US010308953B2

(12) United States Patent
Aponte et al.

(10) Patent No.: US 10,308,953 B2
(45) Date of Patent: Jun. 4, 2019

(54) PLANTS HAVING INCREASED TOLERANCE TO HERBICIDES

(71) Applicant: BASF AGRO B.V., EA Arnheim (NL)

(72) Inventors: Raphael Aponte, Ludwigshafen (DE); Stefan Tresch, Kirchheim (DE); Matthias Witschel, Bad Duerkheim (DE); Jens Lerchl, Potsdam OT Golm (DE); Dario Massa, Mannheim (DE); Tobias Seiser, Mannheim (DE); Thomas Mietzner, Annweiler (DE); Jill Marie Paulik, Cary, NC (US); Chad Brommer, Raleigh, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 15/105,270

(22) PCT Filed: Dec. 17, 2014

(86) PCT No.: PCT/IB2014/067018

§ 371 (c)(1),
(2) Date: Jun. 16, 2016

(87) PCT Pub. No.: WO2015/092706

PCT Pub. Date: Jun. 25, 2015

(65) Prior Publication Data

US 2016/0374339 A1 Dec. 29, 2016

Related U.S. Application Data

(60) Provisional application No. 61/917,360, filed on Dec. 18, 2013.

(51) Int. Cl.

| | |
|---|---|
| ***C12N 15/82*** | (2006.01) |
| ***A01N 43/54*** | (2006.01) |
| ***C12N 9/02*** | (2006.01) |
| ***A01N 37/10*** | (2006.01) |
| ***A01N 43/653*** | (2006.01) |
| ***A01N 43/84*** | (2006.01) |
| ***A01H 5/00*** | (2018.01) |

(52) U.S. Cl.

CPC .......... *C12N 15/8274* (2013.01); *A01H 5/00* (2013.01); *A01N 37/10* (2013.01); *A01N 43/54* (2013.01); *A01N 43/653* (2013.01); *A01N 43/84* (2013.01); *C12N 9/001* (2013.01); *C12Y 103/03004* (2013.01)

(58) Field of Classification Search

None

See application file for complete search history.

(56) References Cited

U.S. PATENT DOCUMENTS

| | | | |
|---|---|---|---|
| 4,940,935 | A | 7/1990 | Riley |
| 5,188,642 | A | 2/1993 | Shah et al. |
| 5,276,268 | A | 1/1994 | Strauch et al. |
| 5,366,892 | A | 11/1994 | Foncerrada et al. |
| 5,561,236 | A | 10/1996 | Leemans et al. |
| 5,593,881 | A | 1/1997 | Thompson et al. |
| 5,723,756 | A | 3/1998 | Peferoen et al. |
| 5,737,514 | A | 4/1998 | Stiffler |
| 5,747,450 | A | 5/1998 | Ohba et al. |
| 5,767,373 | A | 6/1998 | Ward et al. |
| 5,792,931 | A | 8/1998 | Duvick et al. |
| 5,939,602 | A | 8/1999 | Volrath et al. |
| 5,981,722 | A | 11/1999 | Chen et al. |
| 8,119,784 | B2 | 2/2012 | Zhu et al. |
| 2005/0060767 | A1 | 3/2005 | Subramanian et al. |
| 2005/0246798 | A1 | 11/2005 | Castle et al. |
| 2007/0004912 | A1 | 1/2007 | Castle et al. |
| 2008/0155705 | A1 | 6/2008 | Zank et al. |
| 2010/0100988 | A1 | 4/2010 | Tranel et al. |
| 2014/0082772 | A1 | 3/2014 | Vantieghem et al. |
| 2015/0252379 | A1 | 9/2015 | Hutzler et al. |

FOREIGN PATENT DOCUMENTS

| | | | |
|---|---|---|---|
| CN | 1860211 | A | 11/2006 |
| CN | 101980595 | A | 2/2011 |
| CN | 102947443 | A | 2/2013 |
| CN | 103261424 | A | 8/2013 |
| EP | 239956 | A2 | 10/1987 |
| EP | 242236 | A1 | 10/1987 |
| EP | 337899 | A1 | 10/1989 |

(Continued)

OTHER PUBLICATIONS

Arondel et al, Map-based cloning of a gene controlling omega-3 fatty acid desaturation in *Arabidopsis*, Science, 258(5086) : 1353-5 (1992) (Prior Art).

Balvo, et al, Genetic connection between fatty acid metabolism and sporulation in Aspergillus nidulans, J.Biol. Chem, 276(28):25766-74 (2001) (Prior Art).

Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (2002).

Broun et al., Catalytic plasticity of fatty acid modification enzymes underlying chemical diversity of plant lipids, Science, 282(5392):1315-7 (1998).

Cases et al., Identification of a gene encoding an acyl CoA:diacylglycerol acyltransferase, a key enzyme in triacylglycerol synthesis, Proc. Natl. Acad. Sci. USA, 95(22): 13018-23 (1998).

(Continued)

*Primary Examiner* — Eileen B O Hara

(74) *Attorney, Agent, or Firm* — Marshall, Gerstein & Borun LLP

(57) ABSTRACT

The present invention refers to a method for controlling undesired vegetation at a plant cultivation site, the method comprising the steps of providing, at said site, a plant that comprises at least one nucleic acid comprising a nucleotide sequence encoding a wild-type or a mutated protoporphyrinogen oxidase (PPO) which is resistant or tolerant to a PPO-inhibiting herbicide by applying to said site an effective amount of said herbicide. The invention further refers to plants comprising wild-type or mutated PPO enzymes, and methods of obtaining such plants.

10 Claims, 24 Drawing Sheets

Specification includes a Sequence Listing.

(56) References Cited

FOREIGN PATENT DOCUMENTS

| | | | | |
|---|---|---|---|---|
| EP | 2861742 A2 | 4/2015 | | |
| EP | 3033426 A2 | 6/2016 | | |
| WO | WO-2007/024739 A2 | 3/2007 | | |
| WO | WO-2008/022963 A2 | 2/2008 | | |
| WO | WO-2011/114232 A2 | 9/2011 | | |
| WO | WO-2012/052468 A2 | 4/2012 | | |
| WO | WO-2012/080975 A1 | 6/2012 | | |
| WO | WO-2012080975 A1 * | 6/2012 | ........... | C12N 9/0059 |
| WO | WO-2012/163824 A1 | 12/2012 | | |
| WO | WO-2013/006472 A1 | 1/2013 | | |
| WO | WO-2013/017402 A1 | 2/2013 | | |
| WO | WO-2013/072528 A2 | 5/2013 | | |
| WO | WO-2013/076315 A2 | 5/2013 | | |
| WO | WO-2013/076316 A2 | 5/2013 | | |
| WO | WO-2013/083859 A2 | 6/2013 | | |
| WO | WO-2013/092244 A1 | 6/2013 | | |
| WO | WO-2013/104561 A1 | 7/2013 | | |
| WO | WO-2013/139752 A1 | 9/2013 | | |
| WO | WO-2013/139753 A1 | 9/2013 | | |
| WO | WO-2013/139765 A1 | 9/2013 | | |
| WO | WO-2013/139779 A1 | 9/2013 | | |
| WO | WO-2013/174693 A1 | 11/2013 | | |
| WO | WO-2013/174694 A1 | 11/2013 | | |
| WO | WO-2013/178585 A1 | 12/2013 | | |
| WO | WO-2013/182472 A1 | 12/2013 | | |
| WO | WO-2013/189777 A1 | 12/2013 | | |
| WO | WO-2013/189984 A2 | 12/2013 | | |
| WO | WO-2014/020533 A2 | 2/2014 | | |
| WO | WO-2014/030090 A1 | 2/2014 | | |
| WO | WO-2014/064094 A1 | 5/2014 | | |
| WO | WO-2014/097085 A1 | 6/2014 | | |
| WO | WO-2014/124850 A1 | 8/2014 | | |
| WO | WO-2014/177990 A2 | 11/2014 | | |
| WO | WO-2014/177991 A2 | 11/2014 | | |
| WO | WO-2014/177992 A2 | 11/2014 | | |
| WO | WO-2014/177993 A2 | 11/2014 | | |
| WO | WO-2014/177999 A2 | 11/2014 | | |
| WO | WO-2014/184014 A1 | 11/2014 | | |
| WO | WO-2014/184015 A1 | 11/2014 | | |
| WO | WO-2014/184016 A1 | 11/2014 | | |
| WO | WO-2014/184017 A1 | 11/2014 | | |
| WO | WO-2014/184019 A1 | 11/2014 | | |
| WO | WO-2014/184073 A1 | 11/2014 | | |
| WO | WO-2014/184074 | 11/2014 | | |
| WO | WO-2014/187705 A1 | 11/2014 | | |
| WO | WO-2014/206835 A1 | 12/2014 | | |
| WO | WO-2015/007564 A1 | 1/2015 | | |
| WO | WO-2015/007711 A1 | 1/2015 | | |
| WO | WO-2015/022634 A2 | 2/2015 | | |
| WO | WO-2015/022636 | 2/2015 | | |
| WO | WO-2015/022639 A2 | 2/2015 | | |
| WO | WO-2015/052152 A1 | 4/2015 | | |
| WO | WO-2015/052153 A1 | 4/2015 | | |
| WO | WO-2015/052173 A1 | 4/2015 | | |
| WO | WO-2015/052178 A1 | 4/2015 | | |
| WO | WO-2015/092706 A1 | 6/2015 | | |

OTHER PUBLICATIONS

Castle et al., Discovery and directed evolution of a glyphosate tolerance gene, Science, 304:1151-4 (2004).

Che et al., Localization of target-site of the protoporphyrinogen oxidase-inhibiting herbicide, S-23142, in *Spinacia oleracea* L., Z. Naturforsch., 49:350-5 (1993).

Dailey et al., Expression of a cloned protoporphyrinogen oxidase, J. Biol. Chem., 269(2):813-5 (1994).

Duke et al., Protoporphyrinogen oxidase-inhibiting herbicides, Weed Sci., 39:465-73 (1991).

Frentzen, Acyltransferases from basic science to modified seed oils, Fett/Lipid, pp. 161-166, vol. 100 (1998) (Prior Art).

Geiser et al., The hypervariable region in the genes coding for entomopathogenic crystal proteins of Bacillus thuringiensis: nucleotide sequence of the kurhd1 gene of subsp. *kurstaki* HD1, Gene, 48(1):109-18 (1986).

Genbank AAQ98793, delta-4 fatty acid desaturase [*Pavlova lutheri*] (Nov. 7, 2003).

Genbank Accession No. ABD52326.1, mitochondrial protoporphyrinogen oxidase [*Amaranthus tuberculatus*] (Aug. 18, 2006).

Genbank AY926606.1, Pavlova salina delta-4 desaturase (D4Des) mRNA, complete cds (Dec. 1, 2006).

International Preliminary Report on Patentability, International Application No. PCT/IB2013/056243, dated Feb. 3, 2015.

International Preliminary Report on Patentability, International Application No. PCT/IB2014/067018, dated Jun. 21, 2016.

International Search Report, International Application No. PCT/IB2013/056243, dated Feb. 6, 2014.

International Search Report, International application No. PCT/IB2014/067018, dated May 6, 2015.

Jones et al., Isolation of the tomato Cf-9 gene for resistance to Cladosporium fulvum by transposon tagging, Science, 266(5186):789-93 (1994).

Kataoka et al., Isolation and partial characterization of mutant chlanzydoronas reinhardtii resistant to herbicide S-23142, J. Pesticide Sci., 15:449-51 (1990).

Kayastha, Book review of "Protein Biotechnology" edited by G. Walsh and D. Headon, Biochemical Education, 23(2):105-6 (1995).

Knutzon et al., Identification of Delta5-desaturase from Mortierella alpina by heterologous expression in Bakers' yeast and canola, J. Biol. Chem., 273(45):29360-6 (1998).

Lee et al., Cellular localization of protoporphyrinogen-oxidizing activities of etiolated barley (*Hordeum vulgare* L) Leaves, Plant Physiol., 102:881-9 (1993).

Lermontova et al., Overexpression of plastidic protoporphyrinogen IX oxidase leads to resistance to the diphenyl-ether herbicide acifluorfen, Plant Physiol., 122(1):75-84 (2000).

Li et al., Development of PPO inhibitor-resistant cultures and crops, Pest Manag. Sci., 61(3)277-85 (2005).

Lu et al., An enzyme regulating triacylglycerol composition is encoded by the ROD1 gene of *Arabidopsis*, Proc. Natl. Acad. Sci. USA, 106(44): 18837-42 (2009).

Mantle et al., Differentiation of Claviceps purpurea in axenic culture, J. Gen. Microbiol., 93(2):321-34 (1976).

Martin et al., Map-based cloning of a protein kinase gene conferring disease resistance in tomato, Science, 262(5138):1432-6 (1993).

Matringe et al., Protoporphyrinogen oxidase as a molecular target for diphenyl ether herbicides, Biochem. J., 260(1):231-5 (1989).

Matringe et al., Protoporphyrinogen oxidase inhibition by three peroxidizing herbicides: oxadiazon, LS 82-556 and M&B 39279, FEBS Lett., 245(1-2):35-8 (1989).

Mey et al., The biotrophic, non-appressorium-forming grass pathogen *Claviceps purpurea* needs a Fus3/Pmk1 homologous mitogen-activated protein kinase for colonization of rye ovarian tissue, Mol. Plant Microbe Interact. 15(4):303-12 (2002).

Mindrinos et al., The *A. thaliana* disease resistance gene RPS2 encodes a protein containing a nucleotide-binding site and leucine-rich repeats, Cell, 78(6):1089-99 (1994).

Nandihalli et al., Quantitative structure-activity relationships of protoporphyrinogen oxidase-inhibiting diphenyl ether herbicides, Pesticide Biochemistry and Physiology, 43:193-211 (1992).

Okuley et al., *Arabidopsis* FAD2 gene encodes the enzyme that is essential for polyunsaturated lipid synthesis, Plant Cell, 6(1):147-58 (1994).

Oshio et al., Isolation and characterization of a *Chlamydomonas reinhardtii* mutant resistant to photobleaching herbicides, Z. Naturforsch., 48c:339-44 (1993).

Padgette et al., Site-directed mutagenesis of a conserved region of the 5-enolpyruvylshikimate-3-phosphate synthase active site, J. Biol. Chem., 266(33):22364-9 (1991).

Partial Supplementary European Search Report, European patent application No. 14872551.8, dated May 2, 2017 (15 pages).

Qi et al, Production of very long chain polyunsaturated omega-3 and omega-6 fatty acids in plants, Nat. Biotechnol., 22:739-45, vo. 22 (2004).

(56) References Cited

OTHER PUBLICATIONS

Qui et al., Identification of a delta4 fatty acid desaturase from *Thraustochystrium* sp. involved in the biosynthesis of docosahexanoic acid by heterologous expression in *Saccharomyces cerevisiae* adn *Brassica juncea*, J. Biol. Chem., 276(34):31561-6 (2001).
Sasarman et al., Nucleotide sequence of the hemG gene involved in the protoporphyrinogen oxidase activity of *Escherichia coli* K12, Can. J. Microbiol., 39(12):1155-61 (1993).
Sato et al., Characterization of a mutant of Chlamydomonas reinhardtii resistant to protoporphyrinogen oxidase inhibitors, Washington DC: ACS Press, pp. 91-104 (1994).
Shanklin et al, Desaturation and related modifications of fatty acids, Plant Physiol. Plant Mol. Biol., 49:611-41 (1998).
Shibata et al., Isolation and characterization of a Chlamydomonas reinhardtii mutant resistant to an experimental herbicide S-23142, which inhibits chlorophyll synthesis, pp. 567-570 in: Murata (ed.), Research in Photosynthesis, vol. III, Netherlands: Kluwer Acadmic Publishers (1992).
Slabas, Acyltransferases and their role in the biosynthesis of lipids—opportunities for new oils, J.Plant Physiology, 158:505-13 (2001).
Tonon et al., Identification of a very long chain polyunsaturated fatty acid delta4-desaturase from the microalga *Pavlova lutheri*, FEBS Lett., 553:440-4 (2003).
Tudzinski et al, Biotechnology and genetics of ergot alkaloids, App. Microbiol. Biotechnol., 57:593-605 (2001).
UniProt No. D6NSTO, Delta-4 fatty acid desaturase [*Pavlova viridis*].
Van Damme et al., Molecular cloning of mannose-binding lectins from Clivia miniata, Plant Mol. Biol., 24:825-30 (1994).
Vrinten et al., Biosynthesis of long chain polyunsaturated fatty acids in the marine ichtyosporean *Sphaeroforma aractica*, Lipids, 48:263-74 (2013).
Xu et al., Heterologous overexpression of a novel delta-4 desaturase gene from the marine microalga *Pavlova viridis* in *Escherichia coli* as a Mistic fusion, World J. Microbiol. Biotechnol., 27:2931-7 (2011).
Yanase et al., Porphyrin synthesis involvement in diphenyl ether-like mode of action of TNPP-ethyl, a novel phenylpyrazole herbicide, Pesticide Biochem. Physiol., 35:70-80 (1989).
Zank, Cloning and functional expression of the first plant fatty acid elongase specific for delta6-polyunsaturated fatty acids, Biochemical Society Transactions, 28:654-8 (2000).
Extended European Search Report for EP Patent No. 14872551.8, dated Sep. 8, 2017, 18 pages.
Li, et al., "Development of Protoporphyrinogen Oxidase as an Efficient Selection Marker for Agrobacterium tumefaciens-Mediated Transformation of Maize", Plant Physiol., 133(2):436-47 (2003).

* cited by examiner

```
                              10         20         30         40         50         60         70
88809979[Amaranthus   ................................MVIQSITHLSPNLALPSPLSVSTKNYPVAVMGNISERE
88809985[Amaranthus   ................................MVIQSITHLSPNLALPSPLSVSTKNYPVAVMGNISERE
88809983[Amaranthus   ................................MVIQSITHLSPNLALPSPLSVSTKNYPVAVMGNISERE
88809987[Amaranthus   ................................MVIQSITHLSPNLALPSPLSVSTKNYPVAVMGNISERE
154269386[Amaranthu   ................................MVIQSITHLSPKLALPSPLSVSTKNYPVAVMGNISERE
88809977[Amaranthus   ..............................................................MGNISERD
14349153[Spinacia o   ................................MVILPVSQLSTNLGLS..LVSPTKNNP..VMGNVSERN
296090240[Vitis vin   ..............................................................MAEKSDAQ
223549447[Ricinus c   ..............................................................MSSVIKED
508710828[Theobroma   ..............................................................MAAAKNKD
4586308[Glycine max   ..............................................................MASSATDD
462413867[Prunus pe   ..............................................................MTSLTTKE
355497217[Medicago    ..............................................................MASSAKDD
470136421[Fragaria    ..............................................................MASPSQPH
557549728[Citrus cl   ..............................................................MASAPGED
557549727[Citrus cl   ..............................................................MTNKWRVD
502174085[Cicer ari   ..............................................................MASSAKDN
449521337[Cucumis s   ..............................................................MASPAKQD
449441382[Cucumis s   ..............................................................MKS.....
4105188[Nicotiana t   ..............................................................MAPSAGED
460376434[Solanum l   ..............................................................MAPSAGED
332004618[Arabidops   ..............................................................MASGAVAD
297319493[Arabidops   ..............................................................MESGAVGD
7573447[Arabidopsis   ..............................................................MASGAVAD
9757803[Arabidopsis   ................MGLIKNGTLYCRFGISWNFAAVFFSTYFRHCFRLVRDFDSELLQIAMASGAVAD
386276657[Ambrosia    ......................................................................
514802270[Setaria i   ...............................MLSSSTTTASPAS.SHPYRPAYPR.ASLRPVLAMAGSDD
241937893[Sorghum b   ...............................MLARTATVSSTSSHSHPYRPTSARSLRLRPVLAMAGSDD
332004619[Arabidops   ..............................................................MASGAVAD
414586622[Zea mays]   ...............................MLALTASASSASSHPYRHASAHTRRPRLRAVLAMAGSDD
9857979[Zea mays]     ...............................MLALTASASSASSHPYRHASAHTRRPRLRAVLAMAGSDD
g005961[LEMPA]        .......................................................MEADAGKGSAGGAQI
g009128[LEMPA]        .....................MASSAAISPLHFSPAPPRRHELSHRCRVRCSIAGKPPATAANDSSATSV
224055695[Populus t   ..............................................................MTAAAKDD
482556086[Capsella   MHDAGDSHDPFEIHKHVDVELKSGLDAKTLNKGPLDKRLKIIGPEELKTRFDAELSWLLLITMASAKVAD
357167874[Brachypod   ...........................MLTSATASPSASTRFSSTCRPCRSDSVPARRPRPVLAMAASDD
38347440[Oryza sati   ................................................................MAASDD
148909790[Picea sit   ..............................................................MAEHIHTD
3093412[Solanum tub   ..............................................................MAPSAGED
218195102[Oryza sat   ................................................................MAASDD
222629104[Oryza sat   ................................................................MAASDD
557101022[Eutrema s   ..............................................................MAPDAVAD
300153442[Selaginel   ..............................................................MAMAEGET
300147553[Selaginel   ..............................................................MAMAEGET
88862006[Amaranthus   ................................MVIQSITHLSPNLALPSPLSVSTKNYPVAVMGNISERE
88862008[Amaranthus   ................................MVIQSITHLSPNLALPSPLSVSTKNYPVAVMGNISERE
414586624[Zea mays]   ......................................................................
475622332[Aegilops    ......................................................................
527193040[Genlisea    ..............................................................GFP.....
548847660[Amborella   ......................................................................
```

Figure 1a

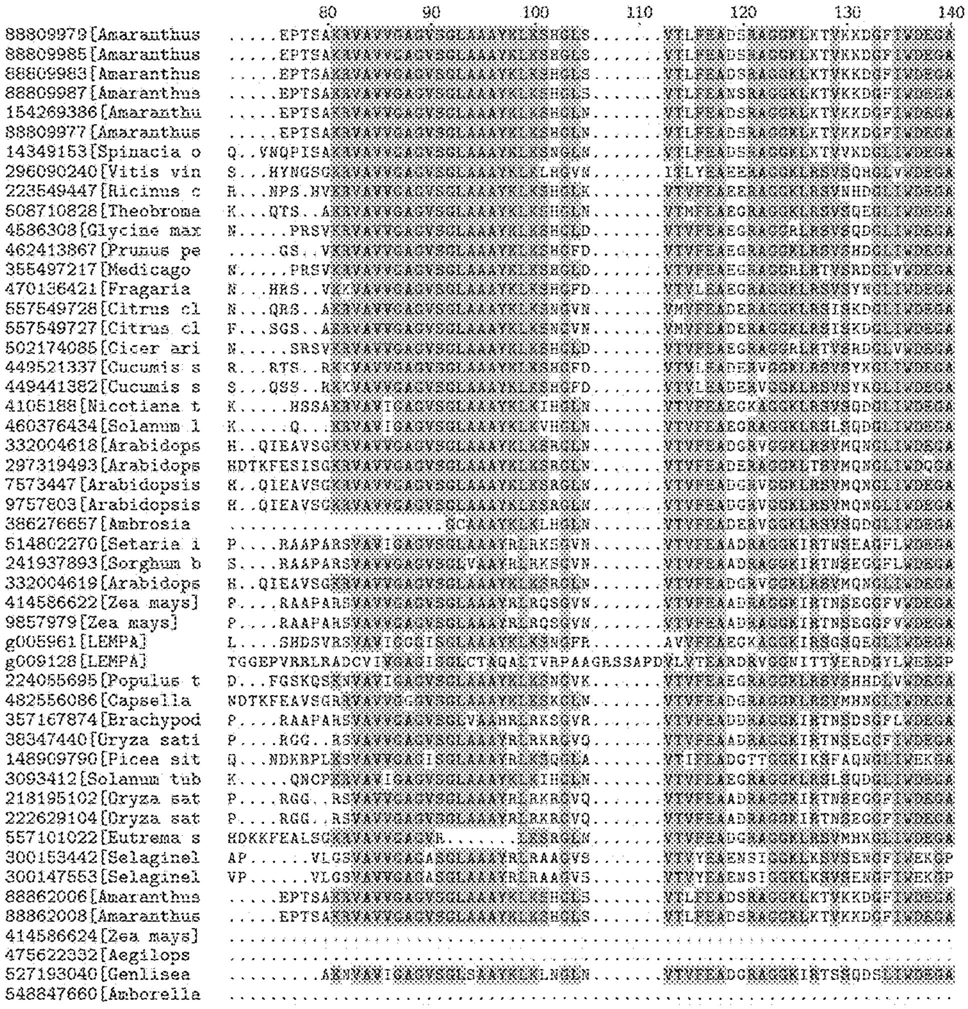
Figure 1a - continued

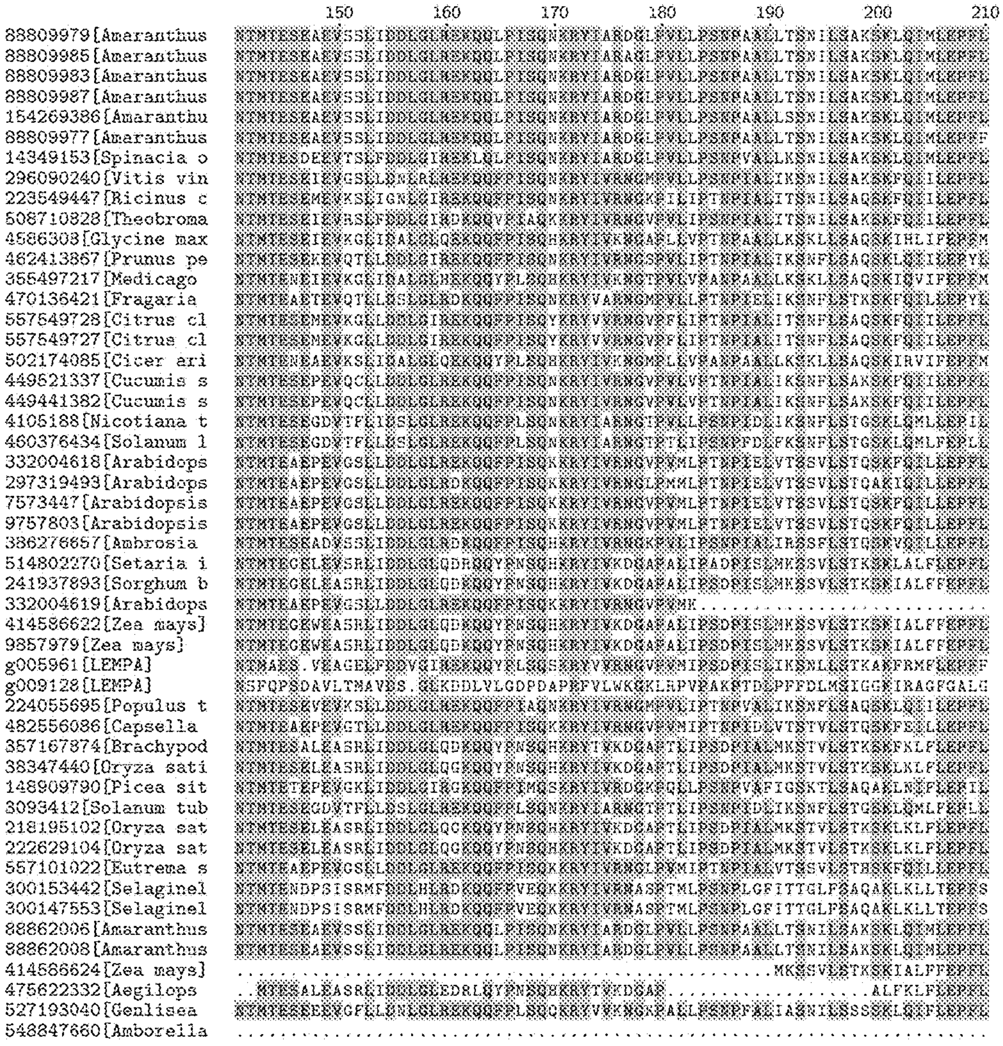
Figure 1a - continued

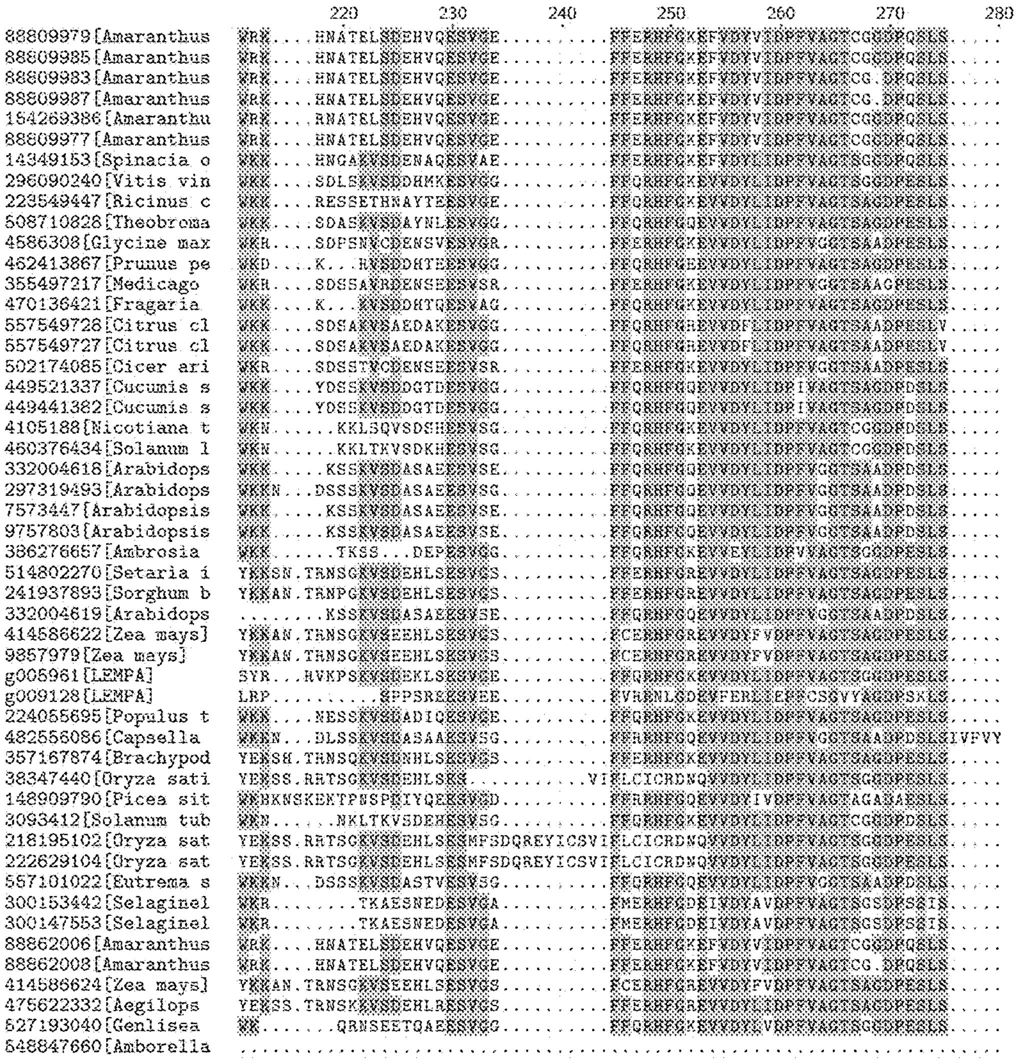
Figure 1a - continued

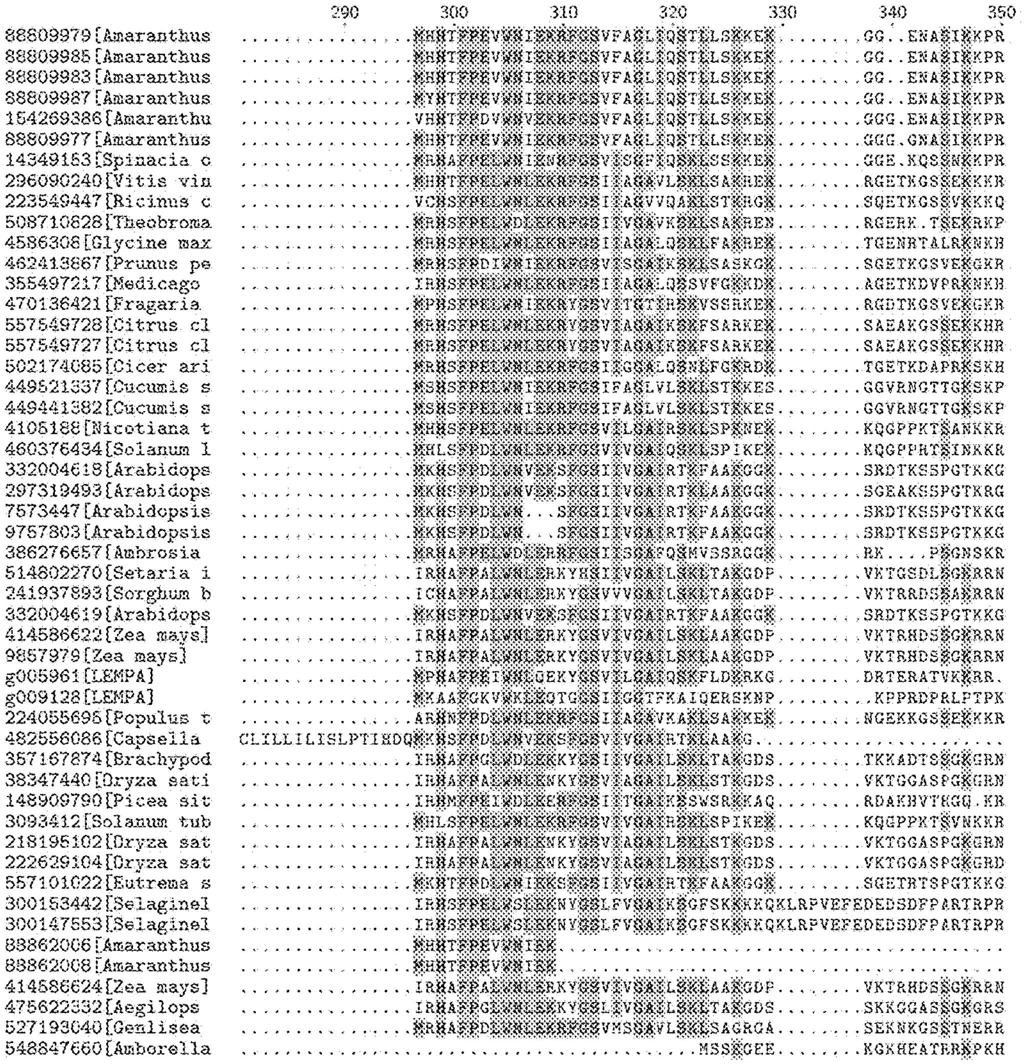
Figure 1a - continued

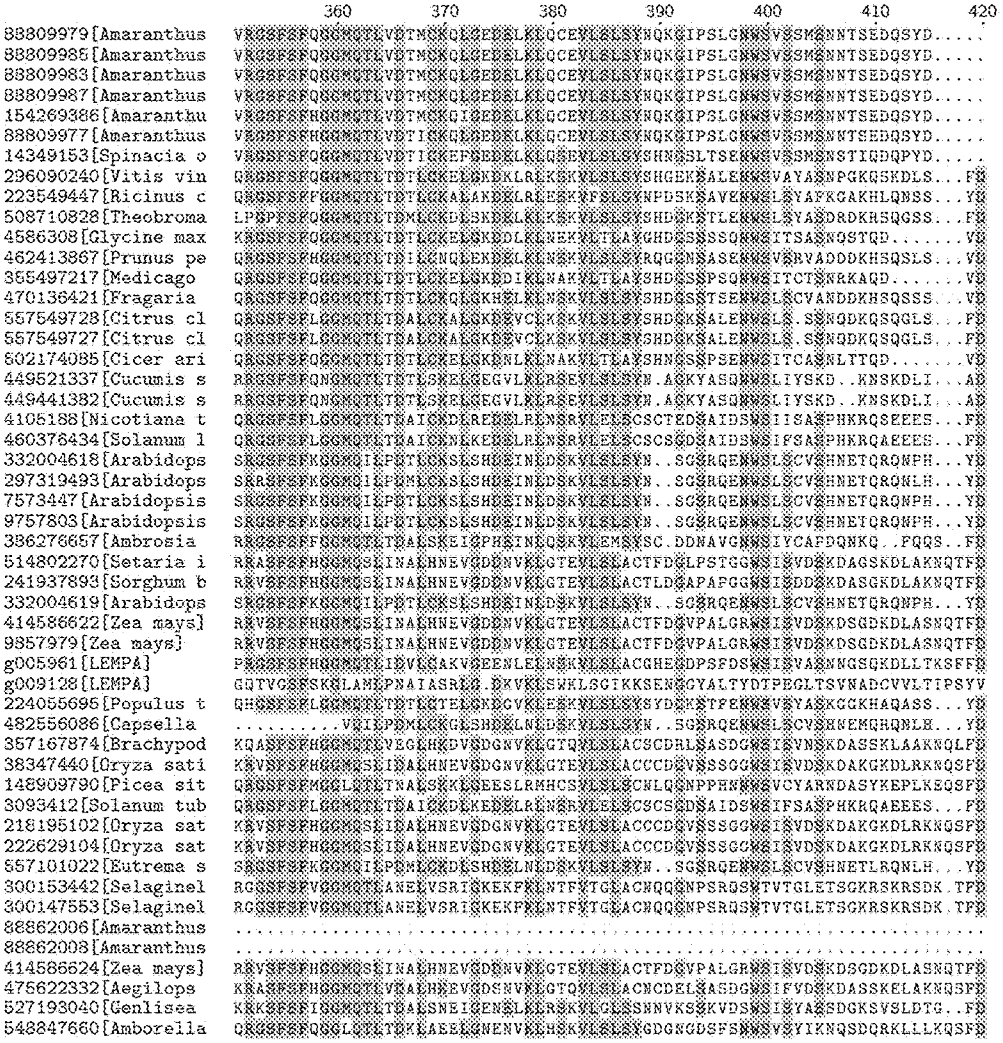
Figure 1a - continued

```
                                 430       440       450       460       470       480       490
88809979[Amaranthus    AVVVTAPIRNVKEMKIMKFGNPFSLDFIPEVTYVPLSVMITAFKKDKVKR.PLEGFGVLIPSKEQH.NGL
88809985[Amaranthus    AVVVTAPIRNVKEMKIMKFGNPFSLDFIPEVTYVPLSVMITAFKKDKVKR.PLEGFGVLIPSKEQH.NGL
88809983[Amaranthus    AVVVTAPIRNVKEMKIMKFGNPFSLDFIPEVTYVPLSVMITAFKKDKVKR.PLEGFGVLIPSKEQH.NGL
88809987[Amaranthus    AVVVTAPIRNVKEMKIMKFGNPFSLDFIPEVTYVPLSVMITAFKKDKVKR.PLEGFGVLIPSKEQH.NGL
154269386[Amaranthu    AVVVTAPIRNVKEMKIMKFGNPFSLDFIPEVTYVPLSVMITAFKKDKVKR.PLEGFGVLIPSKEQH.NGL
88809977[Amaranthus    AVVVTAPIRNVKEMKIMKFGNPFSLDFIPEVSYVPLSVMITAFKKDKVKR.PLEGFGVLIPSKEQH.NGL
14349153[Spinacia o    AVVVTAPINNVKELKIMKVENPFSLDFIPEVSCLPLSVIITTFKKTNVKR.PLEGFGVLVPSNKQH.NGL
296090240[Vitis vin    AVIMTAPLCNVREMKIMKKGNPFLLDFLPEVSYLPLSVIITTFKKENVKR.PLEGFGVLVPSKEQQ.NGL
223549447[Ricinus c    AIVMTAPLCNVKEMKITKNRNIFSLNFLPEVSYMPLSVVITTFKKDNVKS.PLEGFGVLVPSKEQQ.NGL
508710828[Theobroma    AVVMTAPLCNVKEMKIMKGGKLFPLNFIPQVSYMPLSVIITTFKKENVKK.PLEGFGVLVPSKEQQ.NGL
4586308[Glycine max    AVIMTAPLYNVKDIKITKRGTPFPLNFLPEVSYVPISVMITTFKKENVKR.PLEGFGVLVPSKEQK.NGL
462413867[Prunus pe    ALIMTAPLCNVKEMKITKRGTRFPLDFIPEVVYMPLSVIITTFKKENVKR.PLEGFGVLVPSKEQK.NGL
355497217[Medicago     AVIMTAPLGNVRDIQIKKKGNPFPLNFLPEVTYLPLSVLITTFKKENVKR.PLEGFGVLVPSKEQQ.NGF
470136421[Fragaria     AIIMTAPLCSIKEMKITRRGTIFPLDFLPEVNYMPLSVLITSFKKENIKR.PLEGFGVLVPSKEQE.NGL
557549728[Citrus cl    AVIMTASLCNVKEMKITKGGNLFPLDFLPEVIYMPLSVFITAFKKENVGK.PLQGFGVLVPSKEQQ.NGL
557549727[Citrus cl    AVIMTASLCNVKEMKITKGGNLFPLDFLPEVIYMPLSVFITAFKKENVGK.PLQGFGVLVPSKEQQ.NGL
502174085[Cicer ari    AVIMTAPLGNVKDIQITKRGTPFTLNFFPEVTYLPLSVLITTFKKENVKR.PLEGFGVLVPSKEEQ.NGF
449521337[Cucumis s    AVIMTAPVCSVREMKFMKGGIPFSLNFLPEVAYMPLSVMITTFRKESVKR.PLEGFGVLVPSSEQQ.NGL
449441382[Cucumis s    AVIMTAPVCSVREMKFMKGGIPFSLNFLPEVAYMPLSVMITTFRKESVKR.PLEGFGVLVPSSEQQ.NGL
4105188[Nicotiana t    AVIMTAPLCDVKSMKIAKRGNPFLLNFIPEVDYVPLSVVITTFKRENVKY.PLEGFGVLVPSKEQQ.HGL
460376434[Solanum l    AVIMTAPLCDVKSMKIAKRGNPFLLNFIPEVDYVPLSVVITTFKKESVKH.PLEGFGVLVPSQEQK.HGL
332004618[Arabidops    AVIMTAPLCNVKEMKVMKGGQPFQLNFLPEINYMPLSVLITTFTKEKVKR.PLEGFGVLIPSKEQK.HGF
297319493[Arabidops    AVVMTAPLCNVKEMKVTKGGQPFLLNFLPEINYMPLSVLITTFTKEKVKR.PLEGFGVLIPSKEKK.HGF
7573447[Arabidopsis    A....APLCNVKEMKVMKGGQPFQLNFLPEINYMPLSVLITTFTKEKVKR.PLEGFGVLIPSKEQK.HGF
9757803[Arabidopsis    A....APLCNVKEMKVMKGGQPFQLNFLPEINYMPLSVLITTFTKEKVKR.PLEGFGVLIPSKEQK.HGF
386276657[Ambrosia     AVIMTAPLNNLKEMKITKTGSPFLLNFIPEVSYLPISVIISTFKKENVKQ.PLEGFGVLVPAKEQE.NGL
514802270[Setaria i    AVIMTAPLSNVQRMKFRKGGAPFVLDFLPKVNYLPLSLMVTAFKKEDVKK.PLEGFGVLIPYKEQQKHGL
241937893[Sorghum b    AVIMTAPLSNVQRMKFTKGGAPFVLDFLPKVDYLPLSLMVTAFKKEDVKK.PLEGFGVLIPYKEQQKHGL
332004619[Arabidops    AVIMTAPLCNVKEMKVMKGGQPFQLNFLPEINYMPLSVLITTFTKEKVKR.PLEGFGVLIPSKEQK.HGF
414586622[Zea mays]    AVIMTAPLSNVRRMKFTKGGAPVVLDFLPKMDYLPLSLMVTAFKKDDVKK.PLEGFGVLIPYKEQQKHGL
9857979[Zea mays]      AVIMTAPLSNVRRMKFTKGGAPVVLDFLPKMDYLPLSLMVTAFKKDDVKK.PLEGFGVLIPYKEQQKHGL
g005961[LEMPA]         AVIMTAPLGNVEDMKFTKKGSPFALDFLPQVTYLPLSVLITSFKRENVKR.PLEGFGVLVPSKEQE.GGF
g009128[LEMPA]         AGDLLRPLSN.......EAADALTKFYYFPVAAVTISYPSDSIRSSCLIDGQLKSEGQLHP....RSQSV
224055695[Populus t    AVIMTAPLCNVKEINIKGRNRFSLDFLPQMSYMPLSVIITTFKKEDVKR.PLEGFGVLVPSKEQQ.NGL
482556086[Capsella     AVIMTAPLCNVKEMDVMKGGQPFQLNFLPEIKYMPLSVIITTFTKEKVKR.PLEGFGVLIPSKEQK.HGF
357167874[Brachypod    AVIMTAPLSNVQRMKFTKGGVPFVLDFLPKVDYLPLSLMVTAFRKEDVKR.PLEGFGVLIPYKEQQKYGL
38347440[Oryza sati    AVIMTAPLSNVQRMKFTKGGVPFVLDFLPKVDYLPLSLMVTAFKKEDVKK.PLEGFGALIPYKEQQKHGL
148909790[Picea sit    AVVM.........................TVTYLPMSIIITTFKKQDVKH.PLEGFGILVPSKEEK.NGF
3093412[Solanum tub    AVIMTAPLCDVKSMKIAKRGNPFLLNFIPEVDYVPLSVVITTFKKESVKH.PLEGFGVLVPSQEQK.HGL
218195102[Oryza sat    AVIMTAPLSNVQRMKFTKGGVPFVLDFLPKVDYLPLSLMVTAFKKEDVKK.PLEGFGALIPYKEQQKHGL
222629104[Oryza sat    AVIMTAPLSNVQRMKFTKGGVPFVLDFLPKVDYLPLSLMVTAFKKEDVKK.PLEGFGALIPYKEQQKHGL
557101022[Eutrema s    AVVMTAPLCNVKEMKVVKGGQPFQLNFIPEIKYMPLSVIITTFTKEKVKR.PLEGFGVLIPSKEEK.HGF
300153442[Selaginel    AVIMTAPVDDVRAMKVVKDGKPYALDYLPTVIYEPMSVLITMFNKDSVKR.ALPGFGVLVPSKEQQANGF
300147553[Selaginel    AVIMTAPVDDVRTMKVVKDGKPYALDYLPTVIYEPMSVLITMFNKDSVKR.ALPGFGVLVPSKEQQANGF
88862006[Amaranthus    ......................................................................
88862008[Amaranthus    ......................................................................
414586624[Zea mays]    AVIMTAPLSNVRRMKFTKGGAPVVLDFLPKMDYLPLSLMVTAFKKDDVKK.PLEGFGVLIPYKEQQKHGL
475622332[Aegilops     AVIMTAPLSNVQRMRFTKGGAPFVLDFLPKVDYLPLSLMVTAFKKEDVKR.PLEGFGVLIPFKEQQKHGL
527193040[Genlisea     AVIMTAPLSDVKQMK.......................................................
548847660[Amborella    AVVMTAPIRNMQEMQISKCGKPYMLDFLPNVMYLPLSIIVTTFKKENVKL.PLEGFGVLVPSKEQG.SGL
```

Figure 1a - continued

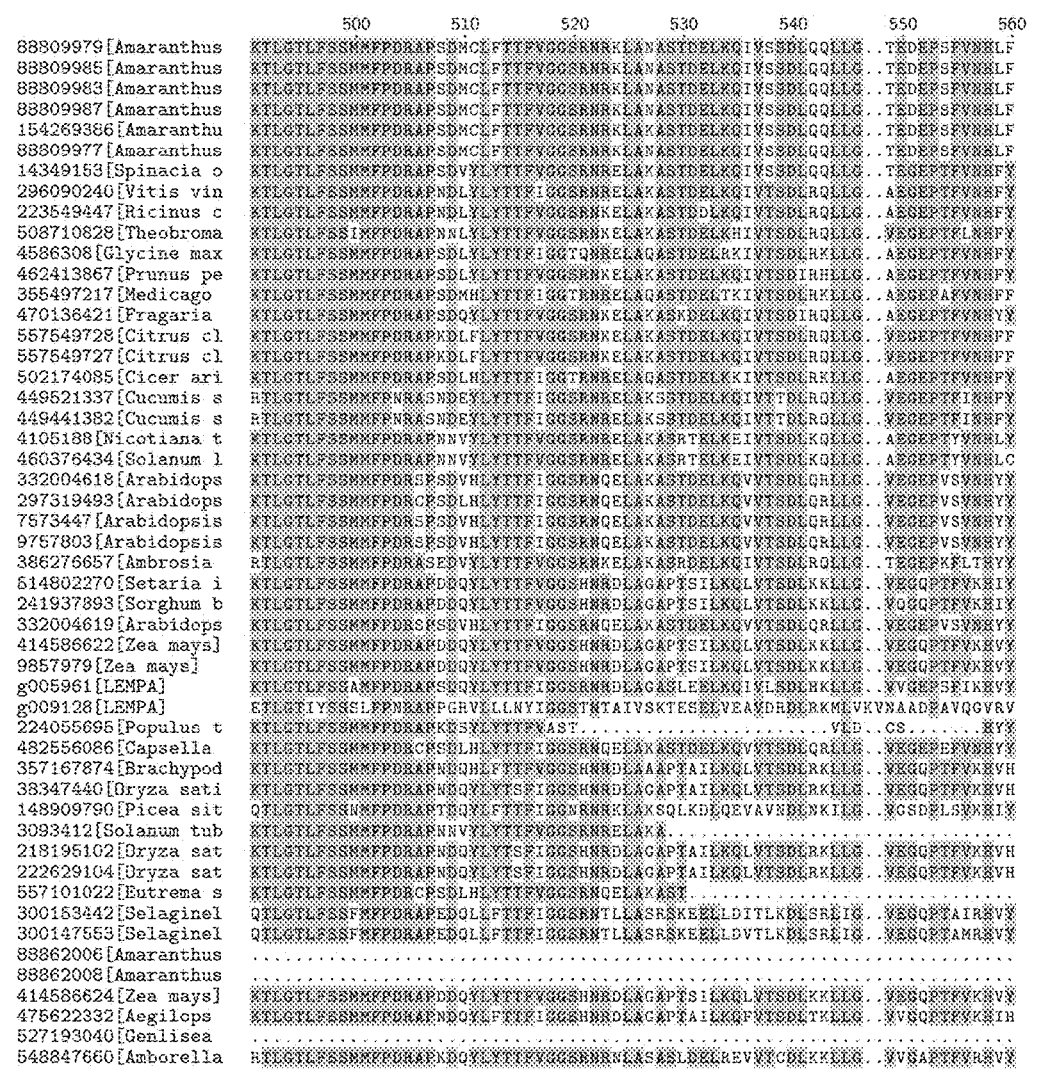

```
                             500        510        520        530        540        550        560
88809979[Amaranthus   KTLGTLFSSNMFPDRAPSDMCLFTTFVGGSRNRKLANASTDELKQIVSSDLQQLLG..TEDEPSFVNHLF
88809985[Amaranthus   KTLGTLFSSNMFPDRAPSDMCLFTTFVGGSRNRKLANASTDELKQIVSSDLQQLLG..TEDEPSFVNHLF
88809983[Amaranthus   KTLGTLFSSNMFPDRAPSDMCLFTTFVGGSRNRKLANASTDELKQIVSSDLQQLLG..TEDEPSFVNHLF
88809987[Amaranthus   KTLGTLFSSNMFPDRAPSDMCLFTTFVGGSRNRKLANASTDELKQIVSSDLQQLLG..TEDEPSFVNHLF
154269386[Amaranthu   KTLGTLFSSNMFPDRAPSDMCLFTTFVGGSRNRKLAKASTDELKQIVSSDLQQLLG..TEDEPSFVNHLF
88809977[Amaranthus   KTLGTLFSSNMFPDRAPSDMCLFTTFVGGSRNRKLANASTDELKQIVSSDLQQLLG..TEDEPSFVNHLF
14349153[Spinacia o   KTLGTLFSSNMFPDRAPSDVYLYTTFVGGSRNRELAKASTDELKQIVSSDLQQLLG..TEGEPTFVNHFY
296090240[Vitis vin   KTLGTLFSSNMFPDRAPNDLYLYTTFIGGSRNRELAKASTDELKQIVTSDLRQLLG..AEGEPTFVNHFY
223549447[Ricinus c   KTLGTLFSSNMFPDRAPNDLYLYTTFVGGSRNKELAKASTDDLKQIVTSDLRQLLG..AEGEPTFVNHFY
508710828[Theobroma   KTLGTLFSSIMFPDRAPNNLYLYTTFVGGSRNKELAKASTDELKHIVTSDLRQLLG..VEGEPTFLNHFY
4586308[Glycine max   KTLGTLFSSNMFPDRAPSDLYLYTTFIGGTQNRELAQASTDELRKIVTSDLRKLLG..AEGEPTFVNHFY
462413867[Prunus pe   KTLGTLFSSNMFPDRAPSDLYLYTTFVGGSRNKELAKASTDELKQIVTSDIRHLLG..AEGEPTFVNHFY
355497217[Medicago    KTLGTLFSSNMFPDRAPSDMHLYTTFIGGTRNRELAQASTDELTKIVTSDLRKLLG..AEGEPAFVNHFF
470136421[Fragaria    KTLGTLFSSNMFPDRAPSDQYLYTTFVGGSRNKELAKASKDELKQIVTSDIRQLLG..AEGEPTFVNHYY
557549728[Citrus cl   KTLGTLFSSNMFPDRAPKDLFLYTTFVGGSRNKELAKASTDELKQIVTSDLRQLLG..VEGEPTFVNHFF
557549727[Citrus cl   KTLGTLFSSNMFPDRAPKDLFLYTTFVGGSRNKELAKASTDELKQIVTSDLRQLLG..VEGEPTFVNHFF
502174085[Cicer ari   KTLGTLFSSNMFPDRAPSDLHLYTTFIGGTRNRELAQASTDELKKIVTSDLRKLLG..AEGEPTFVNHFY
449521337[Cucumis s   RTLGTLFSSNMFPNRASNDEYLYTTFIGGSRNRELAKSSTDELKQIVTTDLRQLLG..VEGEPTFINHFY
449441382[Cucumis s   RTLGTLFSSNMFPNRASNDEYLYTTFIGGSRNRELAKSSTDELKQIVTTDLRQLLG..VEGEPTFINHFY
4105188[Nicotiana t   KTLGTLFSSNMFPDRAPNNVYLYTTFVGGSRNRELAKASRTELKEIVTSDLKQLLG..AEGEPTYVNHLY
460376434[Solanum l   KTLGTLFSSNMFPDRAPNNVYLYTTFVGGSRNRELAKASRTELKEIVTSDLKQLLG..AEGEPTYVNHLC
332004618[Arabidops   KTLGTLFSSNMFPDRSPSDVHLYTTFIGGSRNQELAKASTDELKQVVTSDLQRLLG..VEGEPVSVNHYY
297319493[Arabidops   KTLGTLFSSNMFPDRCPSDLHLYTTFIGGSRNQELAKASTDELKQVVTSDLQRLLG..VEGEPVSVNHYY
7573447[Arabidopsis   KTLGTLFSSNMFPDRSPSDVHLYTTFIGGSRNQELAKASTDELKQVVTSDLQRLLG..VEGEPVSVNHYY
9757803[Arabidopsis   KTLGTLFSSNMFPDRSPSDVHLYTTFIGGSRNQELAKASTDELKQVVTSDLQRLLG..VEGEPVSVNHYY
386276657[Ambrosia    RTLGTLFSSNMFPDRASEDVYLYTTFVGGSRNKELAKASRDELKQIVTSDLRQLLG..TEGEPKFLTHYY
514802270[Setaria i   KTLGTLFSSNMFPDRAPDDQYLYTTFVGGSHNRDLAGAPTSILKQLVTSDLKKLLG..VEGQPTFVKHIY
241937893[Sorghum b   KTLGTLFSSNMFPDRAPDDQYLYTTFVGGSHNRDLAGAPTSILKQLVTSDLKKLLG..VQGQPTFVKHIY
332004619[Arabidops   KTLGTLFSSNMFPDRSPSDVHLYTTFIGGSRNQELAKASTDELKQVVTSDLQRLLG..VEGEPVSVNHYY
414586622[Zea mays]   KTLGTLFSSNMFPDRAPDDQYLYTTFVGGSHNRDLAGAPTSILKQLVTSDLKKLLG..VEGQPTFVKHVY
9857979[Zea mays]     KTLGTLFSSNMFPDRAPDDQYLYTTFVGGSHNRDLAGAPTSILKQLVTSDLKKLLG..VEGQPTFVKHVY
g005961[LEMPA]        KTLGTLFSSAMFPDRAPSDQYLYTTFIGGSRNRDLAGASLEELKQIVLSDLHKLLG..VVGEPSFIKHVY
g009128[LEMPA]        ETLGTIYSSSLFPNRAPPGRVLLLNYIGGSTNTAIVSKTESELVEAVDRDLRKMLVKVNAADPAVQGVRV
224055695[Populus t   KTLGTLFSSNMFPDRAPKDSYLYTTFVAST.......................VLD..CS.......HYY
482556086[Capsella    KTLGTLFSSNMFPDRCPSDLHLYTTFIGGSRNQELAKASTDELKQVVTSDLQRLLG..VEGEPEFVNHYY
357167874[Brachypod   KTLGTLFSSNMFPDRAPNDQHLFTTFVGGSHNRDLAAAPTAILKQLVTSDLRKLLG..VEGQPTFVKHVH
38347440[Oryza sati   KTLGTLFSSNMFPDRAPNDQYLYTSFIGGSHNRDLAGAPTAILKQLVTSDLRKLLG..VEGQPTFVKHVH
148909790[Picea sit   QTLGTLFSSNMFPDRAPTDQYLFTTFIGGNRNRKLAKSQLKDLQEVAVNDLNKILG..VGSDPLSVKHIY
3093412[Solanum tub   KTLGTLFSSNMFPDRAPNNVYLYTTFVGGSRNRELAKA................................
218195102[Oryza sat   KTLGTLFSSNMFPDRAPNDQYLYTSFIGGSHNRDLAGAPTAILKQLVTSDLRKLLG..VEGQPTFVKHVH
222629104[Oryza sat   KTLGTLFSSNMFPDRAPNDQYLYTSFIGGSHNRDLAGAPTAILKQLVTSDLRKLLG..VEGQPTFVKHVH
557101022[Eutrema s   KTLGTLFSSNMFPDRCPSDLHLYTTFVGGSRNQELAKAST..............................
300153442[Selaginel   QTLGTLFSSFMFPDRAPEDQLLFTTFIGGSRNTLLASRSKEELLDITLKDLSRLIG..VEGQPTAIRHVY
300147553[Selaginel   QTLGTLFSSFMFPDRAPEDQLLFTTFIGGSRNTLLASRSKEELLDVTLKDLSRLIG..VEGQPTAMRHVY
88862006[Amaranthus   ......................................................................
88862008[Amaranthus   ......................................................................
414586624[Zea mays]   KTLGTLFSSNMFPDRAPDDQYLYTTFVGGSHNRDLAGAPTSILKQLVTSDLKKLLG..VEGQPTFVKHVY
475622332[Aegilops    KTLGTLFSSNMFPDRAPNDQYLFTTFIGGSHNRDLAGAPTAILKQFVTSDLTKLLG..VVGQPTFVKHIH
527193040[Genlisea    ......................................................................
548847660[Amborella   RTLGTLFSSNMFPDRAPKDQYLYTTFVGGSRNRNLASASLDELREVVTCDLKKLLG..VVGAPTFVRHVY
```

Figure 1a - continued

```
                         570       580       590       600       610       620       630
88809979[Amaranthus   WSNAFFLYGHNYDSVLRAIDKMEKDL..PGFFYAGNHKGGLSVGKAMASGCKAAELVISYLDSHIYVKMD
88809985[Amaranthus   WSNAFFLYGHNYDSVLRAIDKMEKDL..PGFFYAGNHKGGLSVGKAMASGCKAAELVISYLDSHIYVKMD
88809983[Amaranthus   WSNAFFLYGHNYDCVLRAIDKMEKDL..PGFFYAGNHKGGLSVGKAMASGCKAAELVISYLDSHIYVKMD
88809987[Amaranthus   WSNAFFLYGHNYDSVLRAIDKMEKDL..PGFFYAGNHKGGLSVGKAMASGCKAAELVISYLDSHIYVKMD
154269386[Amaranthu   WSNAFFLYGHNYDSVLRAIDKMEKDL..PGFFYAGNHKGGLSVGKAMASGCKAAELVISYLDSHLYVKMN
88809977[Amaranthus   WSNAFFLYGHNYDSVLRAIDKMEKDL..PGFFYAGNHKGGLSVGKAMASGCKAAELVISYLDSHIYVKMD
14349153[Spinacia o   WSKAFFLYGRNYDSVLRAIEKMERDL..PGLFYAGNHKGGLSVGKSIASGYKAAELAISYLESN...KMT
296090240[Vitis vin   WSKAFFLFGHNYDSVLEAIDKMEKDL..PGFFYAGNHKGGLSVGKAIASGCKAADLVISYLNSSSDGKMF
223549447[Ricinus c   WSKAFFLYGRNYDAVLEAIDTMEKDL..PGFFYAGNHKGGLSVGKAIASGCKAADLVISYLESSSDDKML
508710828[Theobroma   WSKAFFLYGRNYASVLKAIEKMETDL..PGFFYAGNHKGGLSVGKAIASGCKAADLVISYLESS.HQKLL
4586308[Glycine max   WSKGFFLYGRNYGSVLQAIDKIEKDL..PGFFFAGNYKGGLSVGKAIASGCKAADLVISYLNSASDNTVP
462413867[Prunus pe   WSNAFFLYGRDYDSVIEAIENMEKNL..PGFFYAGNHRGGLSVGKSIASGCKAAELVISYLESPSDEKTR
355497217[Medicago    WSKGFFLYGHNYGSVLEAIDKMEKDL..PGFFYAGNHRGGLSVGRAIASGCKAADLVISYLNNASDNSV.
470136421[Fragaria    WSKAFFLYGHNYDSVIEAIEKMEKNL..PGLFYAGNHRGGLSVGKAIASGCKAADLVISYLESSSDGKIL
557549728[Citrus cl   WSKAFFLYGRDYDSVLEAIEKMEKNL..PGFFYAGNHKGGLSVGKSIASGCKAAELVISYLENSSDDKML
557549727[Citrus cl   WSKAFFLYGRDYDSVLEAIEKMEKNL..PGFFYAGNHKGGLSVGKSIASGCKAAELVISYLENSSDDKML
502174085[Cicer ari   WSKGFFLYGHNYGLVLEAIDKMEKGL..PGFFYAGNHRGGLSVGRAIASGCKAADLVISYLNNASDNTVA
449521337[Cucumis s   WSKAFFLYGRNYDSVVKAIETMEKNL..PGFFYAGNHRDGLSVGKSIASGCKAADLVISYLESSTDQSCA
449441382[Cucumis s   WSKAFFLYGRNYDSVVKAIETMEKNL..PGFFYAGNHRDGLSVGKSIASGCKAADLVISYLESSTDQSCA
4105188[Nicotiana t   WSKAFFLYGHNYDSVLDAIDKMEKNL..PGLFYAGNHRGGLSVGKALSSGCNAADLVISYLESVSTDSKR
460376434[Solanum l   WSKAFFLYGHNYDSVLDAIDKMEKSL..PGLFYAGNHKGGLSVGKALSSGCNAADLVISYLEAVSADTKN
332004618[Arabidops   WRKAFFLYDSSYDSVMEAIDKMENDL..PGFFYAGNHRGGLSVGKSIASGCKAADLVISYLESCSNDKKP
297319493[Arabidops   WRKAFFLYDSSYGSVMEAIDKMEKDL..PGFFYAGNHRGGLSIGKSIASGCKAADLVISYLESCSNDKKP
7573447[Arabidopsis   WRKAFFLYDSSYDSVMEAIDKMENDL..PGFFYAGNHRGGLSVGKSIASGCKAADLVISYLESCSNDKKP
9757803[Arabidopsis   WRKAFFLYDSSYDSVMEAIDKMENDL..PGFFYAGNHRGGLSVGKSIASGCKAADLVISYLESCSNDKKP
386276657[Ambrosia    WSKAFFLYGRDYGSVIEAIEKMEKEL..PGYFYAGNHKGGLSVGKAISSGCKAAESVIAYLDSYSNQK..
514802270[Setaria i   WRNAFFLYGRDYGSVLDAIEKMEKNL..PGFFYAGNNKDGLAVGNVIASGSKAAELAISYLESQTKHNNS
241937893[Sorghum b   WGNAFFLYGHDYNSVLEAIEKMEKNL..PGFFYAGNNKDGLAVGSVIASGSKAADLAISYLESHTKHNNL
332004619[Arabidops   WRKAFFLYDSSYDSVMEAIDKMENDL..PGFFYAGNHRGGLSVGKSIASGCKAADLVISYLESCSNDKKP
414586622[Zea mays]   WGNAFFLYGHDYSSVLEAIEKMEKNL..PGFFYAGNNKDGLAVGSVIASGSKAADLAISYLESHTKHNNS
9857979[Zea mays]     WGNAFFLYGHDYSSVLEAIEKMEKNL..PGFFYAGNSKDGLAVGSVIASGSKAADLAISYLESHTKHNNS
g005961[LEMPA]        WSKAFFLYGRDYGLVMEAIDRMERNL..PGFYYAGNHRDGLSVGKAIASGFRAADLAISYINSSV.....
g009128[LEMPA]        WPRAIPQFLIGHTDLEDAATRSLDRAGYGGLILGENYVAGVALGRCIEGAYDTAAKVNSFESKYARSF..
224055695[Populus t   WSKAFFLYGKNYDLVLEGIERMEKNL..PGFFYAGNHRGGLSVGKAIASGCKAADLVISHENSSADDKML
482556086[Capsella    WRKAFFLYDSSYDSVMEAIDKMEKDL..PGFFYAGNHRGGLSVGKSIASGCKAADLVISYLESCSNDKKP
357167874[Brachypod   WKNAFFLYGHDYDLALEAIGKMENEL..PGFFYAGNNKDGLAVGNVIASGSKTADLVISYLES..HQAR.
38347440[Oryza sati   WRNAFFLYGQNYDLVLEAIAKMENNL..PGFFYAGNNKDGLAVGNVIASGSKAADLVISYLESCTDQDN.
148909790[Picea sit   WNEAFFLYSLDYNSVVAAIDKLGKSL..PGIYFAGNYRGGLSVGKALTSGFKAADLAISDFNSKGLCTMI
3093412[Solanum tub   ......................................................................
218195102[Oryza sat   WRNAFFLYGQNYDLVLEAIAKMENNL..PGFFYAGKS..........MKAPLLYKRNLRYEKHIPVD...
222629104[Oryza sat   WRNAFFLYGQNYDLVLEAIAKMENNL..PGFFYAGKS..........MKAPLLYKRNLRYEKHIPVD...
557101022[Eutrema s   ......................................................................
300153442[Selaginel   WEKAFFRYSIGYDNVLHSIQKLESDL..PGLFYAGNHRGGLAVGKTIVSGLDAAEQVLQYLQGSGGKKVF
300147553[Selaginel   WEKAFFRYSIGYDNVLNSIQKLESDL..PGLFYAGNHRGGLAVGKTIVSGLDAAEQVLQYLQGSGGKKVF
88862006[Amaranthus   ......................................................................
88862008[Amaranthus   ......................................................................
414586624[Zea mays]   WGNAFFLYGHDYSSVLEAIEKMEKNL..PGFFYAGNNKDGLAVGSVIASGSKAADLAISYLESHTKHNNS
475622332[Aegilops    WRNAFFLYGHDYDSALEAIGKME...........RNNKDGLAVGNVIASGSNTADLVISYLESGIKQVS.
527193040[Genlisea    ......................................................................
548847660[Amborella   WGDAFFLYGHNYDMVLKAIEKMEQNL..PGFFYAGKFSLWC.............................
```

Figure 1a - continued

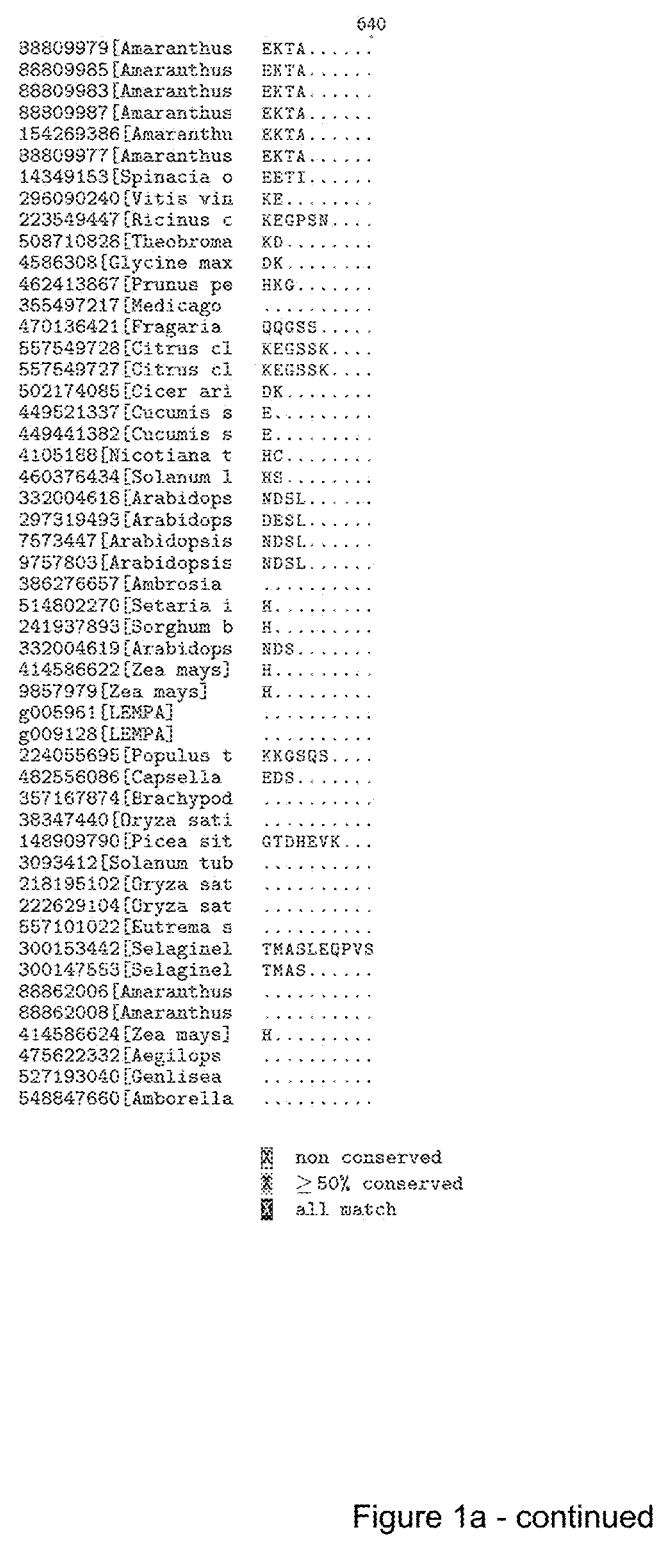

```
                             640
88809979[Amaranthus     EKTA......
88809985[Amaranthus     EKTA......
88809983[Amaranthus     EKTA......
88809987[Amaranthus     EKTA......
154269386[Amaranthu     EKTA......
88809977[Amaranthus     EKTA......
14349153[Spinacia o     EETI......
296090240[Vitis vin     KE........
223549447[Ricinus c     KEGPSN....
508710828[Theobroma     KD........
4586308[Glycine max     DK........
462413867[Prunus pe     HKG.......
355497217[Medicago      ..........
470136421[Fragaria      QQGSS.....
557549728[Citrus cl     KEGSSK....
557549727[Citrus cl     KEGSSK....
502174085[Cicer ari     DK........
449521337[Cucumis s     E.........
449441382[Cucumis s     E.........
4105188[Nicotiana t     HC........
460376434[Solanum l     HS........
332004618[Arabidops     NDSL......
297319493[Arabidops     DESL......
7573447[Arabidopsis     NDSL......
9757803[Arabidopsis     NDSL......
386276657[Ambrosia      ..........
514802270[Setaria i     H.........
241937893[Sorghum b     H.........
332004619[Arabidops     NDS.......
414586622[Zea mays]     H.........
9857979[Zea mays]       H.........
g005961[LEMPA]          ..........
g009128[LEMPA]          ..........
224055695[Populus t     KKGSQS....
482556086[Capsella      EDS.......
357167874[Brachypod     ..........
38347440[Oryza sati     ..........
148909790[Picea sit     GTDHEVK...
3093412[Solanum tub     ..........
218195102[Oryza sat     ..........
222629104[Oryza sat     ..........
557101022[Eutrema s     ..........
300153442[Selaginel     TMASLEQPVS
300147553[Selaginel     TMAS......
88862006[Amaranthus     ..........
88862008[Amaranthus     ..........
414586624[Zea mays]     H.........
475622332[Aegilops      ..........
527193040[Genlisea      ..........
548847660[Amborella     ..........
```

non conserved
≥ 50% conserved
all match

Figure 1a - continued

```
                                 10         20         30         40         50         60         70
88809979[Amaranthus    MVIQSITHLSPNLALPSPLSVSTKNYPVAVMGNISEREEPTSAKRVAVVGAGVSGLAAAYKLKSHG....
88809985[Amaranthus    MVIQSITHLSPNLALPSPLSVSTKNYPVAVMGNISEREEPTSAKRVAVVGAGVSGLAAAYKLKSHG....
88809983[Amaranthus    MVIQSITHLSPNLALPSPLSVSTKNYPVAVMGNISEREEPTSAKRVAVVGAGVSGLAAAYKLKSHG....
262334755[Rhodother    ..........................................MASVGIIGAGIAGLTAAYELHRRG....
83756210[Salinibact    ..........................................MPNVGIIGAGISGLAAAYRLQEHG....
294343547[Salinibac    ..........................................MPNVGIIGAGISGLAAAYRLQEHG....
414586625[Zea mays]    ......................................................................
345112217[Rhodother    ..........................................MASVGIISAGIAGLAAAYELHRRG....
371721543[Caldithri    ...........................................MTVAVIGAGISGLTTAYYLKQQG....
177641723[Opitutus     ..........................MSTSPFNPSATASGRPPKTFAVLGAGITGLTAAHRLTQLG....
518880016[Verrucomi    ......................................MGNPNKTIAILGGGITGLTAAYELLKLG....
383800862[Ignavibac    .........................................MTKTIVVIGAGISGLTTAYLLSKRG....
524787385[Coralioma    .........................................MEKKAIVIGAGISGLCAAIELKKSG....
551206374[Salisaeta    ..........................................MARIGIIGAGIAGLTAAYQLQQQG....
386276661[Ambrosia     ..............................MASPTIVDNQKPAKRVAIVGAGVSGCAAAYKLKLHG....
395811099[Melioriba    .........................................MSKKIVVLGAGISGLSTAYWLVKKG....
261835678[Halothiob    ...............................MNTHSNASEPINCPYLVIGGGISGLATAYHLSRMG....
507112914[Chondrus     .....................................MPEPVKRNVAVLGGGPAGLSAAFRLLHDLPPGL
517800408[Rubritale    .........................................MRKHIAIIGAGVSGLSTAYHLQQAG....
374849760[unculture    .........................................MGVEVAIIGAGISGLSVAFFLKRAG....
293613131[Coralioma    ..........................................MPDTCIIGAGITGLATAWQYQRKG....
308227147[Oscilloch    ........................................MNSYDVVVVGAGISGLSAAYTLFKRG....
391219071[Opitutace    ...........................................MPVAVIGGGITGLTAAWRLAREG....
548847659[Amborella    .........................................STKSVAVVGGGVSGLTTAYRLKSHG....
372475085[Opitutace    ........................MSASLPPPPPPPHTHTQARLPVAVIGGGITGLTAAWRLAREG....
222447859[Chlorofle    ......................................MMAGYDSVVIIGGGIAGLAAAYTLHKRG....
206602621[Leptospir    ......................................MAGFDCDTLVVGGGVSGLAAALTLKNRG....
406774425[Leptospir    ......................................MAGFDCDTLVVGGGVSGLAAALTLKNRG....
518823277[Verrucomi    ........................................MNTKKVCILGAGLSGISLGLSHENKG....
219544473[Chlorofle    .....................................MMMANYDSVVIIGGGIGGLAAAYTLYKRG....
325064935[Desulfuro    ...........................................MKVAVIGAGISGLSVAFYLKKGG....
551218349[Desulfuro    ..........................................MKKVAVVGAGVSGLSTAFYIEKFSGD..
406714610[Arthrospi    .......................................MTNLVDSLIVGAGISGLSLAYSLNREKSVRE
387222448[Leptospir    ......................................MAGFDCDTLVVGGGISGLAAALTLKNHG....
198258436[Verrucomi    ..........................................MQDAIILGGGISGLTAGYLAQKDG....
518821883[Verrucomi    ........................................MNTKKVCILGAGLSGISLGLSHENKG....
86554332[Synechococ    .................................MNPATPEPLNAEVVVIGAGISGLTLAWRLQQGLSARG
551197846[Hymenobac    ...........................................MTIAILGGGISGLVVAWQLQKAG....
394453687[Pontibact    ...........................................MRVAIIGAGISGLSLAYYLQRQG....
251772217[Leptospir    ......................................MATEDVETLVIGGGIAGLACASHLKLAG....
355369310[Prevotell    .......................................MERQRKIIVIGAGLTGLTCAAHLRHKG....
522018329[Flexithri    ............................................MVGIIGAGISGLSLAYHLQKLG....
403378183[Geobacter    ..........................................MKKVIVVGGGISGLATAFELRNKGAEAG
86557434|[Synechoco    .........................................MQAEVVVVGAGISGLTLALRLQQGLSPKD
428246331[Crinalium    ..........................................MVDTLIIGAGISGLSLAYALHQDG....
148843553[Planctomy    ....................................MNQSAPAKRIAVVGGGITGLSAAFHLQELAQEKN
146395727[Geobacter    ..........................................MKKAIVVGGGISGLASAYLLREKAKNSG
343775775[Aciditbio    ...............................MEDV...........IIIGAGISGLATAYFLRKQG....
288335658[Prevotell    .......................................ME.ERKIVVVGAGLTGLTCAAYLRRKG....
317114493[Thermovib    ...........................................MRVCVIGGGVSGLSTAFYLKRGG....
```

Figure 1b

```
                          80        90        100       110       120       130       140
88809979[Amaranthus   ...LSYTLFEADSRAGGKLKTV.KKDGFIWDEGANTMTESEAEVSSLIDDLGLREKQQLPIS..QNKAYI
88809985[Amaranthus   ...LSYTLFEADSRAGGKLKTV.KKDGFIWDEGANTMTESEAEVSSLIDDLGLREKQQLPIS..QNKAYI
88809983[Amaranthus   ...LSYTLFEADSRAGGKLKTV.KKDGFIWDEGANTMTESEAEVSSLIDDLGLREKQQLPIS..QNKAYI
262334755[Rhodother   ...LEYTVFEATDRIGGFIQSE.RIDGFLVELGPQTLQRTSGDFEELLRQV.DLEDACIPARPVAANAFI
83756210[Salinibact   ...HSYRLLEASGHTGGVIRSE.SSEGFLVEHGPNSIRAGAAGLETLIDAL.DLHEDRVWANDAADTAYV
294343547[Salinibac   ...HSYRVLEASGHTGGVIRSE.SSEGFLVEHGPNSIRAGAAGLETLIDAL.DLHEDRVWANDAADTAYV
414586625[Zea mays]   .....................................................................
345112217[Rhodother   ...LEYTVFEATDRIGGFIQSE.RIDGFLVEHGPQTLQRTSGDFEELLRQV.DLEDACITARPIAANAFI
371721543[Caldithri   ...VDYQVFEKNNYIGGSVITE.KKDGFLIDLGPNSTLETSQVLRQLIDQI.GLQSGKVYASDVSNKAYV
177841723[Opitutus    ...HKYRVFEQSDRVGGSIKTE.EVDGWLIEGGPNTLLSGELAVDKLIDEL.GLNGERIAADPAAKNAYI
518880016[Verrucomi   ...HKPTVFESSSRIGGAIETI.RQNDFLAECGPNTLLETSPRISALISDL.GLDSRKRYANPSMKNAYI
383800862[Ignavibac   ...FNIRILERKSEVGGSIESI.KENGFLFDRGPNSALETTPLISQLVEEL.NLKDELLYANKAANKAYI
524787385[Coralioma   ...FNYTVVEKREKAGGVIGTT.ARDGFRAESGSNTVMVNSQKTLDFLMEI.GLKDKIVNSSPAAKKAFF
551206374[Salisaeta   ...HMYRVWEARGVAGGAIRSERTSDGFLVEHGPNSLRATTPIVPRLLEDL.GLERARLSAAPAATKAFI
386276661[Ambrosia    ...LNYTVFEADEKVGGKPRSV.SQDGLIWDEGANTMTESEADASSLIDELGLRDKQQFPIS..QHKAYI
395811099[Melioriba   ...YDYTILETKNEPGGSMISR.RLDNFLIDYGPNSGLETTPLIRKLVEEV.NLSDKMIYANAAASKAYI
261835678[Halothiob   ...KTYTVLEATSRVGGAVGSI.EEDGWLRELGPNSLVQTPEMA.ALMSAL.DLVSEIIEANTVAKKAFV
507112914[Chondrus   S..VKYDLYEATGRLGGAVTSA.CDAGFCYELGPNSMNAKHPSVADLIQEKLRLKPRMLPRSPYAKRYYF
517800408[Rubritale   ...HSYVVFESSKRAGGVIQTI.REDDYLCEWGPNSLMIGDKRIEALLKSI.GLDDEILEANTASKKAFI
374849760[unculture   ...AGYLVLEAEEDVGGTMRSR.RFKGYLIELGPNSALETTPLFQELIAAA.GLAGERVYASEAARNAYI
293613131[Coralioma   ...KDCVVLESGPQVGGAIQSI.LQDGYLAEEGPNSIQLNSLEIEDFLTSIPGLEAQIIEANPAAQKAYI
308227147[Oscilloch   ...LDYLVVEAGAEVGGVMRSIVTPEGYVLDCGPNTLASKDPRMWAEFDDL.GMRDRLVVAGRAGKRAYF
391219071[Opitutace   ...HPYRLFEASPRPGGLIRSE.RDGEWLSEAGPNSLLDNKPELAALLAEL.GLEDARQYAQPAAKKAFI
548847659[Amborella   ...LNYTLYESEGTAGGRIRSI.AYGGLIWEEGANTMTESEMEVKRLIDDLGLREKQQFPIS..QNKAFI
372475085[Opitutace   ...HPYRLFEASPRPGGLIRSE.RDGEWLSEAGPNSLLDNKPELAALLAEL.GLEEARQYAQPAAKKAFI
222447859[Chlorofle   ...YRYLVIESTNRVGGVIQTITTPEGYILDCGPNTVGTGDARLWQELIDL.GLRERITPAAPCSKRAFI
206602621[Leptospir   ...VDYRLLESRGYLGGAIRTV.REDGYLLEFGPNSLMVRPEDAIDTVLGDPELRARIVPASGLSKNAYV
406774425[Leptospir   ...VDYRLLESRGYLGGAIRTV.REDGYLLEFGPNSLMVRPEDAIDTVLGDPELRARIVPASGLSKNAYV
518823277[Verrucomi   ...NQYTIFEKDLRVGGVLQSI.KSEGFLMDYGANTLSIRTKKTVDFLKQY.EILEHAMDANQESSKAFI
219544473[Chlorofle   ...YRYLVIEAANRVGGVIHSITTPEGFTLDCGPNTIGTNDVRLWQELIDL.GLRDRIRPAARCGRRAYI
325064935[Desulfuro   ...AEYKVFEKEKTVGGKMKTI.HEDGYIIETGPNGFLDGKPYTLNLVK.ELGIESKLYRSSDKARKAFI
551218349[Desulfuro   ..NVSYTIFEKENVPGGKMLTV.QKDGFIIETGPNGFLDNKPYTLDLVK.DLKIEDRLYRSSDKARKAFV
406714610[Arthrospi   ..PLKYLVTESQNRVGGNITTGRA.RDFLWEEGPNSFAPTPELLGLAVDLG..LKEELIFADRKLP.AYV
387222448[Leptospir   ...VDYRLLESRGYLGGAVRTV.REEGYLLEFGPNSLMVRPDDAIDAVLGDPELRARIVAASGLSKNAYV
198258436[Verrucomi   ...QDISVIEKGKIPGGPISSF.REEGYLVERGPNSLLLPDPWVETFIEEL.GLRDQLQETNPIASKAYI
518821833[Verrucomi   ...NQYTIFEKDLRVGGVLQSI.KSEGFLMDYGGNTLSIRTKKTVDFLKQY.EILEHAMDANQESSKAFI
86554332[Synechococ   GSPQAYLLAEASSRVGGCISTQSK.RGYRWEEGPNSFTPTPALLNLIAEVG..LTDQLVLADAKLP.AYI
551197846[Hymenobac   ...VAYDLFEAETTPGGCLRSVSHPRGYLVETGPNSLQLSDELLELITELG..LVDEIQDAAAVSKNAYV
394453687[Pontibact   ...VAYDLFEAGSEVGGNMRTLRK.NGYTFELGPNTLQMNEELLQLITELK..LETELLPLTPRNNKAYV
251772217[Leptospir   ...RTYRLVERNDYLGGVIRTL.SDSGYRIETGPNSLLVRTEEPLLKYLSRPEIAARIQLAGRMGKKAFI
355369310[Prevotell   ...QDYEVLEATEKIGGLMQTE.DFDGFIMEQGPSTGTIKYPEVAELFDML..GDKCTLEVAQSSAKCRL
522018329[Flexithri   ...KAYCLFEAGDKPGGNICSVKK.EGFLLEKGPNSLLADSEIIDLVKELG..LEDQMIIPETVSKKAYI
403378183[Geobacter   I.ELDYTLLEKEEKVGGKIWSI.KEEGYLCEWGPNGFLDSKPQTLDLCR.DLGASERLLRSNDNARKAFI
86557434|[Synechoco   ESTQPLLLAEASSRVGGCISTQSK.DSYRWEEGPNSFTPVPALLNLIAEVG..LAEHLVLADAKLP.AYI
428246331[Crinalium   ...RKYLLCERQEKVGGNITTGKA.GGFLWEEGRTSFTPTPALLKLAVDVG..LREELVLADHRLP.AFV
148843553[Planctomy   Q.PVEYTLFESQPEAGGWIGTI.SQDGYRIDTGADMFITNKPAAIELCQ.RLGLEDQLISTNQQYRGALI
146395727[Geobacter   M.ELEITIVEKEDRTGGKIRSI.KEDGYLCEWGPNGFLDSKPQTLDLCR.ELKVDSQLLRSNDNARKAFI
343775775[Acidithio   ...WSPLLLEAAAKPGGNLQSR.QEEGYLRDMGPNSLMLKGHIVPEWLREL.RLEEDIVEANPLAKRAYI
288335658[Prevotell   ...QDYVVLEAADKIGGLMQTE.EVDGFVMEQGPSTGTIKYPEVAELFDML..GDDCTLEVAQSSAKCRL
317114493[Thermovib   ...AQYKLLERENYPGGKARTY.YEKGYIVESGPNGFLDGKPDTLELVK.LLGAEKLLYRSSDKARKAFI
```

Figure 1b - continued

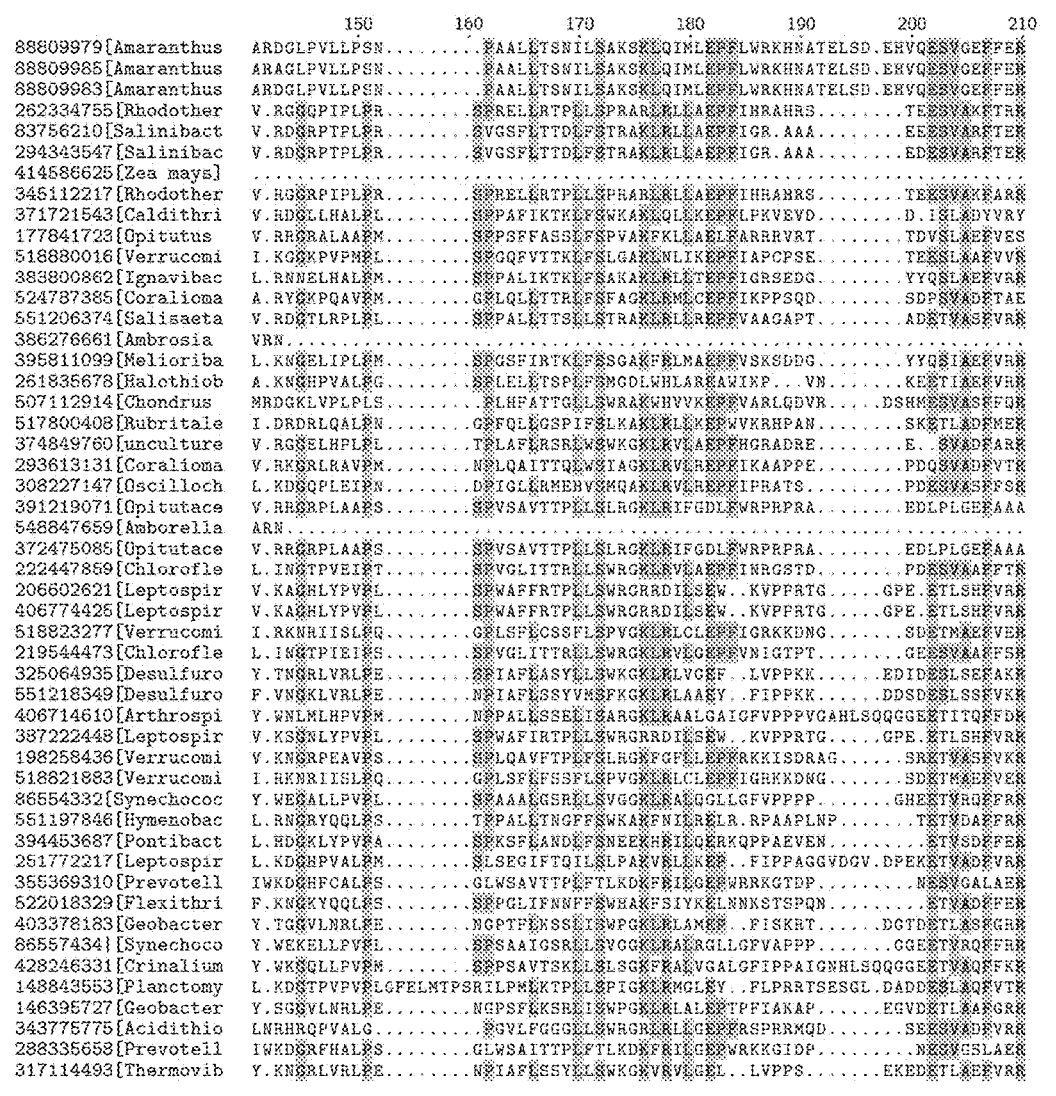

```
                         150       160       170       180       190       200       210
88809979[Amaranthus  ARDGLPVLLPSN.........PAALETSNILSAKSKLQIMLEPFLWRKHNATELSD.EHVQESVGEFFER
88809985[Amaranthus  ARAGLPVLLPSN.........PAALETSNILSAKSKLQIMLEPFLWRKHNATELSD.EHVQESVGEFFER
88809983[Amaranthus  ARDGLPVLLPSN.........PAALETSNILSAKSKLQIMLEPFLWRKHNATELSD.EHVQESVGEFFER
262334755[Rhodother  V.RGSQPIPLPR........SPRELLRTPLLSPRARLKLLAEPFIHRAHRS........TEESVAKFTRR
83756210[Salinibact  V.RDSRPTPLPR........SVGSFLTTDLFSTRAKLKLLAEPFIGR.AAA........EEESVARFTER
294343547[Salinibac  V.RDSRPTPLPR........SVGSFLTTDLFSTRAKLKLLAEPFIGR.AAA........EDESVARFTER
414586625[Zea mays]  ......................................................................
345112217[Rhodother  V.RGSRPIPLPR........SPRELLRTPLLSPRARLRLLAEPFIHRAHRS........TEKSVAKFARR
371721543[Caldithri  V.RDSLLHALPL........SPPAFIKTKLFSWKAKLQLLKEPKLPKVEVD........D.ISLADYVRY
177841723[Opitutus   V.RRGRALAAPM........SPPSFFASSLFSPVAKFKLLAELFARRRVRT........TDVSLAEFVES
518880016[Verrucomi  I.KGSKPVPMPL........SPGQFVTTKLFSLGAKLNLIKEPFIAPCPSE........TEESLAAFVVS
383800862[Ignavibac  L.RNNELHALPM........SPPALIKTKLFSAKAKLRLLTEPFIGRSEDG........YYQSLAEFVRR
524787385[Coralioma  A.RYGKPQAVPM........GPLQLLTTRLFSFAGKLRMLCEPFIKPPSQD........SDPSVADFTAE
551206374[Salisaeta  V.RDGTLRPLPL........SPPALLTTSLLSTRAKLRLLREPFVAAGAPT........ADETVASFVRR
386276661[Ambrosia   VRN...................................................................
395811099[Melioriba  L.KNGELIPLPM........SPGSFIRTKLFSSGAKFRLMAEPFVSKSDDG........YYQSIAEFVRR
261835678[Halothiob  A.KNGHPVALPG........SPLELLTSPLFSMGDLWHLARKAWIKP...VN........KEETIAEFVRR
507112914[Chondrus   MRDGKLVPLPLS.........PLHFATTGLLSWRAKWHVVKEPFVARLQDVR....DSHMESVASFFQR
517800408[Rubritale  I.DRDRLQALPN........GPFQLLGSPIFSLKAKLKLLKSPWVKRHPAN........SKETLADFMEK
374849760[unculture  V.RGSELHPLPL........TPLAFLRSRLWSWKGKLKVLAEPFHGRADRE........E..SVADFARR
293613131[Coralioma  V.RKGRLRAVPM........NPLQAITTQLWSIAGKLRVLREPFIKAAPPE........PDQSVADFVTK
308227147[Oscilloch  L.KDGQPLEIPN........DPIGLLRMEHVSMQAKLRVLREPFIPRATS.........PDESVASFFSR
391219071[Opitutace  V.RRGRPLAAPS........SPVSAVTTPLLSLRGKLRIFGDLFWRPRPRA........EDLPLGEFAAA
548847659[Amborella  ARN...................................................................
372475085[Opitutace  V.RRGRPLAAPS........SPVSAVTTPLLSLRGKLRIFGDLFWRPRPRA........EDLPLGEFAAA
222447859[Chlorofle  L.INGTPVEIPT........SPVGLITTRLLSWRGKLRVLAEPFINRGSTD........PDESVAAFFTR
206602621[Leptospir  V.KAGHLYPVPL........SPWAFFRTPLLSWRGRRDILSEW..KVPPRTG.....GPE.ETLSHFVRR
406774425[Leptospir  V.KAGHLYPVPL........SPWAFFRTPLLSWRGRRDILSEW..KVPPRTG.....GPE.ETLSHFVRR
518823277[Verrucomi  I.RKNHIISLPQ........GPLSFLCSSFLSPVGKLRLCLEPFIGRKKDNG.......SDETMAEFVER
219544473[Chlorofle  L.INGTPIEIPS........SPVGLITTRLLSWRGKLRVLGEPFVNIGTPT........GEESVAAFFSR
325064935[Desulfuro  Y.TNGRLVRLPE........SPIAFLASYLLSWKGKLKLVCEF..LVPPKK.....EDIDESLSEFAKR
551218349[Desulfuro  F.VNSKLVRLPE........NPIAFLSSYVMSFKGKLKLAASY..FIPPKK.....DDSDESLSSFVKK
406714610[Arthrospi  Y.WNLMLHPVPM........NPPALLSSELISARGKLKAALGAIGFVPPPVGAHLSQQGGEETITQFFDK
387222448[Leptospir  V.KSSNLYPVPL........SPWAFIRTPLLSWRGRRDILSEW..KVPPRTG.....GPE.ETLSHFVRK
198258436[Verrucomi  V.KNGRPEAVPS........SPLQAVFTPLFSLRGKFGFLLEPFRKKISDRAG.....SRETVASFVKR
518821883[Verrucomi  I.RKNRIISLPQ........GPLSFLFSSFLSPVGKLRLCLEPKIGRKKDNG.......SDETMAEFVER
86554332[Synechococ  Y.WEGALLPVPL........SPAAALGSRLLSVGGKLRALQGLLGFVPPPP.......GHEETVRQFFRR
551197846[Hymenobac  L.RNGRYQQLPS........TPPALLTNGFFSWKAKFNILRELR.RPAAPLNP.......TETVDAFFRR
394453687[Pontibact  L.HDGKLYPVPA........SPKSFLANDLFSNEEKHRILQERKQPPAEVEN.........ETVSDFFER
251772217[Leptospir  L.KDGHPVALPM........SLSEGIFTQILSLPAKVRLLKEP..FIPPAGGVDGV.DPEKETVADFVRR
355369310[Prevotell  IWKDGHFCALPS........GLWSAVTTPLFTLKDKFRILGEPWRRKGTDP.........NESVGALAER
522018329[Flexithri  F.KNGKYQQLPS........SPPGLIFNNFFSWHAKFSIYKELNNKSTSPQN.........ETVADFFER
403378183[Geobacter  Y.TGGVLNRLPE........NGPTFLKSSLISWPGKLRLAMEP..FISKRT.....DGTDETLASFGRR
86557434][Synechoco  Y.WEKELLPVPL........SPSAAIGSRLLSVGGKLRALRGLLGFVAPPP.......GGEETVRQFFRR
428246331[Crinalium  Y.WKSQLLPVPM........SPPSAVTSKLLSLSGKFKALVGALGFIPPAIGNHLSQQGGEETVAQFFKR
148843553[Planctomy  L.KDSTPVPVPLGFELMTPSRILPMLKTPLLSPIGKLKMGLSY..FLPRRTSESGL.DADDESLAQFVTK
146395727[Geobacter  Y.SGGVLNRLPE........NGPSFLKSRLISWPGKLRLALEPTPFIAKAP.....EGVDETLAAFGRR
343775775[Acidithio  LNRHRQPVALG.........PGVLFGGGLLSWRGRLRLLGEPFRSPRRMQD.......SEESVADFVRR
288335658[Prevotell  IWKDGRFHALPS........GLWSAITTPLFTLKDKFRILGEPWRKKGIDP.........NESVGSLAER
317114493[Thermovib  Y.KNGRLVRLPE........NPIAFLSSYLLSWKGKVRVLGEL..LVPPS.......EKEDETLAEFVRR
```

Figure 1b - continued

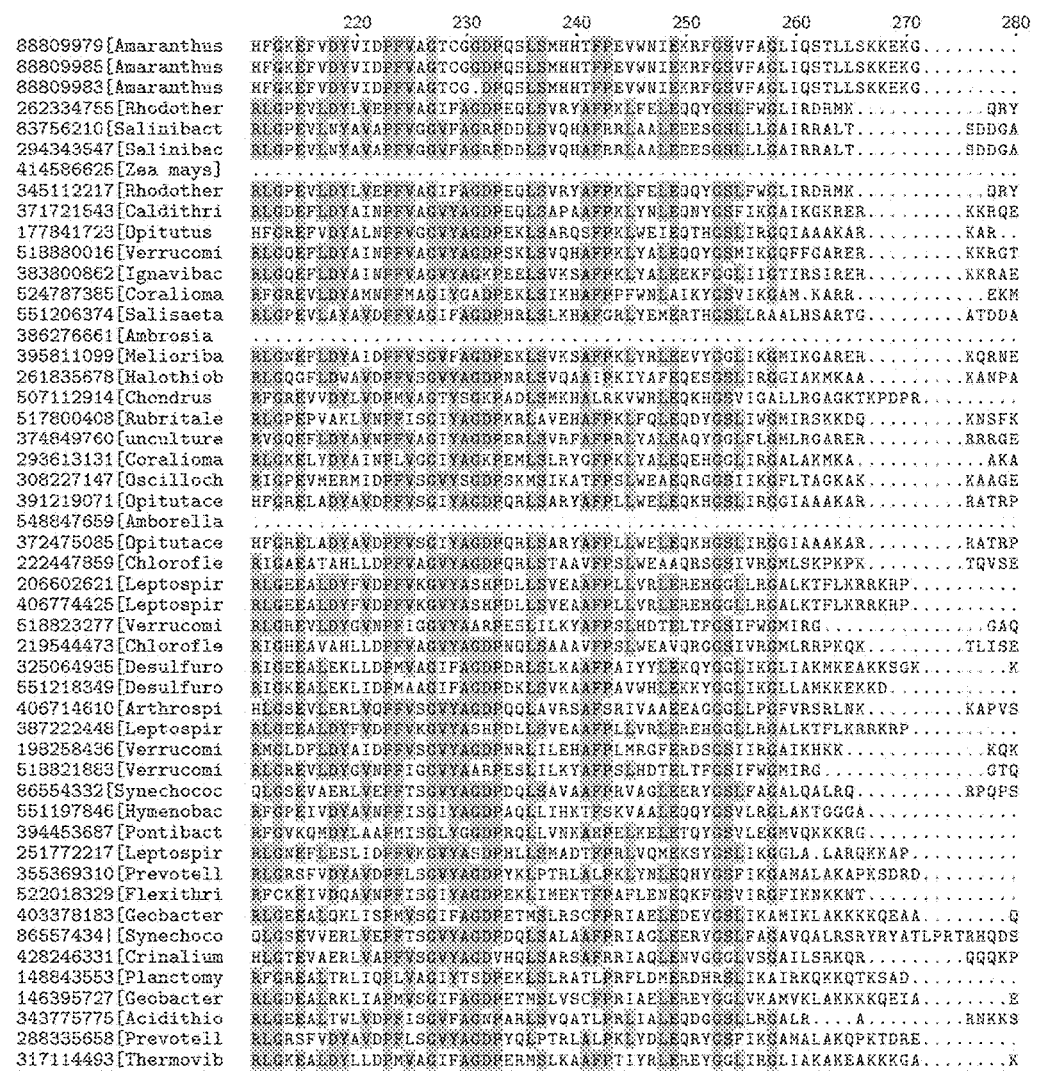

```
                                 220        230        240        250        260        270        280
88809979[Amaranthus   HFGKEFVDYVIDPFVAGTCGGDPQSLSMHHTFPEVWNIEKRFGSVFAGLIQSTLLSKKEKG........
88809985[Amaranthus   HFGKEFVDYVIDPFVAGTCGGDPQSLSMHHTFPEVWNIEKRFGSVFAGLIQSTLLSKKEKG........
88809983[Amaranthus   HFGKEFVDYVIDPFVAGTCG.DPQSLSMHHTFPEVWNIEKRFGSVFAGLIQSTLLSKKEKG........
262334755[Rhodother   RLGPEVLDYLVEPFVAGIFAGDPEQLSVRYAFPKLFELEQQYGSLFWGLIRDRMK...........QRY
83756210[Salinibact   RLGPEVLNYAVAPFVGGVFAGRPDDLSVQHAFRRLAALEEESGSLLLGAIRRALT.........SDDGA
294343547[Salinibac   RLGPEVLNYAVAPFVGGVFAGRPDDLSVQHAFRRLAALEEESGSLLLGAIRRALT.........SDDGA
414586625[Zea mays]   .....................................................................
345112217[Rhodother   RLGPEVLDYLVEPFVAGIFAGDPEQLSVRYAFPKLFELEQQYGSLFWGLIRDRMK...........QRY
371721543[Caldithri   RLGDEFLDYAINPFVAGVYAGDPEQLSAPAAFPKLYNLEQNYGSFIKGAIKGKRER........KKRQE
177841723[Opitutus    HFGREFVDYALNPFVGGVYAGDPEKLSARQSFPKLWEIEQTHGSLIRGQIAAAKAR........KAR..
518880016[Verrucomi   RLGQEFLDYAINPFVAGVYAGDPSKLSVQHAFPKLYALEQQYGSMIKGQFFGARER........KKRGT
383800862[Ignavibac   RLGQEFLDYAINPFVAGVYAGKPEELSVKSAFPKLYALEEKFGGLIIGTIRSIRER........KKRAE
524787385[Coralioma   RFGREVLDYAMNPFMAGIYGADPEKLSIKHAFPPFWNLAIKYGSVIKGAM.KARR...........EKM
551206374[Salisaeta   RLGPEVLAYAVDPFVAGIFAGDPHRLSLKHAFGRLYEMERTHGSLLRAALHSARTG........ATDDA
386276661[Ambrosia    .....................................................................
395811099[Melioriba   RLGNEFLDYAIDPFVSGVFAGDPEKLSVKSAFPKLYRLEEVYGGLIKGMIKGARER........KQRNE
261835678[Halothiob   RLGQGFLDWAVDPFVSGVYAGDPNRLSVQAAIPKIYAFEQESGSLIRGGIAKMKAA........KANPA
507112914[Chondrus    RFGREVVDYLVDPMVAGTYSGKPADLSMKHALRKVWRLEQKHGSVIGALLRGAGKTKPDPR........
517800408[Rubritale   RLGPEPVAKLVNPFISGIYAGDPKRLAVEHAFPKLFQLEQDYGSLIWGMIRSKKDQ........KNSFK
374849760[unculture   RVGQEFLDYAVNPFVAGIYAGDPERLSVRFAFPRLYALEAQYGGLFLGMLRGARER........RRRGE
293613131[Coralioma   RLGKELYDYAINPLVGGIYAGKPEMLSLRYGFPKLYALEQEHGGLIRGALAKMKA...........AKA
308227147[Oscilloch   RIGPEVMERMIDPFVSGVYSGDPSKMSIKATFPSLWEAEQRGGSIIKGFLTAGKAK........KAAGE
391219071[Opitutace   HFGRELADYAVDPFVSGIYAGDPQRLSARYAFPLLWELEQKHGSLIRGGIAAAKAR........RATRP
548847659[Amborella   .....................................................................
372475085[Opitutace   HFGRELADYAVDPFVSGIYAGDPQRLSARYAFPLLWELEQKHGSLIRGGIAAAKAR........RATRP
222447859[Chlorofle   RIGAEATAHLLDPFVAGVYAGDPQRLSTAAVFPSLWEAAQRSGSIVRGMLSKPKPK........TQVSE
206602621[Leptospir   RLGEEALDYFVDPFVKGVYASHPDLLSVEAAFPLLVRLERENGGLLRGALKTFLKRRKRP.........
406774425[Leptospir   RLGEEALDYFVDPFVKGVYASHPDLLSVEAAFPLLVRLERENGGLLRGALKTFLKRRKRP.........
518823277[Verrucomi   RLGREVLDYGVNPFIGGVYAARPESLILKYAFPSLHDTELTFGSIFWGMIRG.............GAQ
219544473[Chlorofle   RIGHEAVAHLLDPFVAGVYAGDPNQLSAAAVFPSLWEAVQRGGSIVRGMLRRPKQK........TLISE
325064935[Desulfuro   RIGEEALEKLLDPMVAGIFAGDPDRLSLKAAFPAIYYLEKQYGGLIKGLIAKMKEAKKSGK.......K
551218349[Desulfuro   RIGKEALEKLIDPMAAGIFAGDPDKLSVKAAFPAVWHLEKKYGGLIKGLLAMKKEKKD..........
406714610[Arthrospi   HLGSEVLERLVQPFVSGVYAGDPQQLAVRSAFSRIVAAEEAGGGLLPGFVRSRLNK........KAPVS
387222448[Leptospir   RLGEEALDYFVDPFVKGVYASHPDLLSVEAAFPLLVRLERENGGLLRGALKTFLKRRKRP.........
198258436[Verrucomi   RMGLDFLDYAIDPFVSGVYAGDPNRLILEHAFPLMRGFERDSGSIIRGAIKHKK...........KQK
518821883[Verrucomi   RLGREVLDYGVNPFIGGVYAARPESLILKYAFPSLHDTELTFGSIFWGMIRG.............GTQ
86554332[Synechococ   QLGSEVAERLVEPFTSGVYAGDPDQLSAVAAFPRVAGLEERYGSLFAGALQALRQ.........RPQPS
551197846[Hymenobac   RFGPEIVDYAVNPFISGIYAGDPAQLLIHKTFSKVAALEQQYGSVLRGLAKTGGGA.............
394453687[Pontibact   RFGVKQMDYLAAPMISGLYGGDPRQLLVNKAHPELKELETQYGSVLEGMVQKKKRG.............
251772217[Leptospir   RLGNEFLESLIDPFVKGVYASDPHLLSMADTFPRLVQMEKSYGSLIKGGLA.LARQKKAP.........
355369310[Prevotell   RLGRSFVDYAVDPFLSGVYAGDPYKLPTRLALPKLYNLEQHYGSFIKGAMALAKAPKSDRD........
522018329[Flexithri   RFCKEIVDQAVNPFISGIYAGDPEKLIMEKTFPAFLENEQKFGSVIRGFIKNKKNT.............
403378183[Geobacter   RLGEEALQKLISPMVSGIFAGDPETMSLRSCFPRIAELEDEYGSLIKAMIKLAKKKKQEAA.......Q
86557434|[Synechoco   QLGSEVVERLVEPFTSGVYAGDPDQLSALAAFPRIAGLEERYGSLFASAVQALRSRYRYATLPRTRHQDS
428246331[Crinalium   HLGTEVAERLVAPFVSGVYAGDVHQLSARSAFRRIAQLENVGGGLVSGAILSRKQR........QQQKP
148843553[Planctomy   RFGREALTRLIQPLVAGIYTSDPEKLSLRATLPRFLDMERDHRSLIKAIRKQKKQTKSAD.........
146395727[Geobacter   RLGDEALRKLIAPMVSGIFAGDPETMSLVSCFPRIAELEREYGGLVKAMVKLAKKKKQEIA.......E
343775775[Acidithio   RLGEEALTWLVDPFISGVFAGNPARLSVQATLPRLIALEQDGGSLLRGALR....A........RNKKS
288335658[Prevotell   RLGRSFVDYAVDPFLSGVYAGDPYQLPTRLALPKLYDLEQRYGSFIKSAMALAKQPKTDRE........
317114493[Thermovib   RLGKEALDYLLDPMVAGIFAGDPERMSLKAAFPTIYRLEREYGGLIRGLIAKAKEAKKKGA.......K
```

Figure 1b - continued

```
                            290       300       310       320       330       340       350
88809979{Amaranthus   ..GENASIKKPRVRGSFSFQGGMQTLVDTMCKQLGEDELKLQCEVLSLSYNQKGIPSLGNWSVSSMS...
88809985{Amaranthus   ..GENASIKKPRVRGSFSFQGGMQTLVDTMCKQLGEDELKLQCEVLSLSYNQKGIPSLGNWSVSSMS...
88809983{Amaranthus   ..GENASIKKPRVRGSFSFQGGMQTLVDTMCKQLGEDELKLQCEVLSLSYNQKGIPSLGNWSVSSMS...
262334755{Rhodother   HP......APRRSMFSFVEGLHMLPRALAERLPAHAIVRNAEVLAIRWD....EKNPWTLTFRQHG....
83756210{Salinibact   PP......DTPSGLFSFRNGLQTLPNALADTL.GDRIRLNAPVHALAHD....GTAWRVTVSPPDA....
294343547{Salinibac   PP......DTPSGLFSFRNGLQTLPNALADTL.GDRIRLNAPVHALTHD....GTAWRVTVSPPDA....
414586625{Zea mays}   ......................................................................
345112217{Rhodother   HP......APRRSMFSFVEGLHMLPRALADRLPAHAIVRNAEVLAIRWD....EKNPWTLTFRQHG....
371721543{Caldithri   VA......KDRAKMFSFLDGMQVFPQALARQL.GEVIRLNCEVREVIPH....GKG.FKVVLEQDS....
177841723{Opitutus    .......GEPRPGIFSFKHGLHVLPEALAARLPAGAITLGASLDAIVP......GDKWNVVWHDDV....
518880016{Verrucomi   VS......KDKAKLVSFDQGLEVLVDGLGQKI.EDTINISTVIESVEKA....EEK.....WVVQG....
383800862{Ignavibac   KS......KQSARMLSFKSGMISLPKAIANYF.ADKLILSAEVISVDKT....AEG.FIVSYRHSG....
524787385{Coralioma   AA....GNFFKPVMISFKSGMHTLTDALAAELGD.SVKCGAKVISI..DSN..CDG.WEVSWGTET....
551206374{Salisaeta   ST......ATDRRIFSLRDGLQMLPHALADAL.GEAIRYEAPVTALRQM....PDGTWTVATETDA....
386276661{Ambrosia    ......................................................................
395811099{Melioriba   ES......KQSAKMFSFLEGMQSLPNAIADKL.KDNIVFSAKVLNVTGA....NDKQWKVTYELNG....
261835678{Halothiob   PVTLP.....AKGKLFSFKRGLQTLTDALATAITS.SGRGNIQLDSAITNIQRLPEGGWSVKTVQG.....
507112914{Chondrus    ..YKPYTGKELRASFTYDKGMEVVTDALVANIN........DLNPRGGRLYTHGKVRTLDRDPNGAW...
517800408{Rubritale   SK....HKLQKRRIVSFKQGMEALPQAMAAALDEGTLIFEAKIGGISQNRN..NKR.WHMDWKCPN....
374849760{unculture   AP......KIAARLFSFREGMGALPRALAAAL.GNTVWCATRALCVERA....GAA.FEIAFERDG....
293613131{Coralioma   NK....GPKAKKYILSFKDGLQTLPQSIANNLNE.PVQTGVSIESI..RQI..EDM.WAVRWN.......
308227147{Oscilloch   KKAKPIGPKMRSVTFNFKGGVAEWPKTIAKVLGDQRVWKNARVTTLYPE.....STGWTLVVERDG....
391219071{Opitutace   AGPAEKPRPPRARIFSFAEGLETIPAALAERLPAGCVETGARVVRLVPPVA..RGGAWEVVWERKDEKDE
548847659{Amborella   ......................................................................
372475085{Opitutace   AGPAEKPRPPRARIFSFAEGLETIPAALAERLPAGCVETGARVVRLVPPVA..RGGAWEVVWERKD...E
222447859{Chlorofle   .......PKMRSRTFTFRGGLAEWPRALAQALGAGNVWTERRVVKLQPR.....DSWWEVTIDGVN....
206602621{Leptospir   .....SGSSPRGIFS.FAGGMTDLVEAMGKRLG..EDVGTNVDVIKYTR....LEEGFRVALMYDE....
406774425{Leptospir   .....SGSSPRGIFS.FAGGMTDLVEAMGKRLG..EDVGTNVDVIKYTR....LEEGFRVALMYDE....
518823277{Verrucomi   PS....EKISKSRLISFREGMQELPNRLAARMHN.PPVLGCEIKKI.EFKD..DVQ.WCVQGEKHD....
219544473{Chlorofle   .......PKMRSRTFSFQGGLADWPRAIARALGTGNVWTGRRAVGLRDL.....GTYWEVTVDGTG....
325064935{Desulfuro   S....GPAGPGGVLTSFKGGVKDLIDSLSEFLG..DSIETEVEILGLDR....IEKGWKVKYKKEN....
551218349{Desulfuro   .....ATAGPGGVLTSFKGGVKDLIDALVANIK..GEIHPGTTVKKLIP....ENGKWKIVYEKDD....
406714610{Arthrospi   TPDPNIPKTRPGELGSFRYGLQTLPETLASKLGDRVKLNWTIDRFYPTDHQTYIAEFST..........
387222448{Leptospir   .....SGSAPRGIFS.FTGGMGDLVEAMGKRLG..EDVGTNVDVIKYTR....LEEGFRVALMYDE....
198258436{Verrucomi   RE....GTAYKKRSISFKDGLGILPQTIARKLGN.RLWLGSEVVAV..NRV..EDH.WQVTWK.RE....
518821883{Verrucomi   PS....EKISKSRLISFREGMQELPNRLATRMHN.PPVLGCEIKKI.EFKD..DVQ.WCVQGETRD....
86554332{Synechococ   P.AAIQPPPKRGQLGNLRQGLQQLPEALAQKLGDSLRLGWRALQLKR.AGELYWVGFET..........
551197846{Hymenobac   .........GRRRIISLQGGIQKLTDTLAAKLTHHHVHQRVLALHRTTKGGYQVQTSA...........
394453687{Pontibact   .........VFQRAFSFRNGMSTLPHAIADKLISLHLDHK.VEFITRIKGKFIISCASN..........
251772217{Leptospir   .....APAFAREILS.FSEGMGTLPESLANILD..DDAGTNAEVIGCAP....SESGFRTALLFEE....
355369310{Prevotell   .......KRATKEVFSTRGGFRSLVSALAKTIGDDRITTGCAHLHVEPLG.....DKWKLSWGENT....
522018329{Flexithri   .........QRKLTFSFKEGLGILADKLAENLSVNYNSP..IKEIRQEAGGFLLIT............
403378183{Geobacter   GKAVSSAAGPGGVLTSFRWGIQELTDILAEQLGS.ATVVTGQPVTGLTR....GSS...VPWRLKT....
86557434|{Synechoco   ANSPIQPPPKRGQLGNLRQGLQQLPEAIAQKLGSALRLGWRAVHLKR.DETGYRVGFVIHDSGAEH....
428246331{Crinalium   PTDPSLPTVRRGELGSFKEGLQSLPKAIASHLGENIKLNWTLTELRQTANQTYIAEFST..........
148843553{Planctomy   .....ATGARYGLFAAFKEGMQTLIRTLADRVSSTGTILYEHRVTHVAA....ADSGYDLTIESTV....
146395727{Geobacter   GKQVASAAGPGGVLTSFRDGIQTLTDILNERLGK.DMLVIGAEVTGVSH....GNS...TPYRVQT....
343775775{Aciditihio  PDTP......KTRLISFREGLQTLPLRVASALGD.ALRCNTPVEQLGN.....SDGSWQVSSGS......
288335658{Prevotell   .......KRATKAVFSTRGGFRSLVSALGRVIGDERIRTNCKELSIEPLG.....DKWKLSWGENT....
317114493{Thermovib   SS...GPAGPGGVLTSFVKGMSQFTQLLAQELG..ESFTPEAQVKTLEK.....KKDKWLVTYTLRG....
```

Figure 1b - continued

```
                            360       370       380       390       400       410       420
88809979{Amaranthus   .....NNTSEDQSYDAYVVTAPIRNVKEMKIMKFGNPFSLDFIPEVTYVPLSVMITAAKKDKVKRPLEGF
88809985{Amaranthus   .....NNTSEDQSYDAYVVTAPIRNVKEMKIMKFGNPFSLDFIPEVTYVPLSVMITAAKKDKVKRPLEGF
88809983{Amaranthus   .....NNTSEDQSYDAYVVTAPIRNVKEMKIMKFGNPFSLDFIPEVTYVPLSVMITAAKKDKVKRPLEGF
262334755{Rhodother   .......RASTRFFDIIVCAVPLHRLAQLRIHP..PVDRRP.LSTVEHPPIALVALGFRREQVAAPLDGF
83756210{Salinibact   .......PAHTRSFDALVCTVPLHRLAAMEIDT..PVDLAP.LGEVTYPPLSVLALGYGRDAIDAALDGF
294343547{Salinibac   .......PAHTRSFDALVCTVPLHRLAAMEIDT..PVDLAP.LGEVTYPPLSVLALGYERDAIDAALDGF
414586625{Zea mays}   ..................MTAPLSNVHRMKFTKGGAPVVLDFLPKMDYLPLSLMVTAAKKDDVKKPLEGF
345112217{Rhodother   .......RASTRFFDIIVCAVPLHRLAQLRIHP..PVDRRP.LSTVEHPPIALVALGFRREQVAAPLDGF
371721543{Caldithri   .......GEQECFFERYVISVPTY.VQAKILNSILKERAAL.LADVLHPPIAVVFMGFKKDDVAAALDGF
177841723{Opitutus    .......ATHTQSFDSYVVALPAPALARLQIGTLGEKPLAA.LALIEHPPYSSLFLGFRREQVAAPLDGF
518880016{Verrucomi   .......RKIRESFDAYITAIPTHRMTKMTFRDESDLDNSI.LRDLIYPPYSSVVMGFRRDQIQASLEGF
383800862{Ignavibac   .......IDEAIVCDAYLSTVPSY.VAGNLFSKFDKKFKVH.SDELYYPPYLVYFLAYEKKNIGQTLDGF
524787385{Coralioma   ......EDVCEN.YDALVVAVPAPEISGLPFGGMLAAALAP.LAKLQYAPYATYTMGFKRQDVSAPLDGF
551206374{Salisaeta   .......TQVN....ALISTVPLHALGSIDWAP..AVDTSP.LQRVPYPPYRVVALGFRRADVAAPLDGF
386276661{Ambrosia    ....................................................................GK
395811099{Melioriba   .......NRESITADTYISTLPAY.IAAGVFGELDGKLAER.LNSLYYPPYMVLYLGYNKKDIKRKLDGF
261835678{Halothiob   .........KTFHTRQLILSTPAHVSAQLLGEV..DGPLAETLAALEYPPYTSVVMGFDRSEVAAPLDGF
507112914{Chondrus    .....RINGRGKYDAVISTIPTHAVKSIYTNMSALGKGFKKLNKSLKYAPYSVVVMGFDKSQVPAPLDGF
517800408{Rubritale   ......GTIGQGSFDAYILTQASHHLNDIP.LDEEVLESLSKLPSLDHAPYTSMLLGFKREQIKAPLDGF
374849760{unculture   .......RRDTLRAERYVLATPAY.AAASLLKHLAPEAARA.LDRLVYPPYSAVILGYPETAIGRPLDGF
293613131{Coralioma   .......GQVKA.FKELIVTVPAHKLPGLPF.....EEPIR.LPALDYPPYSVISLGYPLSAIKGPLDGF
308227147{Oscilloch   .......QVETIEAASYIMAAPAYAAADLIAELD..PAAAKGLRGLRYSSMAVVNLGYRENQVTRPVNGF
391219071{Opitutace   KGASGVEGRLTERVAAYILALPGEALARLEIGANGEHPLAA.LAEVEYPPYASLFIGYRREQARAPLDGF
548847659{Amborella   ....................................................................GT
372475085{Opitutace   KGASGVEGRLTERVAAYILALPGEALARLEIGANGEHPLAA.LAEVEYPPYASLFLGYRREQVRAPLDGF
222447859{Chlorofle   .......GPETLISRSLIIATPAFTAADLIESVD..QRAAGALRGLPYAPYAVVHLGFRRDQISGELSGF
206602621{Leptospir   .......TEYYMTSRRLILATSAPQAAELLEGDP..DGPSSELKSLPYAPYTIAYAGFLREQVTAPLDGF
406774425{Leptospir   .......TEYYMTSRRLILATSAPQAAELLEGDP..DGPSSELKSLPYAPYTIAYAGFLREQVTAPLDGF
518823277{Verrucomi   ......GKIQKEVFDQIICTLPSHALDKIEWVGINSSHLLETLTRAYHPPLALVFQGYQQRQIKAPLDGF
219544473{Chlorofle   .......RLETITTRSYIIATPAYVAAELVEALD..PAAASALRSLPYAPYSVVHLGFRRDQLSAELNGF
325064935{Desulfuro   .......EVFEETFDAIVFSTPAYITAKLLNDLN..LELSKLLSELEYSPISVVALGFEKKGLGADLDGF
551218349{Desulfuro   .......EIFEESFDKYVLSTPSYVAAALVKNFD..EKLAEKLYELEYSPIAVIAFGFIKKGLGAHLDGF
406714610{Arthrospi   .....PDGPQQVEARTLALMTPAHVSARLLQPLH..SPIATALSQLPYPPYACVVLAYPKSALKGQLKGF
387222448{Leptospir   .......TEYYMTSRRLILATSAPQAAELLEGDP..EGPSGELKALPYAPYTIAYAGFLREQITAPLDGF
198258436{Verrucomi   ......GENFEGFAKNLLVCLPSHAIKRIA.WSERIAAPLRSSPNLEYPAYHSLALGFRREQIAAALDGF
518821883{Verrucomi   ......GKIQKEVFDQYICTLPSHALDKIEWVGINSSHLLETLTRAYHPPLALAFQGYQQRQIKAPLDGF
86554332{Synechococ   .....PEGSRWVAARQYVLALPAYEAAALLQELN..PPASQLLAELLYPPYAVVALAYPQEALPGPLRGF
551197846{Hymenobac   ......GSNGGFSYDAYVLALPTFAAAPLLAPLF..PEAAAALAAVHYPPMAAVYTAYRREDVGAPLDGF
394453687{Pontibact   ......GDHDNEEYDKLVLALPAHQAAELIEFTY..PGMSAALQNLNYPPMAVVHTVYNRAEVGAPLQGF
251772217{Leptospir   .......ETYYIRSKHLVLALPAAQTAELIEPMA..PGIPSLLGQLPYAPIAVVYLSYPRDRISAPLDGF
355369310{Prevotell   ...........IIADQYVTTCPAYSLPDLLTFLP..KEQLDDLSNLYYAPYIEIGVGMKHTGNVE.WNAF
522018329{Flexithri   .......ENGETKVTALVFSIPAYAAGKLIKDIS..PESAQAWEGVNYPPICVVHTAFRRKDLGFDFNGF
403378183{Geobacter   .......PTVDIDADVYILASPAHATAGIVSGVD..AANAQVLGELPYASMTVVCFGFERERIAYDLNGF
86557434|{Synechoco   ...TAPEEIHWVAAQQYVLTLPAYAAATLLQDLN..PQASRLLRELPYPPYAVVALAYPEEALPGPLRGF
428246331{Crinalium   .....PEGSQQVEARTYVLTTPAYVTAELLHNLA..PNASIALKELPYPSYACVVLAYPDDALKFPLKGF
148843553{Planctomy   .......ETQTQHFDAYLLTTAAPQAGQMLEAYA..PVLSGLLKQLEYASTAIQVSVYRQENIKAPLHAF
146395727{Geobacter   .......GGRELDADIYVLATPAYATAQALEGID..GGMSATLNQLPYATMTVVCFGYEQEKVAADLNGF
343775776{Acidithio   .........QTWQSKRLILALPAGAAARLLAPT..DAALAHELDALPYPAYGSLSIGFQRMQVQAPLDGF
288335658{Prevotell   ...........IIAEQYITTCPAYALPKLLNFLP..KEQLDDLSNLYYAPYIEIGVGMKNTGDVE.WNAF
317114493{Thermovib   .......KEKSEEFDAYVLSLPAYAAAQVLKETS..RELSELLASLEYSPISVVALGFEKRGLGANLDGF
```

Figure 1b - continued

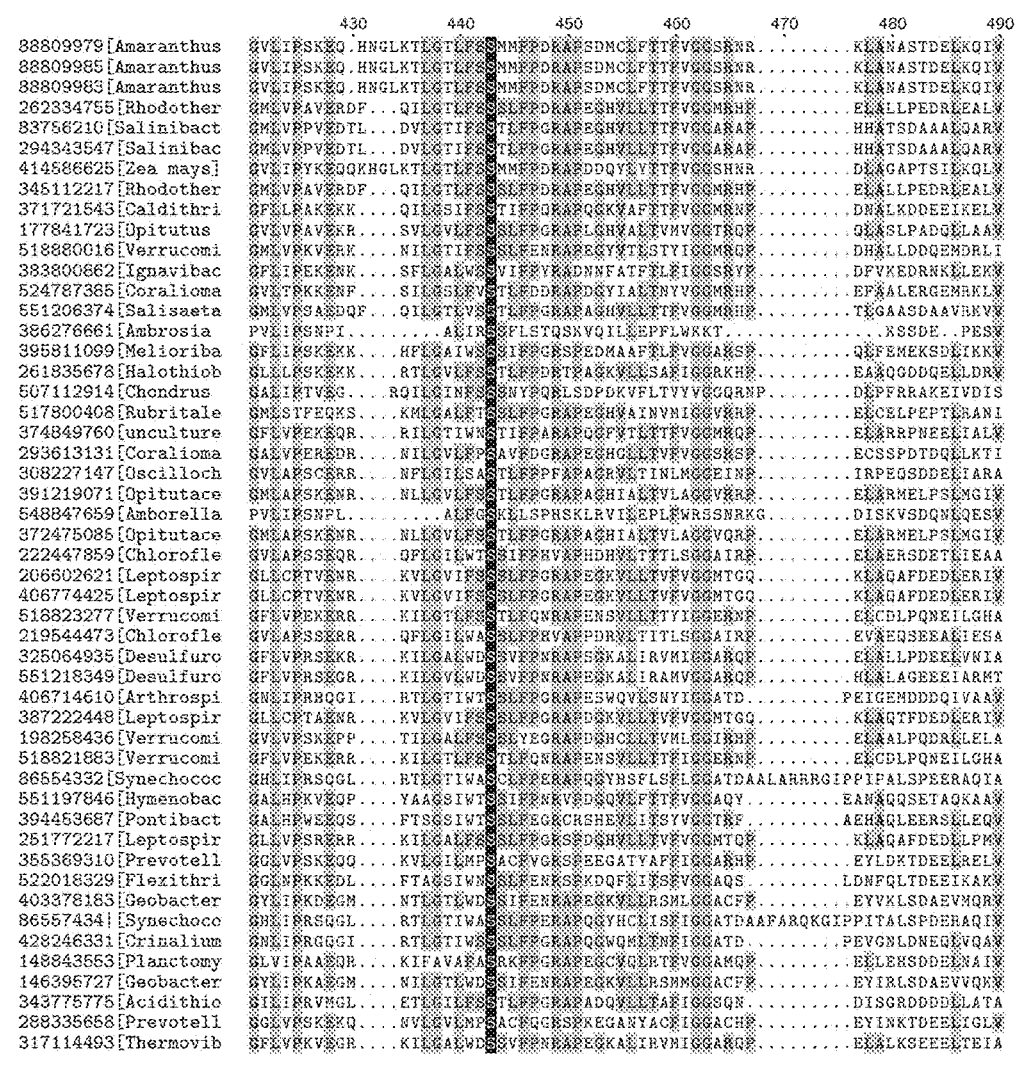

```
                                    430        440        450        460        470        480        490
88809979[Amaranthus   GVLIPSKEQ.HNGLKTLGTLFSSMMFPDKAPSDMCLFTTFVGGSRNR.........KLANASTDELKQIV
88809985[Amaranthus   GVLIPSKEQ.HNGLKTLGTLFSSMMFPDKAPSDMCLFTTFVGGSRNR.........KLANASTDELKQIV
88809983[Amaranthus   GVLIPSKEQ.HNGLKTLGTLFSSMMFPDKAPSDMCLFTTFVGGSRNR.........KLANASTDELKQIV
262334755[Rhodother   GMLVPAVERDF...QILGTLFSSLFPDKAPEGHVLLTTFVGGMRHP.........ELALLPEDRLEALV
83756210[Salinibact   GMLVPPVEDTL...DVLGTIFSTLFPGKAPEGHVLLTTFVGGARAP.........HHATSDAAALQARV
294343547[Salinibac   GMLVPPVEDTL...DVLGTIFSTLFPGKAPEGHVLLTTFVGGARAP.........HHATSDAAALQARV
414586625[Zea mays]   GVLIPYKEQQKHGLKTLGTLFSSMMFPDKAPDDQYLVTTFVGGSHNR.........DLAGAPTSILKQLV
345112217[Rhodother   GMLVPAVERDF...QILGTLFSSLFPDKAPEGHVLLTTFVGGMRHP.........ELALLPEDRLEALV
371721543[Caldithri   GFLLPAKEKK....QILGSIFSTIFPDKAPQGKVAFTTFVGGMRNP.........DNALKDDEEIKELV
177841723[Opitutus    GVLVPAVEKR....SVLGVLFSSLFPGKAPLGHVALTVMVGGTRQP.........QLASLPADQLLAAV
518880016[Verrucomi   GMLVPKVERK....NILGTIFSSLFENKAPEGYVTLSTYIGGMRQP.........DHALLDDQEMDRLI
383800862[Ignavibac   GFLIPEKENK....SFLGALWSVIFPYKADNNFATFTLEIGGSRYP.........DFVKEDRNKLLEKV
524787385[Coralioma   GVLTPKKENF....SILGSLFVSTLFDDKAPDGYIALTNYVGGMRHP.........EFAALERGEMRKLV
551206374[Salisaeta   GMLVPSAEDQF...QILGTLVSSTLFPGRAPAGHVLLTTFVGGMRHP.........TLGAASDAAVRKVV
386276661[Ambrosia    PVLIPSNPI.........ALIRSSFLSTQSKVQILLEPFLWKKT...............KSSDE..PESV
395811099[Melioriba   GFLIPSKEKK....HFLGAIWSSIFPGRSPEDMAAFTLFVGGAKSP.........QLFEMEKSDLIKKV
261835678[Halothiob   GLLLPSKEKK....RTLGVLFSSTLFPDRTPAGKVLLSAFIGGRKHP.........EAAQGDDQELLDRV
507112914[Chondrus    GALIPTVEG....RQILGINFSSNYPQRLSDPDKVFLTVYVGGQRNP........DLPFRRAKEIVDIS
517800408[Rubritale   GMLSTFEQKS....KMLGALFTSLFPGRAPEGHVAINVMIGGVRRP.........ELCELPEPTLRANI
374849760[unculture   GFLVPEKEQR....RILGTIWNTIFPARAPQGFVTLTTFVGGMKQP.........ELARRPNEELIALV
293613131[Coralioma   GALVPEREDR....NILGVLFPSAVFDGRAPEGHGLLTVFVGGSKSP.........ECSSPDTDQLLKTI
308227147[Oscilloch   GVLAPSCERR....NFLGILSASTLFPPFAPAGRVLTINLMGGEINP.........IRPEQSDDELIARA
391219071[Opitutace   GMLAPSKENR....NLLGVLFSSTLFPGRAPAGHIALTVLAGGVRRP.........ELARMELPSLMGIV
548847659[Amborella   PVLIPSNPL.........ALFGSKLLSPHSKLRVILEPLFWRSSNRKG........DISKVSDQNLQESV
372475085[Opitutace   GMLAPSKENR....NLLGVLFSSTLFPGRAPAGHIALTVLAGGVQRP.........ELARMELPSLMGIV
222447859[Chlorofle   GVLAPSSEQR....QFLGILWTSIFPHVAPHDHVLTTTLSGGAIRP.........ELAERSDETLIEAA
206602621[Leptospir   GLLCPTVENR....KVLGVIFSSLFPGRAPEGKVLLTVFVGGMTGQ.........KLAQAFDEDLERIV
406774425[Leptospir   GLLCPTVENR....KVLGVIFSSLFPGRAPEGKVLLTVFVGGMTGQ.........KLAQAFDEDLERIV
518823277[Verrucomi   GFLVPEKERR....KILGTLFSSTLFQNRAPENSVLLTTYIGGERNP.........ELCDLPQNEILGHA
219544473[Chlorofle   GVLAPSSERR....QFLGILWASLFPHVAPPDRVLTITLSGGAIRP.........EVAEQSEEALIESA
325064935[Desulfuro   GFLVPRSEKR....KILGALWDSSVFPNRAPSGKALIRVMIGGARQP.........ELALLPDEELVNIA
551218349[Desulfuro   GFLVPRSEGR....KILGVLWDSVFPNRAPEGKALIRAMVGGARQP.........HLALAGEEEIARMT
406714610[Arthrospi   GNLIPRBQGI....RTLGTIWTSSLFPGRAPESWQVLSNYIGGATD.........PEIGEMDDDQIVAAV
387222448[Leptospir   GLLCPTAENR....KVLGVIFSSLFPGRAPDGKVLLTVFVGGMTGQ.........KLAQTFDEDLERIV
198258436[Verrucomi   GVLVPSKEPP....TILGALFSSLYEGRAPDGHCLLTVMLGGIRHP.........ELAALPQDRLELA
518821883[Verrucomi   GFLVPEKERR....KILGTLFSSTLFQNRAPENSVLLTTFIGGERNP.........ELCDLPQNEILGHA
86554332[Synechococ   GHLIPRSQGL....RTLGTIWASCLFPERAPQGYHSFLSFLGGATDAALARRRGIPPIPALSPEERAQIA
551197846[Hymenobac   GALHPKVEQP....YAAGSIWTSSIFPNKVPDGQVLFTTFVGGAQY.........EANAQQSETAQKAAV
394453687[Pontibact   GALHPWEEQS....FTSGSIWTSSLFEGRCRSHEVLITSYVGGTRF.........AEHAQLEERSLLEQV
251772217[Leptospir   GLLVPSRERR....KILGALFSSLFPGKSPDGHVLLTVFVGGMTQP.........KLAQAFDEDLLPMV
355369310[Prevotell   GGLVPSKEQQ....KVLGILMPSACFVGKSPEEGATYAFFIGGARHP.........EYLDKTDEELRELV
522018329[Flexithri   GGLNPKKEDL....FTAGSIWNSSLFENKSPKDQFLITSFVGGAQS.........LDNFQLTDEEIKAKV
403378183[Geobacter   GYLIPKDEGM....NTLGTLWDSSIFENKAPEGKVLLRSMLGGACFP.........EYVKLSDAEVMQRV
86557434|[Synechoco   GHLIPRSQGL....RTLGTIWASSLFPERAPQGYHCLISFIGGATDAAFARQKGIPPITALSPDERAQIV
428246331[Crinalium   GNLIPRGQGI....RTLGTIWSSSLFPGKAPQGWQMLLNFIGGATD.........PEVGNLDNEQLVQAV
148843553[Planctomy   GLVIPAAEQR....KIFAVAFASRKFPGRAPEGCVGLRTFVGGAMQP.........ELLEHSDDELNAIV
146395727[Geobacter   GYLIPKAEGM....NILGTLWDSSIFENKAPEGKVLLRSMMGGACFP.........EYIRLSDAEVVQKV
343775775[Acidithio   GILIPRVMGL....ETLGILFSSTLFPGRAPADQVLLTAFIGGSQN.........DISGRDDDDLLATA
288335658[Prevotell   GGLVPSKEKQ....NVLGVLMPSACFQGKSPKEGANYACFIGGACHP.........EYINKTDEELIGLV
317114493[Thermovib   GFLVPKVEGR....KILGALWDSSVFPNRAPEGKALIRVMIGGARQP.........ELALKSEEELTEIA
```

Figure 1b - continued

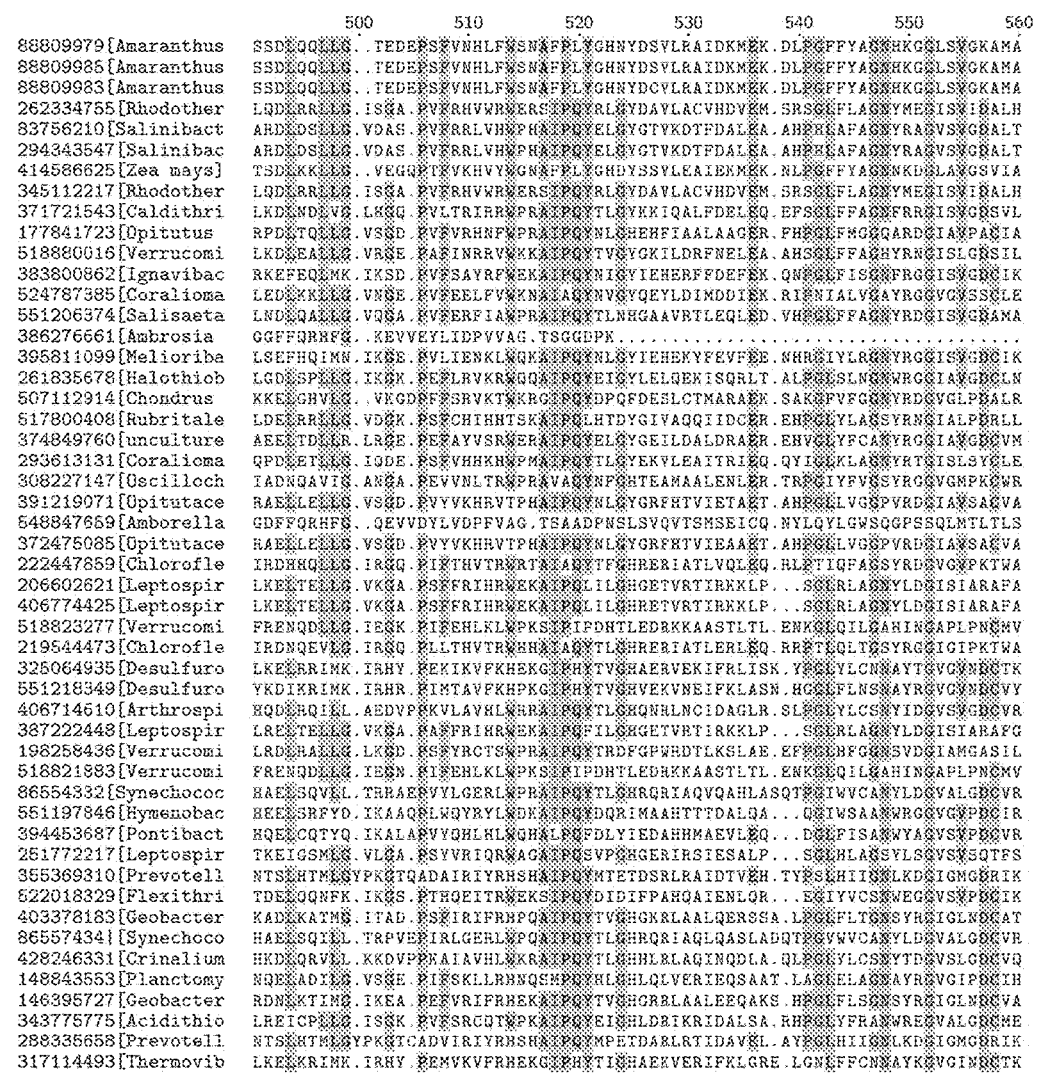

```
                          500       510       520       530       540       550       560
88809979[Amaranthus   SSDLQQLLG..TEDEPSFVNHLFWSNAFPLYGHNYDSVLRAIDKMEK.DLPGFFYAGWHKGGLSYGKAMA
88809985[Amaranthus   SSDLQQLLG..TEDEPSFVNHLFWSNAFPLYGHNYDSVLRAIDKMEK.DLPGFFYAGWHKGGLSYGKAMA
88809983[Amaranthus   SSDLQQLLG..TEDEPSFVNHLFWSNAFPLYGHNYDCVLRAIDKMEK.DLPGFFYAGWHKGGLSYGKAMA
262334755[Rhodother   LQDLRRLLG.ISGA.PVFRHVWRWERSIPQYRLGYDAVLACVHDVEM.SRSGLFLAGNYMEGISYIGALH
83756210[Salinibact   ARDLDSLLG.VDAS.PVFRRLVHWPHAIPQYELGYGTVKDTFDALEA.AHPHLAFAGNYRAGVSYGGALT
294343547[Salinibac   ARDLDSLLG.VDAS.PVFRRLVHWPHAIPQYELGYGTVKDTFDALEA.AHPHLAFAGNYRAGVSYGGALT
414586625[Zea mays]   TSDLKKLLG..VEGQPTFVKHVYWGNAFPLYGHDYSSVLEAIEKMEK.NLPGFFYAGNNKDGLAYGSVIA
345112217[Rhodother   LQDLRRLLG.ISGA.PVFRHVWRWERSIPQYRLGYDAVLACVHDVEM.SRSGLFLAGNYMEGISYIGALH
371721543[Caldithri   LKDLNDLVG.LHGQ.PVLTRIRRWPRAIPQYTLGYKKIQALFDELEQ.EFSGLFFAGNFRRGISYGGSVL
177841723[Opitutus    RPDLTQLLG.VSGD.PVFVRHNFWPRAIPQYNLGHEHFIAALAAGER.FHPGLFMGGQARDGIAYPAGIA
518880016[Verrucomi   LKDLEALLG.VRGE.PAFINRRVWKKAIPQYTVGYGKILDRFNELEA.AHSGLFFAGHYRNGISLGGSIL
383800862[Ignavibac   RKEFEQLMK.IKSD.PVFSAYRFWEKAIPQYNIGYIEHERFFDEFEK.QNPGLFISGNFRGGISYGDCIK
524787385[Coralioma   LEDLKKLLG.VNGE.PVFEELFVWKNAIAQYNVGYQEYLDIMDDIEK.RIPNIALVGAYRGGVGYSSCLE
551206374[Salisaeta   LNDLQALLG.VQGA.PVFERFIAWPRAIPQYTLNHGAAVRTLEQLED.VHPGLFFAGNYRDGISYGGAMA
386276661[Ambrosia    GGFFQRHFG..KEVVEYLIDPVVAG.TSGGDPK.................................
395811099[Melioriba   LSEFHQIMN.IKGE.PVLIENKLWQKAIPQYNLGYIEHEKYFEVFEE.NHRGIYLRGNYRGGISYGDCIK
261835678[Halothiob   LGDLSPLLG.IKGK.PEFLRVKRWQQAIPQYEIGYLELQEKISQRLT.ALPGLSLNGNWRGGIAYGDCLN
507112914[Chondrus    KKELGHVLG..VKGDPFFSRVKTWKRGIPQYDPQFDESLCTMARAEK.SAKGFVFGGNYRDGVGLPGALR
517800408[Rubritale   LDELRRLLG.VDGK.PSFCHIHHTSKAIPQLHTDYGIVAQQIIDCER.EHPGLYLAGSYRNGIALPGRLL
374849760[unculture   AEELTDLLR.LRGE.PEFAYVSRWERAIPQYELGYGEILDALDRAER.EHVGLYFCAGYRGGIAYGDCVM
293613131[Coralioma   QPDLETLLG.IGDE.PSFVHHKHWPMAIPQYTLGYEKVLEAITRIEQ.QYIGLKLAGNYRTGISLSYGLE
308227147[Oscilloch   IADNQAVIG.ANGA.PEVVNLTRWPRAVAQYNFGHTEAMAALENLER.TRPGIYFVGSYRGGVGMPKCWR
391219071[Opitutace   RAELLELLG.VSGD.PVYVKHRVTPHAIPQYNLGYGRFHTVIETAET.AHPGLLVGGPVRDGIAYSAGVA
548847659[Amborella   GDFFQRHFG..QEVVDYLVDPFVAG.TSAADPNSLSVQVTSMSEICQ.NYLQYLGWSQGPSSQLMTLTLS
372475085[Opitutace   RAELLELLG.VSGD.PVYVKHRVTPHAIPQYNLGYGRFHTVIEAAET.AHPGLLVGGPVRDGIAYSAGVA
222447859[Chlorofle   IRDHHQLLG.IRGQ.PIFTHVTRWRTAIAQYTFGHRERIATLVQLEQ.RLPTIQFAGSYRDGVGYPKTWA
206602621[Leptospir   LKELTELLG.VKGA.PSFFRIHRWEKAIPQLILGHGETVRTIRKKLP...SGLRLAGNYLDGISIARAFA
406774425[Leptospir   LKELTELLG.VKGA.PSFFRIHRWEKAIPQLILGHRETVRTIRKKLP...SGLRLAGNYLDGISIARAFA
518823277[Verrucomi   FRENQDLLG.IEGK.PIFEHLKLWPKSIPIPDHTLEDRKKAASTLTL.ENKGLQILGAHINGAPLPNGMV
219544473[Chlorofle   IRDNQEVLG.IRGQ.PLLTHVTRWHHAIAQYTLGHRERIATLERLEQ.RRPTLQLTGSYRGGIGIPKTWA
325064935[Desulfuro   LKELRRIMK.IRHY.PEKIKVFKHEKGIPHYTVGHAERVEKIFRLISK.YPGLYLCNGAYTGVGYNDCTK
551218349[Desulfuro   YKDIKRIMK.IRHR.PIMTAVFKHPKGIPHYTVGHVEKVNEIFKLASN.HGGLFLNSGAYRGVGYNDCVY
406714610[Arthrospi   HQDLRQILL.AEDVPPKVLAVHLWHRAIPQYTLGHQNRLNCIDAGLR.SLPGLYLCSNYIDGVSYGDCVR
387222448[Leptospir   LRELTELLG.VKGA.PAFFRIHRWEKAIPQFILGHGETVRTIRKKLP...SGLRLAGNYLDGISIARAFG
198258436[Verrucomi   LRDLRALLG.LKGD.PSFYRCTSWPRAIPQYTRDFGPWRDTLKSLAE.EFPGLHFGGNSVDGIAMGASIL
518821883[Verrucomi   FRENQDLLG.IEGN.PIFEHLKLWPKSIPIPDHTLEDRKKAASTLTL.ENKGLQILGAHINGAPLPNGMV
86554332[Synechococ   HAELSQVLL.TRRAEPVYLGERLWPRAIPQYTLGHRQRIAQVQAHLASQTPGIWVCAGYLDGVALGDCVR
551197846[Hymenobac   HEELSRFYD.IKAAQPLWQYRYLWDKAIPQYDQRIMAAHTTTDALQA...QGIWSAAGWRGGVGYPDCIR
394453687[Pontibact   HQELCQTYQ.IKALAPVYQHLHLWQHALPQFDLYIEDAHHMAEVLEQ...DGLFISAGWYAGVSYPDCVR
251772217[Leptospir   TKEIGSMLG.VLGA.PSYVRIQRWAGAIPQSVPGHGERIRSIESALP...SGLHLAGSYLSGVSYSQTFS
355369310[Prevotell   NTSLHTMLGYPKGTQADAIRIYRHSHAIPQYMTETDSRLRAIDTVEH.TYPSLHIIGNLKDGIGMGGRIK
522018329[Flexithri   TDELQQNFK.IKGS.PTHQEITRWEKSIPQYDIDIFPAHQAIENLQR...EGIYVCSGWEGGVSYPDGIK
403378183[Geobacter   KADLKATMG.ITAD.PSFIRIFRHPQAIPQYTVGHGKRLAALQERSSA.LPGLFLTGNSYRGIGLNDCAT
86557434|[Synechoco   HAELSQILL.TRPVEPIRLGERLWPQAIPQYTLGHRQRIAQLQASLADQTPGVWVCAGYLDGVALGDCVR
428246331[Crinalium   HKDLQRVLL.KKDVPPKAIAVHLWKRAIPQYTLGHHLRLAQINQDLA.QLPGLYLCSGYTDGVSLGDCVQ
148843553[Planctomy   NQELADILG.VSGE.PIFSKLLRHNQSMPQYHLGHLQLVERIEQSAAT.LAGLELAGNAYRGVGIPDCIH
146395727[Geobacter   RDNLKTIMG.IKEA.PEFVRIFRHEKAIPQYTVGHGRRLAALEEQAKS.HPGLFLSGNSYRGIGLNDCVA
343775775[Acidithio   LREICPLLG.ISGK.PVFSRCQTWPKAIPQYEIGHLDRIKRIDALSA.RHPGLYFRAGWREGVALGGCME
288335658[Prevotell   NTSLHTMLGYPKGTCADVIRIYRHSHAIPQYMPETDARLRTIDAVEL.AYPGLHIIGNLKDGIGMGGRIK
317114493[Thermovib   LKELKRIMK.IRHY.PEMVKVFRHEKGIPHYTIGHAEKVERIFKLGRE.LGNGFFCNGAYKGVGINDCTK
```

Figure 1b - continued

```
                                     570          580
88809979[Amaranthus   SGCKAAELVISYLDSHIYVKMDEKTA..
88809985[Amaranthus   SGCKAAELVISYLDSHIYVKMDEKTA..
88809983[Amaranthus   SGCKAAELVISYLDSHIYVKMDEKTA..
262334755[Rhodother   TGLKAARAIIQHLREEAAGGLAKLVLGD
83756210[Salinibact   SGLEAA...DRLLETDERAAQPH.....
294343547[Salinibac   SGLEAA...DRLLETDERATQPH.....
414586625[Zea mays]   SGSKAADLAISYLESHTKHNNSH.....
345112217[Rhodother   TGLKAARAIIQHLREEAAGGLAKLVLGD
371721543[Caldithri   SAFETSEKMLKEK...............
177841723[Opitutus    AGEKLAERAGQ.................
518880016[Verrucomi   AGLDVAQRINQQ................
383800862[Ignavibac   NAELVANKICVQFTMHNVQ.........
524787385[Coralioma   NGLLSAAKLAGRISD.............
551206374[Salisaeta   SGEDAARRVDAHLAGADRAVAATGP...
386276661[Ambrosia    ............................
395811099[Melioriba   NSELEIK.....................
261835678[Halothiob   NGNKLAERLIENTRTEES..........
507112914[Chondrus    SGILSAEKTLQYLKTL............
517800408[Rubritale   EGISLTEKINQSL...............
374849760[unculture   SAHATAERILRDRARS............
293613131[Coralioma   SAIASTN.....................
308227147[Oscilloch   NGVNMAERVATYLKTRSAVASLR.....
391219071[Opitutace   AGEKLARRVVA.................
548847659[Amborella   PSSVIDQMLSERMVTFLQVMLSPLLM..
372475065[Opitutace   AGEKLARRVVA.................
222447859[Chlorofle   SGVQAGERIAAALAAHGTTAVSTETASG
206602621[Leptospir   SGVRAAEELLSEDGGTPG..........
406774425[Leptospir   SGVRAAEELLSEDGGTPG..........
518823277[Verrucomi   L...........................
219544473[Chlorofle   SGVGAGERIAAALDAQGTTADTLEQARG
325064935[Desulfuro   AAEEVARRILDG................
551218349[Desulfuro   NSLKTAEMVTSE................
406714610[Arthrospi   RGQQWASKIQSHLHDCQTAN........
387222448[Leptospir   SGVRAAEELLSEDGGTPG..........
198258436[Verrucomi   SGKRLAECLDKDIDV.............
518821863[Verrucomi   L...........................
86554332[Synechococ   RAEALAQQLLSQV...............
551197846[Hymenobac   HARHVADQLTGK................
394453687[Pontibact   EAKAIAAKINTRAASRSIA.........
251772217[Leptospir   SGIRAAEKILAQ...SPG..........
355369310[Prevotell   QAVDLAERIG..................
522018329[Flexithri   KGKQLAERIKENKF..............
403378183[Geobacter   AANRTTDEVVAYLKGR............
86557434|[Synechoco   RAEALAQQILSVRR..............
428246331[Crinalium   RAYDQLPIINKQLSIINDN.........
148843553[Planctomy   SAEQAAERLLVDLTARV...........
146395727[Geobacter   AANRTADEVVAFLQSR............
343775775[Acidithio   EAYRFSQDVGWQR...............
288335658[Prevotell   QAVDMAEKISLSVS..............
317114493[Thermovib   SARETAEEVLNSLC..............
```

X non conserved

X ≥ 50% conserved

X all match

Figure 1b - continued

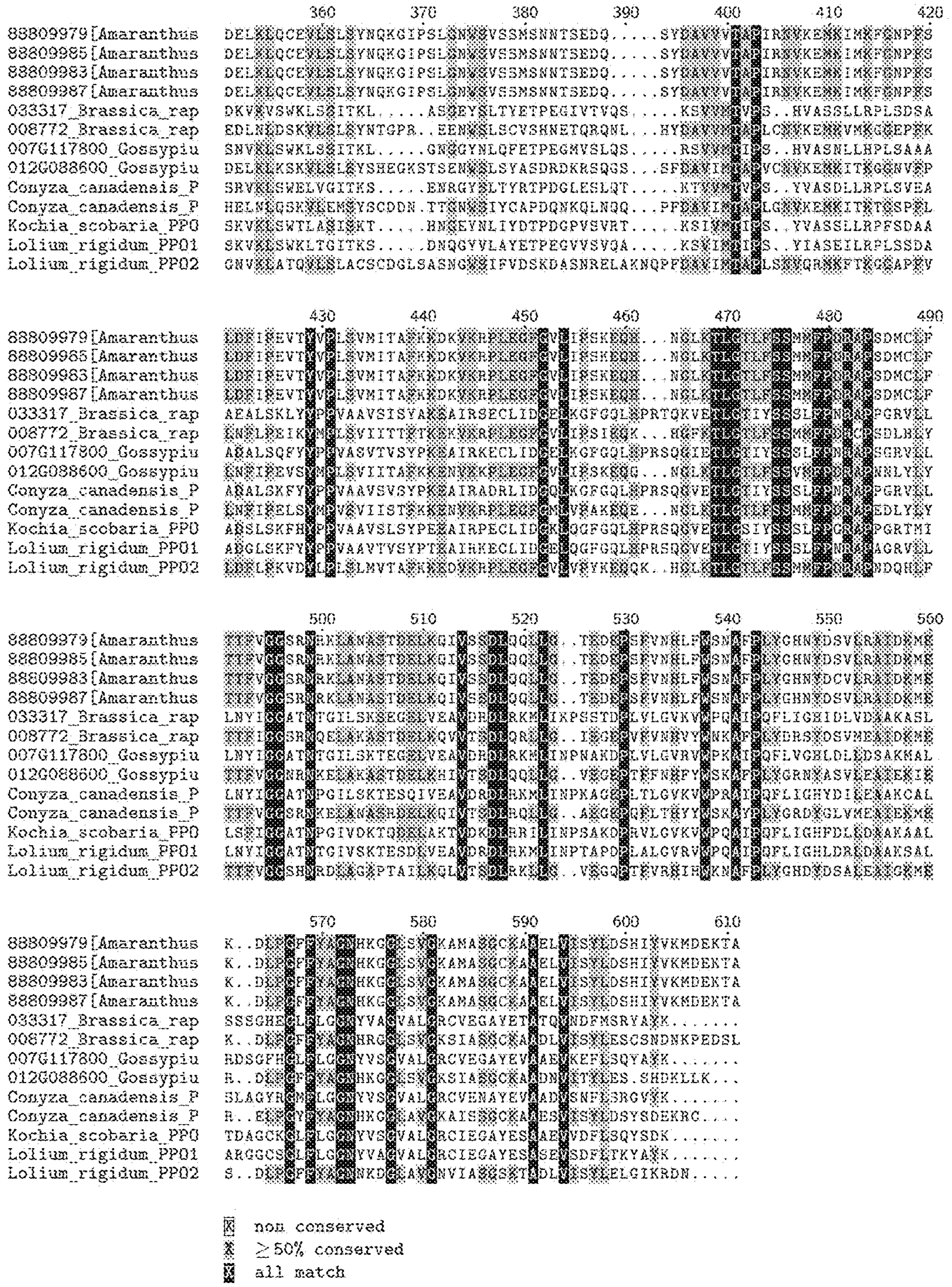

Figure 1c - continued

```
                         360       370       380       390       400       410       420
88809979[Amaranthus   DELXLQCEXLSLYNQKGIPSLXNXXVSSMSNNTSEDQ.....SYXXXVXIRXXKEXXIMKFXNPXS
88809985[Amaranthus   DELXLQCEXLSLYNQKGIPSLXNXXVSSMSNNTSEDQ.....SYXXXVXIRXXKEXXIMKFXNPXS
88809983[Amaranthus   DELXLQCEXLSLYNQKGIPSLXNXXVSSMSNNTSEDQ.....SYXXXVXIRXXKEXXIMKFXNPXS
88809987[Amaranthus   DELXLQCEXLSLYNQKGIPSLXNXXVSSMSNNTSEDQ.....SYXXXVXIRXXKEXXIMKFXNPXS
033317_Brassica_rap   DKVXVSWKLSXITKL.....ASXEYXLTYETPEGIVTVQS.....KSVXXXVQS..HVASSLLRPLSDSA
008772_Brassica_rap   EDLNXDSKXXSLXYNTGPR..EENXSLSCVSHNETQRQNL..HYXXXXXXLCXXKEXXVMKGXEPXK
007G117800_Gossypiu   SNVXLSWKLSXITKL.....GNXGYNLQFETPEGMVSLQS.....RSVXXXIXS..HVASNLLHPLSAAA
012G088600_Gossypiu   DELXLKSKXLXLXYSHEGKSTSENXXLSYASDRDKRSQGS...SFXXXIXXVCXXKEXXITXGXNVXP
Conyza_canadensis_P   SRVXLSWELVGITKS.....ENRGYXLTYRTPDGLESLQT.....KTXXXXVXS..YVASDLLRPLSVEA
Conyza_canadensis_P   HELNXQSKXXEMXYSCDDN.TTXNXXIYCAPDQNKQLNQQ...PFXXXIXXLGXXKEXXITXTXSPXL
Kochia_scobaria_PPO   SKVXLSWTLAXIXKT.....HNXEYNLIYDTPDGPVSVRT.....KSIXXXIXS..YVASSLLRPFSDAA
Lolium_rigidum_PPO1   SKVXLSWKLTGITKS.....DNQGYVLAYETPEGVVSVQA.....KSIXXXIXS..YIASEILRPLSSDA
Lolium_rigidum_PPO2   GNVXLATQXXSLACSCDGLSASNGXXIFVDSKDASNRELAKNQPFXXXIXXLSXXQRXXFTXGXAPXV

                         430       440       450       460       470       480       490
88809979[Amaranthus   LXXIXEVTXVXLSVMITAXKRDKXXRPXXGXXGVIXSKEXX...NGLXXXXXLFXSMXXXXXXSDMCXF
88809985[Amaranthus   LXXIXEVTXVXLSVMITAXKRDKXXRPXXGXXGVIXSKEXX...NGLXXXXXLFXSMXXXXXXSDMCXF
88809983[Amaranthus   LXXIXEVTXVXLSVMITAXKRDKXXRPXXGXXGVIXSKEXX...NGLXXXXXLFXSMXXXXXXSDMCXF
88809987[Amaranthus   LXXIXEVTXVXLSVMITAXKRDKXXRPXXGXXGVIXSKEXX...NGLXXXXXLFXSMXXXXXXSDMCXF
033317_Brassica_rap   AEALSKLYXXPXVAAVSISYAXXAIRSECLIDXXXKGFGQLXPRTQKVEXXXIYXSLXXXXXPGRVXL
008772_Brassica_rap   ENXLPEIKXMXLXSVIITTXTKXXXXRXXGXXGVIXSIXGK...HGPXXXXXLFXXXXXXXCXSDLBXY
007G117800_Gossypiu   AXALSQFYXXPXVASVTVSYPXXAIRKECLIDXXXKGFGQLXPRSQXIEXXXIYXSLXXXXXSGRVXL
012G088600_Gossypiu   XXXLXEVSXMXLXSVIITAXKXXXXXIXSKXGG...KLXXXXXLFXXVXXXXXANNLYXY
Conyza_canadensis_P   AXALSXFYXXPXVAAVSVSYPXXAIRADRLIDXXXKGFGQLXPRSQXVEXXXIYXSLXXXXXPGRVXL
Conyza_canadensis_P   ENXIXELSXMXVXVIISTXKKXNXXRPXXGXXMVXAKEXE...NGLXXXXXLFXSMXXXAXEDLYXY
Kochia_scobaria_PPO   AXSLSKFHXXPXVAAVSLSYPEXAIRPECLIDXXGFGQLXPRSQXVEXXXSIYXSLXXCXXXPGRTMI
Lolium_rigidum_PPO1   AXGLSKFYXXPXVAAVTVSYPTXAIRKECLIDXXXQGFGQLXPRSQXVEXXXIYXSLXXXXXAGRVXL
Lolium_rigidum_PPO2   LXXLXKVDXXLXLSLMVTAXKXXXXXIXSKXXK..HXLXXXXXLFXXXXXXXXNDQHXF

                         500       510       520       530       540       550       560
88809979[Amaranthus   XXXVGXSRXRKLANAXTDXLKGIXVSXXQQIXX..TXDXXSXVNHLFXSNXXFXYCHNXDSVXRAXDXMX
88809985[Amaranthus   XXXVGXSRXRKLANAXTDXLKGIXVSXXQQIXX..TXDXXSXVNHLFXSNXXFXYCHNXDSVXRAXDXMX
88809983[Amaranthus   XXXVGXSRXRKLANAXTDXLKGIXVSXXQQIXX..TXDXXSXVNHLFXSNXXFXYCHNXDCVXRAXDXMX
88809987[Amaranthus   XXXVGXSRXRKLANAXTDXLKGIXVSXXQQIXX..TXDXXSXVNHLFXSNXXFXYCHNXDSVXRXXDXMX
033317_Brassica_rap   LNYIXGATXTGILSKXEGXLVEAXDRXXRKMXIXPSSTDXLYLGVKVXPQAIXQFLIGHIDLVDXAKASL
008772_Brassica_rap   XXXIXGSRXQELXKAXSTXLXQVXTXXQRXXX..IXGXXVXVNRXYXNKXPXXDRSXDSVMEXXDKMX
007G117800_Gossypiu   LNYIXGATXTGILSKXTEGXIVEAXDRXXRKMXINPNAKDXLVLGVKVXPKIXGQFLVGHLDLXDSAKMAL
012G088600_Gossypiu   XXXVGXNRXKELXKAXSTXLKHIXTXXQQLXX..VXGXXTXFNHFYXSKXFXYGRNXASVLEXXEKIX
Conyza_canadensis_P   LNYIXGATXPGILSKXTESQIVEAXDRXXRKMXINPKAGXPLTLGVKVXPRAIXQFLIGHYDIXEXAKCAL
Conyza_canadensis_P   XXXVGXSRXKELANASRDXXKQIXTXXRQXX..AXGXXQXLTHYYXSKXYYXGRDXGLVMEXXEXMX
Kochia_scobaria_PPO   LSXIXGATXPGIVDKTQXXLAKTXDKXDRXBRIXIPSAKOXRVLGVKVXPQAIXQFLIGHFDLXDXAKAAL
Lolium_rigidum_PPO1   LNYIXGATXTGIVSKTESDXVEAXDRXXRKMXINPTAPDXLALGVRVXPQAIXQFLIGHLDRXDXAKSAL
Lolium_rigidum_PPO2   XXXVGXSHXRDXXGXPTAILXQLXTXXXRKXX..VXGQXTXVRXIHXXKNXFXYGHDXDSAXEXXGXMX

                         570       580       590       600       610
88809979[Amaranthus   K..DLXXXCFXXXXHKGXXSVXKAMAXXCKAXXELXXSXXDSHIXVKMDEKTA
88809985[Amaranthus   K..DLXXXCFXXXXHKGXXSVXKAMAXXCKAXXELXXSXXDSHIXVKMDEKTA
88809983[Amaranthus   K..DLXXXCFXXXXHKGXXSVXKAMAXXCKAXXELXXSXXDSHIXVKMDEKTA
88809987[Amaranthus   K..DLXXXCFXXXXHKGXXSVXKAMAXXCKAXXELXXSXXDSHIXVKMDEKTA
033317_Brassica_rap   SSSGHEXLXLGXXYVAXXVALXRCVEGAYETXTQXNDFMSRYAXK.......
008772_Brassica_rap   K..DLXXXCFXXXXHRGXXSVXKSIAXXCKAXXDLXXSXXESCSNDNKPEDSL
007G117800_Gossypiu   RDSGFHXLXLGXXYVSXXVALXRCVEGAYEVXAEXXKEFXSQYAXK.......
012G088600_Gossypiu   R..DLXXXFXXXXXHKGXXSVXKSIAXXCKAXXDNXXTXXES.SHDKLLX...
Conyza_canadensis_P   SLAGYRXMXLGXXYVSXXVALXRCVENAYEVXAAXXSNFXSRGVXK.......
Conyza_canadensis_P   R..ELXXXXXXXXXXHKGXXAVXKAISXXCKAXXESXXSXXDSYSDEKRC....
Kochia_scobaria_PPO   TDAGCKXLXLGXXYVSXXVALXRCIEGAYESXAEXXVDFXSQYSDK.......
Lolium_rigidum_PPO1   ARGGCSXLXLGXXYVAXXVALXRCIEGAYESXSEXXSDFXTKYAXK.......
Lolium_rigidum_PPO2   S..DLXXXFXXXXXNKDXXAVXNVIAXXSXTXXDLXXSXXELGIKRDN.....
```

X non conserved
    X ≥50% conserved
    X all match

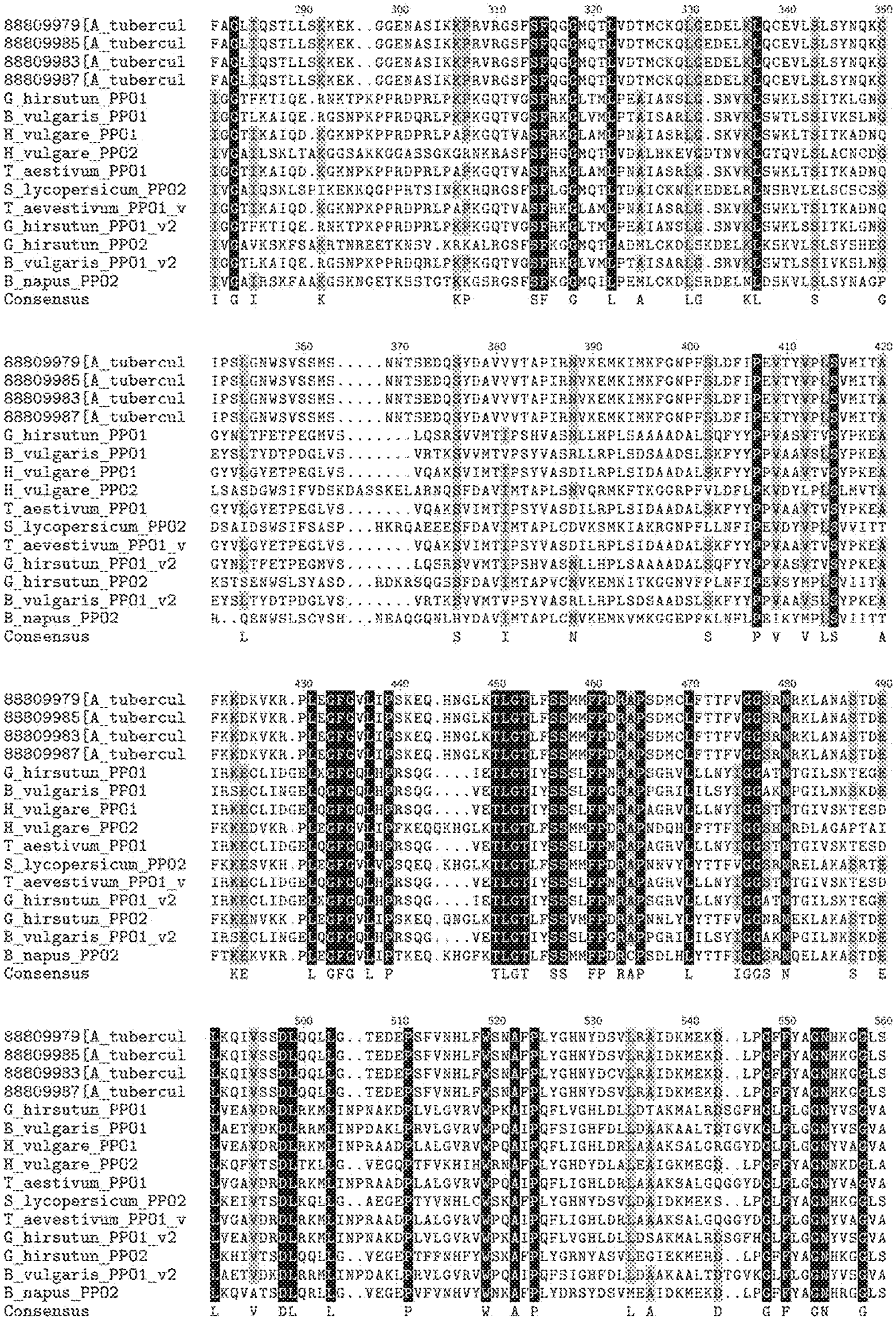
Figure 1d - continued

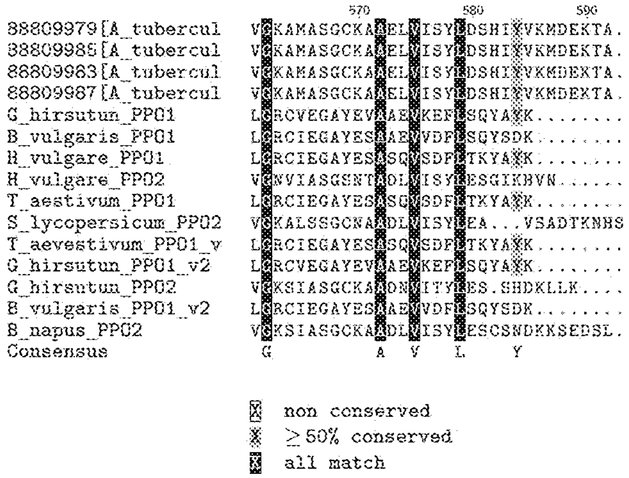
Figure 1d - continued

SEQUENCE LISTING

<160> NUMBER OF SEQ ID NOS: 129

<210> SEQ ID NO 1
<211> LENGTH: 534
<212> TYPE: PRT
<213> ORGANISM: Amaranthus tuberculatus

<400> SEQUENCE: 1

Met Val Ile Gln Ser Ile Thr His Leu Ser Pro Asn Leu Ala Leu Pro
1 5 10 15

Ser Pro Leu Ser Val Ser Thr Lys Asn Tyr Pro Val Ala Val Met Gly
20 25 30

Asn Ile Ser Glu Arg Glu Glu Pro Thr Ser Ala Lys Arg Val Ala Val
35 40 45

Val Gly Ala Gly Val Ser Gly Leu Ala Ala Ala Tyr Lys Leu Lys Ser
50 55 60

His Gly Leu Ser Val Thr Leu Phe Glu Ala Asp Ser Arg Ala Gly Gly
65 70 75 80

Lys Leu Lys Thr Val Lys Lys Asp Gly Phe Ile Trp Asp Glu Gly Ala
85 90 95

Asn Thr Met Thr Glu Ser Glu Ala Glu Val Ser Ser Leu Ile Asp Asp
100 105 110

Leu Gly Leu Arg Glu Lys Gln Gln Leu Pro Ile Ser Gln Asn Lys Arg

-continued

```
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530
```

<210> SEQ ID NO 2
<211> LENGTH: 534
<212> TYPE: PRT
<213> ORGANISM: Amaranthus tuberculatus

<400> SEQUENCE: 2

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Ala Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
```

```
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530


<210> SEQ ID NO 3
<211> LENGTH: 533
<212> TYPE: PRT
<213> ORGANISM: Amaranthus tuberculatus

<400> SEQUENCE: 3

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205
```

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530

<210> SEQ ID NO 4
<211> LENGTH: 533
<212> TYPE: PRT
<213> ORGANISM: Amaranthus tuberculatus

<400> SEQUENCE: 4

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

-continued

```
Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met Tyr His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460
```

-continued

```
Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530


<210> SEQ ID NO 5
<211> LENGTH: 535
<212> TYPE: PRT
<213> ORGANISM: Amaranthus hypochondriacus

<400> SEQUENCE: 5

Met Val Ile Gln Ser Ile Thr His Leu Ser Pro Lys Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Asn Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Ser Ser Asn Ile Leu Ser Ala Lys Ser Lys Leu Gln Ile
145                 150                 155                 160

Met Leu Glu Pro Phe Leu Trp Arg Lys Arg Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Val His His Thr Phe Pro Asp
    210                 215                 220

Val Trp Asn Val Glu Lys Arg Phe Gly Ser Val Phe Ala Gly Leu Ile
225                 230                 235                 240

Gln Ser Thr Leu Leu Ser Lys Lys Glu Lys Gly Gly Gly Glu Asn Ala
                245                 250                 255

Ser Ile Lys Lys Pro Arg Val Arg Gly Ser Phe Ser Phe His Gly Gly
            260                 265                 270

Met Gln Thr Leu Val Asp Thr Met Cys Lys Gln Ile Gly Glu Asp Glu
        275                 280                 285

Leu Lys Leu Gln Cys Glu Val Leu Ser Leu Ser Tyr Asn Gln Lys Gly
    290                 295                 300
```

-continued

Ile Pro Ser Leu Gly Asn Trp Ser Val Ser Ser Met Ser Asn Asn Thr
305 310 315 320

Ser Glu Asp Gln Ser Tyr Asp Ala Val Val Val Thr Ala Pro Ile Arg
325 330 335

Asn Val Lys Glu Met Lys Ile Met Lys Phe Gly Asn Pro Phe Ser Leu
340 345 350

Asp Phe Ile Pro Glu Val Thr Tyr Val Pro Leu Ser Val Met Ile Thr
355 360 365

Ala Phe Lys Lys Asp Lys Val Lys Arg Pro Leu Glu Gly Phe Gly Val
370 375 380

Leu Ile Pro Ser Lys Glu Gln His Asn Gly Leu Lys Thr Leu Gly Thr
385 390 395 400

Leu Phe Ser Ser Met Met Phe Pro Asp Arg Ala Pro Ser Asp Met Cys
405 410 415

Leu Phe Thr Thr Phe Val Gly Gly Ser Arg Asn Arg Lys Leu Ala Lys
420 425 430

Ala Ser Thr Asp Glu Leu Lys Gln Ile Val Ser Ser Asp Leu Gln Gln
435 440 445

Leu Leu Gly Thr Glu Asp Glu Pro Ser Phe Val Asn His Leu Phe Trp
450 455 460

Ser Asn Ala Phe Pro Leu Tyr Gly His Asn Tyr Asp Ser Val Leu Arg
465 470 475 480

Ala Ile Asp Lys Met Glu Lys Asp Leu Pro Gly Phe Phe Tyr Ala Gly
485 490 495

Asn His Lys Gly Gly Leu Ser Val Gly Lys Ala Met Ala Ser Gly Cys
500 505 510

Lys Ala Ala Glu Leu Val Ile Ser Tyr Leu Asp Ser His Leu Tyr Val
515 520 525

Lys Met Asn Glu Lys Thr Ala
530 535

<210> SEQ ID NO 6
<211> LENGTH: 505
<212> TYPE: PRT
<213> ORGANISM: Amaranthus tuberculatus

<400> SEQUENCE: 6

Met Gly Asn Ile Ser Glu Arg Asp Glu Pro Thr Ser Ala Lys Arg Val
1 5 10 15

Ala Val Val Gly Ala Gly Val Ser Gly Leu Ala Ala Ala Tyr Lys Leu
20 25 30

Lys Ser His Gly Leu Asn Val Thr Leu Phe Glu Ala Asp Ser Arg Ala
35 40 45

Gly Gly Lys Leu Lys Thr Val Lys Lys Asp Gly Phe Ile Trp Asp Glu
50 55 60

Gly Ala Asn Thr Met Thr Glu Ser Glu Ala Glu Val Ser Ser Leu Ile
65 70 75 80

Asp Asp Leu Gly Leu Arg Glu Lys Gln Gln Leu Pro Ile Ser Gln Asn
85 90 95

Lys Arg Tyr Ile Ala Arg Asp Gly Leu Pro Val Leu Leu Pro Ser Asn
100 105 110

Pro Ala Ala Leu Leu Thr Ser Asn Ile Leu Ser Ala Lys Ser Lys Leu
115 120 125

Gln Ile Met Leu Glu Pro Phe Phe Trp Arg Lys His Asn Ala Thr Glu 130 135 140

Leu Ser Asp Glu His Val Gln Glu Ser Val Gly Glu Phe Phe Glu Arg
145 150 155 160

His Phe Gly Lys Glu Phe Val Asp Tyr Val Ile Asp Pro Phe Val Ala
165 170 175

Gly Thr Cys Gly Gly Asp Pro Gln Ser Leu Ser Met His His Thr Phe
180 185 190

Pro Glu Val Trp Asn Ile Glu Lys Arg Phe Gly Ser Val Phe Ala Gly
195 200 205

Leu Ile Gln Ser Thr Leu Leu Ser Lys Lys Glu Lys Gly Gly Gly Gly
210 215 220

Asn Ala Ser Ile Lys Lys Pro Arg Val Arg Gly Ser Phe Ser Phe His
225 230 235 240

Gly Gly Met Gln Thr Leu Val Asp Thr Ile Cys Lys Gln Leu Gly Glu
245 250 255

Asp Glu Leu Lys Leu Gln Cys Glu Val Leu Ser Leu Ser Tyr Asn Gln
260 265 270

Lys Gly Ile Pro Ser Leu Gly Asn Trp Ser Val Ser Ser Met Ser Asn
275 280 285

Asn Thr Ser Glu Asp Gln Ser Tyr Asp Ala Val Val Val Thr Ala Pro
290 295 300

Ile Arg Asn Val Lys Glu Met Lys Ile Met Lys Phe Gly Asn Pro Phe
305 310 315 320

Ser Leu Asp Phe Ile Pro Glu Val Ser Tyr Val Pro Leu Ser Val Met
325 330 335

Ile Thr Ala Phe Lys Lys Asp Lys Val Lys Arg Pro Leu Glu Gly Phe
340 345 350

Gly Val Leu Ile Pro Ser Lys Glu Gln His Asn Gly Leu Lys Thr Leu
355 360 365

Gly Thr Leu Phe Ser Ser Met Met Phe Pro Asp Arg Ala Pro Ser Asp
370 375 380

Met Cys Leu Phe Thr Thr Phe Val Gly Gly Ser Arg Asn Arg Lys Leu
385 390 395 400

Ala Asn Ala Ser Thr Asp Glu Leu Lys Gln Ile Val Ser Ser Asp Leu
405 410 415

Gln Gln Leu Leu Gly Thr Glu Asp Glu Pro Ser Phe Val Asn His Leu
420 425 430

Phe Trp Ser Asn Ala Phe Pro Leu Tyr Gly His Asn Tyr Asp Ser Val
435 440 445

Leu Arg Ala Ile Asp Lys Met Glu Lys Asp Leu Pro Gly Phe Phe Tyr
450 455 460

Ala Gly Asn His Lys Gly Gly Leu Ser Val Gly Lys Ala Met Ala Ser
465 470 475 480

Gly Cys Lys Ala Ala Glu Leu Val Ile Ser Tyr Leu Asp Ser His Ile
485 490 495

Tyr Val Lys Met Asp Glu Lys Thr Ala
500 505

<210> SEQ ID NO 7
<211> LENGTH: 531
<212> TYPE: PRT
<213> ORGANISM: Spinacia oleracea

<400> SEQUENCE: 7

-continued

```
Met Val Ile Leu Pro Val Ser Gln Leu Ser Thr Asn Leu Gly Leu Ser
1               5                   10                  15

Leu Val Ser Pro Thr Lys Asn Asn Pro Val Met Gly Asn Val Ser Glu
            20                  25                  30

Arg Asn Gln Val Asn Gln Pro Ile Ser Ala Lys Arg Val Ala Val Val
        35                  40                  45

Gly Ala Gly Val Ser Gly Leu Ala Ala Ala Tyr Lys Leu Lys Ser Asn
    50                  55                  60

Gly Leu Asn Val Thr Leu Phe Glu Ala Asp Ser Arg Ala Gly Gly Lys
65                  70                  75                  80

Leu Lys Thr Val Val Lys Asp Gly Leu Ile Trp Asp Glu Gly Ala Asn
                85                  90                  95

Thr Met Thr Glu Ser Asp Glu Glu Val Thr Ser Leu Phe Asp Asp Leu
            100                 105                 110

Gly Ile Arg Glu Lys Leu Gln Leu Pro Ile Ser Gln Asn Lys Arg Tyr
        115                 120                 125

Ile Ala Arg Asp Gly Leu Pro Val Leu Leu Pro Ser Asn Pro Val Ala
    130                 135                 140

Leu Leu Lys Ser Asn Ile Leu Ser Ala Lys Ser Lys Leu Gln Ile Met
145                 150                 155                 160

Leu Glu Pro Phe Leu Trp Lys Lys His Asn Gly Ala Lys Val Ser Asp
                165                 170                 175

Glu Asn Ala Gln Glu Ser Val Ala Glu Phe Phe Glu Arg His Phe Gly
            180                 185                 190

Lys Glu Phe Val Asp Tyr Leu Ile Asp Pro Phe Val Ala Gly Thr Ser
        195                 200                 205

Gly Gly Asp Pro Gln Ser Leu Ser Met Arg His Ala Phe Pro Glu Leu
    210                 215                 220

Trp Asn Ile Glu Asn Arg Phe Gly Ser Val Ile Ser Gly Phe Ile Gln
225                 230                 235                 240

Ser Lys Leu Ser Ser Lys Lys Glu Lys Gly Gly Glu Lys Gln Ser Ser
                245                 250                 255

Asn Lys Lys Pro Arg Val Arg Gly Ser Phe Ser Phe Gln Gly Gly Met
            260                 265                 270

Gln Thr Leu Val Asp Thr Ile Cys Lys Glu Phe Gly Glu Asp Glu Leu
        275                 280                 285

Lys Leu Gln Ser Glu Val Leu Ser Leu Ser Tyr Ser His Asn Gly Ser
    290                 295                 300

Leu Thr Ser Glu Asn Trp Ser Val Ser Ser Met Ser Asn Ser Thr Ile
305                 310                 315                 320

Gln Asp Gln Pro Tyr Asp Ala Val Val Val Thr Ala Pro Ile Asn Asn
                325                 330                 335

Val Lys Glu Leu Lys Ile Met Lys Val Glu Asn Pro Phe Ser Leu Asp
            340                 345                 350

Phe Ile Pro Glu Val Ser Cys Leu Pro Leu Ser Val Ile Ile Thr Thr
        355                 360                 365

Phe Lys Lys Thr Asn Val Lys Arg Pro Leu Glu Gly Phe Gly Val Leu
    370                 375                 380

Val Pro Ser Asn Glu Gln His Asn Gly Leu Lys Thr Leu Gly Thr Leu
385                 390                 395                 400

Phe Ser Ser Met Met Phe Pro Asp Arg Ala Pro Ser Asp Val Tyr Leu
                405                 410                 415

Tyr Thr Thr Phe Val Gly Gly Ser Arg Asn Arg Glu Leu Ala Lys Ala
```

```
            420                 425                 430

Ser Thr Asp Glu Leu Lys Gln Ile Val Ser Ser Asp Leu Gln Gln Leu
        435                 440                 445

Leu Gly Thr Glu Gly Glu Pro Thr Phe Val Asn His Phe Tyr Trp Ser
    450                 455                 460

Lys Ala Phe Pro Leu Tyr Gly Arg Asn Tyr Asp Ser Val Leu Arg Ala
465                 470                 475                 480

Ile Glu Lys Met Glu Arg Asp Leu Pro Gly Leu Phe Tyr Ala Gly Asn
                485                 490                 495

His Lys Gly Gly Leu Ser Val Gly Lys Ser Ile Ala Ser Gly Tyr Lys
            500                 505                 510

Ala Ala Glu Leu Ala Ile Ser Tyr Leu Glu Ser Asn Lys Met Thr Glu
        515                 520                 525

Glu Thr Ile
    530


<210> SEQ ID NO 8
<211> LENGTH: 508
<212> TYPE: PRT
<213> ORGANISM: Vitis vinifera

<400> SEQUENCE: 8

Met Ala Glu Lys Ser Asp Ala Gln Ser His Tyr Asn Gly Ser Gly Lys
1               5                   10                  15

Arg Val Ala Val Val Gly Ala Gly Val Ser Gly Leu Ala Ala Ala Tyr
            20                  25                  30

Lys Leu Lys Leu His Gly Val Asn Ile Thr Leu Tyr Glu Ala Glu Glu
        35                  40                  45

Arg Ala Gly Gly Lys Leu Arg Ser Val Ser Gln His Gly Leu Val Trp
    50                  55                  60

Asp Glu Gly Ala Asn Thr Met Thr Glu Ser Glu Ile Glu Val Gly Ser
65                  70                  75                  80

Leu Leu Asp Asn Leu Arg Leu Arg Glu Lys Gln Gln Phe Pro Ile Ser
                85                  90                  95

Gln Asn Lys Arg Tyr Ile Val Arg Asn Gly Met Pro Val Leu Leu Pro
            100                 105                 110

Ser Asn Pro Ile Ala Leu Ile Lys Ser Asn Ile Leu Ser Ala Lys Ser
        115                 120                 125

Lys Phe Gln Ile Ile Leu Glu Pro Phe Leu Trp Lys Lys Ser Asp Leu
    130                 135                 140

Ser Lys Val Ser Asp Asp His Met Lys Glu Ser Val Gly Gly Phe Phe
145                 150                 155                 160

Gln Arg His Phe Gly Lys Glu Val Val Asp Tyr Leu Ile Asp Pro Phe
                165                 170                 175

Val Ala Gly Thr Ser Gly Gly Asp Pro Glu Ser Leu Ser Met His His
            180                 185                 190

Thr Phe Pro Glu Leu Trp Asn Leu Glu Lys Arg Phe Gly Ser Ile Ile
        195                 200                 205

Ala Gly Ala Val Leu Ser Lys Leu Ser Ala Lys Arg Glu Lys Arg Gly
    210                 215                 220

Glu Thr Lys Gly Ser Ser Glu Lys Lys Lys Arg Gln Arg Gly Ser Phe
225                 230                 235                 240

Ser Phe Gln Gly Gly Met Gln Thr Leu Thr Asp Thr Leu Cys Lys Glu
                245                 250                 255
```

-continued

Leu Gly Lys Asp Lys Leu Arg Leu Lys Ser Lys Val Leu Ser Leu Ser
260 265 270

Tyr Ser His Gly Glu Lys Ser Ala Leu Glu Asn Trp Ser Val Ala Tyr
275 280 285

Ala Ser Asn Pro Gly Lys Gln Ser Lys Asp Leu Ser Phe Asp Ala Val
290 295 300

Ile Met Thr Ala Pro Leu Cys Asn Val Arg Glu Met Lys Ile Met Lys
305 310 315 320

Lys Gly Asn Pro Phe Leu Leu Asp Phe Leu Pro Glu Val Ser Tyr Leu
325 330 335

Pro Leu Ser Val Ile Ile Thr Thr Phe Lys Lys Glu Asn Val Lys Arg
340 345 350

Pro Leu Glu Gly Phe Gly Val Leu Val Pro Ser Lys Glu Gln Gln Asn
355 360 365

Gly Leu Lys Thr Leu Gly Thr Leu Phe Ser Ser Met Met Phe Pro Asp
370 375 380

Arg Ala Pro Asn Asp Leu Tyr Leu Tyr Thr Thr Phe Ile Gly Gly Ser
385 390 395 400

Arg Asn Arg Glu Leu Ala Lys Ala Ser Thr Asp Glu Leu Lys Gln Ile
405 410 415

Val Thr Ser Asp Leu Arg Gln Leu Leu Gly Ala Glu Gly Glu Pro Thr
420 425 430

Phe Val Asn His Phe Tyr Trp Ser Lys Ala Phe Pro Leu Phe Gly His
435 440 445

Asn Tyr Asp Ser Val Leu Glu Ala Ile Asp Lys Met Glu Lys Asp Leu
450 455 460

Pro Gly Phe Phe Tyr Ala Gly Asn His Lys Gly Gly Leu Ser Val Gly
465 470 475 480

Lys Ala Ile Ala Ser Gly Cys Lys Ala Ala Asp Leu Val Ile Ser Tyr
485 490 495

Leu Asn Ser Ser Ser Asp Gly Lys Met Phe Lys Glu
500 505

<210> SEQ ID NO 9
<211> LENGTH: 511
<212> TYPE: PRT
<213> ORGANISM: Ricinus communis

<400> SEQUENCE: 9

Met Ser Ser Val Ile Lys Glu Asp Arg Asn Pro Ser His Val Lys Arg
1 5 10 15

Val Ala Val Val Gly Ala Gly Val Ser Gly Leu Ala Ala Ala Tyr Lys
20 25 30

Leu Lys Ser His Gly Leu Lys Val Thr Val Phe Glu Ala Glu Glu Arg
35 40 45

Ala Gly Gly Lys Leu Arg Ser Val Asn His Asp Gly Leu Ile Trp Asp
50 55 60

Glu Gly Ala Asn Thr Met Thr Glu Ser Glu Met Glu Val Lys Ser Leu
65 70 75 80

Ile Gly Asn Leu Gly Ile Arg Glu Lys Gln Gln Phe Pro Ile Ser Gln
85 90 95

Asn Lys Arg Tyr Ile Val Arg Asn Gly Lys Pro Ile Leu Ile Pro Thr
100 105 110

Asn Pro Ile Ala Leu Ile Thr Ser Asn Ile Leu Ser Ala Gln Ser Lys
115 120 125

```
Phe Gln Ile Ile Leu Glu Pro Phe Leu Trp Lys Lys Arg Glu Ser Ser
    130                 135                 140

Glu Thr His Asn Ala Tyr Thr Glu Glu Ser Val Gly Glu Phe Phe Gln
145                 150                 155                 160

Arg His Phe Gly Lys Glu Val Val Asp Tyr Leu Ile Asp Pro Phe Val
                165                 170                 175

Ala Gly Thr Ser Ala Gly Asp Pro Glu Ser Leu Ser Val Cys His Ser
            180                 185                 190

Phe Pro Glu Leu Trp Asn Leu Glu Lys Arg Phe Gly Ser Ile Ile Ala
        195                 200                 205

Gly Val Val Gln Ala Lys Leu Ser Thr Lys Arg Gly Lys Ser Gln Glu
    210                 215                 220

Thr Lys Gly Ser Ser Val Lys Lys Lys Gln Gln Arg Gly Ser Phe Ser
225                 230                 235                 240

Phe Phe Gly Gly Met Gln Thr Leu Thr Asp Thr Leu Cys Lys Ala Leu
                245                 250                 255

Ala Lys Asp Glu Leu Arg Leu Glu Ser Lys Val Phe Ser Leu Ser Tyr
            260                 265                 270

Asn Pro Asp Ser Lys Ser Ala Val Glu Asn Trp Ser Leu Ser Tyr Ala
        275                 280                 285

Phe Lys Gly Ala Lys His Leu Gln Asn Ser Ser Tyr Asp Ala Ile Val
    290                 295                 300

Met Thr Ala Pro Leu Cys Asn Val Lys Glu Met Lys Ile Thr Lys Asn
305                 310                 315                 320

Arg Asn Ile Phe Ser Leu Asn Phe Leu Pro Glu Val Ser Tyr Met Pro
                325                 330                 335

Leu Ser Val Val Ile Thr Thr Phe Lys Lys Asp Asn Val Lys Ser Pro
            340                 345                 350

Leu Glu Gly Phe Gly Val Leu Val Pro Ser Lys Glu Gln Gln Asn Gly
        355                 360                 365

Leu Lys Thr Leu Gly Thr Leu Phe Ser Ser Met Met Phe Pro Asp Arg
    370                 375                 380

Ala Pro Asn Asp Leu Tyr Leu Tyr Thr Thr Phe Val Gly Gly Ser Arg
385                 390                 395                 400

Asn Lys Glu Leu Ala Lys Ala Ser Thr Asp Asp Leu Lys Gln Ile Val
                405                 410                 415

Thr Ser Asp Leu Arg Gln Leu Leu Gly Ala Glu Gly Glu Pro Thr Phe
            420                 425                 430

Val Asn His Phe Tyr Trp Ser Lys Ala Phe Pro Leu Tyr Gly Arg Asn
        435                 440                 445

Tyr Asp Ala Val Leu Glu Ala Ile Asp Thr Met Glu Lys Asp Leu Pro
    450                 455                 460

Gly Phe Phe Tyr Ala Gly Asn His Lys Gly Gly Leu Ser Val Gly Lys
465                 470                 475                 480

Ala Ile Ala Ser Gly Cys Lys Ala Ala Asp Leu Val Ile Ser Tyr Leu
                485                 490                 495

Glu Ser Ser Ser Asp Asp Lys Met Leu Lys Glu Gly Pro Ser Asn
            500                 505                 510
```

<210> SEQ ID NO 10
<211> LENGTH: 504
<212> TYPE: PRT
<213> ORGANISM: Theobroma cacao

<400> SEQUENCE: 10

```
Met Ala Ala Ala Lys Asn Lys Asp Lys Gln Thr Ser Ala Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asn Val Thr Met Phe Glu Ala Glu Gly Arg Ala
        35                  40                  45

Gly Gly Lys Leu Arg Ser Val Ser Gln Glu Gly Leu Ile Trp Asp Glu
    50                  55                  60

Gly Ala Asn Thr Met Thr Glu Ser Glu Ile Glu Val Arg Ser Leu Phe
65                  70                  75                  80

Asp Asp Leu Gly Ile Arg Asp Lys Gln Gln Val Pro Ile Ala Gln Lys
                85                  90                  95

Lys Arg Tyr Ile Val Arg Asn Gly Val Pro Val Leu Ile Pro Ser Asn
            100                 105                 110

Pro Ile Ala Leu Ile Thr Ser Asn Ile Leu Ser Ala Lys Ser Lys Phe
        115                 120                 125

Gln Ile Ile Leu Glu Pro Phe Leu Trp Lys Lys Ser Asp Ala Ser Lys
    130                 135                 140

Val Ser Asp Ala Tyr Asn Leu Glu Ser Val Gly Gly Phe Phe Gln Arg
145                 150                 155                 160

His Phe Gly Gln Glu Val Val Asp Tyr Leu Ile Asp Pro Phe Val Ala
                165                 170                 175

Gly Thr Ser Ala Gly Asp Pro Glu Ser Leu Ser Met Arg His Ser Phe
            180                 185                 190

Pro Glu Leu Trp Asp Leu Glu Lys Arg Phe Gly Ser Ile Ile Val Gly
        195                 200                 205

Ala Val Lys Ser Lys Leu Ser Ala Lys Arg Glu Asn Arg Gly Glu Arg
    210                 215                 220

Lys Thr Ser Glu Lys Arg Lys Pro Leu Pro Gly Pro Phe Ser Phe Gln
225                 230                 235                 240

Gly Gly Met Gln Thr Leu Thr Asp Met Leu Cys Lys Asp Leu Ser Lys
                245                 250                 255

Asp Glu Leu Lys Leu Lys Ser Lys Val Leu Ser Leu Ser Tyr Ser His
            260                 265                 270

Asp Gly Lys Ser Thr Leu Glu Asn Trp Ser Leu Ser Tyr Ala Ser Asp
        275                 280                 285

Arg Asp Lys Arg Ser Gln Gly Ser Ser Phe Asp Ala Val Val Met Thr
    290                 295                 300

Ala Pro Leu Cys Asn Val Lys Glu Met Lys Ile Met Lys Gly Gly Lys
305                 310                 315                 320

Leu Phe Pro Leu Asn Phe Ile Pro Gln Val Ser Tyr Met Pro Leu Ser
                325                 330                 335

Val Ile Ile Thr Thr Phe Lys Lys Glu Asn Val Lys Lys Pro Leu Glu
            340                 345                 350

Gly Phe Gly Val Leu Val Pro Ser Lys Glu Gln Gln Asn Gly Leu Lys
        355                 360                 365

Thr Leu Gly Thr Leu Phe Ser Ser Ile Met Phe Pro Asp Arg Ala Pro
    370                 375                 380

Asn Asn Leu Tyr Leu Tyr Thr Thr Phe Val Gly Gly Ser Arg Asn Lys
385                 390                 395                 400

Glu Leu Ala Lys Ala Ser Thr Asp Glu Leu Lys His Ile Val Thr Ser
                405                 410                 415
```

```
Asp Leu Arg Gln Leu Leu Gly Val Glu Gly Glu Pro Thr Phe Leu Asn
            420                 425                 430

His Phe Tyr Trp Ser Lys Ala Phe Pro Leu Tyr Gly Arg Asn Tyr Ala
        435                 440                 445

Ser Val Leu Lys Ala Ile Glu Lys Met Glu Thr Asp Leu Pro Gly Phe
    450                 455                 460

Phe Tyr Ala Gly Asn His Lys Gly Gly Leu Ser Val Gly Lys Ala Ile
465                 470                 475                 480

Ala Ser Gly Cys Lys Ala Ala Asp Leu Val Ile Ser Tyr Leu Glu Ser
                485                 490                 495

Ser His Gln Lys Leu Leu Lys Asp
            500


<210> SEQ ID NO 11
<211> LENGTH: 502
<212> TYPE: PRT
<213> ORGANISM: Glycine max

<400> SEQUENCE: 11

Met Ala Ser Ser Ala Thr Asp Asp Asn Pro Arg Ser Val Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asp Val Thr Val Phe Glu Ala Glu Gly Arg Ala
        35                  40                  45

Gly Gly Arg Leu Arg Ser Val Ser Gln Asp Gly Leu Ile Trp Asp Glu
    50                  55                  60

Gly Ala Asn Thr Met Thr Glu Ser Glu Ile Glu Val Lys Gly Leu Ile
65                  70                  75                  80

Asp Ala Leu Gly Leu Gln Glu Lys Gln Gln Phe Pro Ile Ser Gln His
                85                  90                  95

Lys Arg Tyr Ile Val Lys Asn Gly Ala Pro Leu Leu Val Pro Thr Asn
            100                 105                 110

Pro Ala Ala Leu Leu Lys Ser Lys Leu Leu Ser Ala Gln Ser Lys Ile
        115                 120                 125

His Leu Ile Phe Glu Pro Phe Met Trp Lys Arg Ser Asp Pro Ser Asn
    130                 135                 140

Val Cys Asp Glu Asn Ser Val Glu Ser Val Gly Arg Phe Phe Glu Arg
145                 150                 155                 160

His Phe Gly Lys Glu Val Val Asp Tyr Leu Ile Asp Pro Phe Val Gly
                165                 170                 175

Gly Thr Ser Ala Ala Asp Pro Glu Ser Leu Ser Met Arg His Ser Phe
            180                 185                 190

Pro Glu Leu Trp Asn Leu Glu Lys Arg Phe Gly Ser Ile Ile Ala Gly
        195                 200                 205

Ala Leu Gln Ser Lys Leu Phe Ala Lys Arg Glu Lys Thr Gly Glu Asn
    210                 215                 220

Arg Thr Ala Leu Arg Lys Asn Lys His Lys Arg Gly Ser Phe Ser Phe
225                 230                 235                 240

Gln Gly Gly Met Gln Thr Leu Thr Asp Thr Leu Cys Lys Glu Leu Gly
                245                 250                 255

Lys Asp Asp Leu Lys Leu Asn Glu Lys Val Leu Thr Leu Ala Tyr Gly
            260                 265                 270

His Asp Gly Ser Ser Ser Ser Gln Asn Trp Ser Ile Thr Ser Ala Ser
```

275 280 285

Asn Gln Ser Thr Gln Asp Val Asp Ala Val Ile Met Thr Ala Pro Leu
290 295 300

Tyr Asn Val Lys Asp Ile Lys Ile Thr Lys Arg Gly Thr Pro Phe Pro
305 310 315 320

Leu Asn Phe Leu Pro Glu Val Ser Tyr Val Pro Ile Ser Val Met Ile
325 330 335

Thr Thr Phe Lys Lys Glu Asn Val Lys Arg Pro Leu Glu Gly Phe Gly
340 345 350

Val Leu Val Pro Ser Lys Glu Gln Lys Asn Gly Leu Lys Thr Leu Gly
355 360 365

Thr Leu Phe Ser Ser Met Met Phe Pro Asp Arg Ala Pro Ser Asp Leu
370 375 380

Tyr Leu Tyr Thr Thr Phe Ile Gly Gly Thr Gln Asn Arg Glu Leu Ala
385 390 395 400

Gln Ala Ser Thr Asp Glu Leu Arg Lys Ile Val Thr Ser Asp Leu Arg
405 410 415

Lys Leu Leu Gly Ala Glu Gly Glu Pro Thr Phe Val Asn His Phe Tyr
420 425 430

Trp Ser Lys Gly Phe Pro Leu Tyr Gly Arg Asn Tyr Gly Ser Val Leu
435 440 445

Gln Ala Ile Asp Lys Ile Glu Lys Asp Leu Pro Gly Phe Phe Phe Ala
450 455 460

Gly Asn Tyr Lys Gly Gly Leu Ser Val Gly Lys Ala Ile Ala Ser Gly
465 470 475 480

Cys Lys Ala Ala Asp Leu Val Ile Ser Tyr Leu Asn Ser Ala Ser Asp
485 490 495

Asn Thr Val Pro Asp Lys
500

<210> SEQ ID NO 12
<211> LENGTH: 502
<212> TYPE: PRT
<213> ORGANISM: Prunus persica

<400> SEQUENCE: 12

Met Thr Ser Leu Thr Thr Lys Glu Gly Ser Val Lys Arg Val Ala Val
1 5 10 15

Val Gly Ala Gly Val Ser Gly Leu Ala Ala Ala Tyr Lys Leu Lys Ser
20 25 30

His Gly Phe Asp Val Thr Val Phe Glu Ala Glu Gly Arg Ala Gly Gly
35 40 45

Lys Leu Arg Ser Val Ser His Asp Gly Leu Ile Trp Asp Glu Gly Ala
50 55 60

Asn Thr Met Thr Glu Ser Glu Lys Glu Val Gln Thr Leu Leu Asp Asp
65 70 75 80

Leu Gly Ile Arg Glu Lys Gln Gln Phe Pro Ile Ser Gln Asn Lys Arg
85 90 95

Tyr Ile Val Arg Asn Gly Ser Pro Val Leu Ile Pro Thr Asn Pro Ile
100 105 110

Ala Leu Ile Lys Ser Asn Phe Leu Ser Ala Gln Ser Lys Leu Gln Ile
115 120 125

Ile Leu Glu Pro Tyr Leu Trp Lys Asp Lys Arg Val Ser Asp Asp His
130 135 140

-continued

Thr Glu Glu Ser Val Gly Gly Phe Phe Gln Arg His Phe Gly Glu Glu
145 150 155 160

Val Val Asp Tyr Leu Ile Asp Pro Phe Val Ala Gly Thr Ser Ala Gly
165 170 175

Asp Pro Glu Ser Leu Ser Met Arg His Ser Phe Pro Asp Ile Trp Asn
180 185 190

Ile Glu Lys Arg Phe Gly Ser Val Ile Ser Gly Ala Ile Lys Ser Lys
195 200 205

Leu Ser Ala Ser Lys Gly Lys Ser Gly Glu Thr Lys Gly Ser Val Glu
210 215 220

Lys Gly Lys Arg Gln Arg Gly Ser Phe Ser Phe His Gly Gly Met Gln
225 230 235 240

Thr Leu Thr Asp Ile Leu Cys Asn Gln Leu Glu Lys Asp Glu Leu Lys
245 250 255

Leu Asn Ser Lys Val Leu Ser Leu Ser Tyr Arg Gln Gly Gly Asn Ser
260 265 270

Ala Ser Glu Asn Trp Ser Val Ser Arg Val Ala Asp Asp Asp Lys His
275 280 285

Ser Gln Ser Leu Ser Val Asp Ala Leu Ile Met Thr Ala Pro Leu Cys
290 295 300

Asn Val Lys Glu Met Lys Ile Thr Lys Arg Gly Thr Arg Phe Pro Leu
305 310 315 320

Asp Phe Ile Pro Glu Val Val Tyr Met Pro Leu Ser Val Ile Ile Thr
325 330 335

Thr Phe Lys Lys Glu Asn Val Lys Arg Pro Leu Glu Gly Phe Gly Val
340 345 350

Leu Val Pro Ser Lys Glu Gln Lys Asn Gly Leu Lys Thr Leu Gly Thr
355 360 365

Leu Phe Ser Ser Met Met Phe Pro Asp Arg Ala Pro Ser Asp Leu Tyr
370 375 380

Leu Tyr Thr Thr Phe Val Gly Gly Ser Arg Asn Lys Glu Leu Ala Lys
385 390 395 400

Ala Ser Thr Asp Glu Leu Lys Gln Ile Val Thr Ser Asp Ile Arg His
405 410 415

Leu Leu Gly Ala Glu Gly Glu Pro Thr Phe Val Asn His Phe Tyr Trp
420 425 430

Ser Asn Ala Phe Pro Leu Tyr Gly Arg Asp Tyr Asp Ser Val Ile Glu
435 440 445

Ala Ile Glu Asn Met Glu Lys Asn Leu Pro Gly Phe Phe Tyr Ala Gly
450 455 460

Asn His Arg Gly Gly Leu Ser Val Gly Lys Ser Ile Ala Ser Gly Cys
465 470 475 480

Lys Ala Ala Glu Leu Val Ile Ser Tyr Leu Glu Ser Pro Ser Asp Glu
485 490 495

Lys Thr Arg His Lys Gly
500

<210> SEQ ID NO 13
<211> LENGTH: 499
<212> TYPE: PRT
<213> ORGANISM: Medicago truncatula

<400> SEQUENCE: 13

Met Ala Ser Ser Ala Lys Asp Asp Asn Pro Arg Ser Val Lys Arg Val
1 5 10 15

-continued

```
Ala Val Val Gly Ala Gly Val Ser Gly Leu Ala Ala Ala Tyr Lys Leu
            20                  25                  30

Lys Ser His Gly Leu Asp Val Thr Val Phe Glu Ala Glu Gly Arg Ala
        35                  40                  45

Gly Gly Arg Leu Arg Thr Val Ser Arg Asp Gly Leu Val Trp Asp Glu
    50                  55                  60

Gly Ala Asn Thr Met Thr Glu Asn Glu Ile Glu Val Lys Gly Leu Ile
65                  70                  75                  80

Asp Ala Leu Gly Leu His Glu Lys Gln Gln Tyr Pro Leu Ser Gln His
                85                  90                  95

Lys Arg Tyr Ile Val Lys Asn Gly Thr Pro Val Leu Val Pro Ala Asn
            100                 105                 110

Pro Ala Ala Leu Leu Lys Ser Lys Leu Leu Ser Ala Gln Ser Lys Ile
        115                 120                 125

Gln Val Ile Phe Glu Pro Phe Met Trp Lys Arg Ser Asp Ser Ser Ala
    130                 135                 140

Val Arg Asp Glu Asn Ser Glu Glu Ser Val Ser Arg Phe Phe Glu Arg
145                 150                 155                 160

His Phe Gly Lys Glu Val Val Asp Tyr Leu Ile Asp Pro Phe Val Gly
                165                 170                 175

Gly Thr Ser Ala Ala Gly Pro Glu Ser Leu Ser Ile Arg His Ser Phe
            180                 185                 190

Pro Glu Leu Trp Asn Leu Glu Lys Arg Phe Gly Ser Ile Ile Ala Gly
        195                 200                 205

Ala Leu Gln Ser Ser Val Phe Gly Lys Lys Asp Lys Ala Gly Glu Thr
    210                 215                 220

Lys Asp Val Pro Arg Lys Asn Lys His Gln Arg Gly Ser Phe Ser Phe
225                 230                 235                 240

Gln Gly Gly Met Gln Thr Leu Thr Asp Thr Leu Cys Lys Glu Leu Gly
                245                 250                 255

Lys Asp Asp Ile Lys Leu Asn Ala Lys Val Leu Thr Leu Ala Tyr Ser
            260                 265                 270

His Asp Gly Ser Ser Pro Ser Gln Asn Trp Ser Ile Thr Cys Thr Ser
        275                 280                 285

Asn Arg Lys Ala Gln Asp Val Asp Ala Val Ile Met Thr Ala Pro Leu
    290                 295                 300

Gly Asn Val Arg Asp Ile Gln Ile Lys Lys Lys Gly Asn Pro Phe Pro
305                 310                 315                 320

Leu Asn Phe Leu Pro Glu Val Thr Tyr Leu Pro Leu Ser Val Leu Ile
                325                 330                 335

Thr Thr Phe Lys Lys Glu Asn Val Lys Arg Pro Leu Glu Gly Phe Gly
            340                 345                 350

Val Leu Val Pro Ser Lys Glu Gln Gln Asn Gly Phe Lys Thr Leu Gly
        355                 360                 365

Thr Leu Phe Ser Ser Met Met Phe Pro Asp Arg Ala Pro Ser Asp Met
    370                 375                 380

His Leu Tyr Thr Thr Phe Ile Gly Gly Thr Arg Asn Arg Glu Leu Ala
385                 390                 395                 400

Gln Ala Ser Thr Asp Glu Leu Thr Lys Ile Val Thr Ser Asp Leu Arg
                405                 410                 415

Lys Leu Leu Gly Ala Glu Gly Glu Pro Ala Phe Val Asn His Phe Phe
            420                 425                 430
```

```
Trp Ser Lys Gly Phe Pro Leu Tyr Gly His Asn Tyr Gly Ser Val Leu
        435                 440                 445

Glu Ala Ile Asp Lys Met Glu Lys Asp Leu Pro Gly Phe Phe Tyr Ala
    450                 455                 460

Gly Asn His Arg Gly Gly Leu Ser Val Gly Arg Ala Ile Ala Ser Gly
465                 470                 475                 480

Cys Lys Ala Ala Asp Leu Val Ile Ser Tyr Leu Asn Asn Ala Ser Asp
                485                 490                 495

Asn Ser Val


<210> SEQ ID NO 14
<211> LENGTH: 506
<212> TYPE: PRT
<213> ORGANISM: Fragaria vesca subsp. vesca

<400> SEQUENCE: 14

Met Ala Ser Pro Ser Gln Pro His Asn His Arg Ser Val Lys Lys Val
1               5                   10                  15

Ala Val Val Gly Ala Gly Val Ser Gly Leu Ala Ala Ala Tyr Lys Leu
            20                  25                  30

Lys Ser His Gly Phe Asp Val Thr Val Leu Glu Ala Glu Gly Arg Ala
        35                  40                  45

Gly Gly Lys Leu Arg Ser Val Ser Tyr Asn Gly Leu Ile Trp Asp Glu
    50                  55                  60

Gly Ala Asn Thr Met Thr Glu Ala Glu Thr Glu Val Gln Thr Leu Leu
65                  70                  75                  80

Asp Ser Leu Gly Leu Arg Asp Lys Gln Gln Phe Pro Ile Ser Gln Asn
                85                  90                  95

Lys Arg Tyr Val Ala Arg Asn Gly Met Pro Val Leu Leu Pro Thr Asn
            100                 105                 110

Pro Ile Glu Leu Ile Lys Ser Asn Phe Leu Ser Thr Lys Ser Lys Phe
        115                 120                 125

Gln Ile Leu Leu Glu Pro Tyr Leu Trp Lys Lys Lys Lys Val Ser Asp
    130                 135                 140

Asp His Thr Gln Glu Ser Val Ala Gly Phe Phe Gln Arg His Phe Gly
145                 150                 155                 160

Lys Glu Val Val Asp Tyr Leu Ile Asp Pro Phe Val Ala Gly Thr Ser
                165                 170                 175

Ala Gly Asp Pro Glu Ser Leu Ser Met Pro His Ser Phe Pro Glu Leu
            180                 185                 190

Trp Asn Ile Glu Lys Arg Tyr Gly Ser Val Ile Thr Gly Thr Ile Arg
        195                 200                 205

Ser Lys Val Ser Ser Arg Lys Glu Lys Arg Gly Asp Thr Lys Gly Ser
    210                 215                 220

Val Glu Lys Gly Lys Arg Gln Arg Gly Ser Phe Ser Phe Gln Gly Gly
225                 230                 235                 240

Met Gln Thr Leu Thr Asp Thr Leu Cys Lys Gln Leu Gly Lys His Glu
                245                 250                 255

Leu Lys Leu Asn Ser Lys Val Leu Ser Leu Ser Tyr Ser His Asp Gly
            260                 265                 270

Ser Ser Thr Ser Glu Asn Trp Ser Leu Ser Cys Val Ala Asn Asp Asp
        275                 280                 285

Lys His Ser Gln Ser Ser Ser Val Asp Ala Ile Ile Met Thr Ala Pro
    290                 295                 300
```

-continued

Leu Cys Ser Ile Lys Glu Met Lys Ile Thr Arg Arg Gly Thr Ile Phe
305 310 315 320

Pro Leu Asp Phe Leu Pro Glu Val Asn Tyr Met Pro Leu Ser Val Leu
325 330 335

Ile Thr Ser Phe Lys Lys Glu Asn Ile Lys Arg Pro Leu Glu Gly Phe
340 345 350

Gly Val Leu Val Pro Ser Lys Glu Gln Glu Asn Gly Leu Lys Thr Leu
355 360 365

Gly Thr Leu Phe Ser Ser Met Met Phe Pro Asp Arg Ala Pro Ser Asp
370 375 380

Gln Tyr Leu Tyr Thr Thr Phe Val Gly Gly Ser Arg Asn Lys Glu Leu
385 390 395 400

Ala Lys Ala Ser Lys Asp Glu Leu Lys Gln Ile Val Thr Ser Asp Ile
405 410 415

Arg Gln Leu Leu Gly Ala Glu Gly Glu Pro Thr Phe Val Asn His Tyr
420 425 430

Tyr Trp Ser Lys Ala Phe Pro Leu Tyr Gly His Asn Tyr Asp Ser Val
435 440 445

Ile Glu Ala Ile Glu Lys Met Glu Lys Asn Leu Pro Gly Leu Phe Tyr
450 455 460

Ala Gly Asn His Arg Gly Gly Leu Ser Val Gly Lys Ala Ile Ala Ser
465 470 475 480

Gly Cys Lys Ala Ala Asp Leu Val Ile Ser Tyr Leu Glu Ser Ser Ser
485 490 495

Asp Gly Lys Ile Leu Gln Gln Gly Ser Ser
500 505

<210> SEQ ID NO 15
<211> LENGTH: 509
<212> TYPE: PRT
<213> ORGANISM: Citrus clementina

<400> SEQUENCE: 15

Met Ala Ser Ala Pro Gly Glu Asp Asn Gln Arg Ser Ala Lys Arg Val
1 5 10 15

Ala Val Val Gly Ala Gly Val Ser Gly Leu Ala Ala Ala Tyr Lys Leu
20 25 30

Lys Ser Asn Gly Val Asn Val Met Val Phe Glu Ala Asp Glu Arg Ala
35 40 45

Gly Gly Lys Leu Arg Ser Ile Ser Lys Asp Gly Leu Ile Trp Asp Glu
50 55 60

Gly Ala Asn Thr Met Thr Glu Ser Glu Met Glu Val Lys Gly Leu Leu
65 70 75 80

Asp Asp Leu Gly Ile Arg Glu Lys Gln Gln Phe Pro Ile Ser Gln Tyr
85 90 95

Lys Arg Tyr Val Val Arg Asn Gly Val Pro Phe Leu Ile Pro Thr Asn
100 105 110

Pro Ile Ala Leu Ile Thr Ser Asn Phe Leu Ser Ala Gln Ser Lys Phe
115 120 125

Gln Ile Ile Leu Glu Pro Phe Leu Trp Lys Lys Ser Asp Ser Ala Lys
130 135 140

Val Ser Ala Glu Asp Ala Lys Glu Ser Val Gly Gly Phe Phe Gln Arg
145 150 155 160

His Phe Gly Arg Glu Val Val Asp Phe Leu Ile Asp Pro Phe Val Ala
165 170 175

```
Gly Thr Ser Ala Ala Asp Pro Glu Ser Leu Val Met Arg His Ser Phe
            180                 185                 190

Pro Glu Leu Trp Asn Leu Glu Lys Arg Tyr Gly Ser Val Ile Ala Gly
        195                 200                 205

Ala Ile Lys Ser Lys Phe Ser Ala Arg Lys Glu Lys Ser Ala Glu Ala
    210                 215                 220

Lys Gly Ser Ser Glu Lys Lys His Arg Gln Arg Gly Ser Phe Ser Phe
225                 230                 235                 240

Leu Gly Gly Met Gln Thr Leu Thr Asp Ala Leu Cys Lys Ala Leu Gly
                245                 250                 255

Lys Asp Glu Val Cys Leu Lys Ser Lys Val Leu Ser Leu Ser Tyr Ser
            260                 265                 270

His Asp Gly Lys Ser Ala Leu Glu Asn Trp Ser Leu Ser Ser Ser Asn
        275                 280                 285

Gln Asp Lys Gln Ser Gln Gly Leu Ser Phe Asp Ala Val Ile Met Thr
    290                 295                 300

Ala Ser Leu Cys Asn Val Lys Glu Met Lys Ile Thr Lys Gly Gly Asn
305                 310                 315                 320

Leu Phe Pro Leu Asp Phe Leu Pro Glu Val Ile Tyr Met Pro Leu Ser
                325                 330                 335

Val Phe Ile Thr Ala Phe Lys Lys Glu Asn Val Gly Lys Pro Leu Gln
            340                 345                 350

Gly Phe Gly Val Leu Val Pro Ser Lys Glu Gln Gln Asn Gly Leu Lys
        355                 360                 365

Thr Leu Gly Thr Leu Phe Ser Ser Met Met Phe Pro Asp Arg Ala Pro
    370                 375                 380

Lys Asp Leu Phe Leu Tyr Thr Thr Phe Val Gly Gly Ser Arg Asn Lys
385                 390                 395                 400

Glu Leu Ala Lys Ala Ser Thr Asp Glu Leu Lys Gln Ile Val Thr Ser
                405                 410                 415

Asp Leu Arg Gln Leu Leu Gly Val Glu Gly Glu Pro Thr Phe Val Asn
            420                 425                 430

His Phe Phe Trp Ser Lys Ala Phe Pro Leu Tyr Gly Arg Asp Tyr Asp
        435                 440                 445

Ser Val Leu Glu Ala Ile Glu Lys Met Glu Lys Asn Leu Pro Gly Phe
    450                 455                 460

Phe Tyr Ala Gly Asn His Lys Gly Gly Leu Ser Val Gly Lys Ser Ile
465                 470                 475                 480

Ala Ser Gly Cys Lys Ala Ala Glu Leu Val Ile Ser Tyr Leu Glu Asn
                485                 490                 495

Ser Ser Asp Asp Lys Met Leu Lys Glu Gly Ser Ser Lys
            500                 505
```

```
<210> SEQ ID NO 16
<211> LENGTH: 509
<212> TYPE: PRT
<213> ORGANISM: Citrus clementina

<400> SEQUENCE: 16

Met Thr Asn Lys Trp Arg Val Asp Phe Ser Gly Ser Ala Lys Arg Val
1               5                   10                  15

Ala Val Val Gly Ala Gly Val Ser Gly Leu Ala Ala Ala Tyr Lys Leu
            20                  25                  30

Lys Ser Asn Gly Val Asn Val Met Val Phe Glu Ala Asp Glu Arg Ala
```

-continued

```
        35                  40                  45

Gly Gly Lys Leu Arg Ser Ile Ser Lys Asp Gly Leu Ile Trp Asp Glu
    50                  55                  60

Gly Ala Asn Thr Met Thr Glu Ser Glu Met Glu Val Lys Gly Leu Leu
65                  70                  75                  80

Asp Asp Leu Gly Ile Arg Glu Lys Gln Gln Phe Pro Ile Ser Gln Tyr
                85                  90                  95

Lys Arg Tyr Val Val Arg Asn Gly Val Pro Phe Leu Ile Pro Thr Asn
            100                 105                 110

Pro Ile Ala Leu Ile Thr Ser Asn Phe Leu Ser Ala Gln Ser Lys Phe
        115                 120                 125

Gln Ile Ile Leu Glu Pro Phe Leu Trp Lys Lys Ser Asp Ser Ala Lys
    130                 135                 140

Val Ser Ala Glu Asp Ala Lys Glu Ser Val Gly Gly Phe Phe Gln Arg
145                 150                 155                 160

His Phe Gly Arg Glu Val Val Asp Phe Leu Ile Asp Pro Phe Val Ala
                165                 170                 175

Gly Thr Ser Ala Ala Asp Pro Glu Ser Leu Val Met Arg His Ser Phe
            180                 185                 190

Pro Glu Leu Trp Asn Leu Glu Lys Arg Tyr Gly Ser Val Ile Ala Gly
        195                 200                 205

Ala Ile Lys Ser Lys Phe Ser Ala Arg Lys Glu Lys Ser Ala Glu Ala
    210                 215                 220

Lys Gly Ser Ser Glu Lys Lys His Arg Gln Arg Gly Ser Phe Ser Phe
225                 230                 235                 240

Leu Gly Gly Met Gln Thr Leu Thr Asp Ala Leu Cys Lys Ala Leu Gly
                245                 250                 255

Lys Asp Glu Val Cys Leu Lys Ser Lys Val Leu Ser Leu Ser Tyr Ser
            260                 265                 270

His Asp Gly Lys Ser Ala Leu Glu Asn Trp Ser Leu Ser Ser Ser Asn
        275                 280                 285

Gln Asp Lys Gln Ser Gln Gly Leu Ser Phe Asp Ala Val Ile Met Thr
    290                 295                 300

Ala Ser Leu Cys Asn Val Lys Glu Met Lys Ile Thr Lys Gly Gly Asn
305                 310                 315                 320

Leu Phe Pro Leu Asp Phe Leu Pro Glu Val Ile Tyr Met Pro Leu Ser
                325                 330                 335

Val Phe Ile Thr Ala Phe Lys Lys Glu Asn Val Gly Lys Pro Leu Gln
            340                 345                 350

Gly Phe Gly Val Leu Val Pro Ser Lys Glu Gln Gln Asn Gly Leu Lys
        355                 360                 365

Thr Leu Gly Thr Leu Phe Ser Ser Met Met Phe Pro Asp Arg Ala Pro
    370                 375                 380

Lys Asp Leu Phe Leu Tyr Thr Thr Phe Val Gly Gly Ser Arg Asn Lys
385                 390                 395                 400

Glu Leu Ala Lys Ala Ser Thr Asp Glu Leu Lys Gln Ile Val Thr Ser
                405                 410                 415

Asp Leu Arg Gln Leu Leu Gly Val Glu Gly Glu Pro Thr Phe Val Asn
            420                 425                 430

His Phe Phe Trp Ser Lys Ala Phe Pro Leu Tyr Gly Arg Asp Tyr Asp
        435                 440                 445

Ser Val Leu Glu Ala Ile Glu Lys Met Glu Lys Asn Leu Pro Gly Phe
    450                 455                 460
```

Phe Tyr Ala Gly Asn His Lys Gly Gly Leu Ser Val Gly Lys Ser Ile
465 470 475 480

Ala Ser Gly Cys Lys Ala Ala Glu Leu Val Ile Ser Tyr Leu Glu Asn
485 490 495

Ser Ser Asp Asp Lys Met Leu Lys Glu Gly Ser Ser Lys
500 505

<210> SEQ ID NO 17
<211> LENGTH: 502
<212> TYPE: PRT
<213> ORGANISM: Cicer arietinum

<400> SEQUENCE: 17

Met Ala Ser Ser Ala Lys Asp Asn Asn Ser Arg Ser Val Lys Arg Val
1 5 10 15

Ala Val Val Gly Ala Gly Val Ser Gly Leu Ala Ala Ala Tyr Lys Leu
20 25 30

Lys Ser His Gly Leu Asp Val Thr Val Phe Glu Ala Glu Gly Arg Ala
35 40 45

Gly Gly Arg Leu Arg Thr Val Ser Arg Asp Gly Leu Val Trp Asp Glu
50 55 60

Gly Ala Asn Thr Met Thr Glu Asn Glu Ala Glu Val Lys Ser Leu Ile
65 70 75 80

Asp Ala Leu Gly Leu Gln Glu Lys Gln Gln Tyr Pro Leu Ser Gln His
85 90 95

Lys Arg Tyr Ile Val Lys Asn Gly Met Pro Leu Leu Val Pro Ala Asn
100 105 110

Pro Ala Ala Leu Leu Lys Ser Lys Leu Leu Ser Ala Gln Ser Lys Ile
115 120 125

Arg Val Ile Phe Glu Pro Phe Met Trp Lys Arg Ser Asp Ser Ser Thr
130 135 140

Val Cys Asp Glu Asn Ser Glu Glu Ser Val Ser Arg Phe Phe Glu Arg
145 150 155 160

His Phe Gly Lys Glu Val Val Asp Tyr Leu Ile Asp Pro Phe Val Gly
165 170 175

Gly Thr Ser Ala Ala Asp Pro Glu Ser Leu Ser Met Arg His Ser Phe
180 185 190

Pro Glu Leu Trp Asn Leu Glu Lys Arg Phe Gly Ser Ile Ile Gly Gly
195 200 205

Ala Leu Gln Ser Asn Leu Phe Gly Lys Arg Asp Lys Thr Gly Glu Thr
210 215 220

Lys Asp Ala Pro Arg Lys Ser Lys His Gln Arg Gly Ser Phe Ser Phe
225 230 235 240

Gln Gly Gly Met Gln Thr Leu Thr Asp Thr Leu Cys Lys Glu Leu Gly
245 250 255

Lys Asp Asn Leu Lys Leu Asn Ala Lys Val Leu Thr Leu Ala Tyr Ser
260 265 270

His Asn Gly Ser Ser Pro Ser Glu Asn Trp Ser Ile Thr Cys Ala Ser
275 280 285

Asn Leu Thr Thr Gln Asp Val Asp Ala Val Ile Met Thr Ala Pro Leu
290 295 300

Gly Asn Val Lys Asp Ile Gln Ile Thr Lys Arg Gly Thr Pro Phe Thr
305 310 315 320

Leu Asn Phe Phe Pro Glu Val Thr Tyr Leu Pro Leu Ser Val Leu Ile

```
                325                 330                 335

Thr Thr Phe Lys Lys Glu Asn Val Lys Arg Pro Leu Glu Gly Phe Gly
            340                 345                 350

Val Leu Val Pro Ser Lys Glu Glu Gln Asn Gly Phe Lys Thr Leu Gly
        355                 360                 365

Thr Leu Phe Ser Ser Met Met Phe Pro Asp Arg Ala Pro Ser Asp Leu
    370                 375                 380

His Leu Tyr Thr Thr Phe Ile Gly Gly Thr Arg Asn Arg Glu Leu Ala
385                 390                 395                 400

Gln Ala Ser Thr Asp Glu Leu Lys Lys Ile Val Thr Ser Asp Leu Arg
                405                 410                 415

Lys Leu Leu Gly Ala Glu Gly Glu Pro Thr Phe Val Asn His Phe Tyr
            420                 425                 430

Trp Ser Lys Gly Phe Pro Leu Tyr Gly His Asn Tyr Gly Leu Val Leu
        435                 440                 445

Glu Ala Ile Asp Lys Met Glu Lys Gly Leu Pro Gly Phe Phe Tyr Ala
    450                 455                 460

Gly Asn His Arg Gly Gly Leu Ser Val Gly Arg Ala Ile Ala Ser Gly
465                 470                 475                 480

Cys Lys Ala Ala Asp Leu Val Ile Ser Tyr Leu Asn Asn Ala Ser Asp
                485                 490                 495

Asn Thr Val Ala Asp Lys
            500


<210> SEQ ID NO 18
<211> LENGTH: 502
<212> TYPE: PRT
<213> ORGANISM: Cucumis sativus

<400> SEQUENCE: 18

Met Ala Ser Pro Ala Lys Gln Asp Arg Arg Thr Ser Arg Lys Lys Val
1               5                   10                  15

Ala Val Val Gly Ala Gly Val Ser Gly Leu Ala Ala Ala Tyr Lys Leu
            20                  25                  30

Lys Ser His Gly Phe Asp Val Thr Val Leu Glu Ala Asp Glu Arg Val
        35                  40                  45

Gly Gly Lys Leu Arg Ser Val Ser Tyr Lys Gly Leu Ile Trp Asp Glu
    50                  55                  60

Gly Ala Asn Thr Met Thr Glu Ser Glu Pro Glu Val Gln Cys Leu Leu
65                  70                  75                  80

Asp Asp Leu Gly Leu Arg Glu Lys Gln Gln Phe Pro Ile Ser Gln Asn
                85                  90                  95

Lys Arg Tyr Ile Val Arg Asn Gly Val Pro Val Leu Val Pro Thr Asn
            100                 105                 110

Pro Ile Ala Leu Ile Lys Ser Asn Phe Leu Ser Ala Lys Ser Lys Phe
        115                 120                 125

Gln Ile Ile Leu Glu Pro Phe Leu Trp Lys Lys Tyr Asp Ser Ser Lys
    130                 135                 140

Val Ser Asp Asp Gly Thr Asp Glu Ser Val Gly Gly Phe Phe Gln Arg
145                 150                 155                 160

His Phe Gly Gln Glu Val Val Asp Tyr Leu Ile Asp Pro Ile Val Ala
                165                 170                 175

Gly Thr Ser Ala Gly Asp Pro Asp Ser Leu Ser Met Ser His Ser Phe
            180                 185                 190
```

```
Pro Glu Leu Trp Asn Ile Glu Lys Arg Phe Gly Ser Ile Phe Ala Gly
        195                 200                 205

Leu Val Leu Ser Lys Leu Ser Thr Lys Lys Glu Ser Gly Gly Val Arg
    210                 215                 220

Asn Gly Thr Thr Gly Lys Ser Lys Pro Arg Arg Gly Ser Phe Ser Phe
225                 230                 235                 240

Gln Asn Gly Met Gln Thr Leu Thr Asp Thr Leu Ser Lys Glu Leu Gly
                245                 250                 255

Glu Gly Val Leu Lys Leu Arg Ser Glu Val Leu Ser Leu Ser Tyr Asn
            260                 265                 270

Ala Gly Lys Tyr Ala Ser Gln Asn Trp Ser Leu Ile Tyr Ser Lys Asp
        275                 280                 285

Lys Asn Ser Lys Asp Leu Ile Ala Asp Ala Val Ile Met Thr Ala Pro
    290                 295                 300

Val Cys Ser Val Arg Glu Met Lys Phe Met Lys Gly Gly Ile Pro Phe
305                 310                 315                 320

Ser Leu Asn Phe Leu Pro Glu Val Ala Tyr Met Pro Leu Ser Val Met
                325                 330                 335

Ile Thr Thr Phe Arg Lys Glu Ser Val Lys Arg Pro Leu Glu Gly Phe
            340                 345                 350

Gly Val Leu Val Pro Ser Ser Glu Gln Gln Asn Gly Leu Arg Thr Leu
        355                 360                 365

Gly Thr Leu Phe Ser Ser Met Met Phe Pro Asn Arg Ala Ser Asn Asp
    370                 375                 380

Glu Tyr Leu Tyr Thr Thr Phe Ile Gly Gly Ser Arg Asn Arg Glu Leu
385                 390                 395                 400

Ala Lys Ser Ser Thr Asp Glu Leu Lys Gln Ile Val Thr Thr Asp Leu
                405                 410                 415

Arg Gln Leu Leu Gly Val Glu Gly Glu Pro Thr Phe Ile Asn His Phe
            420                 425                 430

Tyr Trp Ser Lys Ala Phe Pro Leu Tyr Gly Arg Asn Tyr Asp Ser Val
        435                 440                 445

Val Lys Ala Ile Glu Thr Met Glu Lys Asn Leu Pro Gly Phe Phe Tyr
    450                 455                 460

Ala Gly Asn His Arg Asp Gly Leu Ser Val Gly Lys Ser Ile Ala Ser
465                 470                 475                 480

Gly Cys Lys Ala Ala Asp Leu Val Ile Ser Tyr Leu Glu Ser Ser Thr
                485                 490                 495

Asp Gln Ser Cys Ala Glu
            500


<210> SEQ ID NO 19
<211> LENGTH: 497
<212> TYPE: PRT
<213> ORGANISM: Cucumis sativus

<400> SEQUENCE: 19

Met Lys Ser Ser Gln Ser Ser Arg Lys Lys Val Ala Val Val Gly Ala
1               5                   10                  15

Gly Val Ser Gly Leu Ala Ala Ala Tyr Lys Leu Lys Ser His Gly Phe
            20                  25                  30

Asp Val Thr Val Leu Glu Ala Asp Glu Arg Val Gly Gly Lys Leu Arg
        35                  40                  45

Ser Val Ser Tyr Lys Gly Leu Ile Trp Asp Glu Gly Ala Asn Thr Met
    50                  55                  60
```

-continued

```
Thr Glu Ser Glu Pro Glu Val Gln Cys Leu Leu Asp Asp Leu Gly Leu
65                  70                  75                  80

Arg Glu Lys Gln Gln Phe Pro Ile Ser Gln Asn Lys Arg Tyr Ile Val
                85                  90                  95

Arg Asn Gly Val Pro Val Leu Val Pro Thr Asn Pro Ile Ala Leu Ile
            100                 105                 110

Lys Ser Asn Phe Leu Ser Ala Lys Ser Lys Phe Gln Ile Ile Leu Glu
        115                 120                 125

Pro Phe Leu Trp Lys Lys Tyr Asp Ser Ser Lys Val Ser Asp Asp Gly
    130                 135                 140

Thr Asp Glu Ser Val Gly Gly Phe Phe Gln Arg His Phe Gly Gln Glu
145                 150                 155                 160

Val Val Asp Tyr Leu Ile Asp Pro Ile Val Ala Gly Thr Ser Ala Gly
                165                 170                 175

Asp Pro Asp Ser Leu Ser Met Ser His Ser Phe Pro Glu Leu Trp Asn
            180                 185                 190

Ile Glu Lys Arg Phe Gly Ser Ile Phe Ala Gly Leu Val Leu Ser Lys
        195                 200                 205

Leu Ser Thr Lys Lys Glu Ser Gly Gly Val Arg Asn Gly Thr Thr Gly
    210                 215                 220

Lys Ser Lys Pro Arg Arg Gly Ser Phe Ser Phe Gln Asn Gly Met Gln
225                 230                 235                 240

Thr Leu Thr Asp Thr Leu Ser Lys Glu Leu Gly Glu Gly Val Leu Lys
                245                 250                 255

Leu Arg Ser Glu Val Leu Ser Leu Ser Tyr Asn Ala Gly Lys Tyr Ala
            260                 265                 270

Ser Gln Asn Trp Ser Leu Ile Tyr Ser Lys Asp Lys Asn Ser Lys Asp
        275                 280                 285

Leu Ile Ala Asp Ala Val Ile Met Thr Ala Pro Val Cys Ser Val Arg
    290                 295                 300

Glu Met Lys Phe Met Lys Gly Gly Ile Pro Phe Ser Leu Asn Phe Leu
305                 310                 315                 320

Pro Glu Val Ala Tyr Met Pro Leu Ser Val Met Ile Thr Thr Phe Arg
                325                 330                 335

Lys Glu Ser Val Lys Arg Pro Leu Glu Gly Phe Gly Val Leu Val Pro
            340                 345                 350

Ser Ser Glu Gln Gln Asn Gly Leu Arg Thr Leu Gly Thr Leu Phe Ser
        355                 360                 365

Ser Met Met Phe Pro Asn Arg Ala Ser Asn Asp Glu Tyr Leu Tyr Thr
    370                 375                 380

Thr Phe Ile Gly Gly Ser Arg Asn Arg Glu Leu Ala Lys Ser Ser Thr
385                 390                 395                 400

Asp Glu Leu Lys Gln Ile Val Thr Thr Asp Leu Arg Gln Leu Leu Gly
                405                 410                 415

Val Glu Gly Glu Pro Thr Phe Ile Asn His Phe Tyr Trp Ser Lys Ala
            420                 425                 430

Phe Pro Leu Tyr Gly Arg Asn Tyr Asp Ser Val Val Lys Ala Ile Glu
        435                 440                 445

Thr Met Glu Lys Asn Leu Pro Gly Phe Phe Tyr Ala Gly Asn His Arg
    450                 455                 460

Asp Gly Leu Ser Val Gly Lys Ser Ile Ala Ser Gly Cys Lys Ala Ala
465                 470                 475                 480
```

```
Asp Leu Val Ile Ser Tyr Leu Glu Ser Ser Thr Asp Gln Ser Cys Ala
                485                 490                 495

Glu


<210> SEQ ID NO 20
<211> LENGTH: 504
<212> TYPE: PRT
<213> ORGANISM: Nicotiana tabacum

<400> SEQUENCE: 20

Met Ala Pro Ser Ala Gly Glu Asp Lys His Ser Ser Ala Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asn Val Thr Val Phe Glu Ala Glu Gly Lys Ala
        35                  40                  45

Gly Gly Lys Leu Arg Ser Val Ser Gln Asp Gly Leu Ile Trp Asp Glu
    50                  55                  60

Gly Ala Asn Thr Met Thr Glu Ser Glu Gly Asp Val Thr Phe Leu Ile
65                  70                  75                  80

Asp Ser Leu Gly Leu Arg Glu Lys Gln Gln Phe Pro Leu Ser Gln Asn
                85                  90                  95

Lys Arg Tyr Ile Ala Arg Asn Gly Thr Pro Val Leu Leu Pro Ser Asn
            100                 105                 110

Pro Ile Asp Leu Ile Lys Ser Asn Phe Leu Ser Thr Gly Ser Lys Leu
        115                 120                 125

Gln Met Leu Leu Glu Pro Ile Leu Trp Lys Asn Lys Lys Leu Ser Gln
    130                 135                 140

Val Ser Asp Ser His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His His Ser Phe Pro Glu
            180                 185                 190

Leu Trp Asn Leu Glu Lys Arg Phe Gly Ser Val Ile Leu Gly Ala Ile
        195                 200                 205

Arg Ser Lys Leu Ser Pro Lys Asn Glu Lys Lys Gln Gly Pro Pro Lys
    210                 215                 220

Thr Ser Ala Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Arg Glu Asp
                245                 250                 255

Glu Leu Arg Leu Asn Ser Arg Val Leu Glu Leu Ser Cys Ser Cys Thr
            260                 265                 270

Glu Asp Ser Ala Ile Asp Ser Trp Ser Ile Ile Ser Ala Ser Pro His
        275                 280                 285

Lys Arg Gln Ser Glu Glu Glu Ser Phe Asp Ala Val Ile Met Thr Ala
    290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Arg Glu Asn Val Lys Tyr Pro Leu Glu Gly
            340                 345                 350
```

-continued

```
Phe Gly Val Leu Val Pro Ser Lys Glu Gln Gln His Gly Leu Lys Thr
        355                 360                 365

Leu Gly Thr Leu Phe Ser Ser Met Met Phe Pro Asp Arg Ala Pro Asn
    370                 375                 380

Asn Val Tyr Leu Tyr Thr Thr Phe Val Gly Gly Ser Arg Asn Arg Glu
385                 390                 395                 400

Leu Ala Lys Ala Ser Arg Thr Glu Leu Lys Glu Ile Val Thr Ser Asp
                405                 410                 415

Leu Lys Gln Leu Leu Gly Ala Glu Gly Glu Pro Thr Tyr Val Asn His
            420                 425                 430

Leu Tyr Trp Ser Lys Ala Phe Pro Leu Tyr Gly His Asn Tyr Asp Ser
        435                 440                 445

Val Leu Asp Ala Ile Asp Lys Met Glu Lys Asn Leu Pro Gly Leu Phe
    450                 455                 460

Tyr Ala Gly Asn His Arg Gly Gly Leu Ser Val Gly Lys Ala Leu Ser
465                 470                 475                 480

Ser Gly Cys Asn Ala Ala Asp Leu Val Ile Ser Tyr Leu Glu Ser Val
                485                 490                 495

Ser Thr Asp Ser Lys Arg His Cys
            500


<210> SEQ ID NO 21
<211> LENGTH: 501
<212> TYPE: PRT
<213> ORGANISM: Solanum lycopersicum

<400> SEQUENCE: 21

Met Ala Pro Ser Ala Gly Glu Asp Lys Gln Lys Arg Val Ala Val Ile
1               5                   10                  15

Gly Ala Gly Val Ser Gly Leu Ala Ala Ala Tyr Lys Leu Lys Val His
            20                  25                  30

Gly Leu Asn Val Thr Val Phe Glu Ala Glu Gly Arg Ala Gly Gly Lys
        35                  40                  45

Leu Arg Ser Leu Ser Gln Asp Gly Leu Ile Trp Asp Glu Gly Ala Asn
    50                  55                  60

Thr Met Thr Glu Ser Glu Gly Asp Val Thr Phe Leu Leu Asp Ser Leu
65                  70                  75                  80

Gly Leu Arg Glu Lys Gln Gln Phe Pro Leu Ser Gln Asn Lys Arg Tyr
                85                  90                  95

Ile Ala Arg Asn Gly Thr Pro Thr Leu Ile Pro Ser Asn Pro Phe Asp
            100                 105                 110

Leu Phe Lys Ser Asn Phe Leu Ser Thr Gly Ser Lys Leu Gln Met Leu
        115                 120                 125

Phe Glu Pro Leu Leu Trp Lys Asn Lys Lys Leu Thr Lys Val Ser Asp
    130                 135                 140

Lys His Glu Ser Val Ser Gly Phe Phe Gln Arg His Phe Gly Lys Glu
145                 150                 155                 160

Val Val Asp Tyr Leu Ile Asp Pro Phe Val Ala Gly Thr Cys Gly Gly
                165                 170                 175

Asp Pro Asp Ser Leu Ser Met His Leu Ser Phe Pro Asp Leu Trp Asn
            180                 185                 190

Leu Glu Lys Arg Phe Gly Ser Val Ile Val Gly Ala Ile Gln Ser Lys
        195                 200                 205

Leu Ser Pro Ile Lys Glu Lys Lys Gln Gly Pro Pro Arg Thr Ser Ile
    210                 215                 220
```

Asn Lys Lys Arg Gln Arg Gly Ser Phe Ser Phe Leu Gly Gly Met Gln
225 230 235 240

Thr Leu Thr Asp Ala Ile Cys Lys Asn Leu Lys Glu Asp Glu Leu Arg
245 250 255

Leu Asn Ser Arg Val Leu Glu Leu Ser Cys Ser Cys Ser Gly Asp Ser
260 265 270

Ala Ile Asp Ser Trp Ser Ile Phe Ser Ala Ser Pro His Lys Arg Gln
275 280 285

Ala Glu Glu Glu Ser Phe Asp Ala Val Ile Met Thr Ala Pro Leu Cys
290 295 300

Asp Val Lys Ser Met Lys Ile Ala Lys Arg Gly Asn Pro Phe Leu Leu
305 310 315 320

Asn Phe Ile Pro Glu Val Asp Tyr Val Pro Leu Ser Val Val Ile Thr
325 330 335

Thr Phe Lys Lys Glu Ser Val Lys His Pro Leu Glu Gly Phe Gly Val
340 345 350

Leu Val Pro Ser Gln Glu Gln Lys His Gly Leu Lys Thr Leu Gly Thr
355 360 365

Leu Phe Ser Ser Met Met Phe Pro Asp Arg Ala Pro Asn Asn Val Tyr
370 375 380

Leu Tyr Thr Thr Phe Val Gly Gly Ser Arg Asn Arg Glu Leu Ala Lys
385 390 395 400

Ala Ser Arg Thr Glu Leu Lys Glu Ile Val Thr Ser Asp Leu Lys Gln
405 410 415

Leu Leu Gly Ala Glu Gly Glu Pro Thr Tyr Val Asn His Leu Cys Trp
420 425 430

Ser Lys Ala Phe Pro Leu Tyr Gly His Asn Tyr Asp Ser Val Leu Asp
435 440 445

Ala Ile Asp Lys Met Glu Lys Ser Leu Pro Gly Leu Phe Tyr Ala Gly
450 455 460

Asn His Lys Gly Gly Leu Ser Val Gly Lys Ala Leu Ser Ser Gly Cys
465 470 475 480

Asn Ala Ala Asp Leu Val Ile Ser Tyr Leu Glu Ala Val Ser Ala Asp
485 490 495

Thr Lys Asn His Ser
500

<210> SEQ ID NO 22
<211> LENGTH: 508
<212> TYPE: PRT
<213> ORGANISM: Arabidopsis thaliana

<400> SEQUENCE: 22

Met Ala Ser Gly Ala Val Ala Asp His Gln Ile Glu Ala Val Ser Gly
1 5 10 15

Lys Arg Val Ala Val Val Gly Ala Gly Val Ser Gly Leu Ala Ala Ala
20 25 30

Tyr Lys Leu Lys Ser Arg Gly Leu Asn Val Thr Val Phe Glu Ala Asp
35 40 45

Gly Arg Val Gly Gly Lys Leu Arg Ser Val Met Gln Asn Gly Leu Ile
50 55 60

Trp Asp Glu Gly Ala Asn Thr Met Thr Glu Ala Glu Pro Glu Val Gly
65 70 75 80

Ser Leu Leu Asp Asp Leu Gly Leu Arg Glu Lys Gln Gln Phe Pro Ile

-continued

```
                85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
        115                 120                 125

Ser Lys Phe Gln Ile Leu Leu Glu Pro Phe Leu Trp Lys Lys Lys Ser
    130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
            180                 185                 190

Ser Phe Pro Asp Leu Trp Asn Val Glu Lys Ser Phe Gly Ser Ile Ile
        195                 200                 205

Val Gly Ala Ile Arg Thr Lys Phe Ala Ala Lys Gly Gly Lys Ser Arg
    210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                245                 250                 255

Leu Ser His Asp Glu Ile Asn Leu Asp Ser Lys Val Leu Ser Leu Ser
            260                 265                 270

Tyr Asn Ser Gly Ser Arg Gln Glu Asn Trp Ser Leu Ser Cys Val Ser
        275                 280                 285

His Asn Glu Thr Gln Arg Gln Asn Pro His Tyr Asp Ala Val Ile Met
    290                 295                 300

Thr Ala Pro Leu Cys Asn Val Lys Glu Met Lys Val Met Lys Gly Gly
305                 310                 315                 320

Gln Pro Phe Gln Leu Asn Phe Leu Pro Glu Ile Asn Tyr Met Pro Leu
                325                 330                 335

Ser Val Leu Ile Thr Thr Phe Thr Lys Glu Lys Val Lys Arg Pro Leu
            340                 345                 350

Glu Gly Phe Gly Val Leu Ile Pro Ser Lys Glu Gln Lys His Gly Phe
        355                 360                 365

Lys Thr Leu Gly Thr Leu Phe Ser Ser Met Met Phe Pro Asp Arg Ser
    370                 375                 380

Pro Ser Asp Val His Leu Tyr Thr Thr Phe Ile Gly Gly Ser Arg Asn
385                 390                 395                 400

Gln Glu Leu Ala Lys Ala Ser Thr Asp Glu Leu Lys Gln Val Val Thr
                405                 410                 415

Ser Asp Leu Gln Arg Leu Leu Gly Val Glu Gly Glu Pro Val Ser Val
            420                 425                 430

Asn His Tyr Tyr Trp Arg Lys Ala Phe Pro Leu Tyr Asp Ser Ser Tyr
        435                 440                 445

Asp Ser Val Met Glu Ala Ile Asp Lys Met Glu Asn Asp Leu Pro Gly
    450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
                485                 490                 495

Ser Cys Ser Asn Asp Lys Lys Pro Asn Asp Ser Leu
            500                 505
```

<210> SEQ ID NO 23
<211> LENGTH: 512
<212> TYPE: PRT
<213> ORGANISM: Arabidopsis lyrata subsp. lyrata

<400> SEQUENCE: 23

```
Met Glu Ser Gly Ala Val Gly Asp His Asp Thr Lys Phe Glu Ser Ile
1               5                   10                  15

Ser Gly Lys Arg Val Ala Val Val Gly Ala Gly Val Ser Gly Leu Ala
            20                  25                  30

Ala Ala Tyr Lys Leu Lys Ser Arg Gly Leu Asn Val Thr Val Phe Glu
        35                  40                  45

Ala Asp Glu Arg Ala Gly Gly Lys Leu Thr Ser Val Met Gln Asn Gly
    50                  55                  60

Leu Ile Trp Asp Gln Gly Ala Asn Thr Met Thr Glu Ala Glu Pro Glu
65                  70                  75                  80

Val Gly Ser Leu Leu Asp Asp Leu Gly Leu Arg Asp Lys Gln Gln Phe
                85                  90                  95

Pro Ile Ser Gln Lys Lys Arg Tyr Ile Val Arg Asn Gly Leu Pro Met
            100                 105                 110

Met Leu Pro Thr Asn Pro Ile Glu Leu Val Thr Ser Ser Val Leu Ser
        115                 120                 125

Thr Gln Ala Lys Ile Gln Ile Leu Leu Glu Pro Phe Leu Trp Lys Lys
    130                 135                 140

Asn Asp Ser Ser Ser Lys Val Ser Asp Ala Ser Ala Glu Glu Ser Val
145                 150                 155                 160

Ser Gly Phe Phe Gln Arg His Phe Gly Gln Glu Val Val Asp Tyr Leu
                165                 170                 175

Ile Asp Pro Phe Val Gly Gly Thr Ser Ala Ala Asp Pro Asp Ser Leu
            180                 185                 190

Ser Met Lys His Ser Phe Pro Asp Leu Trp Asn Val Glu Lys Ser Phe
        195                 200                 205

Gly Ser Ile Ile Val Gly Ala Ile Arg Thr Lys Leu Ala Ala Lys Gly
    210                 215                 220

Gly Lys Ser Gly Glu Ala Lys Ser Ser Pro Gly Thr Lys Arg Gly Ser
225                 230                 235                 240

Arg Arg Ser Phe Ser Phe Lys Gly Gly Met Gln Ile Leu Pro Asp Met
                245                 250                 255

Leu Cys Lys Ser Leu Ser His Asp Glu Ile Asn Leu Asp Ser Lys Val
            260                 265                 270

Leu Ser Leu Ser Tyr Asn Ser Gly Ser Arg Gln Glu Asn Trp Ser Leu
        275                 280                 285

Ser Cys Val Ser His Asn Glu Thr Gln Arg Gln Asn Leu His Tyr Asp
    290                 295                 300

Ala Val Val Met Thr Ala Pro Leu Cys Asn Val Lys Glu Met Lys Val
305                 310                 315                 320

Thr Lys Gly Gly Gln Pro Phe Leu Leu Asn Phe Leu Pro Glu Ile Asn
                325                 330                 335

Tyr Met Pro Leu Ser Val Leu Ile Thr Thr Phe Thr Lys Glu Lys Val
            340                 345                 350

Lys Arg Pro Leu Glu Gly Phe Gly Val Leu Ile Pro Ser Lys Glu Lys
        355                 360                 365

Lys His Gly Phe Lys Thr Leu Gly Thr Leu Phe Ser Ser Met Met Phe
```

```
    370                 375                 380

Pro Asp Arg Cys Pro Ser Asp Leu His Leu Tyr Thr Thr Phe Ile Gly
385                 390                 395                 400

Gly Ser Arg Asn Gln Glu Leu Ala Lys Ala Ser Thr Asp Glu Leu Lys
                405                 410                 415

Gln Val Val Thr Ser Asp Leu Gln Arg Leu Leu Gly Val Glu Gly Glu
            420                 425                 430

Pro Val Ser Val Asn His Tyr Tyr Trp Arg Lys Ala Phe Pro Leu Tyr
        435                 440                 445

Asp Ser Ser Tyr Gly Ser Val Met Glu Ala Ile Asp Lys Met Glu Lys
    450                 455                 460

Asp Leu Pro Gly Phe Phe Tyr Ala Gly Asn His Arg Gly Gly Leu Ser
465                 470                 475                 480

Ile Gly Lys Ser Ile Ala Ser Gly Cys Lys Ala Ala Asp Leu Val Ile
                485                 490                 495

Ser Tyr Leu Glu Ser Cys Ser Asn Asp Lys Lys Pro Asp Glu Ser Leu
            500                 505                 510


<210> SEQ ID NO 24
<211> LENGTH: 501
<212> TYPE: PRT
<213> ORGANISM: Arabidopsis thaliana

<400> SEQUENCE: 24

Met Ala Ser Gly Ala Val Ala Asp His Gln Ile Glu Ala Val Ser Gly
1               5                   10                  15

Lys Arg Val Ala Val Val Gly Ala Gly Val Ser Gly Leu Ala Ala Ala
            20                  25                  30

Tyr Lys Leu Lys Ser Arg Gly Leu Asn Val Thr Val Phe Glu Ala Asp
        35                  40                  45

Gly Arg Val Gly Gly Lys Leu Arg Ser Val Met Gln Asn Gly Leu Ile
    50                  55                  60

Trp Asp Glu Gly Ala Asn Thr Met Thr Glu Ala Glu Pro Glu Val Gly
65                  70                  75                  80

Ser Leu Leu Asp Asp Leu Gly Leu Arg Glu Lys Gln Gln Phe Pro Ile
                85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
        115                 120                 125

Ser Lys Phe Gln Ile Leu Leu Glu Pro Phe Leu Trp Lys Lys Lys Ser
    130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
            180                 185                 190

Ser Phe Pro Asp Leu Trp Asn Ser Phe Gly Ser Ile Ile Val Gly Ala
        195                 200                 205

Ile Arg Thr Lys Phe Ala Ala Lys Gly Gly Lys Ser Arg Asp Thr Lys
    210                 215                 220

Ser Ser Pro Gly Thr Lys Lys Gly Ser Arg Gly Ser Phe Ser Phe Lys
225                 230                 235                 240
```

-continued

```
Gly Gly Met Gln Ile Leu Pro Asp Thr Leu Cys Lys Ser Leu Ser His
                245                 250                 255

Asp Glu Ile Asn Leu Asp Ser Lys Val Leu Ser Leu Ser Tyr Asn Ser
            260                 265                 270

Gly Ser Arg Gln Glu Asn Trp Ser Leu Ser Cys Val Ser His Asn Glu
        275                 280                 285

Thr Gln Arg Gln Asn Pro His Tyr Asp Ala Ala Pro Leu Cys Asn Val
    290                 295                 300

Lys Glu Met Lys Val Met Lys Gly Gly Gln Pro Phe Gln Leu Asn Phe
305                 310                 315                 320

Leu Pro Glu Ile Asn Tyr Met Pro Leu Ser Val Leu Ile Thr Thr Phe
                325                 330                 335

Thr Lys Glu Lys Val Lys Arg Pro Leu Glu Gly Phe Gly Val Leu Ile
            340                 345                 350

Pro Ser Lys Glu Gln Lys His Gly Phe Lys Thr Leu Gly Thr Leu Phe
        355                 360                 365

Ser Ser Met Met Phe Pro Asp Arg Ser Pro Ser Asp Val His Leu Tyr
    370                 375                 380

Thr Thr Phe Ile Gly Gly Ser Arg Asn Gln Glu Leu Ala Lys Ala Ser
385                 390                 395                 400

Thr Asp Glu Leu Lys Gln Val Val Thr Ser Asp Leu Gln Arg Leu Leu
                405                 410                 415

Gly Val Glu Gly Glu Pro Val Ser Val Asn His Tyr Tyr Trp Arg Lys
            420                 425                 430

Ala Phe Pro Leu Tyr Asp Ser Ser Tyr Asp Ser Val Met Glu Ala Ile
        435                 440                 445

Asp Lys Met Glu Asn Asp Leu Pro Gly Phe Phe Tyr Ala Gly Asn His
    450                 455                 460

Arg Gly Gly Leu Ser Val Gly Lys Ser Ile Ala Ser Gly Cys Lys Ala
465                 470                 475                 480

Ala Asp Leu Val Ile Ser Tyr Leu Glu Ser Cys Ser Asn Asp Lys Lys
                485                 490                 495

Pro Asn Asp Ser Leu
            500
```

<210> SEQ ID NO 25
<211> LENGTH: 547
<212> TYPE: PRT
<213> ORGANISM: Arabidopsis thaliana

<400> SEQUENCE: 25

```
Met Gly Leu Ile Lys Asn Gly Thr Leu Tyr Cys Arg Phe Gly Ile Ser
1               5                   10                  15

Trp Asn Phe Ala Ala Val Phe Phe Ser Thr Tyr Phe Arg His Cys Phe
            20                  25                  30

Arg Leu Val Arg Asp Phe Asp Ser Glu Leu Leu Gln Ile Ala Met Ala
        35                  40                  45

Ser Gly Ala Val Ala Asp His Gln Ile Glu Ala Val Ser Gly Lys Arg
    50                  55                  60

Val Ala Val Val Gly Ala Gly Val Ser Gly Leu Ala Ala Ala Tyr Lys
65                  70                  75                  80

Leu Lys Ser Arg Gly Leu Asn Val Thr Val Phe Glu Ala Asp Gly Arg
                85                  90                  95

Val Gly Gly Lys Leu Arg Ser Val Met Gln Asn Gly Leu Ile Trp Asp
            100                 105                 110
```

-continued

```
Glu Gly Ala Asn Thr Met Thr Glu Ala Glu Pro Glu Val Gly Ser Leu
        115                 120                 125

Leu Asp Asp Leu Gly Leu Arg Glu Lys Gln Gln Phe Pro Ile Ser Gln
    130                 135                 140

Lys Lys Arg Tyr Ile Val Arg Asn Gly Val Pro Val Met Leu Pro Thr
145                 150                 155                 160

Asn Pro Ile Glu Leu Val Thr Ser Ser Val Leu Ser Thr Gln Ser Lys
                165                 170                 175

Phe Gln Ile Leu Leu Glu Pro Phe Leu Trp Lys Lys Lys Ser Ser Lys
            180                 185                 190

Val Ser Asp Ala Ser Ala Glu Glu Ser Val Ser Glu Phe Phe Gln Arg
        195                 200                 205

His Phe Gly Gln Glu Val Val Asp Tyr Leu Ile Asp Pro Phe Val Gly
    210                 215                 220

Gly Thr Ser Ala Ala Asp Pro Asp Ser Leu Ser Met Lys His Ser Phe
225                 230                 235                 240

Pro Asp Leu Trp Asn Ser Phe Gly Ser Ile Ile Val Gly Ala Ile Arg
                245                 250                 255

Thr Lys Phe Ala Ala Lys Gly Gly Lys Ser Arg Asp Thr Lys Ser Ser
            260                 265                 270

Pro Gly Thr Lys Lys Gly Ser Arg Gly Ser Phe Ser Phe Lys Gly Gly
        275                 280                 285

Met Gln Ile Leu Pro Asp Thr Leu Cys Lys Ser Leu Ser His Asp Glu
    290                 295                 300

Ile Asn Leu Asp Ser Lys Val Leu Ser Leu Ser Tyr Asn Ser Gly Ser
305                 310                 315                 320

Arg Gln Glu Asn Trp Ser Leu Ser Cys Val Ser His Asn Glu Thr Gln
                325                 330                 335

Arg Gln Asn Pro His Tyr Asp Ala Ala Pro Leu Cys Asn Val Lys Glu
            340                 345                 350

Met Lys Val Met Lys Gly Gly Gln Pro Phe Gln Leu Asn Phe Leu Pro
        355                 360                 365

Glu Ile Asn Tyr Met Pro Leu Ser Val Leu Ile Thr Thr Phe Thr Lys
    370                 375                 380

Glu Lys Val Lys Arg Pro Leu Glu Gly Phe Gly Val Leu Ile Pro Ser
385                 390                 395                 400

Lys Glu Gln Lys His Gly Phe Lys Thr Leu Gly Thr Leu Phe Ser Ser
                405                 410                 415

Met Met Phe Pro Asp Arg Ser Pro Ser Asp Val His Leu Tyr Thr Thr
            420                 425                 430

Phe Ile Gly Gly Ser Arg Asn Gln Glu Leu Ala Lys Ala Ser Thr Asp
        435                 440                 445

Glu Leu Lys Gln Val Val Thr Ser Asp Leu Gln Arg Leu Leu Gly Val
    450                 455                 460

Glu Gly Glu Pro Val Ser Val Asn His Tyr Tyr Trp Arg Lys Ala Phe
465                 470                 475                 480

Pro Leu Tyr Asp Ser Ser Tyr Asp Ser Val Met Glu Ala Ile Asp Lys
                485                 490                 495

Met Glu Asn Asp Leu Pro Gly Phe Phe Tyr Ala Gly Asn His Arg Gly
            500                 505                 510

Gly Leu Ser Val Gly Lys Ser Ile Ala Ser Gly Cys Lys Ala Ala Asp
        515                 520                 525
```

Leu Val Ile Ser Tyr Leu Glu Ser Cys Ser Asn Asp Lys Lys Pro Asn
    530                 535                 540

Asp Ser Leu
545

<210> SEQ ID NO 26
<211> LENGTH: 467
<212> TYPE: PRT
<213> ORGANISM: Ambrosia artemisiifolia

<400> SEQUENCE: 26

Gly Cys Ala Ala Ala Tyr Lys Leu Lys Leu His Gly Leu Asn Val Thr
1               5                   10                  15

Val Phe Glu Ala Asp Glu Arg Val Gly Gly Lys Leu Arg Ser Val Ser
            20                  25                  30

Gln Asp Gly Leu Ile Trp Asp Glu Gly Ala Asn Thr Met Thr Glu Ser
        35                  40                  45

Glu Ala Asp Val Ser Ser Leu Ile Asp Asp Leu Gly Leu Arg Asp Lys
    50                  55                  60

Gln Gln Phe Pro Ile Ser Gln His Lys Arg Tyr Ile Val Arg Asn Gly
65                  70                  75                  80

Lys Pro Val Leu Ile Pro Ser Asn Pro Ile Ala Leu Ile Arg Ser Ser
                85                  90                  95

Phe Leu Ser Thr Gln Ser Lys Val Gln Ile Leu Leu Glu Pro Phe Leu
            100                 105                 110

Trp Lys Lys Thr Lys Ser Ser Asp Glu Pro Glu Ser Val Gly Gly Phe
        115                 120                 125

Phe Gln Arg His Phe Gly Lys Glu Val Val Glu Tyr Leu Ile Asp Pro
    130                 135                 140

Val Val Ala Gly Thr Ser Gly Gly Asp Pro Glu Ser Leu Ser Met Arg
145                 150                 155                 160

His Ala Phe Pro Glu Leu Trp Asp Leu Glu Arg Arg Phe Gly Ser Ile
                165                 170                 175

Ile Ser Gly Ala Phe Gln Ser Met Val Ser Ser Arg Gly Gly Lys Arg
            180                 185                 190

Lys Pro Ser Gly Asn Ser Lys Arg Arg Arg Gly Ser Phe Ser Phe Phe
        195                 200                 205

Gly Gly Met Gln Thr Leu Thr Asp Ala Leu Ser Lys Glu Ile Gly Pro
    210                 215                 220

His Glu Ile Asn Leu Gln Ser Lys Val Leu Glu Met Ser Tyr Ser Cys
225                 230                 235                 240

Asp Asp Asn Ala Val Gly Asn Trp Ser Ile Tyr Cys Ala Pro Asp Gln
                245                 250                 255

Asn Lys Gln Phe Gln Gln Ser Phe Asp Ala Val Ile Met Thr Ala Pro
            260                 265                 270

Leu Asn Asn Leu Lys Glu Met Lys Ile Thr Lys Thr Gly Ser Pro Phe
        275                 280                 285

Leu Leu Asn Phe Ile Pro Glu Val Ser Tyr Leu Pro Ile Ser Val Ile
    290                 295                 300

Ile Ser Thr Phe Lys Lys Glu Asn Val Lys Gln Pro Leu Glu Gly Phe
305                 310                 315                 320

Gly Val Leu Val Pro Ala Lys Glu Gln Glu Asn Gly Leu Arg Thr Leu
                325                 330                 335

Gly Thr Leu Phe Ser Ser Met Met Phe Pro Asp Arg Ala Ser Glu Asp
            340                 345                 350

Val Tyr Leu Tyr Thr Thr Phe Val Gly Gly Ser Arg Asn Lys Glu Leu
355 360 365

Ala Lys Ala Ser Arg Asp Glu Leu Lys Gln Ile Val Thr Ser Asp Leu
370 375 380

Arg Gln Leu Leu Gly Thr Glu Gly Glu Pro Lys Phe Leu Thr His Tyr
385 390 395 400

Tyr Trp Ser Lys Ala Phe Pro Leu Tyr Gly Arg Asp Tyr Gly Ser Val
405 410 415

Ile Glu Ala Ile Glu Lys Met Glu Lys Glu Leu Pro Gly Tyr Phe Tyr
420 425 430

Ala Gly Asn His Lys Gly Gly Leu Ser Val Gly Lys Ala Ile Ser Ser
435 440 445

Gly Cys Lys Ala Ala Glu Ser Val Ile Ala Tyr Leu Asp Ser Tyr Ser
450 455 460

Asn Gln Lys
465

<210> SEQ ID NO 27
<211> LENGTH: 542
<212> TYPE: PRT
<213> ORGANISM: Setaria italica

<400> SEQUENCE: 27

Met Leu Ser Ser Ser Thr Thr Thr Ala Ser Pro Ala Ser Ser His Pro
1 5 10 15

Tyr Arg Pro Ala Tyr Pro Arg Ala Ser Leu Arg Pro Val Leu Ala Met
20 25 30

Ala Gly Ser Asp Asp Pro Arg Ala Ala Pro Ala Arg Ser Val Ala Val
35 40 45

Ile Gly Ala Gly Val Ser Gly Leu Ala Ala Ala Tyr Arg Leu Arg Lys
50 55 60

Ser Gly Val Asn Val Thr Val Phe Glu Ala Ala Asp Arg Ala Gly Gly
65 70 75 80

Lys Ile Arg Thr Asn Ser Glu Ala Gly Phe Leu Trp Asp Glu Gly Ala
85 90 95

Asn Thr Met Thr Glu Gly Glu Leu Glu Val Ser Arg Leu Ile Asp Asp
100 105 110

Leu Gly Leu Gln Asp Arg Gln Gln Tyr Pro Asn Ser Gln His Lys Arg
115 120 125

Tyr Ile Val Lys Asp Gly Ala Pro Ala Leu Ile Pro Ala Asp Pro Ile
130 135 140

Ser Leu Met Lys Ser Ser Val Leu Ser Thr Lys Ser Lys Leu Ala Leu
145 150 155 160

Phe Leu Glu Pro Phe Leu Tyr Lys Lys Ser Asn Thr Arg Asn Ser Gly
165 170 175

Lys Val Ser Asp Glu His Leu Ser Glu Ser Val Gly Ser Phe Phe Glu
180 185 190

Arg His Phe Gly Arg Glu Val Val Asp Tyr Leu Ile Asp Pro Phe Val
195 200 205

Ala Gly Thr Ser Ala Gly Asp Pro Glu Ser Leu Ser Ile Arg His Ala
210 215 220

Phe Pro Ala Leu Trp Asn Leu Glu Arg Lys Tyr His Ser Ile Ile Val
225 230 235 240

Gly Ala Ile Leu Ser Lys Leu Thr Ala Lys Gly Asp Pro Val Lys Thr

```
                245                 250                 255

Gly Ser Asp Leu Ser Gly Lys Arg Arg Asn Arg Arg Ala Ser Phe Ser
            260                 265                 270

Phe His Gly Gly Met Gln Ser Leu Ile Asn Ala Leu His Asn Glu Val
        275                 280                 285

Gly Asp Asp Asn Val Lys Leu Gly Thr Glu Val Leu Ser Leu Ala Cys
    290                 295                 300

Thr Phe Asp Gly Leu Pro Ser Thr Gly Gly Trp Ser Ile Ser Val Asp
305                 310                 315                 320

Ser Lys Asp Ala Gly Ser Lys Asp Leu Ala Lys Asn Gln Thr Phe Asp
                325                 330                 335

Ala Val Ile Met Thr Ala Pro Leu Ser Asn Val Gln Arg Met Lys Phe
            340                 345                 350

Arg Lys Gly Gly Ala Pro Phe Val Leu Asp Phe Leu Pro Lys Val Asn
        355                 360                 365

Tyr Leu Pro Leu Ser Leu Met Val Thr Ala Phe Lys Lys Glu Asp Val
    370                 375                 380

Lys Lys Pro Leu Glu Gly Phe Gly Val Leu Ile Pro Tyr Lys Glu Gln
385                 390                 395                 400

Gln Lys His Gly Leu Lys Thr Leu Gly Thr Leu Phe Ser Ser Met Met
                405                 410                 415

Phe Pro Asp Arg Ala Pro Asp Asp Gln Tyr Leu Tyr Thr Thr Phe Val
            420                 425                 430

Gly Gly Ser His Asn Arg Asp Leu Ala Gly Ala Pro Thr Ser Ile Leu
        435                 440                 445

Lys Gln Leu Val Thr Ser Asp Leu Lys Lys Leu Leu Gly Val Glu Gly
    450                 455                 460

Gln Pro Thr Phe Val Lys His Ile Tyr Trp Arg Asn Ala Phe Pro Leu
465                 470                 475                 480

Tyr Gly Arg Asp Tyr Gly Ser Val Leu Asp Ala Ile Glu Lys Met Glu
                485                 490                 495

Lys Asn Leu Pro Gly Phe Phe Tyr Ala Gly Asn Asn Lys Asp Gly Leu
            500                 505                 510

Ala Val Gly Asn Val Ile Ala Ser Gly Ser Lys Ala Ala Glu Leu Ala
        515                 520                 525

Ile Ser Tyr Leu Glu Ser Gln Thr Lys His Asn Asn Ser His
    530                 535                 540


<210> SEQ ID NO 28
<211> LENGTH: 544
<212> TYPE: PRT
<213> ORGANISM: Sorghum bicolor

<400> SEQUENCE: 28

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Arg Lys Ser Gly Val Asn Val Thr Val Phe Glu Ala Ala Asp Arg Ala
65                  70                  75                  80
```

-continued

```
Gly Gly Lys Ile Arg Thr Asn Ser Glu Gly Gly Phe Leu Trp Asp Glu
                85                  90                  95

Gly Ala Asn Thr Met Thr Glu Gly Glu Leu Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Pro Gly Lys Val Ser Asp Glu His Leu Ser Glu Ser Val Gly Ser Phe
            180                 185                 190

Phe Glu Arg His Phe Gly Arg Glu Val Val Asp Tyr Leu Ile Asp Pro
        195                 200                 205

Phe Val Ala Gly Thr Ser Ala Gly Asp Pro Glu Ser Leu Ser Ile Cys
    210                 215                 220

His Ala Phe Pro Ala Leu Trp Asn Leu Glu Arg Lys Tyr Gly Ser Val
225                 230                 235                 240

Val Val Gly Ala Ile Leu Ser Lys Leu Thr Ala Lys Gly Asp Pro Val
                245                 250                 255

Lys Thr Arg Arg Asp Ser Ser Ala Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Leu Asp Gly Ala Pro Ala Pro Gly Gly Trp Ser Ile Ser
305                 310                 315                 320

Asp Asp Ser Lys Asp Ala Ser Gly Lys Asp Leu Ala Lys Asn Gln Thr
                325                 330                 335

Phe Asp Ala Val Ile Met Thr Ala Pro Leu Ser Asn Val Gln Arg Met
            340                 345                 350

Lys Phe Thr Lys Gly Gly Ala Pro Phe Val Leu Asp Phe Leu Pro Lys
        355                 360                 365

Val Asp Tyr Leu Pro Leu Ser Leu Met Val Thr Ala Phe Lys Lys Glu
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
            420                 425                 430

Phe Val Gly Gly Ser His Asn Arg Asp Leu Ala Gly Ala Pro Thr Ser
        435                 440                 445

Ile Leu Lys Gln Leu Val Thr Ser Asp Leu Lys Lys Leu Leu Gly Val
    450                 455                 460

Gln Gly Gln Pro Thr Phe Val Lys His Ile Tyr Trp Gly Asn Ala Phe
465                 470                 475                 480

Pro Leu Tyr Gly His Asp Tyr Asn Ser Val Leu Glu Ala Ile Glu Lys
                485                 490                 495

Met Glu Lys Asn Leu Pro Gly Phe Phe Tyr Ala Gly Asn Asn Lys Asp
```

```
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Leu His
    530                 535                 540


<210> SEQ ID NO 29
<211> LENGTH: 477
<212> TYPE: PRT
<213> ORGANISM: Arabidopsis thaliana

<400> SEQUENCE: 29

Met Ala Ser Gly Ala Val Ala Asp His Gln Ile Glu Ala Val Ser Gly
1               5                   10                  15

Lys Arg Val Ala Val Val Gly Ala Gly Val Ser Gly Leu Ala Ala Ala
            20                  25                  30

Tyr Lys Leu Lys Ser Arg Gly Leu Asn Val Thr Val Phe Glu Ala Asp
        35                  40                  45

Gly Arg Val Gly Gly Lys Leu Arg Ser Val Met Gln Asn Gly Leu Ile
    50                  55                  60

Trp Asp Glu Gly Ala Asn Thr Met Thr Glu Ala Glu Pro Glu Val Gly
65                  70                  75                  80

Ser Leu Leu Asp Asp Leu Gly Leu Arg Glu Lys Gln Gln Phe Pro Ile
                85                  90                  95

Ser Gln Lys Lys Arg Tyr Ile Val Arg Asn Gly Val Pro Val Met Lys
            100                 105                 110

Lys Ser Ser Lys Val Ser Asp Ala Ser Ala Glu Glu Ser Val Ser Glu
        115                 120                 125

Phe Phe Gln Arg His Phe Gly Gln Glu Val Val Asp Tyr Leu Ile Asp
    130                 135                 140

Pro Phe Val Gly Gly Thr Ser Ala Ala Asp Pro Asp Ser Leu Ser Met
145                 150                 155                 160

Lys His Ser Phe Pro Asp Leu Trp Asn Val Glu Lys Ser Phe Gly Ser
                165                 170                 175

Ile Ile Val Gly Ala Ile Arg Thr Lys Phe Ala Ala Lys Gly Gly Lys
            180                 185                 190

Ser Arg Asp Thr Lys Ser Ser Pro Gly Thr Lys Lys Gly Ser Arg Gly
        195                 200                 205

Ser Phe Ser Phe Lys Gly Gly Met Gln Ile Leu Pro Asp Thr Leu Cys
    210                 215                 220

Lys Ser Leu Ser His Asp Glu Ile Asn Leu Asp Ser Lys Val Leu Ser
225                 230                 235                 240

Leu Ser Tyr Asn Ser Gly Ser Arg Gln Glu Asn Trp Ser Leu Ser Cys
                245                 250                 255

Val Ser His Asn Glu Thr Gln Arg Gln Asn Pro His Tyr Asp Ala Val
            260                 265                 270

Ile Met Thr Ala Pro Leu Cys Asn Val Lys Glu Met Lys Val Met Lys
        275                 280                 285

Gly Gly Gln Pro Phe Gln Leu Asn Phe Leu Pro Glu Ile Asn Tyr Met
    290                 295                 300

Pro Leu Ser Val Leu Ile Thr Thr Phe Thr Lys Glu Lys Val Lys Arg
305                 310                 315                 320

Pro Leu Glu Gly Phe Gly Val Leu Ile Pro Ser Lys Glu Gln Lys His
                325                 330                 335
```

```
Gly Phe Lys Thr Leu Gly Thr Leu Phe Ser Ser Met Met Phe Pro Asp
            340                 345                 350

Arg Ser Pro Ser Asp Val His Leu Tyr Thr Thr Phe Ile Gly Gly Ser
        355                 360                 365

Arg Asn Gln Glu Leu Ala Lys Ala Ser Thr Asp Glu Leu Lys Gln Val
    370                 375                 380

Val Thr Ser Asp Leu Gln Arg Leu Leu Gly Val Glu Gly Glu Pro Val
385                 390                 395                 400

Ser Val Asn His Tyr Tyr Trp Arg Lys Ala Phe Pro Leu Tyr Asp Ser
                405                 410                 415

Ser Tyr Asp Ser Val Met Glu Ala Ile Asp Lys Met Glu Asn Asp Leu
            420                 425                 430

Pro Gly Phe Phe Tyr Ala Gly Asn His Arg Gly Gly Leu Ser Val Gly
        435                 440                 445

Lys Ser Ile Ala Ser Gly Cys Lys Ala Ala Asp Leu Val Ile Ser Tyr
    450                 455                 460

Leu Glu Ser Cys Ser Asn Asp Lys Lys Pro Asn Asp Ser
465                 470                 475


<210> SEQ ID NO 30
<211> LENGTH: 544
<212> TYPE: PRT
<213> ORGANISM: Zea mays

<400> SEQUENCE: 30

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Ala Tyr Arg Leu
    50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240
```

```
Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
        355                 360                 365

Met Asp Tyr Leu Pro Leu Ser Leu Met Val Thr Ala Phe Lys Lys Asp
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
            420                 425                 430

Phe Val Gly Gly Ser His Asn Arg Asp Leu Ala Gly Ala Pro Thr Ser
        435                 440                 445

Ile Leu Lys Gln Leu Val Thr Ser Asp Leu Lys Lys Leu Leu Gly Val
    450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Asn Lys Asp
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Ser His
    530                 535                 540


<210> SEQ ID NO 31
<211> LENGTH: 544
<212> TYPE: PRT
<213> ORGANISM: Zea mays

<400> SEQUENCE: 31

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Ala Tyr Arg Leu
    50                  55                  60

Arg Gln Ser Gly Val Asn Val Thr Val Phe Glu Ala Ala Asp Arg Ala
```

-continued

```
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
        355                 360                 365

Met Asp Tyr Leu Pro Leu Ser Leu Met Val Thr Ala Phe Lys Lys Asp
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
            420                 425                 430

Phe Val Gly Gly Ser His Asn Arg Asp Leu Ala Gly Ala Pro Thr Ser
        435                 440                 445

Ile Leu Lys Gln Leu Val Thr Ser Asp Leu Lys Lys Leu Leu Gly Val
    450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495
```

```
Met Glu Lys Asn Leu Pro Gly Phe Phe Tyr Ala Gly Asn Ser Lys Asp
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Ser His
    530                 535                 540


<210> SEQ ID NO 32
<211> LENGTH: 509
<212> TYPE: PRT
<213> ORGANISM: Lemna paucicostata

<400> SEQUENCE: 32

Met Glu Ala Asp Ala Gly Lys Gly Ser Ala Gly Gly Ala Gln Ile Leu
1               5                   10                  15

Ser His Asp Ser Val Arg Ser Val Ala Val Ile Gly Gly Gly Ile Ser
            20                  25                  30

Gly Leu Ala Ala Ala Tyr Lys Leu Lys Ser Asn Gly Phe Arg Ala Val
        35                  40                  45

Val Phe Glu Ala Glu Gly Lys Ala Gly Gly Lys Ile Arg Ser Gly Ser
    50                  55                  60

Gln Glu Gly Leu Ile Trp Asp Glu Gly Ala Asn Thr Met Ala Glu Ser
65                  70                  75                  80

Val Glu Ala Gly Glu Leu Phe Asp Asp Val Gly Ile Arg Glu Lys Gln
                85                  90                  95

Gln Tyr Pro Leu Ser Gln Ser Lys Arg Tyr Val Val Arg Asn Gly Val
            100                 105                 110

Pro Val Met Ile Pro Ser Asp Pro Ile Ser Leu Ile Lys Ser Asn Leu
        115                 120                 125

Leu Ser Thr Lys Ala Lys Phe Arg Met Phe Leu Glu Pro Phe Phe Ser
    130                 135                 140

Tyr Arg Arg Val Lys Pro Ser Lys Val Ser Asp Glu Lys Leu Ser Glu
145                 150                 155                 160

Ser Val Gly Glu Phe Phe Gln Arg His Phe Gly Lys Glu Val Val Asp
                165                 170                 175

Tyr Leu Ile Asp Pro Phe Val Ala Gly Thr Ser Gly Gly Asp Pro Glu
            180                 185                 190

Ser Leu Ser Met Pro His Ala Phe Pro Glu Ile Trp Asn Leu Gln Glu
        195                 200                 205

Lys Tyr Gly Ser Val Ile Leu Gly Ala Ile Gln Ser Lys Phe Leu Asp
    210                 215                 220

Lys Arg Lys Gly Asp Arg Thr Glu Arg Ala Thr Val Lys Lys Arg Arg
225                 230                 235                 240

Pro Arg Gly Ser Phe Ser Phe His Gly Gly Met Gln Thr Leu Ile Asp
                245                 250                 255

Val Leu Cys Ala Lys Val Gly Glu Glu Asn Leu Glu Leu Asn Ser Lys
            260                 265                 270

Val Leu Ser Leu Ala Cys Gly His Glu Gly Asp Pro Ser Phe Asp Ser
        275                 280                 285

Trp Ser Ile Ser Val Ala Ser Asn Asn Gly Ser Gln Lys Asp Leu Leu
    290                 295                 300

Thr Lys Ser Phe Phe Asp Ala Val Ile Met Thr Ala Pro Leu Gly Asn
305                 310                 315                 320

Val Glu Asp Met Lys Phe Thr Lys Lys Gly Ser Pro Phe Ala Leu Asp
```

```
                325                 330                 335

Phe Leu Pro Gln Val Thr Tyr Leu Pro Leu Ser Val Leu Ile Thr Ser
            340                 345                 350

Phe Lys Arg Glu Asn Val Lys Arg Pro Leu Glu Gly Phe Gly Val Leu
        355                 360                 365

Val Pro Ser Lys Glu Gln Glu Gly Gly Phe Lys Thr Leu Gly Thr Leu
    370                 375                 380

Phe Ser Ser Ala Met Phe Pro Asp Arg Ala Pro Ser Asp Gln Tyr Leu
385                 390                 395                 400

Tyr Thr Thr Phe Ile Gly Gly Ser Arg Asn Arg Asp Leu Ala Gly Ala
                405                 410                 415

Ser Leu Glu Glu Leu Lys Gln Ile Val Leu Ser Asp Leu His Lys Leu
            420                 425                 430

Leu Gly Val Val Gly Glu Pro Ser Phe Ile Lys His Val Tyr Trp Ser
        435                 440                 445

Lys Ala Phe Pro Leu Tyr Gly Arg Asp Tyr Gly Leu Val Met Glu Ala
    450                 455                 460

Ile Asp Arg Met Glu Arg Asn Leu Pro Gly Phe Tyr Tyr Ala Gly Asn
465                 470                 475                 480

His Arg Asp Gly Leu Ser Val Gly Lys Ala Ile Ala Ser Gly Phe Arg
                485                 490                 495

Ala Ala Asp Leu Ala Ile Ser Tyr Ile Asn Ser Ser Val
            500                 505


<210> SEQ ID NO 33
<211> LENGTH: 544
<212> TYPE: PRT
<213> ORGANISM: Lemna paucicostata

<400> SEQUENCE: 33

Met Ala Ser Ser Ala Ala Ile Ser Pro Leu His Phe Ser Pro Ala Pro
1               5                   10                  15

Pro Arg Arg Arg Glu Leu Ser His Arg Cys Arg Val Arg Cys Ser Ile
            20                  25                  30

Ala Gly Lys Pro Pro Ala Thr Ala Ala Asn Asp Ser Ser Ala Thr Ser
        35                  40                  45

Val Thr Gly Gly Glu Pro Val Arg Arg Leu Arg Ala Asp Cys Val Ile
    50                  55                  60

Val Gly Ala Gly Ile Ser Gly Leu Cys Thr Ala Gln Ala Leu Thr Val
65                  70                  75                  80

Arg Pro Ala Ala Gly Arg Ser Ser Ala Pro Asp Val Leu Val Thr Glu
                85                  90                  95

Ala Arg Asp Arg Val Gly Gly Asn Ile Thr Thr Val Glu Arg Asp Gly
            100                 105                 110

Tyr Leu Trp Glu Glu Gly Pro Asn Ser Phe Gln Pro Ser Asp Ala Val
        115                 120                 125

Leu Thr Met Ala Val Asp Ser Gly Leu Lys Asp Asp Leu Val Leu Gly
    130                 135                 140

Asp Pro Asp Ala Pro Arg Phe Val Leu Trp Lys Gly Lys Leu Arg Pro
145                 150                 155                 160

Val Pro Ala Lys Pro Thr Asp Leu Pro Phe Phe Asp Leu Met Ser Ile
                165                 170                 175

Gly Gly Lys Ile Arg Ala Gly Phe Gly Ala Leu Gly Leu Arg Pro Ser
            180                 185                 190
```

Pro Pro Ser Arg Glu Glu Ser Val Glu Glu Phe Val Arg Arg Asn Leu
195 200 205

Gly Asp Glu Val Phe Glu Arg Leu Ile Glu Pro Phe Cys Ser Gly Val
210 215 220

Tyr Ala Gly Asp Pro Ser Lys Leu Ser Met Lys Ala Ala Phe Gly Lys
225 230 235 240

Val Trp Lys Leu Glu Gln Thr Gly Gly Ser Ile Ile Gly Gly Thr Phe
245 250 255

Lys Ala Ile Gln Glu Arg Ser Lys Asn Pro Lys Pro Pro Arg Asp Pro
260 265 270

Arg Leu Pro Thr Pro Lys Gly Gln Thr Val Gly Ser Phe Ser Lys Gly
275 280 285

Leu Ala Met Leu Pro Asn Ala Ile Ala Ser Arg Leu Gly Asp Lys Val
290 295 300

Lys Leu Ser Trp Lys Leu Ser Gly Ile Lys Lys Ser Glu Asn Gly Gly
305 310 315 320

Tyr Ala Leu Thr Tyr Asp Thr Pro Glu Gly Leu Thr Ser Val Asn Ala
325 330 335

Asp Cys Val Val Leu Thr Ile Pro Ser Tyr Val Ala Gly Asp Leu Leu
340 345 350

Arg Pro Leu Ser Asn Glu Ala Ala Asp Ala Leu Thr Lys Phe Tyr Tyr
355 360 365

Pro Pro Val Ala Ala Val Thr Ile Ser Tyr Pro Ser Asp Ser Ile Arg
370 375 380

Ser Glu Cys Leu Ile Asp Gly Gln Leu Lys Gly Phe Gly Gln Leu His
385 390 395 400

Pro Arg Ser Gln Gly Val Glu Thr Leu Gly Thr Ile Tyr Ser Ser Ser
405 410 415

Leu Phe Pro Asn Arg Ala Pro Pro Gly Arg Val Leu Leu Leu Asn Tyr
420 425 430

Ile Gly Gly Ser Thr Asn Thr Ala Ile Val Ser Lys Thr Glu Ser Glu
435 440 445

Leu Val Glu Ala Val Asp Arg Asp Leu Arg Lys Met Leu Val Lys Val
450 455 460

Asn Ala Ala Asp Pro Ala Val Gln Gly Val Arg Val Trp Pro Arg Ala
465 470 475 480

Ile Pro Gln Phe Leu Ile Gly His Thr Asp Leu Leu Asp Ala Ala Thr
485 490 495

Arg Ser Leu Asp Arg Ala Gly Tyr Gly Gly Leu Ile Leu Gly Gly Asn
500 505 510

Tyr Val Ala Gly Val Ala Leu Gly Arg Cys Ile Glu Gly Ala Tyr Asp
515 520 525

Thr Ala Ala Lys Val Asn Ser Phe Leu Ser Lys Tyr Ala Arg Ser Phe
530 535 540

<210> SEQ ID NO 34
<211> LENGTH: 482
<212> TYPE: PRT
<213> ORGANISM: Populus trichocarpa

<400> SEQUENCE: 34

Met Thr Ala Ala Ala Lys Asp Asp Asp Phe Gly Ser Lys Gln Ser Lys
1 5 10 15

Asn Val Ala Val Ile Gly Ala Gly Val Ser Gly Leu Ala Ala Ala Tyr
20 25 30

```
Lys Leu Lys Ser Asn Gly Val Lys Val Thr Val Phe Glu Ala Glu Gly
        35                  40                  45

Arg Ala Gly Gly Lys Leu Arg Ser Val Ser His His Asp Leu Val Trp
    50                  55                  60

Asp Glu Gly Ala Asn Thr Met Thr Glu Ser Glu Val Glu Val Lys Ser
65                  70                  75                  80

Leu Leu Asp Asp Leu Gly Leu Arg Glu Lys Gln Gln Phe Pro Ile Ala
                85                  90                  95

Gln Asn Lys Arg Tyr Ile Val Arg Asn Gly Met Pro Val Leu Ile Pro
            100                 105                 110

Thr Asn Pro Val Ala Leu Ile Lys Ser Asn Phe Leu Ser Ala Gln Ser
        115                 120                 125

Lys Leu Gln Ile Ile Leu Glu Pro Phe Leu Trp Lys Lys Asn Glu Ser
    130                 135                 140

Ser Lys Val Ser Asp Ala Asp Ile Gln Glu Ser Val Gly Glu Phe Phe
145                 150                 155                 160

Gln Arg His Phe Gly Lys Glu Val Val Asp Tyr Leu Ile Asp Pro Phe
                165                 170                 175

Val Ala Gly Thr Ser Ala Gly Asp Pro Glu Ser Leu Ser Ala Arg His
            180                 185                 190

Asn Phe Pro Asp Leu Trp Asn Leu Glu Lys Arg Phe Gly Ser Ile Ile
        195                 200                 205

Ala Gly Ala Val Lys Ala Lys Leu Ser Ala Lys Lys Glu Lys Asn Gly
    210                 215                 220

Glu Lys Lys Gly Ser Ser Glu Lys Lys Lys Arg Gln His Gly Ser Phe
225                 230                 235                 240

Ser Phe Leu Gly Gly Met Gln Thr Leu Thr Asp Thr Leu Cys Thr Glu
                245                 250                 255

Leu Gly Lys Asp Gly Val Lys Leu Glu Ser Lys Val Leu Ser Leu Ser
            260                 265                 270

Tyr Ser Tyr Asp Gly Lys Ser Thr Phe Glu Asn Trp Ser Val Ser Tyr
        275                 280                 285

Ala Ser Lys Gly Gly Lys His Ala Gln Ala Ser Ser Tyr Asp Ala Val
    290                 295                 300

Ile Met Thr Ala Pro Leu Cys Asn Val Lys Glu Ile Asn Ile Asn Lys
305                 310                 315                 320

Gly Arg Asn Arg Phe Ser Leu Asp Phe Leu Pro Gln Met Ser Tyr Met
                325                 330                 335

Pro Leu Ser Val Ile Ile Thr Thr Phe Lys Lys Glu Asp Val Lys Arg
            340                 345                 350

Pro Leu Glu Gly Phe Gly Val Leu Val Pro Ser Lys Glu Gln Gln Asn
        355                 360                 365

Gly Leu Lys Thr Leu Gly Thr Leu Phe Ser Ser Met Met Phe Pro Asp
    370                 375                 380

Arg Ala Pro Lys Asp Ser Tyr Leu Tyr Thr Thr Phe Val Ala Ser Thr
385                 390                 395                 400

Val Leu Asp Cys Ser His Tyr Tyr Trp Ser Lys Ala Phe Pro Leu Tyr
                405                 410                 415

Gly Lys Asn Tyr Asp Leu Val Leu Glu Gly Ile Glu Arg Met Glu Lys
            420                 425                 430

Asn Leu Pro Gly Phe Phe Tyr Ala Gly Asn His Arg Gly Gly Leu Ser
        435                 440                 445
```

```
Val Gly Lys Ala Ile Ala Ser Gly Cys Lys Ala Ala Asp Leu Val Ile
    450                 455                 460

Ser His Leu Asn Ser Ser Ala Asp Asp Lys Met Leu Lys Lys Gly Ser
465                 470                 475                 480

Gln Ser


<210> SEQ ID NO 35
<211> LENGTH: 569
<212> TYPE: PRT
<213> ORGANISM: Capsella rubella

<400> SEQUENCE: 35

Met His Asp Ala Gly Asp Ser His Asp Pro Phe Glu Ile His Lys His
1               5                   10                  15

Val Asp Val Glu Leu Lys Ser Gly Leu Asp Ala Lys Thr Leu Asn Lys
            20                  25                  30

Gly Pro Leu Asp Lys Arg Leu Lys Ile Ile Gly Pro Glu Glu Leu Lys
        35                  40                  45

Thr Arg Phe Asp Ala Glu Leu Ser Trp Leu Leu Leu Ile Thr Met Ala
    50                  55                  60

Ser Ala Lys Val Ala Asp Asn Asp Thr Lys Phe Glu Ala Val Ser Gly
65                  70                  75                  80

Arg Arg Val Ala Val Val Gly Gly Gly Val Ser Gly Leu Ala Ala Ala
                85                  90                  95

Tyr Lys Leu Lys Ser Lys Gly Leu Asn Val Thr Val Phe Glu Ala Asp
            100                 105                 110

Gly Arg Ala Gly Gly Lys Leu Arg Ser Val Met His Asn Gly Leu Ile
        115                 120                 125

Trp Asp Glu Gly Ala Asn Thr Met Thr Glu Ala Glu Pro Glu Val Gly
    130                 135                 140

Thr Leu Leu Asp Asp Leu Gly Leu Arg Glu Lys Gln Gln Phe Pro Ile
145                 150                 155                 160

Ser Gln Lys Lys Arg Tyr Ile Val Arg Asn Gly Val Pro Val Met Ile
                165                 170                 175

Pro Thr Asn Pro Ile Asp Leu Val Thr Ser Thr Val Leu Ser Thr Gln
            180                 185                 190

Ser Lys Phe Glu Ile Leu Leu Glu Pro Phe Leu Trp Lys Lys Asn Asp
        195                 200                 205

Leu Ser Ser Lys Val Ser Asp Ala Ser Ala Ala Glu Ser Val Ser Gly
    210                 215                 220

Phe Phe Arg Arg His Phe Gly Gln Glu Val Val Asp Tyr Leu Ile Asp
225                 230                 235                 240

Pro Phe Val Gly Gly Thr Ser Ala Ala Asp Pro Asp Ser Leu Ser Ile
                245                 250                 255

Val Phe Val Tyr Cys Leu Ile Leu Leu Ile Leu Ile Ser Leu Pro Thr
            260                 265                 270

Ile His Asp Gln Met Lys His Ser Phe Pro Asp Leu Trp Asn Val Glu
        275                 280                 285

Lys Ser Phe Gly Ser Val Ile Val Gly Ala Ile Arg Thr Lys Leu Ala
    290                 295                 300

Ala Lys Gly Val Gln Ile Leu Pro Asp Met Leu Cys Lys Gly Leu Ser
305                 310                 315                 320

His Asp Glu Leu Asn Leu Asp Ser Lys Val Leu Ser Leu Ser Tyr Asn
                325                 330                 335
```

```
Ser Gly Ser Arg Gln Glu Asn Trp Ser Leu Ser Cys Val Ser His Asn
            340                 345                 350

Glu Met Gln Arg Gln Asn Leu His Tyr Asp Ala Val Ile Met Thr Ala
        355                 360                 365

Pro Leu Cys Asn Val Lys Glu Met Asp Val Met Lys Gly Gly Gln Pro
    370                 375                 380

Phe Gln Leu Asn Phe Leu Pro Glu Ile Lys Tyr Met Pro Leu Ser Val
385                 390                 395                 400

Ile Ile Thr Thr Phe Thr Lys Glu Lys Val Lys Arg Pro Leu Glu Gly
                405                 410                 415

Phe Gly Val Leu Ile Pro Ser Lys Glu Gln Lys His Gly Phe Lys Thr
            420                 425                 430

Leu Gly Thr Leu Phe Ser Ser Met Met Phe Pro Asp Arg Cys Pro Ser
        435                 440                 445

Asp Leu His Leu Tyr Thr Thr Phe Ile Gly Gly Ser Arg Asn Gln Glu
    450                 455                 460

Leu Ala Lys Ala Ser Thr Asp Glu Leu Lys Gln Val Val Thr Ser Asp
465                 470                 475                 480

Leu Gln Arg Leu Leu Gly Val Glu Gly Glu Pro Glu Phe Val Asn His
                485                 490                 495

Tyr Tyr Trp Arg Lys Ala Phe Pro Leu Tyr Asp Ser Ser Tyr Asp Ser
            500                 505                 510

Val Met Glu Ala Ile Asp Lys Met Glu Lys Asp Leu Pro Gly Phe Phe
        515                 520                 525

Tyr Ala Gly Asn His Arg Gly Gly Leu Ser Val Gly Lys Ser Ile Ala
    530                 535                 540

Ser Gly Cys Lys Ala Ala Asp Leu Val Ile Ser Tyr Leu Glu Ser Cys
545                 550                 555                 560

Ser Asn Asp Lys Lys Pro Glu Asp Ser
                565


<210> SEQ ID NO 36
<211> LENGTH: 544
<212> TYPE: PRT
<213> ORGANISM: Brachypodium distachyon

<400> SEQUENCE: 36

Met Leu Thr Ser Ala Thr Ala Ser Pro Ser Ala Ser Thr Arg Phe Ser
1               5                   10                  15

Ser Thr Cys Arg Pro Cys Arg Ser Asp Ser Val Pro Ala Arg Arg Pro
            20                  25                  30

Arg Pro Val Leu Ala Met Ala Ala Ser Asp Asp Pro Arg Ala Ala Pro
        35                  40                  45

Ala Arg Ser Val Ala Val Val Gly Ala Gly Val Ser Gly Leu Val Ala
    50                  55                  60

Ala His Arg Leu Arg Lys Ser Gly Val Arg Val Thr Val Phe Glu Ala
65                  70                  75                  80

Asp Asp Arg Ala Gly Gly Lys Ile Arg Thr Asn Ser Asp Ser Gly Phe
                85                  90                  95

Leu Trp Asp Glu Gly Ala Asn Thr Met Thr Glu Ser Ala Leu Glu Ala
            100                 105                 110

Ser Arg Leu Ile Asp Asp Leu Gly Leu Gln Asp Lys Gln Gln Tyr Pro
        115                 120                 125

Asn Ser Gln His Lys Arg Tyr Thr Val Lys Asp Gly Ala Pro Thr Leu
    130                 135                 140
```

```
Ile Pro Ser Asp Pro Ile Ala Leu Met Lys Ser Thr Val Leu Ser Thr
145                 150                 155                 160

Lys Ser Lys Phe Lys Leu Phe Leu Glu Pro Phe Leu Tyr Glu Lys Ser
                165                 170                 175

His Thr Arg Asn Ser Gln Lys Val Ser Asp Asn His Leu Ser Glu Ser
            180                 185                 190

Val Gly Ser Phe Phe Glu Arg His Phe Gly Lys Glu Val Val Asp Tyr
        195                 200                 205

Leu Ile Asp Pro Phe Val Ala Gly Thr Ser Ala Gly Asp Pro Glu Ser
    210                 215                 220

Leu Ser Ile Arg His Ala Phe Pro Gly Leu Trp Asp Leu Glu Lys Lys
225                 230                 235                 240

Tyr Gly Ser Ile Ile Val Gly Ala Ile Leu Ser Lys Leu Thr Ala Lys
                245                 250                 255

Gly Asp Ser Thr Lys Lys Ala Asp Thr Ser Ser Gly Lys Gly Arg Asn
            260                 265                 270

Lys Gln Ala Ser Phe Ser Phe His Gly Gly Met Gln Thr Leu Val Glu
        275                 280                 285

Gly Leu His Lys Asp Val Gly Asp Gly Asn Val Lys Leu Gly Thr Gln
    290                 295                 300

Val Leu Ser Leu Ala Cys Ser Cys Asp Arg Leu Ser Ala Ser Asp Gly
305                 310                 315                 320

Trp Ser Ile Ser Val Asn Ser Lys Asp Ala Ser Ser Lys Leu Ala Ala
                325                 330                 335

Lys Asn Gln Leu Phe Asp Ala Val Ile Met Thr Ala Pro Leu Ser Asn
            340                 345                 350

Val Gln Arg Met Lys Phe Thr Lys Gly Gly Val Pro Phe Val Leu Asp
        355                 360                 365

Phe Leu Pro Lys Val Asp Tyr Leu Pro Leu Ser Leu Met Val Thr Ala
    370                 375                 380

Phe Arg Lys Glu Asp Val Lys Arg Pro Leu Glu Gly Phe Gly Val Leu
385                 390                 395                 400

Ile Pro Tyr Lys Glu Gln Gln Lys Tyr Gly Leu Lys Thr Leu Gly Thr
                405                 410                 415

Leu Phe Ser Ser Met Met Phe Pro Asp Arg Ala Pro Asn Asp Gln His
            420                 425                 430

Leu Phe Thr Thr Phe Val Gly Gly Ser His Asn Arg Asp Leu Ala Ala
        435                 440                 445

Ala Pro Thr Ala Ile Leu Lys Gln Leu Val Thr Ser Asp Leu Arg Lys
    450                 455                 460

Leu Leu Gly Val Glu Gly Gln Pro Thr Phe Val Lys His Val His Trp
465                 470                 475                 480

Lys Asn Ala Phe Pro Leu Tyr Gly His Asp Tyr Asp Leu Ala Leu Glu
                485                 490                 495

Ala Ile Gly Lys Met Glu Asn Glu Leu Pro Gly Phe Phe Tyr Ala Gly
            500                 505                 510

Asn Asn Lys Asp Gly Leu Ala Val Gly Asn Val Ile Ala Ser Gly Ser
        515                 520                 525

Lys Thr Ala Asp Leu Val Ile Ser Tyr Leu Glu Ser His Gln Ala Arg
    530                 535                 540
```

<210> SEQ ID NO 37
<211> LENGTH: 506

<212> TYPE: PRT
<213> ORGANISM: Oryza sativa

<400> SEQUENCE: 37

```
Met Ala Ala Ser Asp Asp Pro Arg Gly Gly Arg Ser Val Ala Val Val
1               5                   10                  15

Gly Ala Gly Val Ser Gly Leu Ala Ala Ala Tyr Arg Leu Arg Lys Arg
            20                  25                  30

Gly Val Gln Val Thr Val Phe Glu Ala Ala Asp Arg Ala Gly Gly Lys
        35                  40                  45

Ile Arg Thr Asn Ser Glu Gly Gly Phe Ile Trp Asp Glu Gly Ala Asn
    50                  55                  60

Thr Met Thr Glu Ser Glu Leu Glu Ala Ser Arg Leu Ile Asp Asp Leu
65                  70                  75                  80

Gly Leu Gln Gly Lys Gln Gln Tyr Pro Asn Ser Gln His Lys Arg Tyr
                85                  90                  95

Ile Val Lys Asp Gly Ala Pro Thr Leu Ile Pro Ser Asp Pro Ile Ala
            100                 105                 110

Leu Met Lys Ser Thr Val Leu Ser Thr Lys Ser Lys Leu Lys Leu Phe
        115                 120                 125

Leu Glu Pro Phe Leu Tyr Glu Lys Ser Ser Arg Arg Thr Ser Gly Lys
    130                 135                 140

Val Ser Asp Glu His Leu Ser Glu Ser Val Ile Phe Leu Cys Ile Cys
145                 150                 155                 160

Arg Asp Asn Gln Val Val Asp Tyr Leu Ile Asp Pro Phe Val Ala Gly
                165                 170                 175

Thr Ser Gly Gly Asp Pro Glu Ser Leu Ser Ile Arg His Ala Phe Pro
            180                 185                 190

Ala Leu Trp Asn Leu Glu Asn Lys Tyr Gly Ser Val Ile Ala Gly Ala
        195                 200                 205

Ile Leu Ser Lys Leu Ser Thr Lys Gly Asp Ser Val Lys Thr Gly Gly
    210                 215                 220

Ala Ser Pro Gly Lys Gly Arg Asn Lys Arg Val Ser Phe Ser Phe His
225                 230                 235                 240

Gly Gly Met Gln Ser Leu Ile Asp Ala Leu His Asn Glu Val Gly Asp
                245                 250                 255

Gly Asn Val Lys Leu Gly Thr Glu Val Leu Ser Leu Ala Cys Cys Cys
            260                 265                 270

Asp Gly Val Ser Ser Ser Gly Gly Trp Ser Ile Ser Val Asp Ser Lys
        275                 280                 285

Asp Ala Lys Gly Lys Asp Leu Arg Lys Asn Gln Ser Phe Asp Ala Val
    290                 295                 300

Ile Met Thr Ala Pro Leu Ser Asn Val Gln Arg Met Lys Phe Thr Lys
305                 310                 315                 320

Gly Gly Val Pro Phe Val Leu Asp Phe Leu Pro Lys Val Asp Tyr Leu
                325                 330                 335

Pro Leu Ser Leu Met Val Thr Ala Phe Lys Lys Glu Asp Val Lys Lys
            340                 345                 350

Pro Leu Glu Gly Phe Gly Ala Leu Ile Pro Tyr Lys Glu Gln Gln Lys
        355                 360                 365

His Gly Leu Lys Thr Leu Gly Thr Leu Phe Ser Ser Met Met Phe Pro
    370                 375                 380

Asp Arg Ala Pro Asn Asp Gln Tyr Leu Tyr Thr Ser Phe Ile Gly Gly
385                 390                 395                 400
```

Ser His Asn Arg Asp Leu Ala Gly Ala Pro Thr Ala Ile Leu Lys Gln
405 410 415

Leu Val Thr Ser Asp Leu Arg Lys Leu Leu Gly Val Glu Gly Gln Pro
420 425 430

Thr Phe Val Lys His Val His Trp Arg Asn Ala Phe Pro Leu Tyr Gly
435 440 445

Gln Asn Tyr Asp Leu Val Leu Glu Ala Ile Ala Lys Met Glu Asn Asn
450 455 460

Leu Pro Gly Phe Phe Tyr Ala Gly Asn Asn Lys Asp Gly Leu Ala Val
465 470 475 480

Gly Asn Val Ile Ala Ser Gly Ser Lys Ala Ala Asp Leu Val Ile Ser
485 490 495

Tyr Leu Glu Ser Cys Thr Asp Gln Asp Asn
500 505

<210> SEQ ID NO 38
<211> LENGTH: 494
<212> TYPE: PRT
<213> ORGANISM: Picea sitchensis

<400> SEQUENCE: 38

Met Ala Glu His Ile His Thr Asp Gln Asn Asp Lys Arg Pro Leu Lys
1 5 10 15

Ser Val Ala Val Val Gly Ala Gly Ile Ser Gly Leu Ala Ala Ala Tyr
20 25 30

Arg Leu Lys Ser Gln Gly Leu Ala Val Thr Ile Phe Glu Ala Asp Gly
35 40 45

Thr Thr Gly Gly Lys Ile Lys Ser Phe Ala Gln Asn Gly Leu Ile Trp
50 55 60

Glu Lys Gly Ala Asn Thr Met Thr Glu Thr Glu Pro Glu Val Gly Lys
65 70 75 80

Leu Ile Asp Asp Leu Gly Ile Arg Gly Lys Gln Gln Phe Pro Ile Met
85 90 95

Gln Ser Lys Arg Tyr Ile Val Arg Asp Gly Lys Pro Gln Leu Leu Pro
100 105 110

Ser Asn Pro Val Ala Phe Ile Gly Ser Lys Thr Leu Ser Ala Gln Ala
115 120 125

Lys Leu Asn Ile Phe Leu Glu Pro Ile Leu Trp Lys His Lys Asn Ser
130 135 140

Lys Glu Lys Thr Pro Asn Ser Pro Asp Ile Tyr Gln Glu Glu Ser Val
145 150 155 160

Gly Asp Phe Phe Arg Arg His Phe Gly Gln Glu Val Val Asp Tyr Ile
165 170 175

Val Asp Pro Phe Val Ala Gly Thr Ala Gly Ala Asp Ala Glu Ser Leu
180 185 190

Ser Ile Arg His Met Phe Pro Glu Ile Trp Asp Leu Glu Glu Arg Phe
195 200 205

Gly Ser Ile Ile Thr Gly Ala Ile Lys Ser Ser Trp Ser Arg Lys Lys
210 215 220

Ala Gln Arg Asp Ala Lys His Val Thr His Gly Gln Lys Arg Gln Arg
225 230 235 240

Gly Ser Phe Ser Phe Met Gly Gly Leu Gln Thr Leu Thr Asn Ala Leu
245 250 255

Ser Lys Lys Leu Gly Glu Glu Ser Leu Arg Met His Cys Ser Val Leu

```
            260                 265                 270

Ser Leu Ser Cys Asn Leu Gln Gly Asn Pro Pro His Asn Asn Trp Ser
        275                 280                 285

Val Cys Tyr Ala Arg Asn Asp Ala Ser Tyr Lys Glu Pro Leu Lys Glu
    290                 295                 300

Gln Ser Phe Asp Ala Val Val Met Thr Val Thr Tyr Leu Pro Met Ser
305                 310                 315                 320

Ile Ile Ile Thr Thr Phe Lys Lys Gln Asp Val Lys His Pro Leu Glu
                325                 330                 335

Gly Phe Gly Ile Leu Val Pro Ser Lys Glu Glu Lys Asn Gly Phe Gln
            340                 345                 350

Thr Leu Gly Thr Leu Phe Ser Ser Asn Met Phe Pro Asp Arg Ala Pro
        355                 360                 365

Thr Asp Gln Tyr Leu Phe Thr Thr Phe Ile Gly Gly Asn Arg Asn Arg
    370                 375                 380

Lys Leu Ala Lys Ser Gln Leu Lys Asp Leu Gln Glu Val Ala Val Asn
385                 390                 395                 400

Asp Leu Asn Lys Ile Leu Gly Val Gly Ser Asp Pro Leu Ser Val Lys
                405                 410                 415

His Ile Tyr Trp Asn Glu Ala Phe Pro Leu Tyr Ser Leu Asp Tyr Asn
            420                 425                 430

Ser Val Val Ala Ala Ile Asp Lys Leu Gly Lys Ser Leu Pro Gly Ile
        435                 440                 445

Tyr Phe Ala Gly Asn Tyr Arg Gly Gly Leu Ser Val Gly Lys Ala Leu
    450                 455                 460

Thr Ser Gly Phe Lys Ala Ala Asp Leu Ala Ile Ser Asp Phe Asn Ser
465                 470                 475                 480

Lys Gly Leu Cys Thr Met Ile Gly Thr Asp His Glu Val Lys
                485                 490


<210> SEQ ID NO 39
<211> LENGTH: 404
<212> TYPE: PRT
<213> ORGANISM: Solanum tuberosum

<400> SEQUENCE: 39

Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asn Val Thr Val Phe Glu Ala Glu Gly Arg Ala
        35                  40                  45

Gly Gly Lys Leu Arg Ser Leu Ser Gln Asp Gly Leu Ile Trp Asp Glu
    50                  55                  60

Gly Ala Asn Thr Met Thr Glu Ser Glu Gly Asp Val Thr Phe Leu Leu
65                  70                  75                  80

Asp Ser Leu Gly Leu Arg Glu Lys Gln Gln Phe Pro Leu Ser Gln Asn
                85                  90                  95

Lys Arg Tyr Ile Ala Arg Asn Gly Thr Pro Thr Leu Ile Pro Ser Asn
            100                 105                 110

Pro Ile Asp Leu Ile Lys Ser Asn Phe Leu Ser Thr Gly Ser Lys Leu
        115                 120                 125

Gln Met Leu Phe Glu Pro Leu Leu Trp Lys Asn Asn Lys Leu Thr Lys
    130                 135                 140
```

-continued

```
Val Ser Asp Glu His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His Leu Ser Phe Pro Glu
            180                 185                 190

Leu Trp Asn Leu Glu Lys Arg Phe Gly Ser Val Ile Val Gly Ala Ile
        195                 200                 205

Arg Ser Lys Leu Ser Pro Ile Lys Glu Lys Lys Gln Gly Pro Pro Lys
    210                 215                 220

Thr Ser Val Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Lys Glu Asp
                245                 250                 255

Glu Leu Arg Leu Asn Ser Arg Val Leu Glu Leu Ser Cys Ser Cys Ser
            260                 265                 270

Gly Asp Ser Ala Ile Asp Ser Trp Ser Ile Phe Ser Ala Ser Pro His
        275                 280                 285

Lys Arg Gln Ala Glu Glu Glu Ser Phe Asp Ala Val Ile Met Thr Ala
    290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Lys Glu Ser Val Lys His Pro Leu Glu Gly
            340                 345                 350

Phe Gly Val Leu Val Pro Ser Gln Glu Gln Lys His Gly Leu Lys Thr
        355                 360                 365

Leu Gly Thr Leu Phe Ser Ser Met Met Phe Pro Asp Arg Ala Pro Asn
    370                 375                 380

Asn Val Tyr Leu Tyr Thr Thr Phe Val Gly Gly Ser Arg Asn Arg Glu
385                 390                 395                 400

Leu Ala Lys Ala


<210> SEQ ID NO 40
<211> LENGTH: 505
<212> TYPE: PRT
<213> ORGANISM: Oryza sativa

<400> SEQUENCE: 40

Met Ala Ala Ser Asp Asp Pro Arg Gly Gly Arg Ser Val Ala Val Val
1               5                   10                  15

Gly Ala Gly Val Ser Gly Leu Ala Ala Ala Tyr Arg Leu Arg Lys Arg
            20                  25                  30

Gly Val Gln Val Thr Val Phe Glu Ala Ala Asp Arg Ala Gly Gly Lys
        35                  40                  45

Ile Arg Thr Asn Ser Glu Gly Gly Phe Ile Trp Asp Glu Gly Ala Asn
    50                  55                  60

Thr Met Thr Glu Ser Glu Leu Glu Ala Ser Arg Leu Ile Asp Asp Leu
65                  70                  75                  80

Gly Leu Gln Gly Lys Gln Gln Tyr Pro Asn Ser Gln His Lys Arg Tyr
                85                  90                  95

Ile Val Lys Asp Gly Ala Pro Thr Leu Ile Pro Ser Asp Pro Ile Ala
            100                 105                 110
```

```
Leu Met Lys Ser Thr Val Leu Ser Thr Lys Ser Lys Leu Lys Leu Phe
        115                 120                 125

Leu Glu Pro Phe Leu Tyr Glu Lys Ser Ser Arg Arg Thr Ser Gly Lys
    130                 135                 140

Val Ser Asp Glu His Leu Ser Glu Ser Met Phe Ser Asp Gln Arg Glu
145                 150                 155                 160

Tyr Ile Cys Ser Val Ile Phe Leu Cys Ile Cys Arg Asp Asn Gln Val
            165                 170                 175

Val Asp Tyr Leu Ile Asp Pro Phe Val Ala Gly Thr Ser Gly Gly Asp
            180                 185                 190

Pro Glu Ser Leu Ser Ile Arg His Ala Phe Pro Ala Leu Trp Asn Leu
        195                 200                 205

Glu Asn Lys Tyr Gly Ser Val Ile Ala Gly Ala Ile Leu Ser Lys Leu
    210                 215                 220

Ser Thr Lys Gly Asp Ser Val Lys Thr Gly Gly Ala Ser Pro Gly Lys
225                 230                 235                 240

Gly Arg Asn Lys Arg Val Ser Phe Ser Phe His Gly Gly Met Gln Ser
            245                 250                 255

Leu Ile Asp Ala Leu His Asn Glu Val Gly Asp Gly Asn Val Lys Leu
            260                 265                 270

Gly Thr Glu Val Leu Ser Leu Ala Cys Cys Cys Asp Gly Val Ser Ser
        275                 280                 285

Ser Gly Gly Trp Ser Ile Ser Val Asp Ser Lys Asp Ala Lys Gly Lys
    290                 295                 300

Asp Leu Arg Lys Asn Gln Ser Phe Asp Ala Val Ile Met Thr Ala Pro
305                 310                 315                 320

Leu Ser Asn Val Gln Arg Met Lys Phe Thr Lys Gly Gly Val Pro Phe
            325                 330                 335

Val Leu Asp Phe Leu Pro Lys Val Asp Tyr Leu Pro Leu Ser Leu Met
            340                 345                 350

Val Thr Ala Phe Lys Lys Glu Asp Val Lys Lys Pro Leu Glu Gly Phe
        355                 360                 365

Gly Ala Leu Ile Pro Tyr Lys Glu Gln Gln Lys His Gly Leu Lys Thr
    370                 375                 380

Leu Gly Thr Leu Phe Ser Ser Met Met Phe Pro Asp Arg Ala Pro Asn
385                 390                 395                 400

Asp Gln Tyr Leu Tyr Thr Ser Phe Ile Gly Gly Ser His Asn Arg Asp
            405                 410                 415

Leu Ala Gly Ala Pro Thr Ala Ile Leu Lys Gln Leu Val Thr Ser Asp
            420                 425                 430

Leu Arg Lys Leu Leu Gly Val Glu Gly Gln Pro Thr Phe Val Lys His
        435                 440                 445

Val His Trp Arg Asn Ala Phe Pro Leu Tyr Gly Gln Asn Tyr Asp Leu
    450                 455                 460

Val Leu Glu Ala Ile Ala Lys Met Glu Asn Asn Leu Pro Gly Phe Phe
465                 470                 475                 480

Tyr Ala Gly Lys Ser Met Lys Ala Pro Leu Leu Tyr Lys Arg Asn Leu
            485                 490                 495

Arg Tyr Leu Lys His Ile Pro Val Asp
            500                 505
```

<210> SEQ ID NO 41
<211> LENGTH: 505
<212> TYPE: PRT

```
<213> ORGANISM: Oryza sativa

<400> SEQUENCE: 41

Met Ala Ala Ser Asp Asp Pro Arg Gly Gly Arg Ser Val Ala Val Val
1               5                   10                  15

Gly Ala Gly Val Ser Gly Leu Ala Ala Ala Tyr Arg Leu Arg Lys Arg
            20                  25                  30

Gly Val Gln Val Thr Val Phe Glu Ala Ala Asp Arg Ala Gly Gly Lys
        35                  40                  45

Ile Arg Thr Asn Ser Glu Gly Gly Phe Ile Trp Asp Glu Gly Ala Asn
    50                  55                  60

Thr Met Thr Glu Ser Glu Leu Glu Ala Ser Arg Leu Ile Asp Asp Leu
65                  70                  75                  80

Gly Leu Gln Gly Lys Gln Gln Tyr Pro Asn Ser Gln His Lys Arg Tyr
                85                  90                  95

Ile Val Lys Asp Gly Ala Pro Thr Leu Ile Pro Ser Asp Pro Ile Ala
            100                 105                 110

Leu Met Lys Ser Thr Val Leu Ser Thr Lys Ser Lys Leu Lys Leu Phe
        115                 120                 125

Leu Glu Pro Phe Leu Tyr Glu Lys Ser Ser Arg Arg Thr Ser Gly Lys
    130                 135                 140

Val Ser Asp Glu His Leu Ser Glu Ser Met Phe Ser Asp Gln Arg Glu
145                 150                 155                 160

Tyr Ile Cys Ser Val Ile Phe Leu Cys Ile Cys Arg Asp Asn Gln Val
                165                 170                 175

Val Asp Tyr Leu Ile Asp Pro Phe Val Ala Gly Thr Ser Gly Gly Asp
            180                 185                 190

Pro Glu Ser Leu Ser Ile Arg His Ala Phe Pro Ala Leu Trp Asn Leu
        195                 200                 205

Glu Asn Lys Tyr Gly Ser Val Ile Ala Gly Ala Ile Leu Ser Lys Leu
    210                 215                 220

Ser Thr Lys Gly Asp Ser Val Lys Thr Gly Gly Ala Ser Pro Gly Lys
225                 230                 235                 240

Gly Arg Asp Lys Arg Val Ser Phe Ser Phe His Gly Gly Met Gln Ser
                245                 250                 255

Leu Ile Asp Ala Leu His Asn Glu Val Gly Asp Gly Asn Val Lys Leu
            260                 265                 270

Gly Thr Glu Val Leu Ser Leu Ala Cys Cys Cys Asp Gly Val Ser Ser
        275                 280                 285

Ser Gly Gly Trp Ser Ile Ser Val Asp Ser Lys Asp Ala Lys Gly Lys
    290                 295                 300

Asp Leu Arg Lys Asn Gln Ser Phe Asp Ala Val Ile Met Thr Ala Pro
305                 310                 315                 320

Leu Ser Asn Val Gln Arg Met Lys Phe Thr Lys Gly Gly Val Pro Phe
                325                 330                 335

Val Leu Asp Phe Leu Pro Lys Val Asp Tyr Leu Pro Leu Ser Leu Met
            340                 345                 350

Val Thr Ala Phe Lys Lys Glu Asp Val Lys Lys Pro Leu Glu Gly Phe
        355                 360                 365

Gly Ala Leu Ile Pro Tyr Lys Glu Gln Gln Lys His Gly Leu Lys Thr
    370                 375                 380

Leu Gly Thr Leu Phe Ser Ser Met Met Phe Pro Asp Arg Ala Pro Asn
385                 390                 395                 400
```

```
Asp Gln Tyr Leu Tyr Thr Ser Phe Ile Gly Gly Ser His Asn Arg Asp
                405                 410                 415

Leu Ala Gly Ala Pro Thr Ala Ile Leu Lys Gln Leu Val Thr Ser Asp
            420                 425                 430

Leu Arg Lys Leu Leu Gly Val Glu Gly Gln Pro Thr Phe Val Lys His
        435                 440                 445

Val His Trp Arg Asn Ala Phe Pro Leu Tyr Gly Gln Asn Tyr Asp Leu
    450                 455                 460

Val Leu Glu Ala Ile Ala Lys Met Glu Asn Asn Leu Pro Gly Phe Phe
465                 470                 475                 480

Tyr Ala Gly Lys Ser Met Lys Ala Pro Leu Leu Tyr Lys Arg Asn Leu
                485                 490                 495

Arg Tyr Leu Lys His Ile Pro Val Asp
            500                 505


<210> SEQ ID NO 42
<211> LENGTH: 405
<212> TYPE: PRT
<213> ORGANISM: Eutrema salsugineum

<400> SEQUENCE: 42

Met Ala Pro Asp Ala Val Ala Asp His Asp Lys Lys Phe Glu Ala Leu
1               5                   10                  15

Ser Gly Lys Arg Val Ala Val Val Gly Ala Gly Val Arg Leu Lys Ser
            20                  25                  30

Arg Gly Leu Asn Val Thr Val Phe Glu Ala Asp Gly Arg Ala Gly Gly
        35                  40                  45

Lys Leu Arg Ser Val Met His Lys Gly Leu Ile Trp Asp Glu Gly Ala
    50                  55                  60

Asn Thr Met Thr Glu Ala Glu Pro Glu Val Gly Ser Leu Leu Asp Asp
65                  70                  75                  80

Leu Gly Leu Arg Glu Lys Gln Gln Phe Pro Ile Ser Gln Lys Lys Arg
                85                  90                  95

Tyr Ile Val Arg Asn Gly Leu Pro Val Met Ile Pro Thr Asn Pro Ile
            100                 105                 110

Ala Leu Val Thr Ser Ser Val Leu Ser Thr His Ser Lys Phe Gln Ile
        115                 120                 125

Leu Leu Glu Pro Phe Leu Trp Lys Lys Asn Asp Ser Ser Ser Lys Val
    130                 135                 140

Ser Asp Ala Ser Thr Val Glu Ser Val Ser Gly Phe Phe Gln Arg His
145                 150                 155                 160

Phe Gly Gln Glu Val Val Asp Tyr Leu Ile Asp Pro Phe Val Gly Gly
                165                 170                 175

Thr Ser Ala Ala Asp Pro Asp Ser Leu Ser Met Lys His Thr Phe Pro
            180                 185                 190

Asp Leu Trp Asn Ile Glu Lys Ser Phe Gly Ser Ile Ile Val Gly Ala
        195                 200                 205

Ile Arg Thr Lys Phe Ala Ala Lys Gly Gly Lys Ser Gly Glu Thr Arg
    210                 215                 220

Thr Ser Pro Gly Thr Lys Lys Gly Ser Arg Gly Ser Phe Ser Phe Lys
225                 230                 235                 240

Gly Gly Met Gln Ile Leu Pro Asp Met Leu Cys Lys Asp Leu Ser His
                245                 250                 255

Asp Glu Leu Asn Leu Asp Ser Lys Val Leu Ser Leu Ser Tyr Asn Ser
            260                 265                 270
```

```
Gly Ser Arg Gln Glu Asn Trp Ser Leu Ser Cys Val Ser His Asn Glu
        275                 280                 285

Thr Leu Arg Gln Asn Leu His Tyr Asp Ala Val Val Met Thr Ala Pro
    290                 295                 300

Leu Cys Asn Val Lys Glu Met Lys Val Val Lys Gly Gly Gln Pro Phe
305                 310                 315                 320

Gln Leu Asn Phe Ile Pro Glu Ile Lys Tyr Met Pro Leu Ser Val Ile
                325                 330                 335

Ile Thr Thr Phe Thr Lys Glu Lys Val Lys Arg Pro Leu Glu Gly Phe
            340                 345                 350

Gly Val Leu Ile Pro Ser Lys Glu Glu Lys His Gly Phe Lys Thr Leu
        355                 360                 365

Gly Thr Leu Phe Ser Ser Met Met Phe Pro Asp Arg Cys Pro Ser Asp
    370                 375                 380

Leu His Leu Tyr Thr Thr Phe Val Gly Gly Ser Arg Asn Gln Glu Leu
385                 390                 395                 400

Ala Lys Ala Ser Thr
                405


<210> SEQ ID NO 43
<211> LENGTH: 520
<212> TYPE: PRT
<213> ORGANISM: Selaginella moellendorffii

<400> SEQUENCE: 43

Met Ala Met Ala Glu Gly Glu Thr Ala Pro Val Leu Gly Ser Val Ala
1               5                   10                  15

Val Val Gly Ala Gly Ala Ser Gly Leu Ala Ala Ala Tyr Arg Leu Arg
            20                  25                  30

Ala Ala Gly Val Ser Val Thr Val Tyr Glu Ala Glu Asn Ser Ile Gly
        35                  40                  45

Gly Lys Leu Lys Ser Val Ser Glu Asn Gly Phe Ile Trp Glu Lys Gly
    50                  55                  60

Pro Asn Thr Met Thr Glu Asn Asp Pro Ser Ile Ser Arg Met Phe Asp
65                  70                  75                  80

Asp Leu His Leu Arg Asp Lys Gln Gln Phe Pro Val Glu Gln Lys Lys
                85                  90                  95

Arg Tyr Ile Val Arg Asn Ala Ser Pro Thr Met Leu Pro Ser Asn Pro
            100                 105                 110

Leu Gly Phe Ile Thr Thr Gly Leu Phe Ser Ala Gln Ala Lys Leu Lys
        115                 120                 125

Leu Leu Thr Glu Pro Phe Ser Trp Lys Arg Thr Lys Ala Glu Ser Asn
    130                 135                 140

Glu Asp Glu Ser Val Gly Ala Phe Met Glu Arg His Phe Gly Asp Glu
145                 150                 155                 160

Ile Val Asp Tyr Ala Val Asp Pro Phe Val Ala Gly Thr Ser Gly Ser
                165                 170                 175

Asp Pro Ser Ser Ile Ser Ile Arg His Ser Phe Pro Glu Leu Trp Ser
            180                 185                 190

Leu Glu Lys Asn Tyr Gly Ser Leu Phe Val Gly Ala Ile Lys Ser Gly
        195                 200                 205

Phe Ser Lys Lys Lys Lys Gln Lys Leu Arg Pro Val Glu Phe Glu Asp
    210                 215                 220

Glu Asp Ser Asp Phe Pro Ala Arg Thr Arg Pro Arg Arg Gly Gly Ser
```

```
225                 230                 235                 240

Phe Ser Phe Val Gly Gly Met Gln Thr Leu Ala Asn Glu Leu Val Ser
                245                 250                 255

Arg Ile Gly Lys Glu Lys Phe Lys Leu Asn Thr Phe Val Thr Gly Leu
            260                 265                 270

Ala Cys Asn Gln Gln Gly Asn Pro Ser Arg Gln Ser Trp Thr Val Thr
        275                 280                 285

Gly Leu Glu Thr Ser Gly Lys Arg Ser Lys Arg Ser Asp Lys Thr Phe
    290                 295                 300

Asp Ala Val Ile Met Thr Ala Pro Val Asp Asp Val Arg Ala Met Lys
305                 310                 315                 320

Val Val Lys Asp Gly Lys Pro Tyr Ala Leu Asp Tyr Leu Pro Thr Val
                325                 330                 335

Ile Tyr Glu Pro Met Ser Val Leu Ile Thr Met Phe Asn Lys Asp Ser
            340                 345                 350

Val Lys Arg Ala Leu Pro Gly Phe Gly Val Leu Val Pro Ser Lys Glu
        355                 360                 365

Gln Gln Ala Asn Gly Phe Gln Thr Leu Gly Thr Leu Phe Ser Ser Phe
    370                 375                 380

Met Phe Pro Asp Arg Ala Pro Glu Asp Gln Leu Leu Phe Thr Thr Phe
385                 390                 395                 400

Ile Gly Gly Ser Arg Asn Thr Leu Leu Ala Ser Arg Ser Lys Glu Glu
                405                 410                 415

Leu Leu Asp Ile Thr Leu Lys Asp Leu Ser Arg Leu Ile Gly Val Glu
            420                 425                 430

Gly Gln Pro Thr Ala Ile Arg His Val Tyr Trp Glu Lys Ala Phe Pro
        435                 440                 445

Arg Tyr Ser Ile Gly Tyr Asp Asn Val Leu His Ser Ile Gln Lys Leu
    450                 455                 460

Glu Ser Asp Leu Pro Gly Leu Phe Tyr Ala Gly Asn His Arg Gly Gly
465                 470                 475                 480

Leu Ala Val Gly Lys Thr Ile Val Ser Gly Leu Asp Ala Ala Glu Gln
                485                 490                 495

Val Leu Gln Tyr Leu Gln Gly Ser Gly Gly Lys Lys Val Phe Thr Met
            500                 505                 510

Ala Ser Leu Glu Gln Pro Val Ser
        515                 520


<210> SEQ ID NO 44
<211> LENGTH: 514
<212> TYPE: PRT
<213> ORGANISM: Selaginella moellendorffii

<400> SEQUENCE: 44

Met Ala Met Ala Glu Gly Glu Thr Val Pro Val Leu Gly Ser Val Ala
1               5                   10                  15

Val Val Gly Ala Gly Ala Ser Gly Leu Ala Ala Ala Tyr Arg Leu Arg
            20                  25                  30

Ala Ala Gly Val Ser Val Thr Val Tyr Glu Ala Glu Asn Ser Ile Gly
        35                  40                  45

Gly Lys Leu Lys Ser Val Ser Glu Asn Gly Phe Ile Trp Glu Lys Gly
    50                  55                  60

Pro Asn Thr Met Thr Glu Asn Asp Pro Ser Ile Ser Arg Met Phe Asp
65                  70                  75                  80
```

-continued

```
Asp Leu His Leu Arg Asp Lys Gln Gln Phe Pro Val Glu Gln Lys Lys
                85                  90                  95

Arg Tyr Ile Val Arg Asn Ala Ser Pro Thr Met Leu Pro Ser Asn Pro
            100                 105                 110

Leu Gly Phe Ile Thr Thr Gly Leu Phe Ser Ala Gln Ala Lys Leu Lys
        115                 120                 125

Leu Leu Thr Glu Pro Phe Ser Trp Lys Arg Thr Lys Ala Glu Ser Asn
    130                 135                 140

Glu Asp Glu Ser Val Gly Ala Phe Met Glu Arg His Phe Gly Asp Glu
145                 150                 155                 160

Ile Val Asp Tyr Ala Val Asp Pro Phe Val Ala Gly Thr Ser Gly Ser
                165                 170                 175

Asp Pro Ser Ser Ile Ser Ile Arg His Ser Phe Pro Glu Leu Trp Ser
            180                 185                 190

Leu Glu Lys Asn Tyr Gly Ser Leu Phe Val Gly Ala Ile Lys Ser Gly
        195                 200                 205

Phe Ser Lys Lys Lys Lys Gln Lys Leu Arg Pro Val Glu Phe Glu Asp
    210                 215                 220

Glu Asp Ser Asp Phe Pro Ala Arg Thr Arg Pro Arg Arg Gly Gly Ser
225                 230                 235                 240

Phe Ser Phe Val Gly Gly Met Gln Thr Leu Ala Asn Glu Leu Val Ser
                245                 250                 255

Arg Ile Gly Lys Glu Lys Phe Lys Leu Asn Thr Phe Val Thr Gly Leu
            260                 265                 270

Ala Cys Asn Gln Gln Gly Asn Pro Ser Arg Gln Ser Trp Thr Val Thr
        275                 280                 285

Gly Leu Glu Thr Ser Gly Lys Arg Ser Lys Arg Ser Asp Lys Thr Phe
    290                 295                 300

Asp Ala Val Ile Met Thr Ala Pro Val Asp Asp Val Arg Thr Met Lys
305                 310                 315                 320

Val Val Lys Asp Gly Lys Pro Tyr Ala Leu Asp Tyr Leu Pro Thr Val
                325                 330                 335

Ile Tyr Glu Pro Met Ser Val Leu Ile Thr Met Phe Asn Lys Asp Ser
            340                 345                 350

Val Lys Arg Ala Leu Pro Gly Phe Gly Val Leu Val Pro Ser Lys Glu
        355                 360                 365

Gln Gln Ala Asn Gly Phe Gln Thr Leu Gly Thr Leu Phe Ser Ser Phe
    370                 375                 380

Met Phe Pro Asp Arg Ala Pro Glu Asp Gln Leu Leu Phe Thr Thr Phe
385                 390                 395                 400

Ile Gly Gly Ser Arg Asn Thr Leu Leu Ala Ser Arg Ser Lys Glu Glu
                405                 410                 415

Leu Leu Asp Val Thr Leu Lys Asp Leu Ser Arg Leu Ile Gly Val Glu
            420                 425                 430

Gly Gln Pro Thr Ala Met Arg His Val Tyr Trp Glu Lys Ala Phe Pro
        435                 440                 445

Arg Tyr Ser Ile Gly Tyr Asp Asn Val Leu Asn Ser Ile Gln Lys Leu
    450                 455                 460

Glu Ser Asp Leu Pro Gly Leu Phe Tyr Ala Gly Asn His Arg Gly Gly
465                 470                 475                 480

Leu Ala Val Gly Lys Thr Ile Val Ser Gly Leu Asp Ala Ala Glu Gln
                485                 490                 495

Val Leu Gln Tyr Leu Gln Gly Ser Gly Gly Lys Lys Val Phe Thr Met
```

500 505 510

Ala Ser

<210> SEQ ID NO 45
<211> LENGTH: 230
<212> TYPE: PRT
<213> ORGANISM: Amaranthus tuberculatus

<400> SEQUENCE: 45

Met Val Ile Gln Ser Ile Thr His Leu Ser Pro Asn Leu Ala Leu Pro
1 5 10 15

Ser Pro Leu Ser Val Ser Thr Lys Asn Tyr Pro Val Ala Val Met Gly
20 25 30

Asn Ile Ser Glu Arg Glu Glu Pro Thr Ser Ala Lys Arg Val Ala Val
35 40 45

Val Gly Ala Gly Val Ser Gly Leu Ala Ala Ala Tyr Lys Leu Lys Ser
50 55 60

His Gly Leu Ser Val Thr Leu Phe Glu Ala Asp Ser Arg Ala Gly Gly
65 70 75 80

Lys Leu Lys Thr Val Lys Lys Asp Gly Phe Ile Trp Asp Glu Gly Ala
85 90 95

Asn Thr Met Thr Glu Ser Glu Ala Glu Val Ser Ser Leu Ile Asp Asp
100 105 110

Leu Gly Leu Arg Glu Lys Gln Gln Leu Pro Ile Ser Gln Asn Lys Arg
115 120 125

Tyr Ile Ala Arg Asp Gly Leu Pro Val Leu Leu Pro Ser Asn Pro Ala
130 135 140

Ala Leu Leu Thr Ser Asn Ile Leu Ser Ala Lys Ser Lys Leu Gln Ile
145 150 155 160

Met Leu Glu Pro Phe Leu Trp Arg Lys His Asn Ala Thr Glu Leu Ser
165 170 175

Asp Glu His Val Gln Glu Ser Val Gly Glu Phe Phe Glu Arg His Phe
180 185 190

Gly Lys Glu Phe Val Asp Tyr Val Ile Asp Pro Phe Val Ala Gly Thr
195 200 205

Cys Gly Gly Asp Pro Gln Ser Leu Ser Met His His Thr Phe Pro Glu
210 215 220

Val Trp Asn Ile Glu Lys
225 230

<210> SEQ ID NO 46
<211> LENGTH: 229
<212> TYPE: PRT
<213> ORGANISM: Amaranthus tuberculatus

<400> SEQUENCE: 46

Met Val Ile Gln Ser Ile Thr His Leu Ser Pro Asn Leu Ala Leu Pro
1 5 10 15

Ser Pro Leu Ser Val Ser Thr Lys Asn Tyr Pro Val Ala Val Met Gly
20 25 30

Asn Ile Ser Glu Arg Glu Glu Pro Thr Ser Ala Lys Arg Val Ala Val
35 40 45

Val Gly Ala Gly Val Ser Gly Leu Ala Ala Ala Tyr Lys Leu Lys Ser
50 55 60

His Gly Leu Ser Val Thr Leu Phe Glu Ala Asp Ser Arg Ala Gly Gly
65 70 75 80

Lys Leu Lys Thr Val Lys Lys Asp Gly Phe Ile Trp Asp Glu Gly Ala
85 90 95

Asn Thr Met Thr Glu Ser Glu Ala Glu Val Ser Ser Leu Ile Asp Asp
100 105 110

Leu Gly Leu Arg Glu Lys Gln Gln Leu Pro Ile Ser Gln Asn Lys Arg
115 120 125

Tyr Ile Ala Arg Asp Gly Leu Pro Val Leu Leu Pro Ser Asn Pro Ala
130 135 140

Ala Leu Leu Thr Ser Asn Ile Leu Ser Ala Lys Ser Lys Leu Gln Ile
145 150 155 160

Met Leu Glu Pro Phe Leu Trp Arg Lys His Asn Ala Thr Glu Leu Ser
165 170 175

Asp Glu His Val Gln Glu Ser Val Gly Glu Phe Phe Glu Arg His Phe
180 185 190

Gly Lys Glu Phe Val Asp Tyr Val Ile Asp Pro Phe Val Ala Gly Thr
195 200 205

Cys Gly Asp Pro Gln Ser Leu Ser Met His His Thr Phe Pro Glu Val
210 215 220

Trp Asn Ile Glu Lys
225

<210> SEQ ID NO 47
<211> LENGTH: 396
<212> TYPE: PRT
<213> ORGANISM: Zea mays

<400> SEQUENCE: 47

Met Lys Ser Ser Val Leu Ser Thr Lys Ser Lys Ile Ala Leu Phe Phe
1 5 10 15

Glu Pro Phe Leu Tyr Lys Lys Ala Asn Thr Arg Asn Ser Gly Lys Val
20 25 30

Ser Glu Glu His Leu Ser Glu Ser Val Gly Ser Phe Cys Glu Arg His
35 40 45

Phe Gly Arg Glu Val Val Asp Tyr Phe Val Asp Pro Phe Val Ala Gly
50 55 60

Thr Ser Ala Gly Asp Pro Glu Ser Leu Ser Ile Arg His Ala Phe Pro
65 70 75 80

Ala Leu Trp Asn Leu Glu Arg Lys Tyr Gly Ser Val Ile Val Gly Ala
85 90 95

Ile Leu Ser Lys Leu Ala Ala Lys Gly Asp Pro Val Lys Thr Arg His
100 105 110

Asp Ser Ser Gly Lys Arg Arg Asn Arg Arg Val Ser Phe Ser Phe His
115 120 125

Gly Gly Met Gln Ser Leu Ile Asn Ala Leu His Asn Glu Val Gly Asp
130 135 140

Asp Asn Val Lys Leu Gly Thr Glu Val Leu Ser Leu Ala Cys Thr Phe
145 150 155 160

Asp Gly Val Pro Ala Leu Gly Arg Trp Ser Ile Ser Val Asp Ser Lys
165 170 175

Asp Ser Gly Asp Lys Asp Leu Ala Ser Asn Gln Thr Phe Asp Ala Val
180 185 190

Ile Met Thr Ala Pro Leu Ser Asn Val Arg Arg Met Lys Phe Thr Lys
195 200 205

Gly Gly Ala Pro Val Val Leu Asp Phe Leu Pro Lys Met Asp Tyr Leu

```
    210                 215                 220

Pro Leu Ser Leu Met Val Thr Ala Phe Lys Lys Asp Asp Val Lys Lys
225                 230                 235                 240

Pro Leu Glu Gly Phe Gly Val Leu Ile Pro Tyr Lys Glu Gln Gln Lys
                245                 250                 255

His Gly Leu Lys Thr Leu Gly Thr Leu Phe Ser Ser Met Met Phe Pro
            260                 265                 270

Asp Arg Ala Pro Asp Asp Gln Tyr Leu Tyr Thr Thr Phe Val Gly Gly
        275                 280                 285

Ser His Asn Arg Asp Leu Ala Gly Ala Pro Thr Ser Ile Leu Lys Gln
    290                 295                 300

Leu Val Thr Ser Asp Leu Lys Lys Leu Leu Gly Val Glu Gly Gln Pro
305                 310                 315                 320

Thr Phe Val Lys His Val Tyr Trp Gly Asn Ala Phe Pro Leu Tyr Gly
                325                 330                 335

His Asp Tyr Ser Ser Val Leu Glu Ala Ile Glu Lys Met Glu Lys Asn
            340                 345                 350

Leu Pro Gly Phe Phe Tyr Ala Gly Asn Asn Lys Asp Gly Leu Ala Val
        355                 360                 365

Gly Ser Val Ile Ala Ser Gly Ser Lys Ala Ala Asp Leu Ala Ile Ser
    370                 375                 380

Tyr Leu Glu Ser His Thr Lys His Asn Asn Ser His
385                 390                 395


<210> SEQ ID NO 48
<211> LENGTH: 414
<212> TYPE: PRT
<213> ORGANISM: Aegilops tauschii

<400> SEQUENCE: 48

Met Thr Glu Ser Ala Leu Glu Ala Ser Arg Leu Ile Asp Asp Leu Gly
1               5                   10                  15

Leu Glu Asp Arg Leu Gln Tyr Pro Asn Ser Gln His Lys Arg Tyr Thr
            20                  25                  30

Val Lys Asp Gly Ala Pro Ala Leu Phe Lys Leu Phe Leu Glu Pro Phe
        35                  40                  45

Leu Tyr Glu Lys Ser Ser Thr Arg Asn Ser Lys Lys Val Ser Asp Glu
    50                  55                  60

His Leu Arg Glu Ser Val Gly Ser Phe Phe Glu Arg His Phe Gly Arg
65                  70                  75                  80

Glu Val Val Asp Tyr Leu Ile Asp Pro Phe Val Ala Gly Thr Ser Ala
                85                  90                  95

Gly Asp Pro Glu Ser Leu Ser Ile Arg His Ala Phe Pro Gly Leu Trp
            100                 105                 110

Asn Leu Glu Lys Lys Tyr Gly Ser Leu Ile Val Gly Ala Ile Leu Ser
        115                 120                 125

Lys Leu Thr Ala Lys Gly Asp Ser Ser Lys Lys Gly Gly Ala Ser Ser
    130                 135                 140

Gly Lys Gly Arg Ser Lys Arg Ala Ser Phe Ser Phe His Gly Gly Met
145                 150                 155                 160

Gln Thr Leu Val Asp Ala Leu His Lys Glu Val Gly Asp Ser Asn Val
                165                 170                 175

Lys Leu Gly Thr Gln Val Leu Ser Leu Ala Cys Asn Cys Asp Glu Leu
            180                 185                 190
```

```
Ser Ala Ser Asp Gly Trp Ser Ile Phe Val Asp Ser Lys Asp Ala Ser
        195                 200                 205

Ser Lys Glu Leu Ala Lys Asn Gln Ser Phe Asp Ala Val Ile Met Thr
    210                 215                 220

Ala Pro Leu Ser Asn Val Gln Arg Met Arg Phe Thr Lys Gly Gly Ala
225                 230                 235                 240

Pro Phe Val Leu Asp Phe Leu Pro Lys Val Asp Tyr Leu Pro Leu Ser
                245                 250                 255

Leu Met Val Thr Ala Phe Lys Lys Glu Asp Val Lys Arg Pro Leu Glu
            260                 265                 270

Gly Phe Gly Val Leu Ile Pro Phe Lys Glu Gln Gln Lys His Gly Leu
        275                 280                 285

Lys Thr Leu Gly Thr Leu Phe Ser Ser Met Met Phe Pro Asp Arg Ala
    290                 295                 300

Pro Asn Asp Gln Tyr Leu Phe Thr Thr Phe Ile Gly Gly Ser His Asn
305                 310                 315                 320

Arg Asp Leu Ala Gly Ala Pro Thr Ala Ile Leu Lys Gln Phe Val Thr
                325                 330                 335

Ser Asp Leu Thr Lys Leu Leu Gly Val Val Gly Gln Pro Thr Phe Val
            340                 345                 350

Lys His Ile His Trp Arg Asn Ala Phe Pro Leu Tyr Gly His Asp Tyr
        355                 360                 365

Asp Ser Ala Leu Glu Ala Ile Gly Lys Met Glu Arg Asn Asn Lys Asp
    370                 375                 380

Gly Leu Ala Val Gly Asn Val Ile Ala Ser Gly Ser Asn Thr Ala Asp
385                 390                 395                 400

Leu Val Ile Ser Tyr Leu Glu Ser Gly Ile Lys Gln Val Ser
                405                 410


<210> SEQ ID NO 49
<211> LENGTH: 304
<212> TYPE: PRT
<213> ORGANISM: Genlisea aurea

<400> SEQUENCE: 49

Gly Phe Pro Ala Lys Asn Val Ala Val Ile Gly Ala Gly Val Ser Gly
1               5                   10                  15

Leu Ser Ala Ala Tyr Lys Leu Lys Leu Asn Gly Leu Asn Val Thr Val
            20                  25                  30

Phe Glu Ala Asp Gly Arg Ala Gly Gly Lys Ile Arg Thr Ser Ser Gln
        35                  40                  45

Asp Ser Leu Ile Trp Asp Glu Gly Ala Asn Thr Met Thr Glu Ser Glu
    50                  55                  60

Glu Glu Val Gly Phe Leu Leu Asp Asn Leu Gly Leu Arg Glu Lys Gln
65                  70                  75                  80

Gln Phe Pro Leu Ser Gln Gln Lys Arg Tyr Val Val Lys Asn Gly Lys
                85                  90                  95

Pro Ala Leu Leu Pro Ser Asn Pro Phe Ala Leu Ile Ala Ser Asn Ile
            100                 105                 110

Leu Ser Ser Ser Ser Lys Leu Gln Ile Phe Leu Glu Pro Phe Leu Trp
        115                 120                 125

Lys Gln Arg Asn Ser Glu Glu Thr Gln Ala Glu Glu Ser Val Gly Gly
    130                 135                 140

Phe Phe Gln Arg His Phe Gly Lys Glu Val Val Asp Tyr Leu Val Asp
145                 150                 155                 160
```

```
Pro Phe Val Ala Gly Thr Ser Gly Gly Asp Pro Glu Ser Leu Ser Met
                165                 170                 175

Arg His Ala Phe Pro Asp Leu Trp Asn Leu Glu Lys Arg Phe Gly Ser
            180                 185                 190

Val Met Ser Gly Ala Val Leu Ser Lys Leu Ser Ala Gly Arg Gly Ala
        195                 200                 205

Ser Glu Lys Asn Lys Gly Ser Ser Thr Asn Glu Arg Arg Lys Arg Lys
    210                 215                 220

Ser Phe Ser Phe Ile Gly Gly Met Gln Thr Leu Thr Asp Ala Leu Ser
225                 230                 235                 240

Asn Glu Ile Gly Glu Asn Glu Leu Lys Leu Arg Ser Lys Val Leu Gly
                245                 250                 255

Leu Ser Ser Asn Asn Val Lys Ser Ser Lys Val Asp Ser Trp Ser Ile
            260                 265                 270

Ser Tyr Ala Ser Ser Asp Gly Lys Ser Val Ser Leu Asp Thr Gly Phe
        275                 280                 285

Asp Ala Val Ile Met Thr Ala Pro Leu Ser Asp Val Lys Gln Met Lys
    290                 295                 300


<210> SEQ ID NO 50
<211> LENGTH: 265
<212> TYPE: PRT
<213> ORGANISM: Amborella trichopoda

<400> SEQUENCE: 50

Met Ser Ser Lys Gly Glu Glu Lys Gly Lys His Glu Ala Thr Arg Arg
1               5                   10                  15

Lys Pro Lys His Gln Arg Gly Ser Phe Ser Phe Gln Gly Gly Leu Gln
            20                  25                  30

Thr Leu Thr Asp Lys Leu Ala Glu Glu Leu Gly Asn Glu Asn Val Lys
        35                  40                  45

Leu His Ser Lys Val Leu Ser Leu Ser Tyr Gly Asp Gly Asn Gly Asp
    50                  55                  60

Ser Phe Ser Asn Trp Ser Val Ser Tyr Ile Lys Asn Gln Ser Asp Gln
65                  70                  75                  80

Arg Lys Leu Leu Leu Lys Gln Ser Phe Asp Ala Val Val Met Thr Ala
                85                  90                  95

Pro Ile Arg Asn Met Gln Glu Met Gln Ile Ser Lys Cys Gly Lys Pro
            100                 105                 110

Tyr Met Leu Asp Phe Leu Pro Asn Val Met Tyr Leu Pro Leu Ser Ile
        115                 120                 125

Ile Val Thr Thr Phe Lys Lys Glu Asn Val Lys Leu Pro Leu Glu Gly
    130                 135                 140

Phe Gly Val Leu Val Pro Ser Lys Glu Gln Gly Ser Gly Leu Arg Thr
145                 150                 155                 160

Leu Gly Thr Leu Phe Ser Ser Met Met Phe Pro Asp Arg Ala Pro Lys
                165                 170                 175

Asp Gln Tyr Leu Tyr Thr Thr Phe Val Gly Gly Ser Arg Asn Arg Asn
            180                 185                 190

Leu Ala Ser Ala Ser Leu Asp Glu Leu Arg Glu Val Val Thr Cys Asp
        195                 200                 205

Leu Lys Lys Leu Leu Gly Val Val Gly Ala Pro Thr Phe Val Arg His
    210                 215                 220

Val Tyr Trp Gly Asp Ala Phe Pro Leu Tyr Gly His Asn Tyr Asp Met
```

```
225                 230                 235                 240

Val Leu Lys Ala Ile Glu Lys Met Glu Gln Asn Leu Pro Gly Phe Phe
                245                 250                 255

Tyr Ala Gly Lys Phe Ser Leu Trp Cys
            260                 265


<210> SEQ ID NO 51
<211> LENGTH: 469
<212> TYPE: PRT
<213> ORGANISM: Rhodothermus marinus

<400> SEQUENCE: 51

Met Ala Ser Val Gly Ile Ile Gly Ala Gly Ile Ala Gly Leu Thr Ala
1               5                   10                  15

Ala Tyr Glu Leu His Arg Arg Gly Leu Glu Val Thr Val Phe Glu Ala
            20                  25                  30

Thr Asp Arg Ile Gly Gly Phe Ile Gln Ser Glu Arg Ile Asp Gly Phe
        35                  40                  45

Leu Val Glu Leu Gly Pro Gln Thr Leu Gln Arg Thr Ser Gly Asp Phe
    50                  55                  60

Glu Glu Leu Leu Arg Gln Val Asp Leu Glu Asp Ala Cys Ile Pro Ala
65                  70                  75                  80

Arg Pro Val Ala Ala Asn Arg Phe Ile Val Arg Gly Gly Gln Pro Ile
                85                  90                  95

Pro Leu Pro Arg Ser Pro Arg Glu Leu Leu Arg Thr Pro Leu Leu Ser
            100                 105                 110

Pro Arg Ala Arg Leu Arg Leu Leu Ala Glu Pro Phe Ile His Arg Ala
        115                 120                 125

His Arg Ser Thr Glu Glu Ser Val Ala Lys Phe Thr Arg Arg Arg Leu
    130                 135                 140

Gly Pro Glu Val Leu Asp Tyr Leu Val Glu Pro Phe Val Ala Gly Ile
145                 150                 155                 160

Phe Ala Gly Asp Pro Glu Gln Leu Ser Val Arg Tyr Ala Phe Pro Lys
                165                 170                 175

Leu Phe Glu Leu Glu Gln Gln Tyr Gly Ser Leu Phe Trp Gly Leu Ile
            180                 185                 190

Arg Asp Arg Met Lys Gln Arg Tyr His Pro Ala Pro Arg Arg Ser Met
        195                 200                 205

Phe Ser Phe Val Glu Gly Leu His Met Leu Pro Arg Ala Leu Ala Glu
    210                 215                 220

Arg Leu Pro Ala His Ala Ile Val Arg Asn Ala Glu Val Leu Ala Ile
225                 230                 235                 240

Arg Trp Asp Glu Lys Asn Pro Trp Thr Leu Thr Phe Arg Gln His Gly
                245                 250                 255

Arg Ala Ser Thr Arg Phe Phe Asp Ile Ile Val Cys Ala Val Pro Leu
            260                 265                 270

His Arg Leu Ala Gln Leu Arg Ile His Pro Pro Val Asp Arg Arg Pro
        275                 280                 285

Leu Ser Thr Val Glu His Pro Pro Ile Ala Leu Val Ala Leu Gly Phe
    290                 295                 300

Arg Arg Glu Gln Val Ala His Pro Leu Asp Gly Phe Gly Met Leu Val
305                 310                 315                 320

Pro Ala Val Glu Arg Asp Phe Gln Ile Leu Gly Thr Leu Phe Ser Ser
                325                 330                 335
```

-continued

```
Ser Leu Phe Pro Asp Arg Ala Pro Glu Gly His Val Leu Leu Thr Thr
            340                 345                 350

Phe Val Gly Gly Met Arg His Pro Glu Leu Ala Leu Leu Pro Glu Asp
        355                 360                 365

Arg Leu Glu Ala Leu Val Leu Gln Asp Leu Arg Arg Leu Leu Gly Ile
    370                 375                 380

Ser Gly Ala Pro Val Phe Arg His Val Trp Arg Trp Glu Arg Ser Ile
385                 390                 395                 400

Pro Gln Tyr Arg Leu Gly Tyr Asp Ala Val Leu Ala Cys Val His Asp
                405                 410                 415

Val Glu Met Ser Arg Ser Gly Leu Phe Leu Ala Gly Asn Tyr Met Glu
            420                 425                 430

Gly Ile Ser Val Ile Asp Ala Leu His Thr Gly Leu Lys Ala Ala Arg
        435                 440                 445

Ala Ile Ile Gln His Leu Arg Glu Glu Ala Ala Gly Gly Leu Ala Lys
    450                 455                 460

Leu Val Leu Gly Asp
465


<210> SEQ ID NO 52
<211> LENGTH: 461
<212> TYPE: PRT
<213> ORGANISM: Salinibacter ruber

<400> SEQUENCE: 52

Met Pro Asn Val Gly Ile Ile Gly Ala Gly Ile Ser Gly Leu Ala Ala
1               5                   10                  15

Ala Tyr Arg Leu Gln Glu His Gly His Ser Val Arg Leu Leu Glu Ala
            20                  25                  30

Ser Gly His Thr Gly Gly Val Ile Arg Ser Glu Ser Ser Glu Gly Phe
        35                  40                  45

Leu Val Glu His Gly Pro Asn Ser Ile Arg Ala Gly Ala Ala Gly Leu
    50                  55                  60

Glu Thr Leu Ile Asp Ala Leu Asp Leu His Glu Asp Arg Val Trp Ala
65                  70                  75                  80

Asn Asp Ala Ala Asp Thr Arg Tyr Val Val Arg Asp Gly Arg Pro Thr
                85                  90                  95

Pro Leu Pro Arg Ser Val Gly Ser Phe Leu Thr Thr Asp Leu Phe Ser
            100                 105                 110

Thr Arg Ala Lys Leu Arg Leu Leu Ala Glu Pro Phe Ile Gly Arg Ala
        115                 120                 125

Ala Ala Glu Glu Glu Ser Val Ala Arg Phe Thr Glu Arg Arg Leu Gly
    130                 135                 140

Pro Glu Val Leu Asn Tyr Ala Val Ala Pro Phe Val Gly Gly Val Phe
145                 150                 155                 160

Ala Gly Arg Pro Asp Asp Leu Ser Val Gln His Ala Phe Arg Arg Leu
                165                 170                 175

Ala Ala Leu Glu Glu Glu Ser Gly Ser Leu Leu Leu Gly Ala Ile Arg
            180                 185                 190

Arg Ala Leu Thr Ser Asp Asp Gly Ala Pro Pro Asp Thr Pro Ser Gly
        195                 200                 205

Leu Phe Ser Phe Arg Asn Gly Leu Gln Thr Leu Pro Asn Ala Leu Ala
    210                 215                 220

Asp Thr Leu Gly Asp Arg Ile Arg Leu Asn Ala Pro Val His Ala Leu
225                 230                 235                 240
```

Ala His Asp Gly Thr Ala Trp Arg Val Thr Val Ser Pro Pro Asp Ala
245 250 255

Pro Ala His Thr Arg Ser Phe Asp Ala Leu Val Cys Thr Val Pro Leu
260 265 270

His Arg Leu Ala Ala Met Glu Ile Asp Thr Pro Val Asp Leu Ala Pro
275 280 285

Leu Gly Glu Val Thr Tyr Pro Pro Leu Ser Val Leu Ala Leu Gly Tyr
290 295 300

Gly Arg Asp Ala Ile Asp His Ala Leu Asp Gly Phe Gly Met Leu Val
305 310 315 320

Pro Pro Val Glu Asp Thr Leu Asp Val Leu Gly Thr Ile Phe Ser Ser
325 330 335

Thr Leu Phe Pro Gly Arg Ala Pro Glu Gly His Val Leu Leu Thr Thr
340 345 350

Phe Val Gly Gly Ala Arg Ala Pro His His Ala Thr Ser Asp Ala Ala
355 360 365

Ala Leu Gln Ala Arg Val Ala Arg Asp Leu Asp Ser Leu Leu Gly Val
370 375 380

Asp Ala Ser Pro Val Phe Arg Arg Leu Val His Trp Pro His Ala Ile
385 390 395 400

Pro Gln Tyr Glu Leu Gly Tyr Gly Thr Val Lys Asp Thr Phe Asp Ala
405 410 415

Leu Glu Ala Ala His Pro His Leu Ala Phe Ala Gly Asn Tyr Arg Ala
420 425 430

Gly Val Ser Val Gly Asp Ala Leu Thr Ser Gly Leu Glu Ala Ala Asp
435 440 445

Arg Leu Leu Glu Thr Asp Glu Arg Ala Ala Gln Pro His
450 455 460

<210> SEQ ID NO 53
<211> LENGTH: 461
<212> TYPE: PRT
<213> ORGANISM: Salinibacter ruber

<400> SEQUENCE: 53

Met Pro Asn Val Gly Ile Ile Gly Ala Gly Ile Ser Gly Leu Ala Ala
1 5 10 15

Ala Tyr Arg Leu Gln Glu His Gly His Ser Val Arg Val Leu Glu Ala
20 25 30

Ser Gly His Thr Gly Gly Val Ile Arg Ser Glu Ser Ser Glu Gly Phe
35 40 45

Leu Val Glu His Gly Pro Asn Ser Ile Arg Ala Gly Ala Ala Gly Leu
50 55 60

Glu Thr Leu Ile Asp Ala Leu Asp Leu His Glu Asp Arg Val Trp Ala
65 70 75 80

Asn Asp Ala Ala Asp Thr Arg Tyr Val Val Arg Asp Gly Arg Pro Thr
85 90 95

Pro Leu Pro Arg Ser Val Gly Ser Phe Leu Thr Thr Asp Leu Phe Ser
100 105 110

Thr Arg Ala Lys Leu Arg Leu Leu Ala Glu Pro Phe Ile Gly Arg Ala
115 120 125

Ala Ala Glu Asp Glu Ser Val Ala Arg Phe Thr Glu Arg Arg Leu Gly
130 135 140

Pro Glu Val Leu Asn Tyr Ala Val Ala Pro Phe Val Gly Gly Val Phe

```
145                 150                 155                 160

Ala Gly Arg Pro Asp Asp Leu Ser Val Gln His Ala Phe Arg Arg Leu
                165                 170                 175

Ala Ala Leu Glu Glu Glu Ser Gly Ser Leu Leu Leu Gly Ala Ile Arg
            180                 185                 190

Arg Ala Leu Thr Ser Asp Asp Gly Ala Pro Pro Asp Thr Pro Ser Gly
        195                 200                 205

Leu Phe Ser Phe Arg Asn Gly Leu Gln Thr Leu Pro Asn Ala Leu Ala
    210                 215                 220

Asp Thr Leu Gly Asp Arg Ile Arg Leu Asn Ala Pro Val His Ala Leu
225                 230                 235                 240

Thr His Asp Gly Thr Ala Trp Arg Val Thr Val Ser Pro Pro Asp Ala
                245                 250                 255

Pro Ala His Thr Arg Ser Phe Asp Ala Leu Val Cys Thr Val Pro Leu
            260                 265                 270

His Arg Leu Ala Ala Met Glu Ile Asp Thr Pro Val Asp Leu Ala Pro
        275                 280                 285

Leu Gly Glu Val Thr Tyr Pro Pro Leu Ser Val Leu Ala Leu Gly Tyr
    290                 295                 300

Glu Arg Asp Ala Ile Asp His Ala Leu Asp Gly Phe Gly Met Leu Val
305                 310                 315                 320

Pro Pro Val Glu Asp Thr Leu Asp Val Leu Gly Thr Ile Phe Ser Ser
                325                 330                 335

Thr Leu Phe Pro Gly Arg Ala Pro Glu Gly His Val Leu Leu Thr Thr
            340                 345                 350

Phe Val Gly Gly Ala Arg Ala Pro His His Ala Thr Ser Asp Ala Ala
        355                 360                 365

Ala Leu Gln Ala Arg Val Ala Arg Asp Leu Asp Ser Leu Leu Gly Val
    370                 375                 380

Asp Ala Ser Pro Val Phe Arg Arg Leu Val His Trp Pro His Ala Ile
385                 390                 395                 400

Pro Gln Tyr Glu Leu Gly Tyr Gly Thr Val Lys Asp Thr Phe Asp Ala
                405                 410                 415

Leu Glu Ala Ala His Pro His Leu Ala Phe Ala Gly Asn Tyr Arg Ala
            420                 425                 430

Gly Val Ser Val Gly Asp Ala Leu Thr Ser Gly Leu Glu Ala Ala Asp
        435                 440                 445

Arg Leu Leu Glu Thr Asp Glu Arg Ala Thr Gln Pro His
    450                 455                 460
```

<210> SEQ ID NO 54
<211> LENGTH: 203
<212> TYPE: PRT
<213> ORGANISM: Zea mays

<400> SEQUENCE: 54

```
Met Thr Ala Pro Leu Ser Asn Val Arg Arg Met Lys Phe Thr Lys Gly
1               5                   10                  15

Gly Ala Pro Val Val Leu Asp Phe Leu Pro Lys Met Asp Tyr Leu Pro
            20                  25                  30

Leu Ser Leu Met Val Thr Ala Phe Lys Lys Asp Asp Val Lys Lys Pro
        35                  40                  45

Leu Glu Gly Phe Gly Val Leu Ile Pro Tyr Lys Glu Gln Gln Lys His
    50                  55                  60
```

-continued

Gly Leu Lys Thr Leu Gly Thr Leu Phe Ser Ser Met Met Phe Pro Asp
65 70 75 80

Arg Ala Pro Asp Asp Gln Tyr Leu Tyr Thr Thr Phe Val Gly Gly Ser
85 90 95

His Asn Arg Asp Leu Ala Gly Ala Pro Thr Ser Ile Leu Lys Gln Leu
100 105 110

Val Thr Ser Asp Leu Lys Lys Leu Leu Gly Val Glu Gly Gln Pro Thr
115 120 125

Phe Val Lys His Val Tyr Trp Gly Asn Ala Phe Pro Leu Tyr Gly His
130 135 140

Asp Tyr Ser Ser Val Leu Glu Ala Ile Glu Lys Met Glu Lys Asn Leu
145 150 155 160

Pro Gly Phe Phe Tyr Ala Gly Asn Asn Lys Asp Gly Leu Ala Val Gly
165 170 175

Ser Val Ile Ala Ser Gly Ser Lys Ala Ala Asp Leu Ala Ile Ser Tyr
180 185 190

Leu Glu Ser His Thr Lys His Asn Asn Ser His
195 200

<210> SEQ ID NO 55
<211> LENGTH: 469
<212> TYPE: PRT
<213> ORGANISM: Rhodothermus marinus

<400> SEQUENCE: 55

Met Ala Ser Val Gly Ile Ile Gly Ala Gly Ile Ala Gly Leu Ala Ala
1 5 10 15

Ala Tyr Glu Leu His Arg Arg Gly Leu Glu Val Thr Val Phe Glu Ala
20 25 30

Thr Asp Arg Ile Gly Gly Phe Ile Gln Ser Glu Arg Ile Asp Gly Phe
35 40 45

Leu Val Glu His Gly Pro Gln Thr Leu Gln Arg Thr Ser Gly Asp Phe
50 55 60

Glu Glu Leu Leu Arg Gln Val Asp Leu Glu Asp Ala Cys Ile Thr Ala
65 70 75 80

Arg Pro Ile Ala Ala Asn Arg Phe Ile Val Arg Gly Gly Arg Pro Ile
85 90 95

Pro Leu Pro Arg Ser Pro Arg Glu Leu Leu Arg Thr Pro Leu Leu Ser
100 105 110

Pro Arg Ala Arg Leu Arg Leu Leu Ala Glu Pro Phe Ile His Arg Ala
115 120 125

His Arg Ser Thr Glu Glu Ser Val Ala Lys Phe Ala Arg Arg Arg Leu
130 135 140

Gly Pro Glu Val Leu Asp Tyr Leu Val Glu Pro Phe Val Ala Gly Ile
145 150 155 160

Phe Ala Gly Asp Pro Glu Gln Leu Ser Val Arg Tyr Ala Phe Pro Lys
165 170 175

Leu Phe Glu Leu Glu Gln Gln Tyr Gly Ser Leu Phe Trp Gly Leu Ile
180 185 190

Arg Asp Arg Met Lys Gln Arg Tyr His Pro Ala Pro Arg Arg Ser Met
195 200 205

Phe Ser Phe Val Glu Gly Leu His Met Leu Pro Arg Ala Leu Ala Asp
210 215 220

Arg Leu Pro Ala His Ala Ile Val Arg Asn Ala Glu Val Leu Ala Ile
225 230 235 240

Arg Trp Asp Glu Lys Asn Pro Trp Thr Leu Thr Phe Arg Gln His Gly
245 250 255

Arg Ala Ser Thr Arg Phe Phe Asp Ile Ile Val Cys Ala Val Pro Leu
260 265 270

His Arg Leu Ala Gln Leu Arg Ile His Pro Pro Val Asp Arg Arg Pro
275 280 285

Leu Ser Thr Val Glu His Pro Pro Ile Ala Leu Val Ala Leu Gly Phe
290 295 300

Arg Arg Glu Gln Val Ala His Pro Leu Asp Gly Phe Gly Met Leu Val
305 310 315 320

Pro Ala Val Glu Arg Asp Phe Gln Ile Leu Gly Thr Leu Phe Ser Ser
325 330 335

Ser Leu Phe Pro Asp Arg Ala Pro Glu Gly His Val Leu Leu Thr Thr
340 345 350

Phe Val Gly Gly Met Arg His Pro Glu Leu Ala Leu Leu Pro Glu Asp
355 360 365

Arg Leu Glu Ala Leu Val Leu Gln Asp Leu Arg Arg Leu Leu Gly Ile
370 375 380

Ser Gly Ala Pro Val Phe Arg His Val Trp Arg Trp Glu Arg Ser Ile
385 390 395 400

Pro Gln Tyr Arg Leu Gly Tyr Asp Ala Val Leu Ala Cys Val His Asp
405 410 415

Val Glu Met Ser Arg Ser Gly Leu Phe Leu Ala Gly Asn Tyr Met Glu
420 425 430

Gly Ile Ser Val Ile Asp Ala Leu His Thr Gly Leu Lys Ala Ala Arg
435 440 445

Ala Ile Ile Gln His Leu Arg Glu Glu Ala Ala Gly Gly Leu Ala Lys
450 455 460

Leu Val Leu Gly Asp
465

<210> SEQ ID NO 56
<211> LENGTH: 453
<212> TYPE: PRT
<213> ORGANISM: Caldithrix abyssi

<400> SEQUENCE: 56

Met Thr Val Ala Val Ile Gly Ala Gly Ile Ser Gly Leu Thr Thr Ala
1 5 10 15

Tyr Tyr Leu Lys Gln Gln Gly Val Asp Val Gln Val Phe Glu Lys Asn
20 25 30

Asn Tyr Ile Gly Gly Ser Val Ile Thr Glu Lys Lys Asp Gly Phe Leu
35 40 45

Ile Asp Leu Gly Pro Asn Ser Thr Leu Glu Thr Ser Gln Val Leu Arg
50 55 60

Gln Leu Ile Asp Gln Ile Gly Leu Gln Ser Gln Lys Val Tyr Ala Ser
65 70 75 80

Asp Val Ser Asn Lys Arg Tyr Val Val Arg Asp Gly Leu Leu His Ala
85 90 95

Leu Pro Leu Ser Pro Pro Ala Phe Ile Lys Thr Lys Leu Phe Ser Trp
100 105 110

Lys Ala Lys Leu Gln Leu Leu Lys Glu Pro Phe Leu Pro Lys Val Glu
115 120 125

Val Asp Asp Ile Ser Leu Ala Asp Tyr Val Arg Tyr Arg Leu Gly Asp 130 135 140

Glu Phe Leu Asp Tyr Ala Ile Asn Pro Phe Val Ala Gly Val Tyr Ala
145 150 155 160

Gly Asp Pro Glu Gln Leu Ser Ala Pro Ala Ala Phe Pro Lys Leu Tyr
165 170 175

Asn Leu Glu Gln Asn Tyr Gly Ser Phe Ile Lys Gly Ala Ile Lys Gly
180 185 190

Lys Arg Glu Arg Lys Lys Arg Gln Glu Val Ala Lys Asp Arg Ala Lys
195 200 205

Met Phe Ser Phe Leu Asp Gly Met Gln Val Phe Pro Gln Ala Leu Ala
210 215 220

Arg Gln Leu Gly Glu Val Ile His Leu Asn Cys Glu Val Arg Glu Val
225 230 235 240

Ile Pro His Gly Lys Gly Phe Lys Val Val Leu Glu Gln Asp Ser Gly
245 250 255

Glu Gln Glu Cys Phe Phe Glu Arg Val Val Ile Ser Val Pro Thr Tyr
260 265 270

Val Gln Ala Lys Ile Leu Asn Ser Ile Leu Lys Glu Arg Ala Ala Leu
275 280 285

Leu Ala Asp Val Leu His Pro Pro Ile Ala Val Val Phe Met Gly Phe
290 295 300

Lys Arg Asp Asp Val Ala His Ala Leu Asp Gly Phe Gly Phe Leu Leu
305 310 315 320

Pro Ala Lys Glu Lys Lys Gln Ile Leu Gly Ser Ile Phe Ser Ser Thr
325 330 335

Ile Phe Pro Gln Arg Ala Pro Gln Gly Lys Val Ala Phe Thr Thr Phe
340 345 350

Val Gly Gly Met Arg Asn Pro Asp Asn Ala Leu Lys Asp Asp Glu Glu
355 360 365

Ile Lys Glu Leu Val Leu Lys Asp Leu Asn Asp Leu Val Gly Leu His
370 375 380

Gly Gln Pro Val Leu Thr Arg Ile Arg Arg Trp Pro Arg Ala Ile Pro
385 390 395 400

Gln Tyr Thr Leu Gly Tyr Lys Lys Ile Gln Ala Leu Phe Asp Glu Leu
405 410 415

Glu Gln Glu Phe Ser Gly Leu Phe Phe Ala Gly Asn Phe Arg Arg Gly
420 425 430

Ile Ser Val Gly Asp Ser Val Leu Ser Ala Phe Glu Thr Ser Glu Lys
435 440 445

Met Leu Lys Glu Lys
450

<210> SEQ ID NO 57
<211> LENGTH: 467
<212> TYPE: PRT
<213> ORGANISM: Opitutus terrae

<400> SEQUENCE: 57

Met Ser Thr Ser Pro Phe Asn Pro Ser Ala Thr Ala Ser Gly Arg Pro
1 5 10 15

Pro Lys Thr Phe Ala Val Leu Gly Ala Gly Ile Thr Gly Leu Thr Ala
20 25 30

Ala His Arg Leu Thr Gln Leu Gly His Lys Val Arg Val Phe Glu Gln
35 40 45

```
Ser Asp Arg Val Gly Gly Ser Ile Lys Thr Glu Glu Val Asp Gly Trp
    50                  55                  60

Leu Ile Glu Gly Gly Pro Asn Thr Leu Leu Ser Gly Glu Leu Ala Val
65                  70                  75                  80

Asp Lys Leu Ile Asp Glu Leu Gly Leu Asn Gly Glu Arg Ile Ala Ala
                85                  90                  95

Asp Pro Ala Ala Lys Asn Arg Tyr Ile Val Arg Arg Gly Arg Ala Leu
            100                 105                 110

Ala Ala Pro Met Ser Pro Pro Ser Phe Phe Ala Ser Ser Leu Phe Ser
        115                 120                 125

Pro Val Ala Lys Phe Lys Leu Leu Ala Glu Leu Phe Ala Arg Arg Arg
    130                 135                 140

Val Arg Thr Thr Asp Val Ser Leu Ala Glu Phe Val Glu Ser His Phe
145                 150                 155                 160

Gly Arg Glu Phe Val Asp Tyr Ala Leu Asn Pro Phe Val Gly Gly Val
                165                 170                 175

Tyr Ala Gly Asp Pro Glu Lys Leu Ser Ala Arg Gln Ser Phe Pro Lys
            180                 185                 190

Leu Trp Glu Ile Glu Gln Thr His Gly Ser Leu Ile Arg Gly Gln Ile
        195                 200                 205

Ala Ala Ala Lys Ala Arg Lys Ala Arg Gly Glu Pro Arg Pro Gly Ile
    210                 215                 220

Phe Ser Phe Lys His Gly Leu His Val Leu Pro Glu Ala Leu Ala Ala
225                 230                 235                 240

Arg Leu Pro Ala Gly Ala Ile Thr Leu Gly Ala Ser Leu Asp Ala Ile
                245                 250                 255

Val Pro Gly Asp Lys Trp Asn Val Val Trp His Asp Asp Val Ala Thr
            260                 265                 270

His Thr Gln Ser Phe Asp Ser Val Val Val Ala Leu Pro Ala Pro Ala
        275                 280                 285

Leu Ala Arg Leu Gln Ile Gly Thr Leu Gly Glu Lys Pro Leu Ala Ala
    290                 295                 300

Leu Ala Leu Ile Glu His Pro Pro Val Ser Ser Leu Phe Leu Gly Phe
305                 310                 315                 320

Arg Arg Glu Gln Val Ala His Pro Leu Asp Gly Phe Gly Val Leu Val
                325                 330                 335

Pro Ala Val Glu Lys Arg Ser Val Leu Gly Val Leu Phe Ser Ser Ser
            340                 345                 350

Leu Phe Pro Gly Arg Ala Pro Leu Gly His Val Ala Leu Thr Val Met
        355                 360                 365

Val Gly Gly Thr Arg Gln Pro Gln Leu Ala Ser Leu Pro Ala Asp Gln
    370                 375                 380

Leu Leu Ala Ala Val Arg Pro Asp Leu Thr Gln Leu Leu Gly Val Ser
385                 390                 395                 400

Gly Asp Pro Val Phe Val Arg His Asn Phe Trp Pro Arg Ala Ile Pro
                405                 410                 415

Gln Tyr Asn Leu Gly His Glu His Phe Ile Ala Ala Leu Ala Ala Gly
            420                 425                 430

Glu Arg Phe His Pro Gly Leu Phe Met Gly Gly Gln Ala Arg Asp Gly
        435                 440                 445

Ile Ala Val Pro Ala Cys Ile Ala Ala Gly Glu Lys Leu Ala Glu Arg
    450                 455                 460

Ala Gly Gln
```

465

<210> SEQ ID NO 58
<211> LENGTH: 455
<212> TYPE: PRT
<213> ORGANISM: Verrucomicrobia bacterium

<400> SEQUENCE: 58

```
Met Gly Asn Pro Asn Lys Thr Ile Ala Ile Leu Gly Gly Gly Ile Thr
1               5                   10                  15

Gly Leu Thr Ala Ala Tyr Glu Leu Leu Lys Leu Gly His Lys Pro Thr
            20                  25                  30

Val Phe Glu Ser Ser Ser Arg Ile Gly Gly Ala Ile Glu Thr Ile Arg
        35                  40                  45

Gln Asn Asp Phe Leu Ala Glu Cys Gly Pro Asn Thr Leu Leu Glu Thr
    50                  55                  60

Ser Pro Arg Ile Ser Ala Leu Ile Ser Asp Leu Gly Leu Asp Ser Arg
65                  70                  75                  80

Lys Arg Tyr Ala Asn Pro Ser Met Lys Asn Arg Tyr Ile Ile Lys Gly
                85                  90                  95

Gly Lys Pro Val Pro Met Pro Leu Ser Pro Gly Gln Phe Val Thr Thr
            100                 105                 110

Lys Leu Phe Ser Leu Gly Ala Lys Leu Asn Leu Ile Lys Glu Pro Phe
        115                 120                 125

Ile Ala Pro Cys Pro Ser Glu Thr Glu Glu Ser Leu Ala Ala Phe Val
    130                 135                 140

Val Arg Arg Leu Gly Gln Glu Phe Leu Asp Tyr Ala Ile Asn Pro Phe
145                 150                 155                 160

Val Ala Gly Val Tyr Ala Gly Asp Pro Ser Lys Leu Ser Val Gln His
                165                 170                 175

Ala Phe Pro Lys Leu Tyr Ala Leu Glu Gln Gln Tyr Gly Ser Met Ile
            180                 185                 190

Lys Gly Gln Phe Phe Gly Ala Arg Glu Arg Lys Lys Arg Gly Thr Val
        195                 200                 205

Ser Lys Asp Lys Ala Lys Leu Val Ser Phe Asp Gln Gly Leu Glu Val
    210                 215                 220

Leu Val Asp Gly Leu Gly Gln Lys Ile Glu Asp Thr Ile Asn Ile Ser
225                 230                 235                 240

Thr Val Ile Glu Ser Val Glu Lys Ala Glu Glu Lys Trp Val Val Gln
                245                 250                 255

Gly Arg Lys Ile Arg Glu Ser Phe Asp Ala Val Ile Thr Ala Ile Pro
            260                 265                 270

Thr His Arg Met Thr Lys Met Thr Phe Arg Asp Glu Ser Asp Leu Asp
        275                 280                 285

Met Ser Ile Leu Arg Asp Ile Ile Tyr Pro Pro Val Ser Ser Val Val
    290                 295                 300

Met Gly Phe Arg Arg Asp Gln Ile Gln His Ser Leu Glu Gly Phe Gly
305                 310                 315                 320

Met Leu Val Pro Lys Val Glu Arg Lys Asn Ile Leu Gly Thr Ile Phe
                325                 330                 335

Ser Ser Ser Leu Phe Glu Asn Arg Ala Pro Glu Gly Tyr Val Thr Leu
            340                 345                 350

Ser Thr Tyr Ile Gly Gly Met Arg Gln Pro Asp His Ala Leu Leu Asp
        355                 360                 365
```

-continued

```
Asp Gln Glu Met Asp Arg Leu Ile Leu Lys Asp Leu Glu Ala Leu Leu
    370                 375                 380

Gly Val Arg Gly Glu Pro Ala Phe Ile Asn Arg Arg Val Trp Lys Lys
385                 390                 395                 400

Ala Ile Pro Gln Tyr Thr Val Gly Tyr Gly Lys Ile Leu Asp Arg Phe
                405                 410                 415

Asn Glu Leu Glu Ala Ala His Ser Gly Leu Phe Phe Ala Gly His Tyr
            420                 425                 430

Arg Asn Gly Ile Ser Leu Gly Asp Ser Ile Leu Ala Gly Leu Asp Val
        435                 440                 445

Ala Gln Arg Ile Asn Gln Gln
    450                 455


<210> SEQ ID NO 59
<211> LENGTH: 462
<212> TYPE: PRT
<213> ORGANISM: Ignavibacterium album

<400> SEQUENCE: 59

Met Thr Lys Thr Ile Val Val Ile Gly Ala Gly Ile Ser Gly Leu Thr
1               5                   10                  15

Thr Ala Tyr Leu Leu Ser Lys Arg Gly Phe Asn Ile Arg Ile Leu Glu
            20                  25                  30

Arg Lys Ser Glu Val Gly Gly Ser Ile Glu Ser Ile Lys Glu Asn Gly
        35                  40                  45

Phe Leu Phe Asp Arg Gly Pro Asn Ser Ala Leu Glu Thr Thr Pro Leu
    50                  55                  60

Ile Ser Gln Leu Val Glu Glu Leu Asn Leu Lys Asp Glu Leu Leu Tyr
65                  70                  75                  80

Ala Asn Lys Ala Ala Asn Lys Arg Tyr Ile Leu Arg Asn Asn Glu Leu
                85                  90                  95

His Ala Leu Pro Met Ser Pro Pro Ala Leu Ile Lys Thr Lys Leu Phe
            100                 105                 110

Ser Ala Lys Ala Lys Leu Arg Leu Leu Thr Glu Pro Phe Ile Gly Arg
        115                 120                 125

Ser Glu Asp Gly Tyr Tyr Gln Ser Leu Ala Glu Phe Val Arg Arg Arg
    130                 135                 140

Leu Gly Gln Glu Phe Leu Asp Tyr Ala Ile Asn Pro Phe Val Ala Gly
145                 150                 155                 160

Val Tyr Ala Gly Lys Pro Glu Glu Leu Ser Val Lys Ser Ala Phe Pro
                165                 170                 175

Lys Leu Tyr Ala Leu Glu Glu Lys Phe Gly Gly Leu Ile Ile Gly Thr
            180                 185                 190

Ile Arg Ser Ile Arg Glu Arg Lys Lys Arg Ala Glu Lys Ser Lys Gln
        195                 200                 205

Ser Ala Arg Met Leu Ser Phe Lys Ser Gly Met Ile Ser Leu Pro Lys
    210                 215                 220

Ala Ile Ala Asn Tyr Phe Ala Asp Lys Leu Ile Leu Ser Ala Glu Val
225                 230                 235                 240

Ile Ser Val Asp Lys Thr Ala Glu Gly Phe Ile Val Ser Tyr Arg His
                245                 250                 255

Ser Gly Ile Asp Glu Ala Ile Val Cys Asp Ala Val Leu Ser Thr Val
            260                 265                 270

Pro Ser Tyr Val Ala Gly Asn Leu Phe Ser Lys Phe Asp Lys Lys Phe
        275                 280                 285
```

```
Lys Val His Ser Asp Glu Ile Tyr Tyr Pro Pro Val Leu Val Tyr Phe
    290                 295                 300

Leu Ala Tyr Glu Lys Lys Asn Ile Gly Gln Thr Leu Asp Gly Phe Gly
305                 310                 315                 320

Phe Leu Ile Pro Glu Lys Glu Asn Lys Ser Phe Leu Gly Ala Leu Trp
                325                 330                 335

Ser Ser Val Ile Phe Pro Tyr Arg Ala Asp Asn Asn Phe Ala Thr Phe
            340                 345                 350

Thr Leu Phe Ile Gly Gly Ser Arg Tyr Pro Asp Phe Val Lys Glu Asp
        355                 360                 365

Arg Asn Lys Leu Leu Glu Lys Val Arg Lys Glu Phe Glu Gln Leu Met
    370                 375                 380

Lys Ile Lys Ser Asp Pro Val Phe Ser Ala Tyr Arg Phe Trp Glu Lys
385                 390                 395                 400

Ala Ile Pro Gln Tyr Asn Ile Gly Tyr Ile Glu His Glu Arg Phe Phe
                405                 410                 415

Asp Glu Phe Glu Lys Gln Asn Pro Gly Leu Phe Ile Ser Gly Asn Phe
            420                 425                 430

Arg Gly Gly Ile Ser Val Gly Asp Cys Ile Lys Asn Ala Glu Leu Val
        435                 440                 445

Ala Asn Lys Ile Cys Val Gln Phe Thr Met His Asn Val Gln
    450                 455                 460


<210> SEQ ID NO 60
<211> LENGTH: 457
<212> TYPE: PRT
<213> ORGANISM: Coraliomargarita spec

<400> SEQUENCE: 60

Met Glu Lys Lys Ala Ile Val Ile Gly Ala Gly Ile Ser Gly Leu Cys
1               5                   10                  15

Ala Ala Ile Glu Leu Lys Lys Ser Gly Phe Asn Val Thr Val Val Glu
            20                  25                  30

Lys Arg Glu Arg Ala Gly Gly Val Ile Gly Thr Thr Ala Arg Asp Gly
        35                  40                  45

Phe Arg Ala Glu Ser Gly Ser Asn Thr Val Met Val Asn Ser Gln Lys
    50                  55                  60

Thr Leu Asp Phe Leu Met Glu Ile Gly Leu Lys Asp Lys Ile Val Asn
65                  70                  75                  80

Ser Ser Pro Ala Ala Lys Lys Arg Phe Phe Ala Arg Tyr Gly Lys Pro
                85                  90                  95

Gln Ala Val Pro Met Gly Pro Leu Gln Leu Leu Thr Thr Arg Leu Phe
            100                 105                 110

Ser Phe Ala Gly Lys Leu Arg Met Leu Cys Glu Pro Phe Ile Lys Pro
        115                 120                 125

Pro Ser Gln Asp Ser Asp Pro Ser Val Ala Asp Phe Thr Ala Glu Arg
    130                 135                 140

Phe Gly Arg Glu Val Leu Asp Tyr Ala Met Asn Pro Phe Met Ala Gly
145                 150                 155                 160

Ile Tyr Gly Ala Asp Pro Glu Lys Leu Ser Ile Lys His Ala Phe Pro
                165                 170                 175

Pro Phe Trp Asn Leu Ala Ile Lys Tyr Gly Ser Val Ile Lys Gly Ala
            180                 185                 190

Met Lys Ala Arg Arg Glu Lys Met Ala Ala Gly Asn Phe Phe Lys Pro
```

-continued

```
        195                 200                 205

Val Met Ile Ser Phe Lys Ser Gly Met His Thr Leu Thr Asp Ala Leu
    210                 215                 220

Ala Ala Glu Leu Gly Asp Ser Val Lys Cys Gly Ala Lys Val Ile Ser
225                 230                 235                 240

Ile Asp Ser Asn Cys Asp Gly Trp Glu Val Ser Trp Gly Thr Glu Thr
                245                 250                 255

Glu Asp Val Cys Glu Asn Tyr Asp Ala Leu Val Val Ala Val Pro Ala
            260                 265                 270

Pro Glu Ile Ser Gly Leu Pro Phe Gly Gly Met Leu Ala Ala Ala Leu
        275                 280                 285

Ala Pro Leu Ala Lys Ile Gln Tyr Ala Pro Val Ala Thr Tyr Thr Met
    290                 295                 300

Gly Phe Lys Arg Gln Asp Val Ser His Pro Leu Asp Gly Phe Gly Val
305                 310                 315                 320

Leu Thr Pro Lys Lys Glu Asn Phe Ser Ile Leu Gly Ser Leu Phe Val
                325                 330                 335

Ser Thr Leu Phe Asp Asp Arg Ala Pro Asp Gly Tyr Ile Ala Leu Thr
            340                 345                 350

Asn Tyr Val Gly Gly Met Arg His Pro Glu Phe Ala Ala Leu Glu Arg
        355                 360                 365

Gly Glu Met Arg Lys Leu Val Leu Glu Asp Leu Lys Lys Leu Leu Gly
    370                 375                 380

Val Asn Gly Glu Pro Val Phe Glu Glu Leu Phe Val Trp Lys Asn Ala
385                 390                 395                 400

Ile Ala Gln Tyr Asn Val Gly Tyr Gln Glu Tyr Leu Asp Ile Met Asp
                405                 410                 415

Asp Ile Glu Lys Arg Ile Pro Asn Ile Ala Leu Val Gly Ala Tyr Arg
            420                 425                 430

Gly Gly Val Gly Val Ser Ser Cys Leu Glu Asn Gly Leu Leu Ser Ala
        435                 440                 445

Ala Lys Leu Ala Gly Arg Ile Ser Asp
    450                 455


<210> SEQ ID NO 61
<211> LENGTH: 465
<212> TYPE: PRT
<213> ORGANISM: Salisaeta longa

<400> SEQUENCE: 61

Met Ala Arg Ile Gly Ile Ile Gly Ala Gly Ile Ala Gly Leu Thr Ala
1               5                   10                  15

Ala Tyr Gln Leu Gln Gln Gln Gly His Met Val Arg Val Trp Glu Ala
            20                  25                  30

Arg Gly Val Ala Gly Gly Ala Ile Arg Ser Glu Arg Thr Ser Asp Gly
        35                  40                  45

Phe Leu Val Glu His Gly Pro Asn Ser Leu Arg Ala Thr Thr Pro Ile
    50                  55                  60

Val Pro Arg Leu Leu Glu Asp Leu Gly Leu Glu Arg Ala Arg Leu Ser
65                  70                  75                  80

Ala Ala Pro Ala Ala Thr Lys Arg Phe Ile Val Arg Asp Gly Thr Leu
                85                  90                  95

Arg Pro Leu Pro Leu Ser Pro Pro Ala Leu Leu Thr Thr Ser Leu Leu
            100                 105                 110
```

-continued

```
Ser Thr Arg Ala Lys Leu Arg Leu Leu Arg Glu Pro Phe Val Ala Ala
        115                 120                 125

Gly Ala Pro Thr Ala Asp Glu Thr Val Ala Ser Phe Val Arg Arg Arg
    130                 135                 140

Leu Gly Pro Glu Val Leu Ala Tyr Ala Val Asp Pro Phe Val Ala Gly
145                 150                 155                 160

Ile Phe Ala Gly Asp Pro His Arg Leu Ser Leu Lys His Ala Phe Gly
                165                 170                 175

Arg Leu Tyr Glu Met Glu Arg Thr His Gly Ser Leu Leu Arg Ala Ala
            180                 185                 190

Leu His Ser Ala Arg Thr Gly Ala Thr Asp Asp Ala Ser Thr Ala Thr
        195                 200                 205

Asp Arg Arg Ile Phe Ser Leu Arg Asp Gly Leu Gln Met Leu Pro His
    210                 215                 220

Ala Leu Ala Asp Ala Leu Gly Glu Ala Ile Arg Tyr Glu Ala Pro Val
225                 230                 235                 240

Thr Ala Leu Arg Gln Met Pro Asp Gly Thr Trp Thr Val Ala Thr Glu
                245                 250                 255

Thr Asp Ala Thr Gln Val Asn Ala Leu Ile Ser Thr Val Pro Leu His
            260                 265                 270

Ala Leu Gly Ser Ile Asp Trp Ala Pro Ala Val Asp Thr Ser Pro Leu
        275                 280                 285

Gln Arg Val Pro Tyr Pro Pro Val Arg Val Val Ala Leu Gly Phe Arg
    290                 295                 300

Arg Ala Asp Val Ala His Pro Leu Asp Gly Phe Gly Met Leu Val Pro
305                 310                 315                 320

Ser Ala Glu Asp Gln Phe Gln Ile Leu Gly Thr Leu Val Ser Ser Thr
                325                 330                 335

Leu Phe Pro Gly Arg Ala Pro Ala Gly His Val Leu Leu Thr Thr Phe
            340                 345                 350

Val Gly Gly Met Arg His Pro Thr Leu Gly Ala Ala Ser Asp Ala Ala
        355                 360                 365

Val Arg Lys Val Val Leu Asn Asp Leu Gln Ala Leu Leu Gly Val Gln
    370                 375                 380

Gly Ala Pro Val Phe Glu Arg Phe Ile Ala Trp Pro Arg Ala Ile Pro
385                 390                 395                 400

Gln Tyr Thr Leu Asn His Gly Ala Ala Val Arg Thr Leu Glu Gln Leu
                405                 410                 415

Glu Asp Val His Pro Gly Leu Phe Phe Ala Gly Asn Tyr Arg Asp Gly
            420                 425                 430

Ile Ser Val Gly Asp Ala Met Ala Ser Gly Glu Asp Ala Ala Arg Arg
        435                 440                 445

Val Asp Ala His Leu Ala Gly Ala Asp Arg Ala Val Ala Ala Thr Gly
    450                 455                 460

Pro
465
```

<210> SEQ ID NO 62
<211> LENGTH: 179
<212> TYPE: PRT
<213> ORGANISM: Ambrosia artemisiifolia

<400> SEQUENCE: 62

```
Met Ala Ser Pro Thr Ile Val Asp Asn Gln Lys Pro Ala Lys Arg Val
1               5                   10                  15
```

Ala Ile Val Gly Ala Gly Val Ser Gly Cys Ala Ala Ala Tyr Lys Leu
20 25 30

Lys Leu His Gly Leu Asn Val Thr Val Phe Glu Ala Asp Glu Arg Val
35 40 45

Gly Gly Lys Pro Arg Ser Val Ser Gln Asp Gly Leu Ile Trp Asp Glu
50 55 60

Gly Ala Asn Thr Met Thr Glu Ser Glu Ala Asp Ala Ser Ser Leu Ile
65 70 75 80

Asp Glu Leu Gly Leu Arg Asp Lys Gln Gln Phe Pro Ile Ser Gln His
85 90 95

Lys Arg Tyr Ile Val Arg Asn Gly Lys Pro Val Leu Ile Pro Ser Asn
100 105 110

Pro Ile Ala Leu Ile Arg Ser Ser Phe Leu Ser Thr Gln Ser Lys Val
115 120 125

Gln Ile Leu Leu Glu Pro Phe Leu Trp Lys Lys Thr Lys Ser Ser Asp
130 135 140

Glu Pro Glu Ser Val Gly Gly Phe Phe Gln Arg His Phe Gly Lys Glu
145 150 155 160

Val Val Glu Tyr Leu Ile Asp Pro Val Val Ala Gly Thr Ser Gly Gly
165 170 175

Asp Pro Lys

<210> SEQ ID NO 63
<211> LENGTH: 451
<212> TYPE: PRT
<213> ORGANISM: Melioribacter roseus

<400> SEQUENCE: 63

Met Ser Lys Lys Ile Val Val Leu Gly Ala Gly Ile Ser Gly Leu Ser
1 5 10 15

Thr Ala Tyr Trp Leu Val Lys Lys Gly Tyr Asp Val Thr Ile Leu Glu
20 25 30

Thr Lys Asn Glu Pro Gly Gly Ser Met Ile Ser Arg Arg Leu Asp Asn
35 40 45

Phe Leu Ile Asp Tyr Gly Pro Asn Ser Gly Leu Glu Thr Thr Pro Leu
50 55 60

Ile Arg Lys Leu Val Glu Glu Val Asn Leu Ser Asp Lys Met Ile Tyr
65 70 75 80

Ala Asn Ala Ala Ala Ser Lys Arg Tyr Ile Leu Lys Asn Gly Glu Leu
85 90 95

Ile Pro Leu Pro Met Ser Pro Gly Ser Phe Ile Arg Thr Lys Leu Phe
100 105 110

Ser Ser Gly Ala Lys Phe Arg Leu Met Ala Glu Pro Phe Val Ser Lys
115 120 125

Ser Asp Asp Gly Tyr Tyr Gln Ser Ile Ala Glu Phe Val Arg Arg Arg
130 135 140

Leu Gly Asn Glu Phe Leu Asp Tyr Ala Ile Asp Pro Phe Val Ser Gly
145 150 155 160

Val Phe Ala Gly Asp Pro Glu Lys Leu Ser Val Lys Ser Ala Phe Pro
165 170 175

Lys Leu Tyr Arg Leu Glu Glu Val Tyr Gly Gly Leu Ile Lys Gly Met
180 185 190

Ile Lys Gly Ala Arg Glu Arg Lys Gln Arg Asn Glu Glu Ser Lys Gln
195 200 205

```
Ser Ala Lys Met Phe Ser Phe Leu Glu Gly Met Gln Ser Leu Pro Asn
    210                 215                 220

Ala Ile Ala Asp Lys Leu Lys Asp Asn Ile Val Phe Ser Ala Lys Val
225                 230                 235                 240

Leu Asn Val Thr Gly Ala Asn Asp Lys Gln Trp Lys Val Thr Tyr Glu
                245                 250                 255

Leu Asn Gly Asn Arg Glu Ser Ile Thr Ala Asp Thr Val Ile Ser Thr
            260                 265                 270

Leu Pro Ala Tyr Ile Ala Ala Gly Val Phe Gly Glu Leu Asp Gln Lys
        275                 280                 285

Leu Ala Glu Arg Leu Asn Ser Ile Tyr Tyr Pro Pro Val Met Val Leu
    290                 295                 300

Tyr Leu Gly Tyr Asn Lys Lys Asp Ile Lys Arg Lys Leu Asp Gly Phe
305                 310                 315                 320

Gly Phe Leu Ile Pro Ser Lys Glu Lys Lys His Phe Leu Gly Ala Ile
                325                 330                 335

Trp Ser Ser Ser Ile Phe Pro Gly Arg Ser Pro Glu Asp Met Ala Ala
            340                 345                 350

Phe Thr Leu Phe Val Gly Gly Ala Arg Ser Pro Gln Leu Phe Glu Met
        355                 360                 365

Glu Lys Ser Asp Leu Ile Lys Lys Val Leu Ser Glu Phe His Gln Ile
    370                 375                 380

Met Asn Ile Lys Gly Glu Pro Val Leu Ile Glu Asn Lys Leu Trp Gln
385                 390                 395                 400

Lys Ala Ile Pro Gln Tyr Asn Leu Gly Tyr Ile Glu His Glu Lys Tyr
                405                 410                 415

Phe Glu Val Phe Glu Glu Asn His Arg Gly Ile Tyr Leu Arg Gly Asn
            420                 425                 430

Tyr Arg Gly Gly Ile Ser Val Gly Asp Cys Ile Lys Asn Ser Glu Leu
        435                 440                 445

Glu Ile Lys
    450


<210> SEQ ID NO 64
<211> LENGTH: 472
<212> TYPE: PRT
<213> ORGANISM: Halothiobacillus neapolitanus

<400> SEQUENCE: 64

Met Asn Thr His Ser Asn Ala Ser Glu Pro Ile Asn Cys Pro Tyr Leu
1               5                   10                  15

Val Ile Gly Gly Gly Ile Ser Gly Leu Ala Thr Ala Tyr His Leu Ser
            20                  25                  30

Arg Met Gly Lys Thr Val Thr Val Leu Glu Ala Thr Ser Arg Val Gly
        35                  40                  45

Gly Ala Val Gly Ser Ile Glu Glu Asp Gly Trp Leu Arg Glu Leu Gly
    50                  55                  60

Pro Asn Ser Leu Val Gln Thr Pro Glu Met Ala Ala Leu Met Ser Ala
65                  70                  75                  80

Leu Asp Leu Val Ser Glu Ile Ile Glu Ala Asn Thr Val Ala Lys Lys
                85                  90                  95

Arg Phe Val Ala Lys Asn Gly His Pro Val Ala Leu Pro Gly Ser Pro
            100                 105                 110

Leu Glu Leu Leu Thr Ser Pro Leu Phe Ser Met Gly Asp Leu Trp His
```

```
        115                 120                 125

Leu Ala Arg Glu Ala Trp Ile Lys Pro Val Asn Lys Glu Glu Thr Ile
    130                 135                 140

Ala Glu Phe Val Arg Arg Arg Leu Gly Gln Gly Phe Leu Asp Trp Ala
145                 150                 155                 160

Val Asp Pro Phe Val Ser Gly Val Tyr Ala Gly Asp Pro Asn Arg Leu
                165                 170                 175

Ser Val Gln Ala Ala Ile Pro Lys Ile Tyr Ala Phe Glu Gln Glu Ser
            180                 185                 190

Gly Ser Leu Ile Arg Gly Gly Ile Ala Lys Met Lys Ala Ala Lys Ala
        195                 200                 205

Asn Pro Ala Pro Val Thr Leu Pro Ala Lys Gly Lys Leu Phe Ser Phe
    210                 215                 220

Lys Arg Gly Leu Gln Thr Leu Thr Asp Ala Leu Ala Thr Ala Ile Thr
225                 230                 235                 240

Ser Ser Gly Arg Gly Asn Ile Gln Leu Asp Ser Ala Ile Thr Asn Ile
                245                 250                 255

Gln Arg Leu Pro Glu Gly Gly Trp Ser Val Lys Thr Val Gln Gly Lys
            260                 265                 270

Thr Phe His Thr Arg Gln Leu Ile Leu Ser Thr Pro Ala His Val Ser
        275                 280                 285

Ala Gln Leu Leu Gly Glu Val Asp Gly Pro Leu Ala Glu Thr Leu Ala
    290                 295                 300

Ala Ile Glu Tyr Pro Pro Val Thr Ser Val Val Met Gly Phe Asp Arg
305                 310                 315                 320

Ser Glu Val Ala His Pro Leu Asp Gly Phe Gly Leu Leu Leu Pro Ser
                325                 330                 335

Lys Glu Lys Lys Arg Thr Leu Gly Val Leu Phe Ser Ser Thr Leu Phe
            340                 345                 350

Pro Asp Arg Thr Pro Ala Gly Lys Val Leu Leu Ser Ala Phe Ile Gly
        355                 360                 365

Gly Arg Lys His Pro Glu Ala Ala Gln Gly Asp Asp Gln Glu Leu Leu
    370                 375                 380

Asp Arg Val Leu Gly Asp Leu Ser Pro Leu Leu Gly Ile Lys Gly Lys
385                 390                 395                 400

Pro Glu Phe Leu Arg Val Lys Arg Trp Gln Gln Ala Ile Pro Gln Tyr
                405                 410                 415

Glu Ile Gly Tyr Leu Glu Leu Gln Glu Lys Ile Ser Gln Arg Leu Thr
            420                 425                 430

Ala Leu Pro Gly Leu Ser Leu Asn Gly Asn Trp Arg Gly Gly Ile Ala
        435                 440                 445

Val Gly Asp Cys Leu Asn Asn Gly Asn Lys Leu Ala Glu Arg Leu Ile
    450                 455                 460

Glu Asn Thr Arg Thr Glu Glu Ser
465                 470


<210> SEQ ID NO 65
<211> LENGTH: 480
<212> TYPE: PRT
<213> ORGANISM: Chondrus crispus

<400> SEQUENCE: 65

Met Pro Glu Pro Val Lys Arg Asn Val Ala Val Leu Gly Gly Gly Pro
1               5                   10                  15
```

-continued

```
Ala Gly Leu Ser Ala Ala Phe Arg Leu Leu His Asp Leu Pro Pro Gly
            20                  25                  30

Leu Ser Val Lys Val Asp Leu Tyr Glu Ala Thr Gly Arg Leu Gly Gly
        35                  40                  45

Ala Val Thr Ser Ala Cys Asp Ala Gly Phe Cys Tyr Glu Leu Gly Pro
    50                  55                  60

Asn Ser Met Asn Ala Lys His Pro Ser Val Ala Asp Leu Ile Gln Glu
65                  70                  75                  80

Lys Leu Arg Leu Lys Pro Arg Met Leu Pro Arg Ser Pro Tyr Ala Lys
                85                  90                  95

Arg Tyr Tyr Phe Met Arg Asp Gly Lys Leu Val Pro Leu Pro Leu Ser
            100                 105                 110

Pro Leu His Phe Ala Thr Thr Gly Leu Leu Ser Trp Arg Ala Lys Trp
        115                 120                 125

His Val Val Lys Glu Pro Phe Val Ala Arg Leu Gln Asp Val Arg Asp
    130                 135                 140

Ser His Met Glu Ser Val Ala Ser Phe Phe Gln Arg Arg Phe Gly Arg
145                 150                 155                 160

Glu Val Val Asp Tyr Leu Val Asp Pro Met Val Ala Gly Thr Tyr Ser
                165                 170                 175

Gly Lys Pro Ala Asp Leu Ser Met Lys His Ala Leu Arg Lys Val Trp
            180                 185                 190

Arg Leu Glu Gln Lys His Gly Ser Val Ile Gly Ala Leu Leu Arg Gly
        195                 200                 205

Ala Gly Lys Thr Lys Pro Asp Pro Arg Tyr Lys Pro Tyr Thr Gly Lys
    210                 215                 220

Glu Leu Arg Ala Ser Phe Thr Tyr Asp Lys Gly Met Glu Val Val Thr
225                 230                 235                 240

Asp Ala Leu Val Ala Asn Ile Asn Asp Leu Asn Pro Arg Gly Gly Arg
                245                 250                 255

Leu Tyr Thr His Gly Lys Val Arg Thr Leu Asp Arg Asp Pro Asn Gly
            260                 265                 270

Ala Trp Arg Ile Asn Gly Arg Gly Lys Tyr Asp Ala Val Ile Ser Thr
        275                 280                 285

Ile Pro Thr His Ala Val Lys Ser Ile Tyr Thr Asn Met Ser Ala Leu
    290                 295                 300

Gly Lys Gly Phe Lys Lys Leu Asn Lys Ser Ile Lys Tyr Ala Pro Val
305                 310                 315                 320

Ser Val Val Val Met Gly Phe Asp Lys Ser Gln Val Pro His Pro Leu
                325                 330                 335

Asp Gly Phe Gly Ala Leu Ile Pro Thr Val Glu Gly Arg Gln Ile Leu
            340                 345                 350

Gly Ile Asn Phe Ser Ser Ser Asn Tyr Pro Gln Arg Leu Ser Asp Pro
        355                 360                 365

Asp Lys Val Phe Leu Thr Val Tyr Val Gly Gly Gln Arg Asn Pro Asp
    370                 375                 380

Leu Pro Phe Arg Arg Ala Lys Glu Ile Val Asp Ile Ser Lys Lys Glu
385                 390                 395                 400

Leu Gly His Val Leu Gly Val Lys Gly Asp Pro Phe Phe Ser Arg Val
                405                 410                 415

Lys Thr Trp Lys Arg Gly Ile Pro Gln Tyr Asp Pro Gln Phe Asp Glu
            420                 425                 430

Ser Leu Cys Thr Met Ala Arg Ala Glu Lys Ser Ala Lys Gly Phe Val
```

```
        435                 440                 445

Phe Gly Gly Asn Tyr Arg Asp Gly Val Gly Leu Pro Asp Ala Leu Arg
    450                 455                 460

Ser Gly Ile Leu Ser Ala Glu Lys Thr Leu Gln Tyr Leu Lys Thr Leu
465                 470                 475                 480


<210> SEQ ID NO 66
<211> LENGTH: 463
<212> TYPE: PRT
<213> ORGANISM: Rubritalea marina

<400> SEQUENCE: 66

Met Arg Lys His Ile Ala Ile Ile Gly Ala Gly Val Ser Gly Leu Ser
1               5                   10                  15

Thr Ala Tyr His Leu Gln Gln Ala Gly His Ser Val Val Val Phe Glu
            20                  25                  30

Ser Ser Lys Arg Ala Gly Gly Val Ile Gln Thr Ile Arg Glu Asp Asp
        35                  40                  45

Tyr Leu Cys Glu Trp Gly Pro Asn Ser Leu Met Ile Gly Asp Lys Arg
    50                  55                  60

Ile Glu Ala Leu Leu Lys Ser Ile Gly Leu Asp Asp Glu Ile Leu Glu
65                  70                  75                  80

Ala Asn Thr Ala Ser Lys Lys Arg Phe Ile Ile Asp Arg Asp Arg Leu
                85                  90                  95

Gln Ala Leu Pro Asn Gly Pro Phe Gln Leu Leu Gly Ser Pro Ile Phe
            100                 105                 110

Ser Leu Lys Ala Lys Leu Arg Leu Leu Lys Glu Pro Trp Val Lys Arg
        115                 120                 125

His Pro Ala Asn Ser Lys Glu Thr Leu Ala Asp Phe Met Glu Arg Arg
    130                 135                 140

Leu Gly Pro Glu Pro Val Ala Lys Leu Val Asn Pro Phe Ile Ser Gly
145                 150                 155                 160

Ile Tyr Ala Gly Asp Pro Lys Arg Leu Ala Val Glu His Ala Phe Pro
                165                 170                 175

Lys Leu Phe Gln Leu Glu Gln Asp Tyr Gly Ser Leu Ile Trp Gly Met
            180                 185                 190

Ile Arg Ser Lys Lys Asp Gln Lys Asn Ser Phe Lys Ser Lys His Lys
        195                 200                 205

Leu Gln Lys Arg Arg Ile Val Ser Phe Lys Gln Gly Met Glu Ala Leu
    210                 215                 220

Pro Gln Ala Met Ala Ala Ala Leu Asp Glu Gly Thr Leu Ile Phe Glu
225                 230                 235                 240

Ala Lys Ile Gly Gly Ile Ser Gln Asn Arg Asn Asn Lys Arg Trp His
                245                 250                 255

Met Asp Trp Lys Cys Pro Asn Gly Thr Ile Gly Gln Gly Ser Phe Asp
            260                 265                 270

Ala Val Ile Leu Thr Gln Ala Ser His His Leu Asn Asp Ile Pro Leu
        275                 280                 285

Asp Glu Glu Val Leu Glu Ser Leu Ser Lys Leu Pro Ser Ile Asp His
    290                 295                 300

Ala Pro Val Thr Ser Met Leu Leu Gly Phe Lys Arg Glu Gln Ile Lys
305                 310                 315                 320

His Pro Leu Asp Gly Phe Gly Met Leu Ser Thr Phe Glu Gln Lys Ser
                325                 330                 335
```

Lys Met Leu Gly Ala Leu Phe Thr Ser Ser Leu Phe Pro Gly Arg Ala
340 345 350

Pro Glu Gly His Val Ala Ile Asn Val Met Ile Gly Gly Val Arg Arg
355 360 365

Pro Glu Leu Cys Glu Leu Pro Glu Pro Thr Leu Arg Ala Asn Ile Leu
370 375 380

Asp Glu Leu Arg Arg Leu Leu Gly Val Asp Gly Lys Pro Ser Phe Cys
385 390 395 400

His Ile His His Thr Ser Lys Ala Ile Pro Gln Leu His Thr Asp Tyr
405 410 415

Gly Ile Val Ala Gln Gln Ile Ile Asp Cys Glu Arg Glu His Pro Gly
420 425 430

Leu Tyr Leu Ala Gly Ser Tyr Arg Asn Gly Ile Ala Leu Pro Asp Arg
435 440 445

Leu Leu Glu Gly Ile Ser Leu Thr Glu Lys Ile Asn Gln Ser Leu
450 455 460

<210> SEQ ID NO 67
<211> LENGTH: 457
<212> TYPE: PRT
<213> ORGANISM: Acidobacteria bacterium

<400> SEQUENCE: 67

Met Gly Val Glu Val Ala Ile Ile Gly Ala Gly Ile Ser Gly Leu Ser
1 5 10 15

Val Ala Phe Phe Leu Lys Arg Ala Gly Ala Gly Val Leu Val Leu Glu
20 25 30

Ala Glu Glu Asp Val Gly Gly Thr Met Arg Ser Arg Arg Phe Lys Gly
35 40 45

Tyr Leu Ile Glu Leu Gly Pro Asn Ser Ala Leu Glu Thr Thr Pro Leu
50 55 60

Phe Gln Glu Leu Ile Ala Ala Ala Gly Leu Ala Gly Glu Arg Val Tyr
65 70 75 80

Ala Ser Glu Ala Ala Arg Asn Arg Tyr Ile Val Arg Gly Gly Glu Leu
85 90 95

His Pro Leu Pro Leu Thr Pro Leu Ala Phe Leu Arg Ser Arg Leu Trp
100 105 110

Ser Trp Lys Gly Lys Leu Arg Val Leu Ala Glu Pro Phe His Gly Arg
115 120 125

Ala Asp Arg Glu Glu Ser Val Ala Asp Phe Ala Arg Arg Arg Val Gly
130 135 140

Gln Glu Phe Leu Asp Tyr Ala Val Asn Pro Phe Val Ala Gly Ile Tyr
145 150 155 160

Ala Gly Asp Pro Glu Arg Leu Ser Val Arg Phe Ala Phe Pro Arg Leu
165 170 175

Tyr Ala Leu Glu Ala Gln Tyr Gly Gly Leu Phe Leu Gly Met Leu Arg
180 185 190

Gly Ala Arg Glu Arg Arg Arg Arg Gly Glu Ala Pro Lys Ile Ala Ala
195 200 205

Arg Leu Phe Ser Phe Arg Glu Gly Met Gly Ala Leu Pro Arg Ala Leu
210 215 220

Ala Ala Ala Leu Gly Asn Thr Val Trp Cys Ala Thr Arg Ala Leu Cys
225 230 235 240

Val Glu Arg Ala Gly Ala Ala Phe Glu Ile Ala Phe Glu Arg Asp Gly
245 250 255

Arg Arg Asp Thr Leu Arg Ala Glu Arg Val Val Leu Ala Thr Pro Ala
260 265 270

Tyr Ala Ala Ala Ser Leu Leu Lys Arg Leu Ala Pro Glu Ala Ala Arg
275 280 285

Ala Leu Asp Arg Ile Val Tyr Pro Pro Val Ser Ala Val Ile Leu Gly
290 295 300

Tyr Pro Glu Thr Ala Ile Gly Arg Pro Leu Asp Gly Phe Gly Phe Leu
305 310 315 320

Val Pro Glu Lys Glu Gln Arg Arg Ile Leu Gly Thr Ile Trp Asn Ser
325 330 335

Thr Ile Phe Pro Ala Arg Ala Pro Gln Gly Phe Val Thr Leu Thr Thr
340 345 350

Phe Val Gly Gly Met Arg Gln Pro Glu Leu Ala Arg Arg Pro Asn Glu
355 360 365

Glu Leu Ile Ala Leu Val Ala Glu Glu Leu Thr Asp Leu Leu Arg Leu
370 375 380

Arg Gly Glu Pro Glu Phe Ala Tyr Val Ser Arg Trp Glu Arg Ala Ile
385 390 395 400

Pro Gln Tyr Glu Leu Gly Tyr Gly Glu Ile Leu Asp Ala Leu Asp Arg
405 410 415

Ala Glu Arg Glu His Val Gly Leu Tyr Phe Cys Ala Asn Tyr Arg Gly
420 425 430

Gly Ile Ala Val Gly Asp Cys Val Met Ser Ala His Ala Thr Ala Glu
435 440 445

Arg Ile Leu Arg Asp Arg Ala Arg Ser
450 455

<210> SEQ ID NO 68
<211> LENGTH: 441
<212> TYPE: PRT
<213> ORGANISM: Coraliomargarita akajimensis

<400> SEQUENCE: 68

Met Pro Asp Thr Cys Ile Ile Gly Ala Gly Ile Thr Gly Leu Ala Thr
1 5 10 15

Ala Trp Gln Tyr Gln Arg Lys Gly Lys Asp Cys Val Val Leu Glu Ser
20 25 30

Gly Pro Gln Val Gly Gly Ala Ile Gln Ser Ile Leu Gln Asp Gly Tyr
35 40 45

Leu Ala Glu Glu Gly Pro Asn Ser Ile Gln Leu Asn Ser Leu Glu Ile
50 55 60

Glu Asp Phe Leu Thr Ser Ile Pro Gly Leu Glu Ala Gln Ile Ile Glu
65 70 75 80

Ala Asn Pro Ala Ala Gln Lys Arg Tyr Ile Val Arg Lys Gly Arg Leu
85 90 95

Arg Ala Val Pro Met Asn Pro Leu Gln Ala Ile Thr Thr Gln Leu Trp
100 105 110

Ser Ile Ala Gly Lys Leu Arg Val Leu Arg Glu Pro Phe Ile Lys Ala
115 120 125

Ala Pro Pro Glu Pro Asp Gln Ser Val Ala Asp Phe Val Thr Arg Arg
130 135 140

Leu Gly Lys Glu Leu Tyr Asp Tyr Ala Ile Asn Pro Leu Val Gly Gly
145 150 155 160

Ile Tyr Ala Gly Lys Pro Glu Met Leu Ser Leu Arg Tyr Gly Phe Pro

```
                165                 170                 175

Lys Leu Tyr Ala Leu Glu Gln Glu His Gly Gly Leu Ile Arg Gly Ala
            180                 185                 190

Leu Ala Lys Met Lys Ala Ala Lys Ala Asn Lys Gly Pro Lys Ala Lys
        195                 200                 205

Lys Tyr Ile Leu Ser Phe Lys Asp Gly Leu Gln Thr Leu Pro Gln Ser
    210                 215                 220

Ile Ala Asn Asn Leu Asn Glu Pro Val Gln Thr Gly Val Ser Ile Glu
225                 230                 235                 240

Ser Ile Arg Gln Ile Glu Asp Met Trp Ala Val Arg Trp Asn Gly Gln
                245                 250                 255

Val Lys Ala Phe Lys Glu Leu Ile Val Thr Val Pro Ala His Lys Leu
            260                 265                 270

Pro Gly Leu Pro Phe Glu Glu Pro Ile Arg Leu Pro Ala Ile Asp Tyr
        275                 280                 285

Pro Pro Val Ser Val Ile Ser Leu Gly Tyr Pro Leu Ser Ala Ile Lys
    290                 295                 300

Gln Pro Leu Asp Gly Phe Gly Ala Leu Val Pro Glu Arg Glu Asp Arg
305                 310                 315                 320

Asn Ile Leu Gly Val Leu Phe Pro Ser Ala Val Phe Asp Gly Arg Ala
                325                 330                 335

Pro Glu Gly His Gly Leu Leu Thr Val Phe Val Gly Gly Ser Arg Ser
            340                 345                 350

Pro Glu Cys Ser Ser Pro Asp Thr Asp Gln Leu Leu Lys Thr Ile Gln
        355                 360                 365

Pro Asp Leu Glu Thr Leu Leu Gly Ile Gln Asp Glu Pro Ser Phe Val
    370                 375                 380

His His Lys His Trp Pro Met Ala Ile Pro Gln Tyr Thr Leu Gly Tyr
385                 390                 395                 400

Glu Lys Val Leu Glu Ala Ile Thr Arg Ile Glu Gln Gln Tyr Ile Gly
                405                 410                 415

Leu Lys Leu Ala Gly Asn Tyr Arg Thr Gly Ile Ser Leu Ser Tyr Cys
            420                 425                 430

Leu Glu Ser Ala Ile Ala Ser Thr Asn
        435                 440


<210> SEQ ID NO 69
<211> LENGTH: 474
<212> TYPE: PRT
<213> ORGANISM: Oscillochloris trichoides

<400> SEQUENCE: 69

Met Asn Ser Tyr Asp Val Val Val Val Gly Ala Gly Ile Ser Gly Leu
1               5                   10                  15

Ser Ala Ala Tyr Thr Leu Phe Lys Arg Gly Leu Asp Val Leu Val Val
            20                  25                  30

Glu Ala Gly Ala Glu Val Gly Gly Val Met Arg Ser Ile Val Thr Pro
        35                  40                  45

Glu Gly Tyr Val Leu Asp Cys Gly Pro Asn Thr Leu Ala Ser Lys Asp
    50                  55                  60

Pro Arg Met Trp Ala Glu Phe Asp Asp Leu Gly Met Arg Asp Arg Leu
65                  70                  75                  80

Val Val Ala Gly Arg Ala Gly Lys Arg Arg Tyr Phe Leu Lys Asp Gly
                85                  90                  95
```

-continued

```
Gln Pro Leu Glu Ile Pro Asn Asp Pro Ile Gly Leu Leu Arg Met Glu
            100                 105                 110

His Val Ser Met Gln Ala Lys Leu Arg Val Leu Arg Glu Pro Phe Ile
        115                 120                 125

Pro Arg Ala Thr Ser Pro Asp Glu Ser Val Ala Ser Phe Phe Ser Arg
    130                 135                 140

Arg Ile Gly Pro Glu Val Met Glu Arg Met Ile Asp Pro Phe Val Ser
145                 150                 155                 160

Gly Val Tyr Ser Gly Asp Pro Ser Lys Met Ser Ile Lys Ala Thr Phe
                165                 170                 175

Pro Ser Leu Trp Glu Ala Glu Gln Arg Gly Gly Ser Ile Ile Lys Gly
            180                 185                 190

Phe Leu Thr Ala Gly Lys Ala Lys Lys Ala Ala Gly Glu Lys Lys Ala
        195                 200                 205

Lys Pro Ile Gly Pro Lys Met Arg Ser Val Thr Phe Asn Phe Lys Gly
    210                 215                 220

Gly Val Ala Glu Trp Pro Lys Thr Ile Ala Lys Val Leu Gly Asp Gln
225                 230                 235                 240

Arg Val Trp Lys Asn Ala Arg Val Thr Thr Leu Tyr Pro Glu Ser Thr
                245                 250                 255

Gly Trp Thr Leu Val Val Glu Arg Asp Gly Gln Val Glu Thr Ile Glu
            260                 265                 270

Ala Ala Ser Val Ile Met Ala Ala Pro Ala Tyr Ala Ala Ala Asp Leu
        275                 280                 285

Ile Ala Glu Leu Asp Pro Ala Ala Ala Lys Gly Leu Arg Gly Ile Arg
    290                 295                 300

Tyr Ser Ser Met Ala Val Val Asn Leu Gly Tyr Arg Glu Asn Gln Val
305                 310                 315                 320

Thr Arg Pro Val Asn Gly Phe Gly Val Leu Ala Pro Ser Cys Glu Arg
                325                 330                 335

Arg Asn Phe Leu Gly Ile Leu Ser Ala Ser Thr Leu Phe Pro Pro Phe
            340                 345                 350

Ala Pro Ala Gly Arg Val Leu Thr Ile Asn Leu Met Gly Gly Glu Ile
        355                 360                 365

Asn Pro Ile Arg Pro Glu Gln Ser Asp Asp Glu Leu Ile Ala Arg Ala
    370                 375                 380

Ile Ala Asp Asn Gln Ala Val Ile Gly Ala Asn Gly Ala Pro Glu Val
385                 390                 395                 400

Val Asn Leu Thr Arg Trp Pro Arg Ala Val Ala Gln Tyr Asn Phe Gly
                405                 410                 415

His Thr Glu Ala Met Ala Ala Leu Glu Asn Leu Glu Arg Thr Arg Pro
            420                 425                 430

Gly Ile Tyr Phe Val Gly Ser Tyr Arg Gly Gly Val Gly Met Pro Lys
        435                 440                 445

Cys Trp Arg Asn Gly Val Asn Met Ala Glu Arg Val Ala Thr Tyr Leu
    450                 455                 460

Lys Thr Arg Ser Ala Val Ala Ser Leu Arg
465                 470
```

<210> SEQ ID NO 70
<211> LENGTH: 474
<212> TYPE: PRT
<213> ORGANISM: Opitutaceae bacterium

<400> SEQUENCE: 70

-continued

```
Met Pro Val Ala Val Ile Gly Gly Gly Ile Thr Gly Leu Thr Ala Ala
1               5                   10                  15

Trp Arg Leu Ala Arg Glu Gly His Pro Val Arg Leu Phe Glu Ala Ser
            20                  25                  30

Pro Arg Pro Gly Gly Leu Ile Arg Ser Glu Arg Asp Gly Glu Trp Leu
        35                  40                  45

Ser Glu Ala Gly Pro Asn Ser Leu Leu Asp Asn Lys Pro Glu Leu Ala
    50                  55                  60

Ala Leu Leu Ala Glu Leu Gly Leu Glu Asp Ala Arg Gln Tyr Ala Gln
65                  70                  75                  80

Pro Ala Ala Lys Lys Arg Phe Ile Val Arg Arg Gly Arg Pro Leu Ala
                85                  90                  95

Ala Pro Ser Ser Pro Val Ser Ala Val Thr Thr Pro Leu Leu Ser Leu
            100                 105                 110

Arg Gly Lys Leu Arg Ile Phe Gly Asp Leu Phe Trp Arg Pro Arg Pro
        115                 120                 125

Arg Ala Glu Asp Leu Pro Leu Gly Glu Phe Ala Ala Ala His Phe Gly
    130                 135                 140

Arg Glu Leu Ala Asp Tyr Ala Val Asp Pro Phe Val Ser Gly Ile Tyr
145                 150                 155                 160

Ala Gly Asp Pro Gln Arg Leu Ser Ala Arg Tyr Ala Phe Pro Leu Leu
                165                 170                 175

Trp Glu Leu Glu Gln Lys His Gly Ser Leu Ile Arg Gly Gly Ile Ala
            180                 185                 190

Ala Ala Lys Ala Arg Arg Ala Thr Arg Pro Ala Gly Pro Ala Glu Lys
        195                 200                 205

Pro Arg Pro Pro Arg Ala Arg Ile Phe Ser Phe Ala Glu Gly Leu Glu
    210                 215                 220

Thr Ile Pro Ala Ala Leu Ala Glu Arg Leu Pro Ala Gly Cys Val Glu
225                 230                 235                 240

Thr Gly Ala Arg Val Val Arg Leu Val Pro Pro Val Ala Arg Gly Gly
                245                 250                 255

Ala Trp Glu Val Val Trp Glu Arg Lys Asp Glu Lys Asp Glu Lys Gly
            260                 265                 270

Ala Ser Gly Val Glu Gly Arg Leu Thr Glu Arg Val Ala Ala Val Ile
        275                 280                 285

Leu Ala Leu Pro Gly Glu Ala Leu Ala Arg Leu Glu Ile Gly Ala Asn
    290                 295                 300

Gly Glu His Pro Leu Ala Ala Leu Ala Glu Val Glu Tyr Pro Pro Val
305                 310                 315                 320

Ala Ser Leu Phe Ile Gly Tyr Arg Arg Glu Gln Ala Arg His Pro Leu
                325                 330                 335

Asp Gly Phe Gly Met Leu Ala Pro Ser Lys Glu Asn Arg Asn Leu Leu
            340                 345                 350

Gly Val Leu Phe Ser Ser Thr Leu Phe Pro Gly Arg Ala Pro Ala Gly
        355                 360                 365

His Ile Ala Leu Thr Val Leu Ala Gly Gly Val Arg Arg Pro Glu Leu
    370                 375                 380

Ala Arg Met Glu Leu Pro Ser Leu Met Gly Ile Val Arg Ala Glu Leu
385                 390                 395                 400

Leu Glu Leu Leu Gly Val Ser Gly Asp Pro Val Tyr Val Lys His Arg
                405                 410                 415
```

Val Thr Pro His Ala Ile Pro Gln Tyr Asn Leu Gly Tyr Gly Arg Phe
420 425 430

His Thr Val Ile Glu Thr Ala Glu Thr Ala His Pro Gly Leu Leu Val
435 440 445

Gly Gly Pro Val Arg Asp Gly Ile Ala Val Ser Ala Cys Val Ala Ala
450 455 460

Gly Glu Lys Leu Ala Arg Arg Val Val Ala
465 470

<210> SEQ ID NO 71
<211> LENGTH: 239
<212> TYPE: PRT
<213> ORGANISM: Amborella trichopoda

<400> SEQUENCE: 71

Ser Thr Lys Ser Val Ala Val Val Gly Gly Gly Val Ser Gly Leu Thr
1 5 10 15

Thr Ala Tyr Arg Leu Lys Ser His Gly Leu Asn Val Thr Leu Tyr Glu
20 25 30

Ser Glu Gly Thr Ala Gly Gly Arg Ile Arg Ser Ile Ala Tyr Gly Gly
35 40 45

Leu Ile Trp Glu Glu Gly Ala Asn Thr Met Thr Glu Ser Glu Met Glu
50 55 60

Val Lys Arg Leu Ile Asp Asp Leu Gly Leu Arg Glu Lys Gln Gln Phe
65 70 75 80

Pro Ile Ser Gln Asn Lys Arg Phe Ile Ala Arg Asn Gly Thr Pro Val
85 90 95

Leu Ile Pro Ser Asn Pro Leu Ala Leu Phe Gly Ser Lys Leu Leu Ser
100 105 110

Pro His Ser Lys Leu Arg Val Ile Leu Glu Pro Leu Phe Trp Arg Ser
115 120 125

Ser Asn Arg Lys Gly Asp Ile Ser Lys Val Ser Asp Gln Asn Leu Gln
130 135 140

Glu Ser Val Gly Asp Phe Phe Gln Arg His Phe Gly Gln Glu Val Val
145 150 155 160

Asp Tyr Leu Val Asp Pro Phe Val Ala Gly Thr Ser Ala Ala Asp Pro
165 170 175

Asn Ser Leu Ser Val Gln Val Thr Ser Met Ser Glu Ile Cys Gln Asn
180 185 190

Tyr Leu Gln Tyr Leu Gly Trp Ser Gln Gly Pro Ser Ser Gln Leu Met
195 200 205

Thr Leu Thr Leu Ser Pro Ser Ser Val Ile Asp Gln Met Leu Ser Glu
210 215 220

Arg Met Val Thr Phe Leu Gln Val Met Leu Ser Pro Leu Leu Met
225 230 235

<210> SEQ ID NO 72
<211> LENGTH: 490
<212> TYPE: PRT
<213> ORGANISM: Opitutaceae bacterium

<400> SEQUENCE: 72

Met Ser Ala Ser Leu Pro Pro Pro Pro Pro Pro Pro His Thr His Thr
1 5 10 15

Gln Ala Arg Leu Pro Val Ala Val Ile Gly Gly Gly Ile Thr Gly Leu
20 25 30

-continued

```
Thr Ala Ala Trp Arg Leu Ala Arg Glu Gly His Pro Val Arg Leu Phe
        35                  40                  45

Glu Ala Ser Pro Arg Pro Gly Gly Leu Ile Arg Ser Glu Arg Asp Gly
    50                  55                  60

Glu Trp Leu Ser Glu Ala Gly Pro Asn Ser Leu Leu Asp Asn Lys Pro
65                  70                  75                  80

Glu Leu Ala Ala Leu Leu Ala Glu Leu Gly Leu Glu Glu Ala Arg Gln
                85                  90                  95

Tyr Ala Gln Pro Ala Ala Lys Lys Arg Phe Ile Val Arg Arg Gly Arg
            100                 105                 110

Pro Leu Ala Ala Pro Ser Ser Pro Val Ser Ala Val Thr Thr Pro Leu
        115                 120                 125

Leu Ser Leu Arg Gly Lys Leu Arg Ile Phe Gly Asp Leu Phe Trp Arg
    130                 135                 140

Pro Arg Pro Arg Ala Glu Asp Leu Pro Leu Gly Glu Phe Ala Ala Ala
145                 150                 155                 160

His Phe Gly Arg Glu Leu Ala Asp Tyr Ala Val Asp Pro Phe Val Ser
                165                 170                 175

Gly Ile Tyr Ala Gly Asp Pro Gln Arg Leu Ser Ala Arg Tyr Ala Phe
            180                 185                 190

Pro Leu Leu Trp Glu Leu Glu Gln Lys His Gly Ser Leu Ile Arg Gly
        195                 200                 205

Gly Ile Ala Ala Ala Lys Ala Arg Arg Ala Thr Arg Pro Ala Gly Pro
    210                 215                 220

Ala Glu Lys Pro Arg Pro Pro Arg Ala Arg Ile Phe Ser Phe Ala Glu
225                 230                 235                 240

Gly Leu Glu Thr Ile Pro Ala Ala Leu Ala Glu Arg Leu Pro Ala Gly
                245                 250                 255

Cys Val Glu Thr Gly Ala Arg Val Val Arg Leu Val Pro Pro Val Ala
            260                 265                 270

Arg Gly Gly Ala Trp Glu Val Val Trp Glu Arg Lys Asp Glu Lys Gly
        275                 280                 285

Ala Ser Gly Val Glu Gly Arg Leu Thr Glu Arg Val Ala Ala Val Ile
    290                 295                 300

Leu Ala Leu Pro Gly Glu Ala Leu Ala Arg Leu Glu Ile Gly Ala Asn
305                 310                 315                 320

Gly Glu His Pro Leu Ala Ala Leu Ala Glu Val Glu Tyr Pro Pro Val
                325                 330                 335

Ala Ser Leu Phe Leu Gly Tyr Arg Arg Glu Gln Val Arg His Pro Leu
            340                 345                 350

Asp Gly Phe Gly Met Leu Ala Pro Ser Lys Glu Asn Arg Asn Leu Leu
        355                 360                 365

Gly Val Leu Phe Ser Ser Thr Leu Phe Pro Gly Arg Ala Pro Ala Gly
    370                 375                 380

His Ile Ala Leu Thr Val Leu Ala Gly Gly Val Gln Arg Pro Glu Leu
385                 390                 395                 400

Ala Arg Met Glu Leu Pro Ser Leu Met Gly Ile Val Arg Ala Glu Leu
                405                 410                 415

Leu Glu Leu Leu Gly Val Ser Gly Asp Pro Val Tyr Val Lys His Arg
            420                 425                 430

Val Thr Pro His Ala Ile Pro Gln Tyr Asn Leu Gly Tyr Gly Arg Phe
        435                 440                 445

His Thr Val Ile Glu Ala Ala Glu Thr Ala His Pro Gly Leu Leu Val
```

```
    450                 455                 460

Gly Gly Pro Val Arg Asp Gly Ile Ala Val Ser Ala Cys Val Ala Ala
465                 470                 475                 480

Gly Glu Lys Leu Ala Arg Arg Val Val Ala
                485                 490


<210> SEQ ID NO 73
<211> LENGTH: 474
<212> TYPE: PRT
<213> ORGANISM: Chloroflexus spec

<400> SEQUENCE: 73

Met Met Ala Gly Tyr Asp Ser Val Val Ile Gly Gly Gly Ile Ala Gly
1               5                   10                  15

Leu Ala Ala Ala Tyr Thr Leu His Lys Arg Gly Tyr Arg Val Leu Val
            20                  25                  30

Ile Glu Ser Thr Asn Arg Val Gly Gly Val Ile Gln Thr Ile Thr Thr
        35                  40                  45

Pro Glu Gly Tyr Ile Leu Asp Cys Gly Pro Asn Thr Val Gly Thr Gly
    50                  55                  60

Asp Ala Arg Leu Trp Gln Glu Leu Ile Asp Leu Gly Leu Arg Glu Arg
65                  70                  75                  80

Ile Thr Pro Ala Ala Pro Cys Ser Lys Arg Arg Phe Ile Leu Ile Asn
                85                  90                  95

Gly Thr Pro Val Glu Ile Pro Thr Ser Pro Val Gly Leu Ile Thr Thr
            100                 105                 110

Arg Leu Leu Ser Trp Arg Gly Lys Leu Arg Val Leu Ala Glu Pro Phe
        115                 120                 125

Ile Asn Arg Gly Ser Thr Asp Pro Asp Glu Ser Val Ala Ala Phe Phe
    130                 135                 140

Thr Arg Arg Ile Gly Ala Glu Ala Thr Ala His Leu Leu Asp Pro Phe
145                 150                 155                 160

Val Ala Gly Val Tyr Ala Gly Asp Pro Gln Arg Leu Ser Thr Ala Ala
                165                 170                 175

Val Phe Pro Ser Leu Trp Glu Ala Ala Gln Arg Ser Gly Ser Ile Val
            180                 185                 190

Arg Gly Met Leu Ser Lys Pro Lys Pro Lys Thr Gln Val Ser Glu Pro
        195                 200                 205

Lys Met Arg Ser Arg Thr Phe Thr Phe Arg Gly Gly Leu Ala Glu Trp
    210                 215                 220

Pro Arg Ala Leu Ala Gln Ala Leu Gly Ala Gly Asn Val Trp Thr Glu
225                 230                 235                 240

Arg Arg Val Val Lys Leu Gln Pro Arg Asp Ser Trp Trp Glu Val Thr
                245                 250                 255

Ile Asp Gly Val Asn Gly Pro Glu Thr Leu Ile Ser Arg Ser Leu Ile
            260                 265                 270

Ile Ala Thr Pro Ala Phe Thr Ala Ala Asp Leu Ile Glu Ser Val Asp
        275                 280                 285

Gln Arg Ala Ala Gly Ala Leu Arg Gly Ile Pro Tyr Ala Pro Val Ala
    290                 295                 300

Val Val His Leu Gly Phe Arg Arg Asp Gln Ile Ser Gln Glu Leu Ser
305                 310                 315                 320

Gly Phe Gly Val Leu Ala Pro Ser Ser Glu Gln Arg Gln Phe Leu Gly
                325                 330                 335
```

-continued

Ile Leu Trp Thr Ser Ser Ile Phe Pro His Val Ala Pro His Asp His
340 345 350

Val Leu Thr Thr Thr Leu Ser Gly Gly Ala Ile Arg Pro Glu Leu Ala
355 360 365

Glu Arg Ser Asp Glu Thr Leu Ile Glu Ala Ala Ile Arg Asp His His
370 375 380

Gln Leu Leu Gly Ile Arg Gly Gln Pro Ile Phe Thr His Val Thr Arg
385 390 395 400

Trp Arg Thr Ala Ile Ala Gln Tyr Thr Phe Gly His Arg Glu Arg Ile
405 410 415

Ala Thr Leu Val Gln Leu Glu Gln Arg Leu Pro Thr Ile Gln Phe Ala
420 425 430

Gly Ser Tyr Arg Asp Gly Val Gly Val Pro Lys Thr Trp Ala Ser Gly
435 440 445

Val Gln Ala Gly Glu Arg Ile Ala Ala Ala Leu Ala Ala His Gly Thr
450 455 460

Thr Ala Val Ser Thr Glu Thr Ala Ser Gly
465 470

<210> SEQ ID NO 74
<211> LENGTH: 462
<212> TYPE: PRT
<213> ORGANISM: Leptospirillum spec

<400> SEQUENCE: 74

Met Ala Gly Phe Asp Cys Asp Thr Leu Val Val Gly Gly Gly Val Ser
1 5 10 15

Gly Leu Ala Ala Ala Leu Thr Leu Lys Asn Arg Gly Val Asp Val Arg
20 25 30

Leu Leu Glu Ser Arg Gly Tyr Leu Gly Gly Ala Ile Arg Thr Val Arg
35 40 45

Glu Asp Gly Tyr Leu Leu Glu Phe Gly Pro Asn Ser Leu Met Val Arg
50 55 60

Pro Glu Asp Ala Ile Asp Thr Val Leu Gly Asp Pro Glu Leu Arg Ala
65 70 75 80

Arg Ile Val Pro Ala Ser Gly Leu Ser Lys Asn Arg Tyr Val Val Lys
85 90 95

Ala Gly His Leu Tyr Pro Val Pro Leu Ser Pro Trp Ala Phe Phe Arg
100 105 110

Thr Pro Leu Leu Ser Trp Arg Gly Arg Arg Asp Ile Leu Ser Glu Trp
115 120 125

Lys Val Pro Pro Arg Thr Gly Gly Pro Glu Glu Thr Leu Ser His Phe
130 135 140

Val Arg Arg Arg Leu Gly Glu Glu Ala Leu Asp Tyr Phe Val Asp Pro
145 150 155 160

Phe Val Lys Gly Val Tyr Ala Ser His Pro Asp Leu Leu Ser Val Glu
165 170 175

Ala Ala Phe Pro Leu Leu Val Arg Leu Glu Arg Glu His Gly Gly Leu
180 185 190

Leu Arg Gly Ala Leu Lys Thr Phe Leu Lys Arg Arg Lys Arg Pro Ser
195 200 205

Gly Ser Ser Pro Arg Gly Ile Phe Ser Phe Ala Gly Gly Met Thr Asp
210 215 220

Leu Val Glu Ala Met Gly Lys Arg Leu Gly Glu Asp Val Gly Thr Asn
225 230 235 240

Val Asp Val Ile Lys Tyr Thr Arg Leu Glu Glu Gly Phe Arg Val Ala
245 250 255

Leu Met Tyr Asp Glu Thr Glu Tyr Tyr Met Thr Ser Arg Arg Leu Ile
260 265 270

Leu Ala Thr Ser Ala Pro Gln Ala Ala Glu Leu Leu Glu Gly Asp Pro
275 280 285

Asp Gly Pro Ser Ser Glu Leu Lys Ser Ile Pro Tyr Ala Pro Val Thr
290 295 300

Ile Ala Tyr Ala Gly Phe Leu Arg Glu Gln Val Thr His Pro Leu Asp
305 310 315 320

Gly Phe Gly Leu Leu Cys Pro Thr Val Glu Asn Arg Lys Val Leu Gly
325 330 335

Val Ile Phe Ser Ser Ser Leu Phe Pro Gly Arg Ala Pro Glu Gly Lys
340 345 350

Val Leu Leu Thr Val Phe Val Gly Gly Met Thr Gly Gln Lys Leu Ala
355 360 365

Gln Ala Phe Asp Glu Asp Leu Glu Arg Ile Val Leu Lys Glu Leu Thr
370 375 380

Glu Leu Leu Gly Val Lys Gly Ala Pro Ser Phe Phe Arg Ile His Arg
385 390 395 400

Trp Glu Lys Ala Ile Pro Gln Leu Ile Leu Gly His Gly Glu Thr Val
405 410 415

Arg Thr Ile Arg Lys Lys Leu Pro Ser Gly Leu Arg Leu Ala Gly Asn
420 425 430

Tyr Leu Asp Gly Ile Ser Ile Ala Arg Ala Phe Ala Ser Gly Val Arg
435 440 445

Ala Ala Glu Glu Leu Leu Ser Glu Asp Gly Gly Thr Pro Gly
450 455 460

<210> SEQ ID NO 75
<211> LENGTH: 462
<212> TYPE: PRT
<213> ORGANISM: Leptospirillum ferriphilum

<400> SEQUENCE: 75

Met Ala Gly Phe Asp Cys Asp Thr Leu Val Val Gly Gly Gly Val Ser
1 5 10 15

Gly Leu Ala Ala Ala Leu Thr Leu Lys Asn Arg Gly Val Asp Val Arg
20 25 30

Leu Leu Glu Ser Arg Gly Tyr Leu Gly Gly Ala Ile Arg Thr Val Arg
35 40 45

Glu Asp Gly Tyr Leu Leu Glu Phe Gly Pro Asn Ser Leu Met Val Arg
50 55 60

Pro Glu Asp Ala Ile Asp Thr Val Leu Gly Asp Pro Glu Leu Arg Ala
65 70 75 80

Arg Ile Val Pro Ala Ser Gly Leu Ser Lys Asn Arg Tyr Val Val Lys
85 90 95

Ala Gly His Leu Tyr Pro Val Pro Leu Ser Pro Trp Ala Phe Phe Arg
100 105 110

Thr Pro Leu Leu Ser Trp Arg Gly Arg Arg Asp Ile Leu Ser Glu Trp
115 120 125

Lys Val Pro Pro Arg Thr Gly Gly Pro Glu Glu Thr Leu Ser His Phe
130 135 140

Val Arg Arg Arg Leu Gly Glu Glu Ala Leu Asp Tyr Phe Val Asp Pro

-continued 145 150 155 160

Phe Val Lys Gly Val Tyr Ala Ser His Pro Asp Leu Leu Ser Val Glu
165 170 175

Ala Ala Phe Pro Leu Leu Val Arg Leu Glu Arg Glu His Gly Gly Leu
180 185 190

Leu Arg Gly Ala Leu Lys Thr Phe Leu Lys Arg Arg Lys Arg Pro Ser
195 200 205

Gly Ser Ser Pro Arg Gly Ile Phe Ser Phe Ala Gly Gly Met Thr Asp
210 215 220

Leu Val Glu Ala Met Gly Lys Arg Leu Gly Glu Asp Val Gly Thr Asn
225 230 235 240

Val Asp Val Ile Lys Tyr Thr Arg Leu Glu Glu Gly Phe Arg Val Ala
245 250 255

Leu Met Tyr Asp Glu Thr Glu Tyr Tyr Met Thr Ser Arg Arg Leu Ile
260 265 270

Leu Ala Thr Ser Ala Pro Gln Ala Ala Glu Leu Leu Glu Gly Asp Pro
275 280 285

Asp Gly Pro Ser Ser Glu Leu Lys Ser Ile Pro Tyr Ala Pro Val Thr
290 295 300

Ile Ala Tyr Ala Gly Phe Leu Arg Glu Gln Val Thr His Pro Leu Asp
305 310 315 320

Gly Phe Gly Leu Leu Cys Pro Thr Val Glu Asn Arg Lys Val Leu Gly
325 330 335

Val Ile Phe Ser Ser Ser Leu Phe Pro Gly Arg Ala Pro Glu Gly Lys
340 345 350

Val Leu Leu Thr Val Phe Val Gly Gly Met Thr Gly Gln Lys Leu Ala
355 360 365

Gln Ala Phe Asp Glu Asp Leu Glu Arg Ile Val Leu Lys Glu Leu Thr
370 375 380

Glu Leu Leu Gly Val Lys Gly Ala Pro Ser Phe Phe Arg Ile His Arg
385 390 395 400

Trp Glu Lys Ala Ile Pro Gln Leu Ile Leu Gly His Arg Glu Thr Val
405 410 415

Arg Thr Ile Arg Lys Lys Leu Pro Ser Gly Leu Arg Leu Ala Gly Asn
420 425 430

Tyr Leu Asp Gly Ile Ser Ile Ala Arg Ala Phe Ala Ser Gly Val Arg
435 440 445

Ala Ala Glu Glu Leu Leu Ser Glu Asp Gly Gly Thr Pro Gly
450 455 460

<210> SEQ ID NO 76
<211> LENGTH: 446
<212> TYPE: PRT
<213> ORGANISM: Verrucomicrobia bacterium

<400> SEQUENCE: 76

Met Asn Thr Lys Lys Val Cys Ile Leu Gly Ala Gly Leu Ser Gly Ile
1 5 10 15

Ser Leu Gly Leu Ser His Glu Asn Lys Gly Asn Gln Val Thr Ile Phe
20 25 30

Glu Lys Asp Leu Arg Val Gly Gly Val Leu Gln Ser Ile Lys Ser Glu
35 40 45

Gly Phe Leu Met Asp Tyr Gly Ala Asn Thr Leu Ser Ile Arg Thr Lys
50 55 60

-continued

```
Lys Thr Val Asp Phe Leu Lys Gln Tyr Glu Ile Leu Glu His Ala Met
65                  70                  75                  80

Asp Ala Asn Gln Glu Ser Ser Lys Arg Phe Ile Ile Arg Lys Asn Arg
                85                  90                  95

Ile Ile Ser Leu Pro Gln Gly Pro Leu Ser Phe Leu Cys Ser Ser Phe
            100                 105                 110

Leu Ser Pro Val Gly Lys Leu Arg Leu Cys Leu Glu Pro Phe Ile Gly
        115                 120                 125

Arg Lys Lys Asp Asn Gly Ser Asp Glu Thr Met Ala Glu Phe Val Glu
    130                 135                 140

Arg Arg Leu Gly Arg Glu Val Leu Asp Tyr Gly Val Asn Pro Phe Ile
145                 150                 155                 160

Gly Gly Val Tyr Ala Ala Arg Pro Glu Ser Leu Ile Leu Lys Tyr Ala
                165                 170                 175

Phe Pro Ser Leu His Asp Thr Glu Leu Thr Phe Gly Ser Ile Phe Trp
            180                 185                 190

Gly Met Ile Arg Gly Gly Ala Gln Pro Ser Glu Lys Ile Ser Lys Ser
        195                 200                 205

Arg Leu Ile Ser Phe Arg Glu Gly Met Gln Glu Leu Pro Asn Arg Leu
    210                 215                 220

Ala Ala Arg Met His Asn Pro Pro Val Leu Gly Cys Glu Ile Lys Lys
225                 230                 235                 240

Ile Glu Phe Lys Asp Asp Val Gln Trp Cys Val Gln Gly Glu Lys His
                245                 250                 255

Asp Gly Lys Ile Gln Lys Glu Val Phe Asp Gln Ile Ile Cys Thr Leu
            260                 265                 270

Pro Ser His Ala Leu Asp Lys Ile Glu Trp Val Gly Ile Asn Ser Ser
        275                 280                 285

His Leu Leu Glu Thr Leu Thr Arg Ala Tyr His Pro Pro Leu Ala Leu
    290                 295                 300

Val Phe Gln Gly Tyr Gln Gln Arg Gln Ile Lys His Pro Leu Asp Gly
305                 310                 315                 320

Phe Gly Phe Leu Val Pro Glu Lys Glu Arg Arg Lys Ile Leu Gly Thr
                325                 330                 335

Leu Phe Ser Ser Thr Leu Phe Gln Asn Arg Ala Pro Glu Asn Ser Val
            340                 345                 350

Leu Leu Thr Thr Tyr Ile Gly Gly Glu Arg Asn Pro Glu Leu Cys Asp
        355                 360                 365

Leu Pro Gln Asn Glu Ile Leu Gly His Ala Phe Arg Glu Asn Gln Asp
    370                 375                 380

Leu Leu Gly Ile Glu Gly Lys Pro Ile Phe Glu His Leu Lys Leu Trp
385                 390                 395                 400

Pro Lys Ser Ile Pro Ile Pro Asp His Thr Leu Glu Asp Arg Lys Lys
                405                 410                 415

Ala Ala Ser Thr Leu Thr Leu Glu Asn Lys Gly Leu Gln Ile Leu Gly
            420                 425                 430

Ala His Ile Asn Gly Ala Pro Leu Pro Asn Cys Met Val Leu
        435                 440                 445
```

<210> SEQ ID NO 77
<211> LENGTH: 475
<212> TYPE: PRT
<213> ORGANISM: Chloroflexus aggregans

<400> SEQUENCE: 77

```
Met Met Met Ala Asn Tyr Asp Ser Val Val Ile Gly Gly Gly Ile Gly
1               5                   10                  15

Gly Leu Ala Ala Ala Tyr Thr Leu Tyr Lys Arg Gly Tyr Arg Val Leu
            20                  25                  30

Val Ile Glu Ala Ala Asn Arg Val Gly Gly Val Ile His Ser Ile Thr
        35                  40                  45

Thr Pro Glu Gly Phe Thr Leu Asp Cys Gly Pro Asn Thr Ile Gly Thr
    50                  55                  60

Asn Asp Val Arg Leu Trp Gln Glu Leu Ile Asp Leu Gly Leu Arg Asp
65                  70                  75                  80

Arg Ile Arg Pro Ala Ala Arg Cys Gly Arg Arg Arg Tyr Ile Leu Ile
                85                  90                  95

Asn Gly Thr Pro Ile Glu Ile Pro Ser Ser Pro Val Gly Leu Ile Thr
            100                 105                 110

Thr Arg Leu Leu Ser Trp Arg Gly Lys Leu Arg Val Leu Gly Glu Pro
        115                 120                 125

Phe Val Asn Ile Gly Thr Pro Thr Gly Glu Glu Ser Val Ala Ala Phe
    130                 135                 140

Phe Ser Arg Arg Ile Gly His Glu Ala Val Ala His Leu Leu Asp Pro
145                 150                 155                 160

Phe Val Ala Gly Val Tyr Ala Gly Asp Pro Asn Gln Leu Ser Ala Ala
                165                 170                 175

Ala Val Phe Pro Ser Leu Trp Glu Ala Val Gln Arg Gly Gly Ser Ile
            180                 185                 190

Val Arg Gly Met Leu Arg Arg Pro Lys Gln Lys Thr Leu Ile Ser Glu
        195                 200                 205

Pro Lys Met Arg Ser Arg Thr Phe Ser Phe Gln Gly Gly Leu Ala Asp
    210                 215                 220

Trp Pro Arg Ala Ile Ala Arg Ala Leu Gly Thr Gly Asn Val Trp Thr
225                 230                 235                 240

Gly Arg Arg Ala Val Gly Leu Arg Asp Leu Gly Thr Tyr Trp Glu Val
                245                 250                 255

Thr Val Asp Gly Thr Gly Arg Leu Glu Thr Ile Thr Thr Arg Ser Val
            260                 265                 270

Ile Ile Ala Thr Pro Ala Tyr Val Ala Ala Glu Leu Val Glu Ala Leu
        275                 280                 285

Asp Pro Ala Ala Ala Ser Ala Leu Arg Ser Ile Pro Tyr Ala Pro Val
    290                 295                 300

Ser Val Val His Leu Gly Phe Arg Arg Asp Gln Leu Ser His Glu Leu
305                 310                 315                 320

Asn Gly Phe Gly Val Leu Ala Pro Ser Ser Glu Arg Arg Gln Phe Leu
                325                 330                 335

Gly Ile Leu Trp Ala Ser Ser Leu Phe Pro His Val Ala Pro Pro Asp
            340                 345                 350

Arg Val Leu Thr Ile Thr Leu Ser Gly Gly Ala Ile Arg Pro Glu Val
        355                 360                 365

Ala Glu Gln Ser Glu Glu Ala Leu Ile Glu Ser Ala Ile Arg Asp Asn
    370                 375                 380

Gln Glu Val Leu Gly Ile Arg Gly Gln Pro Leu Leu Thr His Val Thr
385                 390                 395                 400

Arg Trp His His Ala Ile Ala Gln Tyr Thr Leu Gly His Arg Glu Arg
                405                 410                 415
```

```
Ile Ala Thr Leu Glu Arg Leu Glu Gln Arg Arg Pro Thr Leu Gln Leu
            420                 425                 430

Thr Gly Ser Tyr Arg Gly Gly Ile Gly Ile Pro Lys Thr Trp Ala Ser
        435                 440                 445

Gly Val Gly Ala Gly Glu Arg Ile Ala Ala Ala Leu Asp Ala Gln Gly
    450                 455                 460

Thr Thr Ala Asp Thr Leu Glu Gln Ala Arg Gly
465                 470                 475


<210> SEQ ID NO 78
<211> LENGTH: 456
<212> TYPE: PRT
<213> ORGANISM: Desulfurobacterium thermolithotrophum

<400> SEQUENCE: 78

Met Lys Val Ala Val Ile Gly Ala Gly Ile Ser Gly Leu Ser Val Ala
1               5                   10                  15

Phe Tyr Leu Lys Lys Gly Gly Ala Glu Val Lys Val Phe Glu Lys Glu
            20                  25                  30

Lys Thr Val Gly Gly Lys Met Lys Thr Ile His Glu Asp Gly Tyr Ile
        35                  40                  45

Ile Glu Thr Gly Pro Asn Gly Phe Leu Asp Gly Lys Pro Tyr Thr Leu
    50                  55                  60

Asn Leu Val Lys Glu Leu Gly Ile Glu Ser Lys Leu Tyr Arg Ser Ser
65                  70                  75                  80

Asp Lys Ala Arg Lys Arg Phe Ile Tyr Thr Asn Gly Arg Leu Val Arg
                85                  90                  95

Leu Pro Glu Ser Pro Ile Ala Phe Leu Ala Ser Tyr Leu Leu Ser Trp
            100                 105                 110

Lys Gly Lys Leu Arg Leu Val Gly Glu Phe Leu Val Pro Pro Lys Lys
        115                 120                 125

Glu Asp Ile Asp Glu Ser Leu Ser Glu Phe Ala Lys Arg Arg Ile Gly
    130                 135                 140

Glu Glu Ala Leu Glu Lys Leu Leu Asp Pro Met Val Ala Gly Ile Phe
145                 150                 155                 160

Ala Gly Asp Pro Asp Arg Leu Ser Leu Lys Ala Ala Phe Pro Ala Ile
                165                 170                 175

Tyr Tyr Leu Glu Lys Gln Tyr Gly Gly Leu Ile Lys Gly Leu Ile Ala
            180                 185                 190

Lys Met Lys Glu Ala Lys Lys Ser Gly Lys Lys Ser Gly Pro Ala Gly
        195                 200                 205

Pro Gly Gly Val Leu Thr Ser Phe Lys Gly Gly Val Lys Asp Leu Ile
    210                 215                 220

Asp Ser Leu Ser Glu Phe Leu Gly Asp Ser Ile Glu Thr Glu Val Glu
225                 230                 235                 240

Ile Leu Gly Leu Asp Arg Ile Glu Lys Gly Trp Lys Val Lys Tyr Lys
                245                 250                 255

Lys Glu Asn Glu Val Phe Glu Glu Thr Phe Asp Ala Ile Val Phe Ser
            260                 265                 270

Thr Pro Ala Tyr Ile Thr Ala Lys Leu Leu Asn Asp Leu Asn Leu Glu
        275                 280                 285

Leu Ser Lys Leu Leu Ser Glu Ile Glu Tyr Ser Pro Ile Ser Val Val
    290                 295                 300

Ala Leu Gly Phe Glu Lys Lys Gly Leu Gly His Asp Leu Asp Gly Phe
305                 310                 315                 320
```

Gly Phe Leu Val Pro Arg Ser Glu Lys Arg Lys Ile Leu Gly Ala Leu
325 330 335

Trp Asp Ser Ser Val Phe Pro Asn Arg Ala Pro Ser Gly Lys Ala Leu
340 345 350

Ile Arg Val Met Ile Gly Gly Ala Arg Gln Pro Glu Leu Ala Leu Leu
355 360 365

Pro Asp Glu Glu Leu Val Asn Ile Ala Leu Lys Glu Leu Arg Arg Ile
370 375 380

Met Lys Ile Arg His Tyr Pro Glu Lys Ile Lys Val Phe Lys His Glu
385 390 395 400

Lys Gly Ile Pro His Tyr Thr Val Gly His Ala Glu Arg Val Glu Lys
405 410 415

Ile Phe Arg Leu Ile Ser Lys Tyr Pro Gly Leu Tyr Leu Cys Asn Asn
420 425 430

Ala Tyr Thr Gly Val Gly Val Asn Asp Cys Thr Lys Ala Ala Glu Glu
435 440 445

Val Ala Arg Arg Ile Leu Asp Gly
450 455

<210> SEQ ID NO 79
<211> LENGTH: 455
<212> TYPE: PRT
<213> ORGANISM: Desulfurobacterium spec

<400> SEQUENCE: 79

Met Lys Lys Val Ala Val Val Gly Ala Gly Val Ser Gly Leu Ser Thr
1 5 10 15

Ala Phe Tyr Ile Glu Lys Phe Gly Gly Asp Asn Val Ser Val Thr Ile
20 25 30

Phe Glu Lys Glu Asn Val Pro Gly Gly Lys Met Leu Thr Val Gln Lys
35 40 45

Asp Gly Phe Ile Ile Glu Thr Gly Pro Asn Gly Phe Leu Asp Asn Lys
50 55 60

Pro Tyr Thr Leu Asp Leu Val Lys Asp Leu Lys Ile Glu Asp Arg Leu
65 70 75 80

Tyr Arg Ser Ser Asp Lys Ala Arg Lys Arg Phe Val Phe Val Asn Gly
85 90 95

Lys Leu Val Arg Leu Pro Glu Asn Pro Ile Ala Phe Leu Ser Ser Tyr
100 105 110

Val Met Ser Phe Lys Gly Lys Leu Arg Leu Ala Ala Glu Tyr Phe Ile
115 120 125

Pro Pro Lys Lys Asp Asp Ser Asp Glu Ser Leu Ser Ser Phe Val Lys
130 135 140

Arg Arg Ile Gly Lys Glu Ala Leu Glu Lys Leu Ile Asp Pro Met Ala
145 150 155 160

Ala Gly Ile Phe Ala Gly Asp Pro Asp Lys Leu Ser Val Lys Ala Ala
165 170 175

Phe Pro Ala Val Trp His Leu Glu Lys Lys Tyr Gly Gly Leu Ile Lys
180 185 190

Gly Leu Leu Ala Met Lys Lys Glu Lys Lys Asp Ala Thr Ala Gly Pro
195 200 205

Gly Gly Val Leu Thr Ser Phe Lys Gly Gly Val Lys Asp Leu Ile Asp
210 215 220

Ala Leu Val Ala Asn Ile Lys Gly Glu Ile His Pro Gly Thr Thr Val

-continued

```
225                 230                 235                 240

Lys Lys Leu Ile Pro Glu Asn Gly Lys Trp Lys Ile Val Tyr Glu Lys
                245                 250                 255

Asp Asp Glu Ile Phe Glu Glu Ser Phe Asp Lys Val Val Leu Ser Thr
            260                 265                 270

Pro Ser Tyr Val Ala Ala Ala Leu Val Lys Asn Phe Asp Glu Lys Leu
        275                 280                 285

Ala Glu Lys Leu Tyr Glu Ile Glu Tyr Ser Pro Ile Ala Val Ile Ala
    290                 295                 300

Phe Gly Phe Ile Lys Lys Gly Leu Gly His His Leu Asp Gly Phe Gly
305                 310                 315                 320

Phe Leu Val Pro Arg Ser Glu Gly Arg Lys Ile Leu Gly Val Leu Trp
                325                 330                 335

Asp Ser Ser Val Phe Pro Asn Arg Ala Pro Glu Gly Lys Ala Leu Ile
            340                 345                 350

Arg Ala Met Val Gly Gly Ala Arg Gln Pro His Leu Ala Leu Ala Gly
        355                 360                 365

Glu Glu Glu Ile Ala Arg Met Thr Tyr Lys Asp Ile Lys Arg Ile Met
    370                 375                 380

Lys Ile Arg His Arg Pro Ile Met Thr Ala Val Phe Lys His Pro Lys
385                 390                 395                 400

Gly Ile Pro His Tyr Thr Val Gly His Val Glu Lys Val Asn Glu Ile
                405                 410                 415

Phe Lys Leu Ala Ser Asn His Gly Gly Leu Phe Leu Asn Ser Asn Ala
            420                 425                 430

Tyr Arg Gly Val Gly Val Asn Asp Cys Val Tyr Asn Ser Leu Lys Thr
        435                 440                 445

Ala Glu Met Val Thr Ser Glu
    450                 455


<210> SEQ ID NO 80
<211> LENGTH: 484
<212> TYPE: PRT
<213> ORGANISM: Arthrospira platensis

<400> SEQUENCE: 80

Met Thr Asn Leu Val Asp Ser Leu Ile Val Gly Ala Gly Ile Ser Gly
1               5                   10                  15

Leu Ser Leu Ala Tyr Ser Leu Asn Arg Glu Lys Ser Val Arg Glu Pro
            20                  25                  30

Leu Lys Val Leu Val Thr Glu Ser Gln Asn Arg Val Gly Gly Asn Ile
        35                  40                  45

Thr Thr Gly Arg Ala Asp Asp Phe Leu Trp Glu Glu Gly Pro Asn Ser
    50                  55                  60

Phe Ala Pro Thr Pro Glu Leu Leu Gly Leu Ala Val Asp Leu Gly Leu
65                  70                  75                  80

Lys Glu Glu Leu Ile Phe Ala Asp Arg Lys Leu Pro Arg Tyr Val Tyr
                85                  90                  95

Trp Asn Leu Met Leu His Pro Val Pro Met Asn Pro Pro Ala Leu Leu
            100                 105                 110

Ser Ser Glu Leu Ile Ser Ala Arg Gly Lys Leu Arg Ala Ala Leu Gly
        115                 120                 125

Ala Ile Gly Phe Val Pro Pro Pro Val Gly Ala His Leu Ser Gln Gln
    130                 135                 140
```

-continued

Gly Gly Glu Glu Thr Ile Thr Gln Phe Phe Asp Arg His Leu Gly Ser
145 150 155 160

Glu Val Leu Glu Arg Leu Val Gln Pro Phe Val Ser Gly Val Tyr Ala
165 170 175

Gly Asp Pro Gln Gln Leu Ala Val Arg Ser Ala Phe Ser Arg Ile Val
180 185 190

Ala Ala Glu Glu Ala Gly Gly Gly Leu Leu Pro Gly Phe Val Arg Ser
195 200 205

Arg Leu Asn Lys Lys Ala Pro Val Ser Thr Pro Asp Pro Asn Ile Pro
210 215 220

Lys Thr Arg Pro Gly Glu Leu Gly Ser Phe Arg Tyr Gly Leu Gln Thr
225 230 235 240

Leu Pro Glu Thr Leu Ala Ser Lys Leu Gly Asp Arg Val Lys Leu Asn
245 250 255

Trp Thr Ile Asp Arg Phe Tyr Pro Thr Asp His Gln Thr Tyr Ile Ala
260 265 270

Glu Phe Ser Thr Pro Asp Gly Pro Gln Gln Val Glu Ala Arg Thr Leu
275 280 285

Ala Leu Met Thr Pro Ala His Val Ser Ala Arg Leu Leu Gln Pro Leu
290 295 300

His Ser Pro Ile Ala Thr Ala Leu Ser Gln Ile Pro Tyr Pro Pro Val
305 310 315 320

Ala Cys Val Val Leu Ala Tyr Pro Lys Ser Ala Leu Lys Gln Gln Leu
325 330 335

Lys Gly Phe Gly Asn Leu Ile Pro Arg His Gln Gly Ile Arg Thr Leu
340 345 350

Gly Thr Ile Trp Thr Ser Ser Leu Phe Pro Gly Arg Ala Pro Glu Ser
355 360 365

Trp Gln Val Leu Ser Asn Tyr Ile Gly Gly Ala Thr Asp Pro Glu Ile
370 375 380

Gly Glu Met Asp Asp Asp Gln Ile Val Ala Ala Val His Gln Asp Leu
385 390 395 400

Arg Gln Ile Leu Leu Ala Glu Asp Val Pro Pro Lys Val Leu Ala Val
405 410 415

His Leu Trp Arg Arg Ala Ile Pro Gln Tyr Thr Leu Gly His Gln Asn
420 425 430

Arg Leu Asn Cys Ile Asp Ala Gly Leu Arg Ser Leu Pro Gly Leu Tyr
435 440 445

Leu Cys Ser Asn Tyr Ile Asp Gly Val Ser Val Gly Asp Cys Val Arg
450 455 460

Arg Gly Gln Gln Trp Ala Ser Lys Ile Gln Ser His Leu His Asp Cys
465 470 475 480

Gln Thr Ala Asn

<210> SEQ ID NO 81
<211> LENGTH: 462
<212> TYPE: PRT
<213> ORGANISM: Leptospirillum spec

<400> SEQUENCE: 81

Met Ala Gly Phe Asp Cys Asp Thr Leu Val Val Gly Gly Gly Ile Ser
1 5 10 15

Gly Leu Ala Ala Ala Leu Thr Leu Lys Asn Arg Gly Val Asp Val Arg
20 25 30

```
Leu Leu Glu Ser Arg Gly Tyr Leu Gly Gly Ala Val Arg Thr Val Arg
        35                  40                  45

Glu Glu Gly Tyr Leu Leu Glu Phe Gly Pro Asn Ser Leu Met Val Arg
    50                  55                  60

Pro Asp Asp Ala Ile Asp Ala Val Leu Gly Asp Pro Glu Leu Arg Ala
65                  70                  75                  80

Arg Ile Val Ala Ala Ser Gly Leu Ser Lys Asn Arg Tyr Val Val Lys
                85                  90                  95

Ser Gly Asn Leu Tyr Pro Val Pro Leu Ser Pro Trp Ala Phe Ile Arg
            100                 105                 110

Thr Pro Leu Leu Ser Trp Arg Gly Arg Arg Asp Ile Leu Ser Glu Trp
        115                 120                 125

Lys Val Pro Pro Arg Thr Gly Gly Pro Glu Glu Thr Leu Ser His Phe
    130                 135                 140

Val Arg Arg Arg Leu Gly Glu Glu Ala Leu Asp Tyr Phe Val Asp Pro
145                 150                 155                 160

Phe Val Lys Gly Val Tyr Ala Ser His Pro Asp Leu Leu Ser Val Glu
                165                 170                 175

Ala Ala Phe Pro Leu Leu Val Arg Leu Glu Arg Glu His Gly Gly Leu
            180                 185                 190

Leu Arg Gly Ala Leu Lys Thr Phe Leu Lys Arg Arg Lys Arg Pro Ser
        195                 200                 205

Gly Ser Ala Pro Arg Gly Ile Phe Ser Phe Thr Gly Gly Met Gly Asp
    210                 215                 220

Leu Val Glu Ala Met Gly Lys Arg Leu Gly Glu Asp Val Gly Thr Asn
225                 230                 235                 240

Val Asp Val Ile Lys Tyr Thr Arg Leu Glu Glu Gly Phe Arg Val Ala
                245                 250                 255

Leu Met Tyr Asp Glu Thr Glu Tyr Tyr Met Thr Ser Arg Arg Leu Ile
            260                 265                 270

Leu Ala Thr Ser Ala Pro Gln Ala Ala Glu Leu Leu Glu Gly Asp Pro
        275                 280                 285

Glu Gly Pro Ser Gly Glu Leu Lys Ala Ile Pro Tyr Ala Pro Val Thr
    290                 295                 300

Ile Ala Tyr Ala Gly Phe Leu Arg Glu Gln Ile Thr His Pro Leu Asp
305                 310                 315                 320

Gly Phe Gly Leu Leu Cys Pro Thr Ala Glu Asn Arg Lys Val Leu Gly
                325                 330                 335

Val Ile Phe Ser Ser Ser Leu Phe Pro Gly Arg Ala Pro Asp Gly Lys
            340                 345                 350

Val Leu Leu Thr Val Phe Val Gly Gly Met Thr Gly Gln Lys Leu Ala
        355                 360                 365

Gln Thr Phe Asp Glu Asp Leu Glu Arg Ile Val Leu Arg Glu Leu Thr
    370                 375                 380

Glu Leu Leu Gly Val Lys Gly Ala Pro Ala Phe Phe Arg Ile His Arg
385                 390                 395                 400

Trp Glu Lys Ala Ile Pro Gln Phe Ile Leu Gly His Gly Glu Thr Val
                405                 410                 415

Arg Thr Ile Arg Lys Lys Leu Pro Ser Gly Leu Arg Leu Ala Gly Asn
            420                 425                 430

Tyr Leu Asp Gly Ile Ser Ile Ala Arg Ala Phe Gly Ser Gly Val Arg
        435                 440                 445

Ala Ala Glu Glu Leu Leu Ser Glu Asp Gly Gly Thr Pro Gly
```

450 455 460

<210> SEQ ID NO 82
<211> LENGTH: 458
<212> TYPE: PRT
<213> ORGANISM: Verrucomicrobiae bacterium

<400> SEQUENCE: 82

Met Gln Asp Ala Ile Ile Leu Gly Gly Gly Ile Ser Gly Leu Thr Ala
1 5 10 15

Gly Tyr Leu Ala Gln Lys Gln Gly Gln Asp Ile Ser Val Ile Glu Lys
20 25 30

Gly Lys Ile Pro Gly Gly Pro Ile Ser Ser Phe Arg Glu Glu Gly Tyr
35 40 45

Leu Val Glu Arg Gly Pro Asn Ser Leu Leu Leu Pro Asp Pro Trp Val
50 55 60

Glu Thr Phe Ile Glu Glu Leu Gly Leu Arg Asp Gln Leu Gln Glu Thr
65 70 75 80

Asn Pro Ile Ala Ser Lys Arg Tyr Ile Val Lys Asn Gly Arg Pro Glu
85 90 95

Ala Val Pro Ser Ser Pro Leu Gln Ala Val Phe Thr Pro Leu Phe Ser
100 105 110

Leu Arg Gly Lys Phe Gly Phe Leu Leu Glu Pro Phe Arg Lys Lys Ile
115 120 125

Ser Asp Arg Ala Gly Ser Arg Glu Thr Val Ala Ser Phe Val Lys Arg
130 135 140

Arg Met Gly Leu Asp Phe Leu Asp Tyr Ala Ile Asp Pro Phe Val Ser
145 150 155 160

Gly Val Tyr Ala Gly Asp Pro Asn Arg Leu Ile Leu Glu His Ala Phe
165 170 175

Pro Leu Met Arg Gly Phe Glu Arg Asp Ser Gly Ser Ile Ile Arg Gly
180 185 190

Ala Ile Lys His Lys Lys Lys Gln Lys Arg Glu Gly Thr Ala Tyr Lys
195 200 205

Lys Arg Ser Ile Ser Phe Lys Asp Gly Leu Gly Ile Leu Pro Gln Thr
210 215 220

Ile Ala Arg Lys Leu Gly Asn Arg Leu Trp Leu Gly Ser Glu Val Val
225 230 235 240

Ala Val Asn Arg Val Glu Asp His Trp Gln Val Thr Trp Lys Arg Glu
245 250 255

Gly Glu Asn Phe Glu Gly Phe Ala Lys Asn Leu Leu Val Cys Leu Pro
260 265 270

Ser His Ala Ile Lys Arg Ile Ala Trp Ser Glu Arg Ile Ala Ala Pro
275 280 285

Leu Arg Ser Ser Pro Asn Leu Glu Tyr Pro Ala Val His Ser Leu Ala
290 295 300

Leu Gly Phe Arg Arg Glu Gln Ile Ala His Ala Leu Asp Gly Phe Gly
305 310 315 320

Val Leu Val Pro Ser Lys Glu Pro Pro Thr Ile Leu Gly Ala Leu Phe
325 330 335

Ser Ser Ser Leu Tyr Glu Gly Arg Ala Pro Asp Gly His Cys Leu Leu
340 345 350

Thr Val Met Leu Gly Gly Ile Arg His Pro Glu Leu Ala Ala Leu Pro
355 360 365

-continued

```
Gln Asp Arg Leu Leu Glu Leu Ala Leu Arg Asp Leu Arg Ala Leu Leu
    370                 375                 380

Gly Leu Lys Gly Asp Pro Ser Phe Tyr Arg Cys Thr Ser Trp Pro Arg
385                 390                 395                 400

Ala Ile Pro Gln Tyr Thr Arg Asp Phe Gly Pro Trp Arg Asp Thr Leu
                405                 410                 415

Lys Ser Leu Ala Glu Glu Phe Pro Gly Leu His Phe Gly Gly Asn Ser
            420                 425                 430

Val Asp Gly Ile Ala Met Gly Ala Ser Ile Leu Ser Gly Lys Arg Leu
        435                 440                 445

Ala Glu Cys Leu Asp Lys Asp Ile Asp Val
    450                 455


<210> SEQ ID NO 83
<211> LENGTH: 446
<212> TYPE: PRT
<213> ORGANISM: Verrucomicrobia bacterium

<400> SEQUENCE: 83

Met Asn Thr Lys Lys Val Cys Ile Leu Gly Ala Gly Leu Ser Gly Ile
1               5                   10                  15

Ser Leu Gly Leu Ser His Glu Asn Lys Gly Asn Gln Val Thr Ile Phe
            20                  25                  30

Glu Lys Asp Leu Arg Val Gly Gly Val Leu Gln Ser Ile Lys Ser Glu
        35                  40                  45

Gly Phe Leu Met Asp Tyr Gly Gly Asn Thr Leu Ser Ile Arg Thr Lys
    50                  55                  60

Lys Thr Val Asp Phe Leu Lys Gln Tyr Glu Ile Leu Glu His Ala Met
65                  70                  75                  80

Asp Ala Asn Gln Glu Ser Ser Lys Arg Phe Ile Ile Arg Lys Asn Arg
                85                  90                  95

Ile Ile Ser Leu Pro Gln Gly Pro Leu Ser Phe Leu Phe Ser Ser Phe
            100                 105                 110

Leu Ser Pro Val Gly Lys Leu Arg Leu Cys Leu Glu Pro Phe Ile Gly
        115                 120                 125

Arg Lys Lys Asp Asn Gly Ser Asp Glu Thr Met Ala Glu Phe Val Glu
    130                 135                 140

Arg Arg Leu Gly Arg Glu Val Leu Asp Tyr Gly Val Asn Pro Phe Ile
145                 150                 155                 160

Gly Gly Val Tyr Ala Ala Arg Pro Glu Ser Leu Ile Leu Lys Tyr Ala
                165                 170                 175

Phe Pro Ser Leu His Asp Thr Glu Leu Thr Phe Gly Ser Ile Phe Trp
            180                 185                 190

Gly Met Ile Arg Gly Gly Thr Gln Pro Ser Glu Lys Ile Ser Lys Ser
        195                 200                 205

Arg Leu Ile Ser Phe Arg Glu Gly Met Gln Glu Leu Pro Asn Arg Leu
    210                 215                 220

Ala Thr Arg Met His Asn Pro Pro Val Leu Gly Cys Glu Ile Lys Lys
225                 230                 235                 240

Ile Glu Phe Lys Asp Asp Val Gln Trp Cys Val Gln Gly Glu Thr Arg
                245                 250                 255

Asp Gly Lys Ile Gln Lys Glu Val Phe Asp Gln Val Ile Cys Thr Leu
            260                 265                 270

Pro Ser His Ala Leu Asp Lys Ile Glu Trp Val Gly Ile Asn Ser Ser
        275                 280                 285
```

His Leu Leu Glu Thr Leu Thr Arg Ala Tyr His Pro Pro Leu Ala Leu
290 295 300

Ala Phe Gln Gly Tyr Gln Gln Arg Gln Ile Lys His Pro Leu Asp Gly
305 310 315 320

Phe Gly Phe Leu Val Pro Glu Lys Glu Arg Arg Lys Ile Leu Gly Thr
325 330 335

Leu Phe Ser Ser Thr Leu Phe Gln Asn Arg Ala Pro Glu Asn Ser Val
340 345 350

Leu Leu Thr Thr Phe Ile Gly Gly Glu Arg Asn Pro Glu Leu Cys Asp
355 360 365

Leu Pro Gln Asn Glu Ile Leu Gly His Ala Phe Arg Glu Asn Gln Asp
370 375 380

Leu Leu Gly Ile Glu Gly Asn Pro Ile Phe Glu His Leu Lys Leu Trp
385 390 395 400

Pro Lys Ser Ile Pro Ile Pro Asp His Thr Leu Glu Asp Arg Lys Lys
405 410 415

Ala Ala Ser Thr Leu Thr Leu Glu Asn Lys Gly Leu Gln Ile Leu Gly
420 425 430

Ala His Ile Asn Gly Ala Pro Leu Pro Asn Cys Met Val Leu
435 440 445

<210> SEQ ID NO 84
<211> LENGTH: 485
<212> TYPE: PRT
<213> ORGANISM: Synechococcus spec

<400> SEQUENCE: 84

Met Asn Pro Ala Thr Pro Glu Pro Leu Asn Ala Glu Val Val Val Ile
1 5 10 15

Gly Ala Gly Ile Ser Gly Leu Thr Leu Ala Trp Arg Leu Gln Gln Gly
20 25 30

Leu Ser Ala Arg Gly Gly Ser Pro Gln Ala Val Leu Leu Ala Glu Ala
35 40 45

Ser Ser Arg Val Gly Gly Cys Ile Ser Thr Gln Ser Lys Asp Gly Tyr
50 55 60

Arg Trp Glu Glu Gly Pro Asn Ser Phe Thr Pro Thr Pro Ala Leu Leu
65 70 75 80

Asn Leu Ile Ala Glu Val Gly Leu Thr Asp Gln Leu Val Leu Ala Asp
85 90 95

Ala Lys Leu Pro Arg Tyr Ile Tyr Trp Glu Gly Ala Leu Leu Pro Val
100 105 110

Pro Leu Ser Pro Ala Ala Ala Leu Gly Ser Arg Leu Leu Ser Val Gly
115 120 125

Gly Lys Leu Arg Ala Leu Gln Gly Leu Leu Gly Phe Val Pro Pro Pro
130 135 140

Pro Gly His Glu Glu Thr Val Arg Gln Phe Phe Arg Arg Gln Leu Gly
145 150 155 160

Ser Glu Val Ala Glu Arg Leu Val Glu Pro Phe Thr Ser Gly Val Tyr
165 170 175

Ala Gly Asp Pro Asp Gln Leu Ser Ala Val Ala Ala Phe Pro Arg Val
180 185 190

Ala Gly Leu Glu Glu Arg Tyr Gly Ser Leu Phe Ala Gly Ala Leu Gln
195 200 205

Ala Leu Arg Gln Arg Pro Gln Pro Ser Pro Ala Ala Ile Gln Pro Pro

```
    210                 215                 220

Pro Lys Arg Gly Gln Leu Gly Asn Leu Arg Gln Gly Leu Gln Gln Leu
225                 230                 235                 240

Pro Glu Ala Leu Ala Gln Lys Leu Gly Asp Ser Leu Arg Leu Gly Trp
                245                 250                 255

Arg Ala Leu Gln Leu Lys Arg Ala Gly Glu Leu Tyr Trp Val Gly Phe
            260                 265                 270

Glu Thr Pro Glu Gly Ser Arg Trp Val Ala Ala Arg Gln Val Val Leu
        275                 280                 285

Ala Leu Pro Ala Tyr Glu Ala Ala Ala Leu Leu Gln Glu Leu Asn Pro
    290                 295                 300

Pro Ala Ser Gln Leu Leu Ala Glu Ile Leu Tyr Pro Pro Val Ala Val
305                 310                 315                 320

Val Ala Leu Ala Tyr Pro Gln Glu Ala Leu Pro Gln Pro Leu Arg Gly
                325                 330                 335

Phe Gly His Leu Ile Pro Arg Ser Gln Gly Leu Arg Thr Leu Gly Thr
            340                 345                 350

Ile Trp Ala Ser Cys Leu Phe Pro Glu Arg Ala Pro Gln Gly Tyr His
        355                 360                 365

Ser Phe Leu Ser Phe Leu Gly Gly Ala Thr Asp Ala Ala Leu Ala Arg
    370                 375                 380

Arg Arg Gly Ile Pro Pro Ile Pro Ala Leu Ser Pro Glu Glu Arg Ala
385                 390                 395                 400

Gln Ile Ala His Ala Glu Leu Ser Gln Val Leu Leu Thr Arg Arg Ala
                405                 410                 415

Glu Pro Val Tyr Leu Gly Glu Arg Leu Trp Pro Arg Ala Ile Pro Gln
            420                 425                 430

Tyr Thr Leu Gly His Arg Gln Arg Ile Ala Gln Val Gln Ala His Leu
        435                 440                 445

Ala Ser Gln Thr Pro Gly Ile Trp Val Cys Ala Asn Tyr Leu Asp Gly
    450                 455                 460

Val Ala Leu Gly Asp Cys Val Arg Arg Ala Glu Ala Leu Ala Gln Gln
465                 470                 475                 480

Leu Leu Ser Gln Val
                485


<210> SEQ ID NO 85
<211> LENGTH: 443
<212> TYPE: PRT
<213> ORGANISM: Hymenobacter norwichensis

<400> SEQUENCE: 85

Met Thr Ile Ala Ile Leu Gly Gly Gly Ile Ser Gly Leu Val Val Ala
1               5                   10                  15

Trp Gln Leu Gln Lys Ala Gly Val Ala Tyr Asp Leu Phe Glu Ala Glu
            20                  25                  30

Thr Thr Pro Gly Gly Cys Leu Arg Ser Val Ser His Pro Asp Gly Tyr
        35                  40                  45

Leu Val Glu Thr Gly Pro Asn Ser Leu Gln Leu Ser Asp Glu Leu Leu
    50                  55                  60

Glu Leu Ile Thr Glu Leu Gly Leu Val Asp Glu Ile Gln Asp Ala Ala
65                  70                  75                  80

Ala Val Ser Lys Asn Arg Tyr Val Leu Arg Asn Gly Arg Tyr Gln Gln
                85                  90                  95
```

-continued

Leu Pro Ser Thr Pro Pro Ala Leu Leu Thr Asn Gly Phe Phe Ser Trp
100 105 110

Lys Ala Lys Phe Asn Ile Leu Arg Glu Leu Arg Arg Pro Ala Ala Pro
115 120 125

Leu Asn Pro Thr Glu Thr Val Asp Ala Phe Phe Arg Arg Arg Phe Gly
130 135 140

Pro Glu Ile Val Asp Tyr Ala Val Asn Pro Phe Ile Ser Gly Ile Tyr
145 150 155 160

Ala Gly Asp Pro Ala Gln Leu Leu Ile His Lys Thr Phe Ser Lys Val
165 170 175

Ala Ala Leu Glu Gln Gln Tyr Gly Ser Val Leu Arg Gly Leu Ala Lys
180 185 190

Thr Gly Gly Gly Ala Gly Arg Arg Arg Ile Ile Ser Leu Gln Gly Gly
195 200 205

Ile Gln Lys Leu Thr Asp Thr Leu Ala Ala Lys Leu Thr His His His
210 215 220

Val Arg Gln Arg Val Leu Ala Leu His Arg Thr Thr Lys Gly Gly Tyr
225 230 235 240

Gln Val Gln Thr Ser Ala Gly Ser Asn Gly Gly Phe Ser Tyr Asp Ala
245 250 255

Val Val Leu Ala Leu Pro Thr Phe Ala Ala Ala Pro Leu Leu Ala Pro
260 265 270

Leu Phe Pro Glu Ala Ala Ala Ala Leu Ala Ala Val His Tyr Pro Pro
275 280 285

Met Ala Ala Val Tyr Thr Ala Tyr Arg Arg Glu Asp Val Gly His Pro
290 295 300

Leu Asp Gly Phe Gly Ala Leu His Pro Lys Val Glu Gln Pro Tyr Ala
305 310 315 320

Ala Gly Ser Ile Trp Thr Ser Ser Ile Phe Pro Asn Arg Val Pro Asp
325 330 335

Gly Gln Val Leu Phe Thr Thr Phe Val Gly Gly Ala Gln Tyr Glu Ala
340 345 350

Asn Ala Gln Gln Ser Glu Thr Ala Gln Lys Ala Ala Val His Glu Glu
355 360 365

Leu Ser Arg Phe Tyr Asp Ile Lys Ala Ala Gln Pro Leu Trp Gln Tyr
370 375 380

Arg Tyr Leu Trp Asp Lys Ala Ile Pro Gln Tyr Asp Gln Arg Ile Met
385 390 395 400

Ala Ala His Thr Thr Thr Asp Ala Leu Gln Ala Gln Gly Ile Trp Ser
405 410 415

Ala Ala Asn Trp Arg Gly Gly Val Gly Val Pro Asp Cys Ile Arg His
420 425 430

Ala Arg His Val Ala Asp Gln Leu Thr Gly Lys
435 440

<210> SEQ ID NO 86
<211> LENGTH: 448
<212> TYPE: PRT
<213> ORGANISM: Pontibacter spec

<400> SEQUENCE: 86

Met Arg Val Ala Ile Ile Gly Ala Gly Ile Ser Gly Leu Ser Leu Ala
1 5 10 15

Tyr Tyr Leu Gln Arg Gln Gly Val Ala Tyr Asp Leu Phe Glu Ala Gly
20 25 30

```
Ser Glu Val Gly Gly Asn Met Arg Thr Leu Arg Lys Asn Gly Tyr Thr
        35                  40                  45

Phe Glu Leu Gly Pro Asn Thr Leu Gln Met Asn Glu Glu Leu Leu Gln
    50                  55                  60

Leu Ile Thr Glu Leu Lys Leu Glu Thr Glu Leu Leu Pro Leu Thr Pro
65                  70                  75                  80

Arg Asn Asn Lys Arg Tyr Val Leu His Asp Gly Lys Leu Tyr Pro Val
                85                  90                  95

Pro Ala Ser Pro Lys Ser Phe Leu Ala Asn Asp Leu Phe Ser Asn Glu
            100                 105                 110

Glu Lys His Arg Ile Leu Gln Glu Arg Lys Gln Pro Pro Ala Glu Val
        115                 120                 125

Glu Asn Glu Thr Val Ser Asp Phe Phe Glu Arg Arg Phe Gly Val Lys
    130                 135                 140

Gln Met Asp Tyr Leu Ala Ala Pro Met Ile Ser Gly Leu Tyr Gly Gly
145                 150                 155                 160

Asp Pro Arg Gln Leu Leu Val Asn Lys Ala His Pro Glu Leu Lys Glu
                165                 170                 175

Leu Glu Thr Gln Tyr Gly Ser Val Leu Glu Gly Met Val Gln Lys Lys
            180                 185                 190

Lys Arg Gly Val Phe Gln Arg Ala Phe Ser Phe Arg Asn Gly Met Ser
        195                 200                 205

Thr Leu Pro His Ala Ile Ala Asp Lys Leu Ile Ser Leu His Leu Asp
    210                 215                 220

His Lys Val Glu Phe Ile Thr Arg Ile Lys Gly Lys Phe Ile Ile Ser
225                 230                 235                 240

Cys Ala Ser Asn Gly Asp His Asp Asn Glu Glu Tyr Asp Lys Leu Val
                245                 250                 255

Leu Ala Leu Pro Ala His Gln Ala Ala Glu Leu Ile Glu Phe Thr Tyr
            260                 265                 270

Pro Gly Met Ser Ala Ala Leu Gln Asn Ile Asn Tyr Pro Pro Met Ala
        275                 280                 285

Val Val His Thr Val Tyr Asn Arg Ala Glu Val Gly His Pro Leu Gln
    290                 295                 300

Gly Phe Gly Ala Leu His Pro Trp Glu Glu Gln Ser Phe Thr Ser Gly
305                 310                 315                 320

Ser Ile Trp Thr Ser Ser Leu Phe Glu Gly Arg Cys Arg Ser His Glu
                325                 330                 335

Val Leu Ile Thr Ser Tyr Val Gly Gly Thr Arg Phe Ala Glu His Ala
            340                 345                 350

Gln Leu Glu Glu Arg Ser Leu Leu Glu Gln Val His Gln Glu Leu Cys
        355                 360                 365

Gln Thr Tyr Gln Ile Lys Ala Leu Ala Pro Val Tyr Gln His Leu His
    370                 375                 380

Leu Trp Gln His Ala Leu Pro Gln Phe Asp Leu Tyr Ile Glu Asp Ala
385                 390                 395                 400

His His Met Ala Glu Val Leu Glu Gln Asp Gly Leu Phe Ile Ser Ala
                405                 410                 415

Asn Trp Tyr Ala Gly Val Ser Val Pro Asp Cys Val Arg Glu Ala Lys
            420                 425                 430

Ala Ile Ala Ala Lys Ile Asn Thr Arg Ala Ala Ser Arg Ser Ile Ala
        435                 440                 445
```

<210> SEQ ID NO 87
<211> LENGTH: 463
<212> TYPE: PRT
<213> ORGANISM: Leptospirillum ferrodiazotrophum

<400> SEQUENCE: 87

```
Met Ala Thr Glu Asp Val Glu Thr Leu Val Ile Gly Gly Gly Ile Ala
1               5                   10                  15

Gly Leu Ala Cys Ala Ser His Leu Lys Leu Ala Gly Arg Thr Val Arg
            20                  25                  30

Leu Val Glu Arg Asn Asp Tyr Leu Gly Gly Val Ile Arg Thr Leu Ser
        35                  40                  45

Asp Ser Gly Tyr Arg Ile Glu Thr Gly Pro Asn Ser Leu Leu Val Arg
    50                  55                  60

Thr Glu Glu Pro Leu Leu Lys Tyr Leu Ser Arg Pro Glu Ile Ala Ala
65                  70                  75                  80

Arg Ile Gln Leu Ala Gly Arg Met Gly Lys Lys Arg Phe Ile Leu Lys
                85                  90                  95

Asp Gly His Pro Val Ala Leu Pro Met Ser Leu Ser Glu Gly Ile Phe
            100                 105                 110

Thr Gln Ile Leu Ser Leu Pro Ala Lys Val Arg Leu Leu Lys Glu Pro
        115                 120                 125

Phe Ile Pro Pro Ala Gly Gly Val Asp Gly Val Asp Pro Glu Lys Glu
    130                 135                 140

Thr Val Ala Asp Phe Val Arg Arg Arg Leu Gly Asn Glu Phe Leu Glu
145                 150                 155                 160

Ser Leu Ile Asp Pro Phe Val Lys Gly Val Tyr Ala Ser Asp Pro His
                165                 170                 175

Leu Leu Ser Met Ala Asp Thr Phe Pro Arg Leu Val Gln Met Glu Lys
            180                 185                 190

Ser Tyr Gly Ser Leu Ile Lys Gly Gly Leu Ala Leu Ala Arg Gln Lys
        195                 200                 205

Lys Ala Pro Ala Pro Ala Phe Ala Arg Glu Ile Leu Ser Phe Ser Glu
    210                 215                 220

Gly Met Gly Thr Leu Pro Glu Ser Leu Ala Asn Ile Leu Asp Asp Asp
225                 230                 235                 240

Ala Gly Thr Asn Ala Glu Val Ile Gly Cys Ala Pro Ser Glu Ser Gly
                245                 250                 255

Phe Arg Thr Ala Leu Leu Phe Glu Glu Glu Thr Tyr Tyr Ile Arg Ser
            260                 265                 270

Lys His Leu Val Leu Ala Leu Pro Ala Ala Gln Thr Ala Glu Leu Ile
        275                 280                 285

Glu Pro Met Ala Pro Gly Ile Pro Ser Leu Leu Gly Gln Ile Pro Tyr
    290                 295                 300

Ala Pro Ile Ala Val Val Tyr Leu Gly Tyr Pro Arg Asp Arg Ile Ser
305                 310                 315                 320

His Pro Leu Asp Gly Phe Gly Leu Leu Val Pro Ser Arg Glu Arg Arg
                325                 330                 335

Lys Ile Leu Gly Ala Leu Phe Ser Ser Ser Leu Phe Pro Gly Arg Ser
            340                 345                 350

Pro Asp Gly His Val Leu Leu Thr Val Phe Val Gly Gly Met Thr Gln
        355                 360                 365

Pro Lys Leu Ala Gln Ala Phe Asp Glu Asp Leu Leu Pro Met Val Thr
    370                 375                 380
```

Lys Glu Ile Gly Ser Met Leu Gly Val Leu Gly Ala Pro Ser Tyr Val
385 390 395 400

Arg Ile Gln Arg Trp Ala Gly Ala Ile Pro Gln Ser Val Pro Gly His
405 410 415

Gly Glu Arg Ile Arg Ser Ile Glu Ser Ala Leu Pro Ser Gly Leu His
420 425 430

Leu Ala Gly Ser Tyr Leu Ser Gly Val Ser Val Ser Gln Thr Phe Ser
435 440 445

Ser Gly Ile Arg Ala Ala Glu Lys Ile Leu Ala Gln Ser Pro Gly
450 455 460

<210> SEQ ID NO 88
<211> LENGTH: 451
<212> TYPE: PRT
<213> ORGANISM: Prevotella histicola

<400> SEQUENCE: 88

Met Glu Arg Gln Arg Lys Ile Ile Val Ile Gly Ala Gly Leu Thr Gly
1 5 10 15

Leu Thr Cys Ala Ala His Leu Arg His Lys Gly Gln Asp Val Glu Val
20 25 30

Leu Glu Ala Thr Glu Arg Ile Gly Gly Leu Met Gln Thr Glu Asp Phe
35 40 45

Asp Gly Phe Ile Met Glu Gln Gly Pro Ser Thr Gly Thr Ile Lys Tyr
50 55 60

Pro Glu Val Ala Glu Leu Phe Asp Met Leu Gly Asp Lys Cys Thr Leu
65 70 75 80

Glu Val Ala Gln Ser Ser Ala Lys Cys Arg Leu Ile Trp Lys Asp Gly
85 90 95

His Phe Cys Ala Leu Pro Ser Gly Leu Trp Ser Ala Val Thr Thr Pro
100 105 110

Leu Phe Thr Leu Lys Asp Lys Phe Arg Ile Leu Gly Glu Pro Trp Arg
115 120 125

Arg Lys Gly Thr Asp Pro Asn Glu Ser Val Gly Ala Leu Ala Glu Arg
130 135 140

Arg Leu Gly Arg Ser Phe Val Asp Tyr Ala Val Asp Pro Phe Leu Ser
145 150 155 160

Gly Val Tyr Ala Gly Asp Pro Tyr Lys Leu Pro Thr Arg Leu Ala Leu
165 170 175

Pro Lys Leu Tyr Asn Leu Glu Gln His Tyr Gly Ser Phe Ile Lys Gly
180 185 190

Ala Met Ala Leu Ala Lys Ala Pro Lys Ser Asp Arg Asp Lys Arg Ala
195 200 205

Thr Lys Glu Val Phe Ser Thr Arg Gly Gly Phe Arg Ser Leu Val Ser
210 215 220

Ala Leu Ala Lys Thr Ile Gly Asp Asp Arg Ile Thr Thr Gly Cys Ala
225 230 235 240

His Leu His Val Glu Pro Leu Gly Asp Lys Trp Lys Leu Ser Trp Gly
245 250 255

Glu Asn Thr Ile Ile Ala Asp Gln Val Val Thr Thr Cys Pro Ala Tyr
260 265 270

Ser Leu Pro Asp Leu Leu Thr Phe Leu Pro Lys Glu Gln Leu Asp Asp
275 280 285

Leu Ser Asn Leu Tyr Tyr Ala Pro Val Ile Glu Ile Gly Val Gly Met 290 295 300

Lys His Thr Gly Asn Val His Trp Asn Ala Phe Gly Gly Leu Val Pro
305 310 315 320

Ser Lys Glu Gln Gln Lys Val Leu Gly Ile Leu Met Pro Ser Ala Cys
325 330 335

Phe Val Gly Arg Ser Pro Glu Glu Gly Ala Thr Tyr Ala Phe Phe Ile
340 345 350

Gly Gly Ala Arg His Pro Glu Tyr Leu Asp Lys Thr Asp Glu Glu Leu
355 360 365

Arg Glu Leu Val Asn Thr Ser Leu His Thr Met Leu Gly Tyr Pro Lys
370 375 380

Gly Thr Gln Ala Asp Ala Ile Arg Ile Tyr Arg His Ser His Ala Ile
385 390 395 400

Pro Gln Tyr Met Thr Glu Thr Asp Ser Arg Leu Arg Ala Ile Asp Thr
405 410 415

Val Glu His Thr Tyr Pro Ser Leu His Ile Ile Gly Asn Leu Lys Asp
420 425 430

Gly Ile Gly Met Gly Asp Arg Ile Lys Gln Ala Val Asp Leu Ala Glu
435 440 445

Arg Ile Gly
450

<210> SEQ ID NO 89
<211> LENGTH: 436
<212> TYPE: PRT
<213> ORGANISM: Flexithrix dorotheae

<400> SEQUENCE: 89

Met Val Gly Ile Ile Gly Ala Gly Ile Ser Gly Leu Ser Leu Ala Tyr
1 5 10 15

His Leu Gln Lys Leu Gly Lys Ala Tyr Cys Leu Phe Glu Ala Gly Asp
20 25 30

Lys Pro Gly Gly Asn Ile Cys Ser Val Lys Lys Glu Gly Phe Leu Leu
35 40 45

Glu Lys Gly Pro Asn Ser Leu Leu Ala Asp Ser Glu Ile Ile Asp Leu
50 55 60

Val Lys Glu Leu Gly Leu Glu Asp Gln Met Ile Ile Pro Glu Thr Val
65 70 75 80

Ser Lys Lys Arg Tyr Ile Phe Lys Asn Gly Lys Tyr Gln Gln Leu Pro
85 90 95

Ser Ser Pro Pro Gly Leu Ile Phe Asn Asn Phe Phe Ser Trp His Ala
100 105 110

Lys Phe Ser Ile Tyr Lys Glu Leu Asn Asn Lys Ser Thr Ser Pro Gln
115 120 125

Asn Glu Thr Val Ala Asp Phe Phe Glu Arg Arg Phe Cys Lys Glu Ile
130 135 140

Val Asp Gln Ala Val Asn Pro Phe Ile Ser Gly Ile Tyr Ala Gly Asp
145 150 155 160

Pro Glu Lys Leu Ile Met Glu Lys Thr Phe Pro Ala Phe Leu Glu Asn
165 170 175

Glu Gln Lys Phe Gly Ser Val Ile Arg Gly Phe Ile Lys Asn Lys Lys
180 185 190

Asn Thr Gln Arg Lys Leu Thr Phe Ser Phe Lys Glu Gly Leu Gly Ile
195 200 205

Leu Ala Asp Lys Leu Ala Glu Asn Leu Ser Val Asn Tyr Asn Ser Pro
    210                 215                 220

Ile Lys Glu Ile Arg Gln Glu Ala Gly Gly Phe Leu Leu Ile Thr Glu
225                 230                 235                 240

Asn Gly Glu Thr Lys Val Thr Ala Leu Val Phe Ser Ile Pro Ala Tyr
                245                 250                 255

Ala Ala Gly Lys Leu Ile Lys Asp Ile Ser Pro Glu Ser Ala Gln Ala
            260                 265                 270

Trp Glu Gly Val Asn Tyr Pro Pro Ile Cys Val Val His Thr Ala Phe
        275                 280                 285

Arg Arg Lys Asp Leu Gly Phe Asp Phe Asn Gly Phe Gly Gly Leu Asn
    290                 295                 300

Pro Lys Lys Glu Asp Leu Phe Thr Ala Gly Ser Ile Trp Asn Ser Ser
305                 310                 315                 320

Leu Phe Glu Asn Arg Ser Pro Lys Asp Gln Phe Leu Ile Thr Ser Phe
                325                 330                 335

Val Gly Gly Ala Gln Ser Leu Asp Asn Phe Gln Leu Thr Asp Glu Glu
            340                 345                 350

Ile Lys Ala Lys Val Thr Asp Glu Leu Gln Gln Asn Phe Lys Ile Lys
        355                 360                 365

Gly Ser Pro Thr His Gln Glu Ile Thr Arg Trp Glu Lys Ser Ile Pro
    370                 375                 380

Gln Tyr Asp Ile Asp Ile Phe Pro Ala His Gln Ala Ile Glu Asn Leu
385                 390                 395                 400

Gln Arg Glu Gly Ile Tyr Val Cys Ser Asn Trp Glu Gly Gly Val Ser
                405                 410                 415

Val Pro Asp Cys Ile Lys Lys Gly Lys Gln Leu Ala Glu Arg Ile Lys
            420                 425                 430

Glu Asn Lys Phe
        435

<210> SEQ ID NO 90
<211> LENGTH: 469
<212> TYPE: PRT
<213> ORGANISM: Geobacter metallireducens

<400> SEQUENCE: 90

Met Lys Lys Val Ile Val Val Gly Gly Gly Ile Ser Gly Leu Ala Thr
1               5                   10                  15

Ala Phe Glu Leu Arg Asn Lys Gly Ala Glu Ala Gly Ile Glu Leu Asp
            20                  25                  30

Val Thr Leu Leu Glu Lys Glu Glu Arg Val Gly Gly Lys Ile Trp Ser
        35                  40                  45

Ile Lys Glu Glu Gly Tyr Leu Cys Glu Trp Gly Pro Asn Gly Phe Leu
    50                  55                  60

Asp Ser Lys Pro Gln Thr Leu Asp Leu Cys Arg Asp Leu Gly Ala Ser
65                  70                  75                  80

Glu Arg Leu Leu Arg Ser Asn Asp Asn Ala Arg Lys Arg Phe Ile Tyr
                85                  90                  95

Thr Gly Gly Val Leu Asn Arg Leu Pro Glu Asn Gly Pro Thr Phe Leu
            100                 105                 110

Lys Ser Ser Leu Ile Ser Trp Pro Gly Lys Leu Arg Leu Ala Met Glu
        115                 120                 125

Pro Phe Ile Ser Lys Arg Thr Asp Gly Thr Asp Glu Thr Leu Ala Ser
    130                 135                 140

```
Phe Gly Arg Arg Arg Leu Gly Glu Glu Ala Leu Gln Lys Leu Ile Ser
145                 150                 155                 160

Pro Met Val Ser Gly Ile Phe Ala Gly Asp Pro Glu Thr Met Ser Leu
                165                 170                 175

Arg Ser Cys Phe Pro Arg Ile Ala Glu Leu Glu Asp Glu Tyr Gly Ser
            180                 185                 190

Leu Ile Lys Ala Met Ile Lys Leu Ala Lys Lys Lys Lys Gln Glu Ala
        195                 200                 205

Ala Gln Gly Lys Ala Val Ser Ser Ala Ala Gly Pro Gly Gly Val Leu
    210                 215                 220

Thr Ser Phe Arg Trp Gly Ile Gln Glu Leu Thr Asp Ile Leu Ala Glu
225                 230                 235                 240

Gln Leu Gly Ser Ala Thr Val Val Thr Gly Gln Pro Val Thr Gly Leu
                245                 250                 255

Thr Arg Gly Ser Ser Val Pro Trp Arg Leu Lys Thr Pro Thr Val Asp
            260                 265                 270

Ile Asp Ala Asp Val Val Ile Leu Ala Ser Pro Ala His Ala Thr Ala
        275                 280                 285

Gly Ile Val Ser Gly Val Asp Ala Ala Met Ala Gln Val Leu Gly Glu
    290                 295                 300

Ile Pro Tyr Ala Ser Met Thr Val Val Cys Phe Gly Phe Glu Arg Glu
305                 310                 315                 320

Arg Ile Ala Tyr Asp Leu Asn Gly Phe Gly Tyr Leu Ile Pro Lys Asp
                325                 330                 335

Glu Gly Met Asn Thr Leu Gly Thr Leu Trp Asp Ser Ser Ile Phe Glu
            340                 345                 350

Asn Arg Ala Pro Glu Gly Lys Val Leu Leu Arg Ser Met Leu Gly Gly
        355                 360                 365

Ala Cys Phe Pro Glu Tyr Val Lys Leu Ser Asp Ala Glu Val Met Gln
    370                 375                 380

Arg Val Lys Ala Asp Leu Lys Ala Thr Met Gly Ile Thr Ala Asp Pro
385                 390                 395                 400

Ser Phe Ile Arg Ile Phe Arg His Pro Gln Ala Ile Pro Gln Tyr Thr
                405                 410                 415

Val Gly His Gly Lys Arg Leu Ala Ala Leu Gln Glu Arg Ser Ser Ala
            420                 425                 430

Leu Pro Gly Leu Phe Leu Thr Gly Asn Ser Tyr Arg Gly Ile Gly Leu
        435                 440                 445

Asn Asp Cys Ala Thr Ala Ala Asn Arg Thr Thr Asp Glu Val Val Ala
    450                 455                 460

Tyr Leu Lys Gly Arg
465
```

<210> SEQ ID NO 91
<211> LENGTH: 498
<212> TYPE: PRT
<213> ORGANISM: Synechococcus spec

<400> SEQUENCE: 91

```
Met Gln Ala Glu Val Val Val Val Gly Ala Gly Ile Ser Gly Leu Thr
1               5                   10                  15

Leu Ala Leu Arg Leu Gln Gln Gly Leu Ser Pro Lys Asp Glu Ser Thr
            20                  25                  30

Gln Pro Leu Leu Leu Ala Glu Ala Ser Ser Arg Val Gly Gly Cys Ile
```

```
        35                  40                  45

Ser Thr Gln Ser Lys Asp Ser Tyr Arg Trp Glu Glu Gly Pro Asn Ser
    50                  55                  60

Phe Thr Pro Val Pro Ala Leu Leu Asn Leu Ile Ala Glu Val Gly Leu
65                  70                  75                  80

Ala Glu His Leu Val Leu Ala Asp Ala Lys Leu Pro Arg Tyr Ile Tyr
                85                  90                  95

Trp Glu Lys Glu Leu Leu Pro Val Pro Leu Ser Pro Ser Ala Ala Ile
            100                 105                 110

Gly Ser Arg Leu Leu Ser Val Gly Gly Lys Leu Arg Ala Leu Arg Gly
        115                 120                 125

Leu Leu Gly Phe Val Ala Pro Pro Pro Gly Gly Glu Glu Thr Val Arg
    130                 135                 140

Gln Phe Phe Arg Arg Gln Leu Gly Ser Glu Val Val Glu Arg Leu Val
145                 150                 155                 160

Glu Pro Phe Thr Ser Gly Val Tyr Ala Gly Asp Pro Asp Gln Leu Ser
                165                 170                 175

Ala Leu Ala Ala Phe Pro Arg Ile Ala Gly Leu Glu Glu Arg Tyr Gly
            180                 185                 190

Ser Leu Phe Ala Gly Ala Val Gln Ala Leu Arg Ser Arg Tyr Arg Tyr
        195                 200                 205

Ala Thr Leu Pro Arg Thr Arg His Gln Asp Ser Ala Asn Ser Pro Ile
    210                 215                 220

Gln Pro Pro Pro Lys Arg Gly Gln Leu Gly Asn Leu Arg Gln Gly Leu
225                 230                 235                 240

Gln Gln Leu Pro Glu Ala Ile Ala Gln Lys Leu Gly Ser Ala Leu Arg
                245                 250                 255

Leu Gly Trp Arg Ala Val His Leu Lys Arg Asp Glu Thr Gly Tyr Arg
            260                 265                 270

Val Gly Phe Val Ile His Asp Ser Gly Ala Glu His Thr Ala Pro Glu
        275                 280                 285

Glu Ile His Trp Val Ala Ala Gln Gln Val Val Leu Thr Leu Pro Ala
    290                 295                 300

Tyr Ala Ala Ala Thr Leu Leu Gln Asp Leu Asn Pro Gln Ala Ser Arg
305                 310                 315                 320

Leu Leu Arg Glu Ile Pro Tyr Pro Pro Val Ala Val Val Ala Leu Ala
                325                 330                 335

Tyr Pro Glu Glu Ala Leu Pro Gln Pro Leu Arg Gly Phe Gly His Leu
            340                 345                 350

Ile Pro Arg Ser Gln Gly Leu Arg Thr Leu Gly Thr Ile Trp Ala Ser
        355                 360                 365

Ser Leu Phe Pro Glu Arg Ala Pro Gln Gly Tyr His Cys Leu Ile Ser
    370                 375                 380

Phe Ile Gly Gly Ala Thr Asp Ala Ala Phe Ala Arg Gln Lys Gly Ile
385                 390                 395                 400

Pro Pro Ile Thr Ala Leu Ser Pro Asp Glu Arg Ala Gln Ile Val His
                405                 410                 415

Ala Glu Leu Ser Gln Ile Leu Leu Thr Arg Pro Val Glu Pro Ile Arg
            420                 425                 430

Leu Gly Glu Arg Leu Trp Pro Gln Ala Ile Pro Gln Tyr Thr Leu Gly
        435                 440                 445

His Arg Gln Arg Ile Ala Gln Leu Gln Ala Ser Leu Ala Asp Gln Thr
    450                 455                 460
```

Pro Gly Val Trp Val Cys Ala Asn Tyr Leu Asp Gly Val Ala Leu Gly
465 470 475 480

Asp Cys Val Arg Arg Ala Glu Ala Leu Ala Gln Gln Ile Leu Ser Val
485 490 495

Arg Arg

<210> SEQ ID NO 92
<211> LENGTH: 475
<212> TYPE: PRT
<213> ORGANISM: Crinalium epipsammum

<400> SEQUENCE: 92

Met Val Asp Thr Leu Ile Ile Gly Ala Gly Ile Ser Gly Leu Ser Leu
1 5 10 15

Ala Tyr Ala Leu His Gln Asp Gly Arg Lys Val Leu Leu Cys Glu Arg
20 25 30

Gln Glu Arg Val Gly Gly Asn Ile Thr Thr Gly Lys Ala Gly Gly Phe
35 40 45

Leu Trp Glu Glu Gly Pro Thr Ser Phe Thr Pro Thr Pro Ala Leu Leu
50 55 60

Lys Leu Ala Val Asp Val Gly Leu Arg Glu Glu Leu Val Leu Ala Asp
65 70 75 80

His Arg Leu Pro Arg Phe Val Tyr Trp Lys Gly Gln Leu Leu Pro Val
85 90 95

Pro Met Ser Pro Pro Ser Ala Val Thr Ser Lys Leu Leu Ser Leu Ser
100 105 110

Gly Lys Phe Arg Ala Leu Val Gly Ala Leu Gly Phe Ile Pro Pro Ala
115 120 125

Ile Gly Asn His Leu Ser Gln Gln Gly Gly Glu Glu Thr Val Ala Gln
130 135 140

Phe Phe Lys Arg His Leu Gly Thr Glu Val Ala Glu Arg Leu Val Ala
145 150 155 160

Pro Phe Val Ser Gly Val Tyr Ala Gly Asp Val His Gln Leu Ser Ala
165 170 175

Arg Ser Ala Phe Arg Arg Ile Ala Gln Leu Glu Asn Val Gly Gly Gly
180 185 190

Leu Val Ser Gly Ala Ile Leu Ser Arg Lys Gln Arg Gln Gln Gln Lys
195 200 205

Pro Pro Thr Asp Pro Ser Leu Pro Thr Val Arg Arg Gly Glu Leu Gly
210 215 220

Ser Phe Lys Glu Gly Leu Gln Ser Leu Pro Lys Ala Ile Ala Ser His
225 230 235 240

Leu Gly Glu Asn Ile Lys Leu Asn Trp Thr Leu Thr Glu Leu Arg Gln
245 250 255

Thr Ala Asn Gln Thr Tyr Ile Ala Glu Phe Ser Thr Pro Glu Gly Ser
260 265 270

Gln Gln Val Glu Ala Arg Thr Val Val Leu Thr Thr Pro Ala Tyr Val
275 280 285

Thr Ala Glu Leu Leu His Asn Leu Ala Pro Asn Ala Ser Ile Ala Leu
290 295 300

Lys Glu Ile Pro Tyr Pro Ser Val Ala Cys Val Val Leu Ala Tyr Pro
305 310 315 320

Asp Asp Ala Leu Lys Phe Pro Leu Lys Gly Phe Gly Asn Leu Ile Pro
325 330 335

```
Arg Gly Gln Gly Ile Arg Thr Leu Gly Thr Ile Trp Ser Ser Ser Leu
            340                 345                 350

Phe Pro Gly Arg Ala Pro Gln Gly Trp Gln Met Leu Thr Asn Phe Ile
        355                 360                 365

Gly Gly Ala Thr Asp Pro Glu Val Gly Asn Leu Asp Asn Glu Gln Leu
    370                 375                 380

Val Gln Ala Val His Lys Asp Leu Gln Arg Val Leu Leu Lys Lys Asp
385                 390                 395                 400

Val Pro Pro Lys Ala Ile Ala Val His Leu Trp Lys Arg Ala Ile Pro
                405                 410                 415

Gln Tyr Thr Leu Gly His His Leu Arg Leu Ala Gln Ile Asn Gln Asp
            420                 425                 430

Leu Ala Gln Leu Pro Gly Leu Tyr Leu Cys Ser Asn Tyr Thr Asp Gly
        435                 440                 445

Val Ser Leu Gly Asp Cys Val Gln Arg Ala Tyr Asp Gln Leu Pro Ile
    450                 455                 460

Ile Asn Lys Gln Leu Ser Ile Ile Asn Asp Asn
465                 470                 475


<210> SEQ ID NO 93
<211> LENGTH: 486
<212> TYPE: PRT
<213> ORGANISM: Planctomyces maris

<400> SEQUENCE: 93

Met Asn Gln Ser Ala Pro Ala Lys Arg Ile Ala Val Val Gly Gly Gly
1               5                   10                  15

Ile Thr Gly Leu Ser Ala Ala Phe His Leu Gln Glu Leu Ala Gln Glu
            20                  25                  30

Lys Asn Gln Pro Val Glu Val Thr Leu Phe Glu Ser Gln Pro Glu Ala
        35                  40                  45

Gly Gly Trp Ile Gly Thr Ile Ser Gln Asp Gly Tyr Arg Ile Asp Thr
    50                  55                  60

Gly Ala Asp Met Phe Ile Thr Asn Lys Pro Ala Ala Ile Glu Leu Cys
65                  70                  75                  80

Gln Arg Leu Gly Leu Glu Asp Gln Leu Ile Ser Thr Asn Gln Gln Tyr
                85                  90                  95

Arg Gly Ala Leu Ile Leu Lys Asp Gly Thr Pro Val Pro Val Pro Leu
            100                 105                 110

Gly Phe Glu Leu Met Thr Pro Ser Arg Ile Leu Pro Met Leu Lys Thr
        115                 120                 125

Pro Leu Leu Ser Pro Ile Gly Lys Leu Arg Met Gly Leu Glu Tyr Phe
    130                 135                 140

Leu Pro Arg Arg Thr Ser Glu Ser Gly Leu Asp Ala Asp Asp Glu Ser
145                 150                 155                 160

Leu Ala Gln Phe Val Thr Arg Arg Phe Gly Arg Glu Ala Leu Thr Arg
                165                 170                 175

Leu Ile Gln Pro Leu Val Ala Gly Ile Tyr Thr Ser Asp Pro Glu Lys
            180                 185                 190

Leu Ser Leu Arg Ala Thr Leu Pro Arg Phe Leu Asp Met Glu Arg Asp
        195                 200                 205

His Arg Ser Leu Ile Lys Ala Ile Arg Lys Gln Lys Lys Gln Thr Lys
    210                 215                 220

Ser Ala Asp Ala Thr Gly Ala Arg Tyr Gly Leu Phe Ala Ala Phe Lys
```

-continued 225 230 235 240

Glu Gly Met Gln Thr Leu Ile Arg Thr Leu Ala Asp Arg Val Ser Ser
245 250 255

Thr Gly Thr Ile Leu Tyr Glu His Arg Val Thr His Val Ala Ala Ala
260 265 270

Asp Ser Gly Tyr Asp Leu Thr Ile Glu Ser Thr Val Glu Thr Gln Thr
275 280 285

Gln His Phe Asp Ala Val Leu Leu Thr Thr Ala Ala Pro Gln Ala Gly
290 295 300

Gln Met Leu Glu Ala Tyr Ala Pro Val Leu Ser Gly Leu Leu Lys Gln
305 310 315 320

Ile Glu Tyr Ala Ser Thr Ala Ile Gln Val Ser Val Tyr Arg Gln Glu
325 330 335

Asn Ile Lys His Pro Leu His Ala Phe Gly Leu Val Ile Pro Ala Ala
340 345 350

Glu Gln Arg Lys Ile Phe Ala Val Ala Phe Ala Ser Arg Lys Phe Pro
355 360 365

Gly Arg Ala Pro Glu Gly Cys Val Gln Leu Arg Thr Phe Val Gly Gly
370 375 380

Ala Met Gln Pro Glu Leu Leu Glu His Ser Asp Asp Glu Leu Asn Ala
385 390 395 400

Ile Val Asn Gln Glu Leu Ala Asp Ile Leu Gly Val Ser Gly Glu Pro
405 410 415

Ile Phe Ser Lys Leu Leu Arg His Asn Gln Ser Met Pro Gln Tyr His
420 425 430

Leu Gly His Leu Gln Leu Val Glu Arg Ile Glu Gln Ser Ala Ala Thr
435 440 445

Leu Ala Gly Leu Glu Leu Ala Gly Asn Ala Tyr Arg Gly Val Gly Ile
450 455 460

Pro Asp Cys Ile His Ser Ala Glu Gln Ala Ala Glu Arg Leu Leu Val
465 470 475 480

Asp Leu Thr Ala Arg Val
485

<210> SEQ ID NO 94
<211> LENGTH: 471
<212> TYPE: PRT
<213> ORGANISM: Geobacter uraniireducens

<400> SEQUENCE: 94

Met Lys Lys Ala Ile Val Val Gly Gly Gly Ile Ser Gly Leu Ala Ser
1 5 10 15

Ala Tyr Leu Leu Arg Glu Lys Ala Lys Asn Ser Gly Met Glu Leu Glu
20 25 30

Ile Thr Ile Val Glu Lys Glu Asp Arg Thr Gly Gly Lys Ile Arg Ser
35 40 45

Ile Lys Glu Asp Gly Tyr Leu Cys Glu Trp Gly Pro Asn Gly Phe Leu
50 55 60

Asp Ser Lys Pro Gln Thr Leu Asp Leu Cys Arg Glu Leu Lys Val Asp
65 70 75 80

Ser Gln Leu Leu Arg Ser Asn Asp Asn Ala Arg Lys Arg Phe Ile Tyr
85 90 95

Ser Gly Gly Val Leu Asn Arg Leu Pro Glu Asn Gly Pro Ser Phe Leu
100 105 110

```
Lys Ser Arg Leu Ile Ser Trp Pro Gly Lys Leu Arg Leu Ala Leu Glu
        115                 120                 125

Pro Thr Pro Phe Ile Ala Lys Ala Pro Glu Gly Val Asp Glu Thr Leu
    130                 135                 140

Ala Ala Phe Gly Arg Arg Arg Leu Gly Asp Glu Ala Leu Arg Lys Leu
145                 150                 155                 160

Ile Ala Pro Met Val Ser Gly Ile Phe Ala Gly Asp Pro Glu Thr Met
                165                 170                 175

Ser Leu Val Ser Cys Phe Pro Arg Ile Ala Glu Leu Glu Arg Glu Tyr
            180                 185                 190

Gly Gly Leu Val Lys Ala Met Val Lys Leu Ala Lys Lys Lys Lys Gln
        195                 200                 205

Glu Ile Ala Glu Gly Lys Gln Val Ala Ser Ala Ala Gly Pro Gly Gly
    210                 215                 220

Val Leu Thr Ser Phe Arg Asp Gly Ile Gln Thr Leu Thr Asp Ile Leu
225                 230                 235                 240

Asn Glu Arg Leu Gly Lys Asp Met Leu Val Ile Gly Ala Glu Val Thr
                245                 250                 255

Gly Val Ser Arg Gly Asn Ser Thr Pro Tyr Arg Val Gln Thr Gly Gly
            260                 265                 270

Arg Glu Leu Asp Ala Asp Ile Val Val Leu Ala Thr Pro Ala Tyr Ala
        275                 280                 285

Thr Ala Gln Ala Leu Glu Gly Ile Asp Gly Gly Met Ser Ala Thr Leu
    290                 295                 300

Asn Gln Ile Pro Tyr Ala Thr Met Thr Val Val Cys Phe Gly Tyr Glu
305                 310                 315                 320

Gln Glu Lys Val Ala His Asp Leu Asn Gly Phe Gly Tyr Leu Ile Pro
                325                 330                 335

Lys Ala Glu Gly Met Asn Ile Leu Gly Thr Leu Trp Asp Ser Ser Ile
            340                 345                 350

Phe Glu Asn Arg Ala Pro Glu Gly Lys Val Leu Leu Arg Ser Met Met
        355                 360                 365

Gly Gly Ala Cys Phe Pro Glu Tyr Ile Arg Leu Ser Asp Ala Glu Val
    370                 375                 380

Val Gln Lys Val Arg Asp Asn Leu Lys Thr Ile Met Gly Ile Lys Glu
385                 390                 395                 400

Ala Pro Glu Phe Val Arg Ile Phe Arg His Glu Lys Ala Ile Pro Gln
                405                 410                 415

Tyr Thr Val Gly His Gly Arg Arg Leu Ala Ala Leu Glu Glu Gln Ala
            420                 425                 430

Lys Ser His Pro Gly Leu Phe Leu Ser Gly Asn Ser Tyr Arg Gly Ile
        435                 440                 445

Gly Leu Asn Asp Cys Val Ala Ala Ala Asn Arg Thr Ala Asp Glu Val
    450                 455                 460

Val Ala Phe Leu Gln Ser Arg
465                 470


<210> SEQ ID NO 95
<211> LENGTH: 446
<212> TYPE: PRT
<213> ORGANISM: Acidithiobacillus ferrivorans

<400> SEQUENCE: 95

Met Glu Asp Val Ile Ile Ile Gly Ala Gly Ile Ser Gly Leu Ala Thr
1               5                   10                  15
```

-continued

```
Ala Tyr Phe Leu Arg Lys Gln Gly Trp Ser Pro Leu Leu Leu Glu Ala
            20                  25                  30

Ala Ala Lys Pro Gly Gly Asn Leu Gln Ser Arg Gln Glu Glu Gly Tyr
        35                  40                  45

Leu Arg Asp Met Gly Pro Asn Ser Leu Met Leu Lys Gly His Ile Val
    50                  55                  60

Pro Glu Trp Leu Arg Glu Leu Arg Leu Glu Glu Asp Ile Val Glu Ala
65                  70                  75                  80

Asn Pro Leu Ala Lys Arg Arg Tyr Ile Leu Asn Arg His Arg Gln Pro
                85                  90                  95

Val Ala Leu Gly Pro Gly Val Leu Phe Gly Gly Gly Leu Leu Ser Trp
            100                 105                 110

Arg Gly Arg Leu Arg Leu Leu Gly Glu Pro Phe Arg Ser Pro Arg Arg
        115                 120                 125

Met Gln Asp Ser Glu Glu Ser Val Ala Asp Phe Val Arg Arg Arg Leu
    130                 135                 140

Gly Glu Glu Ala Leu Thr Trp Leu Val Asp Pro Phe Ile Ser Gly Val
145                 150                 155                 160

Phe Ala Gly Asn Pro Ala Arg Leu Ser Val Gln Ala Thr Leu Pro Arg
                165                 170                 175

Leu Ile Ala Leu Glu Gln Asp Gly Gly Ser Leu Leu Arg Gly Ala Leu
            180                 185                 190

Arg Ala Arg Asn Lys Lys Ser Pro Asp Thr Pro Lys Thr Arg Leu Ile
        195                 200                 205

Ser Phe Arg Glu Gly Leu Gln Thr Leu Pro Leu Arg Val Ala Ser Ala
    210                 215                 220

Leu Gly Asp Ala Leu Arg Cys Asn Thr Pro Val Glu Gln Leu Gly Asn
225                 230                 235                 240

Ser Asp Gly Ser Trp Gln Val Ser Ser Gly Ser Gln Thr Trp Gln Ser
                245                 250                 255

Lys Arg Leu Ile Leu Ala Leu Pro Ala Gly Ala Ala Ala Arg Leu Leu
            260                 265                 270

Ala Pro Thr Asp Ala Ala Leu Ala His Glu Leu Asp Ala Ile Pro Tyr
        275                 280                 285

Pro Ala Val Gly Ser Leu Ser Ile Gly Phe Gln Arg Met Gln Val Gln
    290                 295                 300

His Pro Leu Asp Gly Phe Gly Ile Leu Ile Pro Arg Val Met Gly Leu
305                 310                 315                 320

Glu Thr Leu Gly Ile Leu Phe Ser Ser Thr Leu Phe Pro Gly Arg Ala
                325                 330                 335

Pro Ala Asp Gln Val Leu Leu Thr Ala Phe Ile Gly Gly Ser Gln Asn
            340                 345                 350

Asp Ile Ser Gly Arg Asp Asp Asp Asp Leu Leu Ala Thr Ala Leu Arg
        355                 360                 365

Glu Ile Cys Pro Leu Leu Gly Ile Ser Gly Lys Pro Val Phe Ser Arg
    370                 375                 380

Cys Gln Thr Trp Pro Lys Ala Ile Pro Gln Tyr Glu Ile Gly His Leu
385                 390                 395                 400

Asp Arg Ile Lys Arg Ile Asp Ala Leu Ser Ala Arg His Pro Gly Leu
                405                 410                 415

Tyr Phe Arg Ala Asn Trp Arg Glu Gly Val Ala Leu Gly Asp Cys Met
            420                 425                 430
```

```
Glu Glu Ala Tyr Arg Phe Ser Gln Asp Val Gly Trp Gln Arg
        435                 440                 445


<210> SEQ ID NO 96
<211> LENGTH: 454
<212> TYPE: PRT
<213> ORGANISM: Prevotella melaninogenica

<400> SEQUENCE: 96

Met Glu Glu Arg Lys Ile Val Val Val Gly Ala Gly Leu Thr Gly Leu
1               5                   10                  15

Thr Cys Ala Ala Tyr Leu Arg Arg Lys Gly Gln Asp Val Val Val Leu
            20                  25                  30

Glu Ala Ala Asp Arg Ile Gly Gly Leu Met Gln Thr Glu Glu Val Asp
        35                  40                  45

Gly Phe Val Met Glu Gln Gly Pro Ser Thr Gly Thr Ile Lys Tyr Pro
    50                  55                  60

Glu Val Ala Glu Leu Phe Asp Met Leu Gly Asp Asp Cys Thr Leu Glu
65                  70                  75                  80

Val Ala Gln Ser Ser Ala Lys Cys Arg Leu Ile Trp Lys Asp Gly Arg
                85                  90                  95

Phe His Ala Leu Pro Ser Gly Leu Trp Ser Ala Ile Thr Thr Pro Leu
            100                 105                 110

Phe Thr Leu Lys Asp Lys Phe Arg Ile Leu Gly Glu Pro Trp Arg Lys
        115                 120                 125

Lys Gly Ile Asp Pro Asn Glu Ser Val Gly Ser Leu Ala Glu Arg Arg
    130                 135                 140

Leu Gly Arg Ser Phe Val Asp Tyr Ala Val Asp Pro Phe Leu Ser Gly
145                 150                 155                 160

Val Tyr Ala Gly Asp Pro Tyr Gln Leu Pro Thr Arg Leu Ala Leu Pro
                165                 170                 175

Lys Leu Tyr Asp Leu Glu Gln Arg Tyr Gly Ser Phe Ile Lys Gly Ala
            180                 185                 190

Met Ala Leu Ala Lys Gln Pro Lys Thr Asp Arg Glu Lys Arg Ala Thr
        195                 200                 205

Lys Ala Val Phe Ser Thr Arg Gly Gly Phe Arg Ser Leu Val Ser Ala
    210                 215                 220

Leu Gly Arg Val Ile Gly Asp Glu Arg Ile Arg Thr Asn Cys Lys Glu
225                 230                 235                 240

Leu Ser Ile Glu Pro Leu Gly Asp Lys Trp Lys Leu Ser Trp Gly Glu
                245                 250                 255

Asn Thr Ile Ile Ala Glu Gln Val Ile Thr Thr Cys Pro Ala Tyr Ala
            260                 265                 270

Leu Pro Lys Leu Leu Asn Phe Leu Pro Lys Glu Gln Leu Asp Asp Leu
        275                 280                 285

Ser Asn Leu Tyr Tyr Ala Pro Val Ile Glu Ile Gly Val Gly Met Lys
    290                 295                 300

Asn Thr Gly Asp Val His Trp Asn Ala Phe Gly Gly Leu Val Pro Ser
305                 310                 315                 320

Lys Glu Lys Gln Asn Val Leu Gly Val Leu Met Pro Ser Ala Cys Phe
                325                 330                 335

Gln Gly Arg Ser Pro Lys Glu Gly Ala Asn Tyr Ala Cys Phe Ile Gly
            340                 345                 350

Gly Ala Cys His Pro Glu Tyr Ile Asn Lys Thr Asp Glu Glu Leu Ile
        355                 360                 365
```

```
Gly Leu Val Asn Thr Ser Leu His Thr Met Leu Gly Tyr Pro Lys Gly
    370                 375                 380

Thr Cys Ala Asp Val Ile Arg Ile Tyr Arg His Ser His Ala Ile Pro
385                 390                 395                 400

Gln Tyr Met Pro Glu Thr Asp Ala Arg Leu Arg Thr Ile Asp Ala Val
                405                 410                 415

Glu Leu Ala Tyr Pro Gly Leu His Ile Ile Gly Asn Leu Lys Asp Gly
            420                 425                 430

Ile Gly Met Gly Asp Arg Ile Lys Gln Ala Val Asp Met Ala Glu Lys
        435                 440                 445

Ile Ser Leu Ser Val Ser
    450


<210> SEQ ID NO 97
<211> LENGTH: 458
<212> TYPE: PRT
<213> ORGANISM: Thermovibrio ammonificans

<400> SEQUENCE: 97

Met Arg Val Cys Val Ile Gly Gly Gly Val Ser Gly Leu Ser Thr Ala
1               5                   10                  15

Phe Tyr Leu Lys Arg Gly Gly Ala Gln Val Lys Leu Leu Glu Arg Glu
            20                  25                  30

Asn Tyr Pro Gly Gly Lys Ala Arg Thr Tyr Tyr Glu Lys Gly Tyr Ile
        35                  40                  45

Val Glu Ser Gly Pro Asn Gly Phe Leu Asp Gly Lys Pro Asp Thr Leu
    50                  55                  60

Glu Leu Val Lys Leu Leu Gly Ala Glu Lys Leu Leu Tyr Arg Ser Ser
65                  70                  75                  80

Asp Lys Ala Arg Lys Arg Phe Ile Tyr Lys Asn Gly Arg Leu Val Arg
                85                  90                  95

Leu Pro Glu Asn Pro Ile Ala Phe Leu Ser Ser Tyr Leu Leu Ser Trp
            100                 105                 110

Lys Gly Lys Val Arg Val Leu Gly Glu Leu Leu Val Pro Pro Ser Glu
        115                 120                 125

Lys Glu Asp Glu Thr Leu Ala Glu Phe Val Arg Arg Arg Leu Gly Lys
    130                 135                 140

Glu Ala Leu Asp Tyr Leu Leu Asp Pro Met Val Ala Gly Ile Phe Ala
145                 150                 155                 160

Gly Asp Pro Glu Arg Met Ser Leu Lys Ala Ala Phe Pro Thr Ile Tyr
                165                 170                 175

Arg Leu Glu Arg Glu Tyr Gly Gly Leu Ile Arg Gly Leu Ile Ala Lys
            180                 185                 190

Ala Lys Glu Ala Lys Lys Lys Gly Ala Lys Ser Ser Gly Pro Ala Gly
        195                 200                 205

Pro Gly Gly Val Leu Thr Ser Phe Val Lys Gly Met Ser Gln Phe Thr
    210                 215                 220

Gln Leu Leu Ala Gln Glu Leu Gly Glu Ser Phe Thr Pro Glu Ala Gln
225                 230                 235                 240

Val Lys Thr Leu Glu Lys Lys Lys Asp Lys Trp Leu Val Thr Tyr Thr
                245                 250                 255

Leu Arg Gly Lys Glu Lys Ser Glu Glu Phe Asp Ala Val Val Leu Ser
            260                 265                 270

Leu Pro Ala Tyr Ala Ala Ala Gln Val Leu Lys Glu Thr Ser Arg Glu
```

275 280 285

Leu Ser Glu Leu Leu Ala Ser Ile Glu Tyr Ser Pro Ile Ser Val Val
290 295 300

Ala Leu Gly Phe Glu Lys Arg Gly Leu Gly His Asn Leu Asp Gly Phe
305 310 315 320

Gly Phe Leu Val Pro Lys Val Glu Gly Arg Lys Ile Leu Gly Ala Leu
325 330 335

Trp Asp Ser Ser Val Phe Pro Asn Arg Ala Pro Glu Gly Lys Ala Leu
340 345 350

Ile Arg Val Met Ile Gly Gly Ala Arg Gln Pro Glu Leu Ala Leu Lys
355 360 365

Ser Glu Glu Glu Leu Thr Glu Ile Ala Leu Lys Glu Leu Lys Arg Ile
370 375 380

Met Lys Ile Arg His Tyr Pro Glu Met Val Lys Val Phe Arg His Glu
385 390 395 400

Lys Gly Ile Pro His Tyr Thr Ile Gly His Ala Glu Lys Val Glu Arg
405 410 415

Ile Phe Lys Leu Gly Arg Glu Leu Gly Asn Leu Phe Phe Cys Asn Asn
420 425 430

Ala Tyr Lys Gly Val Gly Ile Asn Asp Cys Thr Lys Ser Ala Arg Glu
435 440 445

Thr Ala Glu Glu Val Leu Asn Ser Leu Cys
450 455

<210> SEQ ID NO 98
<211> LENGTH: 536
<212> TYPE: PRT
<213> ORGANISM: Brassica rapa

<400> SEQUENCE: 98

Met Asp Leu Ser Leu Leu Arg Pro Gln Pro Phe Leu Ser Pro Phe Ser
1 5 10 15

Asn Pro Phe Pro Arg Ser Arg Pro Tyr Lys Pro Leu Asn Leu Arg Cys
20 25 30

Ser Val Ser Gly Gly Ser Val Val Gly Ser Ser Thr Ile Glu Gly Gly
35 40 45

Gly Gly Gly Lys Thr Val Thr Ala Asp Cys Val Ile Val Gly Gly Gly
50 55 60

Ile Ser Gly Leu Cys Ile Ala Gln Ala Leu Val Thr Lys His Pro Asp
65 70 75 80

Ala Ala Lys Asn Val Met Val Thr Glu Ala Lys Asp Arg Val Gly Gly
85 90 95

Asn Ile Ile Thr Arg Glu Glu Gln Gly Phe Leu Trp Glu Glu Gly Pro
100 105 110

Asn Ser Phe Gln Pro Ser Asp Pro Met Leu Thr Met Val Val Asp Ser
115 120 125

Gly Leu Lys Asp Asp Leu Val Leu Gly Asp Pro Thr Ala Pro Arg Phe
130 135 140

Val Leu Trp Asn Gly Lys Leu Arg Pro Val Pro Ser Lys Leu Thr Asp
145 150 155 160

Leu Pro Phe Phe Asp Leu Met Ser Ile Gly Gly Lys Ile Arg Ala Gly
165 170 175

Phe Gly Ala Ile Gly Ile Arg Pro Ser Pro Pro Gly Arg Glu Glu Ser
180 185 190

```
Val Glu Glu Phe Val Arg Arg Asn Leu Gly Asp Glu Val Phe Glu Arg
        195                 200                 205

Leu Ile Glu Pro Phe Cys Ser Gly Val Tyr Ala Gly Asp Pro Ala Lys
    210                 215                 220

Leu Ser Met Lys Ala Ala Phe Gly Lys Val Trp Lys Leu Glu Glu Asn
225                 230                 235                 240

Gly Gly Ser Ile Ile Gly Gly Ala Phe Lys Ala Ile Gln Ala Lys Asn
                245                 250                 255

Lys Ala Pro Lys Thr Thr Arg Asp Pro Arg Leu Pro Lys Pro Lys Gly
            260                 265                 270

Gln Thr Val Gly Ser Phe Arg Lys Gly Leu Thr Met Leu Pro Glu Ala
        275                 280                 285

Ile Ser Ala Arg Leu Gly Asp Lys Val Lys Val Ser Trp Lys Leu Ser
    290                 295                 300

Ser Ile Thr Lys Leu Ala Ser Gly Glu Tyr Ser Leu Thr Tyr Glu Thr
305                 310                 315                 320

Pro Glu Gly Ile Val Thr Val Gln Ser Lys Ser Val Val Met Thr Val
                325                 330                 335

Pro Ser His Val Ala Ser Ser Leu Leu Arg Pro Leu Ser Asp Ser Ala
            340                 345                 350

Ala Glu Ala Leu Ser Lys Leu Tyr Tyr Pro Pro Val Ala Ala Val Ser
        355                 360                 365

Ile Ser Tyr Ala Lys Glu Ala Ile Arg Ser Glu Cys Leu Ile Asp Gly
    370                 375                 380

Glu Leu Lys Gly Phe Gly Gln Leu His Pro Arg Thr Gln Lys Val Glu
385                 390                 395                 400

Thr Leu Gly Thr Ile Tyr Ser Ser Ser Leu Phe Pro Asn Arg Ala Pro
                405                 410                 415

Pro Gly Arg Val Leu Leu Leu Asn Tyr Ile Gly Gly Ala Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Ser Ser Thr Asp Pro Leu Val
    450                 455                 460

Leu Gly Val Lys Val Trp Pro Gln Ala Ile Pro Gln Phe Leu Ile Gly
465                 470                 475                 480

His Ile Asp Leu Val Asp Ala Ala Lys Ala Ser Leu Ser Ser Ser Gly
                485                 490                 495

His Glu Gly Leu Phe Leu Gly Gly Asn Tyr Val Ala Gly Val Ala Leu
            500                 505                 510

Gly Arg Cys Val Glu Gly Ala Tyr Glu Thr Ala Thr Gln Val Asn Asp
        515                 520                 525

Phe Met Ser Arg Tyr Ala Tyr Lys
    530                 535
```

<210> SEQ ID NO 99
<211> LENGTH: 521
<212> TYPE: PRT
<213> ORGANISM: Brassica rapa

<400> SEQUENCE: 99

```
Met Ala Ser Asn Ala Val Ala Asp His Asp Lys Pro Val Ser Gly Lys
1               5                   10                  15

Arg Val Ala Val Val Gly Ala Gly Val Ser Gly Leu Ala Ala Ala Tyr
            20                  25                  30
```

```
Lys Leu Lys Ser Lys Gly Val Asn Val Thr Val Phe Glu Ala Asp Gly
        35                  40                  45

Arg Val Gly Gly Lys Leu Arg Ser Val Met His Asn Gly Leu Ile Trp
    50                  55                  60

Asp Glu Gly Ala Asn Thr Met Thr Glu Ala Glu Pro Glu Val Gly Ser
65                  70                  75                  80

Leu Leu Asp Asp Leu Gly Leu Arg Glu Lys Gln Gln Phe Val Ser Thr
                85                  90                  95

Phe His Ala Leu Ser Ile Met Phe Gln Pro Leu Ser Gln Lys Lys Arg
            100                 105                 110

Tyr Ile Val Arg Asn Gly Leu Pro Val Met Ile Pro Thr Asn Pro Ile
        115                 120                 125

Ala Leu Val Thr Ser Ser Val Leu Ser Thr Gln Ser Lys Phe Gln Ile
    130                 135                 140

Leu Leu Glu Pro Phe Leu Trp Lys Lys Asn Asp Ser Ser Ser Lys Val
145                 150                 155                 160

Ser Asp Ala Ser Val Val Glu Ser Val Ser Gly Phe Phe Gln Arg His
                165                 170                 175

Phe Gly Gln Glu Val Val Asp Tyr Leu Ile Asp Pro Phe Met Gly Gly
            180                 185                 190

Thr Ser Ala Ala Asp Pro Glu Ser Leu Ser Met Lys His Ser Phe Pro
        195                 200                 205

Asp Leu Trp Asn Ile Glu Lys Ser Phe Gly Ser Ile Ile Val Gly Ala
    210                 215                 220

Ile Arg Ser Lys Phe Ala Ala Lys Gly Ser Lys Asn Gly Glu Thr Lys
225                 230                 235                 240

Ser Ser Thr Gly Thr Lys Lys Gly Ser Arg Gly Ser Phe Ser Phe Lys
                245                 250                 255

Gly Gly Met Gln Ile Leu Pro Asp Met Leu Cys Lys Asp Leu Ser Arg
            260                 265                 270

Glu Asp Leu Asn Leu Asp Ser Lys Val Leu Ser Leu Ser Tyr Asn Thr
        275                 280                 285

Gly Pro Arg Glu Glu Asn Trp Ser Leu Ser Cys Val Ser His Asn Glu
    290                 295                 300

Thr Gln Arg Gln Asn Leu His Tyr Asp Ala Val Val Met Thr Ala Pro
305                 310                 315                 320

Leu Cys Asn Val Lys Glu Met Lys Val Met Lys Gly Gly Glu Pro Phe
                325                 330                 335

Lys Leu Asn Phe Leu Pro Glu Ile Lys Tyr Met Pro Leu Ser Val Ile
            340                 345                 350

Ile Thr Thr Phe Thr Lys Glu Lys Val Lys Arg Pro Leu Glu Gly Phe
        355                 360                 365

Gly Val Leu Ile Pro Ser Ile Glu Gln Lys His Gly Phe Lys Thr Leu
    370                 375                 380

Gly Thr Leu Phe Ser Ser Met Met Phe Pro Asp Arg Cys Pro Ser Asp
385                 390                 395                 400

Leu His Leu Tyr Thr Thr Phe Ile Gly Gly Ser Arg Asn Gln Glu Leu
                405                 410                 415

Ala Lys Ala Ser Thr Asp Glu Leu Lys Gln Val Val Thr Ser Asp Leu
            420                 425                 430

Gln Arg Leu Leu Gly Ile Glu Gly Glu Pro Val Phe Val Asn His Val
        435                 440                 445
```

```
Tyr Trp Asn Lys Ala Phe Pro Leu Tyr Asp Arg Ser Tyr Asp Ser Val
    450                 455                 460

Met Glu Ala Ile Asp Lys Met Glu Lys Asp Leu Pro Gly Phe Phe Tyr
465                 470                 475                 480

Ala Gly Asn His Arg Gly Gly Leu Ser Val Gly Lys Ser Ile Ala Ser
                485                 490                 495

Gly Cys Lys Ala Ala Asp Leu Val Ile Ser Tyr Leu Glu Ser Cys Ser
            500                 505                 510

Asn Asp Asn Lys Pro Glu Asp Ser Leu
        515                 520


<210> SEQ ID NO 100
<211> LENGTH: 539
<212> TYPE: PRT
<213> ORGANISM: Gossypium hirsutum

<400> SEQUENCE: 100

Met Thr Ala Leu Ile Asp Leu Ser Leu Leu Arg Ser Ser Pro Ser Val
1               5                   10                  15

Ser Pro Phe Ser Ile Pro His His Gln His Pro Pro Arg Phe Arg Lys
            20                  25                  30

Pro Phe Lys Leu Arg Cys Ser Leu Ala Glu Gly Pro Thr Ile Ser Ser
        35                  40                  45

Ser Lys Ile Asp Gly Gly Glu Ser Ser Ile Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300
```

Lys Leu Ser Ser Ile Thr Lys Leu Gly Asn Gly Gly Tyr Asn Leu Gln
305 310 315 320

Phe Glu Thr Pro Glu Gly Met Val Ser Leu Gln Ser Arg Ser Val Val
325 330 335

Met Thr Ile Pro Ser His Val Ala Ser Asn Leu Leu His Pro Leu Ser
340 345 350

Ala Ala Ala Ala Asp Ala Leu Ser Gln Phe Tyr Tyr Pro Pro Val Ala
355 360 365

Ser Val Thr Val Ser Tyr Pro Lys Glu Ala Ile Arg Lys Glu Cys Leu
370 375 380

Ile Asp Gly Glu Leu Lys Gly Phe Gly Gln Leu His Pro Arg Ser Gln
385 390 395 400

Gly Ile Glu Thr Leu Gly Thr Ile Tyr Ser Ser Ser Leu Phe Pro Asn
405 410 415

Arg Ala Pro Ser Gly Arg Val Leu Leu Leu Asn Tyr Ile Gly Gly Ala
420 425 430

Thr Asn Thr Gly Ile Leu Ser Lys Thr Glu Gly Glu Leu Val Glu Ala
435 440 445

Val Asp Arg Asp Leu Arg Lys Met Leu Ile Asn Pro Asn Ala Lys Asp
450 455 460

Pro Leu Val Leu Gly Val Arg Val Trp Pro Lys Ala Ile Pro Gln Phe
465 470 475 480

Leu Val Gly His Leu Asp Leu Leu Asp Ser Ala Lys Met Ala Leu Arg
485 490 495

Asp Ser Gly Phe His Gly Leu Phe Leu Gly Gly Asn Tyr Val Ser Gly
500 505 510

Val Ala Leu Gly Arg Cys Val Glu Gly Ala Tyr Glu Val Ala Ala Glu
515 520 525

Val Lys Glu Phe Leu Ser Gln Tyr Ala Tyr Lys
530 535

<210> SEQ ID NO 101
<211> LENGTH: 503
<212> TYPE: PRT
<213> ORGANISM: Gossypium hirsutum

<400> SEQUENCE: 101

Met Ala Ser Thr Glu Asn Lys Asp Asp His Ser Ser Ala Lys Arg Val
1 5 10 15

Ala Val Ile Gly Ala Gly Val Ser Gly Leu Ala Ala Ala Tyr Lys Leu
20 25 30

Lys Ser Gln Gly Leu His Val Thr Val Phe Glu Ser Glu Gly Arg Ala
35 40 45

Gly Gly Lys Leu Arg Ser Val Ser Arg Glu Gly Leu Ile Trp Asp Glu
50 55 60

Gly Ala Asn Thr Met Thr Glu Ser Glu Ile Glu Val Arg Ser Leu Phe
65 70 75 80

Asp Asp Leu Gly Ile Gln Asp Lys Glu Gln Val Pro Ile Ala Gln Asn
85 90 95

Lys Arg Tyr Ile Val Arg Asn Gly Val Pro Val Leu Ile Pro Ser Asn
100 105 110

Pro Leu Ala Leu Phe Thr Ser Ser Ile Leu Ser Ala Lys Ser Lys Phe
115 120 125

Gln Ile Ile Leu Glu Pro Phe Leu Trp Arg Lys Ser Glu Ala Ser Lys

```
    130                 135                 140

Val Ser Asp Ala Tyr Asn Gln Glu Ser Val Gly Gly Phe Phe Gln Arg
145                 150                 155                 160

His Phe Gly Gln Glu Val Val Asp Tyr Leu Val Asp Pro Phe Val Ala
                165                 170                 175

Gly Thr Ser Ala Gly Asp Pro Glu Ser Leu Ser Met Cys His Ser Phe
            180                 185                 190

Pro Glu Leu Trp Asp Leu Glu Gln Arg Phe Gly Ser Ile Ile Val Gly
        195                 200                 205

Ala Val Lys Ser Lys Phe Ser Ala Lys Arg Thr Asn Arg Glu Glu Thr
    210                 215                 220

Lys Asn Ser Val Lys Arg Lys Ala Leu Arg Gly Ser Phe Ser Phe Gln
225                 230                 235                 240

Gly Gly Met Gln Thr Leu Ala Asp Met Leu Cys Lys Asp Leu Ser Lys
                245                 250                 255

Asp Glu Leu Lys Leu Lys Ser Lys Val Leu Ser Leu Ser Tyr Ser His
            260                 265                 270

Glu Gly Lys Ser Thr Ser Glu Asn Trp Ser Leu Ser Tyr Ala Ser Asp
        275                 280                 285

Arg Asp Lys Arg Ser Gln Gly Ser Ser Phe Asp Ala Val Ile Met Thr
    290                 295                 300

Ala Pro Val Cys Asn Val Lys Glu Met Lys Ile Thr Lys Gly Gly Asn
305                 310                 315                 320

Val Phe Pro Leu Asn Phe Ile Pro Glu Val Ser Tyr Met Pro Leu Ser
                325                 330                 335

Val Ile Ile Thr Ala Phe Lys Lys Glu Asn Val Lys Lys Pro Leu Glu
            340                 345                 350

Gly Phe Gly Val Leu Ile Pro Ser Lys Glu Gln Gln Asn Gly Leu Lys
        355                 360                 365

Thr Leu Gly Thr Leu Phe Ser Ser Val Met Phe Pro Asp Arg Ala Pro
    370                 375                 380

Asn Asn Leu Tyr Leu Tyr Thr Thr Phe Val Gly Gly Asn Arg Asn Lys
385                 390                 395                 400

Glu Leu Ala Lys Ala Ser Thr Asp Glu Leu Lys His Ile Val Thr Ser
                405                 410                 415

Asp Leu Gln Gln Leu Leu Gly Val Glu Gly Glu Pro Thr Phe Phe Asn
            420                 425                 430

His Phe Tyr Trp Ser Lys Ala Phe Pro Leu Tyr Gly Arg Asn Tyr Ala
        435                 440                 445

Ser Val Leu Glu Ala Ile Glu Lys Ile Glu Arg Asp Leu Pro Gly Phe
    450                 455                 460

Phe Tyr Ala Gly Asn His Lys Gly Gly Leu Ser Val Gly Lys Ser Ile
465                 470                 475                 480

Ala Ser Gly Cys Lys Ala Ala Asp Asn Val Ile Thr Tyr Leu Glu Ser
                485                 490                 495

Ser His Asp Lys Leu Leu Lys
            500
```

<210> SEQ ID NO 102
<211> LENGTH: 535
<212> TYPE: PRT
<213> ORGANISM: Conyza canadensis

<400> SEQUENCE: 102

-continued

```
Met Thr Ser Leu Thr Asn Phe Thr Pro Leu Lys Leu Thr Asn Pro Asn
1               5                   10                  15

Tyr Leu Thr Thr Thr Thr Thr Tyr Asn His Arg Lys Leu Ser Asn Phe
            20                  25                  30

Arg Phe Arg Cys Ser Ile Ala Arg Asp Ser Pro Thr Ala Pro Ser Ile
        35                  40                  45

Ser Gly Asp Ser Ser Ser Arg Pro Leu Leu Asp Cys Val Val Val Gly
    50                  55                  60

Ala Gly Ile Ser Gly Leu Cys Ile Ala Gln Ala Leu Ser Thr Lys His
65                  70                  75                  80

Gly Gly Asp Val Val Val Thr Glu Ala Arg Glu Arg Val Gly Gly Asn
                85                  90                  95

Ile Ser Thr Val Glu Arg Asp Gly Tyr Leu Trp Glu Glu Gly Pro Asn
            100                 105                 110

Ser Phe Gln Pro Ser Asp Pro Met Leu Thr Met Val Val Asp Ser Gly
        115                 120                 125

Leu Lys Asp Asp Leu Val Leu Gly Asp Pro Thr Ala Pro Arg Phe Val
    130                 135                 140

Leu Trp Asp Gly Asp Leu Lys Pro Val Pro Ser Ser Pro Ser Asp Leu
145                 150                 155                 160

Pro Thr Phe Asp Leu Met Ser Leu Gly Gly Lys Leu Arg Ala Gly Phe
                165                 170                 175

Gly Ala Leu Gly Ile Arg Pro Pro Pro Pro Asp Arg Glu Glu Ser Val
            180                 185                 190

Glu Glu Phe Val Arg Arg Asn Leu Gly Asp Glu Val Phe Glu Arg Leu
        195                 200                 205

Ile Glu Pro Phe Cys Ser Gly Val Tyr Ala Gly Asp Pro Ser Lys Leu
    210                 215                 220

Ser Met Lys Ala Ala Phe Gly Lys Val Trp Lys Leu Glu Gln Asn Gly
225                 230                 235                 240

Gly Ser Ile Val Gly Gly Ala Phe Lys Ala Ile Gln Ala Lys Asn Lys
                245                 250                 255

Ser Thr Lys Pro Pro Arg Asp Pro Arg Leu Pro Thr Pro Lys Gly Gln
            260                 265                 270

Thr Val Gly Ser Phe Arg Lys Gly Gln Ala Met Leu Pro Asn Ala Ile
        275                 280                 285

Ser Lys Gly Leu Gly Ser Arg Val Lys Leu Ser Trp Glu Leu Val Gly
    290                 295                 300

Ile Thr Lys Ser Glu Asn Arg Gly Tyr Ser Leu Thr Tyr Arg Thr Pro
305                 310                 315                 320

Asp Gly Leu Glu Ser Leu Gln Thr Lys Thr Val Val Met Thr Val Pro
                325                 330                 335

Ser Tyr Val Ala Ser Asp Leu Leu Arg Pro Leu Ser Val Glu Ala Ala
            340                 345                 350

Asp Ala Leu Ser Lys Phe Tyr Tyr Pro Pro Val Ala Ala Val Ser Val
        355                 360                 365

Ser Tyr Pro Lys Glu Ala Ile Arg Ala Asp Arg Leu Ile Asp Gly Gln
    370                 375                 380

Leu Lys Gly Phe Gly Gln Leu His Pro Arg Ser Gln Gly Val Glu Thr
385                 390                 395                 400

Leu Gly Thr Ile Tyr Ser Ser Ser Leu Phe Pro Asn Arg Ala Pro Pro
                405                 410                 415

Gly Arg Val Leu Leu Leu Asn Tyr Ile Gly Gly Ala Thr Asn Pro Gly
```

```
            420                 425                 430

Ile Leu Ser Lys Thr Glu Ser Gln Ile Val Glu Ala Val Asp Arg Asp
        435                 440                 445

Leu Arg Lys Met Leu Ile Asn Pro Lys Ala Gly Glu Pro Leu Thr Leu
    450                 455                 460

Gly Val Lys Val Trp Pro Arg Ala Ile Pro Gln Phe Leu Ile Gly His
465                 470                 475                 480

Tyr Asp Ile Leu Glu Ala Ala Lys Cys Ala Leu Ser Leu Ala Gly Tyr
                485                 490                 495

Arg Gly Met Phe Leu Gly Gly Asn Tyr Val Ser Gly Val Ala Leu Gly
            500                 505                 510

Arg Cys Val Glu Asn Ala Tyr Glu Val Ala Ala Asp Val Ser Asn Phe
        515                 520                 525

Leu Ser Arg Gly Val Tyr Lys
    530                 535


<210> SEQ ID NO 103
<211> LENGTH: 498
<212> TYPE: PRT
<213> ORGANISM: Conyza canadensis

<400> SEQUENCE: 103

Met Ala Ser Pro Thr Thr Thr Thr Asp Asp Asn Lys Glu Lys Ala Pro
1               5                   10                  15

Ala Lys Arg Val Ala Val Val Gly Ala Gly Val Ser Gly Leu Ala Ala
            20                  25                  30

Ala Tyr Lys Leu Lys Leu His Gly Ile Asn Val Thr Val Phe Glu Ala
        35                  40                  45

Gly Glu Ile Ala Gly Gly Lys Leu Arg Ser Ile Ser Gln Asn Gly Leu
    50                  55                  60

Ile Trp Asp Glu Gly Ala Asn Thr Met Thr Glu Ser Glu Pro Asp Val
65                  70                  75                  80

Ser Arg Leu Leu Asp Asp Leu Gly Leu Arg Asp Lys Gln Gln Ser Pro
                85                  90                  95

Leu Ser Gln His Lys Arg Tyr Ile Val Arg Asn Gly Lys Pro Val Leu
            100                 105                 110

Val Pro Ser Asn Pro Ile Ala Leu Ile Gln Ser Ser Leu Leu Ser Thr
        115                 120                 125

Gln Ser Lys Leu Gln Ile Leu Leu Glu Pro Phe Ser Trp Lys Lys Lys
    130                 135                 140

Asn Ser Ser Asp Thr Gln Glu Ser Val Gly Ala Phe Phe Gln Arg His
145                 150                 155                 160

Phe Gly Lys Glu Val Val Glu Tyr Leu Ile Asn Pro Val Val Ala Gly
                165                 170                 175

Thr Ser Gly Gly Asp Pro Glu Ser Leu Ser Met Arg Tyr Ser Phe Pro
            180                 185                 190

Glu Leu Trp Asp Leu Glu Arg Arg Phe Gly Ser Leu Ile Ser Gly Ala
        195                 200                 205

Phe Gln Ser Met Ile Ser Ser Arg Gly Arg Lys Lys Ser Pro Ser Gly
    210                 215                 220

Ser Ser Lys Arg Arg Arg Gly Ser Phe Ser Phe Leu Gly Gly Met Gln
225                 230                 235                 240

Thr Leu Thr Asn Ala Leu Ser Lys Glu Val Gly Gln His Glu Leu Asn
                245                 250                 255
```

```
Leu Gln Ser Lys Val Leu Glu Met Ser Tyr Ser Cys Asp Asp Asn Thr
            260                 265                 270

Thr Gly Asn Trp Ser Ile Tyr Cys Ala Pro Asp Gln Asn Lys Gln Leu
        275                 280                 285

Asn Gln Gln Pro Phe Asp Ala Val Ile Met Thr Ala Pro Leu Gly Asn
    290                 295                 300

Val Lys Glu Met Lys Ile Thr Lys Thr Gly Ser Pro Phe Leu Leu Asn
305                 310                 315                 320

Phe Ile Pro Glu Leu Ser Tyr Met Pro Val Ser Val Ile Ile Ser Thr
                325                 330                 335

Phe Lys Lys Glu Asn Val Lys Arg Pro Leu Glu Gly Phe Gly Met Leu
            340                 345                 350

Val Pro Ala Lys Glu Gln Glu Asn Gly Leu Lys Thr Leu Gly Thr Leu
        355                 360                 365

Phe Ser Ser Met Met Phe Pro Asp Arg Ala Pro Glu Asp Leu Tyr Leu
    370                 375                 380

Tyr Thr Thr Phe Val Gly Gly Ser Arg Asn Lys Glu Leu Ala Asn Ala
385                 390                 395                 400

Ser Arg Asp Glu Leu Lys Gln Ile Val Thr Ser Asp Leu Arg Gln Leu
                405                 410                 415

Leu Gly Ala Glu Gly Glu Pro Gln Phe Leu Thr His Tyr Tyr Trp Ser
            420                 425                 430

Lys Ala Tyr Pro Leu Tyr Gly Arg Asp Tyr Gly Leu Val Met Glu Ala
        435                 440                 445

Ile Glu Lys Met Glu Arg Glu Leu Pro Gly Tyr Phe Tyr Ala Gly Asn
    450                 455                 460

His Lys Gly Gly Leu Ala Val Gly Lys Ala Ile Ser Ser Gly Cys Lys
465                 470                 475                 480

Ala Ala Glu Ser Val Ile Ser Tyr Leu Asp Ser Tyr Ser Asp Glu Lys
                485                 490                 495

Arg Cys


<210> SEQ ID NO 104
<211> LENGTH: 565
<212> TYPE: PRT
<213> ORGANISM: Kochia scobaria

<400> SEQUENCE: 104

Met Ser Ala Met Ala Ser Pro Ser Ile Ile Pro Gln Ser Phe Leu Gln
1               5                   10                  15

Arg Ser Pro Thr Ser Leu Gln Ser Arg Ser Asn Tyr Ser Lys Asn His
            20                  25                  30

Ile Ile Ile Ser Ile Ser Thr Pro Cys Ser His Gly Lys Asn Gln Arg
        35                  40                  45

Arg Phe Leu Arg Lys Thr Thr His Phe Arg Ser Ile His Cys Ser Thr
    50                  55                  60

Ile Ser Thr Ser Thr Pro Thr Ser Ser Ser Asn Pro Gly Thr Leu Gly
65                  70                  75                  80

Glu Gly Gly Leu Leu Asp Cys Val Ile Val Gly Gly Gly Ile Ser Gly
                85                  90                  95

Leu Cys Ile Ala Gln Ala Leu Ser Thr Lys Tyr Ser Ser Leu Ser Thr
            100                 105                 110

Asn Phe Ile Val Thr Glu Ala Lys Asp Arg Val Gly Gly Asn Ile Thr
        115                 120                 125
```

-continued

```
Thr Lys Glu Asp Asp Gly Tyr Ile Trp Glu Glu Gly Pro Asn Ser Phe
    130                 135                 140

Gln Pro Ser Asp Ala Val Leu Thr Met Ala Val Asp Cys Gly Leu Lys
145                 150                 155                 160

Asp Glu Leu Val Phe Gly Asp Pro Lys Ala Pro Arg Phe Val Leu Trp
                165                 170                 175

Asn Gly Lys Leu Arg Arg Val Pro Ser Lys Leu Thr Asp Leu Pro Phe
            180                 185                 190

Phe Asp Leu Met Ser Phe Pro Gly Lys Ile Arg Ala Gly Leu Gly Ala
        195                 200                 205

Leu Gly Phe Arg Pro Ser Pro Pro Gly Arg Glu Glu Ser Val Glu Asp
    210                 215                 220

Phe Val Arg Arg Asn Leu Gly Asp Glu Val Phe Glu Arg Leu Ile Glu
225                 230                 235                 240

Pro Phe Cys Ser Gly Val Tyr Ala Gly Asp Pro Ala Lys Leu Ser Met
                245                 250                 255

Lys Ala Ala Phe Gly Arg Val Trp Val Leu Glu Gln Met Gly Gly Asn
            260                 265                 270

Ile Ile Gly Gly Ala Leu Lys Thr Ile Gln Glu Lys Lys Asn Lys Pro
        275                 280                 285

Lys Pro Pro Arg Asp Pro Arg Leu Pro Lys Pro Lys Gly Gln Thr Val
    290                 295                 300

Gly Ser Phe Arg Lys Gly Leu Ile Met Leu Pro Asn Ala Ile Ser Ala
305                 310                 315                 320

Arg Leu Gly Ser Lys Val Lys Leu Ser Trp Thr Leu Ala Ser Ile Ser
                325                 330                 335

Lys Thr His Asn Gly Glu Tyr Asn Leu Ile Tyr Asp Thr Pro Asp Gly
            340                 345                 350

Pro Val Ser Val Arg Thr Lys Ser Ile Val Met Thr Ile Pro Ser Tyr
        355                 360                 365

Val Ala Ser Ser Leu Leu Arg Pro Phe Ser Asp Ala Ala Ala Asp Ser
    370                 375                 380

Leu Ser Lys Phe His Tyr Pro Pro Val Ala Ala Val Ser Leu Ser Tyr
385                 390                 395                 400

Pro Glu Glu Ala Ile Arg Pro Glu Cys Leu Ile Asp Gly Lys Leu Gln
                405                 410                 415

Gly Phe Gly Gln Leu His Pro Arg Ser Gln Gly Val Glu Thr Leu Gly
            420                 425                 430

Ser Ile Tyr Ser Ser Ser Leu Phe Pro Gly Arg Ala Pro Pro Gly Arg
        435                 440                 445

Thr Met Ile Leu Ser Phe Ile Gly Gly Ala Thr Asn Pro Gly Ile Val
    450                 455                 460

Asp Lys Thr Gln Asp Glu Leu Ala Lys Thr Val Asp Lys Asp Leu Arg
465                 470                 475                 480

Arg Ile Leu Ile Asn Pro Ser Ala Lys Asp Pro Arg Val Leu Gly Val
                485                 490                 495

Lys Val Trp Pro Gln Ala Ile Pro Gln Phe Leu Ile Gly His Phe Asp
            500                 505                 510

Leu Leu Asp Ala Ala Lys Ala Ala Leu Thr Asp Ala Gly Cys Lys Gly
        515                 520                 525

Leu Phe Leu Gly Gly Asn Tyr Val Ser Gly Val Ala Leu Gly Arg Cys
    530                 535                 540

Ile Glu Gly Ala Tyr Glu Ser Ala Ala Glu Val Val Asp Phe Leu Ser
```

```
545                 550                 555                 560

Gln Tyr Ser Asp Lys
                565


<210> SEQ ID NO 105
<211> LENGTH: 531
<212> TYPE: PRT
<213> ORGANISM: Lolium rigidum

<400> SEQUENCE: 105

Met Val Gly Ala Thr Met Ala Thr Ala Thr Val Thr Ala Ala Leu Pro
1               5                   10                  15

Leu Arg Leu Arg Val Pro Ala Arg Ser Arg Arg Gly Gln Thr Arg Cys
            20                  25                  30

Ala Val Ala Ser Asp Ala Thr Glu Ala Pro Ala Val Pro Ser Ala Arg
        35                  40                  45

Leu Ser Ala Asp Cys Val Ile Val Gly Gly Gly Ile Ser Gly Leu Cys
    50                  55                  60

Thr Ala Gln Ala Leu Ala Thr Lys Tyr Gly Val Thr Asp Leu Leu Val
65                  70                  75                  80

Thr Glu Ala Arg Ala Arg Ala Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Gln Gly
    130                 135                 140

Lys Leu Arg Pro Val Pro Ser Lys Pro Gly Asp Leu Pro Phe Phe Asp
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Arg Ala
    210                 215                 220

Ala Phe Gly Lys Val Trp Arg Leu Glu Glu Asn Gly Gly Ser Ile Ile
225                 230                 235                 240

Gly Gly Thr Ile Lys Ala Ile Gln Asp Arg Gly Lys Asn Pro Lys Pro
                245                 250                 255

Pro Arg Asp Pro Arg Leu Pro Thr Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Gly Ile Thr Lys Ser
    290                 295                 300

Asp Asn Gln Gly Tyr Val Leu Ala Tyr Glu Thr Pro Glu Gly Val Val
305                 310                 315                 320

Ser Val Gln Ala Lys Ser Val Ile Met Thr Ile Pro Ser Tyr Ile Ala
                325                 330                 335

Ser Glu Ile Leu Arg Pro Leu Ser Ser Asp Ala Ala Asp Gly Leu Ser
            340                 345                 350
```

```
Lys Phe Tyr Tyr Pro Pro Val Ala Ala Val Thr Val Ser Tyr Pro Thr
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ala Thr Asn Thr Gly Ile Val Ser Lys
            420                 425                 430

Thr Glu Ser Asp Leu Val Glu Ala Val Asp Arg Asp Leu Arg Lys Met
        435                 440                 445

Leu Ile Asn Pro Thr Ala Pro Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Asp Ala Ala Lys Ser Ala Leu Ala Arg Gly Gly Cys Ser Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Glu Val Ser Asp Phe Leu Thr Lys Tyr
        515                 520                 525

Ala Tyr Lys
    530


<210> SEQ ID NO 106
<211> LENGTH: 509
<212> TYPE: PRT
<213> ORGANISM: Lolium rigidum

<400> SEQUENCE: 106

Met Ala Ala Ser Asp Asp Pro Arg Ala Ala Pro Ala Arg Ser Val Ala
1               5                   10                  15

Val Val Gly Ala Gly Val Ser Gly Leu Val Ala Ala Tyr Arg Leu Arg
            20                  25                  30

Lys Ser Gly Val Arg Val Thr Val Phe Glu Ala Asp Asp Arg Ala Gly
        35                  40                  45

Gly Lys Ile Arg Thr Asn Ser Asp Gly Gly Phe Leu Trp Asp Glu Gly
    50                  55                  60

Ala Asn Thr Met Thr Glu Ser Ala Leu Glu Ala Ser Arg Leu Ile Asp
65                  70                  75                  80

Asp Leu Gly Leu Glu Gly Arg Leu Gln Tyr Pro Asn Ser Gln His Lys
                85                  90                  95

Arg Tyr Thr Val Lys Asp Gly Ala Pro Ala Leu Ile Pro Ser Asp Pro
            100                 105                 110

Ile Ala Leu Met Lys Ser Ser Leu Leu Ser Thr Lys Ser Lys Phe Lys
        115                 120                 125

Leu Phe Leu Glu Pro Phe Leu Tyr Glu Lys Ser Ser Thr Asn Asn Ser
    130                 135                 140

Lys Lys Val Ser Asp Glu His Ile Arg Glu Ser Val Gly Ser Phe Phe
145                 150                 155                 160

Glu Arg His Phe Gly Lys Glu Val Val Asp Tyr Leu Ile Asp Pro Phe
                165                 170                 175

Val Ala Gly Thr Ser Ala Gly Asp Pro Glu Ser Leu Ser Ile Arg His
            180                 185                 190
```

Ala Phe Pro Ala Leu Trp Asn Leu Glu Lys Lys Tyr Gly Ser Ile Ile
195 200 205

Ala Gly Ala Ile Leu Ser Lys Leu Thr Ala Lys Gly Asp Ser Thr Lys
210 215 220

Lys Gly Ser Ala Val Ser Gly Lys Gly Arg Asn Lys Arg Val Ser Phe
225 230 235 240

Ser Phe His Gly Gly Met Gln Thr Leu Val Asp Ala Leu His Lys Glu
245 250 255

Ile Gly Asp Gly Asn Val Lys Leu Ala Thr Gln Val Leu Ser Leu Ala
260 265 270

Cys Ser Cys Asp Gly Leu Ser Ala Ser Asn Gly Trp Ser Ile Phe Val
275 280 285

Asp Ser Lys Asp Ala Ser Asn Arg Glu Leu Ala Lys Asn Gln Pro Phe
290 295 300

Asp Ala Val Ile Met Thr Ala Pro Leu Ser Asn Val Gln Arg Met Lys
305 310 315 320

Phe Thr Lys Gly Gly Ala Pro Phe Val Leu Asp Phe Leu Pro Lys Val
325 330 335

Asp Tyr Leu Pro Leu Ser Leu Met Val Thr Ala Phe Lys Lys Glu Asp
340 345 350

Val Lys Arg Pro Leu Glu Gly Phe Gly Val Leu Val Pro Tyr Lys Glu
355 360 365

Gln Gln Lys His Gly Leu Lys Thr Leu Gly Thr Leu Phe Ser Ser Met
370 375 380

Met Phe Pro Asp Arg Ala Pro Asn Asp Gln His Leu Phe Thr Thr Phe
385 390 395 400

Val Gly Gly Ser His Asn Arg Asp Leu Ala Gly Ala Pro Thr Ala Ile
405 410 415

Leu Lys Gln Leu Val Thr Ser Asp Leu Arg Lys Leu Leu Gly Val Glu
420 425 430

Gly Gln Pro Thr Phe Val Arg His Ile His Trp Lys Asn Ala Phe Pro
435 440 445

Leu Tyr Gly His Asp Tyr Asp Ser Ala Leu Glu Ala Ile Gly Lys Met
450 455 460

Glu Ser Asp Leu Pro Gly Phe Phe Tyr Ala Gly Asn Asn Lys Asp Gly
465 470 475 480

Leu Ala Val Gly Asn Val Ile Ala Ser Gly Ser Lys Thr Ala Asp Leu
485 490 495

Val Ile Ser Tyr Leu Glu Leu Gly Ile Lys Arg Asp Asn
500 505

<210> SEQ ID NO 107
<211> LENGTH: 539
<212> TYPE: PRT
<213> ORGANISM: Gossypium hirsutum

<400> SEQUENCE: 107

Met Thr Ala Leu Ile Asp Leu Ser Leu Leu Arg Ser Ser Pro Ser Val
1 5 10 15

Ser Pro Phe Ser Ile Pro His His Gln Leu Pro Pro Arg Ser Arg Lys
20 25 30

Pro Phe Lys Leu Arg Cys Ser Leu Ala Glu Gly Pro Thr Ile Ser Ser
35 40 45

Ser Lys Ile Asp Gly Gly Glu Ser Ser Ile Ala Asp Cys Val Val Val

```
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
            340                 345                 350

Ala Ala Ala Ala Asp Ala Leu Ser Gln Phe Tyr Tyr Pro Pro Val Ala
        355                 360                 365

Ser Val Thr Val Ser Tyr Pro Lys Glu Ala Ile Arg Lys Glu Cys Leu
    370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Ser Leu Phe Pro Asn
                405                 410                 415

Arg Ala Pro Ser Gly Arg Val Leu Leu Leu Asn Tyr Ile Gly Gly Ala
            420                 425                 430

Thr Asn Thr Gly Ile Leu Ser Lys Thr Glu Gly Glu Leu Val Glu Ala
        435                 440                 445

Val Asp Arg Asp Leu Arg Lys Met Leu Ile Asn Pro Asn Ala Lys Asp
    450                 455                 460

Pro Leu Val Leu Gly Val Arg Val Trp Pro Lys Ala Ile Pro Gln Phe
465                 470                 475                 480
```

```
Leu Val Gly His Leu Asp Leu Leu Asp Thr Ala Lys Met Ala Leu Arg
                485                 490                 495

Asp Ser Gly Phe His Gly Leu Phe Leu Gly Gly Asn Tyr Val Ser Gly
            500                 505                 510

Val Ala Leu Gly Arg Cys Val Glu Gly Ala Tyr Glu Val Ala Ala Glu
        515                 520                 525

Val Lys Glu Phe Leu Ser Gln Tyr Ala Tyr Lys
    530                 535


<210> SEQ ID NO 108
<211> LENGTH: 560
<212> TYPE: PRT
<213> ORGANISM: Beta vulgaris

<400> SEQUENCE: 108

Met Lys Ser Met Ala Leu Ser Asn Cys Ile Pro Gln Thr Gln Cys Met
1               5                   10                  15

Pro Leu His Ser Ser Gly His Tyr Arg Gly Asn Cys Ile Met Leu Ser
            20                  25                  30

Ile Pro Cys Ser Leu Ile Gly Arg Arg Gly Tyr Tyr Ser His Lys Lys
        35                  40                  45

Arg Arg Met Ser Met Ser Cys Ser Thr Ser Ser Gly Ser Lys Ser Ala
    50                  55                  60

Val Lys Glu Ala Gly Ser Gly Ser Gly Ser Gly Ala Gly Gly Leu Leu
65                  70                  75                  80

Asp Cys Val Ile Val Gly Gly Gly Ile Ser Gly Leu Cys Ile Ala Gln
                85                  90                  95

Ala Leu Cys Thr Lys Gln Ser Ser Leu Ser Pro Asn Phe Ile Val Thr
            100                 105                 110

Glu Ala Lys Asp Arg Val Gly Gly Asn Ile Val Thr Val Glu Ala Asp
        115                 120                 125

Gly Tyr Ile Trp Glu Glu Gly Pro Asn Ser Phe Gln Pro Ser Asp Ala
    130                 135                 140

Val Leu Thr Met Ala Val Asp Ser Gly Leu Lys Asp Glu Leu Val Leu
145                 150                 155                 160

Gly Asp Pro Asn Ala Pro Arg Phe Val Leu Trp Asn Asp Lys Leu Arg
                165                 170                 175

Pro Val Pro Ser Ser Leu Thr Asp Leu Pro Phe Phe Asp Leu Met Thr
            180                 185                 190

Ile Pro Gly Lys Ile Arg Ala Ala Leu Gly Ala Leu Gly Phe Arg Pro
        195                 200                 205

Ser Pro Pro Pro His Glu Glu Ser Val Glu His Phe Val Arg Arg Asn
    210                 215                 220

Leu Gly Asp Glu Val Phe Glu Arg Leu Ile Glu Pro Phe Cys Ser Gly
225                 230                 235                 240

Val Tyr Ala Gly Asp Pro Ala Lys Leu Ser Met Lys Ala Ala Phe Gly
                245                 250                 255

Lys Val Trp Lys Leu Glu Gln Lys Gly Gly Ser Ile Ile Gly Gly Thr
            260                 265                 270

Leu Lys Ala Ile Gln Glu Arg Gly Ser Asn Pro Lys Pro Pro Arg Asp
        275                 280                 285

Gln Arg Leu Pro Lys Pro Lys Gly Gln Thr Val Gly Ser Phe Arg Lys
    290                 295                 300

Gly Leu Val Met Leu Pro Thr Ala Ile Ser Ala Arg Leu Gly Ser Arg
```

305 310 315 320

Val Lys Leu Ser Trp Thr Leu Ser Ser Ile Val Lys Ser Leu Asn Gly
325 330 335

Glu Tyr Ser Leu Thr Tyr Asp Thr Pro Asp Gly Leu Val Ser Val Arg
340 345 350

Thr Lys Ser Val Val Met Thr Val Pro Ser Tyr Val Ala Ser Arg Leu
355 360 365

Leu Arg Pro Leu Ser Asp Ser Ala Ala Asp Ser Leu Ser Lys Phe Tyr
370 375 380

Tyr Pro Pro Val Ala Ala Val Ser Leu Ser Tyr Pro Lys Glu Ala Ile
385 390 395 400

Arg Ser Glu Cys Leu Ile Asn Gly Glu Leu Gln Gly Phe Gly Gln Leu
405 410 415

His Pro Arg Ser Gln Gly Val Glu Thr Leu Gly Thr Ile Tyr Ser Ser
420 425 430

Ser Leu Phe Pro Gly Arg Ala Pro Pro Gly Arg Ile Leu Ile Leu Ser
435 440 445

Tyr Ile Gly Gly Ala Lys Asn Pro Gly Ile Leu Asn Lys Ser Lys Asp
450 455 460

Glu Leu Ala Glu Thr Val Asp Lys Asp Leu Arg Arg Met Leu Ile Asn
465 470 475 480

Pro Asp Ala Lys Leu Pro Arg Val Leu Gly Val Arg Val Trp Pro Gln
485 490 495

Ala Ile Pro Gln Phe Ser Ile Gly His Phe Asp Leu Leu Asp Ala Ala
500 505 510

Lys Ala Ala Leu Thr Asp Thr Gly Val Lys Gly Leu Phe Leu Gly Gly
515 520 525

Asn Tyr Val Ser Gly Val Ala Leu Gly Arg Cys Ile Glu Gly Ala Tyr
530 535 540

Glu Ser Ala Ala Glu Val Val Asp Phe Leu Ser Gln Tyr Ser Asp Lys
545 550 555 560

<210> SEQ ID NO 109
<211> LENGTH: 530
<212> TYPE: PRT
<213> ORGANISM: Hordeum vulgare

<400> SEQUENCE: 109

Met Ala Gly Ala Gly Ala Thr Met Ala Thr Ala Thr Ala Pro Pro Leu
1 5 10 15

Arg Gly Arg Val Thr Arg Arg Pro His Gly Val Arg Pro Arg Cys Ala
20 25 30

Ala Ala Gly Ser Ala Thr Glu Thr Pro Ala Ala Pro Gly Val Arg Leu
35 40 45

Ser Ala Asp Cys Val Ile Val Gly Ala Gly Ile Ser Gly Leu Cys Thr
50 55 60

Ala Gln Ala Leu Ala Thr Arg His Gly Val Gly Asp Leu Leu Val Thr
65 70 75 80

Glu Ala Arg Asp Arg Pro Gly Gly Asn Ile Thr Thr Val Glu Arg Pro
85 90 95

Asp Glu Gly Tyr Leu Trp Glu Glu Gly Pro Asn Ser Phe Gln Pro Ser
100 105 110

Asp Pro Val Leu Thr Met Ala Val Asp Ser Gly Leu Lys Asp Asp Leu
115 120 125

-continued

```
Val Phe Gly Asp Pro Asn Ala Pro Arg Phe Val Leu Trp Glu Gly Lys
    130                 135                 140

Leu Arg Pro Val Pro Ser Lys Pro Gly Asp Leu Pro Phe Phe Ser Leu
145                 150                 155                 160

Met Ser Val Pro Gly Lys Leu Arg Ala Gly Leu Gly Ala Leu Gly Ile
                165                 170                 175

Arg Pro Pro Pro Pro Gly Arg Glu Glu Ser Val Glu Glu Phe Val Arg
            180                 185                 190

Arg Asn Leu Gly Ala Glu Val Phe Glu Arg Leu Ile Glu Pro Phe Cys
        195                 200                 205

Ser Gly Val Tyr Ala Gly Asp Pro Ser Lys Leu Ser Met Lys Ala Ala
    210                 215                 220

Phe Gly Lys Val Trp Arg Leu Glu Glu Ile Gly Gly Ser Ile Ile Gly
225                 230                 235                 240

Gly Thr Ile Lys Ala Ile Gln Asp Lys Gly Lys Asn Pro Lys Pro Pro
                245                 250                 255

Arg Asp Pro Arg Leu Pro Ala Pro Lys Gly Gln Thr Val Ala Ser Phe
            260                 265                 270

Arg Lys Gly Leu Ala Met Leu Pro Asn Ala Ile Ala Ser Arg Leu Gly
        275                 280                 285

Ser Lys Val Lys Leu Ser Trp Lys Leu Thr Ser Ile Thr Lys Ala Asp
    290                 295                 300

Asn Gln Gly Tyr Val Leu Gly Tyr Glu Thr Pro Glu Gly Leu Val Ser
305                 310                 315                 320

Val Gln Ala Lys Ser Val Ile Met Thr Ile Pro Ser Tyr Val Ala Ser
                325                 330                 335

Asp Ile Leu Arg Pro Leu Ser Ile Asp Ala Ala Asp Ala Leu Ser Lys
            340                 345                 350

Phe Tyr Tyr Pro Pro Val Ala Ala Val Thr Val Ser Tyr Pro Lys Glu
        355                 360                 365

Ala Ile Arg Lys Glu Cys Leu Ile Asp Gly Glu Leu Gln Gly Phe Gly
    370                 375                 380

Gln Leu His Pro Arg Ser Gln Gly Val Glu Thr Leu Gly Thr Ile Tyr
385                 390                 395                 400

Ser Ser Ser Leu Phe Pro Asn Arg Ala Pro Ala Gly Arg Val Leu Leu
                405                 410                 415

Leu Asn Tyr Ile Gly Gly Ser Thr Asn Thr Gly Ile Val Ser Lys Thr
            420                 425                 430

Glu Ser Asp Leu Val Glu Ala Val Asp Arg Asp Leu Arg Lys Met Leu
        435                 440                 445

Ile Asn Pro Arg Ala Ala Asp Pro Leu Ala Leu Gly Val Arg Val Trp
    450                 455                 460

Pro Gln Ala Ile Pro Gln Phe Leu Ile Gly His Leu Asp Arg Leu Ala
465                 470                 475                 480

Ala Ala Lys Ser Ala Leu Gly Arg Gly Gly Tyr Asp Gly Leu Phe Leu
                485                 490                 495

Gly Gly Asn Tyr Val Ala Gly Val Ala Leu Gly Arg Cys Ile Glu Gly
            500                 505                 510

Ala Tyr Glu Ser Ala Ser Gln Val Ser Asp Phe Leu Thr Lys Tyr Ala
        515                 520                 525

Tyr Lys
    530
```

<210> SEQ ID NO 110
<211> LENGTH: 554
<212> TYPE: PRT
<213> ORGANISM: Hordeum vulgare

<400> SEQUENCE: 110

```
Met Leu Thr Ser Ala Thr Ala Pro Pro Ser Ser Ser Ser Cys Ser Ser
1               5                   10                  15

His Ala Pro Ala Arg Phe Ala Ser Pro Ser Arg Pro Arg Arg Ser Ala
            20                  25                  30

Ser Ala Ser Ala Arg Gly Arg Gly Arg Arg Val Arg Pro Val Leu Ala
        35                  40                  45

Met Ala Ala Ser Asp Asp Pro Arg Ala Arg Ser Val Ala Val Val Gly
    50                  55                  60

Ala Gly Val Ser Gly Leu Val Ala Ala Tyr Met Leu Arg Lys Ser Gly
65                  70                  75                  80

Val Arg Val Thr Val Phe Glu Ala Glu Asp Arg Ala Gly Gly Lys Ile
                85                  90                  95

Arg Thr Asn Ser Asp Gly Gly Phe Leu Trp Asp Glu Gly Ala Asn Thr
            100                 105                 110

Met Thr Glu Ser Ala Leu Glu Ala Ser Arg Leu Ile Asp Asp Leu Gly
        115                 120                 125

Leu Gln Asp Arg Leu Gln Tyr Pro Asn Ser Gln His Lys Arg Tyr Thr
    130                 135                 140

Val Lys Asp Gly Ala Pro Ala Leu Ile Pro Ser Asp Pro Ile Ala Leu
145                 150                 155                 160

Met Lys Ser Thr Val Leu Ser Thr Lys Ser Lys Phe Lys Leu Phe Leu
                165                 170                 175

Glu Pro Phe Leu Tyr Glu Lys Ser Ser Thr Arg Asn Ser Lys Lys Val
            180                 185                 190

Ser Asp Glu His Leu Arg Glu Ser Val Gly Ser Phe Phe Glu Arg His
        195                 200                 205

Phe Gly Lys Glu Val Val Asp Tyr Leu Ile Asp Pro Phe Val Ala Gly
    210                 215                 220

Thr Ser Ala Gly Asp Pro Glu Ser Leu Ser Ile Arg His Ala Phe Pro
225                 230                 235                 240

Gly Leu Trp Asn Leu Glu Lys Lys Tyr Gly Ser Leu Ile Val Gly Ala
                245                 250                 255

Ile Leu Ser Lys Leu Thr Ala Lys Gly Gly Ser Ala Lys Lys Gly Gly
            260                 265                 270

Ala Ser Ser Gly Lys Gly Arg Asn Lys Arg Ala Ser Phe Ser Phe His
        275                 280                 285

Gly Gly Met Gln Thr Leu Val Asp Ala Leu His Lys Glu Val Gly Asp
    290                 295                 300

Thr Asn Val Lys Leu Gly Thr Gln Val Leu Ser Leu Ala Cys Asn Cys
305                 310                 315                 320

Asp Gly Leu Ser Ala Ser Asp Gly Trp Ser Ile Phe Val Asp Ser Lys
                325                 330                 335

Asp Ala Ser Ser Lys Glu Leu Ala Arg Asn Gln Ser Phe Asp Ala Val
            340                 345                 350

Ile Met Thr Ala Pro Leu Ser Asn Val Gln Arg Met Lys Phe Thr Lys
        355                 360                 365

Gly Gly Arg Pro Phe Val Leu Asp Phe Leu Pro Lys Val Asp Tyr Leu
    370                 375                 380
```

-continued

Pro Leu Ser Leu Met Val Thr Ala Phe Lys Lys Glu Asp Val Lys Arg
385 390 395 400

Pro Leu Glu Gly Phe Gly Val Leu Ile Pro Phe Lys Glu Gln Gln Lys
405 410 415

His Gly Leu Lys Thr Leu Gly Thr Leu Phe Ser Ser Met Met Phe Pro
420 425 430

Asp Arg Ala Pro Asn Asp Gln His Leu Phe Thr Thr Phe Ile Gly Gly
435 440 445

Ser His Asn Arg Asp Leu Ala Gly Ala Pro Thr Ala Ile Leu Lys Gln
450 455 460

Phe Val Thr Ser Asp Leu Thr Lys Leu Leu Gly Val Glu Gly Gln Pro
465 470 475 480

Thr Phe Val Lys His Ile His Trp Arg Asn Ala Phe Pro Leu Tyr Gly
485 490 495

His Asp Tyr Asp Leu Ala Leu Glu Ala Ile Gly Lys Met Glu Gly Asp
500 505 510

Leu Pro Gly Phe Phe Tyr Ala Gly Asn Asn Lys Asp Gly Leu Ala Val
515 520 525

Gly Asn Val Ile Ala Ser Gly Ser Asn Thr Ala Asp Leu Val Ile Ser
530 535 540

Tyr Leu Glu Ser Gly Ile Lys His Val Asn
545 550

<210> SEQ ID NO 111
<211> LENGTH: 531
<212> TYPE: PRT
<213> ORGANISM: Triticum aestivum

<400> SEQUENCE: 111

Met Ala Gly Ala Thr Met Ala Thr Ala Thr Val Ala Ala Ala Ser Pro
1 5 10 15

Leu Arg Gly Arg Val Thr Gly Arg Pro His Arg Val Arg Pro Arg Cys
20 25 30

Ala Thr Ala Ser Ser Ala Thr Glu Thr Pro Ala Ala Pro Gly Val Arg
35 40 45

Leu Ser Ala Glu Cys Val Ile Val Gly Ala Gly Ile Ser Gly Leu Cys
50 55 60

Thr Ala Gln Ala Leu Ala Thr Arg Tyr Gly Val Ser Asp Leu Leu Val
65 70 75 80

Thr Glu Ala Arg Asp Arg Pro Gly Gly Asn Ile Thr Thr Val Glu Arg
85 90 95

Pro Asp Glu Gly Tyr Leu Trp Glu Glu Gly Pro Asn Ser Phe Gln Pro
100 105 110

Ser Asp Pro Val Leu Thr Met Ala Val Asp Ser Gly Leu Lys Asp Asp
115 120 125

Leu Val Phe Gly Asp Pro Asn Ala Pro Arg Phe Val Leu Trp Glu Gly
130 135 140

Lys Leu Arg Pro Val Pro Ser Lys Pro Gly Asp Leu Pro Phe Phe Ser
145 150 155 160

Leu Met Ser Ile Pro Gly Lys Leu Arg Ala Gly Leu Gly Ala Leu Gly
165 170 175

Ile Arg Pro Pro Pro Pro Gly Arg Glu Glu Ser Val Glu Glu Phe Val
180 185 190

Arg Arg Asn Leu Gly Ala Glu Val Phe Glu Arg Leu Ile Glu Pro Phe
195 200 205

Cys Ser Gly Val Tyr Ala Gly Asp Pro Ser Lys Leu Ser Met Lys Ala
    210                 215                 220

Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ser Thr Asn Thr Gly Ile Val Ser Lys
            420                 425                 430

Thr Glu Ser Asp Leu Val Gly Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Gln Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530

<210> SEQ ID NO 112
<211> LENGTH: 501
<212> TYPE: PRT
<213> ORGANISM: Solanum lycopersicum

<400> SEQUENCE: 112

Met Ala Pro Ser Ala Gly Glu Asp Lys Gln Lys Arg Val Ala Val Ile
1               5                   10                  15

Gly Ala Gly Val Ser Gly Leu Ala Ala Ala Tyr Lys Leu Lys Val His
            20                  25                  30

Gly Leu Asn Val Thr Val Phe Glu Ala Glu Gly Arg Ala Gly Gly Lys

-continued

```
        35                  40                  45

Leu Arg Ser Leu Ser Gln Asp Gly Leu Ile Trp Asp Glu Gly Ala Asn
    50                  55                  60

Thr Met Thr Glu Ser Glu Gly Asp Val Thr Phe Leu Leu Asp Ser Leu
65                  70                  75                  80

Gly Leu Arg Glu Lys Gln Gln Phe Pro Leu Ser Gln Asn Lys Arg Tyr
                85                  90                  95

Ile Ala Arg Asn Gly Thr Pro Thr Leu Ile Pro Ser Asn Pro Phe Asp
            100                 105                 110

Leu Phe Lys Ser Asn Phe Leu Ser Thr Gly Ser Lys Leu Gln Met Leu
        115                 120                 125

Phe Glu Pro Leu Leu Trp Lys Asn Lys Lys Leu Thr Lys Val Ser Asp
    130                 135                 140

Lys His Glu Ser Val Ser Gly Phe Phe Gln Arg His Phe Gly Lys Glu
145                 150                 155                 160

Val Val Asp Tyr Leu Ile Asp Pro Phe Val Ala Gly Thr Cys Gly Gly
                165                 170                 175

Asp Pro Asp Ser Leu Ser Met His Leu Ser Phe Pro Asp Leu Trp Asn
            180                 185                 190

Leu Glu Lys Arg Phe Gly Ser Val Ile Val Gly Ala Ile Gln Ser Lys
        195                 200                 205

Leu Ser Pro Ile Lys Glu Lys Lys Gln Gly Pro Pro Arg Thr Ser Ile
    210                 215                 220

Asn Lys Lys Arg Gln Arg Gly Ser Phe Ser Phe Leu Gly Gly Met Gln
225                 230                 235                 240

Thr Leu Thr Asp Ala Ile Cys Lys Asn Leu Lys Glu Asp Glu Leu Arg
                245                 250                 255

Leu Asn Ser Arg Val Leu Glu Leu Ser Cys Ser Cys Ser Gly Asp Ser
            260                 265                 270

Ala Ile Asp Ser Trp Ser Ile Phe Ser Ala Ser Pro His Lys Arg Gln
        275                 280                 285

Ala Glu Glu Glu Ser Phe Asp Ala Val Ile Met Thr Ala Pro Leu Cys
    290                 295                 300

Asp Val Lys Ser Met Lys Ile Ala Lys Arg Gly Asn Pro Phe Leu Leu
305                 310                 315                 320

Asn Phe Ile Pro Glu Val Asp Tyr Val Pro Leu Ser Val Val Ile Thr
                325                 330                 335

Thr Phe Lys Lys Glu Ser Val Lys His Pro Leu Glu Gly Phe Gly Val
            340                 345                 350

Leu Val Pro Ser Gln Glu Gln Lys His Gly Leu Lys Thr Leu Gly Thr
        355                 360                 365

Leu Phe Ser Ser Met Met Phe Pro Asp Arg Ala Pro Asn Asn Val Tyr
    370                 375                 380

Leu Tyr Thr Thr Phe Val Gly Gly Ser Arg Asn Arg Glu Leu Ala Lys
385                 390                 395                 400

Ala Ser Arg Thr Glu Leu Lys Glu Ile Val Thr Ser Asp Leu Lys Gln
                405                 410                 415

Leu Leu Gly Ala Glu Gly Glu Pro Thr Tyr Val Asn His Leu Cys Trp
            420                 425                 430

Ser Lys Ala Phe Pro Leu Tyr Gly His Asn Tyr Asp Ser Val Leu Asp
        435                 440                 445

Ala Ile Asp Lys Met Glu Lys Ser Leu Pro Gly Leu Phe Tyr Ala Gly
    450                 455                 460
```

```
Asn His Lys Gly Gly Leu Ser Val Gly Lys Ala Leu Ser Ser Gly Cys
465                 470                 475                 480

Asn Ala Ala Asp Leu Val Ile Ser Tyr Leu Glu Ala Val Ser Ala Asp
                485                 490                 495

Thr Lys Asn His Ser
            500


<210> SEQ ID NO 113
<211> LENGTH: 546
<212> TYPE: PRT
<213> ORGANISM: Triticum aestivum

<400> SEQUENCE: 113

Met Gly Ile His Pro Ala Ala Leu Thr Phe Pro Arg Ala Thr Glu Met
1               5                   10                  15

Ala Gly Ala Thr Met Ala Thr Ala Thr Val Ala Ala Ala Ser Pro Leu
            20                  25                  30

Arg Gly Arg Val Thr Gly Arg Pro His Arg Val Arg Pro Arg Cys Ala
        35                  40                  45

Thr Ala Ser Ser Ala Thr Glu Thr Pro Ala Ala Pro Gly Val Arg Leu
    50                  55                  60

Ser Ala Glu Cys Val Ile Val Gly Ala Gly Ile Ser Gly Leu Cys Thr
65                  70                  75                  80

Ala Gln Ala Leu Ala Thr Arg Tyr Gly Val Ser Asp Leu Leu Val Thr
                85                  90                  95

Glu Ala Arg Asp Arg Pro Gly Gly Asn Ile Thr Thr Val Glu Arg Pro
            100                 105                 110

Asp Glu Gly Tyr Leu Trp Glu Glu Gly Pro Asn Ser Phe Gln Pro Ser
        115                 120                 125

Asp Pro Val Leu Thr Met Ala Val Asp Ser Gly Leu Lys Asp Asp Leu
    130                 135                 140

Val Phe Gly Asp Pro Asn Ala Pro Arg Phe Val Leu Trp Glu Gly Lys
145                 150                 155                 160

Leu Arg Pro Val Pro Ser Lys Pro Gly Asp Leu Pro Phe Phe Ser Leu
                165                 170                 175

Met Ser Ile Pro Gly Lys Leu Arg Ala Gly Leu Gly Ala Leu Gly Ile
            180                 185                 190

Arg Pro Pro Pro Pro Gly Arg Glu Glu Ser Val Glu Glu Phe Val Arg
        195                 200                 205

Arg Asn Leu Gly Ala Glu Val Phe Glu Arg Leu Ile Glu Pro Phe Cys
    210                 215                 220

Ser Gly Val Tyr Ala Gly Asp Pro Ser Lys Leu Ser Met Lys Ala Ala
225                 230                 235                 240

Phe Gly Lys Val Trp Arg Leu Glu Glu Ile Gly Gly Ser Ile Ile Gly
                245                 250                 255

Gly Thr Ile Lys Ala Ile Gln Asp Lys Gly Lys Asn Pro Lys Pro Pro
            260                 265                 270

Arg Asp Pro Arg Leu Pro Ala Pro Lys Gly Gln Thr Val Ala Ser Phe
        275                 280                 285

Arg Lys Gly Leu Ala Met Leu Pro Asn Ala Ile Ala Ser Arg Leu Gly
    290                 295                 300

Ser Lys Val Lys Leu Ser Trp Lys Leu Thr Ser Ile Thr Lys Ala Asp
305                 310                 315                 320

Asn Gln Gly Tyr Val Leu Gly Tyr Glu Thr Pro Glu Gly Leu Val Ser
```

325 330 335

Val Gln Ala Lys Ser Val Ile Met Thr Ile Pro Ser Tyr Val Ala Ser
340 345 350

Asp Ile Leu Arg Pro Leu Ser Ile Asp Ala Ala Asp Ala Leu Ser Lys
355 360 365

Phe Tyr Tyr Pro Pro Val Ala Ala Val Thr Val Ser Tyr Pro Lys Glu
370 375 380

Ala Ile Arg Lys Glu Cys Leu Ile Asp Gly Glu Leu Gln Gly Phe Gly
385 390 395 400

Gln Leu His Pro Arg Ser Gln Gly Val Glu Thr Leu Gly Thr Ile Tyr
405 410 415

Ser Ser Ser Leu Phe Pro Asn Arg Ala Pro Ala Gly Arg Val Leu Leu
420 425 430

Leu Asn Tyr Ile Gly Gly Ser Thr Asn Thr Gly Ile Val Ser Lys Thr
435 440 445

Glu Ser Asp Leu Val Gly Ala Val Asp Arg Asp Leu Arg Lys Met Leu
450 455 460

Ile Asn Pro Arg Ala Ala Asp Pro Leu Ala Leu Gly Val Arg Val Trp
465 470 475 480

Pro Gln Ala Ile Pro Gln Phe Leu Ile Gly His Leu Asp Arg Leu Ala
485 490 495

Ala Ala Lys Ser Ala Leu Gly Gln Gly Gly Tyr Asp Gly Leu Phe Leu
500 505 510

Gly Gly Asn Tyr Val Ala Gly Val Ala Leu Gly Arg Cys Ile Glu Gly
515 520 525

Ala Tyr Glu Ser Ala Ser Gln Val Ser Asp Phe Leu Thr Lys Tyr Ala
530 535 540

Tyr Lys
545

<210> SEQ ID NO 114
<211> LENGTH: 539
<212> TYPE: PRT
<213> ORGANISM: Gossypium hirsutum
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid

<400> SEQUENCE: 114

Met Thr Ala Leu Ile Asp Leu Ser Leu Leu Arg Ser Ser Pro Ser Val
1 5 10 15

Ser Pro Phe Ser Ile Pro His His Gln Leu Pro Pro Arg Ser Arg Lys
20 25 30

Pro Phe Arg Leu Arg Cys Ser Val Ala Glu Gly Pro Thr Ile Ser Ser
35 40 45

Ser Lys Ile Asp Gly Gly Glu Ser Ser Ile Ala Asp Cys Val Val Val
50 55 60

Gly Gly Gly Ile Ser Gly Leu Cys Ile Ala Gln Ala Leu Ala Thr Lys
65 70 75 80

```
His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Xaa Val Leu Gly Asp Pro Asn Ala
    130                 135                 140

Pro Arg Phe Val Leu Trp Glu Gly Lys Leu Arg Xaa Val Pro Ser Lys
145                 150                 155                 160

Pro Thr Asp Leu Pro Phe Phe Xaa Leu Met Ser Ile Ala Gly Lys Leu
                165                 170                 175

Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
            340                 345                 350

Ala Ala Ala Ala Asp Ala Leu Ser Gln Phe Tyr Tyr Pro Pro Val Ala
        355                 360                 365

Ser Val Thr Val Ser Tyr Pro Lys Glu Ala Ile Arg Lys Glu Cys Leu
    370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Ser Leu Phe Pro Asn
                405                 410                 415

Arg Ala Pro Ser Gly Arg Val Leu Leu Leu Asn Tyr Ile Gly Gly Ala
            420                 425                 430

Thr Asn Thr Gly Ile Leu Ser Lys Thr Glu Gly Glu Leu Val Glu Ala
        435                 440                 445

Val Asp Arg Asp Leu Arg Lys Met Leu Ile Asn Pro Asn Ala Lys Asp
    450                 455                 460

Pro Leu Val Leu Gly Val Arg Val Trp Pro Lys Ala Ile Pro Gln Phe
465                 470                 475                 480

Leu Val Gly His Leu Asp Leu Leu Asp Ser Ala Lys Met Ala Leu Arg
                485                 490                 495

Asp Ser Gly Phe His Gly Leu Phe Leu Gly Gly Asn Tyr Val Ser Gly
```

```
            500                 505                 510

Val Ala Leu Gly Arg Cys Val Glu Gly Ala Tyr Glu Val Ala Ala Glu
        515                 520                 525

Val Lys Glu Phe Leu Ser Gln Tyr Ala Tyr Lys
    530                 535


<210> SEQ ID NO 115
<211> LENGTH: 503
<212> TYPE: PRT
<213> ORGANISM: Gossypium hirsutum

<400> SEQUENCE: 115

Met Ala Ser Thr Glu Asn Lys Asp Asp His Ser Ser Ala Lys Arg Val
1               5                   10                  15

Ala Val Ile Gly Ala Gly Val Ser Gly Leu Ala Ala Ala Tyr Lys Leu
            20                  25                  30

Lys Ser Gln Gly Leu His Val Thr Val Phe Glu Ser Glu Gly Arg Ala
        35                  40                  45

Gly Gly Lys Leu Arg Ser Val Ser Arg Asp Gly Leu Ile Trp Asp Glu
    50                  55                  60

Gly Ala Asn Thr Met Thr Glu Ser Glu Ile Glu Val Arg Ser Leu Phe
65                  70                  75                  80

Asp Asp Leu Gly Ile Gln Asp Lys Gln Gln Val Pro Ile Ala Gln Asn
                85                  90                  95

Lys Arg Tyr Ile Met Arg Asn Gly Val Pro Val Leu Ile Pro Ser Asn
            100                 105                 110

Pro Leu Ser Leu Phe Thr Ser Ser Ile Leu Ser Ala Lys Ser Lys Phe
        115                 120                 125

Gln Ile Ile Leu Glu Pro Phe Leu Trp Arg Asn Ser Glu Ala Ser Lys
    130                 135                 140

Val Ser Asp Ala Tyr Asn Gln Glu Ser Val Gly Gly Phe Phe Gln Arg
145                 150                 155                 160

His Phe Gly Gln Glu Val Val Asp Tyr Leu Val Asp Pro Phe Val Ala
                165                 170                 175

Gly Thr Ser Ala Gly Asp Pro Glu Ser Leu Ser Met Cys His Ser Phe
            180                 185                 190

Pro Gly Leu Trp Asp Leu Glu Gln Arg Phe Gly Ser Ile Ile Val Gly
        195                 200                 205

Ala Val Lys Ser Lys Phe Ser Ala Lys Arg Thr Asn Arg Glu Glu Thr
    210                 215                 220

Lys Asn Ser Val Lys Arg Lys Ala Leu Arg Gly Ser Phe Ser Phe Lys
225                 230                 235                 240

Gly Gly Met Gln Thr Leu Ala Asp Met Leu Cys Lys Asp Leu Ser Lys
                245                 250                 255

Asp Glu Leu Lys Leu Lys Ser Lys Val Leu Ser Leu Ser Tyr Ser His
            260                 265                 270

Glu Gly Lys Ser Thr Ser Glu Asn Trp Ser Leu Ser Tyr Ala Ser Asp
        275                 280                 285

Arg Asp Lys Arg Ser Gln Gly Ser Ser Phe Asp Ala Val Ile Met Thr
    290                 295                 300

Ala Pro Val Cys Asn Val Lys Glu Met Lys Ile Thr Lys Gly Gly Asn
305                 310                 315                 320

Val Phe Pro Leu Asn Phe Ile Pro Glu Val Ser Tyr Met Pro Leu Ser
                325                 330                 335
```

```
Val Ile Ile Thr Ala Phe Lys Lys Glu Asn Val Lys Lys Pro Leu Glu
            340                 345                 350

Gly Phe Gly Val Leu Ile Pro Ser Lys Glu Gln Gln Asn Gly Leu Lys
        355                 360                 365

Thr Leu Gly Thr Leu Phe Ser Ser Val Met Phe Pro Asp Arg Ala Pro
    370                 375                 380

Asn Asn Leu Tyr Leu Tyr Thr Thr Phe Val Gly Gly Asn Arg Asn Glu
385                 390                 395                 400

Lys Leu Ala Lys Ala Ser Thr Asp Glu Leu Lys His Ile Val Thr Ser
                405                 410                 415

Asp Leu Gln Gln Leu Leu Gly Val Glu Gly Glu Pro Thr Phe Phe Asn
            420                 425                 430

His Phe Tyr Trp Ser Lys Ala Phe Pro Leu Tyr Gly Arg Asn Tyr Ala
        435                 440                 445

Ser Val Leu Glu Gly Ile Glu Lys Met Glu Arg Asp Leu Pro Gly Phe
    450                 455                 460

Phe Tyr Ala Gly Asn His Lys Gly Gly Leu Ser Val Gly Lys Ser Ile
465                 470                 475                 480

Ala Ser Gly Cys Lys Ala Ala Asp Asn Val Ile Thr Tyr Leu Glu Ser
                485                 490                 495

Ser His Asp Lys Leu Leu Lys
            500
```

<210> SEQ ID NO 116
<211> LENGTH: 560
<212> TYPE: PRT
<213> ORGANISM: Beta vulgaris

<400> SEQUENCE: 116

```
Met Lys Ser Met Ala Leu Ser Asn Cys Ile Pro Gln Thr Gln Cys Met
1               5                   10                  15

Pro Leu His Ser Ser Gly His Tyr Arg Gly Asn Cys Ile Met Leu Ser
            20                  25                  30

Ile Pro Cys Ser Leu Ile Gly Arg Arg Gly Tyr Tyr Ser His Lys Lys
        35                  40                  45

Arg Arg Met Ser Met Ser Cys Ser Thr Ser Ser Gly Ser Lys Ser Ala
    50                  55                  60

Val Lys Glu Ala Gly Ser Gly Ser Gly Ser Gly Ala Gly Gly Leu Leu
65                  70                  75                  80

Asp Cys Val Ile Val Gly Gly Gly Ile Ser Gly Leu Cys Ile Ala Gln
                85                  90                  95

Ala Leu Cys Thr Lys Gln Ser Ser Leu Ser Pro Asn Phe Ile Val Thr
            100                 105                 110

Glu Ala Lys Asp Arg Val Gly Gly Asn Ile Val Thr Val Glu Ala Asp
        115                 120                 125

Gly Tyr Ile Trp Glu Glu Gly Pro Asn Ser Phe Gln Pro Ser Asp Ala
    130                 135                 140

Val Leu Thr Met Ala Val Asp Ser Gly Leu Lys Asp Glu Leu Val Leu
145                 150                 155                 160

Gly Asp Pro Asn Ala Pro Arg Phe Val Leu Trp Asn Asp Lys Leu Arg
                165                 170                 175

Pro Val Pro Ser Ser Leu Thr Asn Leu Pro Phe Phe Asp Leu Met Thr
            180                 185                 190

Ile Pro Gly Lys Ile Arg Ala Ala Leu Gly Ala Leu Gly Phe Arg Pro
        195                 200                 205
```

Ser Pro Pro Pro His Glu Glu Ser Val Glu His Phe Val Arg Arg Asn
    210                 215                 220

Leu Gly Asp Glu Val Phe Glu Arg Leu Ile Glu Pro Phe Cys Ser Gly
225                 230                 235                 240

Val Tyr Ala Gly Asp Pro Ala Lys Leu Ser Met Lys Ala Ala Phe Gly
                245                 250                 255

Lys Val Trp Lys Leu Glu Gln Lys Gly Gly Ser Ile Ile Gly Gly Thr
            260                 265                 270

Leu Lys Ala Ile Gln Glu Arg Gly Ser Asn Pro Lys Pro Pro Arg Asp
        275                 280                 285

Gln Arg Leu Pro Lys Pro Lys Gly Gln Thr Val Gly Ser Phe Arg Lys
    290                 295                 300

Gly Leu Val Met Leu Pro Thr Ala Ile Ser Ala Arg Leu Gly Ser Arg
305                 310                 315                 320

Val Lys Leu Ser Trp Thr Leu Ser Ser Ile Val Lys Ser Leu Asn Gly
                325                 330                 335

Glu Tyr Ser Leu Thr Tyr Asp Thr Pro Asp Gly Leu Val Ser Val Arg
            340                 345                 350

Thr Lys Ser Val Val Met Thr Val Pro Ser Tyr Val Ala Ser Arg Leu
        355                 360                 365

Leu Arg Pro Leu Ser Asp Ser Ala Ala Asp Ser Leu Ser Lys Phe Tyr
    370                 375                 380

Tyr Pro Pro Val Ala Ala Val Ser Leu Ser Tyr Pro Lys Glu Ala Ile
385                 390                 395                 400

Arg Ser Glu Cys Leu Ile Asn Gly Glu Leu Gln Gly Phe Gly Gln Leu
                405                 410                 415

His Pro Arg Ser Gln Gly Val Glu Thr Leu Gly Thr Ile Tyr Ser Ser
            420                 425                 430

Ser Leu Phe Pro Gly Arg Ala Pro Pro Gly Arg Ile Leu Ile Leu Ser
        435                 440                 445

Tyr Ile Gly Gly Ala Lys Asn Pro Gly Ile Leu Asn Lys Ser Lys Asp
    450                 455                 460

Glu Leu Ala Glu Thr Val Asp Lys Asp Leu Arg Arg Met Leu Ile Asn
465                 470                 475                 480

Pro Asp Ala Lys Leu Pro Arg Val Leu Gly Val Arg Val Trp Pro Gln
                485                 490                 495

Ala Ile Pro Gln Phe Ser Ile Gly His Phe Asp Leu Leu Asp Ala Ala
            500                 505                 510

Lys Ala Ala Leu Thr Asp Thr Gly Val Lys Gly Leu Phe Leu Gly Gly
        515                 520                 525

Asn Tyr Val Ser Gly Val Ala Leu Gly Arg Cys Ile Glu Gly Ala Tyr
    530                 535                 540

Glu Ser Ala Ala Glu Val Val Asp Phe Leu Ser Gln Tyr Ser Asp Lys
545                 550                 555                 560

<210> SEQ ID NO 117
<211> LENGTH: 508
<212> TYPE: PRT
<213> ORGANISM: Brassica napus

<400> SEQUENCE: 117

Met Ala Ser Asn Ala Val Ala Asp His Asp Lys Leu Ser Gly Lys Arg
1               5                   10                  15

Val Ala Val Val Gly Ala Gly Val Ser Gly Leu Ala Ala Ala Tyr Lys

-continued

```
            20                  25                  30

Leu Lys Ser Lys Gly Val Asn Val Thr Val Phe Glu Ala Asp Gly Arg
        35                  40                  45

Val Gly Gly Lys Leu Arg Ser Val Met His Asn Gly Leu Ile Trp Asp
    50                  55                  60

Glu Gly Ala Asn Thr Met Thr Glu Ala Glu Pro Glu Val Gly Ser Leu
65                  70                  75                  80

Leu Asp Asp Leu Gly Leu Arg Glu Lys Gln Gln Phe Pro Leu Ser Gln
                85                  90                  95

Lys Lys Arg Tyr Ile Val Arg Asn Gly Leu Pro Val Met Ile Pro Thr
            100                 105                 110

Asn Pro Ile Ala Leu Val Thr Ser Ser Val Leu Ser Thr Gln Ser Lys
        115                 120                 125

Phe Gln Ile Leu Leu Glu Pro Phe Leu Trp Lys Lys Asn Asp Ser Ser
    130                 135                 140

Ser Lys Val Ser Asp Ala Ser Val Val Glu Ser Val Ser Gly Phe Phe
145                 150                 155                 160

Gln Arg His Phe Gly Gln Glu Val Val Asp Tyr Leu Ile Asp Pro Phe
                165                 170                 175

Met Gly Gly Thr Ser Ala Ala Asp Pro Glu Ser Leu Ser Met Lys His
            180                 185                 190

Ser Phe Pro Asp Leu Trp Asn Ile Glu Lys Ser Phe Gly Ser Ile Ile
        195                 200                 205

Val Gly Ala Ile Arg Ser Lys Phe Ala Ala Lys Gly Ser Lys Asn Gly
    210                 215                 220

Glu Thr Lys Ser Ser Thr Gly Thr Lys Lys Gly Ser Arg Gly Ser Phe
225                 230                 235                 240

Ser Phe Lys Gly Gly Met Gln Ile Leu Pro Glu Met Leu Cys Lys Asp
                245                 250                 255

Leu Ser Arg Asp Glu Leu Asn Leu Asp Ser Lys Val Leu Ser Leu Ser
            260                 265                 270

Tyr Asn Ala Gly Pro Arg Gln Glu Asn Trp Ser Leu Ser Cys Val Ser
        275                 280                 285

His Asn Glu Ala Gln Gly Gln Asn Leu His Tyr Asp Ala Val Ile Met
    290                 295                 300

Thr Ala Pro Leu Cys Asn Val Lys Glu Met Lys Val Met Lys Gly Gly
305                 310                 315                 320

Glu Pro Phe Lys Leu Asn Phe Leu Pro Glu Ile Lys Tyr Met Pro Leu
                325                 330                 335

Ser Val Ile Ile Thr Thr Phe Thr Lys Glu Lys Val Lys Arg Pro Leu
            340                 345                 350

Glu Gly Phe Gly Val Leu Ile Pro Thr Lys Glu Gln Lys His Gly Phe
        355                 360                 365

Lys Thr Leu Gly Thr Leu Phe Ser Ser Met Met Phe Pro Asp Arg Cys
    370                 375                 380

Pro Ser Asp Leu His Leu Tyr Thr Thr Phe Ile Gly Gly Ser Arg Asn
385                 390                 395                 400

Gln Glu Leu Ala Lys Ala Ser Thr Asp Glu Leu Lys Gln Val Ala Thr
                405                 410                 415

Ser Asp Leu Gln Arg Leu Leu Gly Val Glu Gly Glu Pro Val Phe Val
            420                 425                 430

Asn His Val Tyr Trp Asn Lys Ala Phe Pro Leu Tyr Asp Arg Ser Tyr
        435                 440                 445
```

```
Asp Ser Val Met Glu Ala Ile Asp Lys Met Glu Lys Asp Leu Pro Gly
    450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
                485                 490                 495

Ser Cys Ser Asn Asp Lys Lys Ser Glu Asp Ser Leu
            500                 505
```

<210> SEQ ID NO 118
<211> LENGTH: 1638
<212> TYPE: DNA
<213> ORGANISM: Triticum aestivum

<400> SEQUENCE: 118

```
atggggatcc accccgccgc actgacattc ccccgagcga cagaaatggc cggcgcaaca     60

atggccaccg ccaccgtcgc ggccgcgtcg ccgctccgcg gcagggtcac cgggcgccca    120

caccgcgtcc gcccgcgttg cgctaccgcg agcagcgcga ccgagactcc ggcggcgccc    180

ggcgtgcggc tgtccgcgga atgcgtcatt gtgggcgccg gcatcagcgg cctctgcacc    240

gcgcaggcgc tggccacccg atacggcgtc agcgacctgc tcgtcacgga ggcccgcgac    300

cgcccgggcg gcaacatcac caccgtcgag cgtcccgacg aggggtacct gtgggaggag    360

ggacccaaca gcttccagcc ctccgacccg gtcctcacca tggccgtgga cagcgggctc    420

aaggatgact tggtgttcgg ggaccccaac gcgccccggt tcgtgctgtg ggaggggaag    480

ctgaggccgg tgccgtcgaa gccaggcgac ctgcctttct tcagcctcat gagtatccct    540

gggaagctca gggccggcct tggcgcgctc ggcattcgcc cacctcctcc agggcgcgag    600

gagtcggtgg aggagtttgt gcgccgcaac ctcggtgccg aggtctttga gcgcctcatc    660

gagcctttct gctcaggtgt atatgctggt gatccttcga agcttagtat gaaggctgca    720

tttgggaagg tctggaggtt ggaggagatt ggaggtagta ttattggtgg aaccatcaag    780

gcgattcagg ataaagggaa gaaccccaaa ccgccaaggg atccccgact tccggcacca    840

aagggacaga cggtggcatc tttcaggaag ggtctagcca tgctcccgaa tgccatcgca    900

tctaggctgg gtagtaaagt caagctgtca tggaagctta cgagcattac aaaggcggac    960

aaccaaggat atgtattagg ttatgaaaca ccagaaggac ttgtttcagt gcaggctaaa   1020

agtgttatca tgaccatccc gtcatatgtt gctagtgata tcttgcgccc actttcaatt   1080

gatgcagcag atgcactctc aaaattctat tatccgccag ttgctgctgt aactgtttca   1140

tatccaaaag aagctattag aaaagaatgc ttaattgatg gggagctcca gggtttcggc   1200

cagttgcatc cacgtagcca aggagtcgag actttaggga caatatatag ctcttctctc   1260

tttcctaatc gtgctcctgc tggaagagtg ttacttctga actatatcgg gggttctaca   1320

aatacaggga tcgtctccaa gactgagagt gacttagtag gagccgttga ccgtgacctc   1380

agaaaaatgt tgataaaccc tagagcagca gaccctttag cattaggggt tcgagtgtgg   1440

ccacaagcaa taccacagtt tttgattggg caccttgatc gccttgctgc tgcaaaatct   1500

gcactgggcc aaggcggcta cgacgggmtg ttcctaggag gaaactacgt mgcaggagtt   1560

gccttgggcc gatgcatcga gggtgcgtac gagagtgcct cacaagtatc tgacttcttg   1620

accaagtatg cctacaag                                                  1638
```

<210> SEQ ID NO 119

<211> LENGTH: 1617
<212> TYPE: DNA
<213> ORGANISM: Gossypium hirsutum
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t

<400> SEQUENCE: 119
atgacggctc taatcgacct ttctcttctc cgctcctcgc cctccgtttc ccctttctcc 60
ataccccacc accagcttcc gccccgctct cgtaaacctt tcaggctccg atgctccgtc 120
gccgagggtc ccacgatttc ctcatctaaa atcgacgggg gagaatcatc catcgcggat 180
tgcgtcgtcg ttggaggtgg tatcagtgga ctttgcattg ctcaagctct cgccaccaag 240
caccgtgacg tcgcttccaa tgtgattgtg acggaagcca gagaccgtgt tggtggcaac 300
atcactaccg ttgagagaga tggatatctg tgggaagaag gccccaacag ttttcagccc 360
tccgatccta ttctaaccat ggccgtggat agtggattga aggacgattt ngttttaggt 420
gaccctaatg caccgcgatt tgtactntgg gagggaaaac taaggcntgt gccctccaag 480
ccaaccgact tgccgttttt tganttgatg agcattgctg gaaaacttag ggctgggttc 540
ggggctattg gcattcggcc tccncctccg ggttatgaag aatcggtgga ggagtttgtg 600
cgccgtaatc ttggtgctga ggtttttgaa cgctttattg aaccattttg ttcaggtgtt 660
tatgcagggg atccttcaaa attaagcatg aaagcagcat ttggaagagt atggaagcta 720
gaagagattg gtggcagcat cattggtggc actttcaaga caatccagga gagaaataag 780
acacctaagc cacccagaga cccgcgtctg ccaaaaccga agggccaaac agttggatct 840
tttaggaagg gacttaccat gctgcctgag gcaattgcta acagtttggg tagcaatgta 900
aaattatctt ggaagctntc cagtattacc aaattgggna atggagggta taacttgaca 960
tttgaaacac ctgaaggaat ggtatctctt cagagtagaa gtgttgtnat gaccattcca 1020
tcccatgttg ccagtaactt gttgcatcct ctctcggctg ctgctgcaga tgcattatcc 1080
caattttatt atcctccagt tgcatcagtc acagtctcct atccaaaaga agccattcga 1140
aaagaatgtt tgattgatgg tgaacttaag ggtttggcc agttgcaccc acgcagccaa 1200
ggaattgaaa ctttagggac gatatacagt tcatcacttt tccccaatcg agctccatct 1260
ggcagggtgt tgctcttgaa ctacatagga ggagctacca acactggaat tttgtccaag 1320
actgaagggg aacttgtaga agcagttgat cgtgatttga gaaaaatgct tataaatcct 1380
aatgcaaagg atcctcttgt tttgggtgta agagtatggc caaaagccat tccacagttc 1440
ttggttggtc atttggatct ccttgatagt gcaaaaatgg ctctcaggga ttctgggttt 1500
catggactgt ttcttggggg caactatgta tctggtgtgg cattaggacg gtgtgtggaa 1560
ggtgcttacg aggttgcagc tgaagtgaag gaattcctgt cacaatatgc atacaaa 1617

<210> SEQ ID NO 120
<211> LENGTH: 1509
<212> TYPE: DNA
<213> ORGANISM: Gossypium hirsutum
<220> FEATURE:
<221> NAME/KEY: misc_feature
<222> LOCATION: (630)..(630)
<223> OTHER INFORMATION: n is a, c, g, or t

<400> SEQUENCE: 120
atggcgtcaa ctgaaaacaa agatgaccac tcttctgcta aaagagtagc tgtcattggc 60
gctggtgtta gtggactcgc ggcagcttac aagttgaaat cacaaggttt acatgttacg 120
gtatttgaat ctgaaggaag agctggaggg aagttaagaa gtgtttcgag ggatggtttg 180
atatgggatg aaggagcaaa tacaatgact gaaagtgaga ttgaagtgag aagtttgttt 240
gatgatcttg gtattcaaga taagcaacaa gttccaattg cacagaacaa gcggtatatc 300
atgagaaatg gcgtgcctgt attgatcccc tcaaatcctc tctcattatt cacaagcagc 360
attctttcag caaaatcgaa gtttcagatt attttggagc cttttctgtg gagaaacagt 420
gaagcctcaa aagtatctga tgcttataat caggaaagtg tgggaggatt ttttcagcgc 480
cattttgggc aggaggttgt ggattacctt gttgatccct ttgttgctgg cacaagtgct 540
ggagatcctg aatctctatc tatgtgccat tcctttccgg ggctatggga tcttgagcaa 600
aggtttggct ctatcattgt tggagcagtn aaatctaaat tctctgccaa aaggacaaat 660
cgtgaagaaa caaaaaaattc agtgaaaaga aaggctctac gtggctcatt ttccttcaag 720
ggtggaatgc agacacttgc tgatatgttg tgcaaagatc tttccaaaga tgagcttaaa 780
ctgaaatcaa aggttttgtc attatcttac agtcatgagg ggaagtctac atcagagaac 840
tggtctctct cttatgcttc tgatcgagac aagcgctcac aaggctcatc atttgatgct 900
gtaataatga cggctccggt gtgcaatgtt aaagaaatga aaattactaa aggaggaaat 960
gtctttccac tgaacttcat ccctgaggtg agttatatgc cactatccgt cataattact 1020
gcttttaaga aggagaatgt caagaaaccc ctagaaggtt ttggagttct tataccttca 1080
aaggagcagc aaaatggttt aaaaactctc ggtacacttt tttcatctgt gatgtttcct 1140
gatcgtgcac ctaataattt gtatctctat acaacctttg ttggaggaaa tcgaaatgag 1200
aagctggcaa aagcctcaac agatgaattg aagcatattg ttacttccga ccttcagcag 1260
ttgttgggag tggagggaga accgacattc ttcaatcatt tctattggag caaggcattt 1320
cccttgtatg gccgtaacta tgcttcggtc ttggaaggca ttgaaaagat ggagagagat 1380
ctccctggat tcttctatgc aggtaaccac aaagggggat tatcggtggg caaatcgatt 1440
gcttctggtt gcaaagcagc agataatgta attacatatt tggaatcttc acatgacaag 1500
ctgctgaaa 1509

<210> SEQ ID NO 121

<211> LENGTH: 1680
<212> TYPE: DNA
<213> ORGANISM: Beta vulgaris

<400> SEQUENCE: 121
atgaaatcaa tggcgttatc aaactgcatt ccacagacac agtgcatgcc attgcacagc 60
agcgggcatt acaggggcaa ttgtatcatg ttgtcaattc catgtagttt aattggaaga 120
cgaggttatt attcacataa gaagaggagg atgagcatga gttgcagcac aagctcaggc 180
tcaaagtcag cggttaaaga agcaggatca ggatcaggat caggagcagg aggattgcta 240
gactgcgtaa tcgttggagg tggaattagc gggctttgca tcgcgcaggc tctttgtaca 300
aaacagtcct ctttatcccc aaattttata gtgacagagg ccaaagacag agttggcggc 360
aacatcgtca ctgtggaggc cgatggctat atctgggagg agggacccaa tagcttccag 420
ccttccgacg cggtgctcac catggcggtc gacagtggct tgaaagatga gttggtgctc 480
ggagatccca atgctcctcg ctttgtgctg tggaatgaca aattaaggcc cgtaccttcc 540
agtctcacca acctcccttt cttcgacctc atgaccattc ccggcaagat tagggctgct 600
cttggtgctc tcggatttcg cccttctcct ccacctcatg aggaatctgt tgaacacttt 660
gtgcgtcgta atctcggaga tgaggtcttt gaacgcttga ttgaaccctt ttgttcaggt 720
gtgtatgccg gtgatcctgc caagctgagt atgaaagctg cttttgggaa ggtctggaag 780
ttggagcaaa agggtggcag cataattggt ggcactctca aagctataca ggaaagaggg 840
agtaatccta agccgccccg tgaccagcgc ctccctaaac caaagggtca gactgttgga 900
tcctttagaa agggactcgt tatgttgcct accgccattt ctgctcgact tggcagtaga 960
gtgaaactat cttggaccct ttctagtatc gtaaagtcac tcaatggaga atatagtctg 1020
acttatgata ccccagatgg cttggtttct gtaagaacca aaagtgttgt gatgactgtc 1080
ccatcatatg ttgcaagtag gcttcttcgt ccactttcag actctgctgc agattctctt 1140
tcaaaatttt actatccacc agttgcagca gtgtcacttt cctatcctaa agaagcgatc 1200
agatcagaat gcttgattaa tggtgaactt caaggtttcg ggcaactaca tccccgcagt 1260
cagggtgtgg aaaccttggg aacaatttat agttcgtctc ttttccctgg tcgagcacca 1320
cctggtagga tcttgatctt gagctacatc ggaggtgcta aaaatcctgg catattaaac 1380
aagtcgaaag atgaacttgc cgagacagtt gacaaggacc tgagaagaat gcttataaat 1440
cctgatgcaa aacttcctcg tgtactgggt gtgagagtat ggcctcaagc aatacccccag 1500 ttttctattg ggcactttga tctgctcgat gctgcaaaag ctgctctgac agatacaggg 1560
gtcaaaggac tgtttcttgg tggcaactat gtttcaggtg ttgccttggg gcggtgtata 1620
gagggtgctt atgagtctgc agctgaggta gtagatttcc tctcacagta ctcagacaaa 1680

<210> SEQ ID NO 122
<211> LENGTH: 1593
<212> TYPE: DNA
<213> ORGANISM: Hordeum vulgare

<400> SEQUENCE: 122
atggccggtg caggtgcaac catggccacc gccaccgcgc cgccgctccg cggcagggtc 60
acccggcgcc cgcacggcgt ccgcccgcgt tgcgcggccg cgggcagcgc gaccgagacc 120
cccgcggcgc ccggcgtgcg tctgtccgcg gactgcgtca tcgtgggcgc cggcatcagc 180
ggcctctgca ccgcgcaggc gctggccacc cggcacggcg tcggcgacct gctcgtcacg 240
gaggcccgcg accgcccggg cggcaacatc accaccgtcg agcgccccga cgaggggtac 300

-continued

```
ctctgggagg agggccccaa cagcttccag ccctccgacc ccgtcctcac catggccgtg    360
gacagcgggc tcaaggatga cctggtgttc ggggacccca acgcgccccg gttcgtgctg    420
tgggagggga agctgaggcc ggtgccgtcc aagccaggcg acctgccgtt cttcagcctc    480
atgagcgtcc ccgggaagct cagggccggc ctcggcgccc tcggcattcg cccgcctcct    540
ccagggcgcg aggagtcggt ggaggagttt gtgcgccgca acctcggtgc cgaggtcttt    600
gagcgcctta tcgaaccttt ctgctcaggt gtgtatgctg gtgatccttc gaagctcagt    660
atgaaggctg catttgggaa ggtttggagg ttggaggaga ttgggggtag tattattggt    720
ggaaccatca aggcaattca ggataaaggg aagaacccca aaccgccaag ggatccccga    780
cttccggcac caaagggaca gacggtggca tctttcagga agggtctggc catgctcccg    840
aatgccatcg catctaggtt gggtagtaaa gtcaagctgt catggaagct tacgagcatt    900
acaaaggcgg acaaccaagg atatgtatta ggttatgaaa caccagaagg acttgtttca    960
gtgcaggcta aaagtgttat catgaccatc ccgtcatatg ttgctagtga tatcttacgc   1020
ccactttcaa ttgatgcagc agatgcactc tcaaaattct attatccgcc agttgctgct   1080
gtaactgttt catatccaaa agaagctatt agaaaagaat gcttaattga tggggagctc   1140
cagggtttcg gccagctgca tccacgtagc caaggagtcg agactttagg gacaatatat   1200
agctcttctc tctttcccaa tcgtgctcct gctggaagag tgttacttct gaactatatc   1260
gggggttcta caaatacagg gatcgtctcc aagaccgaga gtgacttagt agaagctgtt   1320
gatcgtgatc tcagaaaaat gttgataaac cctagagcag cagacccttt agcattaggg   1380
gtcagagtgt ggccacaagc aataccacag tttttgattg gacaccttga tcgccttgct   1440
gctgcaaaat ctgcactggg ccgaggcggg tacgacgggt tattcctagg aggaaactac   1500
gtagcaggag ttgccttggg ccgatgcatc gagggtgcgt acgagagtgc ctcacaagta   1560
tctgacttct tgaccaagta tgcctacaag tga                                1593
```

<210> SEQ ID NO 123
<211> LENGTH: 1665
<212> TYPE: DNA
<213> ORGANISM: Hordeum vulgare

<400> SEQUENCE: 123

```
atgctcactt ccgccaccgc tccccccctcc tcctcctcct gctcgtccca cgctcccgcc     60
cgcttcgcct ccccgtcccg gccccgtcgc tccgcgtccg cgtccgcgcg cgggcgaggg    120
cgccgcgtcc gccccgtgct cgccatggcc gcctccgacg acccccgcgc caggtcggtc    180
gccgtcgtcg gcgccggcgt cagtgggctc gtggcggcgt acatgctgag gaagagcggc    240
gtgcgggtca ccgtgttcga ggcggaagac cgcgcgggag ggaagatacg gaccaactcc    300
gacggcggat tcctctggga cgaaggagcc aacaccatga cagaaagtgc actggaggct    360
agtaggctaa tcgacgatct tggtcttcag gacagactgc agtatcctaa ctcccagcac    420
aagcgttaca ccgttaagga tggggcgcca gcactgattc cttcagatcc cattgcgcta    480
atgaaaagca ctgttctttc tacgaaatca aagttcaagt tatttctgga accatttctc    540
tatgaaaaat ctagcacaag gaactccaaa aaagtgtctg acgagcattt gcgcgagagc    600
gttgggagtt tttttgaacg ccattttggg aaagaggttg ttgactatct tattgatcca    660
tttgtagctg gaacaagtgc aggagatccc gagtcattat ctattcgtca tgcatttccg    720
gggttatgga atttagaaaa aaagtatggt tctctcatcg ttggtgccat cttgtcaaaa    780
```

-continued

```
ctaacagcta aaggtggttc agcaaagaaa ggaggcgctt cgtcaggaaa aggaaggaac    840
aagcgggcct cattttcatt tcatggtggc atgcagacac tagtagacgc acttcacaag    900
gaagttggag atactaatgt gaagcttgga acacaagtat tgtcattggc gtgtaactgt    960
gatggactct ctgcatcaga tgggtggtca atttttgttg attcaaagga tgctagtagt   1020
aaggagcttg caaggaacca atcctttgat gctgttataa tgacagctcc actgtccaat   1080
gtccagagga tgaagttcac aaaaggcgga cgtccctttg tgctagactt tcttcctaag   1140
gtggattatc tgccgttgtc cctcatggta acagcattta agaaggaaga cgtcaaaaga   1200
cccctcgaag gatttggggt cttaataccc tttaaggaac aacaaaaaca tggtttgaaa   1260
acgctcggaa ctctcttctc ctctatgatg ttcccagatc gagctcctaa tgaccagcac   1320
ttgtttacaa cattcattgg gggaagccac aatagagatc tcgctggagc tccaacggct   1380
atcttgaaac aatttgtgac atctgacctt acaaagctac tgggggtaga ggggcagcca   1440
acttttgtga aacatataca ttggagaaat gcttttcctt tgtatggcca tgattatgat   1500
ttggcactgg aagctatagg aaagatggaa ggtgatctcc cagggttctt ctatgcagga   1560
aataacaagg atgggttggc tgttggaaat gtcatagctt caggaagtaa cactgcagac   1620
cttgtgatct catacettga gtcaggcatc aagcatgtta attga                   1665
```

<210> SEQ ID NO 124
<211> LENGTH: 1593
<212> TYPE: DNA
<213> ORGANISM: Triticum aestivum

<400> SEQUENCE: 124

```
atggccggcg caacaatggc caccgccacc gtcgcggccg cgtcgccgct ccgcggcagg     60
gtcaccgggc gcccacaccg cgtccgcccg cgttgcgcta ccgcgagcag cgcgaccgag    120
actccggcgg cgcccggcgt gcggctgtcc gcggaatgcg tcattgtggg cgccggcatc    180
agcggcctct gcaccgcgca ggcgctggcc acccgatacg gcgtcagcga cctgctcgtc    240
acggaggccc gcgaccgccc gggcggcaac atcaccaccg tcgagcgtcc cgacgagggg    300
tacctgtggg aggagggacc caacagcttc cagccctccg acccggtcct caccatggcc    360
gtggacagcg ggctcaagga tgacttggtg ttcggggacc ccaacgcgcc ccggttcgtg    420
ctgtgggagg ggaagctgag gccggtgccg tcgaagccag gcgacctgcc tttcttcagc    480
ctcatgagta tccctgggaa gctcagggcc ggccttggcg cgctcggcat tcgcccacct    540
cctccagggc gcgaggagtc ggtggaggag tttgtgcgcc gcaacctcgg tgccgaggtc    600
tttgagcgcc tcatcgagcc tttctgctca ggtgtatatg ctggtgatcc ttcgaagctt    660
agtatgaagg ctgcatttgg gaaggtctgg aggttggagg agattggagg tagtattatt    720
ggtggaacca tcaaggcgat tcaggataaa gggaagaacc ccaaaccgcc aagggatccc    780
cgacttccgg caccaaaggg acagacggtg gcatctttca ggaagggtct agccatgctc    840
ccgaatgcca tcgcatctag gctgggtagt aaagtcaagc tgtcatggaa gcttacgagc    900
attacaaagg cggacaacca aggatatgta ttaggttatg aaacaccaga aggacttgtt    960
tcagtgcagg ctaaaagtgt tatcatgacc atcccgtcat atgttgctag tgatatcttg   1020
cgcccacttt caattgatgc agcagatgca ctctcaaaat tctattatcc gccagttgct   1080
gctgtaactg tttcatatcc aaaagaagct attagaaaag aatgcttaat tgatggggag   1140
ctccagggtt tcggccagtt gcatccacgt agccaaggag tcgagacttt agggacaata   1200
tatagctctt ctctctttcc taatcgtgct cctgctggaa gagtgttact tctgaactat   1260
```

```
atcgggggtt ctacaaatac agggatcgtc tccaagactg agagtgactt agtaggagcc   1320

gttgaccgtg acctcagaaa aatgttgata aaccctagag cagcagaccc tttagcatta   1380

ggggttcgag tgtggccaca agcaatacca cagtttttga ttgggcacct tgatcgcctt   1440

gctgctgcaa aatctgcact gggccaaggc ggctacgacg ggttgttcct aggaggaaac   1500

tacgtcgcag gagttgcctt gggccgatgc atcgagggtg cgtacgagag tgcctcacaa   1560

gtatctgact tcttgaccaa gtatgcctac aag                                1593
```

<210> SEQ ID NO 125
<211> LENGTH: 1506
<212> TYPE: DNA
<213> ORGANISM: Solanum lycopersicum

<400> SEQUENCE: 125

```
atggctccat ctgccggaga agataaacaa aagagagttg cagtcattgg tgctggcgtc     60

agtggacttg ctgcagcata caagttgaaa gttcatggct tgaatgtcac agtatttgaa    120

gcagaaggga gagctggagg gaagttacga agcctgagtc aagatggcct aatatgggat    180

gaaggcgcaa atactatgac tgaaagtgaa ggtgatgtca catttttgct tgattcgctt    240

ggactccgag aaaaacaaca attcccactt tcacagaaca agcgctacat tgccagaaat    300

ggtactccta ctctgatacc ttcaaatcca tttgacctat tcaaaagcaa ttttctttcc    360

actggatcaa agcttcagat gcttttcgag ccacttttgt ggaagaataa aaagcttaca    420

aaggtgtctg acaaacacga aagtgtcagt ggattcttcc agcgtcattt tggaaaggag    480

gttgtcgact atctaattga cccttttgtt gctggaacat gtggtggtga tcctgattcg    540

ctttcaatgc acctttcatt tccagacttg tggaatttag agaaaaggtt tggttcagtc    600

atagttgggg caattcaatc taagttatct cctataaagg aaaagaaaca agggccaccc    660

agaacttcaa taaataagaa gcgccagcgg gggtcctttt catttttggg cggaatgcaa    720

acacttactg acgcaatatg caaaaatctc aaagaagatg aacttaggct aaactctaga    780

gttctggaat tatcttgtag ctgtagtggg gactctgcga tagatagctg gtcaattttt    840

tctgcctctc cacacaagcg gcaagcagaa gaagaatcat ttgatgctgt aattatgacg    900

gcccctctct gtgacgttaa gagtatgaag attgctaaga gaggaaatcc atttctgctc    960

aactttattc ctgaggtcga ttatgtacca ctatctgttg ttataaccac atttaagaag   1020

gagagtgtaa agcatcccct tgagggtttt ggagtgcttg taccctccca ggagcaaaaa   1080

catggtctga agacactagg caccctcttc tcttctatga tgtttccaga tcgtgcaccc   1140

aacaatgtct atctctatac tacatttgtt ggtggaagcc gaaatagaga actcgcgaaa   1200

gcctcgagga ctgagctgaa agagatagta acttctgacc ttaagcagtt gttgggtgct   1260

gagggagagc caacatatgt gaatcattta tgctggagta aagcatttcc attgtacggg   1320

cataactatg attcagtcct agacgcaatt gacaaaatgg agaaaagcct tcctggatta   1380

ttctatgcag gtaaccacaa ggggggattg tcagttggca aagcattatc ttctggatgc   1440

aatgcagcag atcttgttat atcatatctt gaagcggttt cagctgacac caaaaaccat   1500

agctga                                                              1506
```

<210> SEQ ID NO 126
<211> LENGTH: 1677
<212> TYPE: DNA
<213> ORGANISM: Solanum lycopersicum

<400> SEQUENCE: 126

```
atgacaacaa cggccgtcgt caaccatcct agcattttca ctcaccggtc gccgctgccg     60
tcgccgtcct cctcctcatc ctcatcgccg tcatttttat ttttaaatcg tacgaatttt    120
attccatact tttccacctc caagcgcagt agtgtcaatt gcaatggctg gagaacacgg    180
tgttccgttg cgaagaatta tacagttcct ccctcagaag ttgacggtaa tcagttaccg    240
gagctggatt gtgtggtagt cggagcagga attagtggtc tctgcattgc taaggtgata    300
tcggctaatt atcccaattt gatggtgacg gaggcgaggg atcgtgccgg tggaaacata    360
acgacggtgg aaagagatgg atacttatgg gaagaaggtc ctaacagttt ccagccttcg    420
gatcctatgt tgactatggc tgtagattgt ggattgaagg atgatttggt gttgggagat    480
cctgatgcgc ctcgctttgt cttgtggaag gataaactaa ggcctgttcc cggcaagctc    540
actgatcttc ccttctttga tttgatgagt attcctggca agctcagagc tggttttggt    600
gccattggcc ttcgcccttc acctccaggt tatgaggaat cagttgagca gttcgtgcgt    660
cgtaatcttg gtgctgaagt ctttgaacgt ttgattgaac cattttgttc tggtgtttat    720
gctggcgacc catcaaaatt gagtatgaaa gcagcatttg ggaaagtgtg gaagctagaa    780
caaactggtg gtagcattat tggggggaacc tttaaggcaa taaaggagag atccagtaac    840
cctaaaccgc ctcgtgatcc gcgtttacca acaccaaaag gacaaactgt tggttcattt    900
aggaagggtc tgagaatgct gccagatgca atttgtgaaa gactgggaag caaagtgaaa    960
ctatcatgga agctttctag cattacaaag tcagataaag gaggatatct cttgacatac   1020
gagacaccag aaggagtagt ttctctgcga agtcgaagca ttgtcatgac tgttccatcc   1080
tatgtagcaa gcaacatatt acgccctctt tcggtcgccg cagcagatgc actttcaagt   1140
ttctactatc ccccagttgc agcagtgaca atttcatatc ctcaagaggc tattcgtgat   1200
gagcgtctgg ttgatggtga actaaaggga tttgggcagt tgcatccacg ttcacaggga   1260
gtggaaacac taggaacaat atatagttca tcactcttcc ctaaccgtgc tccaaatggc   1320
cgggtgctac tcttgaacta cattggagga gcaacaaata ctgaaattgt gtctaagaca   1380
gagagccaac ttgtggaagc agttgaccgt gacctcagaa agatgcttat aaaacccaaa   1440
gcacaagatc cctttgttac gggtgtgcga gtatggccac aagctatccc acagtttttg   1500
gtcggacatc tggatacact aggtactgct aaagctgctc taagtgataa tgggcttgac   1560
gggctattcc ttgggggtaa ttatgtgtct ggtgtagcat tgggaaggtg tgttgaaggt   1620
gcttatgaaa ttgcatctga agtaactggg tttctgtctc agtatgcata caaatga      1677
```

<210> SEQ ID NO 127
<211> LENGTH: 1620
<212> TYPE: DNA
<213> ORGANISM: Gossypium hirsutum

<400> SEQUENCE: 127

```
atgacggctc taatcgacct ttctcttctc cgctcctcgc cctccgtttc ccctttctcc     60
ataccccacc accagcttcc gccccgctct cgtaaacctt tcaagctccg atgctccctc    120
gccgagggtc ccacgatttc ctcatctaaa atcgacgggg gagaatcatc catcgcggat    180
tgcgtcgtcg ttggaggtgg tatcagtgga ctttgcattg ctcaagctct cgccaccaag    240
caccgtgacg tcgcttccaa tgtgattgtg acggaagcca gagaccgtgt tggtggcaac    300
atcactaccg ttgagagaga tggatatctg tgggaagaag gacccaacag ttttcagccc    360
tccgatccta ttctaaccat ggccgtggat agtggattga aggacgattt agttttaggt    420
```

-continued gaccctaatg caccgcgatt tgtactgtgg gagggaaaac taaggcctgt gccctccaag 480
ccaaccgact tgccgttttt tgacttgatg agcattgctg gaaaacttag ggctgggttc 540
ggggctattg gcattcggcc tccccctccg ggttatgaag aatcggtgga ggagtttgtg 600
cgccgtaatc ttggtgctga ggtttttgaa cgctttattg aaccattttg ttcaggtgtt 660
tatgcagggg atccttcaaa attaagcatg aaagcagcat ttggaagagt atggaagcta 720
gaagagattg gtggcagcat cattggtggc actttcaaga caatccagga gagaaataag 780
acacctaagc cacccagaga cccgcgtctg ccaaaaccga agggccaaac agttggatct 840
tttaggaagg gacttaccat gctgcctgag gcaattgcta acagtttggg tagcaatgta 900
aaattatctt ggaagctctc cagtattacc aaattgggta atggagggta taacttgaca 960
tttgaaacac ctgaaggaat ggtatctctt cagagtagaa gtgttgtcat gaccattcca 1020
tcccatgttg ccagtaactt gttgcatcct ctctcggctg ctgctgcaga tgcattatcc 1080
caattttatt atcctccagt tgcatcagtc acagtctcct atccaaaaga agccattcga 1140
aaagaatgtt tgattgatgg tgaacttaag ggtttggcc agttgcaccc acgcagccaa 1200
ggaatcgaaa ctttagggac gatatacagt tcatcacttt tccccaatcg agctccatct 1260
ggcagggtgt tgctcttgaa ctacatagga ggagctacca acactggaat tttgtccaag 1320
actgaagggg aacttgtaga agcagttgat cgtgatttga gaaaaatgct tataaatcct 1380
aatgcaaagg atcctcttgt tttgggtgta agagtatggc caaaagccat tccacagttc 1440
ttggttggtc atctggatct ccttgatact gcaaaaatgg ctctcaggga ttctgggttt 1500
catggactgt ttcttggggg caactatgta tctggtgtgg cattaggacg gtgtgtggaa 1560
ggtgcttacg aggttgcagc tgaagtgaag gaattcctgt cacaatatgc atacaaataa 1620

<210> SEQ ID NO 128
<211> LENGTH: 1683
<212> TYPE: DNA
<213> ORGANISM: Beta vulgaris

<400> SEQUENCE: 128
atgaaatcaa tggcgttatc aaactgcatt ccacagacac agtgcatgcc attgcacagc 60
agcgggcatt acaggggcaa ttgtatcatg ttgtcaattc catgtagttt aattggaaga 120
cgaggttatt attcacataa gaagaggagg atgagcatga gttgcagcac aagctcaggc 180
tcaaagtcag cggttaaaga agcaggatca ggatcaggat caggagcagg aggattgcta 240
gactgcgtaa tcgttggagg tggaattagc gggctttgca tcgcgcaggc tctttgtaca 300
aaacagtcct ctttatcccc aaattttata gtgacagagg ccaaagacag agttggcggc 360
aacatcgtca ctgtggaggc cgatggctat atctgggagg agggacccaa tagcttccag 420
ccttccgacg cggtgctcac catggcggtc gacagtggct tgaaagatga gttggtgctc 480
ggagatccca atgctcctcg ctttgtgctg tggaatgaca aattaaggcc cgtaccttcc 540
agtctcaccg acctcccttt cttcgacctc atgaccattc ccggcaagat tagggctgct 600
cttggtgctc tcggatttcg cccttctcct ccacctcatg aggaatctgt tgaacacttt 660
gtgcgtcgta atctcggaga tgaggtcttt gaacgcttga ttgaaccctt ttgttcaggt 720
gtgtatgccg gtgatcctgc caagctgagt atgaaagctg cttttgggaa ggtctggaag 780
ttggagcaaa agggtggcag cataattggt ggcactctca aagctataca ggaaagaggg 840
agtaatccta agccgccccg tgaccagcgc ctccctaaac caaagggtca gactgttgga 900

-continued

```
tcctttagaa agggactcgt tatgttgcct accgccattt ctgctcgact tggcagtaga    960

gtgaaactat cttggaccct ttctagtatc gtaaagtcac tcaatggaga atatagtctg   1020

acttatgata ccccagatgg cttggtttct gtaagaacca aaagtgttgt gatgactgtc   1080

ccatcatatg ttgcaagtag gcttcttcgt ccactttcag actctgctgc agattctctt   1140

tcaaaatttt actatccacc agttgcagca gtgtcacttt cctatcctaa agaagcgatc   1200

agatcagaat gcttgattaa tggtgaactt caaggtttcg ggcaactaca tccccgcagt   1260

cagggtgtgg aaaccttggg aacaatttat agttcgtctc ttttccctgg tcgagcacca   1320

cctggtagga tcttgatctt gagctacatc ggaggtgcta aaaatcctgg catattaaac   1380

aagtcgaaag atgaacttgc cgagacagtt gacaaggacc tgagaagaat gcttataaat   1440

cctgatgcaa aacttcctcg tgtactgggt gtgagagtat ggcctcaagc aataccccag   1500

ttttctattg ggcactttga tctgctcgat gctgcaaaag ctgctctgac agatacaggg   1560

gtcaaaggac tgtttcttgg tggcaactat gtttcaggtg ttgccttggg gcggtgtata   1620

gagggtgctt atgagtctgc agctgaggta gtagatttcc tctcacagta ctcagacaaa   1680

tag                                                                 1683
```

<210> SEQ ID NO 129
<211> LENGTH: 155
<212> TYPE: PRT
<213> ORGANISM: Artificial Sequence
<220> FEATURE:
<223> OTHER INFORMATION: Consensus sequence

<400> SEQUENCE: 129

```
Met Ala Ser Asn Ala Val Val Gly Ala Gly Ser Gly Leu Ala Leu Val
1               5                   10                  15

Val Glu Ala Arg Gly Gly Thr Val Asp Gly Ile Trp Glu Gly Asn Ser
            20                  25                  30

Val Asp Gly Leu Asp Arg Gly Pro Ser Pro Leu Ser Lys Leu Leu Arg
        35                  40                  45

Ser Glu Ser Val Glu Phe Arg Gly Glu Val Leu Ile Pro Phe Gly Ala
    50                  55                  60

Gly Asp Pro Leu Ser Met Phe Val Trp Leu Glu Gly Ser Ile Ile Gly
65                  70                  75                  80

Ile Lys Lys Pro Ser Phe Gly Leu Ala Leu Gly Lys Leu Ser Gly Leu
                85                  90                  95

Ser Ile Asn Ser Pro Val Val Leu Ser Ala Lys Glu Leu Gly Phe Gly
            100                 105                 110

Leu Pro Thr Leu Gly Thr Ser Ser Phe Pro Arg Ala Pro Leu Ile Gly
        115                 120                 125

Gly Ser Asn Ser Glu Leu Val Asp Leu Leu Pro Trp Ala Pro Leu Ala
    130                 135                 140

Asp Gly Phe Gly Asn Gly Gly Ala Val Leu Tyr
145                 150                 155
```

PLANTS HAVING INCREASED TOLERANCE TO HERBICIDES

CROSS-REFERENCE TO RELATED APPLICATIONS

This application is a National Stage application of International Application No. PCT/IB2014/067018, filed Dec. 17, 2014, which claims the benefit of U.S. Provisional Application No. 61/917,360, filed on Dec. 18, 2013, the content of which is incorporated herein by reference in its entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "76473_SubSeqListing2.txt" created on Jul. 11, 2018 513, 100 bytes in size. The sequence listing contained in this .txt file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to PPO-inhibiting herbicides. More specifically, the present invention relates to methods and plants obtained by mutagenesis and cross-breeding and transformation that have an increased tolerance to PPO-inhibiting herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidization, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer: Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPO-inhibiting herbicides.

Three main strategies are available for making plants tolerant to herbicides, i.e. (1) detoxifying the herbicide with an enzyme which transforms the herbicide, or its active metabolite, into nontoxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or U.S. Pat. No. 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

WO 2012/080975 discloses plants the tolerance of which to a PPO-inhibiting herbicide named "benzoxazinone-derivative" herbicide (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) had been increased by transforming said plants with nucleic acids encoding mutated PPO mutated enzymes. In particular, WO 2012/080975 discloses that the introduction of nucleic acids which code for a mutated PPO of an *Amaranthus* type II PPO in which the Arginine at position 128 had been replaced by a leucine, alanine, or valine, and the phenylalanine at position 420 had been replaced by a methionine, cysteine, isoleucine, leucine, or threonine, confers increased tolerance/resistance to a benzoxazinone-derivative herbicide. The inventors of the present invention have now surprisingly found that those types of double-mutants and, furthermore, novel substitutions for R128, L397 and F420 which are not disclosed in WO 2012/080975 confer increased tolerance/resistance to a wide variety of PPO inhibitors when transferred to PPO enzymes derived from organisms other than *Amaranthus*, such as those shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117. Thus, to date, the prior art has not described PPO-inhibiting herbicide tolerant plants containing a mutated PPO nucleic acid according to the present invention, which are tolerant/resistant to a broad spectrum of PPO inhibitors. Therefore, what is needed in the art are crop plants and crop plants having increased tolerance to herbicides such as PPO-inhibiting herbicide and containing at least one wildtype and/or mutated PPO nucleic acid according to the present invention. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

The problem is solved by the present invention which refers to a method for controlling undesired vegetation at a plant cultivation site, the method comprising the steps of:

a) providing, at said site, a plant that comprises at least one nucleic acid comprising a nucleotide sequence encoding a wild type protoporphyrinogen oxidase (PPO) or a mutated protoporphyrinogen oxidase (mutated PPO) which is resistant or tolerant to a PPO-inhibiting herbicide, and which comprises the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant thereof
b) applying to said site an effective amount of said herbicide.

Another object refers to a method of identifying a nucleotide sequence encoding a mutated PPO which is resistant or tolerant to a PPO-inhibiting herbicide, the method comprising:

a) generating a library of mutated PPO-encoding nucleic acids,
b) screening a population of the resulting mutated PPO-encoding nucleic acids by expressing each of said nucleic acids in a cell or plant and treating said cell or plant with a PPO-inhibiting herbicide,
c) comparing the PPO-inhibiting herbicide-tolerance levels provided by said population of mutated PPO encoding nucleic acids with the PPO-inhibiting herbicide-tolerance level provided by a control PPO-encoding nucleic acid,
d) selecting at least one mutated PPO-encoding nucleic acid that provides a significantly increased level of tolerance to a PPO-inhibiting herbicide as compared to that provided by the control PPO-encoding nucleic acid.

In a preferred embodiment, the mutated PPO-encoding nucleic acid selected in step d) provides at least 2-fold as much tolerance to a PPO-inhibiting herbicide as compared to that provided by the control PPO-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mutated PPO which is resistant or tolerant to a PPO-inhibiting herbicide, the method comprising:

a) identifying an effective amount of a PPO-inhibiting herbicide in a culture of plant cells or green algae.
b) treating said plant cells or green algae with a mutagenizing agent,
c) contacting said mutagenized cells population with an effective amount of PPO-inhibiting herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, the mutagenizing agent is ethylmethanesulfonate.

Another object refers to an isolated and/or recombinant and/or chemically synthesized nucleic acid encoding a mutated PPO polypeptide comprising the sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant, derivative, orthologue, paralogue or homologue thereof, as defined hereinafter.

Another object refers to a mutated PPO polypeptide, the polypeptide comprising the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, as defined hereinafter.

In a preferred embodiment, the nucleic acid being identifiable by a method as defined above.

In another embodiment, the invention refers to a plant cell transformed by and expressing a wild-type or a mutated PPO nucleic acid according to the present invention or a plant which has been mutated to obtain a plant expressing, preferably over-expressing a wild-type or a mutated PPO nucleic acid according to the present invention, wherein expression of said nucleic acid in the plant cell results in increased resistance or tolerance to a PPO-inhibiting herbicide as compared to a wild type variety of the plant cell.

In another embodiment, the invention refers to a plant that expresses a mutagenized or recombinant mutated PPO polypeptide, and wherein said mutated PPO confers upon the plant increased herbicide tolerance as compared to the corresponding wild-type variety of the plant when expressed therein.

In another embodiment, the invention refers to a plant comprising a plant cell according to the present invention, wherein expression of the nucleic acid in the plant results in the plant's increased resistance to PPO-inhibiting herbicide as compared to a wild type variety of the plant.

The plants of the present invention can be transgenic or non-transgenic.

Preferably, the expression of the nucleic acid of the invention in the plant results in the plant's increased resistance to PPO-inhibiting herbicides as compared to a wild type variety of the plant.

In another embodiment, the invention refers to a method for growing the plant according to the present invention while controlling weeds in the vicinity of said plant, said method comprising the steps of:

a) growing said plant; and
b) applying a herbicide composition comprising a PPO-inhibiting herbicide to the plant and weeds, wherein the herbicide normally inhibits protoporphyrinogen oxidase, at a level of the herbicide that would inhibit the growth of a corresponding wild-type plant.

In another embodiment, the invention refers to a seed produced by a transgenic plant comprising a plant cell of the present invention, or to a seed produced by the non-transgenic plant that expresses a mutagenized PPO polypeptide, wherein the seed is true breeding for an increased resistance to a PPO-inhibiting herbicide as compared to a wild type variety of the seed.

In another embodiment, the invention refers to a method of producing a transgenic plant cell with an increased resistance to a PPO-inhibiting herbicide as compared to a wild type variety of the plant cell comprising, transforming the plant cell with an expression cassette comprising a wild-type or a mutated PPO nucleic acid.

In another embodiment, the invention refers to a method of producing a transgenic plant comprising, (a) transforming a plant cell with an expression cassette comprising a wild-type or a mutated PPO nucleic acid, and (b) generating a plant with an increased resistance to PPO-inhibiting herbicide from the plant cell.

Preferably, the expression cassette further comprises a transcription initiation regulatory region and a translation initiation regulatory region that are functional in the plant.

In another embodiment, the invention relates to using the mutated PPO of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mutated PPO polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one PPO-inhibiting inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mutated PPO proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

In another embodiment, the invention relates to a combination useful for weed control, comprising (a) a polynucleotide encoding a mutated PPO polypeptide according to the present invention, which polynucleotide is capable of being expressed in a plant to thereby provide to that plant tolerance to a PPO inhibiting herbicide; and (b) a PPO inhibiting herbicide.

In another embodiment, the invention relates to a process for preparing a combination useful for weed control comprising (a) providing a polynucleotide encoding a mutated PPO polypeptide according to the present invention, which polynucleotide is capable of being expressed in a plant to thereby provide to that plant tolerance to a PPO inhibiting herbicide; and (b) providing a PPO inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the PPO inhibiting herbicide to the seed.

In another embodiment, the invention relates to the use of a combination useful for weed control, comprising (a) a polynucleotide encoding a mutated PPO polypeptide according to the present invention, which polynucleotide is capable of being expressed in a plant to thereby provide to that plant tolerance to a PPO inhibiting herbicide; and (b) a PPO inhibiting herbicide, to control weeds at a plant cultivation site.

BRIEF DESCRIPTION OF THE DRAWINGS

FIG. 1A-D show an amino acid sequence alignment of various PPO1 and PPO2 sequences. Conserved regions are indicated in light grey, grey and black. FIG. 1A—SEQ ID NOs: 1-50, respectively. Figure 1B—SEQ ID NOs: 1, 2, 3 and 51-97, respectively. FIG. 1C—SEQ ID NOs: 1, 2, 3, 4 and 98-106, respectively. FIG. 1D—SEQ ID NOs: 1, 2, 3, 4, 107-117, and 129, respectively.

DETAILED DESCRIPTION

Figure 1C:
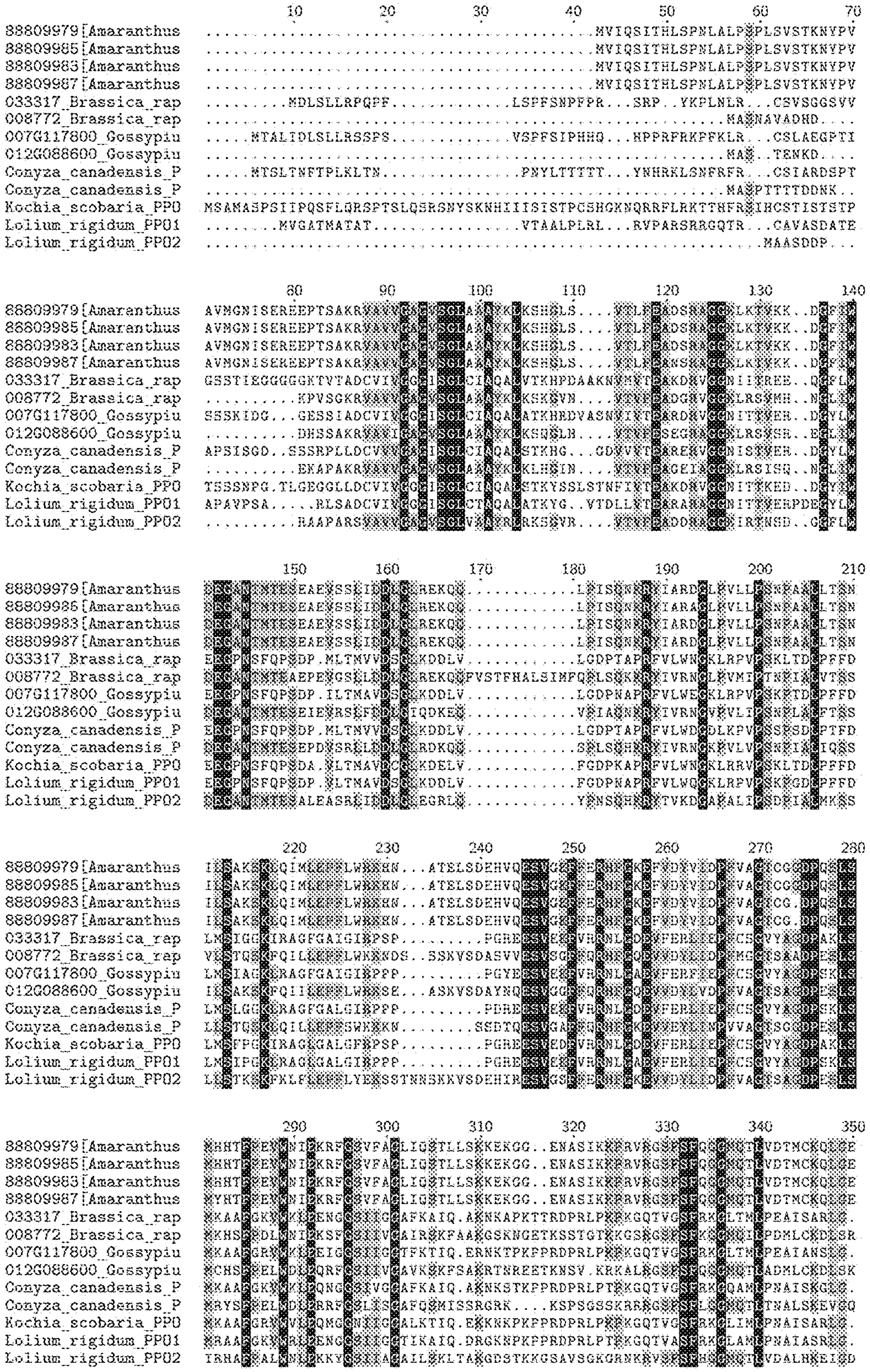
Figure 1D:
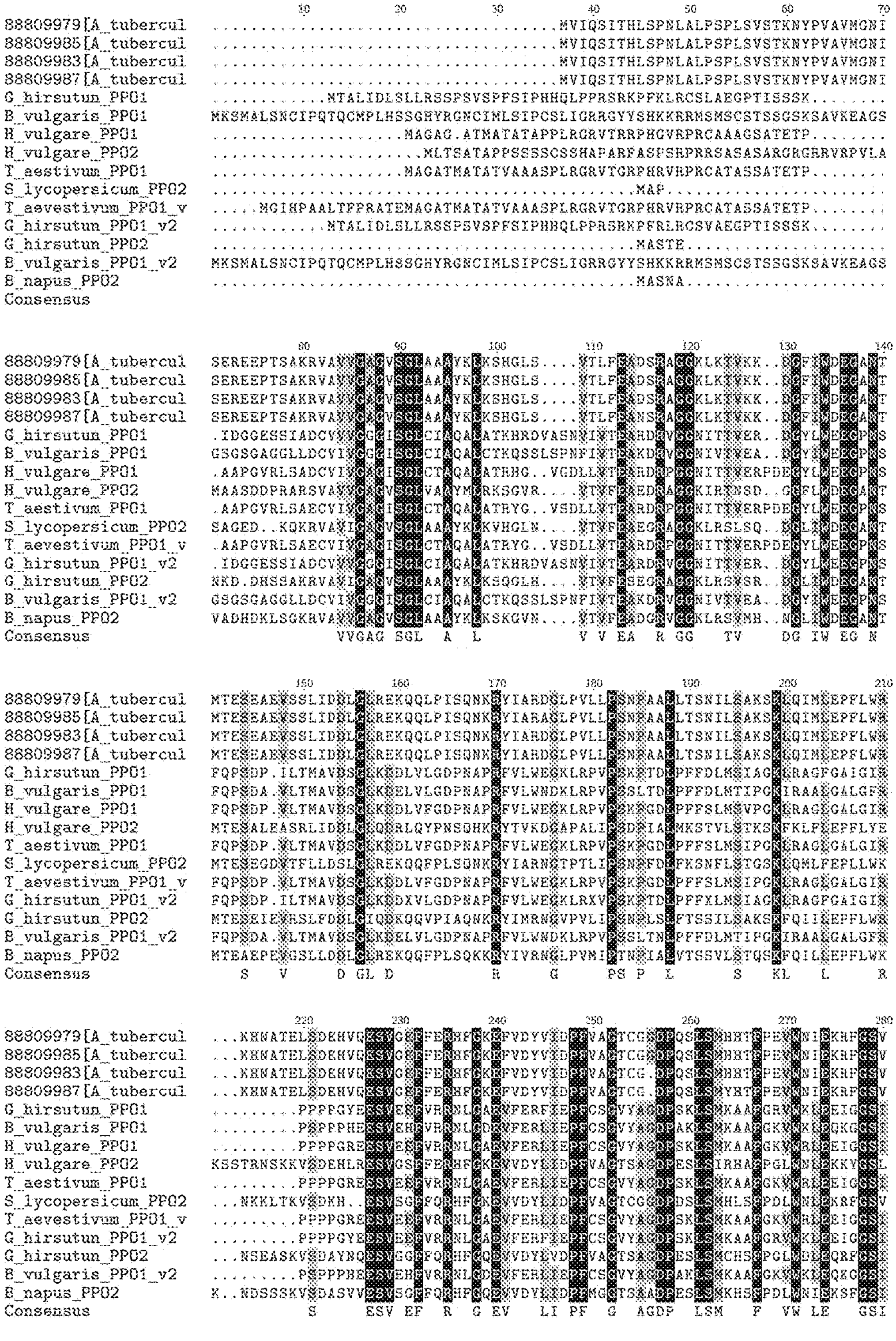

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The inventors of the present invention have found, that the tolerance or resistance of a plant to a PPO-inhibiting herbicide could be remarkably increased by overexpressing a nucleic acid encoding a mutated PPO polypeptide comprising the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof The present invention refers to a method for controlling undesired vegetation at a plant cultivation site, the method comprising the steps of:

a) providing, at said site, a plant that comprises at least one nucleic acid comprising a nucleotide sequence encoding a wild-type protoporphyrinogen oxidase or a mutated protoporphyrinogen oxidase (mutated PPO) which is resistant or tolerant to a PPO-inhibiting herbicide,
b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired, e.g. (crop) plant cultivation sites. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, *asparagus*, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, *sorghum* or oats.

In a preferred embodiment, the plant has been previously produced by a process comprising recombinantly preparing a plant by introducing and over-expressing a wild-type or mutated PPO transgene according to the present invention, as described in greater detail hereinafter.

In another preferred embodiment, the plant has been previously produced by a process comprising in situ mutagenizing plant cells, to obtain plant cells which express a mutated PPO.

As disclosed herein, the nucleic acids of the invention find use in enhancing the herbicide tolerance of plants that comprise in their genomes a gene encoding a herbicide-tolerant wild-type or mutated PPO protein. Such a gene may be an endogenous gene or a transgene, as described hereinafter.

Therefore, in another embodiment the present invention refers to a method of increasing or enhancing the PPO-inhibitor herbicide tolerance or resistance of a plant, the method comprising overexpressing a nucleic acid encoding a mutated PPO polypeptide comprising the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof.

Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109), By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) Science 266:789; Martin et al., (1993) Science 262:1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), cytochrome P450 monooxygenase, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD) and dicamba degrading enzymes as disclosed in WO 02/068607, or phenoxyaceticacid- and phenoxypropionicacid-derivative degrading enzymes as disclosed in WO 2008141154 or WO 2005107437. The combinations generated can also include multiple copies of any one of the polynucleotides of interest.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant wildtype or mutated PPO protein" or "herbicide-resistant wildtype or mutated PPO protein", it is intended that such a PPO protein displays higher PPO activity, relative to the PPO activity of a wild-type PPO protein, when in the presence of at least one herbicide that is known to interfere with PPO activity and at a concentration or level of the herbicide that is known to inhibit the PPO activity of the wild-type mutated PPO protein. Furthermore, the PPO activity of such a herbicide-tolerant or herbicide-resistant mutated PPO protein may be referred to herein as "herbicide-tolerant" or "herbicide-resistant" PPO activity.

Generally, if the PPO-inhibiting herbicides (also referred to as compounds A) and/or the herbicidal compounds B as described herein, which can be employed in the context of the present invention, are capable of forming geometrical isomers, for example E/Z isomers, it is possible to use both, the pure isomers and mixtures thereof, in the compositions useful for the present the invention. If the PPO-inhibiting herbicides A and/or the herbicidal compounds B as described herein have one or more centers of chirality and, as a consequence, are present as enantiomers or diastereomers, it is possible to use both, the pure enantiomers and diastereomers and their mixtures, in the compositions according to the invention. If the PPO-inhibiting herbicides A and/or the herbicidal compounds B as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine. Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The PPO-inhibiting herbicides A and/or the herbicidal compounds B as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Examples of PPO inhibiting herbicides which can be used according to the present invention are acifluorfen, acifluorfen-sodium, aclonifen, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, chlornitrofen, flumipropyn, fluoronitrofen, flupropacil, furyloxyfen, nitrofluorfen, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S3100), N-ethyl-3-2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4), and uracils of formula III

III

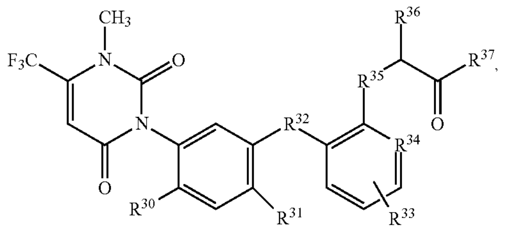

wherein $R^{30}$ and $R^{31}$ independently of one another are F, Cl or CN;

$R^{32}$ is O or S;

$R^{33}$ is H, F, Cl, $CH_3$ or $OCH_3$;

$R^{34}$ is CH or N;

$R^{35}$ is O or S;

$R^{36}$ is H, CN, $CH_3$, $CF_3$, $OCH_3$, $OC_2H_5$, $SCH_3$, $SC_2H_5$, $(CO)OC_2H_5$ or $CH_2R^{38}$, wherein $R^{38}$ is F, Cl, $OCH_3$, $SCH_3$, $SC_2H_5$, $CH_2F$, $CH_2Br$ or $CH_2OH$;

and $R^{37}$ is ($C_1$-$C_6$-alkyl)amino, ($C_1$-$C_6$-dialkyl)amino, (NH)$OR^{39}$, OH, $OR^{40}$ or $SR^{40}$ wherein $R^{39}$ is $CH_3$, $C_2H_5$ or phenyl; and $R^{40}$ is independently of one another $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_6$-cyanoalkyl, $C_1$-$C_4$-alkoxy-carbonyl-$C_1$-$C_4$-alkyl, $C_1$-$C_4$-alkyl-carbonyl-amino, $C_1$-$C_6$-alkylsulfinyl-$C_1$-$C_6$-alkyl, $C_1$-$C_6$-alkyl-sulfonyl-$C_1$-$C_6$-alkyl, $C_1$-$C_6$-dialkoxy-$C_1$-$C_6$-alkyl, $C_1$-$C_6$-alkylcarbonyloxy-$C_1$-$C_6$-alkyl, phenyl-carbonyl-$C_1$-$C_6$-alkyl, tri($C_1$-$C_3$-alkyl)silyl-$C_1$-$C_6$-alkyl, tri($C_1$-$C_3$-alkyl)-silyl-$C_1$-$C_6$-alkenyl, tri($C_1$-$C_3$-alkyl)silyl-$C_1$-$C_6$-alkynyl, tri($C_1$-$C_3$-alkyl)silyl-$C_1$-$C_6$-alkoxy-$C_1$-$C_6$-alkyl, dimethylamino, tetrahydropyranyl, tetrahydrofuranyl-$C_1$-$C_3$-alkyl, phenyl-$C_1$-$C_6$-alkoxy-$C_1$-$C_6$-alkyl, phenyl-$C_1$-$C_3$-alkyl, pyridyl-$C_1$-$C_3$-alkyl, pyridyl, phenyl, which pyridyls and phenyls independently of one another are substituted by one to five substituents selected from the group consisting of halogen, $C_1$-$C_3$-alkyl or $C_1$-$C_2$-haloalkyl;

$C_3$-$C_6$-cycloalkyl or $C_3$-$C_6$-cycloalkyl-$C_1$-$C_4$-alkyl, which cycloalkyls independently of one another are unsubstituted or substituted by one to five substituents selected from the group consisting of halogen, $C_1$-$C_3$-alkyl and $C_1$-$C_2$-haloalkyl;

including their agriculturally acceptable alkali metal salts or ammonium salts.

Preferred PPO-inhibiting herbicides that can be used according to the present invention are: Acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4)

uracils of formula III.1 (corresponding to uracils of formula III, wherein $R^{30}$ is F, $R^{31}$ is Cl, $R^{32}$ is O; $R^{33}$ is H; $R^{34}$ is CH; $R^{35}$ is O and $R^{37}$ is $OR^{40}$)

III.1

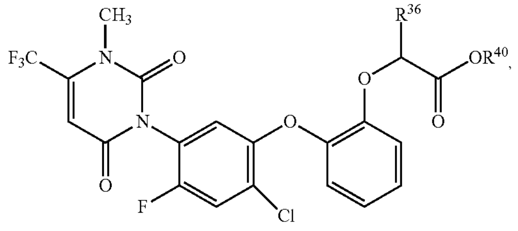

wherein $R^{36}$ is $OCH_3$, $OC_2H_5$, $SCH_3$ or $SC_2H_5$;

and $R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl, which cycloalkyls are unsubstituted or substituted by one to five substituents selected from the group consisting of halogen, $C_1$-$C_3$-alkyl and $C_1$-$C_2$-haloalkyl;

and uracils of formula III.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_1$-$C_6$-alkyl)

III.2

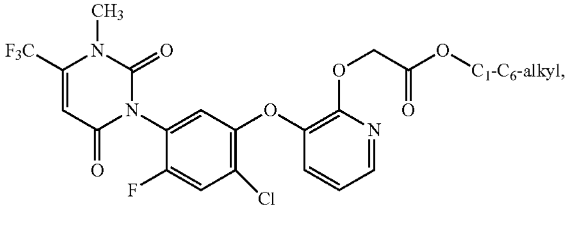

Particularly preferred PPO-inhibiting herbicides that can be used according to the present invention are:

acifluorfen, acifluorfen-sodium, butafenacil, carfentrazone-ethyl, cinidon-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), uracils of formula III.1.1 (corresponding to uracils of formula III, wherein $R^{30}$ is F, $R^{31}$ is Cl, $R^{32}$ is O; $R^{33}$ is H; $R^{34}$ is CH; $R^{35}$ is O, $R^{36}$ is $OCH_3$ and $R^{37}$ is $OR^{40}$)

III.1.1

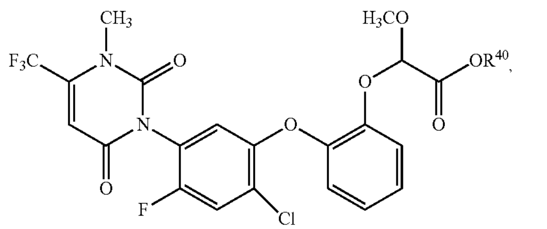

wherein $R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl, which cycloalkyls are unsubstituted or substituted by one to five substituents selected from the group consisting of halogen, $C_1$-$C_3$-alkyl and $C_1$-$C_2$-haloalkyl;

is preferably $CH_3$, $CH_2CH_2OC_2H_5$, $CH_2CHF_2$, cyclohexyl, (1-methylcyclopropyl)methyl or $CH_2$(pyridine-4-yl);

uracils of formula III.2.1 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $CH_3$)

III.2.1

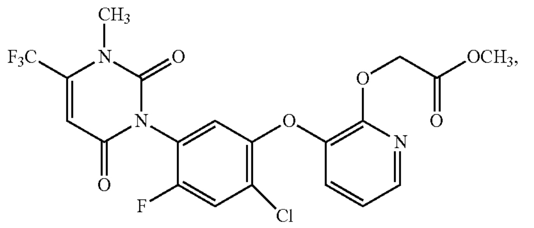

and uracils of formula III.2.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_2H_5$)

III.2.2

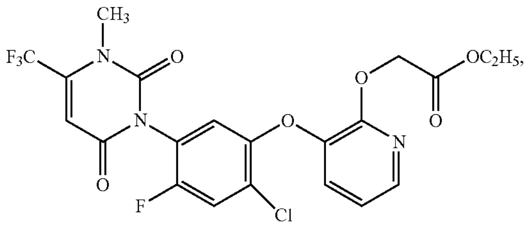

Especially preferred PPO-inhibiting herbicides are the PPO-inhibiting herbicides.1 to A.14 listed below in table A:

TABLE A

| | |
|---|---|
| A.1 | acifluorfen |
| A.2 | butafenacil |
| A.3 | carfentrazone-ethyl |
| A.4 | cinidon-ethyl |
| A.5 | flumioxazin |
| A.6 | fluthiacet-methyl |
| A.7 | fomesafen |
| A.8 | lactofen |
| A.9 | oxadiargyl |
| A.10 | oxyfluorfen |
| A.11 | saflufenacil |
| A.12 | sulfentrazone |
| A.13 | ethyl [3-[2-chloro-4-fluoro-5-(1-methyl-6-trifluoromethyl-2,4-dioxo-1,2,3,4-tetra-hydropyrimidin-3-yl)phenoxy]-2-pyridyloxy]acetate (CAS 353292-31-6) |
| A.14 | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) |

The PPO-inhibiting herbicides described above that are useful to carry out the present invention are often best applied in conjunction with one or more other herbicides to obtain control of a wider variety of undesirable vegetation. For example, PPO-inhibiting herbicides may further be used in conjunction with additional herbicides to which the crop plant is naturally tolerant, or to which it is resistant via expression of one or more additional transgenes as mentioned supra, or to which it is resistant via mutagenesis and breeding methods as described hereinafter. When used in conjunction with other targeting herbicides, the PPO-inhibiting herbicides, to which the plant of the present invention had been made resistant or tolerant, can be formulated with the other herbicide or herbicides, tank mixed with the other herbicide or herbicides, or applied sequentially with the other herbicide or herbicides.

Suitable components for mixtures are, for example, selected from the herbicides of class b1) to b15)

B) herbicides of class b1) to b15):

b1) lipid biosynthesis inhibitors;

b2) acetolactate synthase inhibitors (ALS inhibitors);

b3) photosynthesis inhibitors;

b4) protoporphyrinogen-IX oxidase inhibitors, b5) bleacher herbicides;

b6) enolpyruvyl shikimate 3-phosphate synthase inhibitors (EPSP inhibitors);

b7) glutamine synthetase inhibitors;

b8) 7,8-dihydropteroate synthase inhibitors (DHP inhibitors);

b9) mitosis inhibitors;

b10) inhibitors of the synthesis of very long chain fatty acids (VLCFA inhibitors);

b11) cellulose biosynthesis inhibitors;

b12) decoupler herbicides;

b13) auxinic herbicides;

b14) auxin transport inhibitors; and b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives.

Examples of herbicides B which can be used in combination with the PPO-inhibiting herbicides according to the present invention are:

b1) from the group of the lipid biosynthesis inhibitors: ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofoptefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl-carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors: sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors: amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl) phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides: PDS inhibitors: beflubutamid, diflufenican, fluridone, flurochloridone, flurtamone, norflurazon, picolinafen, and 4-(3-trifluoromethylphenoxy)-2-(4-trifluoromethylphenyl) pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors: glyphosate, glyphosate-isopropylammonium, glyposate-potassium and glyphosate-trimesium (sulfosate);

b7) from the group of the glutamine synthase inhibitors: bilanaphos (bialaphos), bilanaphos-sodium, glufosinate, glufosinate-P and glufosinate-ammonium;

b8) from the group of the DHP synthase inhibitors: asulam;

b9) from the group of the mitosis inhibitors: compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors: chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

II.1

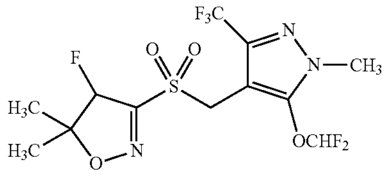

II.2

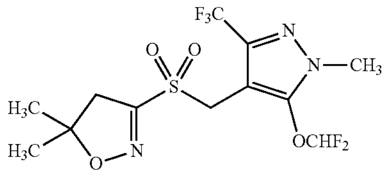

II.3

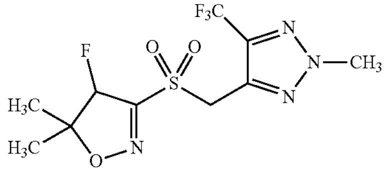

II.4

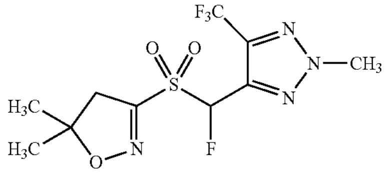

II.5

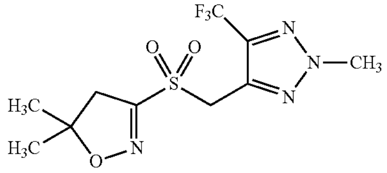

II.6

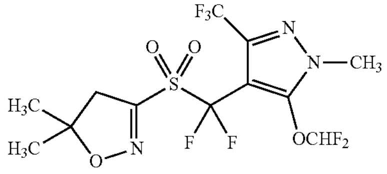

II.7

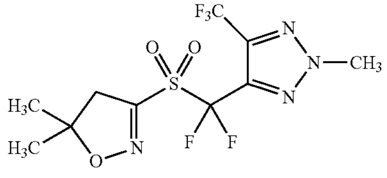

-continued

II.8

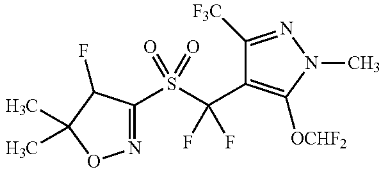

II.9

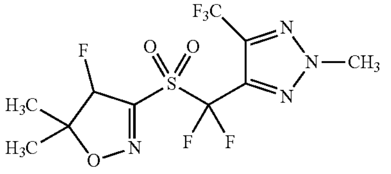

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, triaziflam, isoxaben and 1-Cyclohexyl-5-pentafluorphenyloxy-$1^4$-[1,2,4,6]thiatriazin-3-ylamine;

b12) from the group of the decoupler herbicides: dinoseb, dinoterb and DNOC and its salts;

b13) from the group of the auxinic herbicides: 2,4-D and its salts and esters such as clacyfos, 2,4-DB and its salts and esters, aminocyclopyrachlor and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Preferred herbicides B that can be used in combination with the PPO-inhibiting herbicides according to the present invention are:

b1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors: amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors: ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors: acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl) phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides: aclonifen, beflubutamid, benzobicyclon, clomazone, diflufenican, flurochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors: glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors: benfluralin, dithiopyr, ethalfluralin, oryzalin, pendimethalin, thiazopyr and trifluralin;

b10) from the group of the VLCFA inhibitors: acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, isoxaben and 1-Cyclohexyl-5-pentafluorphenyloxy-$1^4$-[1,2,4,6]thiatriazin-3-ylamine;

b13) from the group of the auxinic herbicides: 2,4-D and its salts and esters, aminocyclopyrachlor and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam and tridiphane.

Particularly preferred herbicides B that can be used in combination with the PPO-inhibiting herbicides according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: clomazone, diflufenican, flurochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Moreover, it may be useful to apply the PPO-inhibiting herbicides, when used in combination with a compound B described SUPRA, in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners C, the PPO-inhibiting herbicides and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro-[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3), and 2,2,5-trimethyl-3-(dichloroacetyl)-1,3-oxazolidine (R-29148, CAS 52836-31-4).

Also preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C, which, as component C, are constituent of the composition according to the invention are the safeners C as defined above; in particular the safeners C.1-C.12 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloro-acetyl)-1,3-oxazolidine (R-29148, CAS 52836-31-4) |

The PPO-inhibiting herbicides (compounds A) and the active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl) methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-Disopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl. Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl. Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl) ammonium.

Suitable salts of glyphosate are for example glyphosate-ammonium, glyphosate-diammonium, glyphosate-di methylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

The preferred embodiments of the invention mentioned herein below have to be understood as being preferred either independently from each other or in combination with one another.

According to a preferred embodiment of the invention, the composition comprises as component B at least one, preferably exactly one herbicide B.

According to another preferred embodiment of the invention, the composition comprises at least two, preferably exactly two, herbicides B different from each other.

According to another preferred embodiment of the invention, the composition comprises at least three, preferably exactly three, herbicides B different from each other.

According to another preferred embodiment of the invention, the composition comprises as component A at least one, preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl) phenoxy]-2-pyridyloxy]acetate (CAS 353292-31-6; S-3100; 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4), and as component B at least one, preferably exactly one, herbicide B.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and at least two, preferably exactly two, herbicides B different from each other.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) and at least three, preferably exactly three, herbicides B different from each other.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b1), in particular selected from the group consisting of clethodim, clodinafop-propargyl, cycloxydim, cyhalofop-butyl, fenoxaprop-P-ethyl, fluazifop, pinoxaden, profoxydim, quizalofop, sethoxydim, tepraloxydim, tralkoxydim, esprocarb, prosulfocarb, thiobencarb and triallate.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b2), in particular selected from the group consisting of bensulfuron-methyl, bispyribac-sodium, cloransulam-methyl, cyclosulfamuron, diclosulam, flumetsulam, flupyrsulfuron-methyl-sodium, foramsulfuron, halosulfuron-methyl, imazamox, imazapic, imazapyr, imazaquin, imazethapyr, imazosulfuron, iodosulfuron, iodosulfuron-methyl-sodium, mesosulfuron-methyl, metazosulfuron, nicosulfuron, penoxsulam, propoxycarbazon-sodium, pyrazosulfuron-ethyl, pyrithiobac-sodium, pyroxsulam, rimsulfuron, sulfosulfuron, thiencarbazon-methyl, thifensulfuron-methyl, trifloxysulfuron and tritosulfuron.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b3), in particular selected from the group consisting of ametryn, atrazine, bentazon, bromoxynil, diuron, fluometuron, hexazinone, isoproturon, linuron, metribuzin, paraquat, paraquat-dichloride, prometryne, propanil, terbutryn and terbuthylazine.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]

acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b4), in particular selected from the group consisting of acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b7), in particular selected from the group consisting of glufosinate, glufosinate-P and glufosinate-ammonium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b9), in particular selected from the group consisting of pendimethalin and trifluralin.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b13), in particular selected from the group consisting of 2,4-D and its salts and esters, aminocyclopyrachlor and its salts and esters, aminopyralid and its salts such as aminopyralid-tris (2-hydroxypropyl)ammonium and its esters, clopyralid and its salts and esters, dicamba and its salts and esters, fluroxypyr-meptyl, quinclorac and quinmerac.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b14), in particular selected from the group consisting of diflufenzopyr and diflufenzopyr-sodium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b15), in particular selected from the group consisting of dymron (=daimuron), indanofan, indaziflam, oxaziclomefone and triaziflam.

Here and below, the term "binary compositions" includes compositions comprising one or more, for example 1, 2 or 3, active compounds of the PPO-inhibiting herbicide and either one or more, for example 1, 2 or 3, herbicides B.

In binary compositions comprising at least one PPO-inhibiting herbicide as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.229 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | fluazifop |
| B.8 | metamifop |
| B.9 | pinoxaden |
| B.10 | profoxydim |
| B.11 | quizalofop |
| B.12 | sethoxydim |
| B.13 | tepraloxydim |
| B.14 | tralkoxydim |
| B.15 | esprocarb |
| B.16 | ethofumesate |
| B.17 | molinate |
| B.18 | prosulfocarb |
| B.19 | thiobencarb |
| B.20 | triallate |
| B.21 | bensulfuron-methyl |
| B.22 | bispyribac-sodium |
| B.23 | cloransulam-methyl |
| B.24 | chlorsulfuron |
| B.25 | clorimuron |
| B.26 | cyclosulfamuron |
| B.27 | diclosulam |
| B.28 | florasulam |
| B.29 | flumetsulam |
| B.30 | flupyrsulfuron-methyl-sodium |
| B.31 | foramsulfuron |
| B.32 | halosulfuron-methyl |
| B.33 | imazamox |
| B.34 | imazamox-ammonium |
| B.35 | imazapic |
| B.36 | imazapic-ammonium |
| B.37 | imazapic-isopropylammonium |
| B.38 | imazapyr |
| B.39 | imazapyr-ammonium |
| B.40 | imazapyr-isopropylammonium |

TABLE B-continued

| | Herbicide B |
|---|---|
| B.41 | imazaquin |
| B.42 | imazaquin-ammonium |
| B.43 | imazethapyr |
| B.44 | imazethapyr-ammonium |
| B.45 | imazethapyr-isopropylammonium |
| B.46 | imazosulfuron |
| B.47 | iodosulfuron-methyl-sodium |
| B.48 | iofensulfuron |
| B.49 | iofensulfuron-sodium |
| B.50 | mesosulfuron-methyl |
| B.51 | metazosulfuron |
| B.52 | metsulfuron-methyl |
| B.53 | metosulam |
| B.54 | nicosulfuron |
| B.55 | penoxsulam |
| B.56 | propoxycarbazon-sodium |
| B.57 | pyrazosulfuron-ethyl |
| B.58 | pyribenzoxim |
| B.59 | pyriftalid |
| B.60 | pyrithiobac-sodium |
| B.61 | pyroxsulam |
| B.62 | propyrisulfuron |
| B.63 | rimsulfuron |
| B.64 | sulfosulfuron |
| B.65 | thiencarbazone-methyl |
| B.66 | thifensulfuron-methyl |
| B.67 | tribenuron-methyl |
| B.68 | trifloxysulfuron |
| B.69 | tritosulfuron |
| B.70 | triafamone |
| B.71 | ametryne |
| B.72 | atrazine |
| B.73 | bentazon |
| B.74 | bromoxynil |
| B.75 | bromoxynil-octanoate |
| B.76 | bromoxynil-heptanoate |
| B.77 | bromoxynil-potassium |
| B.78 | diuron |
| B.79 | fluometuron |
| B.80 | hexazinone |
| B.81 | isoproturon |
| B.82 | linuron |
| B.83 | metamitron |
| B.84 | metribuzin |
| B.85 | prometryne |
| B.86 | propanil |
| B.87 | simazin |
| B.88 | terbuthylazine |
| B.89 | terbutryn |
| B.90 | paraquat-dichloride |
| B.91 | acifluorfen |
| B.92 | acifluorfen-sodium |
| B.93 | azafenidin |
| B.94 | bencarbazone |
| B.95 | benzfendizone |
| B.96 | bifenox |
| B.97 | butafenacil |
| B.98 | carfentrazone |
| B.99 | carfentrazone-ethyl |
| B.100 | chlomethoxyfen |
| B.101 | cinidon-ethyl |
| B.102 | fluazolate |
| B.103 | flufenpyr |
| B.104 | flufenpyr-ethyl |
| B.105 | flumiclorac |
| B.106 | flumiclorac-pentyl |
| B.107 | flumioxazin |
| B.108 | fluoroglycofen |
| B.109 | fluoroglycofen-ethyl |
| B.110 | fluthiacet |
| B.111 | fluthiacet-methyl |
| B.112 | fomesafen |
| B.113 | halosafen |
| B.114 | lactofen |
| B.115 | oxadiargyl |
| B.116 | oxadiazon |
| B.117 | oxyfluorfen |

TABLE B-continued

| | Herbicide B |
|---|---|
| B.118 | pentoxazone |
| B.119 | profluazol |
| B.120 | pyraclonil |
| B.121 | pyraflufen |
| B.122 | pyraflufen-ethyl |
| B.123 | saflufenacil |
| B.124 | sulfentrazone |
| B.125 | thidiazimin |
| B.126 | tiafenacil |
| B.127 | ethyl [3-[2-chloro-4-fluoro-5-(1-methyl-6-trifluoromethyl-2,4-di-oxo-1,2,3,4-tetrahydropyrimidin-3-yl)phenoxy]-2-pyridyl-oxy]acetate (CAS 353292-31-6) |
| B.128 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.129 | N-ethyl-3-(2,6-dichloro-4-trifluoromethylphenoxy)-5-methyl-1H-pyrazole-1-carboxamide (CAS 452098-92-9) |
| B.130 | N-tetrahydrofurfuryl-3-(2,6-dichloro-4-trifluoromethylphenoxy)-5-methyl-1H-pyrazole-1-carboxamide (CAS 915396-43-9) |
| B.131 | N-ethyl-3-(2-chloro-6-fluoro-4-trifluoromethylphenoxy)-5-methyl-1H-pyrazole-1-carboxamide (CAS 452099-05-7) |
| B.132 | N-tetrahydrofurfuryl-3-(2-chloro-6-fluoro-4-trifluoro-methylphenoxy)-5-methyl-1H-pyrazole-1-carboxamide (CAS 452100-03-7) |
| B.133 | 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione |
| B.134 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.135 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.136 | methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3] |
| B.137 | 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4) |
| B.138 | benzobicyclon |
| B.139 | clomazone |
| B.140 | diflufenican |
| B.141 | flurochloridone |
| B.142 | isoxaflutole |
| B.143 | mesotrione |
| B.144 | norflurazone |
| B.145 | picolinafen |
| B.146 | sulcotrione |
| B.147 | tefuryltrione |
| B.148 | tembotrione |
| B.149 | topramezone |
| B.150 | topramezone-sodium |
| B.151 | bicyclopyrone |

TABLE B-continued

| | Herbicide B |
|---|---|
| B.152 | amitrole |
| B.153 | fluometuron |
| B.154 | glyphosate |
| B.155 | glyphosate-ammonium |
| B.156 | glyphosate-dimethylammonium |
| B.157 | glyphosate-isopropylammonium |
| B.158 | glyphosate-trimesium (sulfosate) |
| B.159 | glyphosate-potassium |
| B.160 | glufosinate |
| B.161 | glufosinate-ammonium |
| B.162 | glufosinate-P |
| B.163 | glufosinate-P-ammonium |
| B.164 | pendimethalin |
| B.165 | trifluralin |
| B.166 | acetochlor |
| B.167 | butachlor |
| B.168 | cafenstrole |
| B.169 | dimethenamid-P |
| B.170 | fentrazamide |
| B.171 | flufenacet |
| B.172 | mefenacet |
| B.173 | metazachlor |
| B.174 | metolachlor |
| B.175 | S-metolachlor |
| B.176 | pretilachlor |
| B.177 | fenoxasulfone |
| B.178 | isoxaben |
| B.179 | ipfencarbazone |
| B.180 | pyroxasulfone |
| B.181 | 2,4-D |
| B.182 | 2,4-D-isobutyl |
| B.183 | 2,4-D-dimethylammonium |
| B.184 | 2,4-D-N,N,N-trimethylethanolammonium |
| B.185 | aminopyralid |
| B.186 | aminopyralid-methyl |
| B.187 | aminopyralid-tris(2-hydroxypropyl)ammonium |
| B.188 | clopyralid |
| B.189 | clopyralid-methyl |
| B.190 | clopyralid-olamine |
| B.191 | dicamba |
| B.192 | dicamba-butotyl |
| B.193 | dicamba-diglycolamine |
| B.194 | dicamba-dimethylammonium |
| B.195 | dicamba-diolamine |
| B.196 | dicamba-isopropylammonium |
| B.197 | dicamba-potassium |
| B.198 | dicamba-sodium |
| B.199 | dicamba-trolamine |
| B.200 | dicamba-N,N-bis-(3-aminopropyl)methylamine |
| B.201 | dicamba-diethylenetriamine |
| B.202 | fluroxypyr |
| B.203 | fluroxypyr-meptyl |
| B.204 | MCPA |
| B.205 | MCPA-2-ethylhexyl |
| B.206 | MCPA-dimethylammonium |
| B.207 | quinclorac |
| B.208 | quinclorac-dimethylammonium |
| B.209 | quinmerac |
| B.210 | quinmerac-dimethylammonium |
| B.211 | aminocyclopyrachlor |
| B.212 | aminocyclopyrachlor-potassium |
| B.213 | aminocyclopyrachlor-methyl |
| B.214 | diflufenzopyr |
| B.215 | diflufenzopyr-sodium |
| B.216 | dymron |
| B.217 | indanofan |
| B.218 | indaziflam |
| B.219 | oxaziclomefone |
| B.220 | triaziflam |
| B.221 | II.1 |
| B.222 | II.2 |
| B.223 | II.3 |
| B.224 | II.4 |
| B.225 | II.5 |

TABLE B-continued

| | Herbicide B |
|---|---|
| B.226 | II.6 |
| B.227 | II.7 |
| B.228 | II.8 |
| B.229 | II.9 |

Particularly preferred are compositions 1.1 to 1.229, comprising acifluorfen and the substance(s) as defined in the respective row of table B-1:

TABLE B-1

(compositions 1.1 to 1.229):

| comp. no. | herbicide B |
|---|---|
| 1.1 | B.1 |
| 1.2 | B.2 |
| 1.3 | B.3 |
| 1.4 | B.4 |
| 1.5 | B.5 |
| 1.6 | B.6 |
| 1.7 | B.7 |
| 1.8 | B.8 |
| 1.9 | B.9 |
| 1.10 | B.10 |
| 1.11 | B.11 |
| 1.12 | B.12 |
| 1.13 | B.13 |
| 1.14 | B.14 |
| 1.15 | B.15 |
| 1.16 | B.16 |
| 1.17 | B.17 |
| 1.18 | B.18 |
| 1.19 | B.19 |
| 1.20 | B.20 |
| 1.21 | B.21 |
| 1.22 | B.22 |
| 1.23 | B.23 |
| 1.24 | B.24 |
| 1.25 | B.25 |
| 1.26 | B.26 |
| 1.27 | B.27 |
| 1.28 | B.28 |
| 1.29 | B.29 |
| 1.30 | B.30 |
| 1.31 | B.31 |
| 1.32 | B.32 |
| 1.33 | B.33 |
| 1.34 | B.34 |
| 1.35 | B.35 |
| 1.36 | B.36 |
| 1.37 | B.37 |
| 1.38 | B.38 |
| 1.39 | B.39 |
| 1.40 | B.40 |
| 1.41 | B.41 |
| 1.42 | B.42 |
| 1.43 | B.43 |
| 1.44 | B.44 |
| 1.45 | B.45 |
| 1.46 | B.46 |
| 1.47 | B.47 |
| 1.48 | B.48 |
| 1.49 | B.49 |
| 1.50 | B.50 |
| 1.51 | B.51 |
| 1.52 | B.52 |
| 1.53 | B.53 |
| 1.54 | B.54 |
| 1.55 | B.55 |
| 1.56 | B.56 |
| 1.57 | B.57 |
| 1.58 | B.58. |
| 1.59 | B.59 |
| 1.60 | B.60 |

TABLE B-1-continued (compositions 1.1 to 1.229):

| comp. no. | herbicide B |
|---|---|
| 1.61 | B.61 |
| 1.62 | B.62 |
| 1.63 | B.63 |
| 1.64 | B.64 |
| 1.65 | B.65 |
| 1.66 | B.66 |
| 1.67 | B.67 |
| 1.68 | B.68 |
| 1.69 | B.69 |
| 1.70 | B.70 |
| 1.71 | B.71 |
| 1.72 | B.72 |
| 1.73 | B.73 |
| 1.74 | B.74 |
| 1.75 | B.75 |
| 1.76 | B.76 |
| 1.77 | B.77 |
| 1.78 | B.78 |
| 1.79 | B.79 |
| 1.80 | B.80 |
| 1.81 | B.81 |
| 1.82 | B.82 |
| 1.83 | B.83 |
| 1.84 | B.84 |
| 1.85 | B.85 |
| 1.86 | B.86 |
| 1.87 | B.87 |
| 1.88 | B.88 |
| 1.89 | B.89 |
| 1.90 | B.90 |
| 1.91 | B.91 |
| 1.92 | B.92 |
| 1.93 | B.93 |
| 1.94 | B.94 |
| 1.95 | B.95 |
| 1.96 | B.96 |
| 1.97 | B.97 |
| 1.98 | B.98 |
| 1.99 | B.99 |
| 1.100 | B.100 |
| 1.101 | B.101 |
| 1.102 | B.102 |
| 1.103 | B.103 |
| 1.104 | B.104 |
| 1.105 | B.105 |
| 1.106 | B.106 |
| 1.107 | B.107 |
| 1.108 | B.108 |
| 1.109 | B.109 |
| 1.110 | B.110 |
| 1.111 | B.111 |
| 1.112 | B.112 |
| 1.113 | B.113 |
| 1.114 | B.114 |
| 1.115 | B.115 |
| 1.116 | B.116 |
| 1.117 | B.117 |
| 1.118 | B.118 |
| 1.119 | B.119 |
| 1.120 | B.120 |
| 1.121 | B.121 |
| 1.122 | B.122 |
| 1.123 | B.123 |
| 1.124 | B.124 |
| 1.125 | B.125 |
| 1.126 | B.126 |
| 1.127 | B.127 |
| 1.128 | B.128 |
| 1.129 | B.129 |
| 1.130 | B.130 |
| 1.131 | B.131 |
| 1.132 | B.132 |
| 1.133 | B.133 |
| 1.134 | B.134 |
| 1.135 | B.135 |

TABLE B-1-continued (compositions 1.1 to 1.229):

| comp. no. | herbicide B |
|---|---|
| 1.136 | B.136 |
| 1.137 | B.137 |
| 1.138 | B.138 |
| 1.139 | B.139 |
| 1.140 | B.140 |
| 1.141 | B.141 |
| 1.142 | B.142 |
| 1.143 | B.143 |
| 1.144 | B.144 |
| 1.145 | B.145 |
| 1.146 | B.146 |
| 1.147 | B.147 |
| 1.148 | B.148 |
| 1.149 | B.149 |
| 1.150 | B.150 |
| 1.151 | B.151 |
| 1.152 | B.152 |
| 1.153 | B.153 |
| 1.154 | B.154 |
| 1.155 | B.155 |
| 1.156 | B.156 |
| 1.157 | B.157 |
| 1.158 | B.158 |
| 1.159 | B.159 |
| 1.160 | B.160 |
| 1.161 | B.161 |
| 1.162 | B.162 |
| 1.163 | B.163 |
| 1.164 | B.164 |
| 1.165 | B.165 |
| 1.166 | B.166 |
| 1.167 | B.167 |
| 1.168 | B.168 |
| 1.169 | B.169 |
| 1.170 | B.170 |
| 1.171 | B.171 |
| 1.172 | B.172 |
| 1.173 | B.173 |
| 1.174 | B.174 |
| 1.175 | B.175 |
| 1.176 | B.176 |
| 1.177 | B.177 |
| 1.178 | B.178 |
| 1.179 | B.179 |
| 1.180 | B.180 |
| 1.181 | B.181 |
| 1.182 | B.182 |
| 1.183 | B.183 |
| 1.184 | B.184 |
| 1.185 | B.185 |
| 1.186 | B.186 |
| 1.187 | B.187 |
| 1.188 | B.188 |
| 1.189 | B.189 |
| 1.190 | B.190 |
| 1.191 | B.191 |
| 1.192 | B.192 |
| 1.193 | B.193 |
| 1.194 | B.194 |
| 1.195 | B.195 |
| 1.196 | B.196 |
| 1.197 | B.197 |
| 1.198 | B.198 |
| 1.199 | B.199 |
| 1.200 | B.200 |
| 1.201 | B.201 |
| 1.202 | B.202 |
| 1.203 | B.203 |
| 1.204 | B.204 |
| 1.205 | B.205 |
| 1.206 | B.206 |
| 1.207 | B.207 |
| 1.208 | B.208 |
| 1.209 | B.209 |
| 1.210 | B.210 |

TABLE B-1-continued (compositions 1.1 to 1.229):

| comp. no. | herbicide B |
|---|---|
| 1.211 | B.211 |
| 1.212 | B.212 |
| 1.213 | B.213 |
| 1.214 | B.214 |
| 1.215 | B.215 |
| 1.216 | B.216 |
| 1.217 | B.217 |
| 1.218 | B.218 |
| 1.219 | B.219 |
| 1.220 | B.220 |
| 1.221 | B.221 |
| 1.222 | B.222 |
| 1.223 | B.223 |
| 1.224 | B.224 |
| 1.225 | B.225 |
| 1.226 | B.226 |
| 1.227 | B.227 |
| 1.228 | B.228 |
| 1.229 | B.229 |

Also especially preferred are compositions 2.1. to 2.229 which differ from the corresponding compositions 1.1 to 1.229 only in that they comprise as component A acifluorfen-sodium.

Also especially preferred are compositions 3.1. to 3.229 which differ from the corresponding compositions 1.1 to 1.229 only in that they comprise as component A azafenidin.

Also especially preferred are compositions 4.1. to 4.229 which differ from the corresponding compositions 1.1 to 1.229 only in that they comprise as component A bencarbazone.

Also especially preferred are compositions 5.1. to 5.229 which differ from the corresponding compositions 1.1 to 1.229 only in that they comprise as component A benzfendizone.

Also especially preferred are compositions 6.1. to 6.229 which differ from the corresponding compositions 1.1 to 1.229 only in that they comprise as component A bifenox.

Also especially preferred are compositions 7.1. to 7.229 which differ from the corresponding compositions 1.1 to 1.227 only in that they comprise as component A butafenacil.

Also especially preferred are compositions 8.1. to 8.229 which differ from the corresponding compositions 1.1 to 1.229 only in that they comprise as component A carfentrazone.

Also especially preferred are compositions 9.1. to 9.229 which differ from the corresponding compositions 1.1 to 1.229 only in that they comprise as component A carfentrazone-ethyl.

Also especially preferred are compositions 10.1. to 10.229 which differ from the corresponding compositions 1.1 to 1.229 only in that they comprise as component A chlomethoxyfen.

Also especially preferred are compositions 11.1. to 11.229 which differ from the corresponding compositions 1.1 to 1.229 only in that they comprise as component A cinidon-ethyl.

Also especially preferred are compositions 12.1. to 12.229 which differ from the corresponding compositions 1.1 to 1.229 only in that they comprise as component A fluazolate.

Also especially preferred are compositions 13.1. to 13.229 which differ from the corresponding compositions 1.1 to 1.229 only in that they comprise as component A flufenpyr.

Also especially preferred are compositions 14.1. to 14.229 which differ from the corresponding compositions 1.1 to 1.229 only in that they comprise as component A flufenpyr-ethyl.

Also especially preferred are compositions 15.1. to 15.229 which differ from the corresponding compositions 1.1 to 1.229 only in that they comprise as component A flumiclorac.

Also especially preferred are compositions 16.1. to 16.229 which differ from the corresponding compositions 1.1 to 1.229 only in that they comprise as component A flumiclorac-pentyl.

Also especially preferred are compositions 17.1. to 17.229 which differ from the corresponding compositions 1.1 to 1.229 only in that they comprise as component A flumioxazin.

Also especially preferred are compositions 18.1. to 18.229 which differ from the corresponding compositions 1.1 to 1.229 only in that they comprise as component A fluoroglycofen.

Also especially preferred are compositions 19.1. to 19.229 which differ from the corresponding compositions 1.1 to 1.229 only in that they comprise as component A fluoroglycofen-ethyl.

Also especially preferred are compositions 20.1. to 20.229 which differ from the corresponding compositions 1.1 to 1.229 only in that they comprise as component A fluthiacet.

Also especially preferred are compositions 21.1. to 21.229 which differ from the corresponding compositions 1.1 to 1.229 only in that they comprise as component A fluthiacet-methyl.

Also especially preferred are compositions 22.1. to 22.229 which differ from the corresponding compositions 1.1 to 1.229 only in that they comprise as component A fomesafen.

Also especially preferred are compositions 23.1. to 23.229 which differ from the corresponding compositions 1.1 to 1.229 only in that they comprise as component A halosafen.

Also especially preferred are compositions 24.1. to 24.229 which differ from the corresponding compositions 1.1 to 1.229 only in that they comprise as component A lactofen.

Also especially preferred are compositions 25.1. to 25.229 which differ from the corresponding compositions 1.1 to 1.229 only in that they comprise as component A oxadiargyl.

Also especially preferred are compositions 26.1. to 26.229 which differ from the corresponding compositions 1.1 to 1.229 only in that they comprise as component A oxadiazon.

Also especially preferred are compositions 27.1. to 27.229 which differ from the corresponding compositions 1.1 to 1.229 only in that they comprise as component A oxyfluorfen.

Also especially preferred are compositions 28.1. to 28.229 which differ from the corresponding compositions 1.1 to 1.229 only in that they comprise as component A pentoxazone.

Also especially preferred are compositions 29.1. to 29.229 which differ from the corresponding compositions 1.1 to 1.229 only in that they comprise as component A profluazol.

Also especially preferred are compositions 30.1. to 30.229 which differ from the corresponding compositions 1.1 to 1.229 only in that they comprise as component A pyraclonil.

Also especially preferred are compositions 31.1. to 31.229 which differ from the corresponding compositions 1.1 to 1.229 only in that they comprise as component A pyraflufen.

Also especially preferred are compositions 32.1. to 32.229 which differ from the corresponding compositions 1.1 to 1.229 only in that they comprise as component A pyraflufen-ethyl.

Also especially preferred are compositions 33.1. to 33.229 which differ from the corresponding compositions 1.1 to 1.229 only in that they comprise as component A saflufenacil.

Also especially preferred are compositions 34.1. to 34.229 which differ from the corresponding compositions 1.1 to 1.229 only in that they comprise as component A sulfentrazone.

Also especially preferred are compositions 35.1. to 35.229 which differ from the corresponding compositions 1.1 to 1.229 only in that they comprise as component A thidiazimin.

Also especially preferred are compositions 36.1. to 36.229 which differ from the corresponding compositions 1.1 to 1.229 only in that they comprise as component A tiafenacil.

Also especially preferred are compositions 37.1. to 37.229 which differ from the corresponding compositions 1.1 to 1.229 only in that they comprise as component A ethyl [3-[2-chloro-4-fluoro-5-(1-methyl-6-trifluoromethyl-2,4-di oxo-1,2,3,4-tetrahydropyrimidin-3-yl)phenoxy]-2-pyridyloxy]acetate (CAS 353292-31-6; S-3100).

Also especially preferred are compositions 38.1. to 38.229 which differ from the corresponding compositions 1.1 to 1.229 only in that they comprise as component A 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)

Also especially preferred are compositions 39.1. to 39.229 which differ from the corresponding compositions 1.1 to 1.229 only in that they comprise as component A N-ethyl-3-(2,6-dichloro-4-trifluoromethylphenoxy)-5-methyl-1H-pyrazole-1-carboxamide (CAS 452098-92-9).

Also especially preferred are compositions 40.1. to 40.229 which differ from the corresponding compositions 1.1 to 1.229 only in that they comprise as component A N-tetrahydrofurfuryl-3-(2,6-dichloro-4-trifluoromethylphenoxy)-5-methyl-1H-pyrazole-1-carboxamide (CAS 915396-43-9).

Also especially preferred are compositions 41.1. to 41.229 which differ from the corresponding compositions 1.1 to 1.229 only in that they comprise as component A N-ethyl-3-(2-chloro-6-fluoro-4-trifluoromethylphenoxy)-5-methyl-1H-pyrazole-1-carboxamide (CAS 452099-05-7).

Also especially preferred are compositions 42.1. to 42.229 which differ from the corresponding compositions 1.1 to 1.229 only in that they comprise as component A N-tetrahydrofurfuryl-3-(2-chloro-6-fluoro-4-trifluoromethylphenoxy)-5-methyl-1H-pyrazole-1-carboxamide (CAS 452100-03-7).

Also especially preferred are compositions 43.1. to 43.229 which differ from the corresponding compositions 1.1 to 1.229 only in that they comprise as component A 3-[7-fluoro-3-oxo-4-(prop-2-ynyl)-3,4-dihydro-2H-benzo [1,4]oxazin-6-yl]-1,5-dimethyl-6-thioxo-[1,3,5]triazinan-2,4-dione.

Also especially preferred are compositions 44.1. to 44.229 which differ from the corresponding compositions 1.1 to 1.229 only in that they comprise as component A methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3).

Also especially preferred are compositions 45.1. to 45.229 which differ from the corresponding compositions 1.1 to 1.229 only in that they comprise as component A 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

Also especially preferred are compositions 46.1. to 46.229 which differ from the corresponding compositions 1.1 to 1.229 only in that they comprise as component A 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione.

Also especially preferred are compositions 47.1. to 47.229 which differ from the corresponding compositions 1.1 to 1.229 only in that they comprise as component A 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione Also especially preferred are compositions 48.1. to 48.229 which differ from the corresponding compositions 1.1 to 1.229 only in that they additionally comprise benoxacor as safener C.

Also especially preferred are compositions 49.1. to 49.229 which differ from the corresponding compositions 1.1 to 1.229 only in that they additionally comprise cloquintocet as safener C.

Also especially preferred are compositions 50.1. to 50.229 which differ from the corresponding compositions 1.1 to 1.229 only in that they additionally comprise cyprosulfamide as safener C.

Also especially preferred are compositions 51.1. to 51.229 which differ from the corresponding compositions 1.1 to 1.229 only in that they additionally comprise dichlormid as safener C.

Also especially preferred are compositions 52.1. to 52.229 which differ from the corresponding compositions 1.1 to 1.229 only in that they additionally comprise fenchlorazole as safener C.

Also especially preferred are compositions 53.1. to 53.229 which differ from the corresponding compositions 1.1 to 1.229 only in that they additionally comprise fenclorim as safener C.

Also especially preferred are compositions 54.1. to 54.229 which differ from the corresponding compositions 1.1 to 1.229 only in that they additionally comprise furilazole as safener C.

Also especially preferred are compositions 55.1. to 55.229 which differ from the corresponding compositions 1.1 to 1.229 only in that they additionally comprise isoxadifen as safener C.

Also especially preferred are compositions 56.1. to 56.229 which differ from the corresponding compositions 1.1 to 1.229 only in that they additionally comprise mefenpyr as safener C.

Also especially preferred are compositions 57.1. to 57.229 which differ from the corresponding compositions 1.1 to 1.229 only in that they additionally comprise 4-(dichloroacetyl)-1-oxa-4-azaspiro[4.5]decane (MON4660, CAS 71526-07-3) as safener C.

Also especially preferred are compositions 58.1. to 58.229 which differ from the corresponding compositions 1.1 to 1.229 only in that they additionally comprise 2,2,5-trimethyl-3-(dichloroacetyl)-1,3-oxazolidine (R-29148, CAS 52836-31-4) as safener C.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

It is recognized that the polynucleotide molecules and polypeptides of the invention encompass polypeptides comprising an amino acid sequence that is sufficiently identical to the amino acid sequences set forth in SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated PPO nucleic acid" refers to a PPO nucleic acid having a sequence that is mutated from a wild-type PPO nucleic acid, such as e.g. SEQ ID NO: 118, 119, 120, 121, 122, 123, 124, 125, 126, 127, or 128, or homologues, paralogues and orthologues thereof; and that confers increased PPO-inhibiting herbicide tolerance to a plant in which it is expressed. Furthermore, the term "mutated protoporphyrinogen oxidase (mutated PPO)" refers to the replacement of an amino acid of the wild-type primary sequences SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117 or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the PPO nucleotide sequence encoding a mutated PPO comprises the sequence of SEQ ID NO: 118, 119, 120, 121, 122, 123, 124, 125, 126, 127, or 128, or a variant or derivative thereof.

Furthermore, it will be understood by the person skilled in the art that the PPO nucleotide sequences encompass homologues, paralogues and orthologues of SEQ ID NO: 118, 119, 120, 121, 122, 123, 124, 125, 126, 127, or 128, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein, e.g. the mutated PPO according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence encoding a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116 or 117. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117.

By "variant" polypeptide is intended a polypeptide derived from the protein of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intrasequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have found that by substituting one or more of the key amino acid residues, employing e.g. one of the above described methods to mutate the encoding nucleic acids, the herbicide tolerance or resistance could be remarkably increased as compared to the activity of the wild type PPO enzymes with SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117. Preferred substitutions of mutated PPO are those that increase the herbicide tolerance of the plant, but leave the biological activity of the oxidase activity substantially unaffected.

Accordingly, in another object of the present invention the key amino acid residues of a PPO enzyme comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, is substituted by any other amino acid.

In one embodiment, the key amino acid residues of a PPO enzyme, a variant, derivative, orthologue, paralogue or homologue thereof, is substituted by a conserved amino acid as depicted in Table 1.

It will be understood by the person skilled in the art that amino acids located in a close proximity to the positions of amino acids mentioned below may also be substituted. Thus, in another embodiment the variant of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof comprises a mutated PPO, wherein an amino acid ±3, ±2 or ±1 amino acid positions from a key amino acid is substituted by any other amino acid.

Based on techniques well-known in the art, a highly characteristic sequence pattern can be developed, by means of which further of mutated PPO candidates with the desired activity may be searched.

Searching for further mutated PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum 03/2006, pages 277-279), the inventors of the present invention have identified and generated specific amino acid substitutions and combinations thereof, which—when introduced into a plant by transforming and expressing the respective mutated PPO encoding nucleic acid—confer increased herbicide resistance or tolerance to a PPO inhibiting herbicide to said plant.

Thus, in a particularly preferred embodiment, the variant or derivative of the mutated PPO refers to a polypeptide comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, comprising a single amino acid substitution at positions depicted in the following Table 2a.

TABLE 2a

Single amino acid substitutions within SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117

| SEQ ID | Organism | Mutated site 1 | Mutated site 2 | Mutated site 3 | Mutated site 4 | Mutated site 5 |
|---|---|---|---|---|---|---|
| 1 | *Amaranthus tuberculatus* | R128 | G210 | G211 | L397 | F420 |
| 2 | *Amaranthus tuberculatus* | R128 | G210 | G211 | L397 | F420 |
| 3 | *Amaranthus tuberculatus* | R128 | G210 | — | L396 | F419 |
| 4 | *Amaranthus tuberculatus* | R128 | G210 | — | L396 | F419 |
| 5 | *Amaranthus hypochondriacus* | R128 | G210 | G211 | L398 | F421 |
| 6 | *Amaranthus tuberculatus* | R98 | G180 | G181 | L368 | F391 |

TABLE 2a-continued

Single amino acid substitutions within SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117

| SEQ ID | Organism | Mutated site 1 | Mutated site 2 | Mutated site 3 | Mutated site 4 | Mutated site 5 |
|---|---|---|---|---|---|---|
| 7 | *Spinacia oleracea* | R127 | G209 | G210 | L397 | F420 |
| 8 | *Vitis vinifera* | R100 | G182 | G183 | L373 | F396 |
| 9 | *Ricinus communis* | R99 | A181 | G182 | L372 | F395 |
| 10 | *Theobroma cacao* | R98 | A180 | G181 | L370 | F393 |
| 11 | *Glycine max* | R98 | A180 | A181 | L367 | F390 |
| 12 | *Prunus persica* | R96 | A175 | G176 | L366 | F389 |
| 13 | *Medicago truncatula* | R98 | A180 | A181 | L367 | F390 |
| 14 | *Fragaria vesca* subsp. *vesca* | R98 | A177 | G178 | L368 | F391 |
| 15 | *Citrus clementina* | R98 | A180 | A181 | L370 | F393 |
| 16 | *Citrus clementina* | R98 | A180 | A181 | L370 | F393 |
| 17 | *Cicer arietinum* | R98 | A180 | A181 | L367 | F390 |
| 18 | *Cucumis sativus* | R98 | A180 | G181 | L368 | F391 |
| 19 | *Cucumis sativus* | R93 | A175 | G176 | L363 | F386 |
| 20 | *Nicotiana tabacum* | R98 | G178 | G179 | L369 | F392 |
| 21 | *Solanum lycopersicum* | R95 | G175 | G176 | L366 | F389 |
| 22 | *Arabidopsis thaliana* | R101 | A182 | A183 | L371 | F394 |
| 23 | *Arabidopsis lyrata* subsp. *lyrata* | R103 | A186 | A187 | L375 | F398 |
| 24 | *Arabidopsis thaliana* | R101 | A182 | A183 | L364 | F387 |
| 25 | *Arabidopsis thaliana* | R147 | A228 | A229 | L410 | F433 |
| 26 | *Ambrosia artemisiifolia* | R74 | G151 | G152 | L336 | F359 |
| 27 | *Setaria italica* | R128 | A213 | G214 | L408 | F431 |
| 28 | *Sorghum bicolor* | R130 | A215 | G216 | L410 | F433 |
| 29 | *Arabidopsis thaliana* | R101 | A152 | A153 | L341 | F364 |
| 30 | *Zea mays* | R130 | A215 | G216 | L410 | F433 |
| 31 | *Zea mays* | R130 | A215 | G216 | L410 | F433 |
| 32 | LEMPA | R105 | G188 | G189 | L381 | F404 |
| 33 | LEMPA | R150 | A226 | G227 | L409 | Y432 |
| 34 | *Populus trichocarpa* | R100 | A182 | G183 | L373 | F396 |
| 35 | *Capsella rubella* | R165 | A248 | A249 | L433 | F456 |
| 36 | *Brachypodium distachyon* | R134 | A219 | G220 | L414 | F437 |
| 37 | *Oryza sativa Japonica* Group | R95 | G179 | G180 | L374 | F397 |
| 38 | *Picea sitchensis* | R100 | G186 | A187 | L354 | F377 |
| 39 | *Solanum tuberosum* | R98 | G178 | G179 | L369 | F392 |
| 40 | *Oryza sativa Indica* Group | R95 | G190 | G191 | L385 | F408 |
| 41 | *Oryza sativa Japonica* Group | R95 | G190 | G191 | L385 | F408 |
| 42 | *Eutrema salsugineum* | R96 | A179 | A180 | L368 | F391 |
| 43 | *Selaginella moellendorffii* | R97 | G175 | S176 | L377 | F400 |
| 44 | *Selaginella moellendorffii* | R97 | G175 | S176 | L377 | F400 |
| 45 | *Amaranthus tuberculatus* | R128 | G210 | G211 | — | — |
| 46 | *Amaranthus tuberculatus* | R128 | G210 | — | — | — |
| 47 | *Zea mays* | — | A67 | G68 | L262 | F285 |
| 48 | *Aegilops tauschii* | R30 | A96 | G97 | L291 | F314 |
| 49 | *Genlisea aurea* | R89 | G168 | G169 | — | — |
| 50 | *Amborella trichopoda* | — | — | — | L161 | F184 |
| 51 | *Rhodothermus marinus* | R87 | A162 | G163 | L330 | F353 |
| 52 | *Salinibacter ruber* | R87 | A161 | G162 | L330 | F353 |
| 53 | *Salinibacter ruber* M8 | R87 | A161 | G162 | L330 | F353 |
| 54 | *Zea mays* | — | — | — | L69 | F92 |
| 55 | *Rhodothermus marinus* | R87 | A162 | G163 | L330 | F353 |
| 56 | *Caldithrix abyssi* | R86 | A160 | G161 | L329 | F352 |
| 57 | *Opitutus terrae* PB90-1 | R103 | A178 | G179 | L345 | M368 |
| 58 | *Verrucomicrobia bacterium* | R91 | A166 | G167 | L332 | Y355 |
| 59 | *Ignavibacterium album* | R88 | A163 | G164 | L332 | F355 |
| 60 | *Coraliomargarita* sp. CAG:312 | R88 | G163 | A164 | L331 | Y354 |
| 61 | *Salisaeta longa* | R88 | A163 | G164 | L329 | F352 |
| 62 | *Ambrosia artemisiifolia* | R98 | G175 | G176 | — | — |
| 63 | *Melioribacter roseus* P3M-2 | R88 | A163 | G164 | L333 | F356 |
| 64 | *Halothiobacillus neapolitanus* c2 | R97 | A170 | G171 | L343 | F366 |
| 65 | *Chondrus crispus* | Y98 | S176 | G177 | L352 | Y376 |
| 66 | *Rubritalea marina* | R88 | A163 | G164 | L339 | M362 |
| 67 | *Acidobacteria bacterium* | R88 | A161 | G162 | L330 | F353 |
| 68 | *Coraliomargarita akajimensis* DSM 45221 | R88 | A163 | G164 | L323 | F346 |

TABLE 2a-continued

Single amino acid substitutions within SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117

| SEQ ID | Organism | Mutated site 1 | Mutated site 2 | Mutated site 3 | Mutated site 4 | Mutated site 5 |
|---|---|---|---|---|---|---|
| 69 | *Oscillochloris trichoides* DG6 | R90 | S164 | G165 | L340 | L363 |
| 70 | *Opitutaceae bacterium* TAV1 | R86 | A161 | G162 | L352 | L375 |
| 71 | *Amborella trichopoda* | R87 | A173 | A174 | L230 | — |
| 72 | *Opitutaceae bacterium* TAV5 | R105 | A180 | G181 | L368 | L391 |
| 73 | *Chloroflexus* sp. Y-400-fl | R91 | A166 | G167 | L335 | L358 |
| 74 | *Leptospirillum* sp. Group II '5-way CG' | R92 | A167 | S168 | L335 | F358 |
| 75 | *Leptospirillum ferriphilum* ML-04 | R92 | A167 | S168 | L335 | F358 |
| 76 | *Verrucomicrobia bacterium* SCGC AAA300-O17 | R89 | A165 | A166 | L334 | Y357 |
| 77 | *Chloroflexus aggregans* DSM 9485 | R92 | A167 | G168 | L336 | L359 |
| 78 | *Desulfurobacterium thermolithotrophum* | R86 | A161 | G162 | L333 | M356 |
| 79 | *Desulfurobacterium* sp. TC5-1 | R90 | A165 | G166 | L332 | M355 |
| 80 | *Arthrospira platensis* C1 | R93 | A176 | G177 | L352 | Y375 |
| 81 | *Leptospirillum* sp. Group II 'C75' | R92 | A167 | S168 | L335 | F358 |
| 82 | *Verrucomicrobiae bacterium* DG1235 | R87 | A164 | G165 | L332 | M355 |
| 83 | *Verrucomicrobia bacterium* SCGC AAA300-K03 | R89 | A165 | A166 | L334 | F357 |
| 84 | *Synechococcus* sp. JA-3-3Ab | R101 | A177 | G178 | L350 | F373 |
| 85 | *Hymenobacter norwichensis* | R86 | A161 | G162 | A321 | F344 |
| 86 | *Pontibacter* sp. BAB1700 | R85 | G159 | G160 | S319 | Y342 |
| 87 | *Leptospirillum ferrodiazotrophum* | R92 | A172 | S173 | L339 | F362 |
| 88 | *Prevotella histicola* F0411 | C89 | A164 | G165 | L328 | F351 |
| 89 | *Flexithrix dorotheae* | R84 | A158 | G159 | A313 | F336 |
| 90 | *Geobacter metallireducens* GS-15 | R93 | A168 | G169 | L342 | M365 |
| 91 | *Synechococcus* sp. JA-2-3B'a(2-13) | R93 | A169 | G170 | L362 | F385 |
| 92 | *Crinalium epipsammum* PCC 9333 | R85 | A168 | G169 | L344 | F367 |
| 93 | *Planctomyces maris* | A99 | T187 | S188 | F358 | F381 |
| 94 | *Geobacter uraniireducens* Rf4 | R93 | A170 | G171 | L344 | M367 |
| 95 | *Acidithiobacillus ferrivorans* | R87 | A162 | G163 | L323 | F346 |
| 96 | *Prevotella melaninogenica* | C88 | A163 | G164 | L327 | F350 |
| 97 | *Thermovibrio ammonificans* | R86 | A160 | G161 | L333 | M356 |
| 98 | Brassica_rapa | R143 | A219 | G220 | L402 | Y425 |
| 99 | Brassica_rapa | R112 | A195 | A196 | L384 | F407 |
| 100 | *Gossypium* | R146 | A222 | G223 | L405 | Y428 |
| 101 | *Gossypium* | R98 | A180 | G181 | L370 | F393 |
| 102 | Conyza_canadensis | R142 | A218 | G219 | L401 | Y424 |
| 103 | Conyza_canadensis | R102 | G179 | G180 | L365 | F388 |
| 104 | Kochia_scobaria | R172 | A248 | G249 | L431 | F454 |
| 105 | Lolium_rigidum | R138 | A214 | G215 | L397 | Y420 |
| 106 | Lolium_rigidum | R97 | A182 | G183 | L377 | F400 |
| 107 | *Gossypium hirsutum* PPO1 | R146 | A222 | G223 | L405 | Y428 |
| 108 | *Beta vulgaris* PPO1 | R167 | A243 | G244 | L426 | Y449 |
| 109 | *Hordeum vulgare* PPO1 | R137 | A213 | G214 | L396 | Y419 |
| 110 | *Hordeum vulgare* PPO2 | R142 | A227 | G228 | L422 | F445 |
| 111 | *Triticum aestivum* PPO1 | R138 | A214 | G215 | L397 | Y420 |
| 112 | *Solanum lycopersicum* PPO2 | R95 | G175 | G176 | L366 | F389 |
| 113 | *Triticum aestivum* PPO1_v2 | R153 | A229 | G230 | L412 | Y435 |
| 114 | *Gossypium hirsutum* PPO1_v2 | R146 | A222 | G223 | L405 | Y428 |

TABLE 2a-continued

| Single amino acid substitutions within SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117 | | | | | | |
|---|---|---|---|---|---|---|
| SEQ ID | Organism | Mutated site 1 | Mutated site 2 | Mutated site 3 | Mutated site 4 | Mutated site 5 |
| 115 | *Gossypium hirsutum* PPO2 | R98 | A180 | G181 | L370 | F393 |
| 116 | *Beta vulgaris* PPO1_v2 | R167 | A243 | G244 | L426 | Y449 |
| 117 | Brassica napus_PPO2 | R99 | A182 | A183 | L371 | F394 |

In a further particularly preferred embodiment, the variant or derivative of the mutated PPO refers to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, comprising a single amino acid substitutions at the positions depicted in the following Table 2b.

It should be noted that Mutated site 1 of Table 2a) corresponds to Pos 1 of Table 2b); Mutated site 2 of Table 2a) corresponds to Pos 16 of Table 2b); Mutated site 3 of Table 2a) corresponds to Pos 17 of Table 2b); Mutated site 4 of Table 2a) corresponds to Pos 38 of Table 2b); Mutated site 5 of Table 2a) corresponds to Pos 42 of Table 2b).

TABLE 2B

| ID | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 | Pos 14 | Pos 15 | Pos 16 | Pos 17 | Pos 18 | Pos 19 |
|---|---|---|---|---|---|---|---|---|---|---|---|---|---|---|---|---|---|---|---|
| 1 | R128 | Y129 | A131 | S149 | I151 | A154 | P164 | K169 | E182 | S183 | E189 | F196 | D202 | C209 | G210 | G211 | L216 | M218 | H219 |
| 2 | R128 | Y129 | A131 | S149 | I151 | A154 | P164 | K169 | E182 | S183 | E189 | F196 | D202 | C209 | G210 | G211 | L216 | M218 | H219 |
| 3 | R128 | Y129 | A131 | S149 | I151 | A154 | P164 | K169 | E182 | S183 | E189 | F196 | D202 | C209 | G210 | — | L215 | M217 | H218 |
| 4 | R128 | Y129 | A131 | S149 | I151 | A154 | P164 | K169 | E182 | S183 | E189 | F196 | D202 | C209 | G210 | — | L215 | M217 | Y218 |
| 5 | R128 | Y129 | A131 | S149 | I151 | A154 | P164 | K169 | E182 | S183 | E189 | F196 | D202 | C209 | G210 | G211 | L216 | V218 | H219 |
| 6 | R98 | Y99 | A101 | S119 | I121 | A124 | P134 | K139 | E152 | S153 | E159 | F166 | D172 | C179 | G180 | G181 | L186 | M188 | H189 |
| 7 | R127 | Y128 | A130 | S148 | I150 | A153 | P163 | K168 | E181 | S182 | E188 | F195 | D201 | S208 | G209 | G210 | L215 | M217 | R218 |
| 8 | R100 | Y101 | V103 | S121 | I123 | A126 | P136 | K141 | E154 | S155 | Q161 | V168 | D174 | S181 | G182 | G183 | L188 | M190 | H191 |
| 9 | R99 | Y100 | V102 | S120 | I122 | A125 | P135 | K140 | E153 | S154 | Q160 | V167 | D173 | S180 | A181 | G182 | L187 | V189 | C190 |
| 10 | R98 | Y99 | V101 | S119 | I121 | A124 | P134 | K139 | E152 | S153 | Q159 | V166 | D172 | S179 | A180 | G181 | L186 | M188 | R189 |
| 11 | R98 | Y99 | V101 | S119 | L121 | A124 | P134 | R139 | E152 | S153 | E159 | V166 | D172 | S179 | A180 | A181 | L186 | M188 | R189 |
| 12 | R96 | Y97 | V99 | S117 | F119 | A122 | P132 | D137 | E147 | S148 | Q154 | V161 | D167 | S174 | A175 | G176 | L181 | M183 | R184 |
| 13 | R98 | Y99 | V101 | S119 | L121 | A124 | P134 | R139 | E152 | S153 | E159 | V166 | D172 | S179 | A180 | A181 | L186 | I188 | R189 |
| 14 | R98 | Y99 | A101 | S119 | F121 | T124 | P134 | K139 | E149 | S150 | Q156 | V163 | D169 | S176 | A177 | G178 | L183 | M185 | P186 |
| 15 | R98 | Y99 | V101 | S119 | F121 | A124 | P134 | K139 | E152 | S153 | Q159 | V166 | D172 | S179 | A180 | A181 | L186 | M188 | R189 |
| 16 | R98 | Y99 | V101 | S119 | F121 | A124 | P134 | K139 | E152 | S153 | Q159 | V166 | D172 | S179 | A180 | A181 | L186 | M188 | R189 |
| 17 | R98 | Y99 | V101 | S119 | L121 | A124 | P134 | R139 | E152 | S153 | E159 | V166 | D172 | S179 | A180 | A181 | L186 | M188 | R189 |
| 18 | R98 | Y99 | V101 | S119 | F121 | A124 | P134 | K139 | E152 | S153 | Q159 | V166 | D172 | S179 | A180 | G181 | L186 | M188 | S189 |
| 19 | R93 | Y94 | V96 | S114 | F116 | A119 | P129 | K134 | E147 | S148 | Q154 | V161 | D167 | S174 | A175 | G176 | L181 | M183 | S184 |
| 20 | R98 | Y99 | A101 | S119 | F121 | T124 | P134 | N139 | E150 | S151 | Q157 | V164 | D170 | C177 | G178 | G179 | L184 | M186 | H187 |
| 21 | R95 | Y96 | A98 | S116 | F118 | T121 | P131 | N136 | E147 | S148 | Q154 | V161 | D167 | C174 | G175 | G176 | L181 | M183 | H184 |
| 22 | R101 | Y102 | V104 | S122 | V124 | T127 | P137 | K142 | E154 | S155 | Q161 | V168 | D174 | S181 | A182 | A183 | L188 | M190 | K191 |
| 23 | R103 | Y104 | V106 | S124 | V126 | T129 | P139 | K144 | E158 | S159 | Q165 | V172 | D178 | S185 | A186 | A187 | L192 | M194 | K195 |
| 24 | R101 | Y102 | V104 | S122 | V124 | T127 | P137 | K142 | E154 | S155 | Q161 | V168 | D174 | S181 | A182 | A183 | L188 | M190 | K191 |
| 25 | R147 | Y148 | V150 | S168 | V170 | T173 | P183 | K188 | E200 | S201 | Q207 | V214 | D220 | S227 | A228 | A229 | L234 | M236 | K237 |
| 26 | R74 | Y75 | V77 | S95 | F97 | T100 | P110 | K115 | E123 | S124 | Q130 | V137 | D143 | S150 | G151 | G152 | L157 | M159 | R160 |
| 27 | R128 | Y129 | V131 | S149 | V151 | T154 | P164 | K169 | E185 | S186 | E192 | V199 | D205 | S212 | A213 | G214 | L219 | I221 | R222 |
| 28 | R130 | Y131 | V133 | S151 | V153 | T156 | P166 | K171 | E187 | S188 | E194 | V201 | D207 | S214 | A215 | G216 | L221 | I223 | C224 |
| 29 | R101 | Y102 | V104 | — | — | — | — | — | E124 | S125 | Q131 | V138 | D144 | S151 | A152 | A153 | L158 | M160 | K161 |
| 30 | R130 | Y131 | V133 | S151 | V153 | T156 | P166 | K171 | E187 | S188 | E194 | V201 | D207 | S214 | A215 | G216 | L221 | I223 | R224 |
| 31 | R130 | Y131 | V133 | S151 | V153 | T156 | P166 | K171 | E187 | S188 | E194 | V201 | D207 | S214 | A215 | G216 | L221 | I223 | R224 |
| 32 | R105 | Y106 | V108 | S126 | L128 | T131 | P141 | R146 | E160 | S161 | Q167 | V174 | D180 | S187 | G188 | G189 | L194 | M196 | P197 |
| 33 | R150 | F151 | L153 | F171 | L173 | I176 | A186 | P191 | E201 | E202 | — | V212 | E218 | Y225 | A226 | G227 | L232 | M234 | K235 |
| 34 | R100 | Y101 | V103 | S121 | F123 | A126 | P136 | K141 | E154 | S155 | Q161 | V168 | D174 | S181 | A182 | G183 | L188 | A190 | R191 |
| 35 | R165 | Y166 | V168 | S186 | V188 | T191 | P201 | K206 | E220 | S221 | R227 | V234 | D240 | S247 | A248 | A249 | L254 | M277 | K278 |
| 36 | R134 | Y135 | V137 | S155 | V157 | T160 | P170 | K175 | E191 | S192 | E198 | V205 | D211 | S218 | A219 | G220 | L225 | I227 | R228 |
| 37 | R95 | Y96 | V98 | S116 | V118 | T121 | P131 | K136 | E152 | S153 | C158 | V165 | D171 | S178 | G179 | G180 | L185 | I187 | R188 |
| 38 | R100 | Y101 | V103 | S121 | T123 | A126 | P136 | H141 | E158 | S159 | R165 | V172 | D178 | A185 | G186 | A187 | L192 | I194 | R195 |
| 39 | R98 | Y99 | A101 | S119 | F121 | T124 | P134 | N139 | E150 | S151 | Q157 | V164 | D170 | C177 | G178 | G179 | L184 | M186 | H187 |
| 40 | R95 | Y96 | V98 | S116 | V118 | T121 | P131 | K136 | E152 | S153 | C169 | V176 | D182 | S189 | G190 | G191 | L196 | I198 | R199 |
| 41 | R95 | Y96 | V98 | S116 | V118 | T121 | P131 | K136 | E152 | S153 | C169 | V176 | D182 | S189 | G190 | G191 | L196 | I198 | R199 |
| 42 | R96 | Y97 | V99 | S117 | V119 | T122 | P132 | K137 | E151 | S152 | Q158 | V165 | D171 | S178 | A179 | A180 | L185 | M187 | K188 |
| 43 | R97 | Y98 | V100 | T118 | L120 | A123 | P133 | R138 | E147 | S148 | E154 | I161 | D167 | S174 | G175 | S176 | I181 | I183 | R184 |
| 44 | R97 | Y98 | V100 | T118 | L120 | A123 | P133 | R138 | E147 | S148 | E154 | I161 | D167 | S174 | G175 | S176 | I181 | I183 | R184 |
| 45 | R128 | Y129 | A131 | S149 | I151 | A154 | P164 | K169 | E182 | S183 | E189 | F196 | D202 | C209 | G210 | G211 | L216 | M218 | H219 |
| 46 | R128 | Y129 | A131 | S149 | I151 | A154 | P164 | K169 | E182 | S183 | E189 | F196 | D202 | C209 | G210 | — | L215 | M217 | H218 |
| 47 | — | — | — | S3 | V5 | T8 | P18 | K23 | E39 | S40 | E46 | V53 | D59 | S66 | A67 | G68 | L73 | I75 | R76 |

TABLE 2B-continued

| | | | | | | | | | | | | | | | | | | | |
|---|---|---|---|---|---|---|---|---|---|---|---|---|---|---|---|---|---|---|---|
| 48 | R30 | Y31 | V33 | — | — | — | P47 | K52 | E68 | S69 | E75 | V82 | D88 | S95 | A96 | G97 | L102 | I104 | R105 |
| 49 | R89 | Y90 | V92 | S110 | I112 | S115 | P125 | Q130 | E140 | S141 | Q147 | V154 | D160 | S167 | G168 | G169 | L174 | M176 | R177 |
| 50 | — | — | — | — | — | — | — | — | — | — | — | — | — | — | — | — | — | — | — |
| 51 | R87 | F88 | V90 | T108 | L110 | P113 | P123 | H126 | A137 | K138 | — | V148 | E154 | F161 | A162 | G163 | L168 | V170 | R171 |
| 52 | R87 | Y88 | V90 | T108 | L110 | T113 | P123 | G126 | A136 | R137 | — | V147 | A153 | F160 | A161 | G162 | L167 | V169 | Q170 |
| 53 | R87 | Y88 | V90 | T108 | L110 | T113 | P123 | G126 | A136 | R137 | — | V147 | A153 | F160 | A161 | G162 | L167 | V169 | Q170 |
| 54 | — | — | — | — | — | — | — | — | — | — | — | — | — | — | — | — | — | — | — |
| 55 | R87 | F88 | V90 | T108 | L110 | P113 | P123 | H126 | A137 | K138 | — | V148 | E154 | F161 | A162 | G163 | L168 | V170 | R171 |
| 56 | R86 | Y87 | V89 | T107 | L109 | W112 | P122 | P125 | A135 | D136 | — | F146 | N152 | Y159 | A160 | G161 | L166 | A168 | P169 |
| 57 | R103 | Y104 | V106 | S124 | L126 | P129 | L139 | R142 | A153 | E154 | — | F164 | N170 | Y177 | A178 | G179 | L184 | A186 | R187 |
| 58 | R91 | Y92 | I94 | T112 | L114 | L117 | P127 | A130 | A141 | A142 | — | F152 | N158 | Y165 | A166 | G167 | L172 | V174 | Q175 |
| 59 | R88 | Y89 | L91 | T109 | L111 | A114 | P124 | G127 | A138 | E139 | — | F149 | N155 | Y162 | A163 | G164 | L169 | V171 | K172 |
| 60 | R88 | F89 | A91 | T109 | L111 | F114 | P124 | K127 | A138 | D139 | — | V149 | N155 | Y162 | G163 | A164 | L169 | I171 | K172 |
| 61 | R88 | F89 | V91 | T109 | L111 | T114 | P124 | A127 | A138 | S139 | — | V149 | D155 | F162 | A163 | G164 | L169 | L171 | K172 |
| 62 | R98 | Y99 | V101 | S119 | F121 | T124 | P134 | K139 | E147 | S148 | Q154 | V161 | D167 | S174 | G175 | G176 | — | — | — |
| 63 | R88 | Y89 | L91 | T109 | L111 | S114 | P124 | S127 | A138 | E139 | — | F149 | D155 | F162 | A163 | G164 | L169 | V171 | K172 |
| 64 | R97 | F98 | A100 | S118 | L120 | M123 | A133 | K136 | A145 | E146 | — | F156 | D162 | Y169 | A170 | G171 | L176 | V178 | Q179 |
| 65 | Y98 | Y99 | M101 | T119 | L121 | W124 | P134 | L139 | S149 | V150 | Q155 | V162 | D168 | Y175 | S176 | G177 | L182 | M184 | K185 |
| 66 | R88 | F89 | I91 | S109 | I111 | L114 | P124 | K127 | A138 | D139 | — | P149 | N155 | Y162 | A163 | G164 | L169 | V171 | E172 |
| 67 | R88 | Y89 | V91 | S109 | L111 | W114 | P124 | G127 | A136 | D137 | — | F147 | N153 | Y160 | A161 | G162 | L167 | V169 | R170 |
| 68 | R88 | Y89 | V91 | T109 | L111 | I114 | P124 | K127 | A138 | D139 | — | L149 | N155 | Y162 | A163 | G164 | L169 | L171 | R172 |
| 69 | R90 | Y91 | L93 | M111 | H113 | M116 | P126 | P129 | A139 | S140 | — | V150 | D156 | Y163 | S164 | G165 | M170 | I172 | K173 |
| 70 | R86 | F87 | V89 | T107 | L109 | L112 | L122 | R125 | G136 | E137 | — | L147 | D153 | Y160 | A161 | G162 | L167 | A169 | R170 |
| 71 | R87 | F88 | A90 | S108 | L110 | P113 | P123 | S128 | E145 | S146 | Q152 | V159 | D165 | S172 | A173 | A174 | L179 | — | — |
| 72 | R105 | F106 | V108 | T126 | L128 | L131 | L141 | R144 | G155 | E156 | — | L166 | D172 | Y179 | A180 | G181 | L186 | A188 | R189 |
| 73 | R91 | F92 | L94 | T112 | L114 | W117 | P127 | N130 | A141 | A142 | — | A152 | D158 | Y165 | A166 | G167 | L172 | T174 | A175 |
| 74 | R92 | Y93 | V95 | T113 | L115 | W118 | W128 | P131 | S142 | H143 | — | A153 | D159 | Y166 | A167 | S168 | L173 | V175 | E176 |
| 75 | R92 | Y93 | V95 | T113 | L115 | W118 | W128 | P131 | S142 | H143 | — | A153 | D159 | Y166 | A167 | S168 | L173 | V175 | E176 |
| 76 | R89 | F90 | I92 | S110 | F112 | P115 | P125 | G128 | A140 | E141 | — | V151 | N157 | Y164 | A165 | A166 | L171 | L173 | K174 |
| 77 | R92 | Y93 | L95 | T113 | L115 | W118 | P128 | N131 | A142 | A143 | — | A153 | D159 | Y166 | A167 | G168 | L173 | A175 | A176 |
| 78 | R86 | F87 | Y89 | S107 | L109 | W112 | F122 | P125 | S136 | E137 | — | A147 | D153 | F160 | A161 | G162 | L167 | L169 | K170 |
| 79 | R90 | F91 | F93 | S111 | V113 | F116 | Y126 | P129 | S140 | S141 | — | A151 | D157 | F164 | A165 | G166 | L171 | V173 | K174 |
| 80 | R93 | Y94 | Y96 | S114 | L116 | A119 | A129 | P134 | T151 | Q152 | — | V162 | Q168 | Y175 | A176 | G177 | L182 | V184 | R185 |
| 81 | R92 | Y93 | V95 | T113 | L115 | W118 | W128 | P131 | S142 | H143 | — | A153 | D159 | Y166 | A167 | S168 | L173 | V175 | E176 |
| 82 | R87 | Y88 | V90 | T108 | L110 | L113 | P123 | K126 | A139 | S140 | — | F150 | D156 | Y163 | A164 | G165 | L170 | L172 | E173 |
| 83 | R89 | F90 | I92 | S110 | F112 | P115 | P125 | G128 | A140 | E141 | — | V151 | N157 | Y164 | A165 | A166 | L171 | L173 | K174 |
| 84 | R101 | Y102 | Y104 | S122 | L124 | V127 | L137 | P142 | R152 | Q153 | — | V163 | E169 | Y176 | A177 | G178 | L183 | A185 | V186 |
| 85 | R86 | Y87 | L89 | N107 | F109 | W112 | L122 | A126 | D136 | A137 | — | I147 | N153 | Y160 | A161 | G162 | L167 | I169 | H170 |
| 86 | R85 | Y86 | L88 | N106 | L108 | N111 | R121 | A126 | S134 | D135 | — | Q145 | A151 | Y158 | G159 | G160 | L165 | V167 | N168 |
| 87 | R92 | F93 | L95 | T113 | I115 | L118 | P128 | P131 | A147 | D148 | — | F158 | D164 | Y171 | A172 | S173 | L178 | M180 | A181 |
| 88 | C89 | R90 | I92 | T111 | L113 | L116 | P126 | R129 | G139 | A140 | — | F150 | D156 | Y163 | A164 | G165 | L170 | T172 | R173 |
| 89 | R84 | Y85 | F87 | N105 | F107 | W110 | L120 | T125 | A133 | D134 | — | I144 | N150 | Y157 | A158 | G159 | L164 | M166 | E167 |
| 90 | R93 | F94 | Y96 | S114 | L116 | W119 | P129 | S132 | A143 | S144 | — | A154 | S160 | F167 | A168 | G169 | M174 | L176 | R177 |
| 91 | R93 | Y94 | Y96 | S114 | L116 | V119 | L129 | A134 | R144 | Q145 | — | V155 | E161 | Y168 | A169 | G170 | L175 | A177 | L178 |
| 92 | R85 | F86 | Y88 | S106 | L108 | L111 | A121 | P126 | A143 | Q144 | — | V154 | A160 | Y167 | A168 | G169 | L174 | A176 | R177 |
| 93 | A99 | L100 | L102 | T128 | L130 | P133 | Y143 | P146 | A162 | Q163 | — | A173 | Q179 | Y186 | T187 | S188 | L193 | L195 | R196 |
| 94 | R93 | F94 | Y96 | S114 | L116 | W119 | P129 | A134 | A145 | A146 | — | A156 | A162 | F169 | A170 | G171 | M176 | L178 | V179 |
| 95 | R87 | Y88 | L90 | G107 | L109 | W112 | P122 | S125 | A137 | D138 | — | A148 | D154 | F161 | A162 | G163 | L168 | V170 | Q171 |
| 96 | C88 | R89 | I91 | T110 | L112 | L115 | P125 | K128 | G138 | S139 | — | F149 | D155 | Y162 | A163 | G164 | L169 | T171 | R172 |
| 97 | R86 | F87 | Y89 | S107 | L109 | W112 | L122 | P125 | A135 | E136 | — | A146 | D152 | F159 | A160 | G161 | M166 | L168 | K169 |
| 98 | R143 | F144 | L146 | F164 | L166 | I169 | A179 | P184 | E191 | S192 | R198 | V205 | E211 | Y218 | A219 | G220 | L225 | M227 | K228 |
| 99 | R112 | Y113 | V115 | S133 | V135 | T138 | P148 | K153 | E167 | S168 | Q174 | V181 | D187 | S194 | A195 | A196 | L201 | M203 | K204 |
| 100 | R146 | F147 | L149 | F167 | L169 | I172 | A182 | P187 | E194 | S195 | R201 | V208 | E214 | Y221 | A222 | G223 | L228 | M230 | K231 |
| 101 | R98 | Y99 | V101 | S119 | I121 | A124 | P134 | K139 | E152 | S153 | Q159 | V166 | D172 | S179 | A180 | G181 | L186 | M188 | C189 |
| 102 | R142 | F143 | L145 | F163 | L165 | L168 | A178 | P183 | E190 | S191 | R197 | V204 | E210 | Y217 | A218 | G219 | L224 | M226 | K227 |
| 103 | R102 | Y103 | V105 | S123 | L125 | T128 | P138 | K143 | E151 | S152 | Q158 | V165 | N171 | S178 | G179 | G180 | L185 | M187 | R188 |
| 104 | R172 | F173 | L175 | F193 | L195 | F198 | A208 | P213 | E220 | S221 | R227 | V234 | E240 | Y247 | A248 | G249 | L254 | M256 | K257 |
| 105 | R138 | F139 | L141 | F159 | L161 | I164 | A174 | P179 | E186 | S187 | R193 | V200 | E206 | Y213 | A214 | G215 | L220 | M222 | R223 |
| 106 | R97 | Y98 | V100 | S118 | L120 | T123 | P133 | K138 | E154 | S155 | E161 | V168 | D174 | S181 | A182 | G183 | L188 | I190 | R191 |
| 107 | R146 | F147 | L149 | F167 | L169 | I172 | A182 | P187 | E194 | S195 | R201 | V208 | E214 | Y221 | A222 | G223 | L228 | M230 | K231 |
| 108 | R167 | F168 | L170 | F188 | L190 | I193 | A203 | P208 | E215 | S216 | R222 | V229 | E235 | Y242 | A243 | G244 | L249 | M251 | K252 |
| 109 | R137 | F138 | L140 | F158 | L160 | V163 | A173 | P178 | E185 | S186 | R192 | V199 | E205 | Y212 | A213 | G214 | L219 | M221 | K222 |
| 110 | R142 | Y143 | V145 | S163 | V165 | T168 | P178 | K183 | E199 | S200 | E206 | V213 | D219 | S226 | A227 | G228 | L233 | I235 | R236 |
| 111 | R138 | F139 | L141 | F159 | L161 | I164 | A174 | P179 | E186 | S187 | R193 | V200 | E206 | Y213 | A214 | G215 | L220 | M222 | K223 |
| 112 | R95 | Y96 | A98 | S116 | F118 | T121 | P131 | N136 | E147 | S148 | Q154 | V161 | D167 | C174 | G175 | G176 | L181 | M183 | H184 |
| 113 | R153 | F154 | L156 | F174 | L176 | I179 | A189 | P194 | E201 | S202 | R208 | V215 | E221 | Y228 | A229 | G230 | L235 | M237 | K238 |
| 114 | R146 | F147 | L149 | F167 | L169 | I172 | A182 | P187 | E194 | S195 | R201 | V208 | E214 | Y221 | A222 | G223 | L228 | M230 | K231 |
| 115 | R98 | Y99 | M101 | S119 | I121 | A124 | P134 | N139 | E152 | S153 | Q159 | V166 | D172 | S179 | A180 | G181 | L186 | M188 | C189 |
| 116 | R167 | F168 | L170 | F188 | L190 | I193 | A203 | P208 | E215 | S216 | R222 | V229 | E235 | Y242 | A243 | G244 | L249 | M251 | K252 |
| 117 | R99 | Y100 | V102 | S120 | V122 | T125 | P135 | N141 | E154 | S155 | Q161 | V168 | D174 | S181 | A182 | A183 | L188 | M190 | K191 |

| ID | Pos 20 | Pos 21 | Pos 22 | Pos 23 | Pos 24 | Pos 25 | Pos 26 | Pos 27 | Pos 28 | Pos 29 | Pos 30 | Pos 31 | Pos 32 | Pos 33 | Pos 34 | Pos 35 | Pos 36 | Pos 37 | Pos 38 |
|---|---|---|---|---|---|---|---|---|---|---|---|---|---|---|---|---|---|---|---|
| 1 | H220 | N227 | S234 | S246 | K259 | P260 | R261 | L295 | Q301 | G308 | S324 | R335 | G346 | F349 | L351 | D352 | T358 | L384 | L397 |
| 2 | H220 | N227 | S234 | S246 | K259 | P260 | R261 | L295 | Q301 | G308 | S324 | R335 | G346 | F349 | L351 | D352 | T358 | L384 | L397 |
| 3 | H219 | N226 | S233 | S245 | K258 | P259 | R260 | L294 | Q300 | G307 | S323 | R334 | G345 | F348 | L350 | D351 | T357 | L383 | L396 |
| 4 | H219 | N226 | S233 | S245 | K258 | P259 | R260 | L294 | Q300 | G307 | S323 | R334 | G345 | F348 | L350 | D351 | T357 | L383 | L396 |
| 5 | H220 | N227 | S234 | S246 | K260 | P261 | R262 | L296 | Q302 | G309 | S325 | R336 | G347 | F350 | L352 | D353 | T359 | L385 | L398 |
| 6 | H190 | N197 | S204 | S216 | K230 | P231 | R232 | L266 | Q272 | G279 | S295 | R306 | G317 | F320 | L322 | D323 | S329 | L355 | L368 |

TABLE 2B-continued

| | | | | | | | | | | | | | | | | | | | |
|---|---|---|---|---|---|---|---|---|---|---|---|---|---|---|---|---|---|---|---|
| 7 | H219 | N226 | S233 | S245 | K259 | P260 | R261 | L295 | H301 | E308 | P324 | N335 | E346 | F349 | L351 | D352 | S358 | L384 | L397 |
| 8 | H192 | N199 | S206 | A218 | K232 | K234 | R235 | L269 | H275 | E282 | S300 | C311 | G322 | F325 | L327 | D328 | S334 | L360 | L373 |
| 9 | H191 | N198 | S205 | T217 | K231 | K233 | Q234 | F268 | P274 | E281 | S299 | C310 | R321 | F324 | L326 | N327 | S333 | L359 | L372 |
| 10 | H190 | D197 | S204 | A216 | K229 | K231 | P232 | L266 | H272 | E279 | S297 | C308 | G319 | F322 | L324 | N325 | S331 | L357 | L370 |
| 11 | H190 | N197 | S204 | A216 | K230 | K232 | H233 | L267 | H273 | Q280 | D294 | Y305 | G316 | F319 | L321 | N322 | S328 | L354 | L367 |
| 12 | H185 | N192 | S199 | A211 | K225 | K227 | R228 | L262 | Q268 | E275 | S293 | C304 | G315 | F318 | L320 | D321 | V327 | L353 | L366 |
| 13 | H190 | N197 | S204 | G216 | K230 | K232 | H233 | L267 | H273 | Q280 | D294 | G305 | G316 | F319 | L321 | N322 | T328 | L354 | L367 |
| 14 | H187 | N194 | S201 | S213 | K227 | K229 | R230 | L264 | H270 | E277 | S295 | C306 | G317 | F320 | L322 | D323 | N329 | L355 | L368 |
| 15 | H190 | N197 | S204 | A216 | K230 | H232 | R233 | L267 | H273 | E280 | S297 | C308 | G319 | F322 | L324 | D325 | I331 | L357 | L370 |
| 16 | H190 | N197 | S204 | A216 | K230 | H232 | R233 | L267 | H273 | E280 | S297 | C308 | G319 | F322 | L324 | D325 | I331 | L357 | L370 |
| 17 | H190 | N197 | S204 | G216 | K230 | K232 | H233 | L267 | H273 | E280 | D294 | G305 | G316 | F319 | L321 | N322 | T328 | L354 | L367 |
| 18 | H190 | N197 | S204 | T216 | K230 | K232 | P233 | L267 | — | Q279 | I295 | C306 | G317 | F320 | L322 | N323 | A329 | L355 | L368 |
| 19 | H185 | N192 | S199 | T211 | K225 | K227 | P228 | L262 | — | Q274 | I290 | C301 | G312 | F315 | L317 | N318 | A324 | L350 | L363 |
| 20 | H188 | N195 | S202 | P214 | N228 | K230 | R231 | L265 | C271 | D278 | S296 | C307 | G318 | F321 | L323 | N324 | D330 | L356 | L369 |
| 21 | L185 | N192 | S199 | P211 | N225 | K227 | R228 | L262 | C268 | D275 | S293 | C304 | G315 | F318 | L320 | N321 | D327 | L353 | L366 |
| 22 | H192 | N199 | S206 | A218 | T232 | K234 | G235 | L269 | — | E280 | H298 | C309 | G320 | F323 | L325 | N326 | N332 | L358 | L371 |
| 23 | H196 | N203 | S210 | A222 | T236 | R238 | G239 | L273 | — | E284 | H302 | C313 | G324 | F327 | L329 | N330 | N336 | L362 | L375 |
| 24 | H192 | N199 | S203 | A215 | T229 | K231 | G232 | L266 | — | E277 | H295 | C302 | G313 | F316 | L318 | N319 | N325 | L351 | L364 |
| 25 | H238 | N245 | S249 | A261 | T275 | K277 | G278 | L312 | — | E323 | H341 | C348 | G359 | F362 | L364 | N365 | N371 | L397 | L410 |
| 26 | H161 | D168 | S175 | S187 | N197 | K199 | R200 | L234 | C240 | G246 | S263 | N274 | G285 | F288 | L290 | N291 | S297 | L323 | L336 |
| 27 | H223 | N230 | S237 | A249 | K263 | R265 | N266 | L300 | F306 | G313 | T334 | S345 | G356 | F359 | L361 | D362 | N368 | L394 | L408 |
| 28 | H225 | N232 | S239 | A251 | K265 | R267 | N268 | L302 | L308 | G315 | T336 | S347 | G358 | F361 | L363 | D364 | D370 | L396 | L410 |
| 29 | H162 | N169 | S176 | A188 | T202 | K204 | G205 | L239 | — | E250 | H268 | C279 | G290 | F293 | L295 | N296 | N302 | L328 | L341 |
| 30 | H225 | N232 | S239 | A251 | K265 | R267 | N268 | L302 | F308 | G315 | T336 | S347 | G358 | V361 | L363 | D364 | D370 | L396 | L410 |
| 31 | H225 | N232 | S239 | A251 | K265 | R267 | N268 | L302 | F308 | G315 | T336 | S347 | G358 | V361 | L363 | D364 | D370 | L396 | L410 |
| 32 | H198 | N205 | S212 | D224 | K238 | R240 | — | L274 | H280 | D287 | F308 | G319 | G330 | F333 | L335 | D336 | T342 | L368 | L381 |
| 33 | A236 | K243 | S250 | R262 | P275 | P277 | K278 | G312 | N318 | Y325 | N335 | Y346 | — | N357 | A359 | A360 | Y367 | L399 | L409 |
| 34 | H192 | N199 | S206 | A218 | K232 | K234 | R235 | L269 | Y275 | E282 | S300 | C311 | R322 | F325 | L327 | D328 | S334 | L360 | L373 |
| 35 | H279 | N286 | S293 | A305 | — | — | — | L331 | — | E342 | H360 | C371 | G382 | F385 | L387 | N388 | K394 | L420 | L433 |
| 36 | H229 | D236 | S243 | A255 | K269 | R271 | N272 | L306 | C312 | D319 | L340 | S351 | G362 | F365 | L367 | D368 | D374 | L400 | L414 |
| 37 | H189 | N196 | S203 | T215 | K229 | R231 | N232 | L266 | C272 | G279 | S300 | S311 | G322 | F325 | L327 | D328 | D334 | L360 | L374 |
| 38 | H196 | D203 | S210 | R222 | Q236 | K237 | R238 | L272 | L278 | N285 | S306 | — | — | — | — | — | T315 | L341 | L354 |
| 39 | L188 | N195 | S202 | P214 | N228 | K230 | R231 | L265 | C271 | D278 | S296 | C307 | G318 | F321 | L323 | N324 | D330 | L356 | L369 |
| 40 | H200 | N207 | S214 | T226 | K240 | R242 | N243 | L277 | C283 | G290 | S311 | S322 | G333 | F336 | L338 | D339 | D345 | L371 | L385 |
| 41 | H200 | N207 | S214 | T226 | K240 | R242 | D243 | L277 | C283 | G290 | S311 | S322 | G333 | F336 | L338 | D339 | D345 | L371 | L385 |
| 42 | H189 | N196 | S203 | A215 | T229 | K231 | G232 | L266 | — | E277 | H295 | C306 | G317 | F320 | L322 | N323 | K329 | L355 | L368 |
| 43 | H185 | S192 | S199 | K211 | T233 | P235 | R236 | T270 | Q276 | Q283 | T303 | D314 | G325 | Y328 | L330 | D331 | I337 | L363 | L377 |
| 44 | H185 | S192 | S199 | K211 | T233 | P235 | R236 | T270 | Q276 | Q283 | T303 | D314 | G325 | Y328 | L330 | D331 | I337 | L363 | L377 |
| 45 | H220 | N227 | — | — | — | — | — | — | — | — | — | — | — | — | — | — | — | — | — |
| 46 | H219 | N226 | — | — | — | — | — | — | — | — | — | — | — | — | — | — | — | — | — |
| 47 | H77 | N84 | S91 | A103 | K117 | R119 | N120 | L154 | F160 | G167 | T188 | S199 | G210 | V213 | L215 | D216 | D222 | L248 | L262 |
| 48 | H106 | N113 | S120 | A132 | K146 | R148 | S149 | L183 | C189 | D196 | S217 | S228 | G239 | F242 | L244 | D245 | D251 | L277 | L291 |
| 49 | H178 | N185 | S192 | A204 | N218 | R220 | R221 | L255 | N261 | D268 | G287 | S298 | — | — | — | — | — | — | — |
| 50 | — | — | — | S3 | K17 | K19 | H20 | L54 | D60 | S67 | S88 | R99 | G110 | Y113 | L115 | D116 | M122 | L148 | L161 |
| 51 | Y172 | E179 | S186 | — | — | A203 | P204 | L238 | — | P247 | F262 | H273 | P282 | D285 | — | R286 | E293 | L319 | L330 |
| 52 | H171 | A178 | S185 | — | — | D204 | T205 | H238 | — | W247 | S262 | H273 | T282 | D285 | — | L286 | T293 | L319 | L330 |
| 53 | H171 | A178 | S185 | — | — | D204 | T205 | H238 | — | W247 | S262 | H273 | T282 | D285 | — | L286 | T293 | L319 | L330 |
| 54 | — | — | — | — | — | — | — | — | — | — | — | S6 | G17 | V20 | L22 | D23 | D29 | L55 | L69 |
| 55 | Y172 | E179 | S186 | — | — | A203 | P204 | L238 | — | P247 | F262 | H273 | P282 | D285 | — | R286 | E293 | L319 | L330 |
| 56 | A170 | N177 | S184 | R196 | — | K204 | D205 | R238 | — | — | F261 | Y272 | S280 | K283 | R285 | A286 | L293 | L319 | L329 |
| 57 | Q188 | E195 | S202 | R214 | — | E219 | P220 | D254 | — | K261 | S276 | P287 | T296 | E299 | P301 | L302 | E309 | L335 | L345 |
| 58 | H176 | A183 | S190 | R202 | — | K210 | D211 | E244 | — | — | S263 | H274 | D283 | D286 | D288 | M289 | I296 | L322 | L332 |
| 59 | S173 | A180 | G187 | R199 | — | K207 | Q208 | I241 | — | — | V264 | Y275 | K283 | K286 | F288 | K289 | Y296 | L322 | L332 |
| 60 | H173 | N180 | S187 | — | G203 | F205 | F206 | I239 | S243 | — | — | P273 | M283 | A286 | L288 | A289 | Q295 | L321 | L331 |
| 61 | H173 | E180 | S187 | G199 | — | A207 | T208 | T241 | — | T250 | — | H272 | P281 | D284 | — | T285 | P292 | L318 | L329 |
| 62 | — | — | — | — | — | — | — | — | — | — | — | — | — | — | — | — | — | — | — |
| 63 | S173 | R180 | G187 | R199 | — | K207 | Q208 | L241 | — | Q250 | T265 | Y276 | E284 | Q287 | L289 | A290 | Y297 | L323 | L333 |
| 64 | A180 | A187 | S194 | A206 | — | — | A217 | D250 | I256 | G263 | H275 | H286 | — | G297 | L299 | A300 | E307 | L333 | L343 |
| 65 | H186 | R193 | S200 | T212 | T222 | K224 | E225 | T259 | T265 | G272 | — | H292 | A303 | K306 | F308 | K309 | K316 | L342 | L352 |
| 66 | H173 | Q180 | S187 | Q199 | H207 | L209 | Q210 | G244 | R250 | — | S270 | H281 | E290 | L293 | S295 | L296 | D303 | L329 | L339 |
| 67 | F171 | A178 | G185 | R197 | — | K205 | I206 | L239 | — | — | R262 | Y273 | R281 | P284 | A286 | A287 | V294 | L320 | L330 |
| 68 | Y173 | A180 | G187 | — | G204 | K206 | A207 | E240 | Q244 | — | — | H270 | — | E278 | P280 | I281 | D287 | L313 | L323 |
| 69 | A174 | E181 | S188 | K200 | G212 | K214 | M215 | T249 | — | G257 | E272 | Y283 | — | P294 | A296 | A297 | R304 | L330 | L340 |
| 70 | Y171 | E178 | S185 | R197 | P209 | P211 | P212 | V246 | V252 | A257 | R283 | E294 | A303 | E306 | P308 | L309 | E316 | L342 | L352 |
| 71 | — | — | — | — | — | — | — | T184 | C190 | L197 | — | S213 | — | — | — | — | — | — | L230 |
| 72 | Y190 | E197 | S204 | R216 | P228 | P230 | P231 | V265 | V271 | A276 | R299 | E310 | A319 | E322 | P324 | L325 | E332 | L358 | L368 |
| 73 | A176 | E183 | S190 | K202 | — | K209 | M210 | V244 | — | W252 | I267 | F278 | — | Q289 | A291 | A292 | P299 | L325 | L335 |
| 74 | A177 | R184 | G191 | R203 | G209 | S211 | P212 | V243 | — | G252 | T267 | P278 | — | D289 | P291 | S292 | P299 | L325 | L335 |
| 75 | A177 | R184 | G191 | R203 | G209 | S211 | P212 | V243 | — | G252 | T267 | P278 | — | D289 | P291 | S292 | P299 | L325 | L335 |
| 76 | Y175 | D182 | S189 | — | E203 | I205 | S206 | K239 | K244 | — | V264 | H275 | I285 | S288 | L290 | L291 | Y298 | L324 | L334 |
| 77 | A177 | E184 | S191 | K203 | — | K210 | M211 | V245 | — | Y253 | T268 | Y279 | — | P290 | A292 | A293 | P300 | L326 | L336 |
| 78 | A171 | Y178 | G185 | A197 | P206 | G208 | P209 | I241 | — | G250 | T265 | Y276 | — | L287 | L289 | S290 | E297 | L323 | L333 |
| 79 | A175 | H182 | G189 | K201 | T205 | G207 | P208 | V240 | — | K249 | S264 | Y275 | — | E286 | L288 | A289 | E296 | L322 | L332 |
| 80 | S186 | A193 | G200 | K212 | P224 | T226 | R227 | R261 | H267 | F274 | E284 | H295 | — | S306 | I308 | A309 | P316 | L342 | L352 |
| 81 | A177 | R184 | G191 | R203 | G209 | A211 | P212 | V243 | — | G252 | T267 | P278 | — | E289 | P291 | S292 | P299 | L325 | L335 |
| 82 | H174 | G181 | S188 | — | G204 | A206 | Y207 | V240 | R244 | — | F263 | H274 | E283 | A286 | P288 | L289 | E296 | L322 | L332 |
| 83 | Y175 | D182 | S189 | — | E203 | I205 | S206 | K239 | K244 | — | V264 | H275 | I285 | S288 | L290 | L291 | Y298 | L324 | L334 |
| 84 | A187 | G194 | S201 | — | P223 | P225 | K226 | Q260 | G265 | F272 | A282 | Y293 | — | P304 | A306 | S307 | L314 | L340 | L350 |
| 85 | K171 | A178 | S185 | A197 | — | — | G198 | L232 | G238 | S245 | S253 | F264 | — | P275 | A277 | A278 | H285 | L311 | A321 |
| 86 | K169 | E176 | S183 | G195 | — | — | V196 | F229 | G235 | A242 | E251 | H262 | — | P273 | M275 | S276 | N283 | L309 | S319 |

TABLE 2B-continued

| | | | | | | | | | | | | | | | | | | | |
|---|---|---|---|---|---|---|---|---|---|---|---|---|---|---|---|---|---|---|---|
| 87 | D182 | Q189 | S196 | Q207 | P213 | F215 | A216 | V247 | — | G256 | R271 | A282 | — | P293 | I295 | P296 | P303 | L329 | L339 |
| 88 | L174 | N181 | S188 | P200 | — | R207 | A208 | L242 | G248 | K250 | I261 | Y272 | — | K283 | Q285 | L286 | Y293 | L318 | L328 |
| 89 | K168 | E175 | S182 | T194 | — | — | Q195 | E227 | G233 | — | K245 | Y256 | — | P267 | S269 | A270 | N277 | L303 | A313 |
| 90 | S178 | E185 | S192 | K204 | A217 | G219 | P220 | V253 | — | — | D274 | H285 | — | A296 | M298 | A299 | P306 | L332 | L342 |
| 91 | A179 | G186 | S193 | R205 | P226 | P228 | K229 | H263 | E268 | F275 | A294 | Y305 | — | P316 | A318 | S319 | P326 | L352 | L362 |
| 92 | S178 | Q185 | G192 | R204 | P216 | V218 | R219 | E253 | N259 | F266 | E276 | Y287 | — | P298 | A300 | S301 | P308 | L334 | L344 |
| 93 | A197 | D204 | S211 | T223 | T229 | A231 | R232 | V266 | — | G275 | H290 | P301 | — | P312 | L314 | S315 | E322 | V348 | F358 |
| 94 | S180 | E187 | G194 | K206 | A219 | G221 | P222 | V255 | — | — | D276 | Y287 | — | G298 | M300 | S301 | P308 | L334 | L344 |
| 95 | A172 | A179 | S186 | A194 | — | — | — | E236 | — | S244 | Q255 | G266 | — | A277 | L279 | A280 | P287 | L313 | L323 |
| 96 | L173 | D180 | S187 | P199 | — | R206 | A207 | L241 | G247 | K249 | I260 | Y271 | — | K282 | Q284 | L285 | Y292 | L317 | L327 |
| 97 | A170 | R177 | G184 | A196 | P206 | G208 | P209 | V241 | — | K250 | E265 | Y276 | — | R287 | L289 | S290 | E297 | L323 | L333 |
| 98 | A229 | K236 | S243 | A254 | K269 | P270 | K271 | S304 | — | G312 | — | — | L348 | S351 | A353 | E354 | Y360 | L386 | L402 |
| 99 | H205 | N212 | S219 | A231 | K246 | K247 | G248 | L282 | T288 | E293 | H311 | C322 | G333 | F336 | L338 | N339 | K345 | L371 | L384 |
| 100 | A232 | K239 | S246 | E257 | K272 | P273 | K274 | S307 | — | G315 | — | — | L351 | A354 | A356 | D357 | Y363 | L389 | L405 |
| 101 | H190 | D197 | S204 | A216 | R230 | K231 | A232 | L266 | H272 | E279 | S297 | C308 | G319 | F322 | L324 | N325 | S331 | L357 | L370 |
| 102 | A228 | K235 | S242 | A253 | T268 | P269 | K270 | V303 | — | R311 | — | — | L347 | E350 | A352 | D353 | Y359 | L385 | L401 |
| 103 | Y189 | D196 | S203 | S215 | S226 | K227 | R228 | L262 | C268 | G274 | P292 | G303 | G314 | F317 | L319 | N320 | S326 | L352 | L365 |
| 104 | A258 | V265 | N272 | E283 | K298 | P299 | K300 | A333 | — | G341 | — | — | F377 | A380 | A382 | D383 | H389 | L415 | L431 |
| 105 | A224 | R231 | S238 | D249 | T264 | P265 | K266 | T299 | — | Q307 | — | — | L343 | D346 | A348 | D349 | Y355 | L381 | L397 |
| 106 | H192 | N199 | S206 | A218 | G233 | R234 | N235 | L269 | C275 | N282 | P303 | S314 | G325 | F328 | L330 | D331 | D337 | L363 | L377 |
| 107 | A232 | K239 | S246 | R258 | K272 | P273 | K274 | S307 | G313 | T320 | S334 | S345 | A356 | L359 | Q361 | F362 | A368 | L395 | L405 |
| 108 | A253 | K260 | S267 | R279 | K293 | P294 | K295 | S328 | L334 | T341 | S355 | S366 | A377 | L380 | K382 | F383 | A389 | L416 | L426 |
| 109 | A223 | R230 | S237 | K249 | A263 | P264 | K265 | T298 | D304 | G311 | S325 | S336 | A347 | L350 | K352 | F353 | A359 | L386 | L396 |
| 110 | H237 | N244 | S251 | A263 | G278 | R279 | N280 | L314 | C320 | D327 | S348 | S359 | G370 | F373 | L375 | D376 | D382 | L408 | L422 |
| 111 | A224 | R231 | S238 | K250 | A264 | P265 | K266 | T299 | D305 | G312 | S326 | S337 | A348 | L351 | K353 | F354 | A360 | L387 | L397 |
| 112 | L185 | N192 | S199 | P211 | K226 | K227 | R228 | L262 | C268 | D275 | S293 | C304 | G315 | F318 | L320 | N321 | D327 | L353 | L366 |
| 113 | A239 | R246 | S253 | K265 | A279 | P280 | K281 | T314 | D320 | G327 | S341 | S352 | A363 | L366 | K368 | F369 | A375 | L402 | L412 |
| 114 | A232 | K239 | S246 | R258 | K272 | P273 | K274 | S307 | G313 | T320 | S334 | S345 | A356 | L359 | Q361 | F362 | A368 | L395 | L405 |
| 115 | H190 | D197 | S204 | A216 | R230 | K231 | A232 | L266 | H272 | E279 | S297 | C308 | G319 | F322 | L324 | N325 | S331 | L357 | L370 |
| 116 | A253 | K260 | S267 | R279 | K293 | P294 | K295 | S328 | L334 | T341 | S355 | S366 | A377 | L380 | K382 | F383 | A389 | L416 | L426 |
| 117 | H192 | N199 | S206 | A218 | K233 | K234 | G235 | L269 | A275 | E280 | H298 | C309 | G320 | F323 | L325 | N326 | K332 | L358 | L371 |

| ID | Pos 39 | Pos 40 | Pos 41 | Pos 42 | Pos 43 | Pos 44 | Pos 45 | Pos 46 | Pos 47 | Pos 48 | Pos 49 | Pos 50 | Pos 51 | Pos 52 | Pos 53 | Pos 54 | Pos 55 | Pos 56 |
|---|---|---|---|---|---|---|---|---|---|---|---|---|---|---|---|---|---|---|
| 1 | F417 | T418 | T419 | F420 | A432 | T434 | K438 | L449 | T451 | F462 | Y470 | S476 | V477 | D482 | Y493 | K498 | E515 | K528 |
| 2 | F417 | T418 | T419 | F420 | A432 | T434 | K438 | L449 | T451 | F462 | Y470 | S476 | V477 | D482 | Y493 | K498 | E515 | K528 |
| 3 | F416 | T417 | T418 | F419 | A431 | T433 | K437 | L448 | T450 | F461 | Y469 | C475 | V476 | D481 | Y492 | K497 | E514 | K527 |
| 4 | F416 | T417 | T418 | F419 | A431 | T433 | K437 | L448 | T450 | F461 | Y469 | S475 | V476 | D481 | Y492 | K497 | E514 | K527 |
| 5 | F418 | T419 | T420 | F421 | A433 | T435 | K439 | L450 | T452 | F463 | Y471 | S477 | V478 | D483 | Y494 | K499 | E516 | K529 |
| 6 | F388 | T389 | T390 | F391 | A403 | T405 | K409 | L420 | T422 | F433 | Y441 | S447 | V448 | D453 | Y464 | K469 | E486 | K499 |
| 7 | Y417 | T418 | T419 | F420 | A432 | T434 | K438 | L449 | T451 | Y462 | Y470 | S476 | V477 | E482 | Y493 | K498 | E515 | K525 |
| 8 | Y393 | T394 | T395 | F396 | A408 | T410 | K414 | L425 | A427 | Y438 | F446 | S452 | V453 | D458 | Y469 | K474 | D491 | K504 |
| 9 | Y392 | T393 | T394 | F395 | A407 | T409 | K413 | L424 | A426 | Y437 | Y445 | A451 | V452 | D457 | Y468 | K473 | D490 | K503 |
| 10 | Y390 | T391 | T392 | F393 | A405 | T407 | K411 | L422 | V424 | Y435 | Y443 | S449 | V450 | E455 | Y466 | K471 | D488 | K500 |
| 11 | Y387 | T388 | T389 | F390 | A402 | T404 | R408 | L419 | A421 | Y432 | Y440 | S446 | V447 | D452 | F463 | K468 | D485 | T498 |
| 12 | Y386 | T387 | T388 | F389 | A401 | T403 | K407 | L418 | A420 | Y431 | Y439 | S445 | V446 | E451 | Y462 | R467 | E484 | K497 |
| 13 | Y387 | T388 | T389 | F390 | A402 | T404 | T408 | L419 | A421 | F432 | Y440 | S446 | V447 | D452 | Y463 | R468 | D485 | S498 |
| 14 | Y388 | T389 | T390 | F391 | A403 | K405 | K409 | L420 | A422 | Y433 | Y441 | S447 | V448 | E453 | Y464 | R469 | D486 | K499 |
| 15 | Y390 | T391 | T392 | F393 | A405 | T407 | K411 | L422 | V424 | F435 | Y443 | S449 | V450 | E455 | Y466 | K471 | E488 | K501 |
| 16 | Y390 | T391 | T392 | F393 | A405 | T407 | K411 | L422 | V424 | F435 | Y443 | S449 | V450 | E455 | Y466 | K471 | E488 | K501 |
| 17 | Y387 | T388 | T389 | F390 | A402 | T404 | K408 | L419 | A421 | Y432 | Y440 | L446 | V447 | D452 | Y463 | R468 | D485 | T498 |
| 18 | Y388 | T389 | T390 | F391 | S403 | T405 | K409 | L420 | V422 | Y433 | Y441 | S447 | V448 | E453 | Y464 | R469 | D486 | S499 |
| 19 | Y383 | T384 | T385 | F386 | S398 | T400 | K404 | L415 | V417 | Y428 | Y436 | S442 | V443 | E448 | Y459 | R464 | D481 | S494 |
| 20 | Y389 | T390 | T391 | F392 | A404 | R406 | K410 | L421 | A423 | Y434 | Y442 | S448 | V449 | D454 | Y465 | R470 | D487 | S500 |
| 21 | Y386 | T387 | T388 | F389 | A401 | R403 | K407 | L418 | A420 | C431 | Y439 | S445 | V446 | D451 | Y462 | K467 | D484 | T497 |
| 22 | Y391 | T392 | T393 | F394 | A406 | T408 | K412 | L423 | V425 | Y436 | Y444 | S450 | V451 | D456 | Y467 | R472 | D489 | K502 |
| 23 | Y395 | T396 | T397 | F398 | A410 | T412 | K416 | L427 | V429 | Y440 | Y448 | S454 | V455 | D460 | Y471 | R476 | D493 | K506 |
| 24 | Y384 | T385 | T386 | F387 | A399 | T401 | K405 | L416 | V418 | Y429 | Y437 | S443 | V444 | D449 | Y460 | R465 | D482 | K495 |
| 25 | Y430 | T431 | T432 | F433 | A445 | T447 | K451 | L462 | V464 | Y475 | Y483 | S489 | V490 | D495 | Y506 | R511 | D528 | K541 |
| 26 | Y356 | T357 | T358 | F359 | A371 | R373 | K377 | L388 | T390 | Y401 | Y409 | S415 | V416 | E421 | Y432 | K437 | E454 | K467 |
| 27 | Y428 | T429 | T430 | F431 | A443 | T445 | K449 | L460 | V462 | Y473 | Y481 | S487 | V488 | E493 | Y504 | K509 | E526 | N539 |
| 28 | Y430 | T431 | T432 | F433 | A445 | T447 | K451 | L462 | V464 | Y475 | Y483 | S489 | V490 | E495 | Y506 | K511 | D528 | N541 |
| 29 | Y361 | T362 | T363 | F364 | A376 | T378 | K382 | L393 | V395 | Y406 | Y414 | S420 | V421 | D426 | Y437 | R442 | D459 | K472 |
| 30 | Y430 | T431 | T432 | F433 | A445 | T447 | K451 | L462 | V464 | Y475 | Y483 | S489 | V490 | E495 | Y506 | K511 | D528 | N541 |
| 31 | Y430 | T431 | T432 | F433 | A445 | T447 | K451 | L462 | V464 | Y475 | Y483 | S489 | V490 | E495 | Y506 | K511 | D528 | N541 |
| 32 | Y401 | T402 | T403 | F404 | A416 | L418 | K422 | L433 | V435 | Y446 | Y454 | L460 | V461 | D466 | Y477 | R482 | D499 | — |
| 33 | L429 | L430 | N431 | Y432 | K444 | E446 | V450 | L461 | K463 | V476 | F484 | D490 | L491 | T496 | L509 | V514 | A531 | F544 |
| 34 | Y393 | T394 | T395 | F396 | — | — | — | L402 | C404 | Y408 | Y416 | L422 | V423 | E428 | Y439 | R444 | D461 | K474 |
| 35 | Y453 | T454 | T455 | F456 | A468 | T470 | K474 | L485 | V487 | Y498 | Y506 | S512 | V513 | D518 | Y529 | R534 | D551 | K564 |
| 36 | F434 | T435 | T436 | F437 | A449 | T451 | K455 | L466 | V468 | H479 | Y487 | L493 | A494 | G499 | Y510 | K515 | D532 | A543 |
| 37 | Y394 | T395 | S396 | F397 | A409 | T411 | K415 | L426 | V428 | H439 | Y447 | L453 | V454 | A459 | Y470 | K475 | D492 | D505 |
| 38 | F374 | T375 | T376 | F377 | S389 | L391 | Q395 | L406 | V408 | Y419 | Y427 | S433 | V434 | D439 | F450 | R455 | D472 | T485 |
| 39 | Y389 | T390 | T391 | F392 | A404 | — | — | — | — | — | — | — | — | — | — | — | — | — |
| 40 | Y405 | T406 | S407 | F408 | A420 | T422 | K426 | L437 | V439 | H450 | Y458 | L464 | V465 | A470 | Y481 | — | K493 | — |
| 41 | Y405 | T406 | S407 | F408 | A420 | T422 | K426 | L437 | V439 | H450 | Y458 | L464 | V465 | A470 | Y481 | — | K493 | — |
| 42 | Y388 | T389 | T390 | F391 | A403 | T405 | — | — | — | — | — | — | — | — | — | — | — | — |
| 43 | F397 | T398 | T399 | F400 | R412 | K414 | L418 | I429 | V431 | Y442 | Y450 | N456 | V457 | Q462 | Y473 | R478 | E495 | K508 |
| 44 | F397 | T398 | T399 | F400 | R412 | K414 | L418 | I429 | V431 | Y442 | Y450 | N456 | V457 | Q462 | Y473 | R478 | E495 | K508 |
| 45 | — | — | — | — | — | — | — | — | — | — | — | — | — | — | — | — | — | — |

TABLE 2B-continued

| | | | | | | | | | | | | | | | | | | |
|---|---|---|---|---|---|---|---|---|---|---|---|---|---|---|---|---|---|---|
| 46 | — | — | — | — | — | — | — | — | — | — | — | — | — | — | — | — | — | — |
| 47 | Y282 | T283 | T284 | F285 | A297 | T299 | K303 | L314 | V316 | Y327 | Y335 | S341 | V342 | E347 | Y358 | K363 | D380 | N393 |
| 48 | F311 | T312 | T313 | F314 | A326 | T328 | K332 | L343 | V345 | H356 | Y364 | S370 | A371 | G376 | — | K383 | D400 | V413 |
| 49 | — | — | — | — | — | — | — | — | — | — | — | — | — | — | — | — | — | — |
| 50 | Y181 | T182 | T183 | F184 | A196 | L198 | R202 | L213 | V215 | Y226 | Y234 | M240 | V241 | E246 | Y257 | S262 | — | — |
| 51 | L350 | T351 | T352 | F353 | L365 | E367 | E371 | L382 | I384 | R395 | Y403 | A409 | V410 | H415 | L426 | M431 | R448 | G461 |
| 52 | L350 | T351 | T352 | F353 | S365 | A367 | Q371 | L382 | V384 | H395 | Y403 | T409 | V410 | D415 | F426 | R431 | — | A458 |
| 53 | L350 | T351 | T352 | F353 | S365 | A367 | Q371 | L382 | V384 | H395 | Y403 | T409 | V410 | D415 | F426 | R431 | — | T458 |
| 54 | Y89 | T90 | T91 | F92 | A104 | T106 | K110 | L121 | V123 | Y134 | Y142 | S148 | V149 | E154 | Y165 | K170 | D187 | N200 |
| 55 | L350 | T351 | T352 | F353 | L365 | E367 | E371 | L382 | I384 | R395 | Y403 | A409 | V410 | H415 | L426 | M431 | R448 | G461 |
| 56 | F349 | T350 | T351 | F352 | K364 | D366 | K370 | V381 | L383 | R394 | Y402 | K408 | I409 | D414 | F425 | R430 | E447 | — |
| 57 | L365 | T366 | V367 | M368 | L380 | A382 | L386 | L397 | V399 | F410 | Y418 | H424 | F425 | A430 | M441 | R446 | E463 | — |
| 58 | L352 | S353 | T354 | Y355 | L367 | D369 | D373 | L384 | V386 | V397 | Y405 | K411 | I412 | N417 | F428 | R433 | Q450 | — |
| 59 | F352 | T353 | L354 | F355 | E367 | R369 | L373 | M384 | I386 | F397 | Y405 | E411 | H412 | D417 | I428 | R433 | N450 | — |
| 60 | L351 | T352 | N353 | Y354 | L366 | R368 | R372 | L383 | V385 | V396 | Y404 | E410 | Y411 | D416 | L427 | R432 | A449 | — |
| 61 | L349 | T350 | T351 | F352 | A364 | D366 | R370 | L381 | V383 | A394 | Y402 | A408 | A409 | E414 | F425 | R430 | R447 | V460 |
| 62 | — | — | — | — | — | — | — | — | — | — | — | — | — | — | — | — | — | — |
| 63 | F353 | T354 | L355 | F356 | M368 | K370 | I374 | M385 | I387 | L398 | Y406 | E412 | H413 | E418 | L429 | R434 | K451 | — |
| 64 | L363 | S364 | A365 | F366 | G378 | D380 | L384 | L395 | I397 | R408 | Y416 | E422 | L423 | S428 | L439 | R444 | E461 | — |
| 65 | L373 | T374 | V375 | Y376 | R388 | A390 | V394 | L405 | V407 | T418 | Y426 | E432 | S433 | A438 | F449 | R454 | E471 | — |
| 66 | I359 | N360 | V361 | M362 | L374 | E376 | R380 | L391 | V393 | H404 | L412 | I418 | V419 | I424 | L435 | R440 | E457 | — |
| 67 | L350 | T351 | T352 | F353 | R365 | N367 | I371 | L382 | L384 | R395 | Y403 | E409 | I410 | D415 | F426 | R431 | E448 | — |
| 68 | L343 | T344 | V345 | F346 | P358 | T360 | L364 | L375 | I377 | H388 | Y396 | K402 | V403 | T408 | L419 | R424 | N441 | — |
| 69 | T360 | I361 | N362 | L363 | Q375 | D377 | I381 | I392 | A394 | R405 | Y413 | E419 | A420 | E425 | F436 | R441 | E458 | A471 |
| 70 | L372 | T373 | V374 | L375 | M387 | L389 | M393 | L404 | V406 | V417 | Y425 | R431 | F432 | E437 | V448 | R453 | R470 | — |
| 71 | — | — | — | — | — | — | — | — | — | — | — | — | — | — | — | — | — | — |
| 72 | L388 | T389 | V390 | L391 | M403 | L405 | M409 | L420 | V422 | V433 | Y441 | R447 | F448 | E453 | V464 | R469 | R486 | — |
| 73 | T355 | T356 | T357 | L358 | R370 | D372 | I376 | L387 | I389 | R400 | Y408 | E414 | R415 | V420 | F431 | R436 | E453 | A466 |
| 74 | L355 | T356 | V357 | F358 | A370 | D372 | E376 | L387 | V389 | R400 | L408 | E414 | T415 | R420 | L429 | L434 | E451 | — |
| 75 | L355 | T356 | V357 | F358 | A370 | D372 | E376 | L387 | V389 | R400 | L408 | E414 | T415 | R420 | L429 | L434 | E451 | — |
| 76 | L354 | T355 | T356 | Y357 | L369 | Q371 | L375 | L386 | I388 | L399 | P407 | D413 | R414 | S419 | I430 | I435 | — | — |
| 77 | T356 | I357 | T358 | L359 | Q371 | E373 | I377 | L388 | I390 | R401 | Y409 | E415 | R416 | E421 | L432 | R437 | E454 | A467 |
| 78 | I353 | R354 | V355 | M356 | L368 | D370 | V374 | M385 | I387 | K398 | Y406 | E412 | R413 | F418 | L429 | Y434 | R451 | — |
| 79 | I352 | R353 | A354 | M355 | A367 | E369 | A373 | M384 | I386 | K397 | Y405 | E411 | K412 | F417 | L428 | Y433 | E450 | — |
| 80 | L372 | S373 | N374 | Y375 | M387 | D389 | V393 | L404 | A406 | L418 | Y426 | N432 | R433 | D438 | L449 | I454 | S471 | N484 |
| 81 | L355 | T356 | V357 | F358 | T370 | D372 | E376 | L387 | V389 | R400 | F408 | E414 | T415 | R420 | L429 | L434 | E451 | — |
| 82 | L352 | T353 | V354 | M355 | L367 | Q369 | L373 | L384 | L386 | S397 | Y405 | P411 | W412 | K417 | F428 | V433 | E450 | — |
| 83 | L354 | T355 | T356 | F357 | L369 | Q371 | L375 | L386 | I388 | L399 | P407 | D413 | R414 | S419 | I430 | I435 | — | — |
| 84 | F370 | L371 | S372 | F373 | L394 | P396 | A400 | L411 | T413 | L425 | Y433 | Q439 | R440 | Q445 | V457 | L462 | Q479 | — |
| 85 | F341 | T342 | T343 | F344 | Q356 | E358 | K362 | — | D374 | L387 | Y395 | — | R398 | H403 | S416 | R421 | D438 | — |
| 86 | I339 | T340 | S341 | Y342 | L354 | E356 | L360 | — | Q372 | L385 | F393 | — | Y396 | H401 | I414 | Y419 | A436 | — |
| 87 | L359 | T360 | V361 | F362 | A374 | D376 | L380 | L391 | V393 | R404 | S412 | E418 | R419 | E424 | L433 | L438 | E455 | — |
| 88 | Y348 | A349 | F350 | F351 | K363 | D365 | R369 | L380 | Y382 | R395 | Y403 | S409 | R410 | D415 | I426 | K431 | E448 | — |
| 89 | I333 | T334 | S335 | F336 | L348 | D350 | K354 | — | K366 | R378 | Y386 | — | D389 | H394 | V407 | E412 | E429 | — |
| 90 | L362 | R363 | S364 | M365 | L377 | D379 | M383 | M394 | I396 | R407 | Y415 | K421 | R422 | Q427 | L438 | Y443 | D460 | — |
| 91 | L382 | I383 | S384 | F385 | L406 | P408 | A412 | L423 | T425 | L437 | Y445 | Q451 | R452 | Q457 | V469 | L474 | Q491 | — |
| 92 | L364 | T365 | N366 | F367 | L379 | N381 | V385 | L396 | K398 | L410 | Y418 | L424 | R425 | N430 | L441 | T446 | P463 | — |
| 93 | L378 | R379 | T380 | F381 | H393 | D395 | N399 | L410 | V412 | R423 | Y431 | Q437 | L438 | E443 | L454 | Y459 | E476 | — |
| 94 | L364 | R365 | S366 | M367 | L379 | D381 | V385 | M396 | I398 | R409 | Y417 | R423 | R424 | E429 | L440 | Y445 | D462 | — |
| 95 | L343 | T344 | A345 | F346 | R357 | D359 | L363 | L374 | I376 | T387 | Y395 | D401 | R402 | D407 | F418 | R423 | Q440 | — |
| 96 | Y347 | A348 | C349 | F350 | K362 | D364 | I368 | L379 | Y381 | R394 | Y402 | A408 | R409 | D414 | I425 | K430 | E447 | — |
| 97 | I353 | R354 | V355 | M356 | K368 | E370 | T374 | M385 | I387 | R398 | Y406 | E412 | K413 | F418 | F429 | Y434 | E451 | — |
| 98 | L422 | L423 | N424 | Y425 | K437 | E439 | V443 | L454 | S458 | V469 | F477 | D483 | L484 | K489 | L502 | V507 | T524 | — |
| 99 | Y404 | T405 | T406 | F407 | A419 | T421 | K425 | L436 | I438 | Y449 | Y457 | S463 | V464 | D469 | Y480 | R485 | D502 | N515 |
| 100 | L425 | L426 | N427 | Y428 | K440 | E442 | V446 | L457 | N461 | V472 | F480 | D486 | L487 | K492 | L505 | V510 | A527 | — |
| 101 | Y390 | T391 | T392 | F393 | A405 | T407 | K411 | L422 | V424 | Y435 | Y443 | S449 | V450 | E455 | Y466 | K471 | D488 | K500 |
| 102 | L421 | L422 | N423 | Y424 | K436 | E438 | V442 | L453 | K457 | V468 | F476 | D482 | I483 | K488 | L501 | V506 | A523 | — |
| 103 | Y385 | T386 | T387 | F388 | A400 | R402 | K406 | L417 | A419 | Y430 | Y438 | L444 | V445 | E450 | Y461 | K466 | E483 | K496 |
| 104 | I451 | L452 | S453 | F454 | K466 | Q468 | A472 | L483 | S487 | V498 | F506 | D512 | L513 | K518 | L531 | V536 | A553 | — |
| 105 | L417 | L418 | N419 | Y420 | K432 | E434 | V438 | L449 | T453 | V464 | F472 | D478 | R479 | K484 | L497 | V502 | S519 | — |
| 106 | F397 | T398 | T399 | F400 | A412 | T414 | K418 | L429 | V431 | H442 | Y450 | S456 | A457 | G462 | Y473 | K478 | D495 | D508 |
| 107 | L425 | L426 | N427 | Y428 | K440 | E442 | V446 | L457 | N461 | V472 | F480 | D486 | L487 | K492 | L505 | V510 | A527 | — |
| 108 | I446 | L447 | S448 | Y449 | K461 | K463 | A467 | L478 | D482 | V493 | F501 | D507 | L508 | K513 | L526 | V531 | A548 | — |
| 109 | L416 | L417 | N418 | Y419 | K431 | E433 | V437 | L448 | R452 | V463 | F471 | D477 | R478 | K483 | L496 | V501 | S518 | — |
| 110 | F442 | T443 | T444 | F445 | A457 | T459 | K463 | L474 | V476 | H487 | Y495 | L501 | A502 | G507 | Y518 | K523 | D540 | G549 |
| 111 | L417 | L418 | N419 | Y420 | K432 | E434 | V438 | L449 | R453 | V464 | F472 | D478 | R479 | K484 | L497 | V502 | S519 | — |
| 112 | Y386 | T387 | T388 | F389 | A401 | R403 | K407 | L418 | A420 | C431 | Y439 | S445 | V446 | D451 | Y462 | K467 | D484 | S494 |
| 113 | L432 | L433 | N434 | Y435 | K447 | E449 | V453 | L464 | R468 | V479 | F487 | D493 | R494 | K499 | L512 | V517 | S534 | — |
| 114 | L425 | L426 | N427 | Y428 | K440 | E442 | V446 | L457 | N461 | V472 | F480 | D486 | L487 | K492 | L505 | V510 | A527 | — |
| 115 | Y390 | T391 | T392 | F393 | A405 | T407 | K411 | L422 | V424 | Y435 | Y443 | S449 | V450 | E455 | Y466 | K471 | D488 | S497 |
| 116 | I446 | L447 | S448 | Y449 | K461 | K463 | A467 | L478 | D482 | V493 | F501 | D507 | L508 | K513 | L526 | V531 | A548 | — |
| 117 | Y391 | T392 | T393 | F394 | A406 | T408 | K412 | L423 | V425 | Y436 | Y444 | S450 | V451 | D456 | Y467 | R472 | D489 | K502 |

Assays to test for the functionality of such mutants are readily available in the art, and respectively, described in the Example section of the present invention.

In a preferred embodiment, the mutated PPO refers to a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, in which the amino acid sequence differs at Mutated site 1 (which corresponds to Arg128 of SEQ ID NO: 1) according to Table 2a, and/or at Mutated site 5 (which corresponds to Phe420 of SEQ ID NO: 1) according to Table 2a.

Examples of differences at these amino acid positions include, but are not limited to, one or more of the following:
the amino acid at Mutated site 1 is other than Arginine (or Tryosine, or Cysteine; as the case may be according to Table 2a);
the amino acid at Mutated site 5 is other than Phenylalanine (or Methionine, or Tyrosine, or Leucine, as the case may be according to Table 2a), In particularly preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 (which corresponds to Arg128 of SEQ ID NO: 1) is Leu, Ala, Val, Ile, Met, Tyr, Gly, Asn, Cys, Phe, Ser, Thr, Gln, or His, and the amino acid at Mutated site 5 (which corresponds to Phe420 of SEQ ID NO: 1) is Ala, Leu, Val, Ile, or Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Leu, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Leu, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Leu, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Leu, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Leu, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Ala, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 1 is Ala, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ala, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ala, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ala, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Val, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Val, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Val, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Val, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Val, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ile, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ile, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ile, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ile, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ile, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Met, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Met, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Met, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Met, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Met, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Tyr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Tyr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Tyr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Tyr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Tyr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gly, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gly, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gly, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gly, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gly, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Asn, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Asn, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Asn, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Asn, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Asn, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Cys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Cys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Cys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Cys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Cys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Phe, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Phe, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Phe, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Phe, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Phe, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ser, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ser, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ser, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ser, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Ser, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Thr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Thr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Thr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Thr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Thr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gln, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gln, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gln, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gln, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is Gln, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is His, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is His, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is His, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is His, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 1 is His, and the amino acid at Mutated site 5 is Met.

In another preferred embodiment, the mutated PPO refers to a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, in which the amino acid sequence differs at Mutated site 4 (which corresponds to Leu397 of SEQ ID NO: 1) according to Table 2a, and/or at Mutated site 5 (which corresponds to Phe420 of SEQ ID NO: 1) according to Table 2a.

Examples of differences at these amino acid positions include, but are not limited to, one or more of the following:

the amino acid at Mutated site 4 is other than Leucine (or Alanine, or Serine, or Phenylalanine, as the case may be according to Table 2a);

the amino acid at Mutated site 5 is other than Phenylalanine (or Methionine, or Tyrosine, or Leucine, as the case may be according to Table 2a), In particularly preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 (which corresponds to Leu397 of SEQ ID NO: 1) is Ala, Arg, Val, Ile, Met, His, Lys, Asp, Glu, Ser, Thr, Asn, Gln, Cys, Gly, Pro, Phe, Tyr, or Trp, and the amino acid at Mutated site 5 (which corresponds to Phe420 of SEQ ID NO: 1) is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ala, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Arg, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Arg, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Arg, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Arg, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Met.

In another preferred embodiment, the mutated PPO comprises a sequence of SEQ ID NO: 1, 2,3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Val, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Val, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ile, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Met, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is His, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is His, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Lys, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Lys, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asp, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Asp, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Glu, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Glu, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Glu, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Glu, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Gin.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Ser, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, the amino acid at Mutated site 4 is Thr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Gin.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Thr, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Asn, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gin, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gin, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gin, and the amino acid at Mutated site 5 is Gin.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gin, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gln, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Gin.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Cys, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Gly, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Pro, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Pro, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Phe, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:
the amino acid at Mutated site 4 is Phe, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Phe, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Tyr, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, a variant, derivative, orthologue, paralogue or homologue thereof, in which:

the amino acid at Mutated site 4 is Trp, and the amino acid at Mutated site 5 is Trp.

It will be within the knowledge of the skilled artisan to identify conserved regions and motifs shared between the homologues, orthologues and paralogues of PPO polypeptides comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117. Having identified such conserved regions that may represent suitable binding motifs, amino acids corresponding to the amino acids listed in Table 2a and 2b can be chosen to be substituted by any other amino acid, preferably by the amino acids listed under mutated sites 1, 2, 3, 4, or 5.

In addition, the present invention refers to a method for identifying a PPO-inhibiting herbicide by using a mutated PPO comprising the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant or derivative thereof.

Said method comprises the steps of:

a) generating a transgenic cell or plant comprising a nucleic acid encoding a mutated PPO, wherein the mutated PPO is expressed;
b) applying a PPO-inhibiting herbicide to the transgenic cell or plant of a) and to a control cell or plant of the same variety;
c) determining the growth or the viability of the transgenic cell or plant and the control cell or plant after application of said PPO-inhibiting herbicide, and
d) selecting "PPO-inhibiting herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mutated PPO which is resistant or tolerant to a PPO-inhibiting herbicide, the method comprising:

a) generating a library of mutated PPO-encoding nucleic acids,
b) screening a population of the resulting mutated PPO-encoding nucleic acids by expressing each of said nucleic acids in a cell or plant and treating said cell or plant with a PPO-inhibiting herbicide,
c) comparing the PPO-inhibiting herbicide-tolerance levels provided by said population of mutated PPO encoding nucleic acids with the PPO-inhibiting herbicide-tolerance level provided by a control PPO-encoding nucleic acid,
d) selecting at least one mutated PPO-encoding nucleic acid that provides a significantly increased level of tolerance to a PPO-inhibiting herbicide as compared to that provided by the control PPO-encoding nucleic acid.

In a preferred embodiment, the mutated PPO-encoding nucleic acid selected in step d) provides at least 2-fold as much resistance or tolerance of a cell or plant to a PPO-inhibiting herbicide as compared to that provided by the control PPO-encoding nucleic acid.

In a further preferred embodiment, the mutated PPO-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a PPO-inhibiting herbicide as compared to that provided by the control PPO-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wild-type or mutated PPO which is resistant or tolerant to a PPO-inhibiting herbicide, the method comprising:

a) identifying an effective amount of a PPO-inhibiting herbicide in a culture of plant cells or green algae that leads to death of said cells.
b) treating said plant cells or green algae with a mutagenizing agent,
c) contacting said mutagenized cells population with an effective amount of PPO-inhibiting herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mutated PPO from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mutated PPO-encoding sequences.

Nucleic acids comprising candidate and control PPO encoding sequences can be expressed in yeast, in a bacterial host strain, in an alga or in a higher plant such as tobacco or *Arabidopsis* and the relative levels of inherent tolerance of the PPO encoding sequences screened according to a visible indicator phenotype of the transformed strain or plant in the presence of different concentrations of the selected PPO-inhibiting herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed PPO. For example, in a relatively rapid assay system based upon transformation of a bacterium such as *E. coli*, each mutated PPO encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different PPO sequences. Such strains expressing nucleic acids comprising alternative candidate PPO sequences may be plated out on different concentrations of the selected PPO-inhibiting herbicide in, optionally, a tyrosine supplemented medium and the relative levels of inherent tolerance of the expressed PPO enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected PPO-inhibiting herbicides as described in the Example section hereinafter. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control PPO. Alternatively, an untransformed dicot plant such as *Arabidopsis* or Tobacco can be used as a control since this, in any case, expresses its own endogenous PPO. The average, and distribution, of herbicide tolerance levels of a range of primary plant transformation events or their progeny to PPO-inhibiting herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed PPO. Herbicides can suitably be applied pre-emergence or post-emergence.

Another object of the present invention refers to an isolated and/or recombinant and/or chemically synthesized nucleic acid encoding a mutated PPO comprising an amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117 or a variant or derivative thereof.

In one embodiment, the nucleic acid is identifiable by a method as defined above.

In a preferred embodiment, the encoded mutated PPO is a variant of SEQ ID NO: 1, 11, 30, 31, 37, or 117, or an orthologue thereof, which includes one or more of the following:

the amino acid corresponding to Mutated site 1 is Leu, Ala, Val, Ile, Met, Tyr, Gly, Asn, Cys, Phe, Ser, Thr, Gln, or His;

and/or the amino acid at or corresponding to Mutated site 4 is Ala, Arg, Val, Ile, Met, His, Lys, Asp, Glu, Ser, Thr, Asn, Gln, Cys, Gly, Pro, Phe, Tyr, or Trp, and/or and the amino acid at Mutated site 5 is Ala, Leu, Val, Ile, Met, His, Lys, Asp, Glu, Ser, Thr, Asn, Gln, Cys, Gly, Pro, Arg, Tyr, or Trp.

In another embodiment, the invention refers to a plant cell transformed by a nucleic acid encoding a mutated PPO polypeptide according to the present invention or to a plant cell which has been mutated to obtain a plant expressing a nucleic acid encoding a mutated PPO polypeptide according to the present invention, wherein expression of the nucleic acid in the plant cell results in increased resistance or tolerance to a PPO-inhibiting herbicide as compared to a wild type variety of the plant cell. Preferably, the mutated PPO polypeptide encoding nucleic acid comprises a) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant or derivative thereof; b) a polynucleotide comprising at least 60 consecutive nucleotides of any of a); and c) a polynucleotide complementary to the polynucleotide of any of a) through b).

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the PPO-inhibiting herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mutated PPO nucleic acid comprises a polynucleotide sequence selected from the group consisting of: a) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant or derivative thereof; b) a polynucleotide comprising at least 60 consecutive nucleotides of any of a); and c) a polynucleotide complementary to the polynucleotide of any of a) through b).

Preferably, the expression of the nucleic acid in the plant results in the plant's increased resistance to PPO-inhibiting herbicide as compared to a wild type variety of the plant.

In another embodiment, the invention refers to a plant, preferably a transgenic plant, comprising a plant cell according to the present invention, wherein expression of the nucleic acid in the plant results in the plant's increased resistance to PPO-inhibiting herbicide as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated PPO of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mutated PPO nucleic acids, the nucleic acids can be derived from different genomes or from the same genome. Alternatively, in embodiments wherein the plant is non-transgenic and comprises multiple mutated PPO nucleic acids, the nucleic acids are located on different genomes or on the same genome. As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induce and/or selected by human action. Methods of inducing mutations can induce mutations in random positions in the genetic material or can induce mutations in specific locations in the genetic material (i.e., can be directed mutagenesis techniques), such as by use of a genoplasty technique.

In certain embodiments, the present invention involves herbidicide-resistant plants that are produced by mutation breeding. Such plants comprise a polynucleotide encoding a mutated PPO and are tolerant to one or more PPO-inhibiting herbicides. Such methods can involve, for example, exposing the plants or seeds to a mutagen, particularly a chemical mutagen such as, for example, ethyl methanesulfonate (EMS) and selecting for plants that have enhanced tolerance to at least one or more PPO-inhibiting herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mutated PPO nucleic acid or over-expressed wild-type PPO nucleic acid, and has increased tolerance to a PPO-inhibiting herbicide as compared to a wild-type variety of the plant. It is possible for the plants of the present invention to have multiple wild-type or mutated PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mutated PPO alleles, wherein the plant has increased tolerance to a PPO-inhibiting herbicide as compared to a wild-type variety of the plant. The mutated PPO alleles can comprise a nucleotide sequence selected from the group consisting of a polynucleotide encoding a polypeptide as defined in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

In some embodiments, traditional plant breeding is employed whereby the PPO-inhibiting herbicides-tolerant trait is introduced in the progeny plant resulting therefrom. In one embodiment, the present invention provides a method for producing a PPO-inhibiting herbicides-tolerant progeny plant, the method comprising: crossing a parent plant with a PPO-inhibiting herbicides-tolerant plant to introduce the PPO-inhibiting herbicides-tolerance characteristics of the PPO-inhibiting herbicides-tolerant plant into the germplasm of the progeny plant, wherein the progeny plant has increased tolerance to the PPO-inhibiting herbicides relative to the parent plant. In other embodiments, the method further comprises the step of introgressing the PPO-inhibiting herbicides-tolerance characteristics through traditional plant breeding techniques to obtain a descendent plant having the PPO-inhibiting herbicides-tolerance characteristics.

The herbicide-resistant plants of the invention that comprise polynucleotides encoding mutated PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being tolerant to PPO-inhibiting herbicides, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, PPO-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, PPO-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, PPO-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

PPO-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, PPO-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the PPO-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle

*Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *psylla Cacopsylla pyricola*; the currant aphid *Cryptomyzus ribis*; the grape *phylloxera Daktulosphaira vitifoliae*; the citrus *psylla Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis vires cens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco *thrips Frankliniella fusca*, the flower *thrips Frankliniella intonsa*, the western flower *thrips Frankliniella occidentalism* the cotton bud *thrips Frankliniella schultzei*, the banded greenhouse *thrips Hercinothrips femoralis*, the soybean *thrips Neohydatothrips variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the PPO-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the PPO-inhibiting herbicides-tolerant plants is effective for controlling cabbage seedpod weevil, the Bertha armyworm, *Lygus* bugs, or the diamondback moth.

Furthermore, in one embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, PPO-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, PPO-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, PPO-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2, 2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, PPO-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla. In other embodiments, PPO-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

It is to be understood that the plant of the present invention can comprise a wild type PPO nucleic acid in addition to a mutated PPO nucleic acid. It is contemplated that the PPO-inhibiting herbicide tolerant lines may contain a mutation in only one of multiple PPO isoenzymes. Therefore, the present invention includes a plant comprising one or more mutated PPO nucleic acids in addition to one or more wild type PPO nucleic acids.

In another embodiment, the invention refers to a seed produced by a transgenic plant comprising a plant cell of the present invention, wherein the seed is true breeding for an increased resistance to a PPO-inhibiting herbicide as compared to a wild type variety of the seed.

In another embodiment, the invention refers to a method of producing a transgenic plant cell with an increased resistance to a PPO-inhibiting herbicide as compared to a wild type variety of the plant cell comprising, transforming the plant cell with an expression cassette comprising a mutated PPO nucleic acid.

In another embodiment, the invention refers to a method of producing a transgenic plant comprising, (a) transforming a plant cell with an expression cassette comprising a mutated PPO nucleic acid, and (b) generating a plant with an increased resistance to PPO-inhibiting herbicide from the plant cell.

Consequently, mutated PPO nucleic acids of the invention are provided in expression cassettes for expression in the plant of interest. The cassette will include regulatory sequences operably linked to a mutated PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mutated PPO nucleic acid sequence to be under the transcriptional regulation of the regulatory regions. The expression cassette may additionally contain selectable marker genes.

The expression cassette of the present invention will include in the 5'-3' direction of transcription, a transcriptional and translational initiation region (i.e., a promoter), a mutated PPO encoding nucleic acid sequence of the invention, and a transcriptional and translational termination region (i.e., termination region) functional in plants. The promoter may be native or analogous, or foreign or heterologous, to the plant host and/or to the mutated PPO nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mutated PPO nucleic acid sequence of the invention, it is intended that the promoter is not the native or naturally occurring promoter for the operably linked mutated PPO nucleic acid sequence of the invention. As used herein, a chimeric gene comprises a coding sequence operably linked to a transcription initiation region that is heterologous to the coding sequence.

While it may be preferable to express the mutated PPO nucleic acids of the invention using heterologous promoters, the native promoter sequences may be used. Such constructs would change expression levels of the mutated PPO protein in the plant or plant cell. Thus, the phenotype of the plant or plant cell is altered.

The termination region may be native with the transcriptional initiation region, may be native with the operably linked mutated PPO sequence of interest, may be native with the plant host, or may be derived from another source (i.e., foreign or heterologous to the promoter, the mutated PPO nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballast al. (1989) Nucleic Acids Res. 17:7891-7903; and Joshi et al. (1987) Nucleic Acid Res. 15:9627-

9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize AdhI, intronI gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mutated PPO gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes of the present invention may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced mutated PPO expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka e/[alpha]/. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, “operably linked” means that the nucleic acid sequence encoding a transit peptide (i.e., the chloroplast-targeting sequence) is linked to the mutated PPO nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the mutated PPO proteins of the invention include a native chloroplast transit peptide, any chloroplast transit peptide known in the art can be fused to the amino acid sequence of a mature mutated PPO protein of the invention by operably linking a choloroplast-targeting sequence to the 5'-end of a nucleotide sequence encoding a mature mutated PPO protein of the invention. Chloroplast targeting sequences are known in the art and include the chloroplast small subunit of ribulose-1, 5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the mutated PPO nucleic acid comprises a polynucleotide sequence selected from the group consisting of: a) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, or a variant or derivative thereof; b) a polynucleotide comprising at least 60 consecutive nucleotides of any of a); and c) a polynucleotide complementary to the polynucleotide of any of a) through b)

Preferably, the expression cassette of the present invention further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a mutated PPO nucleic acid as described above, wherein expression of the vector in a host cell results in increased tolerance to a PPO-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated PPO polypeptides, fusion polypeptides, etc.).

In a preferred embodiment of the present invention, the mutated PPO polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A mutated PPO polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased tolerance to PPO-inhibiting herbicides is a general trait wished to be inherited into a wide variety of plants like maize, wheat, rye, oat, triticale, rice, barley, soybean, peanut, cotton, rapeseed and canola, *manihot*, pepper, sunflower and *tagetes*, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mutated PPO polynucleotide into a plant is achieved by *Agrobacterium* mediated gene transfer. One transformation method known to those of skill in the art is the dipping of a flowering plant into an Agrobacteria solution, wherein the Agrobacteria contains the mutated PPO nucleic acid, followed by breeding of the transformed gametes. *Agrobacterium* mediated plant transformation can be performed using for example the GV3101 (pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced mutated PPO polynucleotide may be maintained in the plant cell stably if it is incorporated into a non-chromosomal autonomous replicon or integrated into the plant chromosomes. Alternatively, the introduced mutated PPO polynucleotide may be present on an extra-chromosomal non-replicating vector and be transiently expressed or transiently active. In one embodiment, a homologous recombinant microorganism can be created wherein the mutated PPO polynucleotide is integrated into a chromosome, a vector is prepared which contains at least a portion of an PPO gene into which a deletion, addition, or substitution has been introduced to thereby alter, e.g., functionally disrupt, the endogenous PPO gene and to create a mutated PPO gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240-247). Other homologous recombination procedures in *Triticum* species are also well known in the art and are contemplated for use herein.

In the homologous recombination vector, the mutated PPO gene can be flanked at its 5' and 3' ends by an additional nucleic acid molecule of the PPO gene to allow for homologous recombination to occur between the exogenous mutated PPO gene carried by the vector and an endogenous PPO gene, in a microorganism or plant. The additional flanking PPO nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the mutated PPO gene normally differs from the PPO gene at very few amino acids, a flanking sequence is not always necessary. The homologous recombination vector is introduced into a microorganism or plant cell (e.g., via polyethylene glycol mediated DNA), and cells in which the introduced mutated PPO gene has homologously recombined with the endogenous PPO gene are selected using art-known techniques.

In another embodiment, recombinant microorganisms can be produced that contain selected systems that allow for regulated expression of the introduced gene. For example, inclusion of a mutated PPO gene on a vector placing it under control of the lac operon permits expression of the mutated PPO gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mutated PPO polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mutated PPO polynucleotide. Accordingly, the invention further provides methods for producing mutated PPO polypeptides using the host cells of the invention. In one embodiment, the method comprises culturing the host cell of invention (into which a recombinant expression vector encoding a mutated PPO polypeptide has been introduced, or into which genome has been introduced a gene encoding a wild-type or mutated PPO polypeptide) in a suitable medium until mutated PPO polypeptide is produced. In another embodiment, the method further comprises isolating mutated PPO polypeptides from the medium or the host cell. Another aspect of the invention pertains to isolated mutated PPO polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mutated PPO polypeptide in which the polypeptide is separated from some of the cellular components of the cells in which it is naturally or recombinantly produced. In one embodiment, the language "substantially free of cellular material" includes preparations of a mutated PPO polypeptide having less than about 30% (by dry weight) of non-mutated PPO material (also referred to herein as a "contaminating polypeptide"), more preferably less than about 20% of non-mutated PPO material, still more preferably less than about 10% of non-mutated PPO material, and most preferably less than about 5% non-mutated PPO material.

When the mutated PPO polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mutated PPO polypeptide in which the polypeptide is separated from chemical precursors or other chemicals that are involved in the synthesis of the polypeptide. In one embodiment, the language "substantially free of chemical precursors or other chemicals" includes preparations of a mutated PPO polypeptide having less than about 30% (by dry weight) of chemical precursors or non-mutated PPO chemicals, more preferably less than about 20% chemical precursors or non-mutated PPO chemicals, still more preferably less than about 10% chemical precursors or non-mutated PPO chemicals, and most preferably less than about 5% chemical precursors or non-mutated PPO chemicals. In preferred embodiments, isolated polypeptides, or biologically active portions thereof, lack contaminating polypeptides from the same organism from which the mutated PPO polypeptide is derived. Typically, such polypeptides are produced by recombinant expression of, for example, a mutated PPO polypeptide in plants other than, or in microorganisms such as *C. glutamicum*, ciliates, algae, or fungi.

In other aspects, a method for treating a plant of the present invention is provided.

In some embodiments, the method comprises contacting the plant with an agronomically acceptable composition.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a PPO-inhibiting herbicides herbicidal composition to the descendent plant.

In another embodiment, the invention refers to harvestable parts of the transgenic plant according to the present invention. Preferably, the harvestable parts comprise the PPO nucleic acid or PPO protein of the present invention. The harvestable parts may be seeds, roots, leaves and/or flowers comprising the PPO nucleic acid or PPO protein or parts thereof. Preferred parts of soy plants are soy beans comprising the PPO nucleic acid or PPO protein.

In another embodiment, the invention refers to products derived from a plant according to the present invention, parts thereof or harvestable parts thereof. A preferred plant product is fodder, seed meal, oil, or seed-treatment-coated seeds. Preferably, the meal and/or oil comprises the mutated PPO nucleic acids or PPO proteins of the present invention.

In another embodiment, the invention refers to a method for the production of a product, which method comprises a) growing the plants of the invention or obtainable by the methods of invention and
b) producing said product from or by the plants of the invention and/or parts, e.g. seeds, of these plants.

In a further embodiment the method comprises the steps a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

As described above, the present invention teaches compositions and methods for increasing the PPO-inhibiting tolerance of a crop plant or seed as compared to a wild-type variety of the plant or seed. In a preferred embodiment, the PPO-inhibiting tolerance of a crop plant or seed is increased such that the plant or seed can withstand a PPO-inhibiting herbicide application of preferably approximately 1-1000 g ai $ha^{-1}$, more preferably 1-200 g ai $ha^{-1}$, even more preferably 5-150 g ai $ha^{-1}$, and most preferably 10-100 g ai $ha^{-1}$. As used herein, to "withstand" a PPO-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Furthermore, the present invention provides methods that involve the use of at least one PPO-inhibiting herbicide, optionally in combination with one or more herbicidal compounds B, and, optionally, a safener C, as described in detail supra.

In these methods, the PPO-inhibiting herbicide can be applied by any method known in the art including, but not limited to, seed treatment, soil treatment, and foliar treatment. Prior to application, the PPO-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to PPO-inhibiting herbicide, a wide variety of formulations can be employed for protecting plants from weeds, so as to enhance plant growth and reduce competition for nutrients. A PPO-inhibiting herbicide can be used by itself for pre-emergence, post-emergence, pre-planting, and at-planting control of weeds in areas surrounding the crop plants described herein, or a PPO-inhibiting herbicide formulation can be used that contains other additives. The PPO-inhibiting herbicide can also be used as a seed treatment. Additives found in a PPO-inhibiting herbicide formulation include other herbicides, detergents, adjuvants, spreading agents, sticking agents, stabilizing agents, or the like. The PPO-inhibiting herbicide formulation can be a wet or dry preparation and can include, but is not limited to, flowable powders, emulsifiable concentrates, and liquid concentrates. The PPO-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Site-Directed Mutagenesis PPO

All nucleic acid coding sequence and all single and double mutants encoding a polypeptide comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, are synthesized and cloned by Geneart (Geneart AG, Regensburg, Germany). Rational design mutants are synthesized by Geneart. Random PPO gene libraries are synthesized by Geneart. Plasmids are isolated from *E. coli* TOP10 by performing a plasmid minpreparation and confirmed by DNA sequencing.

Example 2

Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector are transformed into BL21(DE3)-pLysS strain of *E. coli*. Cells are grown in 250 mL of LB with 100 μgmL-1 of carbenicillin, shaking overnight at 37° C. Cultures are diluted in 1 L of LB with antibiotic and grown at 37° C. shaking for 2 h, induced with 1 mM IPTG and grown at 25° C. shaking for 5 more hours. The cells are harvested by centrifugation at 1600×g, washed with 0.09% NaCl, and stored at −80° C. Cells are lysed using a French press at 140 MPa in 50 mM sodium phosphate pH 7.5, 1 M NaCl, 5 mM imidazole, 5% glycerol, and 1 μg mL-1 leupeptin. Following lysis, 0.5 U of benzonase (Novagen, EMD Chemicals, Inc., Gibbstown, N.J.) and PMSF (final concentration of 1 mM) are added. Cell debris is removed by centrifugation at 3000×g. His-tagged PPO proteins are purified on a nickel activated Hitrap Chelating HP column (GE Healthcare Bio-Sciences Corp., Piscataway, N.J.) equilibrated with 20 mM sodium phosphate pH 8.0, 50 mM NaCl, 5 mM imidazole, 5 mM MgCl2, 0.1 mM EDTA, and 17% glycerol. PPO is eluted with 250 mM imidazole. The active protein is desalted on a PD-10 column (GE Healthcare Bio-Sciences Corp., Piscataway, N.J.) equilibrated with a 20 mM sodium phosphate buffer, pH 7.5, 5 mM MgCl2, 1 mM EDTA and 17% glycerol. Each liter of culture provided approximately 10 mg of pure PPO, which is stored at −20° C. until being used in assays.

Example 3

PPO Enzyme Assay (Non-Recombinant)

PPO protein (EC 1.3.3.4) is extracted from coleoptiles or shoots (150 g fresh weight) of dark-grown corn, black nightshade, morning glory, and velvetleaf seedlings as described previously (Grossmann et al. 2010). Before harvesting, the seedlings are allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials are homogenized in the cold with a Braun blender using a fresh-weight-to-volume ratio of 1:4. Homogenization buffer consisted of tris(hydroxymethyl)aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations are obtained after centrifugation at 10 000×g for 5 min and resuspension in homogenization buffer before centrifugation at 150×g for 2 min to remove crude cell debris. The supernatant is centrifuged at 4000×g for 15 min and the pellet fraction is resuspended in 1 ml of a buffer containing Tris-HCl (50 mM; pH 7.3), EDTA (2 mM), leupeptin (2 μM), pepstatin (2 μM) and glycerol (200 ml $L^{-1}$) and stored at −80° C. until use. Protein is determined in the enzyme extract with bovine serum albumin as a standard. PPO activity is assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 μM), and 40 μg extracted protein in a total volume of 200 μl. The reaction is initiated by addition of substrate protoporphyrinogen IX at 22° C. saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control are prepared in dimethyl sulfoxide (DMSO) solution (0.1 mM concentration of DMSO in the assay) and added to the assay mixture in concentrations of 0.005 pM to 5 μM before incubation. Fluorescence is monitored directly from the assay mixture using a POLARstar Optima/Galaxy (BMG) with excitation at 405 nm and emission monitored at 630 nm. Non-enzymatic activity in the presence of heat-inactivated extract is negligible. Inhibition of enzyme activity induced by the herbicide is expressed as percentage inhibition relative to untreated controls. Molar concentrations of compound required for 50% enzyme inhibition (1050 values) are calculated by fitting the values to the dose-response equation using non-linear regression analysis.

Example 4

PPO Enzyme Assay (Recombinant)

Proto is purchased from Sigma-Aldrich (Milwaukee, Wis.). Protogen is prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays are conducted in 100 mM sodium phosphate pH 7.4 with 0.1 mM EDTA, 0.1% Tween 20, 5 μM FAD, and 500 mM imidazole. Dose-response curves with the PPO inhibitors saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, and MC-15608 are obtained in the presence of 150 μM Protogen. The excitation and emission bandwidths are set at 1.5 and 30 nm, respectively. All assays are made in duplicates or triplicates and measured using a POLARstar Optima/Galaxy (BMG) with excitation at 405 nm and emission monitored at 630 nm. Molar concentrations of compound required for 50% enzyme inhibition (1050 values) are calculated by fitting the values to the dose-response equation using non-linear regression analysis. The results are shown in Table x.

Example 5

Engineering PPO-Derivative Herbicide Tolerant Plants Having Wildtype or Mutated PPO Sequences PPO-derivative herbicide tolerant soybean (*Glyceine max*), corn (*Zea mays*), and Canola (*Brassica napus* or *Brassica Rapa* var. or *Brassica campestris* L.) plants are produced by a method as described by Olhoft et al. (US patent 2009/0049567). For transformation of soybean or *Arabidopsis thaliana*, Wildtype or Mutated PPO sequences encoding mutated PPO polypeptides comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOD in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with Agrobacteria, the explants are transferred to shoot introduction media without selection for one week. The explants are subsequently transferred to a shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via *Agrobacterium*-mediated transformation.

Transformed cells are selected in selection media supplemented with 0.5-1.5 μM imazethapyr for 3-4 weeks. Transgenic plantlets are regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with wildtype or mutated PPO sequences by floral dip method as described by McElver and Singh (WO 2008/124495). Transgenic *Arabidopsis* plants are subjected to TaqMan analysis for analysis of the number of integration loci. Transformation of *Oryza sativa* (rice) are done by protoplast transformation as described by Peng et al. (U.S. Pat. No. 6,653,529) T0 or T1 transgenic plant of soybean, corn, and rice containing mutated PPO sequences are tested for improved tolerance to PPO-derived herbicides in greenhouse studies and mini-plot studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Transgenic *Arabidopsis thaliana* plants are assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxide (DMSO) and added to the medium prior solidification (final DMSO concentration 0.1%). Multi well plates are incubated in a growth chamber at 22° C., 75% relative humidity and 110 μmol Phot*$m^{-2}$*$s^{-1}$ with 14:10 h light:dark photoperiod. Growth inhibition is evaluated seven to ten days after seeding in comparison to wild type plants.

Additionally, transgenic T1 *Arabidopsis* plants are tested for improved tolerance to PPO-inhibiting herbicides in greenhouse studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Example 6

Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, (saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli are initiated from 4 different maize or rice cultivars encompassing *Zea mays* and *Japonica* (Taipei 309, Nipponbare, Koshihikari) and Indica (Indica 1) varieties, respectively. Seeds are surface sterilized in 70% ethanol for approximately 1 min followed by 20% commercial Clorox bleach for 20 minutes. Seeds are rinsed with sterile water and plated on callus induction media. Various callus induction media are tested. The ingredient lists for the media tested are presented in Table y.

TABLE Y

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 μg/L | |
| 2,4-D | Sigma | 2.0 mg/L | | | | | 1.0 mg/L |

TABLE Y-continued

| Ingredient | Supplier | R001M | R025M | R026M | R327M | R008M | MS711R |
|---|---|---|---|---|---|---|---|
| $MgCl_2 \cdot 6H_2O$ | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media is selected after testing numerous variations. Cultures are kept in the dark at 30° C. Embryogenic callus is subcultured to fresh media after 10-14 days.

Example 7

Selection of Herbicide-Tolerant Calli

Once tissue culture conditions are determined, further establishment of selection conditions are established through the analysis of tissue survival in kill curves with saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Careful consideration of accumulation of the herbicide in the tissue, as well as its persistence and stability in the cells and the culture media is performed. Through these experiments, a sub-lethal dose has been established for the initial selection of mutated material. After the establishment of the starting dose of saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in selection media, the tissues are selected in a step-wise fashion by increasing the concentration of the PPO inhibitor with each transfer until cells are recovered that grew vigorously in the presence of toxic doses. The resulting calli are further subcultured every 3-4 weeks to R001M with selective agent. Over 26,000 calli are subjected to selection for 4-5 subcultures until the selective pressure is above toxic levels as determined by kill curves and observations of continued culture. Alternatively, liquid cultures initiated from calli in MS711R with slow shaking and weekly subcultures. Once liquid cultures are established, selection agent is added directly to the flask at each subculture. Following 2-4 rounds of liquid selection, cultures are transferred to filters on solid R001M media for further growth.

Example 8

Regeneration of Plants

Tolerant tissue is regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways are also sequenced to characterize mutations. Finally, enzymes that change the fate (e.g. metabolism, translocation, transportation) are also sequence to characterized mutations. Following herbicide selection, calli are regenerated using a media regime of R025M for 10-14 days, R026M for ca. 2 weeks, R327M until well formed shoots are developed, and R008S until shoots are well rooted for transfer to the greenhouse. Regeneration is carried out in the light. No selection agent is included during regeneration. Once strong roots are established, M0 regenerants are transplant to the greenhouse in square or round pots. Transplants are maintained under a clear plastic cup until they are adapted to greenhouse conditions. The greenhouse is set to a day/night cycle of 27° C./21° C. (80° F./70° F.) with 600 W high pressure sodium lights supplementing light to maintain a 14 hour day length. Plants are watered according to need, depending in the weather and fertilized daily.

Example 9

Sequence Analysis

Leaf tissue is collected from clonal plants separated for transplanting and analyzed as individuals. Genomic DNA is extracted using a Wizard® 96 Magnetic DNA Plant System kit (Promega, U.S. Pat. Nos. 6,027,945 & 6,368,800) as directed by the manufacturer. Isolated DNA is PCR amplified using the appropriate forward and reverse primer.

PCR amplification is performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C. PCR products are verified for concentration and fragment size via agarose gel electrophoresis. Dephosphorylated PCR products are analyzed by direct sequence using the PCR primers (DNA Landmarks, or Entelechon). Chromatogram trace files (.scf) are analyzed for mutation relative to the wild-type gene using Vector NTI Advance 10™ (Invitrogen). Based on sequence information, mutations are identified in several individuals. Sequence analysis is performed on the representative chromatograms and corresponding AlignX alignment with default settings and edited to call secondary peaks.

Example 10

Demonstration of Herbicide-tolerance

T0 or T1 transgenic plant of soybean, corn, Canola varieties and rice containing PPO1 and or PPO2 sequences are tested for improved tolerance to herbicides in greenhouse studies and mini-plot studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Transgenic *Arabidopsis thaliana* plants are assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxide (DMSO) and added to the medium prior solidification (final DMSO concentration 0.1%). Multi well plates are incubated in a growth chamber at 22° C., 75% relative humidity and 110 μmol Phot*$m^{-2}$*$s^{-1}$ with 14:10 h light:dark photoperiod. Growth inhibition is evaluated seven to ten days after seeding in comparison to wild type plants. Additionally, transgenic T1 *Arabidopsis* plants are tested for improved tolerance to herbicides in greenhouse studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Example 11

Herbicide Selection Using Tissue Culture

Media is selected for use and kill curves developed as specified above. For selection, different techniques are utilized. Either a step wise selection is applied, or an immediate lethal level of herbicide is applied. In either case, all of the calli are transferred for each new round of selection. Selection is 4-5 cycles of culture with 3-5 weeks for each cycle. Cali are placed onto nylon membranes to facilitate transfer (200 micron pore sheets, Biodesign, Saco, Me.). Membranes are cut to fit 100×20 mm Petri dishes and are autoclaved prior to use 25-35 calli (average weight/calli being 22 mg) are utilized in every plate. In addition, one set of calli are subjected to selection in liquid culture media with weekly subcultures followed by further selection on semi-solid media. Mutant lines are selected using saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Efficiencies of obtaining mutants is high either based on a percentage of calli that gave rise to a regenerable, mutant line or the number of lines as determined by the gram of tissue utilized.

Example 12

Maize Whole Plant Transformation and PPO Inhibitor Tolerance Testing

Immature embryos are transformed according to the procedure outlined in Peng et al. (WO2006/136596). Plants are tested for the presence of the T-DNA by Taqman analysis with the target being the nos terminator which is present in all constructs. Healthy looking plants are sent to the greenhouse for hardening and subsequent spray testing. The plants are individually transplanted into MetroMix 360 soil in 4" pots. Once in the greenhouse (day/night cycle of 27° C./21° C. with 14 hour day length supported by 600 W high pressure sodium lights), they are allowed to grow for 14 days. They are then sprayed with a treatment of 25 to 200 g ai/ha saflufenacil+1.0% v/v methylated seed oil (MSO) and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides are also tested in a similar fashion for confirming cross resistance: flumioxazin, butafenacil, acifluorfen, lactofen, bifenox, sulfentrazone, and photosynthesis inhibitor diuron as negative control. Herbicide injury evaluations are taken at 7, 14 and 21 days after treatment. Herbicide injury evaluations are taken 2, 7, 14 and 21 days post-spray to look for injury to new growth points and overall plant health. The top survivors are transplanted into gallon pots filled with MetroMix 360 for seed production.

Example 13

Soybean Transformation and PPO Inhibitor Tolerance Testing

Soybean cv Jake is transformed as previously described by Siminszky et al., Phytochem Rev. 5:445-458 (2006). After regeneration, transformants are transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events are transplanted to larger pots and allowed to grow in the growth chamber. An optimal shoot for cutting is about 3-4 inches tall, with at least two nodes present. Each cutting is taken from the original transformant (mother plant) and dipped into rooting hormone powder (indole-3-butyric acid, IBA). The cutting is then placed in oasis wedges inside a bio-dome. The mother plant is taken to maturity in the greenhouse and harvested for seed. Wild type cuttings are also taken simultaneously to serve as negative controls. The cuttings are kept in the bio-dome for 5-7 days and then transplanted to 3 inch pots and then acclimated in the growth chamber for two more days. Subsequently, the cuttings are transferred to the greenhouse, acclimated for approximately 4 days, and then sprayed with a treatment of 0-200 g ai/ha saflufenacil plus 1% MSO and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides are also tested in a similar fashion for confirming cross resistance: flumioxazin, butafenacil, acifluorfen, lactofen, bifenox, sulfentrazone, and photosynthesis inhibitor diuron as negative control. Herbicide injury evaluations are taken at 2, 7, 14 and 21 days after treatment. Results are shown in Table xxx.

| Rating | Phenotype (phytotoxicity) of surviving plants |
|---|---|
| 1 | no obvious damage (no phytotoxicity) |
| 2 | minor amount of leaf damage, plant will survive |
| 3 | moderate amount of leaf damage, plant will survive |
| 4 | severe amount of leaf damage, plant will survive |
| 5 | no surviving plants - all plants dead/dying |

The following gives a definition of the injury scores measured above:

| Score | Description of injury |
|---|---|
| 0 | No Injury |
| 1 | Minimal injury, only a few patches of leaf injury or chlorosis. |
| 2 | Minimal injury with slightly stronger chlorosis. Overall growth points remain undamaged. |
| 3 | Slightly stronger injury on secondary leaf tissue, but primary leaf and growth points are still undamaged. |
| 4 | Overall plant morphology is slightly different, some chlorosis and necrosis in secondary growth points and leaf tissue. Stems are intact. Regrowth is highly probable within 1 week. |
| 5 | Overall plant morphology is clearly different, some chlorosis and necrosis on a few leaves and growth points, but primary growth point is intact. Stem tissue is still green. Regrowth is highly probably within 1 week. |
| 6 | Strong injury can be seen on the new leaflet growth. Plant has a high probability to survive only through regrowth at different growth points. Most of the leaves are chlorotic/necrotic but stem tissue is still green. May have regrowth but with noticeable injured appearance. |
| 7 | Most of the active growth points are necrotic. There may be a single growth point that could survive and may be partially chlorotic or green and partially necrotic. Two leaves may still be chlorotic with some green; the rest of the plant including stem is necrotic. |
| 8 | Plant will likely die, and all growth points are necrotic. One leaf may still be chlorotic with some green. The remainder of the plant is necrotic. |
| 9 | Plant is dead. |
| * | Not tested |

Example 14

Transient Protein Expression in Tobacco Leafs

Transient expression of mutated PPO sequences (e.g. SEQ ID NOs: 1, 30, 31, 11, 37, and 117) as wildtype or with respective mutations were done as described previously (Voinnet O., et al., 2003, The Plant Journal 33, 949-956). In brief, cloning of GOI and *Agrobacterium* transformation (strain: GV2260) were done as described in EXAMPLE 5. Young leaves of *Nicotiana benthamiana* were infiltrated with transgenic *Agrobacterium* suspension ($OD^{600}$ of 1.0) harboring binary vector constructs containing a GOI gene controlled by a promoter and terminator sequence. 48 h to 72 h after infiltration punches of leave discs (0.75 cm in diameter) were transferred to 6-well plates with medium (half strength Linsmaier-Skoog (Linsmaier and Skoog (1965) Physiol. Plant. 18: 100-127) nutrient solution or water) containing herbicide of interest in different concentrations. Multi well plates were incubated in a growth chamber at 22° C., 75% relative humidity and 110 μmol Phot*$m^{-2}$*$s^{-1}$ with 14:10 h light:dark photoperiod.

Example 15

Demonstration of Herbicide Tolerance of Transiently Transformed Tobacco Leaf Discs Leaf discs, generated as described in EXAMPLE 14, expressing a protein encoded by GOI, were subjected to analysis on improved tolerance to herbicide treatment. For analysis of herbicide damage, chlorophyll fluorescence were identified as indicative marker (Dayan and Zaccaro (2012)

Pest. Biochem. Physiol. 102: 189-197). In addition to monitor herbicide effect by visual inspection the photosynthetic yield of photosystem II were done with a MAXI imaging PAM machine (IMAGINE-PAM M-Series, Walz, Effeltrich, Germany) 48 h after starting herbicide treatment. PSII yield were measured as per manufacturer instructions. Tolerance factors were calculated based on $IC_{50}$ values of PSII yield inhibition of transformed versus empty vector-transformed leaf discs. $IC_{50}$ of PSII yield inhibition in empty vector-transformed leaf discs treated with Saflufenacil or 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione for 48 h was measured with $1.1*10^{-7}$ M or $1.1*10^{-8}$ M, respectively.

| Origin of gene | Gene | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | SEQ ID |
|---|---|---|---|---|
| *Amaranthus tuberculatus* | AMATU_PPO2_R128L | 170 | 28.7 | 1 |
| *Amaranthus tuberculatus* | AMATU_PPO2_L397E_F420V | 170 | Na | 1 |
| *Zea mays* | Zm_PPO2_R130A_F433V | 618 | 8766 | 30, 31 |
| *Zea mays* | Zm_PPO2_L410Q_F433V | 10 | 15 | 30, 31 |
| *Zea mays* | Zm_PPO2_L410E_F433M | 8 | 8766 | 30, 31 |
| *Zea mays* | Zm_PPO2_L410Q_F433M | 183 | 385 | 30, 31 |
| *Glycine max* | Gm_PPO2_wt | 679 | 1 | 11 |
| *Glycine max* | Gm_PPO2_R98A_F390V | 109 | 14 | 11 |
| *Glycine max* | Gm_PPO2_L367E_F390V | 258 | 15 | 11 |
| *Glycine max* | Gm_PPO2_L367Q_F390V | 679 | 26 | 11 |
| *Glycine max* | Gm_PPO2_L367E_F390M | 38 | 50 | 11 |
| *Glycine max* | Gm_PPO2_L367Q_F390M | 353 | 14 | 11 |
| *Brassica napus* | Bn_PPO2_A_wt | 7 | 1 | 117 |
| *Brassica napus* | Bn_PPO2_A_R99A_F394V | 4 | 1 | 117 |
| *Brassica napus* | Bn_PPO2_A_L371E_F394V | 4 | 13 | 117 |
| *Brassica napus* | Bn_PPO2_A_L371Q_F394V | 244 | 14 | 117 |
| *Brassica napus* | Bn_PPO2_A_L371E_F394M | 26 | 10 | 117 |
| *Brassica napus* | Bn_PPO2_A_L371Q_F394M | 652 | 10 | 117 |
| *Oryza sativa* | Os_PPO2_wt | 88 | Na | 37 |
| *Oryza sativa* | Os_PPO2_L374E_F397V | 8 | 43 | 37 |
| *Oryza sativa* | Os_PPO2_L374E_F397M | 8 | 2454 | 37 |
| *Oryza sativa* | Os_PPO2_L374Q_F397M | 9 | 14 | 37 |

The invention claimed is:

1. A method for controlling undesired vegetation at a plant cultivation site, the method comprising the steps of:

a) providing, at said site, a plant that comprises at least one nucleic acid comprising a nucleotide sequence encoding a mutated protoporphyrinogen oxidase (mutated-PPO) which is resistant or tolerant to a "PPO inhibiting herbicide", and which comprises the amino acid sequence of SEQ ID NO: 11 with a double amino acid substitution selected from the group consisting of R98A/F390V; L367E/F390V; L367Q/F390V; L367E/F390M; and L367Q/F390M; and b) applying to said site an effective amount of said herbicide.

2. The method according to claim 1, wherein the plant comprises at least one additional heterologous nucleic acid comprising a nucleotide sequence encoding a herbicide tolerance enzyme.

3. The method according to claim 1 wherein the PPO inhibiting herbicide is applied in conjunction with one or more additional herbicides.

4. A transgenic plant cell comprising a nucleic acid encoding a mutated-PPO polypeptide, wherein expression of the nucleic acid in the plant cell results in increased resistance or tolerance to a PPO inhibiting herbicide as compared to a wild type variety of the plant cell, and wherein the encoded mutated-PPO comprises the amino acid sequence of SEQ ID NO: 11 with a double amino acid substitution selected from the group consisting of R98A/F390V; L367E/F390V; L367Q/F390V; L367E/F390M; and L367Q/F390M.

5. A transgenic plant comprising a plant cell as defined in claim 4, wherein expression of the mutated-PPO polypeptide encoding nucleic acid in the plant results in the plant's increased resistance to PPO inhibiting herbicide as compared to a wild type plant.

6. A plant that expresses a mutagenized or recombinant mutated-PPO polypeptide comprising the amino acid sequence of SEQ ID NO: 11 with a double amino acid substitution selected from the group consisting of R98A/F390V; L367E/F390V; L367Q/F390V; L367E/F390M; and L367Q/F390M, and wherein said mutated-PPO confers upon the plant increased herbicide tolerance as compared to the corresponding wild-type variety of the plant when expressed therein.

7. A seed produced by a transgenic plant comprising a plant cell as defined in claim 4, wherein the seed is true breeding for an increased resistance to a PPO inhibiting herbicide as compared to a wild type variety of the seed.

8. A method of producing a transgenic plant cell with an increased resistance to a PPO inhibiting herbicide as compared to a wild type variety of the plant cell comprising, transforming the plant cell with an expression cassette comprising a nucleic acid encoding a mutated-PPO polypeptide comprising the amino acid sequence of SEQ ID NO: 11 with a double amino acid substitution selected from the group consisting of R98A/F390V; L367E/F390V; L367Q/F390V; L367E/F390M; and L367Q/F390M.

9. A method of producing a transgenic plant comprising, (a) transforming a plant cell with an expression cassette comprising a nucleic acid encoding a mutated-PPO polypeptide comprising the amino acid sequence of SEQ ID NO: 11 with a double amino acid substitution selected from the group consisting of R98A/F390V; L367E/F390V; L367Q/F390V; L367E/F390M; and L367Q/F390M, and (b) generating a plant with an increased resistance to PPO inhibiting herbicide from the plant cell.

10. The method of claim 9, wherein the expression cassette further comprises a transcription initiation regulatory region and a translation initiation regulatory region that are functional in the plant.

* * * * *